(12) United States Patent
Ehara et al.

(10) Patent No.: US 8,129,411 B2
(45) Date of Patent: Mar. 6, 2012

(54) ORGANIC COMPOUNDS

(75) Inventors: Takeru Ehara, Tsukuba (JP); Philipp Grosche, Inzlingen (DE); Osamu Irie, Tsukuba (JP); Yuki Iwaki, Tsukuba (JP); Takanori Kanazawa, Tsukuba (JP); Shimpei Kawakami, Tsukuba (JP); Kazuhide Konishi, Tsukuba (JP); Muneto Mogi, Tsukuba (JP); Masaki Suzuki, Tsukuba (JP); Fumiaki Yokokawa, Tsukuba (JP)

(73) Assignee: Novartis AG, Basel (CH)

( * ) Notice: Subject to any disclaimer, the term of this patent is extended or adjusted under 35 U.S.C. 154(b) by 590 days.

(21) Appl. No.: 12/159,749

(22) PCT Filed: Dec. 28, 2006

(86) PCT No.: PCT/EP2006/012581
§ 371 (c)(1),
(2), (4) Date: Jun. 30, 2008

(87) PCT Pub. No.: WO2007/077005
PCT Pub. Date: Jul. 12, 2007

(65) Prior Publication Data
US 2009/0192148 A1    Jul. 30, 2009

(30) Foreign Application Priority Data

Dec. 30, 2005  (EP) .................................. 05028771
Mar. 2, 2006   (GB) .................................. 0604223.8
Jun. 8, 2006   (GB) .................................. 0611390.6

(51) Int. Cl.
*A61K 31/454* (2006.01)
*C07D 401/02* (2006.01)
(52) U.S. Cl. ........................ 514/323; 546/201
(58) Field of Classification Search ............... 514/230.5, 514/323, 300, 312; 546/208, 113, 157; 544/105
See application file for complete search history.

(56) References Cited

U.S. PATENT DOCUMENTS

| | | | |
|---|---|---|---|
| 6,150,526 | A | 11/2000 | Binggeli et al. |
| 6,197,959 | B1 | 3/2001 | Breu et al. |
| 6,274,735 | B1 | 8/2001 | Lohri et al. |
| 6,376,672 | B1 | 4/2002 | Breu et al. |
| 2002/0087002 | A1 | 7/2002 | Breu et al. |
| 2004/0019137 | A1 | 1/2004 | Hebrault |
| 2004/0077551 | A1 | 4/2004 | Campbell et al. |
| 2004/0204455 | A1 | 10/2004 | Cody et al. |
| 2007/0167433 | A1 | 7/2007 | Herold et al. |

FOREIGN PATENT DOCUMENTS

| | | |
|---|---|---|
| EP | 1 908 471 A1 | 4/2008 |
| WO | 93/12108 A1 | 6/1993 |
| WO | 95/09858 A1 | 4/1995 |
| WO | 97/09311 A1 | 3/1997 |
| WO | 97/18813 A | 5/1997 |

(Continued)

OTHER PUBLICATIONS

Powell, et al., "Rational design of 6-(2,4-diaminopyrimidiny1)-I,4-benzoxazin-3-ones as small molecule renin inhibitors" Bioorg. Med. Chem. 15(2007) 5912-5949.
Powell, et al., "Equipotent activity in both enantiomers of a series of ketopiperazine-based renin inhibitors" Bioorg med. Chem. Lett. 2005, 15, 2371-2374.
Holsworth, et al., "Discovery of novel non-peptidic ketopiperazine-based renin inhibitors" Bioorg Med. Chem. 2005, 13, 2657-2664.
Powell, et al., "Benzyl ether structure-activity relationships in a series of ketopiperazine-based renin inhibitors" Bioorg Med. Chem. Lett 2005, 15, 4713-4716.
Holsworth, et al., "Ketopiperazine-based renin inhibitors: Optimization of the "C" ring" Bioorg Med. Chem. Lett 2006, 16, 2500-2504.
Holsworth, et al., "Discovery of 6-ethyl-2,4diaminopyrimidine-based small molecule renin inhibitors" Bioorg Med. Chem. Lett, 17 (2007) 3575-3580.
Yokokawa, et al., "Recent advances in the discovery of non-peptidic direct renin inhibitors as antihypertensives: new patent applications in years 2000-2008" Expert Opin. Ther. Patents (2008)18(6), 581-602.
Park J-S, et al: "An efficient synthesis of 3(S)-aminopiperidine-5(R)-carboxylic acid as a cyclic beta, gamma'-diamino acid" Tetrahedon Letters, Elsevier, Amsterdam, NL, vol. 44, No. 8, Feb. 17, 2003. pp. 1611-1614. Cited in the application table 1.

(Continued)

*Primary Examiner* — Kamal Saeed
*Assistant Examiner* — Kristin Bianchi
(74) *Attorney, Agent, or Firm* — Sophie Binet Cross

(57) ABSTRACT

The invention relates to 3,5-substituted piperidine compounds, these compounds for use in the diagnostic and therapeutic treatment of a warm-blooded animal, especially for the treatment of a disease (=disorder) that depends on activity of renin; the use of a compound of that class for the preparation of a pharmaceutical formulation for the treatment of a disease that depends on activity of renin; the use of a compound of that class in the treatment of a disease that depends on activity of renin; pharmaceutical formulations comprising a 3,5-substituted piperidine compound, and/or a method of treatment comprising administering a 3,5-substituted piperidine compound, a method for the manufacture of a 3,5-substituted piperidine compound, and novel intermediates and partial steps for its synthesis.
The compounds have the formula I'

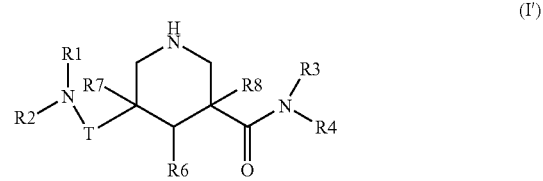

(I')

wherein R1, R2, T, R3 and R4 are as defined in the specification.

20 Claims, No Drawings

FOREIGN PATENT DOCUMENTS

| | | |
|---|---|---|
| WO | 99/09984 A1 | 3/1999 |
| WO | 99/65867 A1 | 12/1999 |
| WO | 00/26211 A1 | 5/2000 |
| WO | 00/51607 A1 | 9/2000 |
| WO | 00/51608 A1 | 9/2000 |
| WO | 00/51610 A1 | 9/2000 |
| WO | 00/63173 A1 | 10/2000 |
| WO | 00/64873 A1 | 11/2000 |
| WO | 00/64887 A1 | 11/2000 |
| WO | 01/70673 A2 | 9/2001 |
| WO | 02/06387 A2 | 1/2002 |
| WO | 02/34716 A2 | 5/2002 |
| WO | 02/076440 A2 | 10/2002 |
| WO | 02/088101 A2 | 11/2002 |
| WO | 03/024899 A2 | 3/2003 |
| WO | 03/031443 A1 | 4/2003 |
| WO | 03/032962 A2 | 4/2003 |
| WO | 03/093267 A1 | 11/2003 |
| WO | 2004/004665 A2 | 1/2004 |
| WO | 2004/089903 A1 | 10/2004 |
| WO | 2004/089915 A1 | 10/2004 |
| WO | 2004/096116 A1 | 11/2004 |
| WO | 2004/096366 A1 | 11/2004 |
| WO | 2004/096769 A1 | 11/2004 |
| WO | 2004/096799 A1 | 11/2004 |
| WO | 2004/096803 A1 | 11/2004 |
| WO | 2004/096804 A1 | 11/2004 |
| WO | 2005/040120 A1 | 5/2005 |
| WO | 2005/051895 A1 | 6/2005 |
| WO | 2005/051911 A | 6/2005 |
| WO | 2005/061457 A | 7/2005 |
| WO | 2005/070870 A2 | 8/2005 |
| WO | 2005/070871 A2 | 8/2005 |
| WO | 2005/070877 A1 | 8/2005 |
| WO | 2005/090304 A1 | 9/2005 |
| WO | 2005/090305 A1 | 9/2005 |
| WO | 2006/005741 A2 | 1/2006 |
| WO | 2006/061426 A1 | 6/2006 |
| WO | 2006/066896 A2 | 6/2006 |
| WO | 2006/069788 A1 | 7/2006 |
| WO | 2006/074924 A1 | 7/2006 |
| WO | 2006/094763 A1 | 9/2006 |
| WO | 2006/095020 A1 | 9/2006 |
| WO | 2006/100036 A1 | 9/2006 |
| WO | 2006/103273 A1 | 10/2006 |
| WO | 2006/103275 A1 | 10/2006 |
| WO | 2006/117183 A | 11/2006 |
| WO | 2006/125621 A1 | 11/2006 |
| WO | 2006/128659 A2 | 12/2006 |
| WO | 2007/006534 A2 | 1/2007 |
| WO | 2007/031557 A2 | 3/2007 |
| WO | 2007/031558 A1 | 3/2007 |
| WO | 2007/059323 A2 | 5/2007 |
| WO | 2007/077005 A1 | 7/2007 |
| WO | 2007/085651 A1 | 8/2007 |
| WO | 2007/141318 A1 | 12/2007 |
| WO | 2007/144128 A1 | 12/2007 |
| WO | 2007/144129 A2 | 12/2007 |

OTHER PUBLICATIONS

Danieli, Bruno, et al: "An expeditious synthesis of dimethyl 1-benzyl-cis-piperidine-3,5-dicarboxylate" Synthetic Communications, 27(1), 1997, pp. 69-77. Scheme 1.

Busch et. al.; "Synthesis and Antimicrobial Evaluation of a Series of 7-[3-amino (or aminomethyl)-4-aryl (or cyclopropyl)-1-pyrrolidinyl]-4-quinolone and -1,8-naphthyridone-3-carboxylic acids"; J. Med. Chem; (1993) 36(26): 4139-51.

Fevig et. al.; "Design and Synthesis of Ring-Constrained Boropeptide Thrombin Inhibitors"; Bioorg. Med. Chem. Lett.; (1996) 6(3): 295-300.

Marki et. al.; "Piperidine Renin Inhibitors: From Leads to Drug Candidates"; IL Farmaco, Rome, IT; (2001) 56: 21-27.

Specker et. al.; "An Old Target Revisited: Two New Privileged Skeletons and an Unexpected Binding Mode for HIV-Protease Inhibitors"; Angew. Chem. Int. Ed.; (2005) 44(20); 3140-44.

Specker; "Dissertation—Rational drug design—Titled: De novo-Design und Synthese neuer Leitstrukturen als Ubergangszustandsmimetika zur selektiven Inhibition der HIV-1 Protease und Cathepsin D"; Fachbereich Pharmazie der Philipps-Universitat Marburg [English Translation of Introduction and issues involved] (2004).

Thomas et. al.; "Beta-Analogs of PLG (L-Prolyl-L-Leucyl-Glycinamide): Ex-Chiral Pool Syntheses and Dopamine D2 Receptor Modulating Effects"; Bioorg. Med. Chem. Lett.; (1998); 8: 2885-2890.

ORGANIC COMPOUNDS

This application is the National Stage of Application No. PCT/EP2006/012581, filed on Dec. 28, 2006, which claims benefit under 35 U.S.C. §119(a)-(d) or (f) or 365(b) of EP Application No. 0517740.7, filed Dec. 30, 2005, and GB Applications No. 0604223.8, filed Mar. 2, 2006, and 0611390.6, filed Jun. 8, 2006, the contents of which are incorporated herein by reference in their entirety.

The invention relates to 3,5-substituted piperidine compounds, these compounds for use in the diagnostic and therapeutic treatment of a warm-blooded animal, especially for the treatment of a disease (=disorder) that depends on activity of renin; the use of a compound of that class for the preparation of a pharmaceutical formulation for the treatment of a disease that depends on activity of renin; the use of a compound of that class in the treatment of a disease that depends on activity of renin; pharmaceutical formulations comprising a 3,5-substituted piperidine compound, and/or a method of treatment comprising administering a 3,5-substituted piperidine compound, a method for the manufacture of a 3,5-substituted piperidine compound, and novel intermediates and partial steps for its synthesis.

The present invention relates to a compound of the formula I'

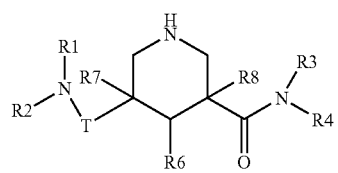
(I')

wherein
R1 is hydrogen, unsubstituted or substituted alkyl, unsubstituted or substituted alkenyl, unsubstituted or substituted alkynyl, unsubstituted or substituted aryl, unsubstituted or substituted heterocyclyl or unsubstituted or substituted cycloalkyl;
R2 is unsubstituted or substituted alkyl, unsubstituted or substituted alkenyl, unsubstituted or substituted alkynyl, unsubstituted or substituted aryl, unsubstituted or substituted heterocyclyl, unsubstituted or substituted cycloalkyl, or acyl;
R3 is hydrogen, unsubstituted or substituted aryl or unsubstituted or substituted alkyl;
R4 is unsubstituted or substituted alkyl, unsubstituted or substituted alkenyl, unsubstituted or substituted alkynyl, unsubstituted or substituted aryl, unsubstituted or substituted heterocyclyl, unsubstituted or substituted cycloalkyl, or acyl;
or R3 and R4 may form together a 3 to 7 membered nitrogen containing saturated hydrocarbon ring which can be unsubstituted or substituted;
R6 is hydrogen, halo, unsubstituted alkyl or unsubstituted alkoxy;
R7 and R8 are independently of each other hydrogen or halo; and
T is methylene or carbonyl;
or a salt thereof.

The present invention also relates to a compound of the formula I

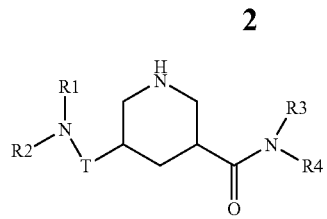
(I)

wherein
R1 is hydrogen, unsubstituted or substituted alkyl, unsubstituted or substituted alkenyl, unsubstituted or substituted alkynyl, unsubstituted or substituted aryl, unsubstituted or substituted heterocyclyl or unsubstituted or substituted cycloalkyl;
R2 is unsubstituted or substituted alkyl, unsubstituted or substituted alkenyl, unsubstituted or substituted alkynyl, unsubstituted or substituted aryl, unsubstituted or substituted heterocyclyl, unsubstituted or substituted cycloalkyl, or acyl;
R3 is hydrogen, unsubstituted or substituted aryl or unsubstituted or substituted alkyl;
R4 is unsubstituted or substituted alkyl, unsubstituted or substituted alkenyl, unsubstituted or substituted alkynyl, unsubstituted or substituted aryl, unsubstituted or substituted heterocyclyl, unsubstituted or substituted cycloalkyl, or acyl;
or R3 and R4 may form together a 3 to 7 membered nitrogen containing saturated hydrocarbon ring which can be unsubstituted or substituted; and
T is methylene or carbonyl;
or a salt thereof.

The compounds of the formula I are preferred embodiments of the formula I' wherein R6, R7 and R8 are each hydrogen.

The compounds of the present invention exhibit inhibitory activity on the natural enzyme renin. Thus, compounds of formula I' or I may be employed for the treatment (this term also including prophylaxis) of one or more disorders or diseases especially selected from the diseases given in detail below, especially as far as these diseases can be modulated (more especially beneficially influenced) by renin inhibition.

Listed below are definitions of various terms used to describe the compounds of the present invention as well as their use and synthesis, starting materials and intermediates and the like. These definitions, either by replacing one, more than one or all general expressions or symbols used in the present disclosure and thus yielding preferred embodiments of the invention, preferably apply to the terms as they are used throughout the specification unless they are otherwise limited in specific instances either individually or as part of a larger group.

The term "lower" or "$C_1$-$C_7$-" defines a moiety with up to and including maximally 7, especially up to and including maximally 4, carbon atoms, said moiety being branched (one or more times) or straight-chained and bound via a terminal or a non-terminal carbon. Lower or $C_1$-$C_7$-alkyl, for example, is n-pentyl, n-hexyl or n-heptyl or preferably $C_1$-$C_4$-alkyl, especially as methyl, ethyl, n-propyl, sec-propyl, n-butyl, isobutyl, sec-butyl or tert-butyl.

Halo or halogen is preferably fluoro, chloro, bromo or iodo, most preferably fluoro, chloro or bromo. If not explicitly or implicitly stated otherwise, halo can also stand for more than one halogen substituent in moieties such as alkyl, alkanoyl and the like (e.g. in trifluoromethyl, trifluoroacetyl).

Unsubstituted or substituted alkyl is preferably $C_1$-$C_{20}$-alkyl, more preferably $C_1$-$C_7$-alkyl, that is straight-chained or branched (one or, where appropriate, more times), which is unsubstituted or substituted by one or more, e.g. up to three moieties selected from unsubstituted or substituted heterocyclyl as described below, especially pyrrolyl, furanyl, thienyl (=thiophenyl), thiazolyl, pyrazolyl, triazolyl, tetrazolyl, oxetidinyl, 3-($C_1$-$C_7$-alkyl)-oxetidinyl, pyridyl, pyrimidinyl, morpholino, thiomorpholino, piperidinyl, piperazinyl, pyrrolidinyl, tetrahydrofuranonyl, tetrahydro-pyranyl, 1H-indazanyl, benzofuranyl, benzothiophenyl, (more preferably) isoquinolinyl, quinolinyl or especially indolyl, each of which is unsubstituted or substituted as described below for unsubstituted or substituted heterocyclyl, e.g. by one to three substitutents independently selected from hydroxy, halo, such as chloro, $C_1$-$C_7$-alkyl, such as methyl, cyano and $C_1$-$C_7$-alkanoyl, such as acetyl; from unsubstituted or substituted cycloalkyl as described below, especially cyclopropyl, cyclobutyl, cyclopentyl or cyclohexyl each of which is unsubstituted or substituted as described below for unsubstituted or substituted cycloalkyl, especially by up to four $C_1$-$C_7$-alkyl moieties; from unsubstituted or substituted aryl as described below, especially unsubstituted or substituted phenyl, naphthyl, indenyl or indanyl; and from the group consisting of $C_2$-$C_7$-alkenyl, $C_2$-$C_7$-alkinyl, halo, hydroxy, $C_1$-$C_7$-alkoxy, halo-$C_1$-$C_7$-alkoxy, such as trifluoromethoxy, hydroxy-$C_1$-$C_7$-alkoxy, $C_1$-$C_7$-alkoxy-$C_1$-$C_7$-alkoxy, phenyl- or naphthyloxy, phenyl- or naphthyl-$C_1$-$C_7$-alkyloxy, $C_1$-$C_7$-alkanoyloxy, ($C_1$-$C_7$-alkyl, hydroxy-$C_2$-$C_7$-alkyl (with the hydroxy not in 1-position), $C_1$-$C_7$-alkoxy-$C_1$-$C_7$-alkyl, phenyl and/or phenyl-$C_1$-$C_7$-alkyl)-aminocarbonyloxy, benzoyl- or naphthoyloxy, $C_1$-$C_7$-alkylthio, halo-$C_1$-$C_7$-alkthio, such as trifluoromethylthio, hydroxy-$C_1$-$C_7$-alkylthio, $C_1$-$C_7$-alkoxy-$C_1$-$C_7$-alkylthio, phenyl- or naphthylthio, phenyl- or naphthyl-$C_1$-$C_7$-alkylthio, nitro, amino, mono- or di-($C_1$-$C_7$-alkyl, phenyl, naphthyl, phenyl-$C_1$-$C_7$-alkyl, naphthyl-$C_1$-$C_7$-alkyl, hydroxy-$C_2$-$C_7$-alkyl (with the hydroxy not in 1-position) and/or $C_1$-$C_7$-alkoxy-$C_1$-$C_7$-alkyl)-amino, $C_1$-$C_7$-alkanoylamino, benzoyl- or naphthoylamino, $C_1$-$C_7$-alkylsulfonylamino, phenyl- or naphthylsulfonylamino, phenyl- or naphthyl-$C_1$-$C_7$-alkylsulfonylamino, phenyl- or naphthyl-$C_1$-$C_7$-alkyl-carbonylamino, carboxyl, $C_1$-$C_7$-alkyl-carbonyl, $C_1$-$C_7$-alkoxy-carbonyl, phenyl- or naphthyloxycarbonyl, phenyl- or naphthyl-$C_1$-$C_7$-alkoxycarbonyl, carbamoyl, N-mono- or N,N-di-($C_1$-$C_7$-alkyl)-aminocarbonyl, N-mono- or N,N-di-(naphthyl- or phenyl-$C_1$-$C_7$-alkyl, hydroxy-$C_2$-$C_7$-alkyl (with the hydroxy not in 1-position) and/or $C_1$-$C_7$-alkoxy-$C_1$-$C_7$-alkyl)-aminocarbonyl, cyano, sulfenyl (—S—OH), sulfonyl (—S(=O)—OH), $C_1$-$C_7$-alkylsulfinyl ($C_1$-$C_7$-alkyl-S(=O)—), phenyl- or naphthylsulfinyl, phenyl- or naphthyl-$C_1$-$C_7$-alkylsulfinyl, sulfonyl, $C_1$-$C_7$-alkylsulfonyl, phenyl- or naphthylsulfonyl, phenyl- or naphthyl-$C_1$-$C_7$-alkylsulfonyl, sulfamoyl, N-mono or N,N-di-($C_1$-$C_7$-alkyl, phenyl-, naphthyl, phenyl-$C_1$-$C_7$-alkyl, naphthyl-$C_1$-$C_7$-alkyl, hydroxy-$C_2$-$C_7$-alkyl and/or $C_1$-$C_7$-alkoxy-$C_1$-$C_7$-alkyl)-aminosulfonyl, N-mono-, N'-mono-, N,N-di- or N,N,N'-tri-($C_1$-$C_7$-alkyl, hydroxy-$C_2$-$C_7$-alkyl (with the hydroxy not in 1-position), $C_1$-$C_7$-alkoxy-$C_1$-$C_7$-alkyl, phenyl and/or phenyl-$C_1$-$C_7$-alkyl)-aminocarbonylamino or -aminocarbonyloxy and N-mono-, N'-mono-, N,N-di- or N,N,N'-tri-($C_1$-$C_7$-alkyl, hydroxy-$C_2$-$C_7$-alkyl (with the hydroxy not in 1-position), $C_1$-$C_7$-alkoxy-$C_1$-$C_7$-alkyl, phenyl and/or phenyl-$C_1$-$C_7$-alkyl)-aminosulfonylamino;

where any phenyl, naphthyl, indenyl, indanyl, pyridyl or indolinyl mentioned as substituent of or as part of a substituent of substituted alkyl (mentioned in the preceding paragraph) is unsubstituted or substituted by one or more, preferably up to three, moieties independently selected from the group consisting of $C_1$-$C_7$-alkyl, $C_1$-$C_7$-alkoxy-$C_1$-$C_7$-alkyl, $C_1$-$C_7$-alkenyl, $C_1$-$C_7$-alkynyl, halo-$C_1$-$C_7$-alkyl, such as trifluoromethyl, halo, especially fluoro, chloro, bromo or iodo, hydroxy, $C_1$-$C_7$-alkoxy, $C_1$-$C_7$-alkoxy-$C_1$-$C_7$-alkoxy, phenyloxy, naphthyloxy, phenyl- or naphthyl-$C_1$-$C_7$-alkoxy, $C_1$-$C_7$-alkanoyloxy, phenyl- or naphthyl-$C_1$-$C_7$-alkanoyloxy, amino, mono- or di-($C_1$-$C_7$-alkyl, phenyl, naphthyl, phenyl-$C_1$-$C_7$-alkyl, naphthyl-$C_1$-$C_7$-alkyl, $C_1$-$C_7$-alkanoyl and/or phenyl- or naphthyl-$C_1$-$C_7$-alkanoyl)-amino, carboxy, $C_1$-$C_7$-alkoxycarbonyl, phenoxycarbonyl, naphthyloxycabonyl, phenyl-$C_1$-$C_7$-alkyloxycarbonyl, naphthyl-$C_1$-$C_7$-alkoxycarbonyl, carbamoyl, N-mono- or N,N-di-($C_1$-$C_7$-alkyl, phenyl, naphthyl, phenyl-$C_1$-$C_7$-alkyl and/or naphthyl-$C_1$-$C_7$-alkyl)-aminocarbonyl, cyano, sulfonyl, sulfamoyl, N-mono- or N,N-di-($C_1$-$C_7$-alkyl, phenyl, naphthyl, phenyl-$C_1$-$C_7$-alkyl and/or naphthyl-$C_1$-$C_7$-alkyl)-aminosulfonyl and nitro, or preferably, where preferred substituents are mentioned, by one or more of these mentioned substituents. Very especially preferred, unsubstituted or substituted alkyl (especially as R2 or as part of acyl R4) is phenylmethyl, 2-cyclohexyl-2-phenyl-ethyl, 2,2-diphenylethyl, 2,2-diphenyl-n-butyl, 2,3-diphenyl-n-propyl, naphthylmethyl, 2-phenyl-2-pyridylethyl, indolylmethyl, 2-$C_1$-$C_7$-alkoxycarbonyl-2,2-diphenyl-ethyl, 4-methyl-2-phenyl-n-pentyl or 5-$C_1$-$C_7$-alkoxy-2-diphenylmethylpentyl, where any phenyl, naphthyl, pyridyl or indolyl mentioned as substituent of substituted alkyl is unsubstituted or substituted by one or more, especially up to three, moieties independently selected from the group consisting of $C_1$-$C_7$-alkyl, hydroxy-$C_1$-$C_7$-alkyl, $C_1$-$C_7$-alkoxy-$C_1$-$C_7$-alkyl, ω-hydroxy-$C_2$-$C_7$-alkoxy-$C_1$-$C_7$-alkyl, halo-$C_1$-$C_7$-alkyl, oxo-$C_1$-$C_7$-alkyl, $C_1$-$C_7$-alkanoyl, phenyl, halo, especially chloro or bromo, hydroxy, $C_1$-$C_7$-alkoxy, $C_1$-$C_7$-alkoxy-$C_1$-$C_7$-alkoxy, phenoxy, halo-$C_1$-$C_7$-alkoxy, amino, $C_1$-$C_7$-alkanoylamino, $C_1$-$C_7$-alkanesulfonyl and cyano (where preferably any moiety mentioned before comprising an O, halo, or S via which it is bound is not bound to a ring nitrogen).

Unsubstituted or substituted alkenyl is preferably $C_2$-$C_{20}$-alkenyl, more preferably $C_2$-$C_7$-alkenyl with one or, if possible, more double bonds, that is straight-chained or branched (one or, where appropriate, more times), which is unsubstituted or substituted by one or more, e.g. up to three moieties selected from those mentioned as substituents for substituted alkyl and from unsubstituted or substituted aryl, each preferably as described above or below. Substituents with an active hydrogen (e.g. hydroxy or amino) are preferably present in the form of tautomers in equilibrium if bound directly to a carbon with a double bond, preferably at such positions substituents with active hydrogen are avoided.

Unsubstituted or substituted alkynyl is preferably $C_2$-$C_{20}$-alkynyl, more preferably $C_2$-$C_7$-alkynyl with one or, if possible, more triple bonds, that is straight-chained or branched (one or, where appropriate, more times), which is unsubstituted or substituted by one or more, e.g. up to three moieties selected from those mentioned as substituents for substituted alkyl and from unsubstituted or substituted aryl, each preferably as described above or below. Substituents with an active hydrogen (e.g. hydroxy or amino) are preferably present in the form of tautomers in equilibrium if bound directly to a carbon with a triple bond, preferably at such positions substituents with active hydrogen are avoided.

Unsubstituted or substituted aryl preferably is a mono- or bicyclic aryl with 6 to 22 carbon atoms, especially phenyl, indenyl, indanyl or naphthyl, and is unsubstituted or substituted by one or more, especially one to three, moieties, preferably independently selected from the group consisting of a substituent of the formula —($C_0$-$C_7$-alkylene)-(X)$_r$—($C_1$-$C_7$-alkylene)-(Y)$_s$—($C_0$-$C_7$-alkylene)-H where $C_0$-alkylene means that a bond is present instead of bound alkylene, alkylene in each case may be straight-chained or branched and unsubstituted or substituted e.g. by one or more moieties as defined for substituted alkyl, especially by halo, especially fluoro, hydroxy, $C_1$-$C_7$-alkoxy, phenyloxy, naphthyloxy, $C_1$-$C_7$-alkanoyloxy, benzoyloxy, naphthoyloxy, amino, mono- or di-($C_1$-$C_7$-alkyl, $C_1$-$C_7$-alkanoyl, phenyl-$C_1$-$C_7$-alkanoyl, naphthyl-$C_1$-$C_7$-alkanoyl, phenyl, naphthyl, phenyl-$C_1$-$C_7$-alkyl and/or naphthyl-$C_1$-$C_7$-alkyl)-amino, carboxy, $C_1$-$C_7$-alkoxycarbonyl or cyano, r and s, each independently of the other, are 0 or 1 and each of X and Y, if present and independently of the others, is —O—, —NV—, —S—, —O—CO—, —CO—O—, —NV—CO—; —CO—NV—; —NV—SO$_2$—, —SO$_2$—NV; —NV—CO—NV—, —NV—CO—O—, —O—CO—NV—, —NV—SO$_2$—NV— wherein V is hydrogen or unsubstituted or substituted alkyl as defined above, especially $C_1$-$C_7$-alkyl, or is phenyl, naphthyl, phenyl- or naphthyl-$C_1$-$C_7$-alkyl or halo-$C_1$-$C_7$-alkyl; where said substituent —($C_0$-$C_7$-alkylene)-(X)$_r$—($C_1$-$C_7$-alkylene)-(Y)$_s$—($C_0$-$C_7$-alkylene)-His preferably $C_1$-$C_7$-alkyl, such as methyl, ethyl, n-propyl, isopropyl, n-butyl, isobutyl, sec-butyl or tert-butyl, halo-$C_1$-$C_7$-alkyl, such as trifluoromethyl, hydroxy-$C_1$-$C_7$-alkyl, $C_1$-$C_7$-alkoxy-$C_1$-$C_7$-alkyl, such as 3-methoxypropyl or 2-methoxyethyl, ω-hydroxy-$C_2$-$C_7$-alkoxy-$C_1$-$C_7$-alkyl, $C_1$-$C_7$-alkoxy-$C_1$-$C_7$-alkoxy-$C_1$-$C_7$-alkyl, phenyloxy- or naphthyloxy-$C_1$-$C_7$-alkyl, $C_1$-$C_7$-alkanoyloxy-$C_1$-$C_7$-alkyl, amino-$C_1$-$C_7$-alkyl, such as aminomethyl, $C_1$-$C_7$-alkoxy-$C_1$-$C_7$-alkylamino-$C_1$-$C_7$-alkyl, mono- or di-($C_1$-$C_7$-alkyl-, naphthyl-, phenyl, naphthyl-$C_1$-$C_7$-alkyl and/or phenyl-$C_1$-$C_7$-alkyl)-amino-$C_1$-$C_7$-alkyl, $C_1$-$C_7$-alkanoylamino-$C_1$-$C_7$-alkyl, $C_1$-$C_7$-alkyl-O—CO—NH—$C_1$-$C_7$-alkyl, $C_1$-$C_7$-alkylsulfonylamino-$C_1$-$C_7$-alkyl, $C_1$-$C_7$-alkyl-NH—CO—NH—$C_1$-$C_7$-alkyl, $C_1$-$C_7$-alkyl-NH—SO$_2$—NH—$C_1$-$C_7$-alkyl, $C_1$-$C_7$-alkoxy, hydroxy-$C_1$-$C_7$-alkoxy, $C_1$-$C_7$-alkoxy-$C_1$-$C_7$-alkoxy, $C_1$-$C_7$-alkanoyloxy, halo-$C_1$-$C_7$-alkoxy, such as trifluoromethoxy, phenyl- or naphthyl-$C_1$-$C_7$-alkanoyloxy, phenyl- or naphthyl-$C_1$-$C_7$-alkylaminocarbonyloxy, halo-$C_1$-$C_7$-alkylthio, such as trifluoromethylthio, phenyl- or naphthyl-$C_1$-$C_7$-alkylthio, mono- or di-($C_1$-$C_7$-alkyl-, naphthyl-$C_1$-$C_7$-alkyl-, phenyl-$C_1$-$C_7$-alkyl- and/or $C_1$-$C_7$-alkoxy-$C_1$-$C_7$-alkyl-)-amino, $C_1$-$C_7$-alkanoylamino, $C_1$-$C_7$-alkylsulfonylamino, phenyl- or naphthyl-$C_1$-$C_7$-alkanoylamino, phenyl- or naphthyl-$C_1$-$C_7$-alkylaminocarbonylamino, carboxy-$C_1$-$C_7$-alkyl, $C_1$-$C_7$-alkoxy-carbonyl, hydroxy-$C_1$-$C_7$-alkoxy-carbonyl, $C_1$-$C_7$-alkoxy-$C_1$-$C_7$-alkoxycarbonyl, amino-$C_1$-$C_7$-alkoxycarbonyl, (N—) mono-($C_1$-$C_7$-alkyl)-amino-$C_1$-$C_7$-alkoxycarbonyl, $C_1$-$C_7$-alkanoylamino-$C_1$-$C_7$-alkoxycarbonyl, N-mono- or N,N-di-($C_1$-$C_7$-alkyl, $C_1$-$C_7$-alkoxy-$C_1$-$C_7$-alkyl, naphthyl-$C_1$-$C_7$-alkyl and/or phenyl-$C_1$-$C_7$-alkyl)-aminocarbonyl, $C_1$-$C_7$-alkylsulfonyl, halo-$C_1$-$C_7$-alkylsulfonyl, hydroxy-$C_1$-$C_7$-alkylsulfonyl, $C_1$-$C_7$-alkoxy-$C_1$-$C_7$-alkylsulfonyl, amino-$C_1$-$C_7$-alkylsulfonyl, N-mono- or di-($C_1$-$C_7$-alkyl)-amino-$C_1$-$C_7$-alkylsulfonyl, $C_1$-$C_7$-alkanoylamino-$C_1$-$C_7$-alkylsulfonyl, N—$C_1$-$C_7$-alkoxy-$C_1$-$C_7$-alkylcarbamoyl or N-mono- or N,N-di-($C_1$-$C_7$-alkyl)-aminosulfonyl;

from $C_2$-$C_7$-alkenyl, $C_2$-$C_7$-alkynyl, phenyl, naphthyl, heterocyclyl, especially as defined below for heterocyclyl, preferably selected from pyrrolyl, furanyl, thienyl, pyrimidine-2,4-dione-1-, -3- or -5-yl and tetrahydrofuranyl, [phenyl- or naphthyl- or heterocyclyl or trihalo(especially trifluoro)methoxy]-$C_1$-$C_7$-alkyl or -$C_1$-$C_7$-alkyloxy wherein phenyl or naphthyl is preferably unsubstituted or substituted, preferably by $C_1$-$C_7$-alkoxy and/or halo and wherein heterocyclyl is as defined below, preferably selected from pyrrolyl, furanyl, tetrahydrofuranyl, tetrahydropyranyl and thienyl; such as benzyl or naphthylmethyl, tetrahydrofuranyl- or tetrahydropyranyl-$C_1$-$C_7$-alkyl, benzoyl- or naphthoylamino-$C_1$-$C_7$-alkyl, (phenyl- or naphthyl- or heterocyclyl)-sulfonylamino-$C_1$-$C_7$-alkyl wherein phenyl or naphthyl or heterocyclyl is unsubstituted or substituted, preferably by one or more, especially one to three, $C_1$-$C_7$-alkyl moieties, (phenyl or naphthyl or heterocyclyl)-$C_1$-$C_7$-alkylsulfonylamino-$C_1$-$C_7$-alkyl, halo, hydroxy, (heterocyclyl or phenyl or naphthyl)-oxy, naphthyl-$C_1$-$C_7$-alkyloxy, benzoyl or naphthoyl or heterocyclylcarbonyl)-oxy, (phenyl or naphthyl or heterocyclyl)-aminocarbonyloxy, (phenyl or naphthyl or heterocyclyl)-thio, (benzoyl or naphthoyl or heterocyclyl)-thio, nitro, amino, di-((naphthyl or phenyl or heterocyclyl)-$C_1$-$C_7$-alkyl)-amino, (benzoyl or naphthoyl or heterocyclyl)-amino, (phenyl or naphthyl or heterocyclyl)-$C_1$-$C_7$-carbonylamino, (phenyl or naphthyl or heterocyclyl)-sulfonylamino wherein phenyl or naphthyl is unsubstituted or substituted preferably by one or more, especially one to three, $C_1$-$C_7$-alkyl moieties, (phenyl or naphthyl or heterocyclyl)-$C_1$-$C_7$-alkylsulfonylamino, (phenyl or naphthyl or heterocyclyl)-aminocarbonylamino, (phenyl or naphthyl or heterocyclyl)-$C_1$-$C_7$-aminocarbonylamino, (phenyl or naphthyl or heterocyclyl)-oxycarbonylamino, (phenyl or naphthyl or heterocyclyl)-$C_1$-$C_7$-alkyloxycarbonylamino, carboxyl, $C_1$-$C_7$-alkyl-carbonyl, halo-$C_1$-$C_7$-alkylcarbonyl, hydroxy-$C_1$-$C_7$-alkylcarbonyl, $C_1$-$C_7$-alkoxy-$C_1$-$C_7$-alkylcarbonyl, amino-$C_1$-$C_7$-alkylcarbonyl, (N—) mono- or (N,N—) di-($C_1$-$C_7$-alkyl)-amino-$C_1$-$C_7$-alkylcarbonyl, $C_1$-$C_7$-alkanoylamino-$C_1$-$C_7$-alkylcarbonyl, halo-$C_1$-$C_7$-alkoxycarbonyl, (phenyl or naphthyl or (especially mono- or bicyclic) heterocyclyl)-oxycarbonyl, (phenyl or naphthyl or heterocyclyl)-$C_1$-$C_7$-alkoxycarbonyl, (N,N—) di-($C_1$-$C_7$-alkyl)-amino-$C_1$-$C_7$-alkoxycarbonyl, carbamoyl, N-mono or N,N-di-(naphthyl or phenyl or heterocyclyl)-aminocarbonyl, cyano, $C_1$-$C_7$-alkylene which is unsubstituted or substituted by up to four $C_1$-$C_7$-alkyl substituents and bound to two adjacent ring atoms of the aryl moiety, sulfenyl, sulfinyl, $C_1$-$C_7$-alkylsulfinyl, (phenyl or naphthyl or heterocyclyl)-sulfinyl wherein phenyl or naphthyl is unsubstituted or substituted preferably by one or more, especially one to three, $C_1$-$C_7$-alkyl moieties, phenyl- or naphthyl-$C_1$-$C_7$-alkylsulfinyl, sulfonyl, (phenyl or naphthyl or heterocyclyl)-sulfonyl wherein phenyl or naphthyl is unsubstituted or substituted preferably by one or more, especially one to three, $C_1$-$C_7$-alkyl moieties, (phenyl or naphthyl or heterocyclyl)-$C_1$-$C_7$-alkylsulfonyl, sulfamoyl and N-mono or N,N-di-($C_1$-$C_7$-alkyl, phenyl-, naphthyl, heterocyclyl, phenyl-$C_1$-$C_7$-alkyl, naphthyl-$C_1$-$C_7$-alkyl and/or heterocyclyl-$C_1$-$C_7$-alkyl)-aminosulfonyl;

where any phenyl or naphthyl or heterocyclyl (which heterocyclyl is preferably as defined for heterocyclyl, more preferably is selected from pyrrolyl, furanyl, tetrahydrofuranyl, tetrahydropyranyl and thienyl) mentioned as substituent of or as part of a substituent of substituted aryl mentioned in one of the two preceding paragraphs is unsubstituted or substituted by one or more, preferably up to three, moieties independently selected from the group consisting of $C_1$-$C_7$-alkyl, $C_1$-$C_7$-alkenyl, $C_1$-$C_7$-alkynyl, halo-$C_1$-$C_7$-alkyl, such as trifluoromethyl, halo, especially fluoro, chloro, bromo or iodo, hydroxy, $C_1$-$C_7$-alkoxy, phenyloxy, naphthyloxy, phenyl- or naphthyl-$C_1$-$C_7$-alkoxy, $C_1$-$C_7$-alkanoyloxy, phenyl- or naphthyl-$C_1$-$C_7$-alkanoyloxy, amino, mono- or di-($C_1$-$C_7$-alkyl, phenyl, naphthyl, phenyl-$C_1$-$C_7$-alkyl, naphthyl-$C_1$-$C_7$-alkyl, $C_1$-$C_7$-alkanoyl and/or phenyl- or naphthyl-$C_1$-$C_7$-alkanoyl)-amino, carboxy, $C_1$-$C_7$-alkoxycarbonyl, phenoxycarbonyl, naphthyloxycabonyl, phenyl-$C_1$-$C_7$-alkyloxycarbonyl, naphthyl-$C_1$-$C_7$-alkoxycarbonyl, carbamoyl, N-mono- or N,N-di-($C_1$-$C_7$-alkyl, phenyl, naphthyl, phenyl-$C_1$-$C_7$-alkyl and/or naphthyl-$C_1$-$C_7$-alkyl)-aminocarbonyl, cyano, sulfonyl, sulfamoyl, N-mono- or N,N-di-($C_1$-$C_7$-alkyl, phenyl, naphthyl, phenyl-$C_1$-$C_7$-alkyl and/or naphthyl-$C_1$-$C_7$-alkyl)-aminosulfonyl and nitro, or preferably, where preferred substituents are mentioned, by one or more of these mentioned substituents.

Unsubstituted or substituted heterocyclyl is preferably a mono- or bicyclic heterocyclic moiety with an unsaturated, partially saturated or saturated ring system with preferably 3 to 22 (more preferably 3 to 14) ring atoms and with one or more, preferably one to four, heteroatoms independently selected from nitrogen (=N—, —NH— or substituted —NH—), oxygen and sulfur (—S—, S(=O)— or S—(=O)$_2$—) which is unsubstituted or substituted by one or more, e.g. up to three, substitutents preferably independently selected from the substitutents mentioned above for aryl (where preferably such substituents that comprise an S, O or halo which binds to heterocyclyl are not bound via a ring nitrogen) and from oxo (=O) and thioxo (=S). Preferably, unsubstituted or substituted heterocyclyl is selected from the following moieties:

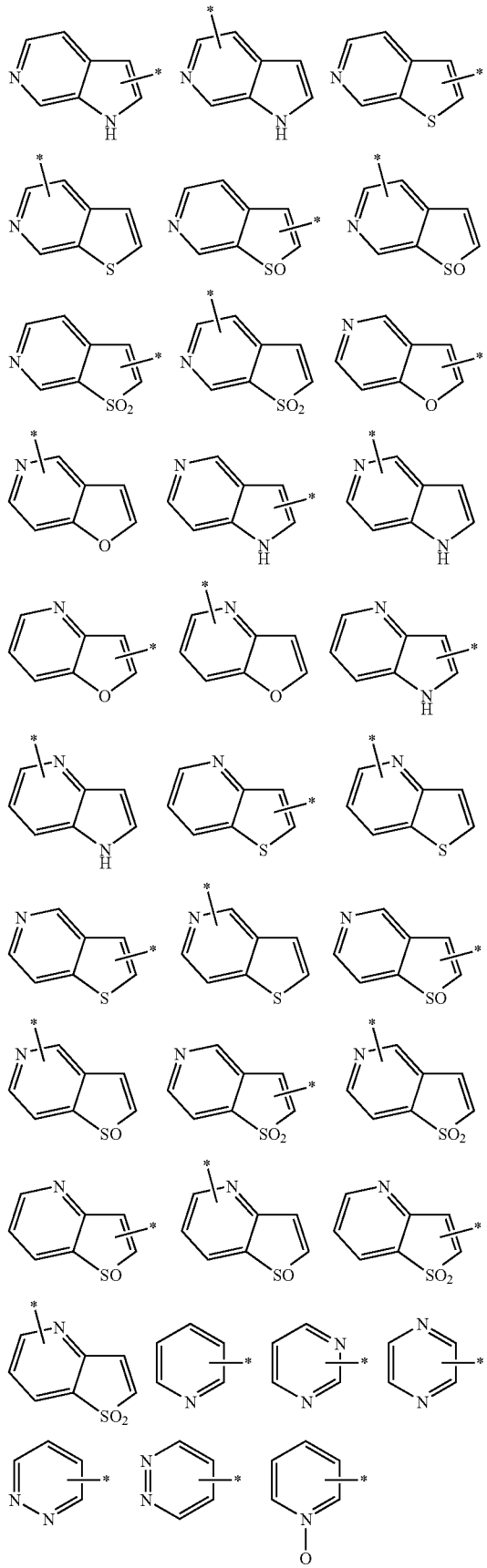

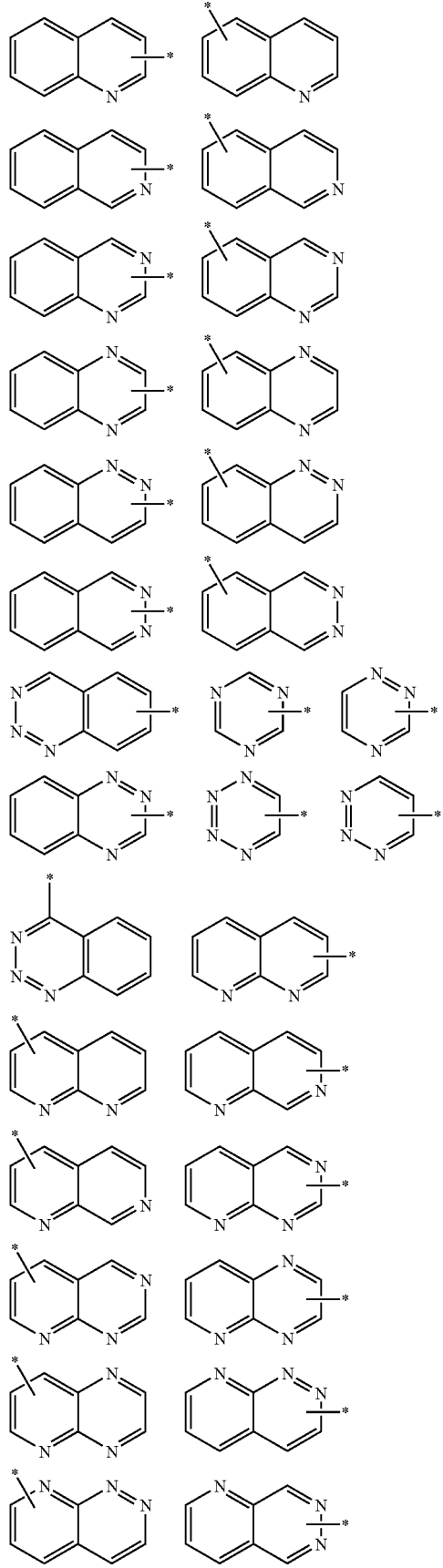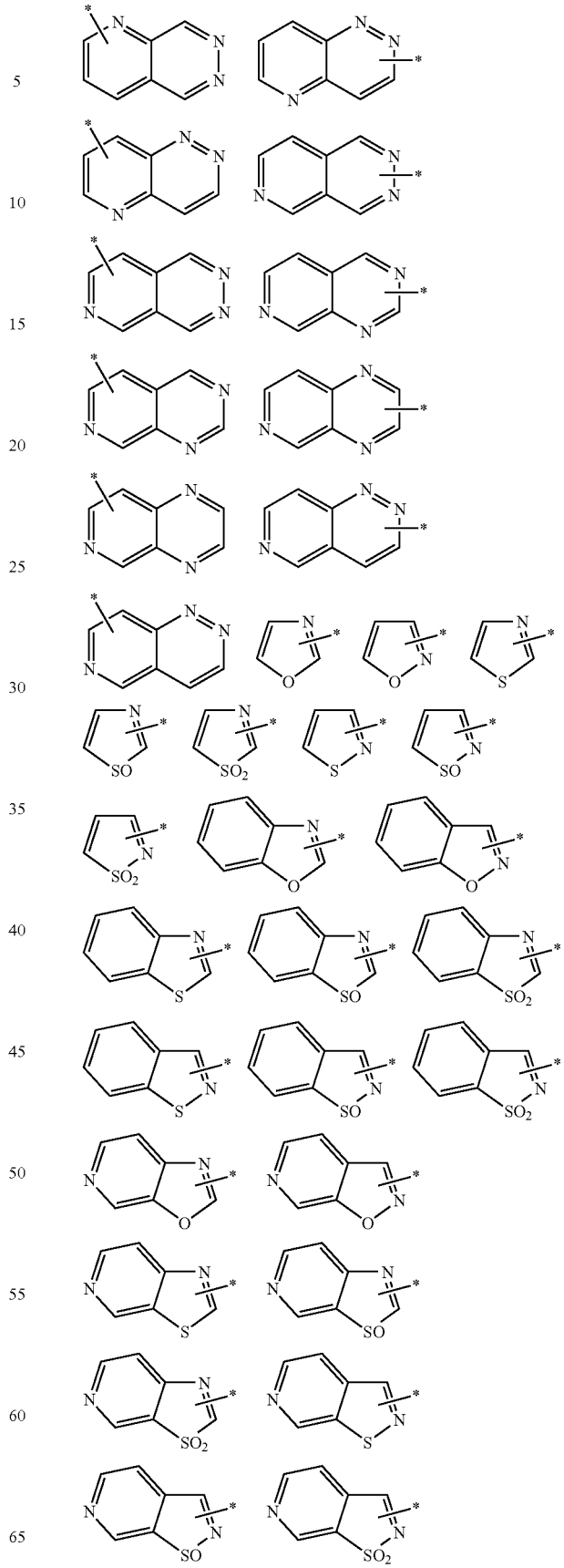

11
-continued
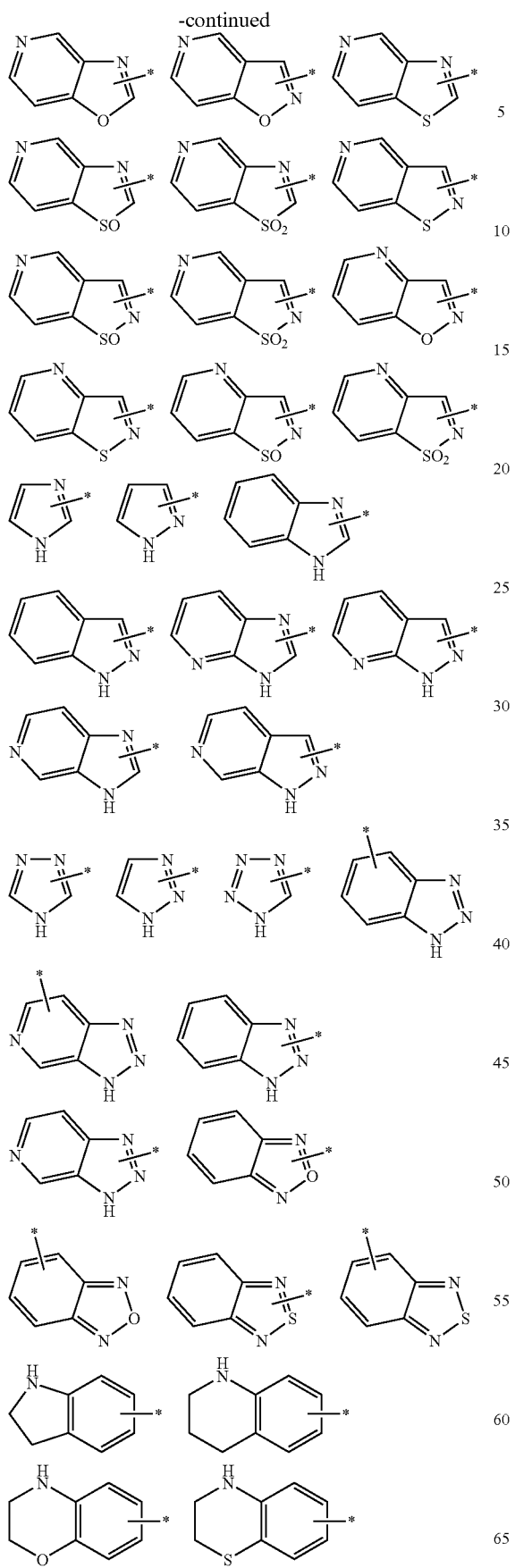
12
-continued
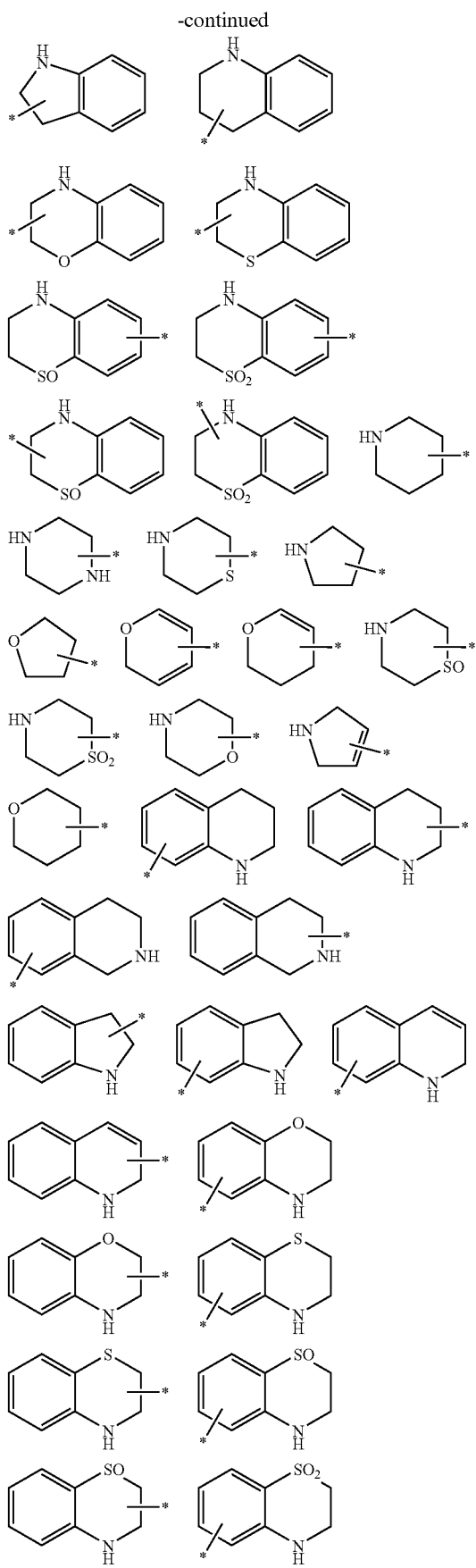

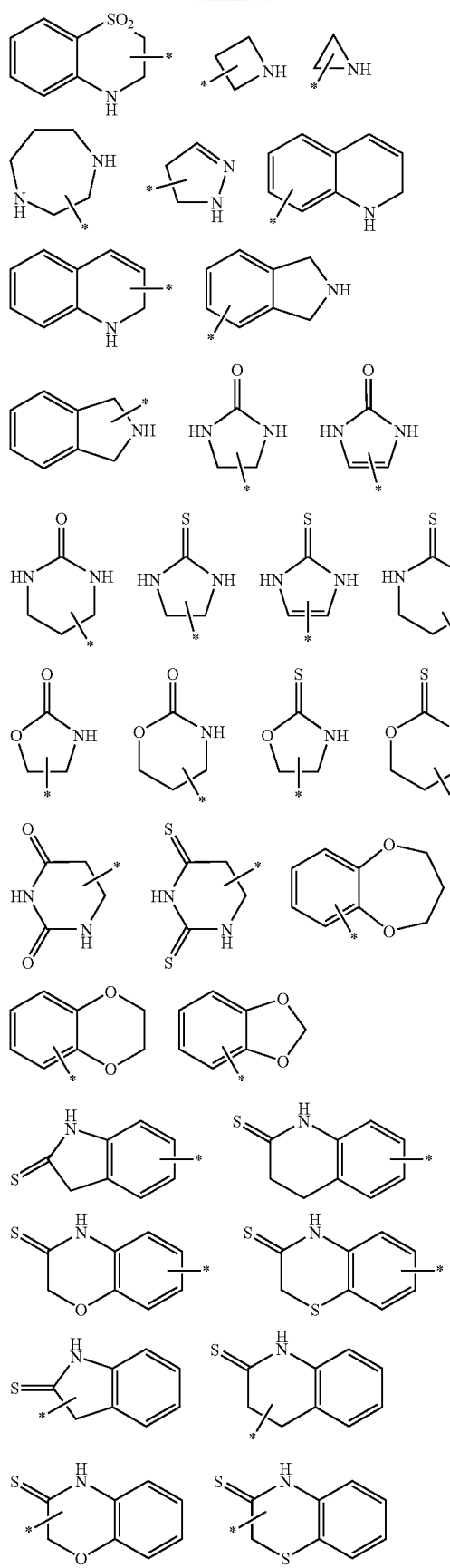
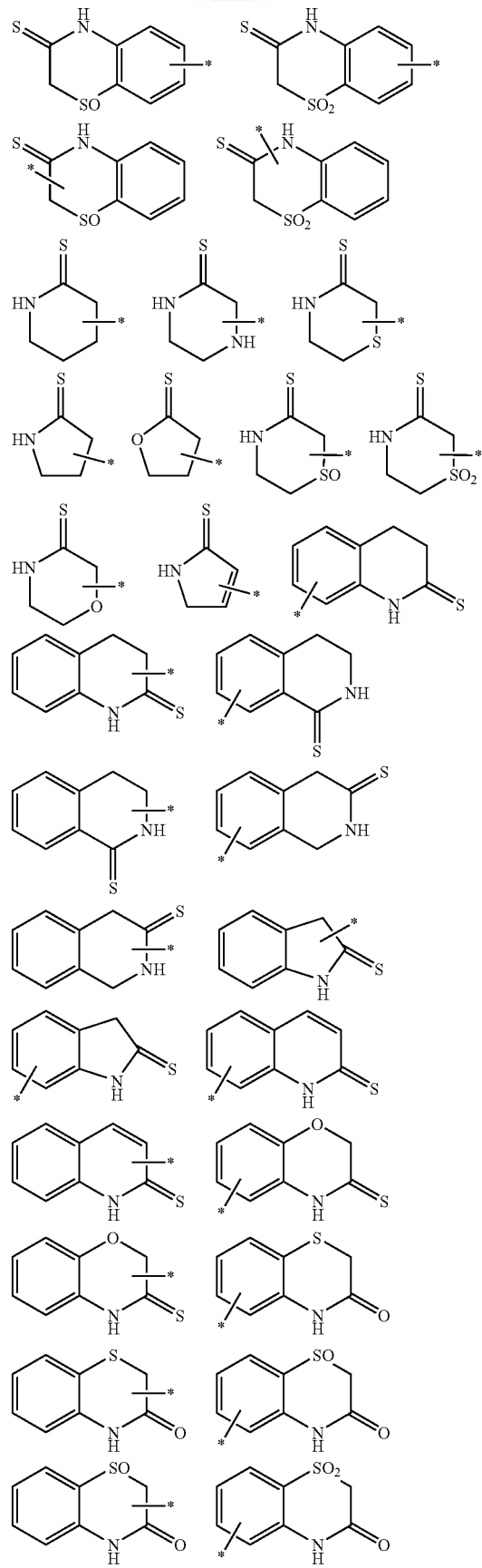

-continued
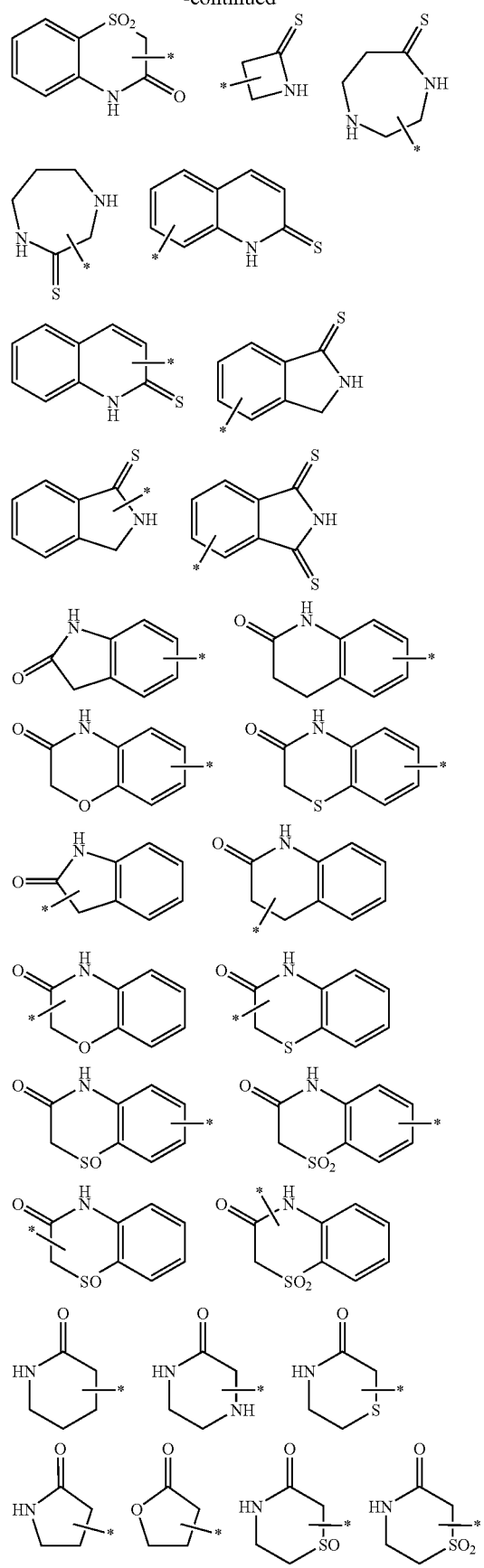
-continued
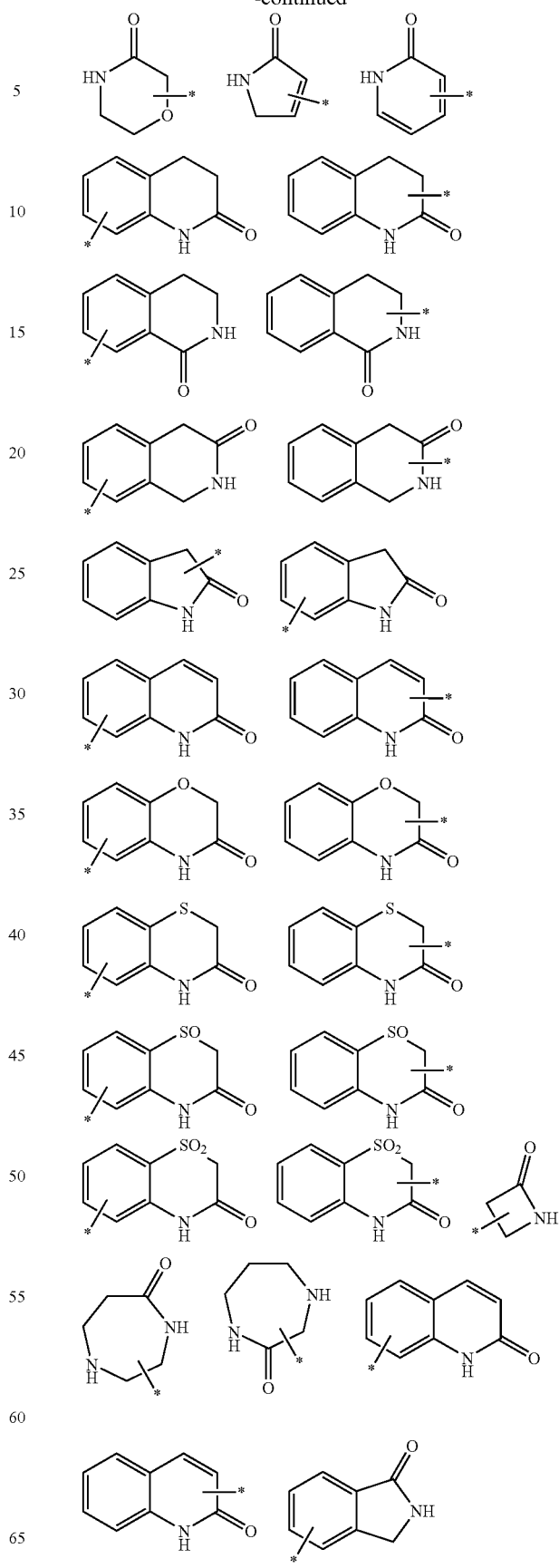

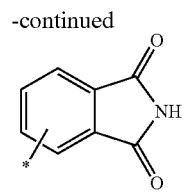

where in each case where an H is present bound to a ring atom the bond with the asterisk connecting the respective heterocyclyl moiety to the rest of the molecule the H may be replaced with said bond and if present one or more further H atoms bound to a ring atom may be replaced by one or more substituents as just described. Very preferred as unsubstituted or substituted heterocyclyl are tetrahydrofuranyl, tetrahydropyranyl, piperidinyl, pyridyl, thiophenyl, thiazolyl, pyrazolyl, indolyl, quinolinyl or 2H-1,4-benzoxazin-3(4H)-onyl, each of which is unsubstituted or substituted by one or more, especially up to three substituents independently selected from the substituents mentioned for substituted aryl above, especially by one or more, especially up to three, moieties independently selected from the group consisting of $C_1$-$C_7$-alkyl, $C_1$-$C_7$-alkoxy-$C_1$-$C_7$-alkyl, halo-$C_1$-$C_7$-alkyl, oxo-$C_1$-$C_7$-alkyl, $C_1$-$C_7$-alkanoyl, phenyl, halo, especially chloro or bromo, hydroxy, $C_1$-$C_7$-alkoxy, $C_1$-$C_7$-alkoxy-$C_1$-$C_7$-alkoxy, phenoxy, halo-$C_1$-$C_7$-alkoxy, amino, $C_1$-$C_7$-alkanoylamino, $C_1$-$C_7$-alkanesulfonyl and cyano.

unsubstituted or substituted cycloalkyl is preferably mono- or bicyclic, more preferably monocyclic, $C_3$-$C_{10}$-cycloalkyl which may include one or more double and/or triple bonds, and is unsubstituted or substituted by one or more, e.g. one to four substitutents preferably independently selected from those mentioned above as substituents for aryl, especially $C_3$-$C_8$-cycloalkyl that is unsubstituted or substituted by up to four substituents selected from $C_1$-$C_7$-alkyl, from phenyl which is unsubstituted or substituted by one or more, especially up to three, substituents independently selected from the group consisting of $C_1$-$C_7$-alkyl, $C_1$-$C_7$-alkoxy-$C_1$-$C_7$-alkyl, halo-$C_1$-$C_7$-alkyl, oxo-$C_1$-$C_7$-alkyl, $C_1$-$C_7$-alkanoyl, phenyl, halo, such as chloro, hydroxy, $C_1$-$C_7$-alkoxy, $C_1$-$C_7$-alkoxy-$C_1$-$C_7$-alkoxy, halo-$C_1$-$C_7$-alkoxy, phenoxy, amino, $C_1$-$C_7$-alkanoylamino, carbamoyl, $C_1$-$C_7$-alkanesulfonyl and cyano, from carbamoyl and from cyano; preferred is cyclopropyl, cyclobutyl, cyclopentyl, cyclohexyl, cycloheptyl or cyclooctyl that is unsubstituted or substituted by up to four moieties selected from hydroxyl, hydroxyl-$C_1$-$C_7$-alkyl, $C_1$-$C_7$-alkyl, carbamoyl and cyano.

Acyl is preferably unsubstituted or substituted aryl-carbonyl or -sulfonyl, unsubstituted or substituted heterocyclylcarbonyl or -sulfonyl, unsubstituted or substituted cycloalkylcarbonyl or -sulfonyl, formyl or (unsubstituted or substituted alkyl, unsubstituted or substituted aryl-$C_1$-$C_7$-alkyl, unsubstituted or substituted heterocyclyl-$C_1$-$C_7$-alkyl or unsubstituted or substituted cycloalkyl-$C_1$-$C_7$-alkyl)-carbonyl or -sulfonyl, or (especially if bound to N, S or O) unsubstituted or substituted alkyloxycarbonyl, unsubstituted or substituted aryl-oxycarbonyl, unsubstituted or substituted heterocyclyloxycarbonyl, unsubstituted or substituted cycloalkyloxycarbonyl, unsubstituted or substituted aryl-$C_1$-$C_7$-oxycarbonyl, unsubstituted or substituted heterocyclyl-$C_1$-$C_7$-oxycarbonyl, unsubstituted or substituted cycloalkyl-$C_1$-$C_7$-oxycarbonyl or N-mono- or N,N-di-(unsubstituted or substituted aryl, unsubstituted or substituted heterocyclyl, unsubstituted or substituted cycloalkyl, unsubstituted or substituted aryl-$C_1$-$C_7$-alkyl, unsubstituted or substituted heterocyclyl-$C_1$-$C_7$-alkyl, unsubstituted or substituted cycloalkyl-$C_1$-$C_7$-alkyl or unsubstituted or substituted alkyl)-aminocarbonyl or -aminosulfonyl, with the proviso that—oxycarbonyl bound moieties are preferably bound to a nitrogen in the rest of the molecule; preferred acyl moieties are $C_1$-$C_7$-alkanoyl that is unsubstituted or substituted by one or more, especially up to three, e.g. one or two moieties independently selected from the group consisting of hydroxy, amino, N-mono- or N,N-di-$C_1$-$C_7$-alkylamino and $C_1$-$C_7$-alkanoylamino, such as acetyl, 2-methyl-propionyl, 2-ethyl-butyryl, 3-methyl-butyryl, 3,3-dimethylbutyryl, 2,2-dimethyl-propionyl, 3,3-dimethyl-butyryl, 3-hydroxy-2,2-dimethyl-propionyl, N,N-dimethyl-aminoacetyl or 2-(N-acetylamino)-4-methyl-butyryl, unsubstituted or mono-, di- or tri-(halo, $C_1$-$C_7$-alkoxy and/or $C_1$-$C_7$-alkyl)-substituted benzoyl or naphthoyl, such as 4-methyl-benzoyl, or 3,4-dimethoxybenzoyl, phenyl- or naphthyl-$C_2$-$C_7$-alkanoyl wherein phenyl or naphthyl is unsubstituted or substituted by one or more, especially up to three, $C_1$-$C_7$-alkoxy substitutents, such as 3-phenyl-propionyl, 2,2,-dimethyl-2-phenylacetyl or 3-ethoxyphenylacetyl, $C_3$-$C_8$-cycloalkylcarbonyl that is unsubstituted or substituted by one or more, e.g. up to four, substituents independently selected from the group consisting of $C_1$-$C_7$-alkyl, carbamoyl and cyano, such as cyclopropylcarbonyl, 2,2,3,3-tetramethyl-cyclopropylcarbonyl, 1-carbamoyl-cyclopropylcarbonyl, cyclobutylcarbonyl or 1-cyano-cyclopropylcarbonyl, benzo[b]thiophenylcarbonyl, such as benzo[b]thiophen-2-carbonyl, tetrahydrofuranylcarbonyl, such as tetrahydrofuran-2-carbonyl, piperidinylcarbonyl which is unsubstituted or substituted by $C_1$-$C_7$-alkanoyl, such as 1-acetyl-piperidine-4-carbonyl, $C_1$-$C_7$-alkylsulfonyl, such as methylsulfonyl, (phenyl- or naphthyl)-$C_1$-$C_7$-alkylsulfonyl, such as phenylmethanesulfonyl, [$C_1$-$C_7$-alkyl-, phenyl-, halo-lower alkyl-, halo, oxo-$C_1$-$C_7$-alkyl-, $C_1$-$C_7$-alkyloxy-, phenyl-$C_1$-$C_7$-alkoxy-, halo-$C_1$-$C_7$-alkyloxy-, phenoxy-, $C_1$-$C_7$-alkanoylamino-, $C_1$-$C_7$-alkylsulfonyl, cyano and/or $C_1$-$C_7$-alkylsulfonyl-]-(mono-, di- or tri-)substituted) (phenyl- or naphthyl)-$C_1$-$C_7$-alkylsulfonyl or (unsubstituted or [$C_1$-$C_7$-alkyl-, phenyl-, halo-lower alkyl-, halo, oxo-$C_1$-$C_7$-alkyl-, $C_1$-$C_7$-alkyloxy-, phenyl-$C_1$-$C_7$-alkoxy-, halo-$C_1$-$C_7$-alkyloxy-, phenoxy-, $C_1$-$C_7$-alkanoylamino-, $C_1$-$C_7$-alkylsulfonyl, cyano and/or $C_1$-$C_7$-alkylsulfonyl-]-(mono-, di- or tri)substituted) (phenyl- or naphthyl)-sulfonyl wherein if more than one substituent is present the substituents are selected independently from those mentioned, such as methanesulfonyl, phenylmethanesulfonyl, phenylsulfonyl, naphthalene-1-sulfonyl, naphthalene-2-sulfonyl, toluene-4-sulfonyl, 4-isopropyl-benzenesulfonyl, biphenyl-4-sulfonyl, 2-trifluoromethylbenzenesulfonyl, 3-trifluoromethyl-benzenesulfonyl, 4-trifluoromethylsulfonyl, 4-chloro-benzenesulfonyl, 3-chloro-benzenesulfonyl, 2-chloro-benzenesulfonyl, 2,4-difluorobenzenesulfonyl, 2,6-difluoro-benzenesulfonyl, 2,5-dichloro-benzenesulfonyl, 2,4-dichlorobenzenesulfonyl, 3,4-dichloro-benzenesulfonyl, 3,5-dichloro-benzenesulfonyl, 2,3-dichloro-benzenesulfonyl, 3-methoxy-benzenesulfonyl, 4-methoxy-benzenesulfonyl, 2,5-dimethoxy-benzenesulfonyl, 2,4-dimethoxybenzenesulfonyl, 4-trifluoromethoxy-benzenesulfonyl, 2-benzyloxy-benzenesulfonyl, 4-phenoxy-benzenesulfonyl, 4-(2-oxo-propyl)-benzenesulfonyl, 3-acetyl-benzenesulfonyl, 4-acetylamino-benzenesulfonyl, 4-cyano-benzenesulfonyl, 3-cyano-benzenesulfonyl, 2-cyano-benzenesulfonyl or 4-methanesulfonyl-benzenesulfonyl; halo-thiophene-2-sulfonyl, such as 5-chloro-thiophene-2-sulfonyl, quinoline-sulfonyl, such as quinoline-8-sulfonyl, ($C_1$-$C_7$-alkanoylamino and/or $C_1$-$C_7$-alkyl)-substituted thiazolsulfonyl, such as 2-acetylamino-4-methyl-thiazole-5-sulfonyl, (halo and/or $C_1$-$C_7$-alkyl)-substituted pyrazolesulfonyl, such as 5-chloro- 1,3-dimethyl-1H-pyrazole-4-sulfonyl, pyridinesulfonyl, such as pyridine-3-sulfonyl, N-mono- or N,N-di-($C_1$-$C_7$-alkyl, (unsubstituted or $C_1$-$C_7$-alkyl- and/or halo-substituted) phenyl or naphthyl, phenyl-$C_1$-$C_7$-alkyl, naphthyl-$C_1$-$C_7$-alkyl or $C_3$-$C_8$-cycloalkyl)-aminocarbonyl, such as $C_1$-$C_7$-alkylaminocarbonyl, especially N-tert-butyl-aminocarbonyl, N-phenyl-aminocarbonyl, N-(3-chloro-phenyl)-aminocarbonyl or phenyl-$C_1$-$C_7$-alkylaminocarbonyl, especially N-benzyl-aminocarbonyl, or ($C_1$-$C_7$-alkyl, phenyl, naphthyl, phenyl-$C_1$-$C_7$-alkyl, napthyl-$C_1$-$C_7$-alkyl and/or $C_1$-$C_7$-alkoxy-$C_1$-$C_7$-alkyl)-oxycarbonyl, e.g. $C_1$-$C_7$-alkoxycarbonyl, such as methoxyethylcarbonyl, isopropyloxycarbonyl, tertbutyloxycarbonyl, isobutyloxycarbonyl or 2-(methoxy)-ethoxycarbonyl, or phenyl-$C_1$-$C_7$-alkyloxycarbonyl, such as benzyloxycarbonyl.

The 3 to 7 membered nitrogen containing saturated hydrocarbon ring formed by R3 and R4 which can be unsubstituted or substituted is preferably unsubstituted or substituted by one or more, e.g. one to four substituents preferably independently selected from those mentioned above as substituents for aryl, especially a 4- to 7-membered ring that is unsubstituted or substituted by up to four substituents, such as one substituent, selected from hydroxy, halo, such as chloro, $C_1$-$C_7$-alkyl, such as methyl, cyano, hydroxy-$C_1$-$C_7$-alkyl, halo-$C_1$-$C_7$-alkyl, $C_1$-$C_7$-alkanoyl, such as acetyl, $C_1$-$C_7$-alkoxy, halo-$C_1$-$C_7$-alkoxy, such as trifluoromethoxy, hydroxy-$C_1$-$C_7$-alkoxy, and $C_1$-$C_7$-alkoxy-$C_1$-$C_7$-alkoxy; preferably a pyrrolidine or piperidine ring is formed by R3 and R4 that is unsubstituted or substituted by up to four moieties selected from $C_1$-$C_7$-alkyl, hydroxyl, halo, hydroxy-$C_1$-$C_7$-alkyl, halo-$C_1$-$C_7$-alkyl and cyano.

T is methylene ($CH_2$) or preferably carbonyl ($C(=O)$).

In all definitions above and below the person having skill in the art will, without undue experimentation or effort, be able to recognize which are especially relevant (e.g. those that if present provide compounds that are sufficiently stable for the manufacture of pharmaceuticals, e.g. having a half-life of more than 30 seconds, preferably of more than a week) and thus are preferably encompassed by the present claims and that only chemically feasible bonds and substitutions (e.g. in the case of double or triple bonds, hydrogen carrying amino or hydroxy groups and the like can be avoided in order to avoid tautomerism) are encompassed, as well as tautomeric forms where present, especially in equilibrium. For example, preferably, for reasons of stability or chemical feasibility, directly vicinal atoms in chains preferably are not selected from oxy plus oxy, thio plus oxy, oxy plus thio or thio plus thio, except where ring systems or the like are present that are sufficiently stable. Substituents binding via an O (e.g. in $C_1$-$C_7$-alkoxy) or S that is part of them are preferably not bound to nitrogen e.g. in rings.

Salts are especially the pharmaceutically acceptable salts of compounds of formula I' or I. They can be formed where salt forming groups, such as basic or acidic groups, are present that can exist in dissociated form at least partially, e.g. in a pH range from 4 to 10 in aqueous solutions, or can be isolated especially in solid, especially crystalline, form.

Such salts are formed, for example, as acid addition salts, preferably with organic or inorganic acids, from compounds of formula I with a basic nitrogen atom (e.g. imino or amino), especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, lactic acid, fumaric acid, succinic acid, citric acid, amino acids, such as glutamic acid or aspartic acid, maleic acid, hydroxymaleic acid, methylmaleic acid, benzoic acid, methane- or ethane-sulfonic acid, ethane-1,2-disulfonic acid, benzenesulfonic acid, 2-naphthalenesulfonic acid, 1,5-naphthalene-disulfonic acid, N-cyclohexylsulfamic acid, N-methyl-, N-ethyl- or N-propyl-sulfamic acid, or other organic protonic acids, such as ascorbic acid.

In the presence of negatively charged radicals, such as carboxy or sulfonyl, salts may also be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethylpiperidine or N,N'-dimethylpiperazine.

When a basic group and an acid group are present in the same molecule, a compound of formula I' or I may also form internal salts.

For isolation or purification purposes it is also possible to use pharmaceutically unacceptable salts, for example picrates or perchlorates. For therapeutic use, only pharmaceutically acceptable salts or free compounds are employed (where applicable comprised in pharmaceutical preparations), and these are therefore preferred.

In view of the close relationship between the compounds in free form and in the form of their salts, including those salts that can be used as intermediates, for example in the purification or identification of the compounds or salts thereof, any reference to "compounds", "starting materials" and "intermediates" hereinbefore and hereinafter, especially to the compound(s) of the formula I' or I or their precursors, is to be understood as referring also to one or more salts thereof or a mixture of a corresponding free compound and one or more salts thereof, each of which is intended to include also any solvate, metabolic precursor such as ester or amide of the compound of formula I' or I, or salt of any one or more of these, as appropriate and expedient and if not explicitly mentioned otherwise. Different crystal forms may be obtainable and then are also included.

Where the plural form is used for compounds, starting materials, intermediates, salts, pharmaceutical preparations, diseases, disorders and the like, this is intended to mean one (preferred) or more single compound(s), salt(s), pharmaceutical preparation(s), disease(s), disorder(s) or the like, where the singular or the indefinite article ("a", "an") is used, this is intended to include the plural (for example also different configuration isomers of the same compound, e.g. enantiomers in racemates or the like) or preferably the singular ("one").

The compounds of the present invention can possess two or more asymmetric centers depending on the choice of the substituents. The preferred absolute configurations are as indicated herein specifically. However, any possible isolated or pure diastereoisomers, enantiomers or geometric enantiomers, and mixtures thereof, e.g., mixtures of enantiomers, such as racemates, are encompassed by the present invention.

As described above, the compounds of the present invention are inhibitors of renin activity and, thus, may be employed for the treatment of hypertension, atherosclerosis, unstable coronary syndrome, congestive heart failure, cardiac hypertrophy, cardiac fibrosis, cardiomyopathy postinfarction, unstable coronary syndrome, diastolic dysfunction, chronic kidney disease, hepatic fibrosis, complications resulting from diabetes, such as nephropathy, vasculopathy and neuropathy, diseases of the coronary vessels, restenosis following angioplasty, raised intra-ocular pressure, glaucoma, abnormal vascular growth and/or hyperaldosteronism, and/or further cognitive impairment, Alzheimer's disease, dementia, anxiety states and cognitive disorders, and the like, especially where inhibition of (especially inappropriate) renin activity is required.

"Inappropriate" renin activity preferably relates to a state of a warm-blooded animal, especially a human, where renin shows a renin activity that is too high in the given situation (e.g. due to one or more of misregulation, overexpression e.g. due to gene amplification or chromosome rearrangement or infection by microorganisms such as virus that express an aberrant gene, abnormal activity e.g. leading to an erroneous substrate specificity or a hyperactive renin e.g. produced in normal amounts, too low activity of renin activity product removing pathways, high substrate concentration and/or the like) and/or leads to or supports a renin dependent disease or disorder as mentioned above and below, e.g. by too high renin activity. Such inappropriate renin activity may, for example, comprise a higher than normal activity, or further an activity in the normal or even below the normal range which, however, due to preceding, parallel and or subsequent processes, e.g. signaling, regulatory effect on other processes, higher substrate or product concentration and the like, leads to direct or indirect support or maintenance of a disease or disorder, and/or an activity that supports the outbreak and/or presence of a disease or disorder in any other way. The inappropriate activity of renin may or may not be dependent on parallel other mechanisms supporting the disorder or disease, and/or the prophylactic or therapeutic effect may or may include other mechanisms in addition to inhibition of renin. Therefore "dependent" can be read as "dependent inter alia", (especially in cases where a disease or disorder is really exclusively dependent only on renin) preferably as "dependent mainly", more preferably as "dependent essentially only". A disease dependent on (especially inappropriate) activity of renin may also be one that simply responds to modulation of renin activity, especially responding in a beneficial way (e.g. lowering the blood pressure) in case of renin inhibition.

Where a disease or disorder dependent on (=that "depends on", "depending") (especially inappropriate) activity of a renin is mentioned (such in the definition of "use" in the following paragraph and also especially where a compound of the formula I' or I is mentioned for use in the diagnostic or therapeutic treatment which is preferably the treatment of a disease or disorder dependent on inappropriate renin activity, this refers preferably to any one or more diseases or disorders that depend on inappropriate activity of natural renin and/or one or more altered or mutated forms thereof.

Where subsequently or above the term "use" is mentioned (as verb or noun) (relating to the use of a compound of the formula I' or I or of a pharmaceutically acceptable salt thereof, or a method of use thereof), this (if not indicated differently or to be read differently in the context) includes any one or more of the following embodiments of the invention, respectively (if not stated otherwise): the use in the treatment of a disease or disorder that depends on (especially inappropriate) activity of renin, the use for the manufacture of pharmaceutical compositions for use in the treatment of a disease or disorder that depends on (especially inappropriate) activity of renin; a method of use of one or more compounds of the formula I' or I in the treatment of a disease or disorder that depends on (especially inappropriate) activity of renin; a pharmaceutical preparation comprising one or more compounds of the formula I' or I for the treatment of a disease or disorder that depends on (especially inappropriate) activity of renin; and one or more compounds of the formula I' or I for use in the treatment of a disease or disorder in a warm-blooded animal, especially a human, preferably a disease that depends on (especially inappropriate) activity of renin; as appropriate and expedient, if not stated otherwise.

The terms "treat", "treatment" or "therapy" refer to the prophylactic (e.g. delaying or preventing the onset of a disease or disorder) or preferably therapeutic (including but not limited to preventive, delay of onset and/or progression, palliative, curing, symptom-alleviating, symptom-reducing, patient condition ameliorating, renin-modulating and/or renin-inhibiting) treatment of said disease(s) or disorder(s), especially of the one or more diseases or disorders mentioned above or below.

PREFERRED EMBODIMENTS ACCORDING TO THE INVENTION

The groups of preferred embodiments of the invention mentioned below are not to be regarded as exclusive, rather, e.g., in order to replace general expressions or symbols with more specific definitions, parts of those groups of compounds can be interchanged or exchanged using the definitions given above, or omitted, as appropriate, and each of the more specific definitions, independent of any others, may be introduced independently of or together with one or more other more specific definitions for other more general expressions or symbols.

The invention preferably relates to a compound of the formula I' or I wherein the moieties T-NR1R2 and NR3R4 are bound in the cis configuration (as pure isomer or mixture of the cis isomers) or alternatively wherein these moieties are bound in trans configuration (as pure isomer of as mixture of the trans isomers) with regard to the central piperidine ring.

The invention thus more preferably relates to a compound of the formula I' or I as defined hereinbefore or hereinafter which has the configuration shown in the following formula IA or I'A,

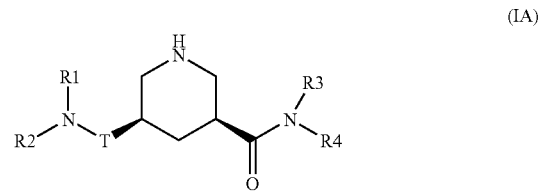

(IA)

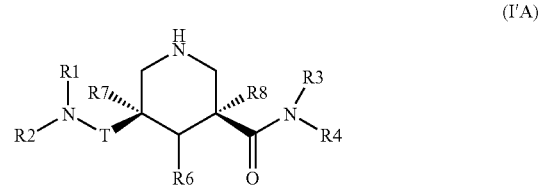

(I'A)

or a (preferably pharmaceutically acceptable salt thereof, or alternatively the configuration shown in the following formula IB or I'B,

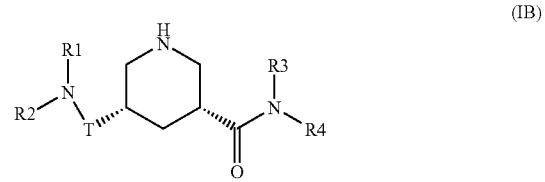

(IB)

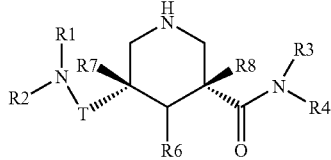

(I'B)

or a (preferably pharmaceutically acceptable) salt thereof, where in formula IA, I'A, IB and formula I'B R1, R2, T, R3 and R4 are as defined above or below for a compound of the formula I or I'.

Alternatively and also more preferably, the invention relates to a compound of the formula I' or I as defined hereinbefore or hereinafter which has the configuration shown in the following formula IC or I'C,

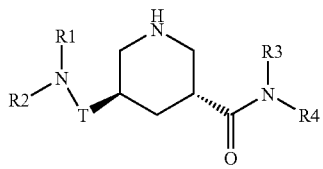

(IC)

(I'C)

or a pharmaceutically acceptable salt thereof, or alternatively the configuration shown in the following formula ID or I'D,

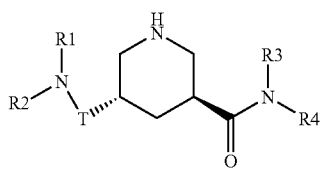

(ID)

(I'D)

or a (preferably pharmaceutically acceptable) salt thereof, where in formula IC, I'C, ID and formula I'D R1, R2, T, R3 and R4 are as defined above or below for a compound of the formula I.

When R6 is other than hydrogen, preferred compounds have the configuration as shown in formula I'E

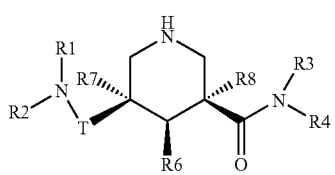

(I'E)

In a first preferred embodiment, the invention especially relates to a compound of the formula I' or I, preferably I, wherein
R1 is hydrogen, unsubstituted or substituted alkyl or unsubstituted or substituted cycloalkyl;
R2 is unsubstituted or substituted alkyl, unsubstituted or substituted aryl, unsubstituted or substituted heterocyclyl or unsubstituted or substituted cycloalkyl;
R3 is hydrogen or unsubstituted or substituted alkyl,
R4 is unsubstituted or substituted alkyl or acyl; and
T is carbonyl (C(═O));
or a (preferably pharmaceutically acceptable) salt thereof;
where preferably unsubstituted or substituted alkyl, unsubstituted or substituted cycloalkyl, unsubstituted or substituted aryl and/or acyl are as defined as given above as preferred definitions.

In another preferred embodiment, the invention especially relates to a compound of the formula I' or I, preferably I, wherein
R1 is hydrogen, unsubstituted or substituted alkyl or unsubstituted or substituted cycloalkyl;
R2 is unsubstituted or substituted alkyl, unsubstituted or substituted aryl, unsubstituted or substituted heterocyclyl or unsubstituted or substituted cycloalkyl;
R3 is hydrogen or unsubstituted or substituted alkyl,
R4 is unsubstituted or substituted alkyl, unsubstituted or substituted aryl, unsubstituted or substituted heterocyclyl, or acyl; and
T is carbonyl (C(═O));
or a (preferably pharmaceutically acceptable) salt thereof;
where preferably unsubstituted or substituted alkyl, unsubstituted or substituted cycloalkyl, unsubstituted or substituted aryl, unsubstituted or substituted heterocyclyl and/or acyl are as defined as given above as preferred definitions.

Highly preferred is a compound of the formula I' or I, preferably I, wherein
R1 is hydrogen, $C_1$-$C_7$-alkyl, $C_3$-$C_8$-cycloalkyl or phenyl-$C_1$-$C_7$-alkyl, preferably $C_1$-$C_7$-alkyl, such as ethyl or isopropyl, or $C_3$-$C_8$-cycloalkyl, such as cyclopropyl;
R2 is phenyl-$C_1$-$C_7$-alkyl, naphthyl-$C_1$-$C_7$-alkyl, pyridyl-$C_1$-$C_7$-alkyl, indolyl-$C_1$-$C_7$-alkyl, 1H-pyrrolo[2,3-b]pyridyl-$C_1$-$C_7$-alkyl, quinolinyl-$C_1$-$C_7$-alkyl, 1H-pyridin-2-onyl-$C_1$-$C_7$-alkyl, thiophenyl-$C_1$-$C_7$-alkyl, chromanyl-$C_1$-$C_7$-alkyl, 2,3-dihydrobenzofuranyl-$C_1$-$C_7$-alkyl, phenyl, 4H-benzo[1,4]oxazin-3-on-yl, 3,4-dihydro-1H-quinolin-2-onyl, or is acyl such as phenylcarbonyl or indolylcarbonyl where each phenyl, naphthyl, pyridyl, indolyl, pyrrolo[2,3-b]pyridyl, quinolinyl 1H-pyridin-2-onyl, thiophenyl, chromanyl, 2,3-dihydrobenzofuranyl, 3,4-dihydro-1H-quinolin-2-onyl or 4H-benzo[1,4]oxazin-3-on-yl mentioned for R2 so far is unsubstituted or substituted by one or more, especially up to three, moieties independently selected from the group consisting of $C_1$-$C_7$-alkyl, $C_1$-$C_7$-alkoxy-$C_1$-$C_7$-alkyl, halo-$C_1$-$C_7$-alkyl, hydroxy-$C_1$-$C_7$-alkyl, phenyl, phenyl which is mono-, di- or tri-substituted with halo, hydroxy, $C_1$-$C_7$-alkoxy, and/or $C_1$-$C_7$-alkyl; halo, hydroxy, $C_1$-$C_7$-alkoxy, cyano, $C_1$-$C_7$-alkoxy-$C_1$-$C_7$-alkoxy-alkyl, $C_1$-$C_7$-alkoxy-$C_1$-$C_7$-alkylamino-$C_1$-$C_7$-alkyl, $C_1$-$C_7$-alkanoylamino, N-mono-$C_1$-$C_7$-alkoxy-$C_1$-$C_7$-alkyl-aminocarbonyl, $C_1$-$C_7$-alkanoyl and $C_1$-$C_7$-alkoxy-$C_1$-$C_7$-alkoxy;
R3 is hydrogen, $C_1$-$C_7$-alkyl such as methyl;
R4 is selected from the group consisting of:
branched $C_4$-$C_{10}$-alkyl which may be unsubstituted or substituted with one or more, such as one or two of the group consisting of:
unsubstituted or substituted heterocyclyl, especially pyrrolyl, furanyl, thienyl, thiazolyl, pyrazolyl, triazolyl, tetrazolyl, pyridyl, or pyrimidinyl, each of which is unsubstituted or substituted as described herein, preferably unsubstituted;

unsubstituted or substituted aryl, especially unsubstituted or substituted phenyl as described herein; halo, hydroxy, $C_1$-$C_7$-alkoxy, halo-$C_1$-$C_7$-alkoxy, such as trifluoromethoxy, hydroxy-$C_1$-$C_7$-alkoxy, and N-mono- or N,N-di-($C_1$-$C_7$-alkyl)-aminocarbonyl;

straight chain $C_1$-$C_7$-alkyl which may be bound to the terminal or non-terminal carbon and which may be unsubstituted or substituted with one or more, such as one or two of the group consisting of:

unsubstituted or substituted heterocyclyl, especially morpholino, thiomorpholino, piperidinyl, piperazinyl, pyrrolidinyl, tetrahydrofuranyl, tetrahydropyranyl, tetrahydrothiophenyl, pyridyl, or pyrrolidin-2-onyl, each of which is unsubstituted or substituted as described herein, preferably unsubstituted; unsubstituted or substituted aryl, especially unsubstituted or substituted phenyl as described herein; unsubstituted or substituted $C_3$-$C_8$-cycloalkyl, such as cycloheptyl, cyclohexyl or cyclopentyl, which is unsubstituted or substituted as described herein; halo, hydroxy, $C_1$-$C_7$-alkoxy, halo-$C_1$-$C_7$-alkoxy, such as trifluoromethoxy, hydroxy-$C_1$-$C_7$-alkoxy, N-mono- or N,N-di-($C_1$-$C_7$-alkyl)-amino, and N-mono- or N,N-di-($C_1$-$C_7$-alkyl)-aminocarbonyl;

unsubstituted or substituted $C_3$-$C_8$-cycloalkyl, such as cyclohexyl or cyclopropyl, which is unsubstituted or substituted as described herein, unsubstituted or substituted aryl, such as phenyl, which is unsubstituted or substituted as described herein, unsubstituted or substituted heterocyclyl, such as pyridyl, pyrrolininyl or piperidinyl, which is unsubstituted or substituted as described herein, or acyl, such as (unsubstituted or substituted alkyl, unsubstituted or substituted aryl-$C_1$-$C_7$-alkyl, unsubstituted or substituted heterocyclyl-$C_1$-$C_7$-alkyl or unsubstituted or substituted cycloalkyl-$C_1$-$C_7$-alkyl)-sulfonyl, especially phenylmethanesulfonyl;

or R3 and R4 form together a pyrrolidine or piperidine ring that is unsubstituted or substituted by up to four moieties selected from $C_1$-$C_7$-alkyl, hydroxyl, halo, hydroxy-$C_1$-$C_7$-alkyl, halo-$C_1$-$C_7$-alkyl and cyano; and T is carbonyl or methylene;

or a (preferably pharmaceutically acceptable) salt thereof.

Also highly preferred is a compound of the formula I' or I, preferably I, wherein R1 is hydrogen, $C_1$-$C_7$-alkyl, $C_3$-$C_8$-cycloalkyl or phenyl-$C_1$-$C_7$-alkyl, preferably $C_1$-$C_7$-alkyl, such as ethyl or isopropyl, or $C_3$-$C_8$-cycloalkyl, such as cyclopropyl;

R2 is phenyl-$C_1$-$C_7$-alkyl, naphthyl-$C_1$-$C_7$-alkyl, pyridyl-$C_1$-$C_7$-alkyl, indolyl-$C_1$-$C_7$-alkyl, 1H-pyrrolo[2,3-b]pyridyl-$C_1$-$C_7$-alkyl, quinolinyl-$C_1$-$C_7$-alkyl, 1H-pyridin-2-onyl-$C_1$-$C_7$-alkyl, 4H-benzo[1,4]oxazin-3-on-yl, 3,4-dihydro-1H-quinolin-2-onyl, where each phenyl, naphthyl, pyridyl, indolyl, pyrrolo[2,3-b]pyridyl, quinolinyl 1H-pyridin-2-onyl 3,4-dihydro-1H-quinolin-2-onyl or 4H-benzo[1,4]oxazin-3-on-yl mentioned for R2 so far is unsubstituted or substituted by one or more, especially up to three, moieties independently selected from the group consisting of $C_1$-$C_7$-alkyl, $C_1$-$C_7$-alkoxy-$C_1$-$C_7$-alkyl, halo-$C_1$-$C_7$-alkyl, phenyl, halo, hydroxy, $C_1$-$C_7$-alkoxy, $C_1$-$C_7$-alkoxy-$C_1$-$C_7$-alkoxy-alkyl, $C_1$-$C_7$-alkoxy-$C_1$-$C_7$-alkylamino-$C_1$-$C_7$-alkyl, $C_1$-$C_7$-alkanoylamino, N-mono-$C_1$-$C_7$-alkoxy-$C_1$-$C_7$-alkyl-aminocarbonyl, and $C_1$-$C_7$-alkoxy-$C_1$-$C_7$-alkoxy;

R3 is hydrogen, $C_1$-$C_7$-alkyl such as methyl;

R4 is selected from the group consisting of:

branched $C_4$-$C_{10}$-alkyl which may be unsubstituted or substituted with one or more, such as one or two of the group consisting of:

unsubstituted or substituted heterocyclyl, especially pyrrolyl, furanyl, thienyl, thiazolyl, pyrazolyl, triazolyl, tetrazolyl, pyridyl, or pyrimidinyl, each of which is unsubstituted or substituted as described herein, preferably unsubstituted; unsubstituted or substituted aryl, especially unsubstituted or substituted phenyl as described herein; halo, hydroxy, $C_1$-$C_7$-alkoxy, halo-$C_1$-$C_7$-alkoxy, such as trifluoromethoxy, hydroxy-$C_1$-$C_7$-alkoxy, and N-mono- or N,N-di-($C_1$-$C_7$-alkyl)-aminocarbonyl;

straight chain $C_1$-$C_7$-alkyl which may be bound to the terminal or non-terminal carbon and which may be unsubstituted or substituted with one or more, such as one or two of the group consisting of:

unsubstituted or substituted heterocyclyl, especially morpholino, thiomorpholino, piperidinyl, piperazinyl, pyrrolidinyl, tetrahydrofuranyl, tetrahydropyranyl or tetrahydrothiophenyl, each of which is unsubstituted or substituted as described herein, preferably unsubstituted;

unsubstituted or substituted aryl, especially unsubstituted or substituted phenyl as described herein; unsubstituted or substituted $C_3$-$C_8$-cycloalkyl, such as cyclohexyl, which is unsubstituted or substituted as described herein; halo, hydroxy, $C_1$-$C_7$-alkoxy, halo-$C_1$-$C_7$-alkoxy, such as trifluoromethoxy, hydroxy-$C_1$-$C_7$-alkoxy, and N-mono- or N,N-di-($C_1$-$C_7$-alkyl)-aminocarbonyl;

unsubstituted or substituted $C_3$-$C_8$-cycloalkyl, such as cyclohexyl, which is unsubstituted or substituted as described herein, or acyl, such as (unsubstituted or substituted alkyl, unsubstituted or substituted aryl-$C_1$-$C_7$-alkyl, unsubstituted or substituted heterocyclyl-$C_1$-$C_7$-alkyl or unsubstituted or substituted cycloalkyl-$C_1$-$C_7$-alkyl)-sulfonyl, especially phenylmethanesulfonyl;

or R3 and R4 form together a pyrrolidine or piperidine ring that is unsubstituted or substituted by up to four moieties selected from $C_1$-$C_7$-alkyl, hydroxyl, halo, hydroxy-$C_1$-$C_7$-alkyl, halo-$C_1$-$C_7$-alkyl and cyano; and T is carbonyl;

or a (preferably pharmaceutically acceptable) salt thereof.

Preferred Definitions for R1

As R1, hydrogen, $C_1$-$C_7$-alkyl, halo-$C_1$-$C_7$-alkyl, phenyl-$C_1$-$C_7$-alkyl, or $C_3$-$C_8$-cycloalkyl is preferred. R1 is more preferably $C_1$-$C_7$-alkyl, such as methyl, ethyl, isopropyl or n-butyl, preferably ethyl, isopropyl or n-butyl or is $C_3$-$C_8$-cycloalkyl, such as $C_3$—, $C_4$—, $C_5$- or $C_6$-cycloalkyl, most preferably R1 is cyclopropyl.

Preferred Definitions for R2

As R2, these or preferably any other mentioned moieties mentioned herein as falling under the definition of R2 are preferred.

In a first preferred embodiment R2 is unsubstituted or substituted, preferably substituted, alkyl.

Preferred examples for alkyl are branched or straight chain $C_1$-$C_7$-alkyl which may be substituted or unsubstituted. Preferred examples include methyl, ethyl, isopropyl, n-propyl, n-butyl, sec-butyl or tert-butyl, more preferably methyl, ethyl or isopropyl, most preferably methyl. The alkyl moiety is preferably mono-, di- or tri-substituted, more preferably mono-substituted. Suitable substituents for the alkyl moiety are as defined herein, preferably $C_1$-$C_4$-alkoxy, halo, hydroxy, unsubstituted or substituted, preferably substituted, phenyl, unsubstituted or substituted, preferably substituted, naphthyl, unsubstituted or substituted, preferably substituted, phenyl- or naphthyloxy, unsubstituted or substituted, preferably substituted, phenyl- or naphthyl-$C_1$-$C_7$-alkyloxy, unsubstituted or substituted, preferably substituted, heterocyclyl, unsubstituted or substituted, preferably unsubstituted, cycloalkyl, nitro, amino, amino-$C_1$-$C_7$-alkyl, N-mono- or N,N-di-substituted aminocarbonyl, carboxyl, and cyano, more preferably unsubstituted or substituted, preferably substituted, phenyl, unsubstituted or substituted, preferably substituted, naphthyl, unsubstituted or substituted, preferably substituted, phenyl- or naphthyloxy, or unsubstituted or substituted, preferably substituted, heterocyclyl, most preferably unsubstituted or substituted, preferably substituted, phenyl or unsubstituted or substituted, preferably substituted, heterocyclyl. The heterocyclyl moiety is in this connection preferably mono- or bicyclic. Preferred are aromatic ring systems, or in particular if a bicyclic moiety is contemplated, partially saturated ring systems, in particular whereby one of the rings is aromatic and the other is saturated or partially saturated, most preferred are aromatic. The heterocyclyl moiety may contain an oxo moiety. The heterocyclyl moiety has preferably 1, 2 or 3, more preferably 1 or 2, most preferably 1, heteroatoms selected from O, N or S, more preferably O or N. Particularly preferred examples include 5- or 6-membered rings preferably containing a nitrogen or sulfur atom, in particular pyridyl or 1H-pyridin-2-onyl or thiophenyl; or bicyclic ring systems preferably containing a N or O atom, in particular indolyl, 1H-indazolyl, quinolyl, isoquinolyl, 1,2,3,4-tetrahydro-1,4-benzoxazinyl, 2H-1,4-benzoxazin-3(4H)-onyl, pyrrolo[2,3-b]pyridyl, chromanyl, or 2,3-dihydrobenzofuranyl.

Each moiety mentioned above as being substituted, in particular phenyl or heterocyclyl, can be substituted by one or more, e.g. up to three, substituents. In one embodiment phenyl is preferably di-substituted. In another embodiment, phenyl is preferably tri-substituted. The heterocyclyl moiety can preferably be mono- or tri-substituted. Suitable substituents for these moieties are preferably independently selected from the group consisting of $C_1$-$C_7$-alkyl, hydroxy-$C_1$-$C_7$-alkyl, $C_1$-$C_7$-alkoxy-$C_1$-$C_7$-alkyl, $C_1$-$C_7$-alkoxy-$C_1$-$C_7$-alkoxy-$C_1$-$C_7$-alkyl, $C_1$-$C_7$-alkanoyloxy-$C_1$-$C_7$-alkyl, amino-$C_1$-$C_7$-alkyl, $C_1$-$C_7$-alkoxy-$C_1$-$C_7$-alkylamino-$C_1$-$C_7$-alkyl, $C_1$-$C_7$-alkanoylamino-$C_1$-$C_7$-alkyl, $C_1$-$C_7$-alkylsulfonylamino-$C_1$-$C_7$-alkyl, carboxy-$C_1$-$C_7$-alkyl, $C_1$-$C_7$-alkoxycarbonyl-$C_1$-$C_7$-alkyl, halo, hydroxy, $C_1$-$C_7$-alkoxy, $C_1$-$C_7$-alkoxy-$C_1$-$C_7$-alkoxy, carboxy-$C_1$-$C_7$-alkoxy, amino-$C_1$-$C_7$-alkoxy, N—$C_1$-$C_7$-alkanoylamino-$C_1$-$C_7$-alkoxy, carbamoyl-$C_1$-$C_7$-alkyl, carbamoyl-$C_1$-$C_7$-alkoxy, N—$C_1$-$C_7$-alkylcarbamoyl-$C_1$-$C_7$-alkoxy, $C_1$-$C_7$-alkanoyl, $C_1$-$C_7$-alkyloxy-$C_1$-$C_7$-alkanoyl, $C_1$-$C_7$-alkoxy-$C_1$-$C_7$-alkanoyl, carboxyl, carbamoyl, N—$C_1$-$C_7$-alkoxy-$C_1$-$C_7$-alkylcarbamoyl, halo-$C_1$-$C_7$-alkyl, phenyl, phenyl which is mono-, di- or tri-substituted with halo, hydroxy, $C_1$-$C_7$-alkoxy, and/or $C_1$-$C_7$-alkyl; cyano, $C_1$-$C_7$-alkanoylamino, and N-mono-$C_1$-$C_7$-alkoxy-$C_1$-$C_7$-alkyl-aminocarbonyl; more preferably $C_1$-$C_7$-alkyl, $C_1$-$C_7$-alkoxy-$C_1$-$C_7$-alkyl, halo-$C_1$-$C_7$-alkyl, hydroxy-$C_1$-$C_7$-alkyl, phenyl, phenyl which is mono-, di- or tri-substituted with halo, hydroxy, $C_1$-$C_7$-alkoxy, and/or $C_1$-$C_7$-alkyl; halo, hydroxy, $C_1$-$C_7$-alkoxy, cyano, $C_1$-$C_7$-alkoxy-$C_1$-$C_7$-alkoxy-alkyl, $C_1$-$C_7$-alkoxy-$C_1$-$C_7$-alkylamino-$C_1$-$C_7$-alkyl, $C_1$-$C_7$-alkanoylamino, N-mono-$C_1$-$C_7$-alkoxy-$C_1$-$C_7$-alkyl-aminocarbonyl, $C_1$-$C_7$-alkanoyl and $C_1$-$C_7$-alkoxy-$C_1$-$C_7$-alkoxy. The heterocyclyl moiety is preferably substituted on the N, if present.

In a second embodiment R2 is preferably unsubstituted or substituted aryl.

Preferred examples of aryl include phenyl or naphthyl, more preferably phenyl. When the aryl moiety is substituted, it is preferably mono- or di-substituted. In one embodiment, the aryl moiety is tri-substituted. Most preferably aryl is di-substituted. Suitable substituents are as defined herein, preferably $C_1$-$C_7$-alkyl, hydroxy-$C_1$-$C_7$-alkyl, $C_1$-$C_7$-alkoxy-$C_1$-$C_7$-alkyl, $C_1$-$C_7$-alkoxy-$C_1$-$C_7$-alkoxy-$C_1$-$C_7$-alkyl, $C_1$-$C_7$-alkanoyloxy-$C_1$-$C_7$-alkyl, amino-$C_1$-$C_7$-alkyl, $C_1$-$C_7$-alkoxy-$C_1$-$C_7$-alkylamino-$C_1$-$C_7$-alkyl, $C_1$-$C_7$-alkanoylamino-$C_1$-$C_7$-alkyl, $C_1$-$C_7$-alkylsulfonylamino-$C_1$-$C_7$-alkyl, carboxy-$C_1$-$C_7$-alkyl, $C_1$-$C_7$-alkoxycarbonyl-$C_1$-$C_7$-alkyl, halo, hydroxy, $C_1$-$C_7$-alkoxy, $C_1$-$C_7$-alkoxy-$C_1$-$C_7$-alkoxy, carboxy-$C_1$-$C_7$-alkoxy, amino-$C_1$-$C_7$-alkoxy, N—$C_1$-$C_7$-alkanoylamino-$C_1$-$C_7$-alkoxy, carbamoyl-$C_1$-$C_7$-alkyl, carbamoyl-$C_1$-$C_7$-alkoxy, N—$C_1$-$C_7$-alkylcarbamoyl-$C_1$-$C_7$-alkoxy, $C_1$-$C_7$-alkanoyl, $C_1$-$C_7$-alkyloxy-$C_1$-$C_7$-alkanoyl, $C_1$-$C_7$-alkoxy-$C_1$-$C_7$-alkanoyl, carboxyl, carbamoyl, N—$C_1$-$C_7$-alkoxy-$C_1$-$C_7$-alkylcarbamoyl, $C_1$-$C_7$-alkoxy-$C_1$-$C_7$-alkanoylamino, halo-$C_1$-$C_7$-alkyl, phenyl, phenyl which is mono-, di- or tri-substituted with halo, hydroxy, $C_1$-$C_7$-alkoxy, and/or $C_1$-$C_7$-alkyl; cyano, $C_1$-$C_7$-alkanoylamino, and N-mono-$C_1$-$C_7$-alkoxy-$C_1$-$C_7$-alkyl-aminocarbonyl;

more preferably $C_1$-$C_7$-alkyl, $C_1$-$C_7$-alkoxy-$C_1$-$C_7$-alkyl, halo-$C_1$-$C_7$-alkyl, hydroxy-$C_1$-$C_7$-alkyl, phenyl, phenyl which is mono-, di- or tri-substituted with halo, hydroxy, $C_1$-$C_7$-alkoxy, and/or $C_1$-$C_7$-alkyl; halo, hydroxy, $C_1$-$C_7$-alkoxy, cyano, $C_1$-$C_7$-alkoxy-$C_1$-$C_7$-alkoxy-alkyl, $C_1$-$C_7$-alkoxy-$C_1$-$C_7$-alkylamino-$C_1$-$C_7$-alkyl, $C_1$-$C_7$-alkanoylamino, N-mono-$C_1$-$C_7$-alkoxy-$C_1$-$C_7$-alkyl-aminocarbonyl, $C_1$-$C_7$-alkoxy-$C_1$-$C_7$-alkanoylamino, halo-$C_1$-$C_7$-alkyl, $C_1$-$C_7$-alkanoyl and $C_1$-$C_7$-alkoxy-$C_1$-$C_7$-alkoxy, still more preferably $C_1$-$C_7$-alkyl, $C_1$-$C_7$-alkoxy, cyano, $C_1$-$C_7$-alkanoyl, $C_1$-$C_7$-alkoxy-$C_1$-$C_7$-alkanoylamino, halo, halo-$C_1$-$C_7$-alkyl and $C_1$-$C_7$-alkoxy-$C_1$-$C_7$-alkoxy, most preferably $C_1$-$C_7$-alkyl, cyano, $C_1$-$C_7$-alkanoyl, $C_1$-$C_7$-alkoxy-$C_1$-$C_7$-alkanoylamino, halo, halo-$C_1$-$C_7$-alkyl and $C_1$-$C_7$-alkoxy-$C_1$-$C_7$-alkoxy.

In a third embodiment R2 is preferably unsubstituted or substituted heterocyclyl.

The heterocyclyl moiety is preferably mono- or bicyclic, more preferably bicyclic. In one embodiment, the heterocyc moiety is preferably monocyclic. Preferred are aromatic ring systems, or partially saturated ring systems, in particular whereby one of the rings is aromatic and the other is saturated or partially saturated, most preferred are partially saturated. The heterocyclyl moiety has preferably 1, 2 or 3, more preferably 1 or 2, most preferably 2, heteroatoms selected from O, N or S, more preferably O or N. The ring system contains preferably an oxo moiety. Preferred examples include bicyclic 10-membered rings preferably containing a nitrogen atom, in particular, quinolyl, isoquinolyl, 1,2,3,4-tetrahydro-1,4-benzoxazinyl, 4H-benzo[1,4]oxazin-3-onyl, 3,4-dihydro-2H-benzo[1,4]oxazyl, 3,4-dihydro-1H-quinolin-2-onyl, or 4H-benzo[1,4]thiazin-3-onyl; more preferably quinolyl, isoquinolyl, 1,2,3,4-tetrahydro-1,4-benzoxazinyl, 4H-benzo[1,4]oxazin-3-on-yl, 3,4-dihydro-1H-quinolin-2-onyl, or 4H-benzo[1,4]thiazin-3-onyl; or bicyclic 9-membered ring systems preferably containing a N atom, in particular indolyl, 1H-indazolyl, benzothiophenyl, imidazo[1,2-a]pyridyl or 3H-benzooxazol-2-onyl, more preferably 4H-benzo[1,4]oxazin-3-onyl, 3,4-dihydro-1H-quinolin-2-onyl. In another embodiment, the heterocyclyl moiety is preferably a monocyclic 6-membered ring, preferably containing a N atom, in particular pyrimidyl and pyridyl. Each heterocyclyl is unsubstituted or substituted by one or more, e.g. up to three, substituents independently selected from the group consisting $C_1$-$C_7$-alkyl, hydroxy-$C_1$-$C_7$-alkyl, $C_1$-$C_7$-alkoxy-$C_1$-$C_7$-alkyl, $C_1$-$C_7$-alkoxy-$C_1$-$C_7$-alkoxy-$C_1$-$C_7$-alkyl, $C_1$-$C_7$-alkanoyloxy-$C_1$-$C_7$-alkyl, amino-$C_1$-$C_7$-alkyl, N-mono or N,N-di($C_1$-$C_7$-alkyl)amino-$C_1$-$C_7$-alkyl, $C_1$-$C_7$-alkoxy-$C_1$-$C_7$-alkylamino-$C_1$-$C_7$-alkyl, $C_1$-$C_7$-alkanoylamino-$C_1$-$C_7$-alkyl, $C_1$-$C_7$-alkylsulfonylamino-$C_1$-$C_7$-alkyl, carboxy-$C_1$-$C_7$-alkyl, $C_1$-$C_7$-alkoxycarbonyl-$C_1$-$C_7$-alkyl, halo, hydroxy, $C_1$-$C_7$-alkoxy, $C_1$-$C_7$-alkoxy-$C_1$-$C_7$-alkoxy, carboxy-$C_1$-$C_7$-alkoxy, amino-$C_1$-$C_7$-alkoxy, N—$C_1$-$C_7$-alkanoylamino-$C_1$-$C_7$-alkoxy, carbamoyl-$C_1$-$C_7$-alkyl, carbamoyl-$C_1$-$C_7$-alkoxy, N—$C_1$-$C_7$-alkylcarbamoyl-$C_1$-$C_7$-alkoxy, $C_1$-$C_7$-alkanoyl, $C_1$-$C_7$-alkoxy-$C_1$-$C_7$-alkanoyl, carboxyl, carbamoyl, N—$C_1$-$C_7$-alkoxy-$C_1$-$C_7$-alkylcarbamoyl, halo-$C_1$-$C_7$-alkyl, phenyl, phenyl which is mono-, di- or tri-substituted with halo, hydroxy, $C_1$-$C_7$-alkoxy, and/or $C_1$-$C_7$-alkyl; cyano, $C_1$-$C_7$-alkanoylamino, and N-mono-$C_1$-$C_7$-alkoxy-$C_1$-$C_7$-alkyl-aminocarbonyl; more preferably selected from the group consisting $C_1$-$C_7$-alkyl, hydroxy-$C_1$-$C_7$-alkyl, $C_1$-$C_7$-alkoxy-$C_1$-$C_7$-alkyl, $C_1$-$C_7$-alkoxy-$C_1$-$C_7$-alkoxy-$C_1$-$C_7$-alkyl, $C_1$-$C_7$-alkanoyloxy-$C_1$-$C_7$-alkyl, amino-$C_1$-$C_7$-alkyl, $C_1$-$C_7$-alkoxy-$C_1$-$C_7$-alkylamino-$C_1$-$C_7$-alkyl, $C_1$-$C_7$-alkanoylamino-$C_1$-$C_7$-alkyl, $C_1$-$C_7$-alkyl-sulfonylamino-$C_1$-$C_7$-alkyl, carboxy-$C_1$-$C_7$-alkyl, $C_1$-$C_7$-alkoxycarbonyl-$C_1$-$C_7$-alkyl, halo, hydroxy, $C_1$-$C_7$-alkoxy, $C_1$-$C_7$-alkoxy-$C_1$-$C_7$-alkoxy, carboxy-$C_1$-$C_7$-alkoxy, amino-$C_1$-$C_7$-alkoxy, N—$C_1$-$C_7$-alkanoylamino-$C_1$-$C_7$-alkoxy, carbamoyl-$C_1$-$C_7$-alkyl, carbamoyl-$C_1$-$C_7$-alkoxy, N—$C_1$-$C_7$-alkylcarbamoyl-$C_1$-$C_7$-alkoxy, $C_1$-$C_7$-alkanoyl, $C_1$-$C_7$-alkyloxy-$C_1$-$C_7$-alkanoyl, carboxyl, carbamoyl, N—$C_1$-$C_7$-alkoxy-$C_1$-$C_7$-alkylcarbamoyl, halo-$C_1$-$C_7$-alkyl, phenyl, phenyl which is mono-, di- or tri-substituted with halo, hydroxy, $C_1$-$C_7$-alkoxy, and/or $C_1$-$C_7$-alkyl; cyano, $C_1$-$C_7$-alkanoylamino, and N-mono-$C_1$-$C_7$-alkoxy-$C_1$-$C_7$-alkyl-aminocarbonyl; still more preferably $C_1$-$C_7$-alkyl, $C_1$-$C_7$-alkoxy-$C_1$-$C_7$-alkyl, halo-$C_1$-$C_7$-alkyl, hydroxy-$C_1$-$C_7$-alkyl, phenyl, phenyl which is mono-, di- or tri-substituted with halo, hydroxy, $C_1$-$C_7$-alkoxy, and/or $C_1$-$C_7$-alkyl; halo, hydroxy, $C_1$-$C_7$-alkoxy, cyano, $C_1$-$C_7$-alkoxy-$C_1$-$C_7$-alkoxy-alkyl, $C_1$-$C_7$-alkoxy-$C_1$-$C_7$-alkylamino-$C_1$-$C_7$-alkyl, $C_1$-$C_7$-alkanoylamino, N-mono-$C_1$-$C_7$-alkoxy-$C_1$-$C_7$-alkyl-aminocarbonyl, $C_1$-$C_7$-alkanoyl and $C_1$-$C_7$-alkoxy-$C_1$-$C_7$-alkoxy, N-mono or N,N-di($C_1$-$C_7$-alkyl)amino-$C_1$-$C_7$-alkyl, amino-$C_1$-$C_7$-alkyl, $C_1$-$C_7$-alkyloxy-$C_1$-$C_7$-alkanoyl; even more preferably $C_1$-$C_7$-alkyl, $C_1$-$C_7$-alkoxy-$C_1$-$C_7$-alkyl, halo-$C_1$-$C_7$-alkyl, hydroxy-$C_1$-$C_7$-alkyl, phenyl, phenyl which is mono-, di- or tri-substituted with halo, hydroxy, $C_1$-$C_7$-alkoxy, and/or $C_1$-$C_7$-alkyl; halo, hydroxy, $C_1$-$C_7$-alkoxy, cyano, $C_1$-$C_7$-alkoxy-$C_1$-$C_7$-alkoxy-alkyl, $C_1$-$C_7$-alkoxy-$C_1$-$C_7$-alkylamino-$C_1$-$C_7$-alkyl, $C_1$-$C_7$-alkanoylamino, N-mono-$C_1$-$C_7$-alkoxy-$C_1$-$C_7$-alkyl-aminocarbonyl, $C_1$-$C_7$-alkanoyl and $C_1$-$C_7$-alkoxy-$C_1$-$C_7$-alkoxy; yet more preferably $C_1$-$C_7$-alkyl, $C_1$-$C_7$-alkoxy-$C_1$-$C_7$-alkyl, $C_1$-$C_7$-alkanoyl, halo-$C_1$-$C_7$-alkyl, hydroxy-$C_1$-$C_7$-alkyl, $C_1$-$C_7$-alkoxy-$C_1$-$C_7$-alkoxy, N-mono or N,N-di($C_1$-$C_7$-alkyl)amino-$C_1$-$C_7$-alkyl, amino-$C_1$-$C_7$-alkyl, $C_1$-$C_7$-alkyloxy-$C_1$-$C_7$-alkanoyl, phenyl, or phenyl which is mono-, di- or tri-substituted with halo, hydroxy, $C_1$-$C_7$-alkoxy, and/or $C_1$-$C_7$-alkyl, most preferably $C_1$-$C_7$-alkyl, $C_1$-$C_7$-alkoxy-$C_1$-$C_7$-alkyl, phenyl, or phenyl which is mono-, di- or tri-substituted with halo, hydroxy, $C_1$-$C_7$-alkoxy, and/or $C_1$-$C_7$-alkyl. The heterocyclyl moiety is preferably substituted on the N, if present.

In a fourth embodiment R2 is preferably acyl wherein acyl is as defined herein.

Acyl is preferably unsubstituted or substituted aryl-carbonyl or -sulfonyl, unsubstituted or substituted heterocyclylcarbonyl or -sulfonyl. Aryl, which is preferably phenyl, and heterocyclyl have the same preferred definitions as phenyl and heterocyclyl disclosed as a substituents of substituted alkyl (see first embodiment). When R2 is acyl, T is preferably methylene. $R_2$ more preferably has one of the meanings given herein other than acyl.

Thus preferably R2 is pyrimidyl, pyridyl, phenyl-$C_1$-$C_7$-alkyl, naphthyl-$C_1$-$C_7$-alkyl, pyridyl-$C_1$-$C_7$-alkyl, indolyl-$C_1$-$C_7$-alkyl, 1H-pyrrolo[2,3-b]pyridyl-$C_1$-$C_7$-alkyl, quinolinyl-$C_1$-$C_7$-alkyl, 1H-pyridin-2-onyl-$C_1$-$C_7$-alkyl, thiophenyl-$C_1$-$C_7$-alkyl, chromanyl-$C_1$-$C_7$-alkyl, 2,3-dihydrobenzofuranyl-$C_1$-$C_7$-alkyl, phenyl, 4H-benzo[1,4]oxazin-3-onyl, 3,4-dihydro-2H-benzo[1,4]oxazyl, 3,4-dihydro-1H-quinolin-2-onyl, or is acyl such as phenylcarbonyl or indolylcarbonyl where each phenyl, naphthyl, pyridyl, pyrimidyl, indolyl, pyrrolo[2,3-b]pyridyl, quinolinyl 1H-pyridin-2-onyl, thiophenyl, chromanyl, 2,3-dihydrobenzofuranyl, 3,4-dihydro-1H-quinolin-2-onyl, 3,4-dihydro-2H-benzo[1,4]oxazyl or 4H-benzo[1,4]oxazin-3-on-yl mentioned for R2 so far as a substituent or part of a substituent is unsubstituted or substituted by one or more, especially up to three, moieties independently selected from the group consisting of $C_1$-$C_7$-alkyl, $C_1$-$C_7$-alkoxy-$C_1$-$C_7$-alkyl, halo-$C_1$-$C_7$-alkyl, hydroxy-$C_1$-$C_7$-alkyl, phenyl, phenyl which is mono-, di- or tri-substituted with halo, hydroxy, $C_1$-$C_7$-alkoxy, and/or $C_1$-$C_7$-alkyl; halo, hydroxy, $C_1$-$C_7$-alkoxy, cyano, $C_1$-$C_7$-alkoxy-$C_1$-$C_7$-alkoxy-$C_1$-$C_7$-alkyl, $C_1$-$C_7$-alkoxy-$C_1$-$C_7$-alkylamino-$C_1$-$C_7$-alkyl, $C_1$-$C_7$-alkanoylamino, N-mono-$C_1$-$C_7$-alkoxy-$C_1$-$C_7$-alkylaminocarbonyl, $C_1$-$C_7$-alkanoyl, $C_1$-$C_7$-alkoxy-$C_1$-$C_7$-alkanoyl, amino-$C_1$-$C_7$-alkyl and $C_1$-$C_7$-alkoxy-$C_1$-$C_7$-alkoxy.

Thus preferably R2 can be phenyl-$C_1$-$C_7$-alkyl, naphthyl-$C_1$-$C_7$-alkyl, pyridyl-$C_1$-$C_7$-alkyl, indolyl-$C_1$-$C_7$-alkyl, 1H-pyrrolo[2,3-b]pyridyl-$C_1$-$C_7$-alkyl, quinolinyl-$C_1$-$C_7$-alkyl, 1H-pyridin-2-onyl-$C_1$-$C_7$-alkyl, thiophenyl-$C_1$-$C_7$-alkyl, chromanyl-$C_1$-$C_7$-alkyl, 2,3-dihydrobenzofuranyl-$C_1$-$C_7$-alkyl, phenyl, 4H-benzo[1,4]oxazin-3-on-yl, 3,4-dihydro-1H-quinolin-2-onyl, or is acyl such as phenylcarbonyl or indolylcarbonyl where each phenyl, naphthyl, pyridyl, indolyl, pyrrolo[2,3-b]pyridyl, quinolinyl 1H-pyridin-2-onyl, thiophenyl, chromanyl, 2,3-dihydrobenzofuranyl, 3,4-dihydro-1H-quinolin-2-onyl or 4H-benzo[1,4]oxazin-3-on-yl mentioned for R2 so far as a substituent or part of a substituent is unsubstituted or substituted by one or more, especially up to three, moieties independently selected from the group consisting of $C_1$-$C_7$-alkyl, $C_1$-$C_7$-alkoxy-$C_1$-$C_7$-alkyl, halo-$C_1$-$C_7$-alkyl, hydroxy-$C_1$-$C_7$-alkyl, phenyl, phenyl which is mono-, di- or tri-substituted with halo, hydroxy, $C_1$-$C_7$-alkoxy, and/or $C_1$-$C_7$-alkyl; halo, hydroxy, $C_1$-$C_7$-alkoxy, cyano, $C_1$-$C_7$-alkoxy-$C_1$-$C_7$-alkoxy-$C_1$-$C_7$-alkyl, $C_1$-$C_7$-alkoxy-$C_1$-$C_7$-alkylamino-$C_1$-$C_7$-alkyl, $C_1$-$C_7$-alkanoylamino, N-mono-$C_1$-$C_7$-alkoxy-$C_1$-$C_7$-alkylaminocarbonyl, $C_1$-$C_7$-alkanoyl and $C_1$-$C_7$-alkoxy-$C_1$-$C_7$-alkoxy.

Particularly preferred examples for R2 are

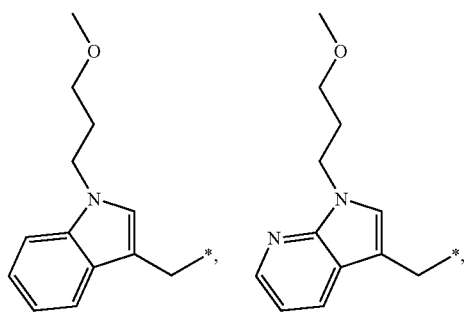

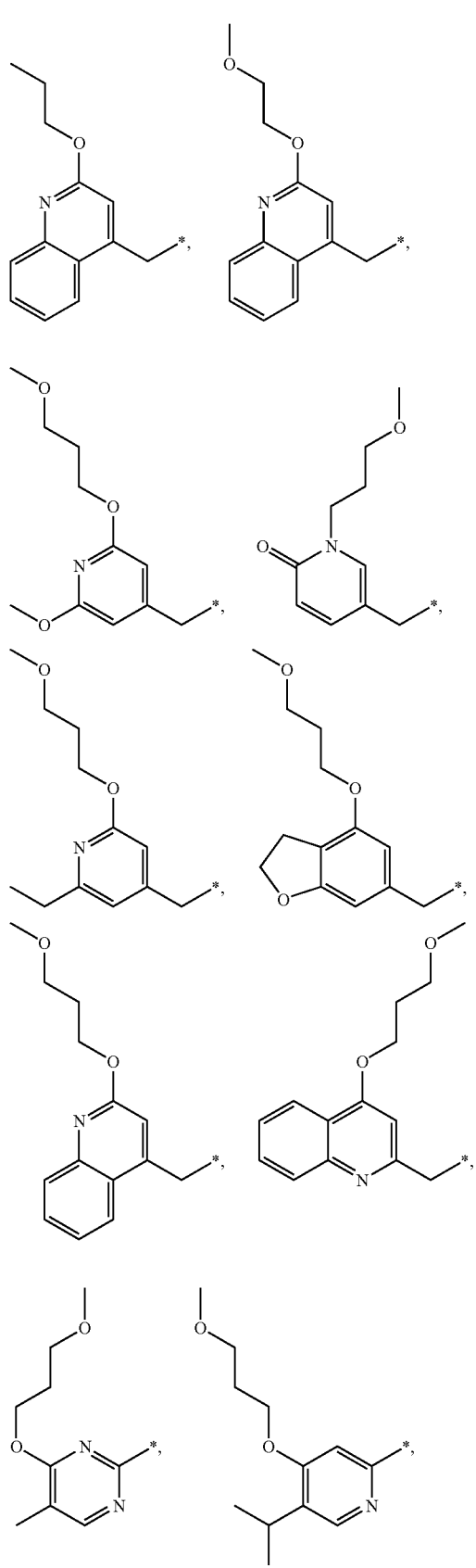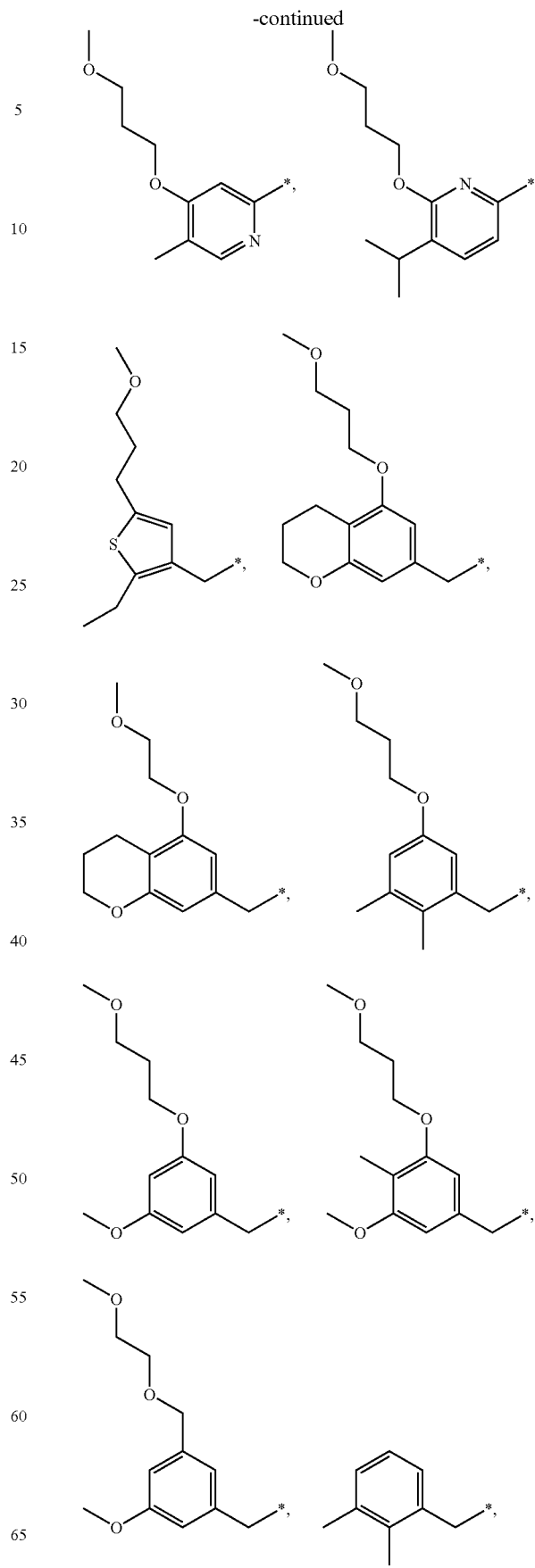

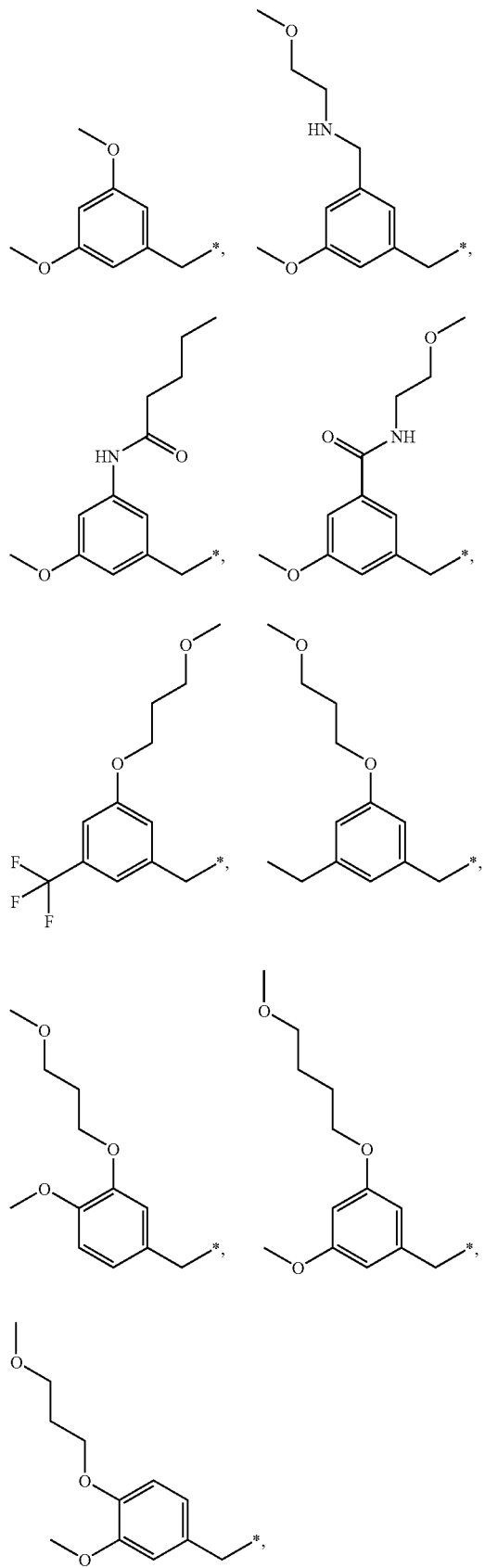
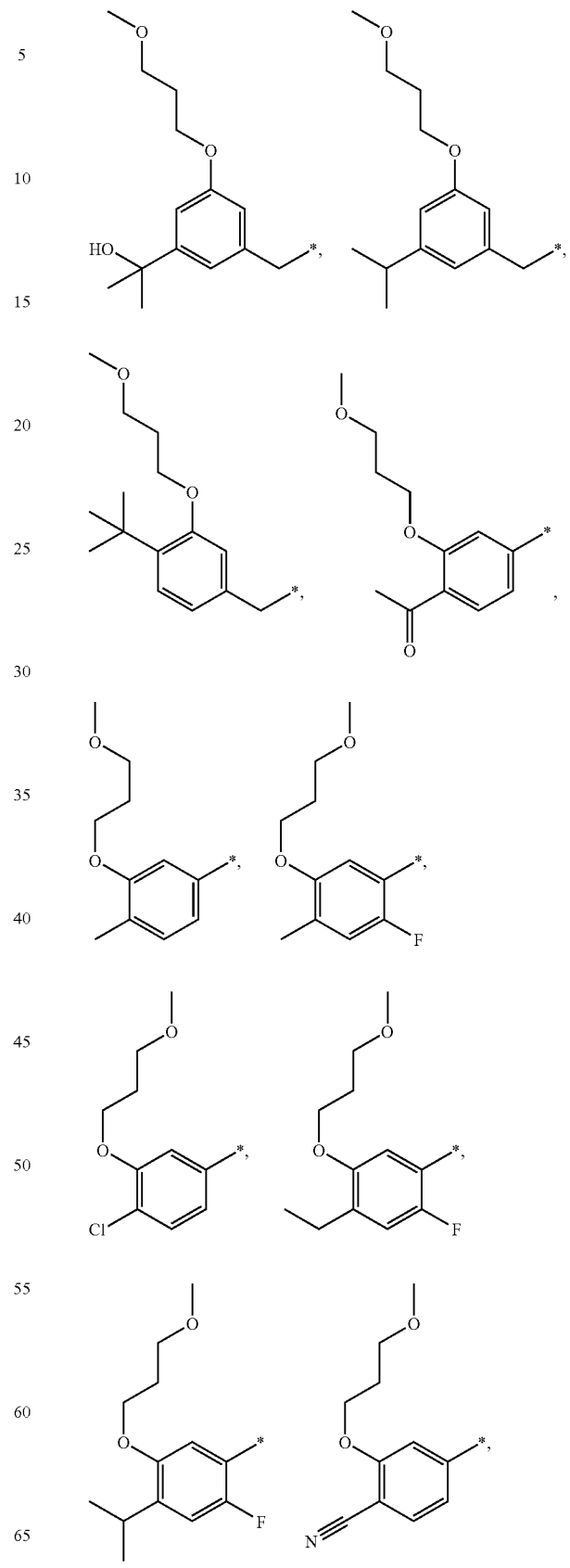

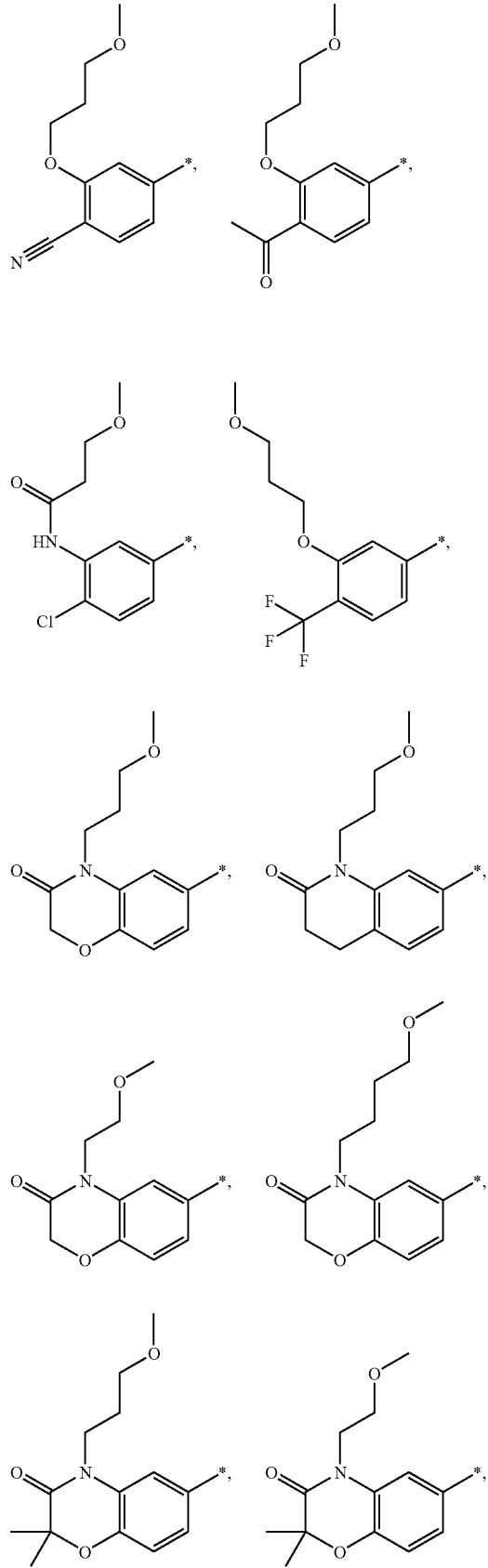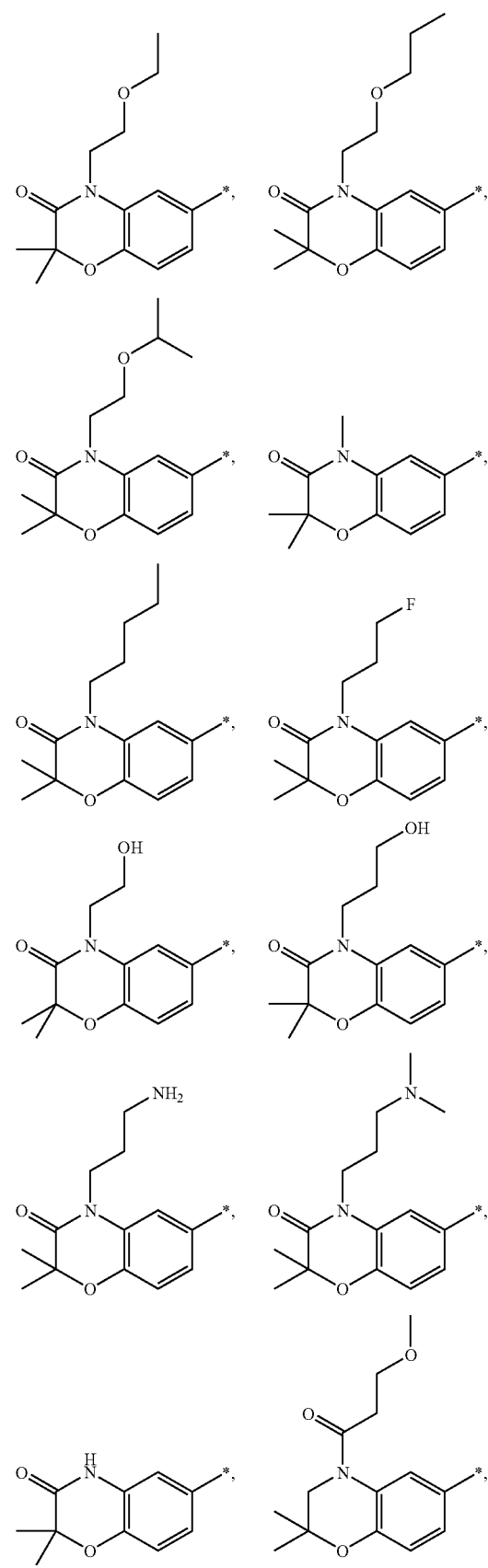

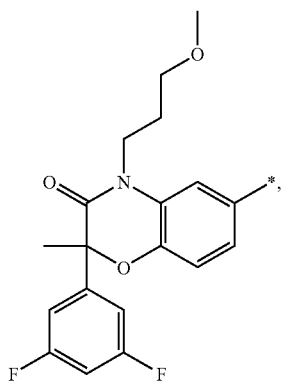
Particularly, more preferred examples for R2 are
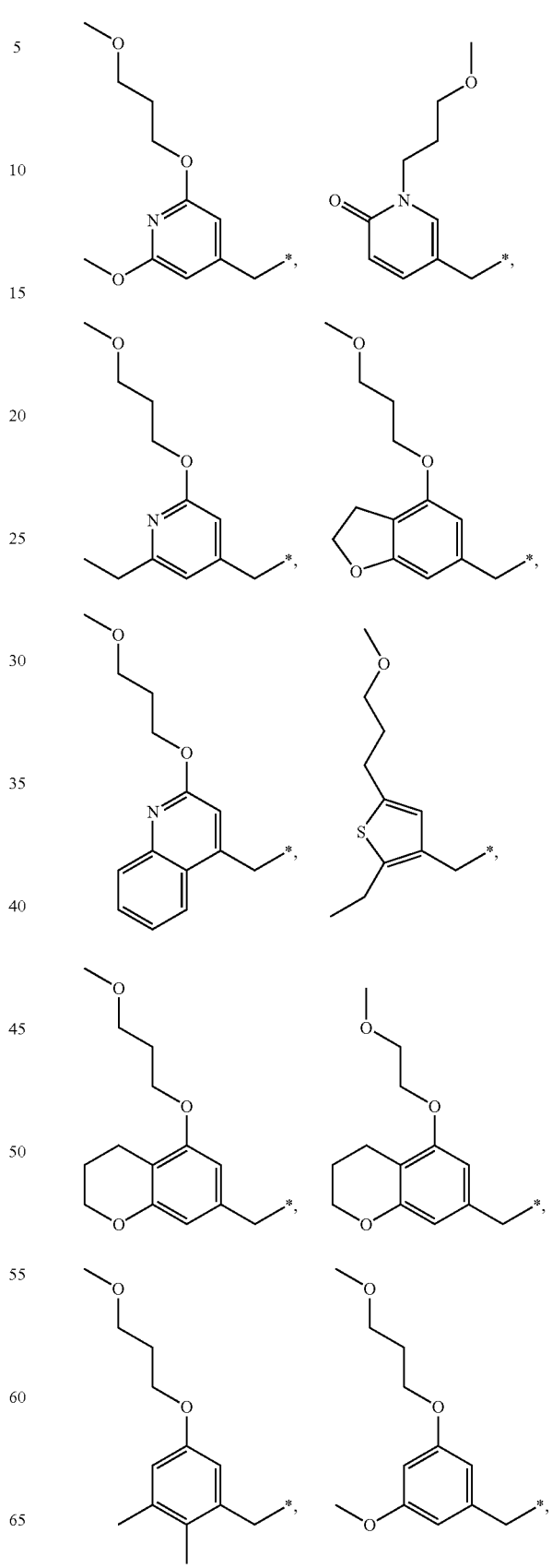

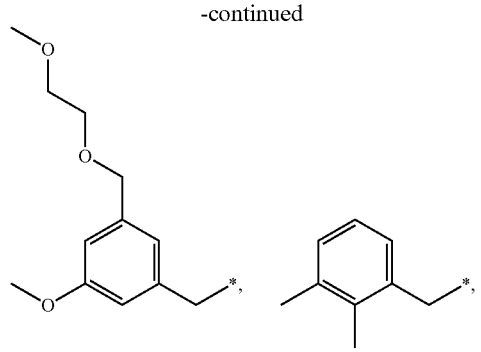
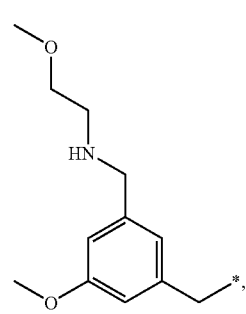
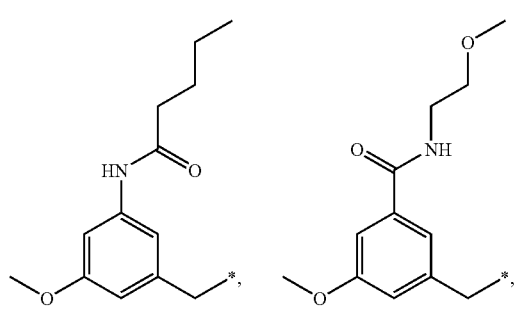
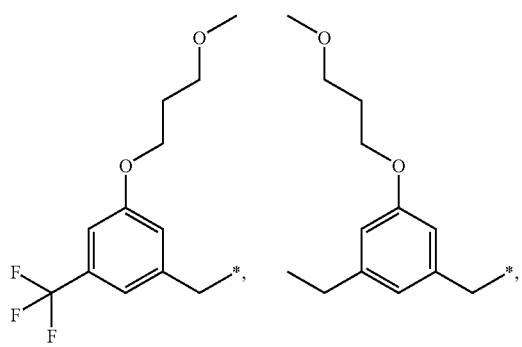
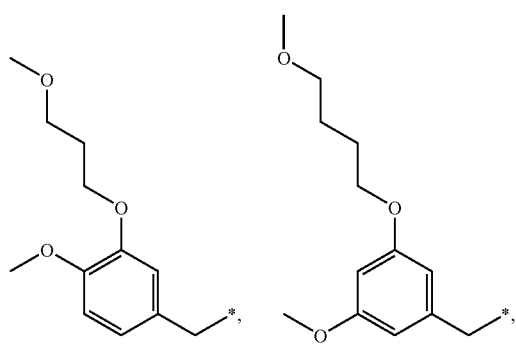
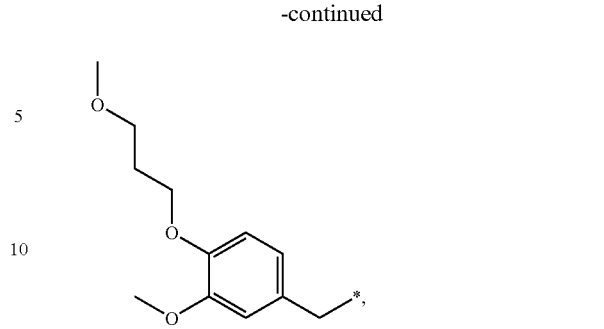
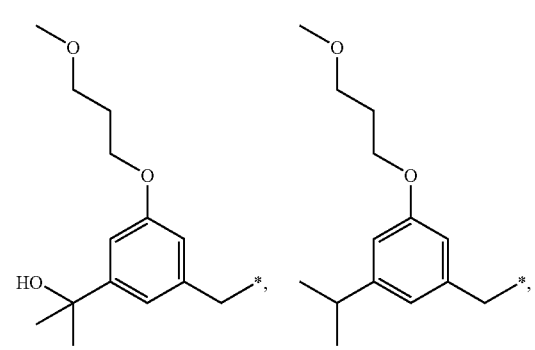
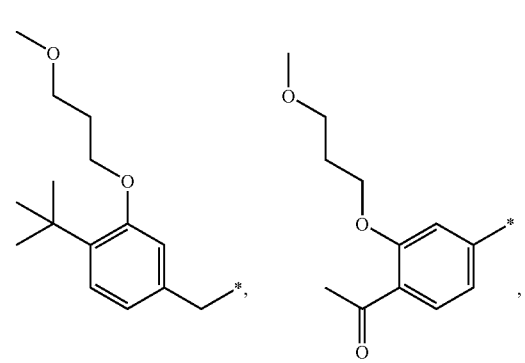
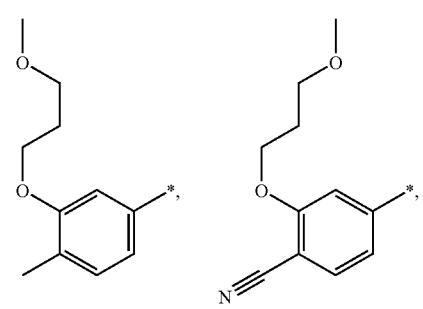
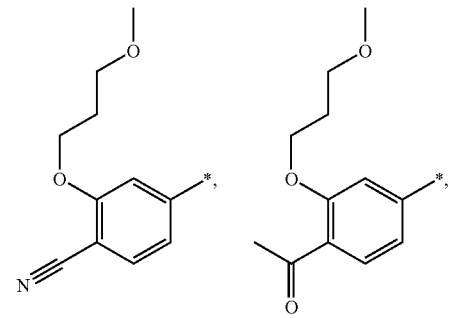

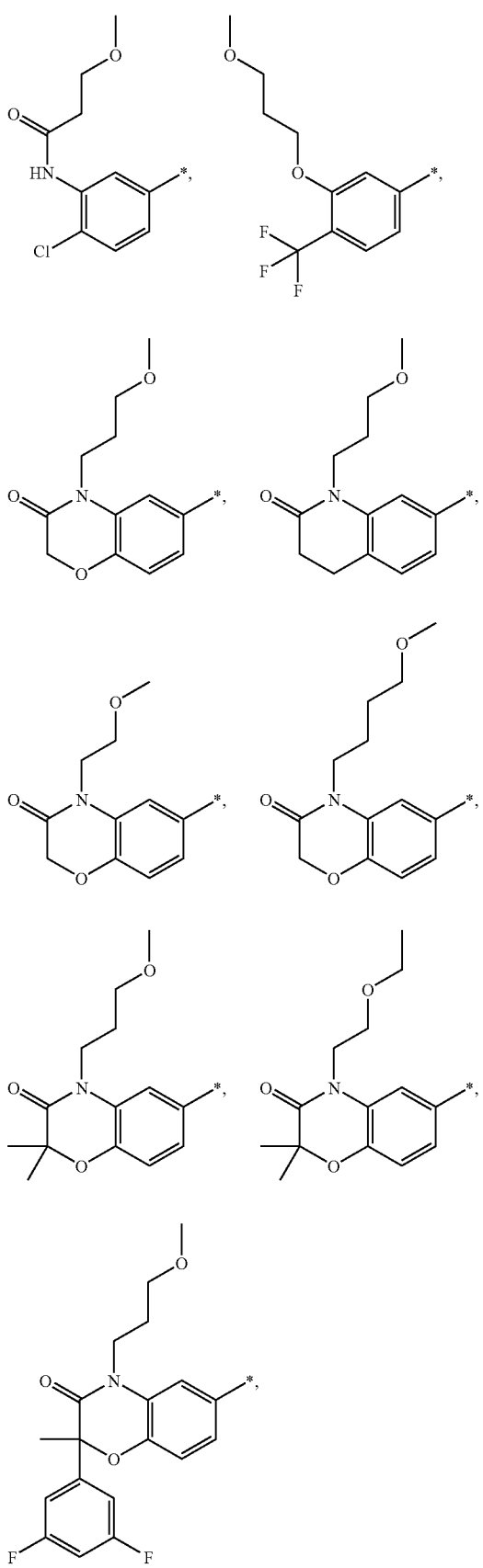

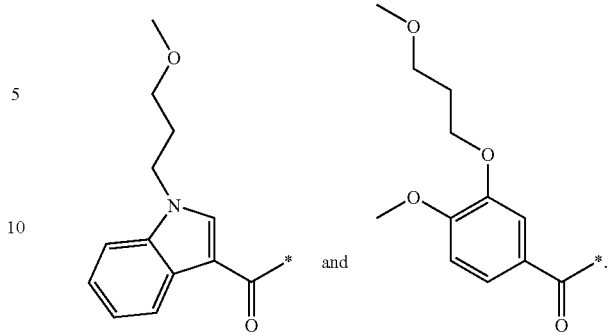

Preferred Definitions for T

T is preferably carbonyl or methylene, more preferably carbonyl. When T is methylene, R2 is preferably acyl.

Preferred Definitions for R3

R3 is preferably hydrogen or $C_1$-$C_7$-alkyl, such as methyl, more preferably hydrogen. When R3 is $C_1$-$C_7$-alkyl, preferably $C_1$-$C_4$-alkyl, such as methyl, then R4 is preferably substituted or unsubstituted $C_1$-$C_7$-alkyl, preferably $C_1$-$C_4$-alkyl, e.g. alkyl substituted with phenyl, most preferably it is isobutyl or benzyl.

Preferred Definitions for R4

As R4, these or preferably any other mentioned moieties mentioned herein as falling under the definition of R4 are preferred.

In a first preferred embodiment R4 is unsubstituted or substituted branched alkyl.

Branched alkyl is a moiety with preferably 3 to 15, more preferably 4 to 10 carbon atoms, such as, isopropyl, isobutyl, sec-butyl, t-butyl, 1-methyl-butyl, 2-methyl-butyl, 3-methyl-butyl, 1-methyl-pentyl, 2-methyl-pentyl, 3-methyl-pentyl, 4-methyl-pentyl, 1-methyl-hexyl, 2-methyl-hexyl, 3-methyl-hexyl, 4-methyl-hexyl, 5-methyl-hexyl, 1-ethyl-propyl, 1-ethyl-butyl, 1-ethyl-pentyl, 1-ethyl-hexyl, 2-ethyl-butyl, 2-ethyl-pentyl, 2-ethyl-hexyl, 3-ethyl-pentyl, 3-ethyl-hexyl, 4-ethyl-hexyl, 1-propyl-butyl, 1-propyl-pentyl, 1-propyl-hexyl, 2-propyl-pentyl, 2-propyl-hexyl, 3-propyl-hexyl, 1,2-dimethyl-propyl, 1,2-dimethyl-butyl, 1,2-dimethyl-pentyl, 1,2-dimethyl-hexyl, 1,3-dimethyl-butyl, 1,3-dimethyl-pentyl, 1,3-dimethyl-hexyl, 1,4-dimethyl-pentyl, 1,4-dimethyl-hexyl, 1,5-dimethyl-hexyl, 2,2-dimethyl-propyl, 2,2-dimethyl-butyl, 2,2-dimethyl-pentyl, 2,2-dimethyl-hexyl, 2,3-dimethyl-butyl, 2,3-dimethyl-pentyl, 2,3-dimethyl-hexyl, 2,4-dimethyl-pentyl, 2,4-dimethyl-hexyl, 2,5-dimethyl-hexyl, 3,3-dimethyl-butyl, 3,3-dimethyl-pentyl, 3,3-dimethyl-hexyl, 3,4-dimethyl-pentyl, 3,4-dimethyl-hexyl, 3,5-dimethyl-hexyl, 4,4-dimethyl-pentyl, 4,4-dimethyl-hexyl, 4,5-dimethyl-hexyl, 1-propyl-3-methyl-propyl, 1-propyl-3-methyl-butyl, 1-propyl-3-methyl-pentyl, 1-propyl-2-methyl-hexyl, 1,2,2-trimethyl-propyl, 1,2,2-trimethyl-butyl, 1,2,2-trimethyl-pentyl, 1,2,2-trimethyl-hexyl, 1,3,3-trimethyl-butyl, 1,3,3-trimethyl-pentyl, 1,3,3-trimethylhexyl, 1,4,4-trimethylpentyl, 1,4,4-trimethyl-hexyl, 1,5,5-trimethylhexyl, 1-ethyl-2-methyl-butyl, 1-ethyl-2-methyl-pentyl, 1-ethyl-2-methyl-hexyl, 1-ethyl-3-methyl-pentyl, 1-ethyl-3-methyl-hexyl, 2-ethyl-4-methyl-pentyl, 3-ethyl-4-methyl-hexyl, 1-isobutyl-3-methyl-butyl, more preferably isobutyl, 1,2-dimethyl-propyl, 1-methyl-butyl, 3-methyl-butyl, 2-ethyl-butyl, 1,3-dimethyl-butyl, 2,2-dimethyl-propyl, 2,2-dimethyl-butyl, 1-propyl-3-methyl-butyl, 1,3,3-trimethyl-butyl, 1-ethyl-3-methyl-hexyl, and 1-isobutyl-3-methyl-butyl. The branched alkyl may be substituted or unsubstituted. When the alkyl moiety is substituted, it is preferably mono-, di- or tri-substituted, more preferably mono-substituted. Suitable substituents for the alkyl moiety are as defined herein, preferably $C_1$-$C_4$-alkoxy, such as methoxy or ethoxy, halo, hydroxy, unsubstituted or substituted, preferably unsubstituted, aryl such as phenyl or naphthyl, unsubstituted or substituted, preferably unsubstituted, heterocyclyl, nitro, amino, amino-$C_1$-$C_7$-alkyl, halo-$C_1$-$C_7$-alkoxy, such as trifluoromethoxy, hydroxy-$C_1$-$C_7$-alkoxy, $C_1$-$C_7$-alkanoylamino, such as —NHCOMe, aminocarbonyl, N-mono- or N,N-di-($C_1$-$C_7$-alkyl)-amino, N-mono- or N,N-di-($C_1$-$C_7$-alkyl)-aminocarbonyl, such as CON(Me)$_2$, carboxyl, $C_1$-$C_7$-alkyloxycarbonyl, and cyano, whereby suitable phenyl or heterocylclyl substituents include $C_1$-$C_7$-alkyl, such as methyl, —O—$C_1$-$C_7$-alkyl, halo-$C_1$-$C_7$-alkyl, halo, hydroxyl and amino; more preferably $C_1$-$C_4$-alkoxy, such as methoxy or ethoxy, halo, hydroxy, unsubstituted or substituted, preferably unsubstituted, aryl such as phenyl or naphthyl, unsubstituted or substituted, preferably unsubstituted, heterocyclyl, nitro, amino, amino-$C_1$-$C_7$-alkyl, halo-$C_1$-$C_7$-alkoxy, such as trifluoromethoxy, hydroxy-$C_1$-$C_7$-alkoxy, $C_1$-$C_7$-alkanoylamino, such as —NHCOMe, aminocarbonyl, N-mono- or N,N-di-($C_1$-$C_7$-alkyl)-aminocarbonyl, such as CON(Me)$_2$, carboxyl, $C_1$-$C_7$-alkyloxycarbonyl, and cyano, whereby suitable phenyl or heterocylclyl substituents include $C_1$-$C_7$-alkyl, such as methyl, —O—$C_1$-$C_7$-alkyl, halo-$C_1$-$C_7$-alkyl, halo, hydroxyl and amino; still more preferably N-mono- or N,N-di-($C_1$-$C_7$-alkyl)-amino, aminocarbonyl, cyano, unsubstituted or substituted heterocyclyl, preferably unsubstituted; unsubstituted or substituted aryl, especially unsubstituted or substituted phenyl as described herein; halo, hydroxy, $C_1$-$C_4$-alkoxy, such as methoxy or ethoxy, halo-$C_1$-$C_7$-alkoxy, such as trifluoromethoxy, hydroxy-$C_1$-$C_7$-alkoxy, and N-mono- or N,N-di-($C_1$-$C_7$-alkyl)-aminocarbonyl; yet more preferable substituents include unsubstituted or substituted heterocyclyl, preferably unsubstituted; unsubstituted or substituted aryl, especially unsubstituted or substituted phenyl as described herein; halo, hydroxy, $C_1$-$C_4$-alkoxy, such as methoxy or ethoxy, halo-$C_1$-$C_7$-alkoxy, such as trifluoromethoxy, hydroxy-$C_1$-$C_7$-alkoxy, and N-mono- or N,N-di-($C_1$-$C_7$-alkyl)-aminocarbonyl; even more preferably N-mono- or N,N-di-($C_1$-$C_7$-alkyl)-amino, aminocarbonyl, cyano, unsubstituted or substituted heterocyclyl, preferably unsubstituted; unsubstituted or substituted aryl, especially unsubstituted or substituted phenyl as described herein; hydroxy, $C_1$-$C_4$-alkoxy, such as methoxy or ethoxy, or N-mono- or N,N-di-($C_1$-$C_7$-alkyl)-aminocarbonyl, such as CON(Me)$_2$; especially hydroxyl or N-mono- or N,N-di-($C_1$-$C_7$-alkyl)-aminocarbonyl, such as CON(Me)$_2$. When the substitutent is heterocylyl, preferred examples for the heterocylyl moiety are mono- or bicyclic rings. Preferred are 3 to 14, more preferably 5 to 11 membered ring systems. The heterocyclyl moiety may be saturated, partially saturated or aromatic, in particular if a monocyclic moiety is contemplated, aromatic or saturated, more preferably saturated, rings, or, in particular if a bicyclic moiety is contemplated, aromatic or partially saturated ring systems, in particular whereby one of the rings is aromatic and the other is saturated or partially saturated. The heterocyclyl moiety has preferably 1, 2 or 3, more preferably 1 or 2 heteroatoms selected from O, N or S, more preferably O or N. Particularly preferred examples include 5- or 6-membered rings preferably containing a nitrogen or an oxygen atom, especially pyrrolyl, furanyl, thienyl, thiazolyl, pyrazolyl, triazolyl, tetrazolyl, tetrahydropyranyl, pyridyl, or pyrimidinyl, in particular tetrahydropyranyl.

In a second preferred embodiment R4 is unsubstituted or substituted straight chain alkyl.

Straight chain alkyl is a moiety with preferably 1 to 7, more preferably 1 to 4 carbon atoms such as methyl, ethyl, n-propyl, n-butyl or n-pentyl, preferably methyl, ethyl, n-propyl or n-pentyl, most preferably methyl. Alkyl is preferably substituted. When the alkyl moiety is substituted, it is preferably mono-, di- or tri-substituted, more preferably mono- or di-substituted. Suitable substituents for the alkyl moiety are as defined herein, preferably $C_1$-$C_4$-alkoxy, such as methoxy, isopropoxy or ethoxy, especially, isopropoxy or ethoxy, halo, hydroxy, unsubstituted or substituted, preferably unsubstituted, aryl such as phenyl or naphthyl, unsubstituted or substituted, preferably unsubstituted, heterocyclyl, unsubstituted or substituted $C_3$-$C_8$-cycloalkyl, such as cycloheptyl, cyclohexyl or cyclopentyl, nitro, amino, amino-$C_1$-$C_7$-alkyl, halo-$C_1$-$C_7$-alkoxy, such as trifluoromethoxy, hydroxy-$C_1$-$C_7$-alkoxy, $C_1$-$C_7$-alkanoylamino, such as —NHCOMe, aminocarbonyl, N-mono- or N,N-di-($C_1$-$C_7$-alkyl)-amino, such as N(Me)$_2$ or N(Et)$_2$, N-mono- or N,N-di-($C_1$-$C_7$-alkyl)-aminocarbonyl, such as CON(Me)$_2$, carboxyl, $C_1$-$C_7$-alkyloxycarbonyl, and cyano, whereby suitable cycloalkyl, phenyl or heterocylclyl substituents include $C_1$-$C_7$-alkyl, such as methyl, $C_1$-$C_7$-alkoxy, halo-$C_1$-$C_7$-alkyl, hydroxy-$C_1$-$C_7$-alkyl, halo, hydroxyl and amino. More preferable, substituents of alkyl include $C_1$-$C_4$-alkoxy, such as isopropoxy or ethoxy, unsubstituted or substituted heterocyclyl, which is unsubstituted or substituted as described herein, preferably unsubstituted; unsubstituted or substituted aryl, especially unsubstituted or substituted phenyl as described herein; unsubstituted or substituted $C_3$-$C_8$-cycloalkyl, such as cycloheptyl, cyclohexyl or cyclopentyl, which is unsubstituted or substituted as described herein; halo, hydroxy, $C_1$-$C_7$-alkoxy, halo-$C_1$-$C_7$-alkoxy, such as trifluoromethoxy, hydroxy-$C_1$-$C_7$-alkoxy, N-mono- or N,N-di-($C_1$-$C_7$-alkyl)-amino, and N-mono- or N,N-di-($C_1$-$C_7$-alkyl)-aminocarbonyl. Still more preferably, substituents of alkyl include substituted or unsubstituted, preferably unsubstituted, heterocyclyl, especially pyrazyl, isoxazolyl, morpholinyl, thiomorpholinyl, piperidinyl, piperazinyl, pyrrolidinyl, tetrahydrofuranyl, tetrahydropyranyl, tetrahydrothiophenyl, pyridyl, or pyrrolidin-2-onyl, unsubstituted or substituted aryl, especially unsubstituted or substituted phenyl as described herein; unsubstituted or substituted $C_3$-$C_8$-cycloalkyl, such as cycloheptyl, cyclohexyl or cyclopentyl, which is unsubstituted or substituted as described herein; hydroxy, $C_1$-$C_7$-alkoxy, and N-mono- or N,N-di-($C_1$-$C_7$-alkyl)-amino. When the substitutent is heterocylyl, preferred examples for the heterocylyl moiety are mono- or bicyclic rings; most preferably substituted or unsubstituted, preferably unsubstituted, heterocyclyl, especially morpholinyl, thiomorpholinyl, piperidinyl, piperazinyl, pyrrolidinyl, tetrahydrofuranyl, tetrahydropyranyl, tetrahydrothiophenyl, pyridyl, or pyrrolidin-2-onyl, unsubstituted or substituted phenyl, unsubstituted or substituted $C_3$-$C_8$-cycloalkyl, such as cycloheptyl, cyclohexyl or cyclopentyl, which is unsubstituted or substituted as described herein; hydroxy, $C_1$-$C_7$-alkoxy, such as methoxy, and N-mono- or N,N-di-($C_1$-$C_7$-alkyl)-amino. When the substitutent is heterocylyl, preferred examples for the heterocylyl moiety are mono- or bicyclic rings. Preferred are 3 to 14, more preferably 5 to 11 membered ring systems. The heterocyclyl moiety may be saturated, partially saturated or aromatic, in particular if a monocyclic moiety is contemplated, aromatic or saturated, more preferably saturated, rings, or, in particular if a bicyclic moiety is contemplated, aromatic or partially saturated ring systems, in particular whereby one of the rings is aromatic and the other is saturated or partially saturated. The heterocyclyl moiety has preferably 1, 2 or 3, more preferably 1 or 2 heteroatoms selected from O, N or S, more preferably O or N. Particularly preferred examples include 5- or 6-membered rings preferably containing a nitrogen or an oxygen atom, more preferably pyrazyl, isoxazolyl, morpholinyl, thiomorpholinyl, piperidinyl, piperazinyl, pyrrolidinyl, tetrahydrofuranyl, tetrahydropyranyl, tetrahydrothiophenyl, pyridyl, or pyrrolidin-2-onyl; most preferably morpholinyl, thiomorpholinyl, piperidinyl, piperazinyl, pyrrolidinyl, tetrahydrofuranyl, tetrahydropyranyl, tetrahydrothiophenyl, pyridyl, or pyrrolidin-2-onyl. If the heterocyclyl moiety is substituted, it is preferably mono-substituted with substituents as defined herein, preferably $C_1$-$C_7$-alkyl such as methyl.

In a third preferred embodiment R4 is unsubstituted or substituted $C_3$-$C_8$-cycloalkyl.

Preferred examples for the cycloalkyl moiety are monocyclic rings, preferably $C_3$-$C_8$-cycloalkyl, more preferably $C_3$, $C_4$, $C_5$, $C_6$, and $C_7$-cycloalkyl, still more preferably $C_3$, $C_5$ and $C_6$-cycloalkyl. The cycloalkyl moiety may be substituted or unsubstituted, preferably substituted. When the cycloalkyl moiety is substituted, it is preferably mono-substituted.

Suitable substituents for the cycloalkyl moiety are as defined herein, preferably $C_1$-$C_7$-alkyl such as methyl and isobutyl, aminocarbonyl, $C_1$-$C_8$-alkoxy-$C_1$-$C_8$-alkyl such as methoxymethyl, ethoxymethyl and isopropoxymethyl, $C_1$-$C_4$-alkoxy, such as OMe, OEt, preferably OMe, halo, hydroxyl, hydroxyl-$C_1$-$C_4$-alkyl, such as $CH_2$—OH, unsubstituted or substituted, preferably unsubstituted, aryl, such as phenyl, substituted or unsubstituted, preferably unsubstituted, heterocyclyl, nitro, amino, amino-$C_1$-$C_7$-alkyl, $C_1$-$C_7$-alkanoylamino, carboxyl, and cyano. More preferably, substituents include $C_1$-$C_4$-alkoxy, such as OMe, OEt, preferably OMe, halo, hydroxyl-$C_1$-$C_4$-alkyl, such as $CH_2$—OH, unsubstituted or substituted, preferably unsubstituted, aryl, such as phenyl, substituted or unsubstituted, preferably unsubstituted, heterocyclyl, nitro, amino, amino-$C_1$-$C_7$-alkyl, $C_1$-$C_7$-alkanoylamino, carboxyl, and cyano. Still more preferably, substituents include $C_1$-$C_8$-alkyl such as methyl and isobutyl, aminocarbonyl, $C_1$-$C_8$-alkoxy-$C_1$-$C_8$-alkyl such as methoxymethyl, ethoxymethyl and isopropoxymethyl, $C_1$-$C_4$-alkoxy, such as OMe, OEt, preferably OMe, hydroxyl, hydroxyl-$C_1$-$C_4$-alkyl, phenyl or heterocyclyl such as pyridyl or tetrahydropyranyl. Most preferably, substituents include hydroxyl, hydroxyl-$C_1$-$C_4$-alkyl, phenyl or heterocyclyl such as pyridyl or tetrahydropyranyl.

When the substituent is heterocylyl, preferred examples for the heterocyclyl moiety are mono- or bicyclic rings. Preferred are 3 to 14, more preferably 5 to 11 membered ring systems. The heterocyclyl moiety may be saturated, partially saturated or aromatic, in particular if a monocyclic moiety is contemplated, aromatic or saturated, more preferably saturated, rings, or, in particular if a bicyclic moiety is contemplated, aromatic or partially saturated ring systems, in particular whereby one of the rings is aromatic and the other is saturated or partially saturated. The heterocyclyl moiety has preferably 1, 2 or 3, more preferably 1 or 2 heteroatoms selected from O, N or S, more preferably O or N. Particularly preferred examples include 5- or 6-membered rings preferably containing a nitrogen or an oxygen atom, especially morpholino, thiomorpholino, piperidinyl, piperazinyl, pyrrolidinyl, tetrahydrofuranyl, tetrahydropyranyl, tetrahydrothiophenyl, pyridyl, or pyrrolidin-2-onyl. The aryl or heterocyclyl moiety may be substituted or unsubstituted. When the aryl or heterocyclyl moiety is substituted, it is preferably mono-substituted. In one embodiment, suitable substituents for the aryl and heterocyclyl moiety are halo, such as fluoro.

In a forth preferred embodiment R4 is unsubstituted or substituted aryl.

Preferred examples of the aryl moiety include mono- or bicyclic aryl with 6 to 22 carbon atoms, especially phenyl, indanyl, indenyl, or naphthyl, more preferably phenyl. In one embodiment, the aryl moiety is indanyl. When the aryl moiety is substituted, it is preferably mono-, di- or tri-substituted, in particular di-substituted. Suitable substituents are as defined herein, preferably $C_1$-$C_7$-alkyl, such as Me, $C_1$-$C_7$-alkoxy, such as OMe and OEt, halo-$C_1$-$C_7$-alkyl, halo, such as F, $C_1$-$C_7$-alkoxy-$C_1$-$C_7$-alkoxy, such as O—$C_3H_6OCH_3$, hydroxy, nitro, amino, amino-$C_1$-$C_7$-alkyl, carboxyl, and cyano; more preferably $C_1$-$C_7$-alkyl, such as Me, $C_1$-$C_7$-alkoxy, such as OMe and OEt, halo-$C_1$-$C_7$-alkyl, or halo, such as F; still more preferably $C_1$-$C_7$-alkyl, such as Me, $C_1$-$C_7$-alkoxy, such as OMe, halo-$C_1$-$C_7$-alkyl, halo, such as F, $C_1$-$C_7$-alkoxy-$C_1$-$C_7$-alkoxy, such as O—$C_3H_6OCH_3$, hydroxy, nitro, amino, amino-$C_1$-$C_7$-alkyl, carboxyl, and cyano; most preferably $C_1$-$C_7$-alkyl, such as Me, $C_1$-$C_7$-alkoxy, such as OMe, halo-$C_1$-$C_7$-alkyl, or halo, such as F.

In a fifth preferred embodiment R4 is unsubstituted or substituted heterocyclyl.

Preferred examples for the heterocyclyl moiety are mono- or bicyclic rings. Preferred are 3 to 14, more preferably 5 to 11 membered ring systems. The heterocyclyl moiety may be saturated, partially saturated or aromatic, in particular if a monocyclic moiety is contemplated, aromatic or saturated, more preferably saturated, rings, or, in particular if a bicyclic moiety is contemplated, aromatic or partially saturated ring systems, in particular whereby one of the rings is aromatic and the other is saturated or partially saturated. The heterocyclyl moiety has preferably 1, 2 or 3, more preferably 1 or 2 heteroatoms selected from O, N or S, more preferably O or N. The heterocyclyl moiety may have an oxo moiety. Preferred examples include 5- 6- or 7-membered rings preferably containing a nitrogen or an oxygen atom, especially azepan-2-onyl, tetrahydropyranyl, 1H-pyridin-2-onyl, pyridyl, piperidinyl, piperazinyl or pyrrolidinyl. Particularly preferred examples include 5- or 6-membered rings preferably containing a nitrogen or an oxygen atom, especially 1H-pyridin-2-onyl, piperidinyl, piperazinyl or pyrrolidinyl. The heterocyclyl moiety may be substituted or unsubstituted. When the heterocyclyl moiety is substituted, it is preferably mono-substituted or di-substituted. Suitable substituents for the heterocyclyl moiety are as defined herein, preferably $C_1$-$C_7$-alkyl, such as methyl, n-propyl, isopropyl or isobutyl, halo, hydroxy, $C_1$-$C_7$-alkanoyl, such as COMe, carboxyl, $C_1$-$C_7$-alkylsulfonyl, such as $SO_2Me$, aryl, substituted or unsubstituted, preferably unsubstituted, such as phenyl, and cyano. More preferably, substituents include $C_1$-$C_7$-alkyl, such as methyl, n-propyl, isopropyl or isobutyl, halo, hydroxy, $C_1$-$C_7$-alkanoyl, such as COMe, carboxyl and cyano. Yet more preferably, substituents include $C_1$-$C_7$-alkyl, hydroxyl, $C_1$-$C_7$-alkanoyl, $C_1$-$C_7$-alkylsulfonyl, such as $SO_2Me$, aryl, substituted or unsubstituted, preferably unsubstituted, such as phenyl, and cyano. Most preferably substituents include $C_1$-$C_7$-alkyl, hydroxyl or $C_1$-$C_7$-alkanoyl.

In a sixth preferred embodiment R4 is acyl.

Preferred examples of acyl are as defined herein, such a (unsubstituted or substituted alkyl, unsubstituted or substituted aryl-$C_1$-$C_7$-alkyl, unsubstituted or substituted heterocyclyl-$C_1$-$C_7$-alkyl or unsubstituted or substituted cycloalkyl-$C_1$-$C_7$-alkyl)-carbonyl or sulfonyl, preferably sulfonyl, more preferably unsubstituted or substituted aryl-$C_1$-$C_7$-alkyl-carbonyl or sulfonyl, more preferably, -sulfonyl, especially phenylmethanesulfonyl.

Thus, R4 is preferably selected from the group consisting of:
branched $C_4$-$C_{10}$-alkyl which may be unsubstituted or substituted with one or more, such as one or two of the group consisting of:
unsubstituted or substituted, preferably unsubstituted, heterocyclyl, especially pyrrolyl, furanyl, thienyl, thiazolyl, pyrazolyl, triazolyl, tetrazolyl, tetrahydropyranyl, pyridyl, or pyrimidinyl, each of which is unsubstituted or substituted as described herein, unsubstituted or substituted, preferably unsubstituted, aryl, especially unsubstituted or substituted phenyl as described herein; halo, hydroxy, $C_1$-$C_7$-alkoxy, halo-$C_1$-$C_7$-alkoxy, especially trifluoromethoxy, hydroxy-$C_1$-$C_7$-alkoxy, and N-mono- or N,N-di-($C_1$-$C_7$-alkyl)-aminocarbonyl; N-mono- or N,N-di-($C_1$-$C_7$-alkyl)-amino, aminocarbonyl, or cyano; especially N-mono- or N,N-di-($C_1$-$C_7$-alkyl)-amino, aminocarbonyl, cyano, unsubstituted or substituted, preferably unsubstituted, heterocyclyl; unsubstituted or substituted, preferably unsubstituted, aryl, especially unsubstituted or substituted phenyl as described herein; hydroxy, $C_1$-$C_4$-alkoxy, such as methoxy or ethoxy, or N-mono- or N,N-di-($C_1$-$C_7$-alkyl)-aminocarbonyl, such as $CON(Me)_2$;
straight chain $C_1$-$C_7$-alkyl which may be bound to the terminal or non-terminal carbon and which may be unsubstituted or substituted with one or more, such as one or two of the group consisting of:
unsubstituted or substituted, preferably unsubstituted, heterocyclyl, especially pyrazyl, isoxazolyl, morpholinyl, thiomorpholinyl, piperidinyl, piperazinyl, pyrrolidinyl, tetrahydrofuranyl, tetrahydropyranyl, tetrahydrothiophenyl, pyridyl, or pyrrolidin-2-onyl, each of which is unsubstituted or substituted as described herein; unsubstituted or substituted, preferably unsubstituted, aryl, especially unsubstituted or substituted phenyl as described herein; unsubstituted or substituted, preferably unsubstituted, $C_3$-$C_8$-cycloalkyl, such as cycloheptyl, cyclohexyl or cyclopentyl, which is unsubstituted or substituted as described herein; halo, hydroxy, $C_1$-$C_7$-alkoxy, halo-$C_1$-$C_7$-alkoxy, such as trifluoromethoxy, hydroxy-$C_1$-$C_7$-alkoxy, N-mono- or N,N-di-($C_1$-$C_7$-alkyl)-amino, and N-mono- or N,N-di-($C_1$-$C_7$-alkyl)-aminocarbonyl; especially unsubstituted or substituted, preferably unsubstituted, heterocyclyl, especially pyrazyl, isoxazolyl, morpholinyl, piperidinyl, tetrahydrofuranyl, tetrahydropyranyl, pyridyl, or pyrrolidin-2-onyl, each of which is unsubstituted or substituted as described herein; unsubstituted or substituted, preferably unsubstituted, aryl, especially unsubstituted or substituted phenyl as described herein; unsubstituted or substituted, preferably unsubstituted, $C_3$-$C_8$-cycloalkyl, such as cycloheptyl or cyclohexyl, which is unsubstituted or substituted as described herein; hydroxy, $C_1$-$C_7$-alkoxy, N-mono- or N,N-di-($C_1$-$C_7$-alkyl)-amino and, N-mono- or N,N-di-($C_1$-$C_7$-alkyl)-aminocarbonyl;
unsubstituted or substituted $C_3$-$C_8$-cycloalkyl, such as cyclopropyl, cyclobutyl, cyclopentyl, cyclohexyl or cyclopropyl, which is unsubstituted or substituted as described herein,
unsubstituted or substituted aryl, such as phenyl and indanyl, which is unsubstituted or substituted as described herein,
unsubstituted or substituted heterocyclyl, such as azepan-2-onyl, tetrahydropyranyl, 1H-pyridin-2-onyl, pyridyl, piperidinyl, piperazinyl or pyrrolidinyl, which is unsubstituted or substituted as described herein, or acyl, such as (unsubstituted or substituted alkyl, unsubstituted or substituted aryl-$C_1$-$C_7$-alkyl, unsubstituted or substituted heterocyclyl-$C_1$-$C_7$-alkyl or unsubstituted or substituted cycloalkyl-$C_1$-$C_7$-alkyl)-sulfonyl, especially phenylmethanesulfonyl.

Thus, R4 can be selected from the group consisting of:
branched $C_4$-$C_{10}$-alkyl which may be unsubstituted or substituted with one or more, such as one or two of the group consisting of:
unsubstituted or substituted heterocyclyl, especially pyrrolyl, furanyl, thienyl, thiazolyl, pyrazolyl, triazolyl, tetrazolyl, pyridyl, or pyrimidinyl, each of which is unsubstituted or substituted as described herein, preferably unsubstituted; unsubstituted or substituted aryl, especially unsubstituted or substituted phenyl as described herein; halo, hydroxy, $C_1$-$C_7$-alkoxy, halo-$C_1$-$C_7$-alkoxy, such as trifluoromethoxy, hydroxy-$C_1$-$C_7$-alkoxy, and N-mono- or N,N-di-($C_1$-$C_7$-alkyl)-aminocarbonyl;
straight chain $C_1$-$C_7$-alkyl which may be bound to the terminal or non-terminal carbon and which may be unsubstituted or substituted with one or more, such as one or two of the group consisting of:
unsubstituted or substituted heterocyclyl, especially morpholino, thiomorpholino, piperidinyl, piperazinyl, pyrrolidinyl, tetrahydrofuranyl, tetrahydropyranyl, tetrahydrothiophenyl, pyridyl, or pyrrolidin-2-onyl, each of which is unsubstituted or substituted as described herein, preferably unsubstituted; unsubstituted or substituted aryl, especially unsubstituted or substituted phenyl as described herein; unsubstituted or substituted $C_3$-$C_8$-cycloalkyl, such as cycloheptyl, cyclohexyl or cyclopentyl, which is unsubstituted or substituted as described herein; halo, hydroxy, $C_1$-$C_7$-alkoxy, halo-$C_1$-$C_7$-alkoxy, such as trifluoromethoxy, hydroxy-$C_1$-$C_7$-alkoxy, N-mono- or N,N-di-($C_1$-$C_7$-alkyl)-amino, and N-mono- or N,N-di-($C_1$-$C_7$-alkyl)-aminocarbonyl;
unsubstituted or substituted $C_3$-$C_8$-cycloalkyl, such as cyclohexyl or cyclopropyl, which is unsubstituted or substituted as described herein,
unsubstituted or substituted aryl, such as phenyl, which is unsubstituted or substituted as described herein,
unsubstituted or substituted heterocyclyl, such as pyridyl, pyrrolininyl or piperidinyl, which is unsubstituted or substituted as described herein, or
acyl, such as (unsubstituted or substituted alkyl, unsubstituted or substituted aryl-$C_1$-$C_7$-alkyl, unsubstituted or substituted heterocyclyl-$C_1$-$C_7$-alkyl or unsubstituted or substituted cycloalkyl-$C_1$-$C_7$-alkyl)-sulfonyl, especially phenylmethanesulfonyl;
Particularly preferred definitions of R4 include

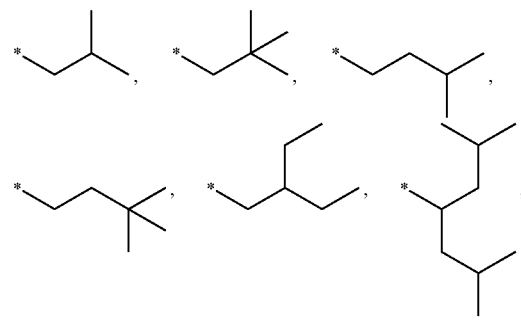

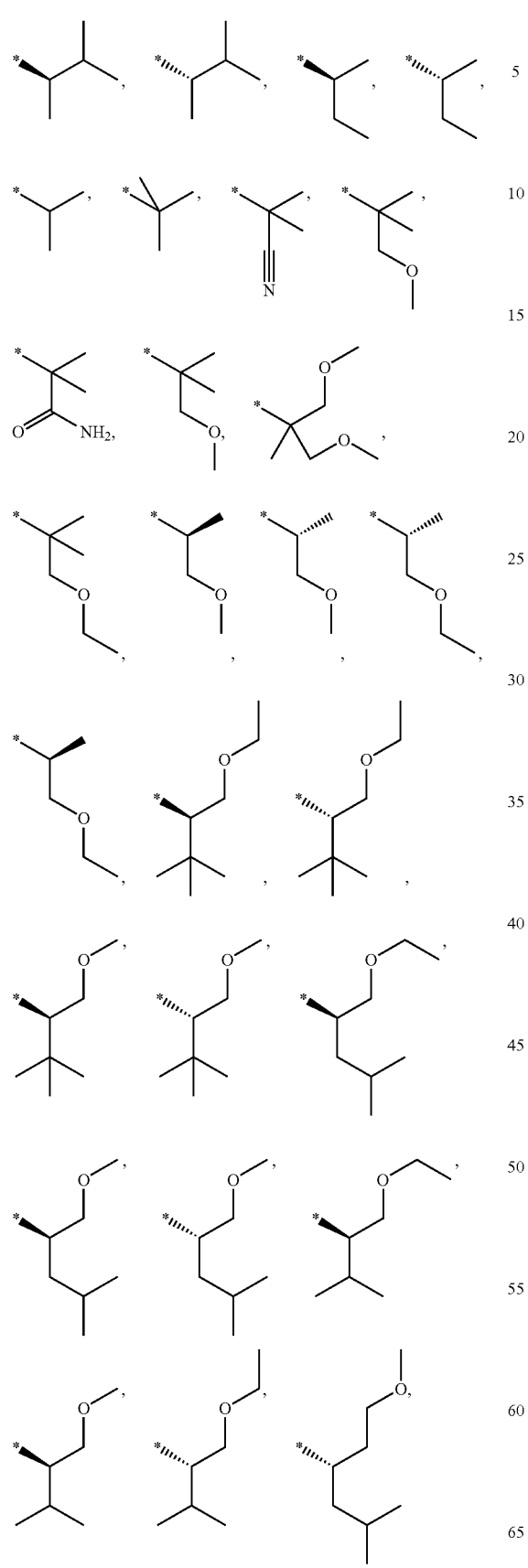
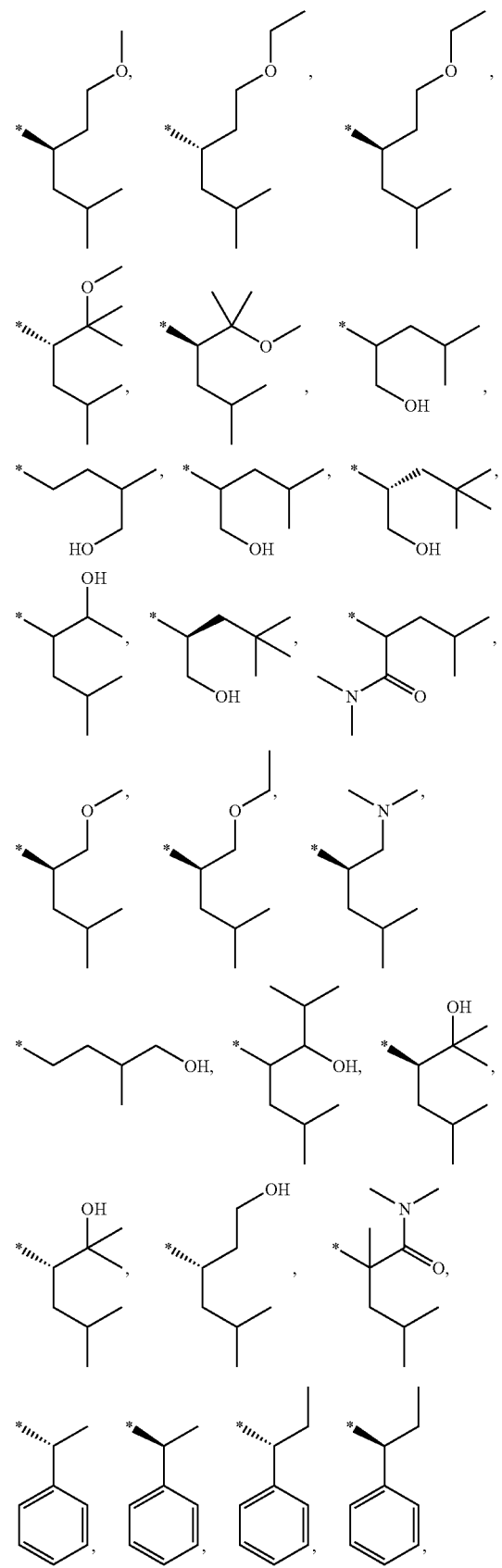

51
-continued
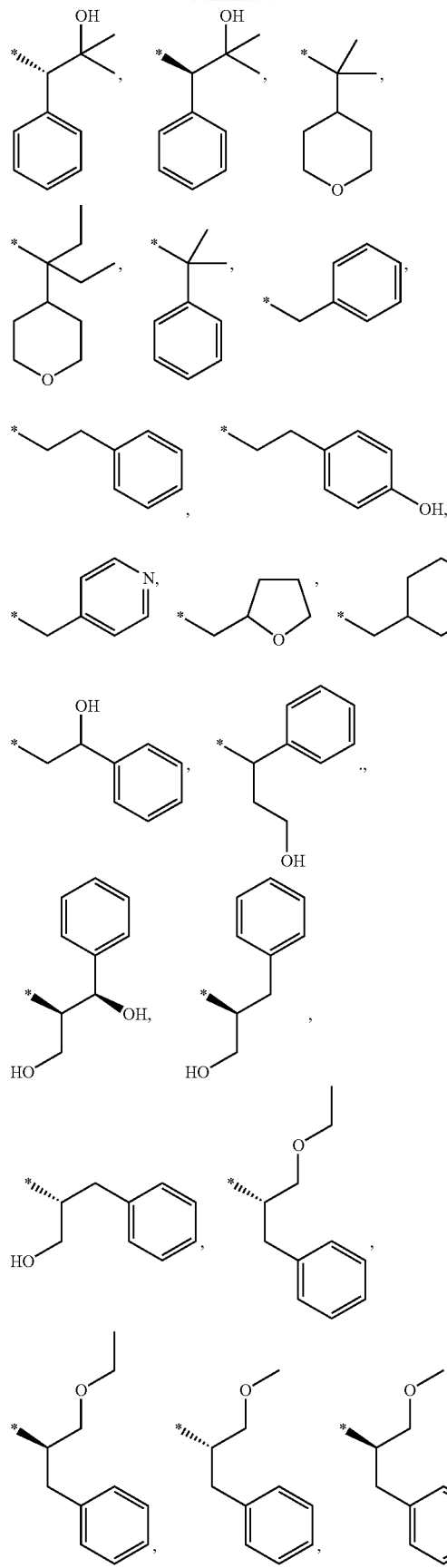
52
-continued
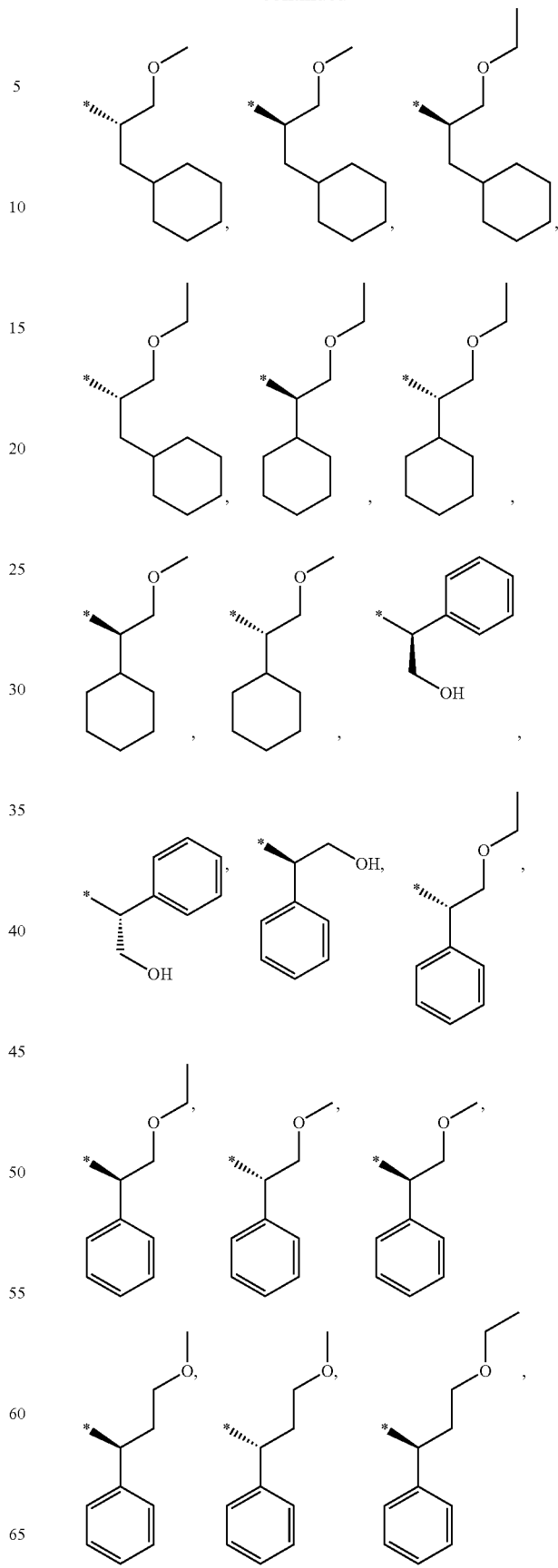

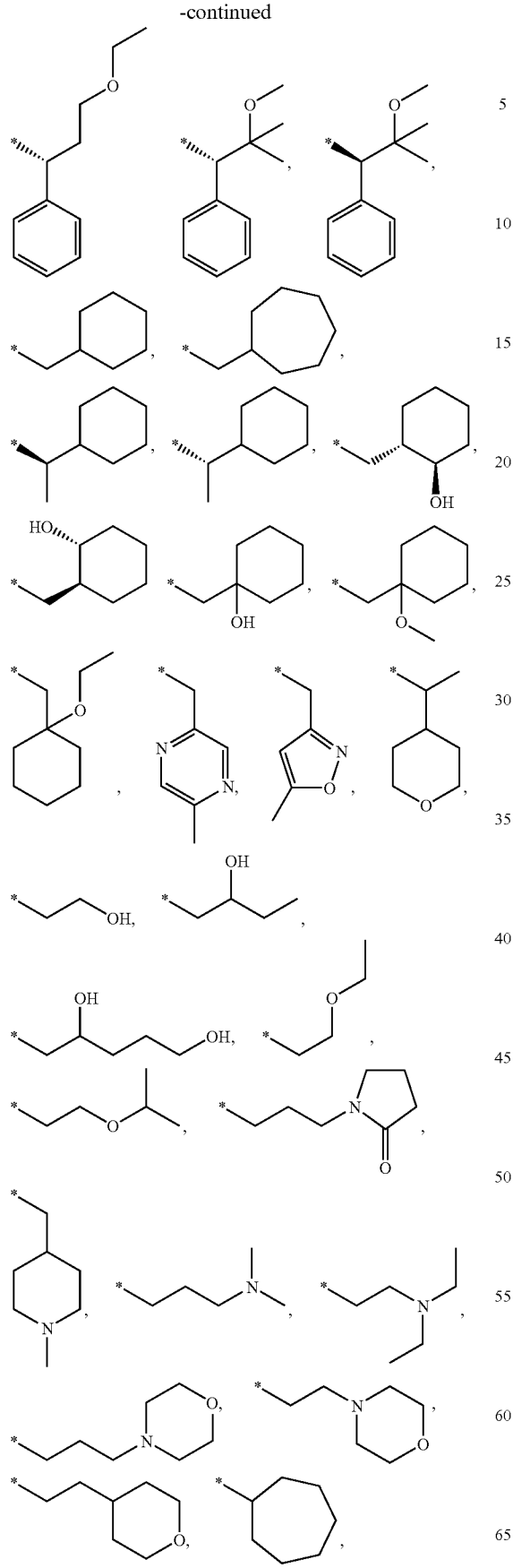
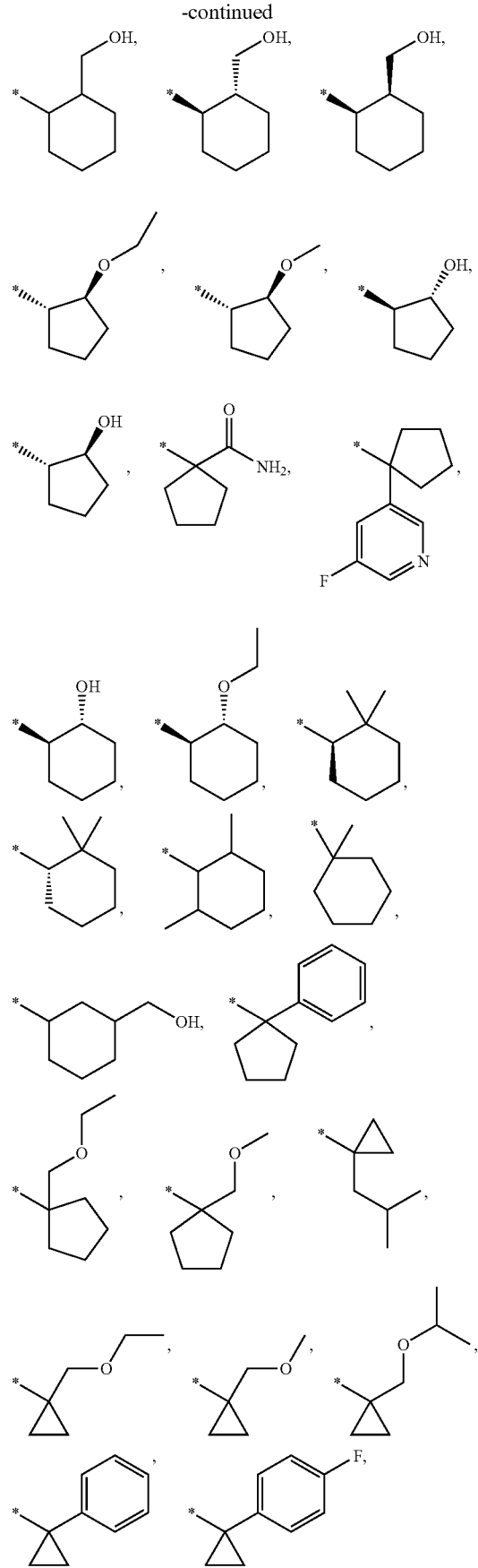

-continued
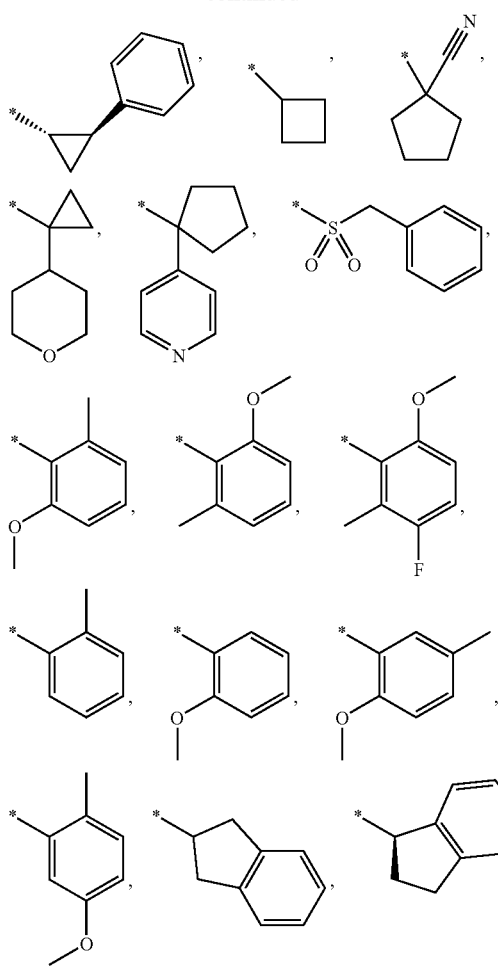
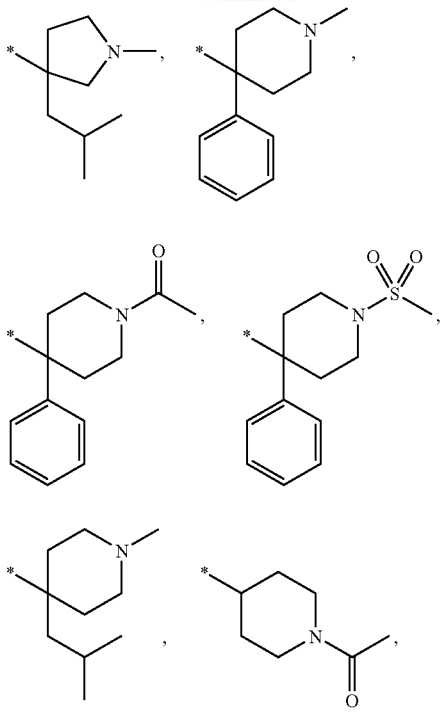
Particularly, more preferred definitions of R4 include
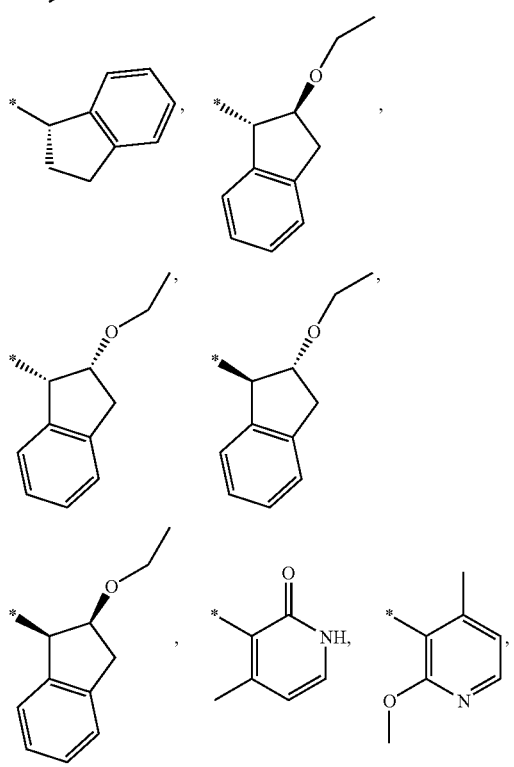
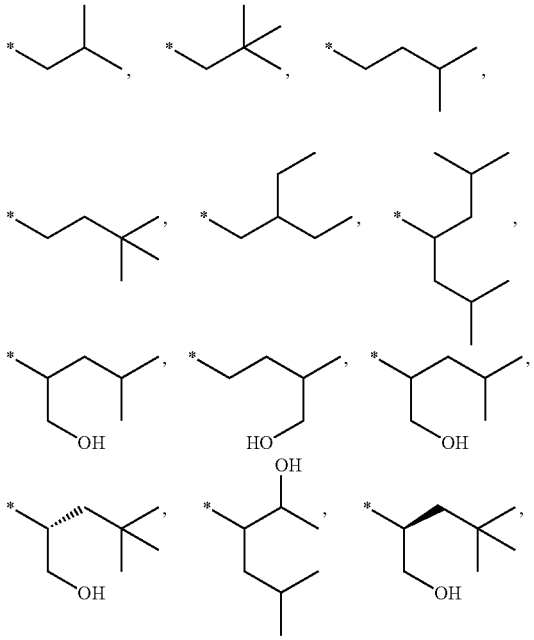

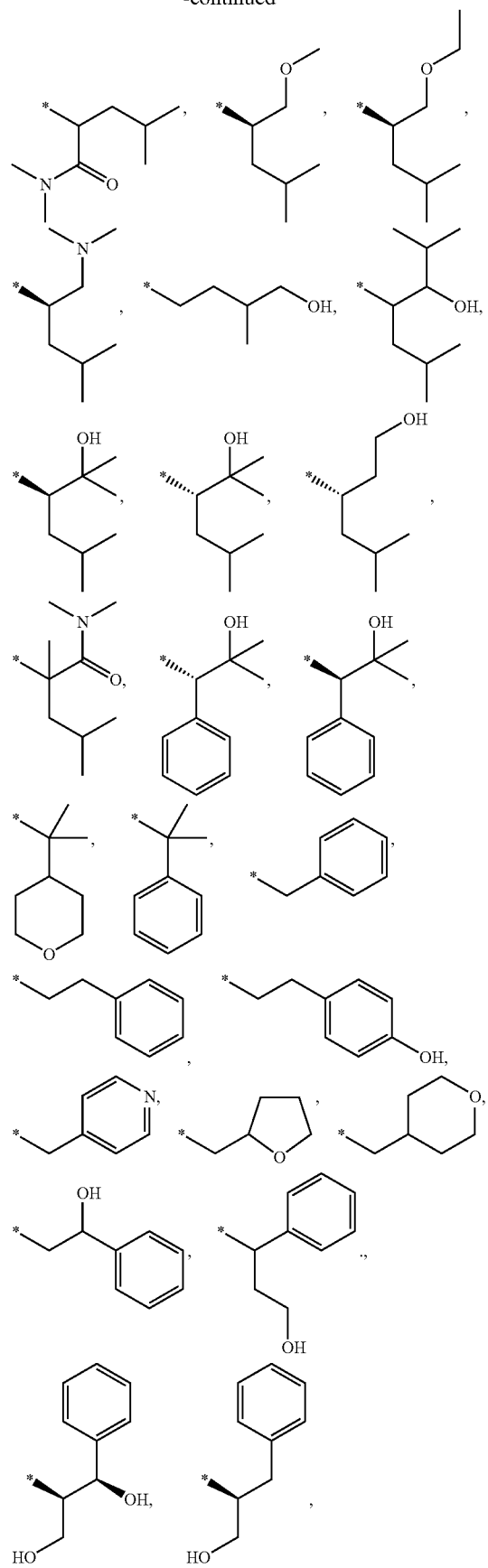
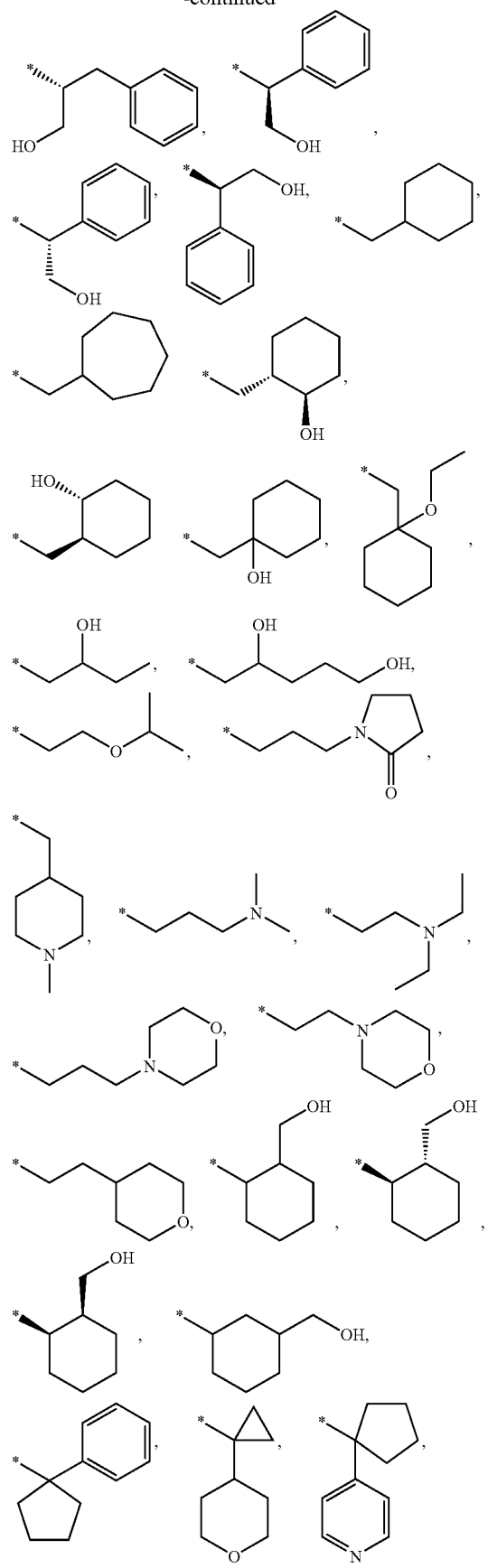

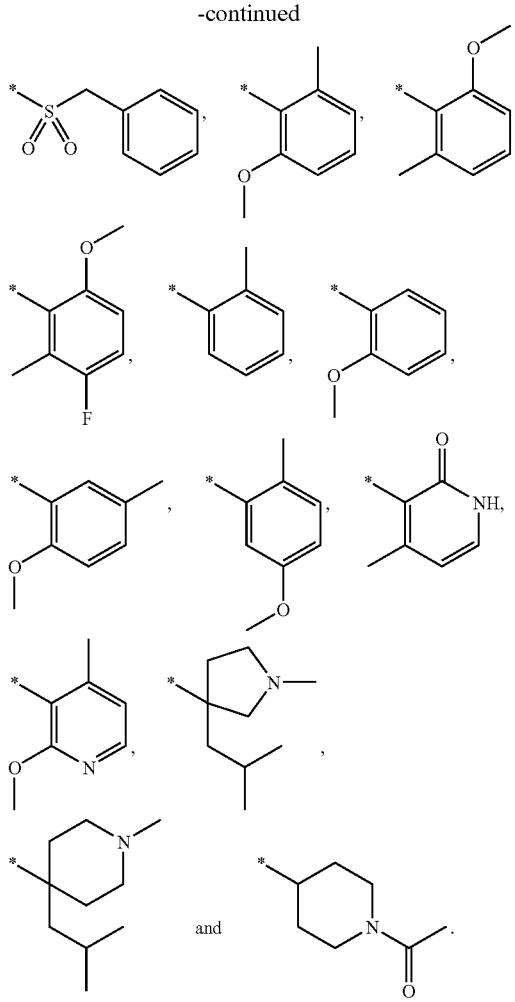

Alternatively, R3 and R4 may form a nitrogen containing ring as described herein, preferably, R3 and R4 form together a pyrrolidine or piperidine ring that is unsubstituted or substituted, preferably by up to four moieties selected from $C_1$-$C_7$-alkyl, hydroxyl, halo, hydroxy-$C_1$-$C_7$-alkyl, halo-$C_1$-$C_7$-alkyl and cyano. Thus, particularly preferred examples of the rings formed by R3 and R4 are

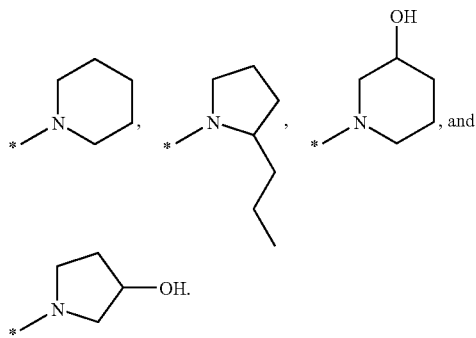

Preferred Definitions for R6

As R6, these or preferably any other mentioned moieties mentioned herein as falling under the definition of R6 are preferred.

Preferably, R6 is hydrogen, OH, F, $C_1$-$C_4$-alkyl or $C_1$-$C_4$-alkoxy, most preferably hydrogen. In one embodiment. R6 is OH, F, $C_1$-$C_4$-alkyl or $C_1$-$C_4$-alkoxy, preferably OH.

Preferred Definitions for R7 and R8

As R5 and R6, these or preferably any other mentioned moieties mentioned herein as falling under the definition of R5 and R6 are preferred.

Preferably both R7 and R8 are hydrogen.

In one embodiment, R7 and R8 are independently of each other halo, such as F. it is preferred in this embodiment, that one of R7 and R8 is hydrogen and the other is F.

Particular embodiments of the invention, especially of compounds of the formula I' or I and/or salts thereof, are provided in the Examples—the invention thus, in a very preferred embodiment, relates to a compound of the formula I' or I, or a salt thereof, selected from the compounds given in the Examples, as well as the use thereof according to the invention.

Process of Manufacture

A compound of formula I, or a salt thereof, is prepared analogously to methods that, for other compounds, are in principle known in the art, so that for the novel compounds of the formula I the process is novel at least as analogy process, especially as described or in analogy to methods described herein in the illustrative Examples, or modifications thereof, preferably in general by a) reacting a compound of the formula II,

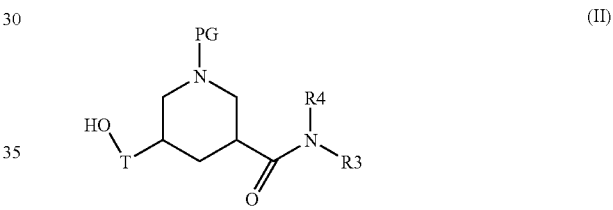 (II)

wherein T is methylene or preferably carbonyl, PG is a protecting group and R3 and R4 are as defined for a compound of the formula I as described above, or (preferably) an activated derivative thereof, with a compound of the formula III,

R1-NH-R2 (III)

wherein R1 and R2 are as defined for a compound of the formula I in any one of claims 1 to 13; or b) reacting a compound of the formula IV,

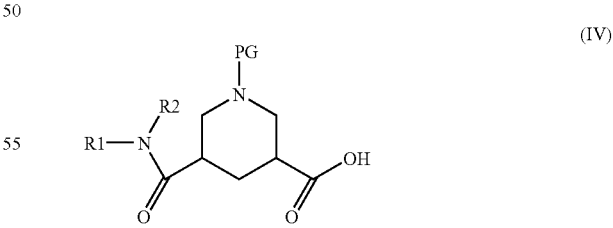 (IV)

wherein PG is a protecting group and R1 and R2 are as defined for a compound of the formula I as described above, or (preferably) an activated derivative thereof, with a compound of the formula V,

R3-NH-R4 (V)

wherein R1 and R2 are as defined for a compound of the formula IV;

and, if desired, subsequent to any one or more of the processes mentioned above converting an obtainable compound of the formula I or a protected form thereof into a different compound of the formula I, converting a salt of an obtainable compound of formula I into the free compound or a different salt, converting an obtainable free compound of formula I into a salt thereof, and/or separating an obtainable mixture of isomers of a compound of formula I into individual isomers;

where in any of the starting materials, in addition to specific protecting groups mentioned, further protecting groups may be present, and any protecting groups or bound resins are removed at an appropriate stage in order to obtain a corresponding compound of the formula I, or a salt thereof.

For the preparation of a chiral scaffold the following methods as set forth below can be followed.

A compound of the formula VI

(VI)

wherein PG is a protecting group, is reacted with an alcohol R5OH, wherein R5 is unsubstituted or substituted alkyl or alkenyl, preferably $C_1$-$C_4$ alkyl, in the presence of a chiral amine catalyst to obtain either a compound of formula VIIa or VIIb:

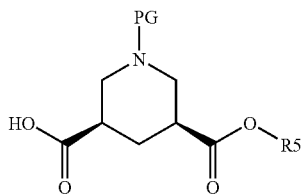

(VIIa)

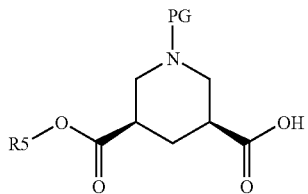

(VIIb)

wherein PG and R5 are as defined in compound of formula VI. A compound of formula VI can be prepared according to methods well known in the art or as described herein.

It was surprisingly found that with this reaction using a chiral amine catalyst a monoester can be prepared in a high stereoselectivity. This is a major improvement to the processes for preparing such a monoester known to date. Reference is made in particular to Park, J.-S.; Yeom, C.-E.; Choi, S. H.; Ahn, Y. S.; Ro, S.; Jeom, Y. H.; Shin, D.-K.; Kim, B. M. Tetrahedron Lett. 2003, 44, 1611-1614, which is herewith incorporated by reference, where the anhydride is enzymatically hydrolysed. Although the desired chiral compound can be obtained, the reaction proceeds rather slowly and with poor selectivity, namely an ee in the range of 20-30%. Such a result is very inferior to the present conversion where a high stereoselectivity is achieved. It is readily apparent that it is vital to obtain a good stereoselectivity since this conversion is at a fairly early stage of the whole manufacture process for preparing compounds of the formula I, since it avoids the production of unwanted side products and drastically reduces the amount of starting material rendering the overall preparation of compounds of the formula I more efficient and economic.

Preferred embodiments of this process of the present invention are described below.

The regioselectivity is dependent on the nature of the chiral amine catalyst. Preferred examples of the chiral amine catalyst are chiral tertiary amines, more preferably cinchona alkaloids, such as quinidine and quinine, most preferably modified cinchona alkaloids.

Examples of such modified cinchona alkaloids are given below. For a more detailed description, reference is made to Tian, S.-K.; Chen, Y.; Hang, J.; Tang, L.; McDiad, P.; Deng, L. Acc. Chem. Res. 2004, 37, 621-631 and references cited therein, which are herewith incorporated by reference.

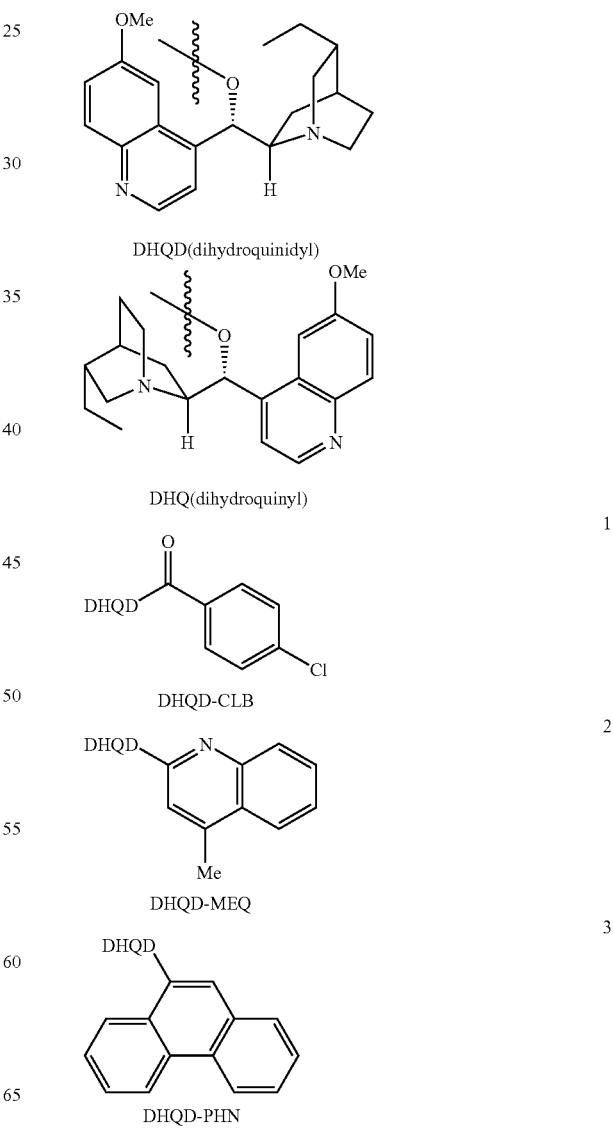

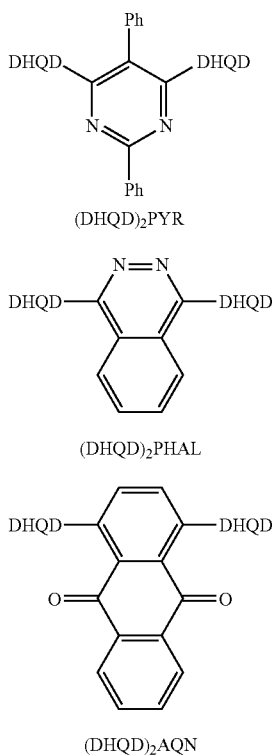

Abbreviations:

| | |
|---|---|
| DHQD-CLB | Hydroquinidine 4-chlorobenzoate |
| DHQ-CLB | Hydroquinine 4-chlorobenzoate |
| DHQD-MEQ | Hydroquinidine 4-methyl-2-quinolyl ether |
| DHQ-MEQ | Hydroquinine 4-methyl-2-quinolyl ether |
| DHQD-PHN | Hydroquinidine 9-O-(9'-phenanthryl)ether |
| DHQ-PHN | Hydroquinine 9-O-(9'-phenanthryl)ether |
| (DHQD)2PYR | Hydroquinidine 2,5-diphenyl-4,6-pyrimidinediyl diether |
| (DHQ)2PYR | Hydroquinine 2,5-diphenyl-4,6-pyrimidinediyl diether |
| (DHQD)2PHAL | Hydroquinidine 1,4-phthalazinediyl diether |
| (DHQ)2PHAL | Hydroquinine 1,4-phthalazinediyl diether |
| (DHQD)2AQN | Hydroquinidine anthraquinone-1,4-diyl diether |
| (DHQ)2AQN | Hydroquinine anthraquinone-1,4-diyl diether |

In the Examples shown above, the modification is only shown with respect to DHQD, however, it is readily apparent that the corresponding derivatives of DHQ such as (DHQ)$_2$AQN can be employed. The nature of the amine governs the position of the ester formation and thus the stereoselectivity. For example when using quinidine, DHQD or a derivative thereof, compounds of formula VIIb can be prepared. Conversely, when using quinine, DHQ or a derivative thereof, compounds of formula VIIa can be prepared. No particular preference is given as to which stereomer is selectively prepared since preferred compounds of the present invention can be prepared from either precursor VIIa and VIIb by chosing the appropriate next reaction sequences and the respective amine reagents therefor. Nevertheless, preferably, a compound of formula VIIb is obtained. The amine catalyst of choice is therefore quinidine, DHQD or a derivative thereof, in particular (DHQD)$_2$AQN. When a compound of formula VIIa is to be prepared, the amine catalyst of choice is therefore quinine, DHQ or a derivative thereof, in particular (DHQ)$_2$AQN.

For reaction conditions, reference is made again to Tian, S.-K. et al. Specifically, the chiral amine catalyst is typically employed in a below-equimolar amount, preferably below 50 mol %, such as 5 to 40 mol %, more preferably 10 to 35 mol %, most preferably 30 mol %.

The alcohol R5OH is a suitable alcohol for esterification on a compound of formula VI and hydrolysis in the presence of an amide as present in a compound of formula VIII, such as unsubstituted or substituted alkyl or alkenyl, preferably $C_1$-$C_4$ alkyl, whereby substituted alkyl is preferably selected from halo or aryl substituted alkyl, in particular fluoro or phenyl. Examples of substituted alkyl include trifluoromethyl, difluoromethyl, difluoroethyl, fluoromethyl, fluoroethyl or benzyl. Most preferably, R5OH is methyl.

Reaction solvents can be chosen as described below, in particular preferred are ethereal solvents such as diethyl ether or tetrahydrofuran (THF) or mixtures of these such as diethyl ether:THF (4:1) or (3:1). The reaction temperature can be chosen so as to bring the reaction to completion in an efficient manner while at the same time suppress the formation of unwanted side products as much as possible. Typical reaction temperatures are −100 to 20° C., such as −80 to 10° C., preferably −40 to 0° C.

The conversion proceeds with high stereoselectivity, preferably more than 60% ee, more preferably more than 70% ee, still more preferably more than 80% ee, most preferably more than 90% ee, such as more than 95% ee. Practically around 100% ee, such as 98% ee can be achieved.

Separation of the desired product can be achieved by suitable recrystallization techniques known in the art. For example, reference is made to the recrystallization methods employed in Park, J.-S.; Yeom, C.-E.; Choi, S. H.; Ahn, Y. S.; Ro, S.; Jeom, Y. H.; Shin, D.-K.; Kim, B. M. *Tetrahedron Lett.* 2003, 44, 1611-1614 and the reference cited therein, which are herewith incorporated by reference. Thus, chiral amines such as α-phenylethylamine can be employed for separation by kinetic resolution.

As a next or individual step, a compound of formula (VIIa)

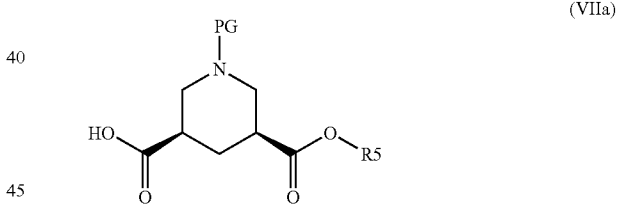

(VIIa)

wherein PG is a protecting group and R5 are is unsubstituted or substituted alkyl or alkenyl, preferably $C_1$-$C_4$ alkyl, or (preferably) an activated derivative thereof, is reacted with a compound of the formula III,

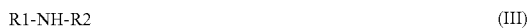

R1-NH-R2    (III)

wherein R1 and R2 are as defined for a compound of the formula I in any one of claims 1 to 13; to obtain the desired amide of formula VIII

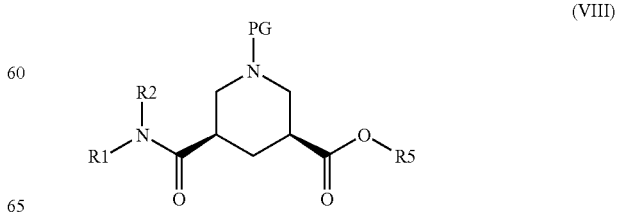

(VIII)

which is subjected to hydrolysis of the ester moiety to obtain a compound of formula IX

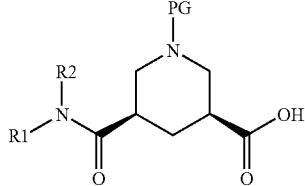
(IX)

which compound or (preferably) an activated derivative thereof, can be in turn reacted with a compound of the formula V,

R3-NH-R4     (V)

wherein R3 and R4 are as defined for a compound of the formula I in any one of claims 1 to 13; to obtain a compound of formula X

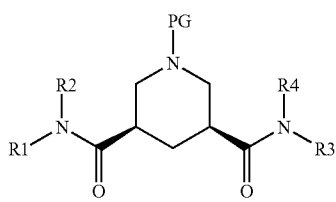
(X)

and, if desired, subsequent to any one or more of the processes mentioned above an obtainable compound of the formula I or a protected form thereof is converted into a different compound of the formula I, a salt of an obtainable compound of formula I is converted into the free compound or a different salt, an obtainable free compound of formula I is converted into a salt thereof, and/or an obtainable mixture of isomers of a compound of formula I is separated into individual isomers; where in any of the starting materials, in addition to specific
  protecting groups mentioned, further protecting groups
  may be present, and any protecting groups or bound resins
  are removed at an appropriate stage in order to obtain a
  corresponding compound of the formula I, or a salt thereof.
  Alternatively, a compound of formula (VIIa)

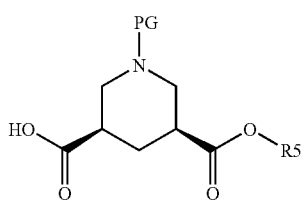
(VIIa)

wherein PG is a protecting group and R5 are is unsubstituted substituted alkyl or alkenyl, preferably $C_1$-$C_4$ alkyl,
or (preferably) an activated derivative thereof, is reacted with
  a compound of the formula V,

R3-NH-R4     (V)

wherein R3 and R4 are as defined for a compound of the formula I in any one of claims 1 to 13;

to obtain the desired amide of formula XI

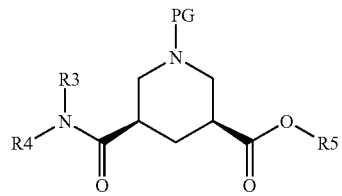
(XI)

which is subjected to hydrolysis of the ester moiety to obtain a compound of formula XI

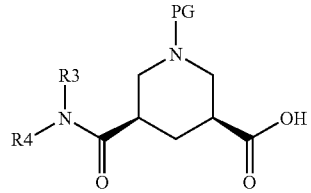
(XII)

which compound or (preferably) an activated derivative thereof, can be in turn reacted with a compound of the formula III,

R1-NH-R2     (III)

wherein R1 and R2 are as defined for a compound of the formula I in any one of claims 1 to 13; to obtain a compound of formula XIII

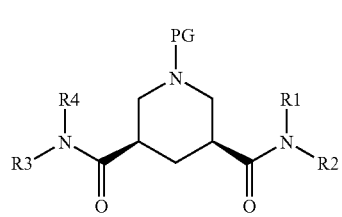
(XIII)

and, if desired, subsequent to any one or more of the processes mentioned above an obtainable compound of the formula I or a protected form thereof is converted into a different compound of the formula I, a salt of an obtainable compound of formula I is converted into the free compound or a different salt, an obtainable free compound of formula I is converted into a salt thereof, and/or an obtainable mixture of isomers of a compound of formula I is separated into individual isomers; where in any of the starting materials, in addition to specific
  protecting groups mentioned, further protecting groups
  may be present, and any protecting groups or bound resins
  are removed at an appropriate stage in order to obtain a
  corresponding compound of the formula I, or a salt thereof.
  Alternatively, as a next or individual step, a compound of
  formula (VIIb)

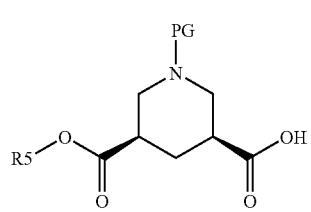
(VIIb)

wherein PG is a protecting group and R5 are is unsubstituted or substituted alkyl or alkenyl, preferably $C_1$-$C_4$ alkyl, or (preferably) an activated derivative thereof, is reacted with a compound of the formula III,

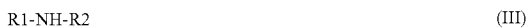

wherein R1 and R2 are as defined for a compound of the formula I in any one of claims 1 to 13; to obtain the desired amide of formula XIV

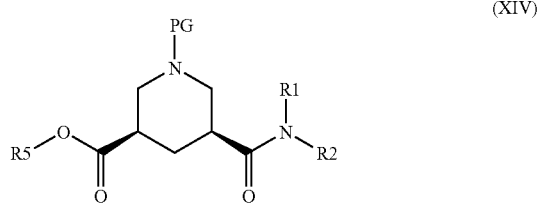

which is subjected to hydrolysis of the ester moiety to obtain a compound of formula XV

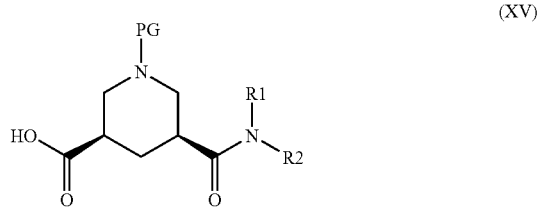

which compound or (preferably) an activated derivative thereof, can be in turn reacted with a compound of the formula V,

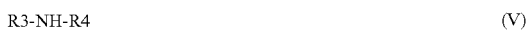

wherein R3 and R4 are as defined for a compound of the formula I in any one of claims 1 to 13; to obtain a compound of formula XIII

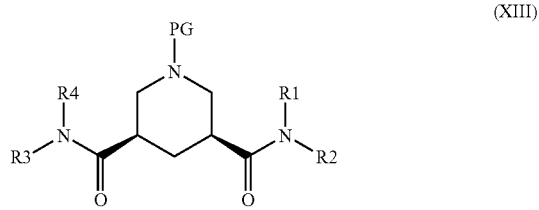

and, if desired, subsequent to any one or more of the processes mentioned above an obtainable compound of the formula I or a protected form thereof is converted into a different compound of the formula I, a salt of an obtainable compound of formula I is converted into the free compound or a different salt, an obtainable free compound of formula I is converted into a salt thereof, and/or an obtainable mixture of isomers of a compound of formula I is separated into individual isomers; where in any of the starting materials, in addition to specific protecting groups mentioned, further protecting groups may be present, and any protecting groups or bound resins are removed at an appropriate stage in order to obtain a corresponding compound of the formula I, or a salt thereof. Alternatively, a compound of formula (VIIb)

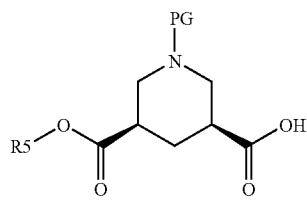

wherein PG is a protecting group and R5 are is unsubstituted or with halo substituted alkyl or alkenyl, preferably $C_1$-$C_4$ alkyl,
or (preferably) an activated derivative thereof, is reacted with a compound of the formula V,

wherein R3 and R4 are as defined for a compound of the formula I in any one of claims 1 to 13;
to obtain the desired amide of formula XVI


which is subjected to hydrolysis of the ester moiety to obtain a compound of formula XVII

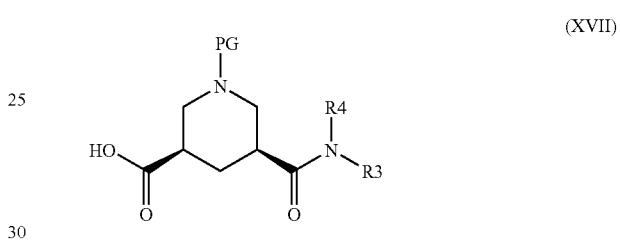

which compound or (preferably) an activated derivative thereof, can be in turn reacted with a compound of the formula III,

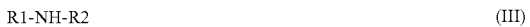

wherein R1 and R2 are as defined for a compound of the formula I in any one of claims 1 to 13; to obtain a compound of formula X

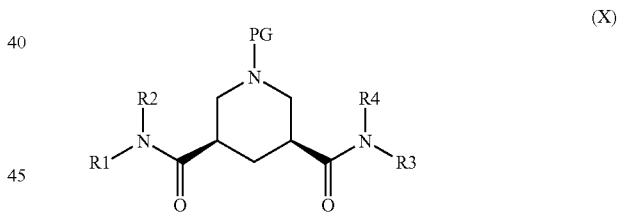

and, if desired, subsequent to any one or more of the processes mentioned above an obtainable compound of the formula I or a protected form thereof is converted into a different compound of the formula I, a salt of an obtainable compound of formula I is converted into the free compound or a different salt, an obtainable free compound of formula I is converted into a salt thereof, and/or an obtainable mixture of isomers of a compound of formula I is separated into individual isomers; where in any of the starting materials, in addition to specific protecting groups mentioned, further protecting groups may be present, and any protecting groups or bound resins are removed at an appropriate stage in order to obtain a corresponding compound of the formula I, or a salt thereof.

Preferably the method for preparing a chiral cis scaffold yields a compound of formula X.

Two of the preferred methods are shown below in Schemes 3a and 3b as a sequence. It should be noted that the brief description on each of the arrows for each conversion has been added for illustration purposes only and should not be regarded as limiting with respect to the sequence or each individual step.

Scheme 3a

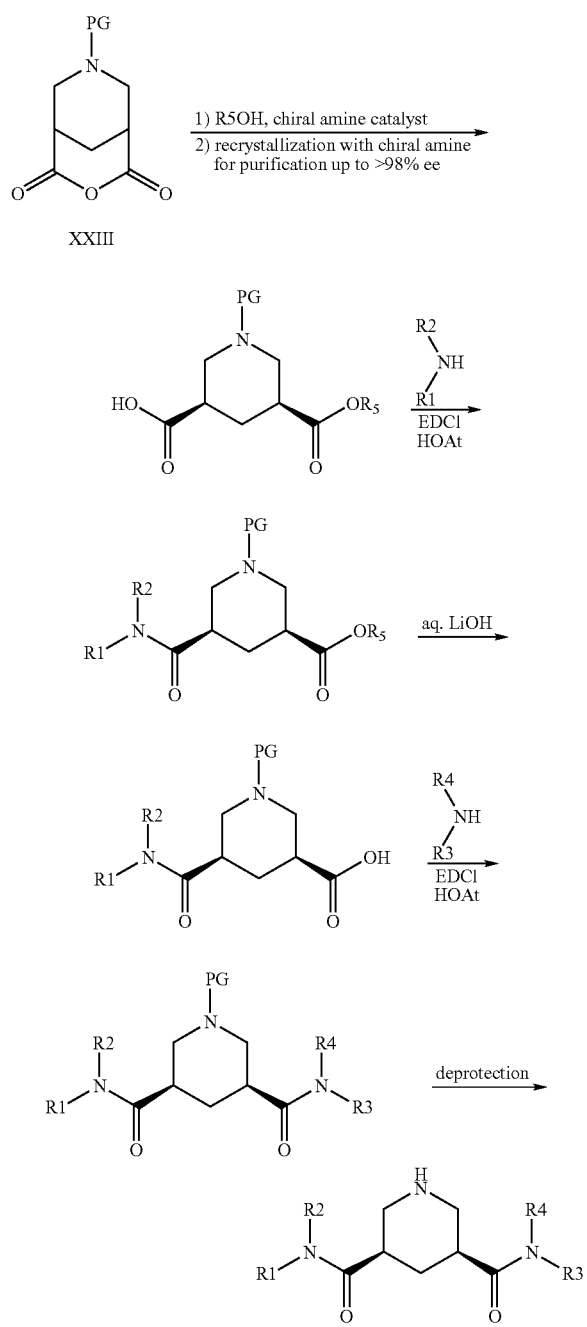

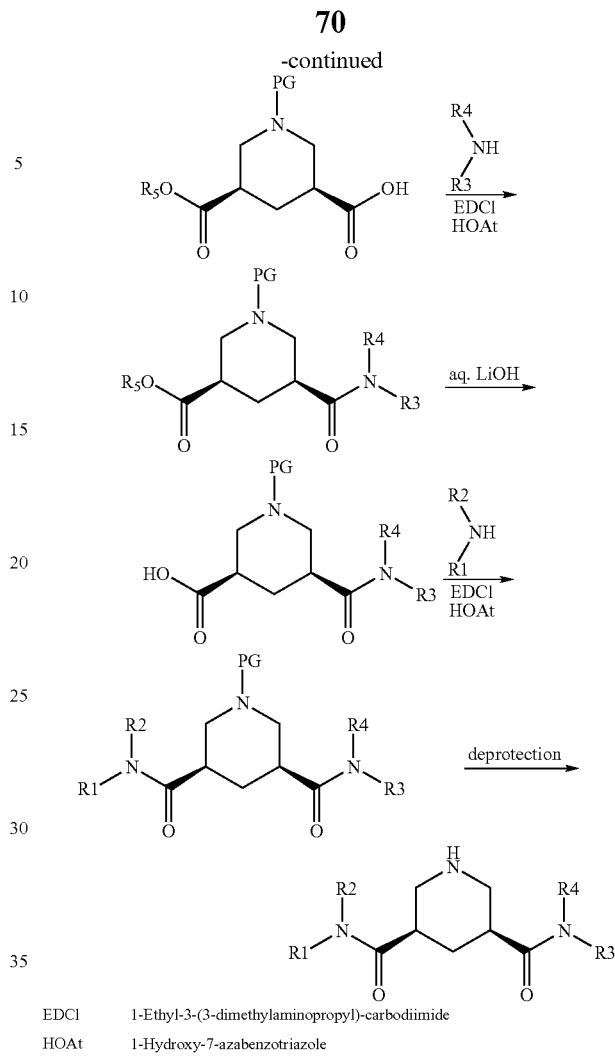

| EDCl | 1-Ethyl-3-(3-dimethylaminopropyl)-carbodiimide |
| HOAt | 1-Hydroxy-7-azabenzotriazole |

Ester hydrolysis and deprotection can be effected according to methods well known in the art, see also the reference made below with respect to protection and deprotection methods.

Preferred Reaction Conditions

The preferred reaction conditions for the reactions mentioned above, as well as for the transformations and conversions, are as follows (or analogous to methods used in the Examples or as described there):

The reaction under a) and b) or for the preparation of compound of formulae VIII, X, XI, and XIII preferably takes place under customary condensation or substitution conditions.

In the case of a compound of the formula II wherein T is carbonyl (that is, the compound of the formula IV is a carbonic acid) in the case of a compound of formula IV, or in the preparation of compound of formulae VIII, X, XI, and XII, the reaction preferably takes place with an activated derivative of the compound of the formula II, IV, VIIa, VIIb, IX, or XII. As an activated derivative of an acid of the formula II, IV, VIIa, VIIb, IX, or XII reactive esters (such as the hydroxybenzotriazole (HOBT), pentafluorophenyl, 4-nitrophenyl or N-hydroxysuccinimide ester), acid halogenides (such as the acid chloride or bromide) or reactive anhydrides (such as mixed anhydrides with lower alkanoic acids or symmetric anhydrides) are preferred. Reactive carbonic acid derivatives can also and preferably be formed in situ. The reaction is

Scheme 3b

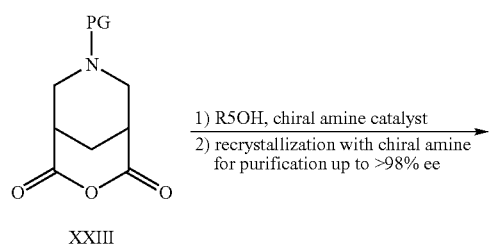

carried out by dissolving the compounds of formulae II, IV, VIIa, VIIb, IX, or XII and III or V in a suitable solvent, for example a halogenated hydrocarbon, such as methylene chloride, N,N-dimethylformamide, N,N-dimethylacetamide, N-methyl-2-pyrrolidone, methylene chloride, acetonitrile or a mixture of two or more such solvents, and by the addition of a suitable base, for example triethylamine, diisopropylethylamine (DIPEA) or N-methylmorpholine and, if the reactive derivative of the acid of the formula IV is formed in situ, a suitable coupling agent that forms a preferred reactive derivative of the carbonic acid of formula II, IV, VIIa, VIIb, IX, or XII in situ, for example dicyclohexylcarbodiimide/1-hydroxybenzotriazole (DCC/HOBT); bis(2-oxo-3-oxazolidinyl)phosphinic chloride (BOPCl); O-(1,2-dihydro-2-oxo-1-pyridyl)-N,N,N',N'-tetramethyluronium tetrafluoroborate (TPTU); O-benzotriazol-1-yl)-N,N,N',N'-tetramethyluronium tetrafluoroborate (TBTU); (benzotriazol-1-yloxy)-tripyrrolidinophosphonium-hexafluorophosphate (PyBOP), 1-(3-dimethylaminopropyl)-3-ethylcarbodiimide hydrochloride/hydroxybenzotriazole or/1-hydroxy-7-azabenzotriazole (EDC/HOBT or EDC/HOAt), HOAt alone, 4-(4,6-dimethoxy-1,3,5-triazin-2-yl)-4-methylmorpholinium chloride (DMT-M M), O-(1H-6-chlorobenzotriazole-1-yl)-1,1,3,3-tetramethyluronium hexafluorophosphate (HCTU), propylphosphonic anhydride or with 1-chloro-2-methyl-propenyl)-dimethylamine (=1-chloro-N,N,2-trimethyl-1-propenylamine). For review of some other possible coupling agents, see e.g. Klauser; Bodansky, *Synthesis* 1972, 453-463. The reaction can take place at a temperature of between approximately −20 and 50° C., especially between 0° C. and 30° C., e.g. at 0° C. to room temperature. The reaction may be carried out under an inert gas, e.g. nitrogen or argon.

In the case of a compound of the formula II wherein T is methylene, in an activated derivative the OH group is preferably replaced by a leaving group, such as halo, e.g. chloro, bromo or iodo, or organic sulfonyloxy, such as tosyloxy or methanesulfonyloxy. The reaction with a compound of the formula III then preferably takes under standard conditions for nucleophilic substitution.

The removal of protecting groups PG and/or other protecting groups can then in either case take place as described under process a) or the general process conditions.

Optional Reactions and Conversions

Compounds of the formula I, or protected forms thereof directly obtained according to any one of the preceding procedures or after introducing protecting groups anew, which are included subsequently as starting materials for conversions as well even if not mentioned specifically, can be converted into different compounds of the formula I according to known procedures, where required after removal of protecting groups.

Where R1 is hydrogen in a compound of the formula I, this can be converted into the corresponding compound wherein R1 has a meaning other than hydrogen given for compounds of the formula I by reaction with a compound of the formula XVIII, $$R1^*-Q \qquad (XVIII)$$

wherein R1* is defined as R1 in a compound of the formula I other than hydrogen and Q is a leaving group (e.g. preferably selected from halo, e.g. chloro, from unsubstituted or substituted aryl-sulfonyloxy, such as toluolsulfonyloxy, from unsubstituted or substituted alkylsulfonyloxy, such as methylsulfonyloxy or trifluoromethylsulfonyloxy, with the reaction allowed to take place e.g. in the presence of a base, such as an alkali metal salt of a weaker acid, e.g. an alkali metal carbonate and/or an alkali metal hydrogencarbonate, such as sodium or potassium carbonate and/or sodium or potassium hydrogencarbonate (NaHCO$_3$ or KHCO$_3$) in an appropriate solvent, e.g. dimethylacetamide, dioxane and/or H$_2$O, at preferred temperatures between −20 and 50° C., e.g. at −5 to 30° C.), or wherein Q is —CHO (so that the compound of the formula IV is an aldehyde) and then R1* is the complementary moiety for a moiety R1 that includes a methylene group (resulting in a group R1 of the formula R1*-CH$_2$—) e.g. under reductive amination conditions as follows: The reaction preferably takes place under customary conditions for reductive amination, e.g. in the presence of an appropriate hydrogenation agent, such as hydrogen in the presence of a catalyst or a complex hydride, e.g. sodium triacetoxyborohydride or sodium cyanoborhydride, in an appropriate solvent, such as a halogenated hydrocarbon, e.g. methylene chloride or 1,2,-dichloroethane, and optionally a carbonic acid, e.g. acetic acid, at preferred temperatures between −10° C. and 50° C., e.g. from 0° C. to room temperature In a compound of the formula I wherein R3 is hydrogen, unsubstituted or substituted alkyl R3 can be introduced by reacting a compound of the formula I wherein R3 is hydrogen and R1, R2, R4 and T are as defined for a compound of the formula I with a compound of the formula XIX, $$R3-Q \qquad XIX$$

wherein R3 is unsubstituted or substituted alkyl and Q is as defined for a compound of the formula XVIII. The reaction conditions are preferably as described for the reaction of a compound of the formula XVIII in the preceding paragraph. The reaction preferably takes place in the presence of a protecting group at the nitrogen of the central piperidine ring, that is, with a compound of the formula I in protected form wherein R3 is hydrogen which is subsequently removed.

In some cases, the conversions preferably take place with compounds of the formula I' or I in protected form; the subsequent removal of protecting group can be achieved as described below and below under "General Process Conditions", yielding a corresponding compound of the formula I' or I. The removal of such a protecting group can take place under customary conditions, e.g. as described in the standard textbooks just referenced. For example, a protecting group 9H-fluoren-9-ylmethyloxycarbonyl may be removed by reacting with an appropriate secondary nitrogen base, such as piperidine, in an appropriate solvent, such as an N,N-di(C$_1$-C$_7$-alkyl)-C$_1$-C$_7$-alkanoylamide, e.g. dimethylacetamide, at customary temperatures, e.g. from 0 to 50° C., for example at room temperature, C$_1$-C$_7$-alkoxycarbonyl, such as tert-butoxycarbonyl, can be removed by reaction with an acid, such as hydrochloric acid, in an appropriate solvent, such as dioxane or methylene chloride, at customary temperatures, e.g. in the range from 0 to 50° C., for example at room temperature, or using CF$_3$SO$_3$Si(CH$_3$)$_3$ or the like in an appropriate solvent, such as methylene chloride, in the presence of 2,6-lutidine, where the temperatures may be in the same range as just described Salts of compounds of formula I' or I having at least one salt-forming group may be prepared in a manner known per se. For example, salts of compounds of formula I' or I having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of formula I' or I are obtained in customary manner, e.g. by treating the compounds with an acid or a suitable anion exchange reagent. Internal salts of compounds of formula I' or I containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

A salt of a compound of the formula I' or I can be converted in customary manner into the free compound; metal and ammonium salts can be converted, for example, by treatment with suitable acids, and acid addition salts, for example, by treatment with a suitable basic agent. In both cases, suitable ion exchangers may be used.

Stereoisomeric mixtures, e.g. mixtures of diastereomers, can be separated into their corresponding isomers in a manner known per se by means of appropriate separation methods.

Diastereomeric mixtures for example may be separated into their individual diastereomers by means of fractionated crystallization, chromatography, solvent distribution, and similar procedures. This separation may take place either at the level of one of the starting compounds or in a compound of formula I' or I itself. Enantiomers may be separated through the formation of diastereomeric salts, for example by salt formation with an enantiomer-pure chiral acid, or by means of chromatography, for example by HPLC, using chromatographic substrates with chiral ligands.

Intermediates and final products can be worked up and/or purified according to standard methods, e.g. using chromatographic methods, distribution methods, (re-) crystallization, and the like.

Starting Materials

In the subsequent description of starting materials (this term including also intermediates) and their synthesis, R1, R1*, R2, T, R3, R4, R5, PG and Q have the meanings given above or in the Examples for the respective starting materials or intermediates, if not indicated otherwise directly or by the context. Protecting groups, if not specifically mentioned, can be introduced and removed at appropriate steps in order to prevent functional groups, the reaction of which is not desired in the corresponding reaction step or steps, employing protecting groups, methods for their introduction and their removal are as described above or below, e.g. in the references mentioned under "General Process Conditions". The person skilled in the art will readily be able to decide whether and which protecting groups are useful or required.

Where for any of the starting materials isomers (e.g. diastereomers, enantiomers) are present, they can be separated according to standard procedures at appropriate stages.

Other starting materials, e.g. compounds of the formula III, V, VI, VIIa, VIIb, XVIII or their synthesis or analogous methods for their synthesis are known in the art, commercially available, and/or they can be found in or derived analogously from the Examples.

General Process Conditions

The following applies in general (where possible) to all processes mentioned hereinbefore and hereinafter, while reaction conditions specifically mentioned above or below are preferred:

In any of the reactions mentioned hereinbefore and hereinafter, protecting groups may be used where appropriate or desired, even if this is not mentioned specifically, to protect functional groups that are not intended to take part in a given reaction, and they can be introduced and/or removed at appropriate or desired stages. Reactions comprising the use of protecting groups are therefore included as possible wherever reactions without specific mentioning of protection and/or deprotection are described in this specification.

Within the scope of this disclosure only a readily removable group that is not a constituent of the particular desired end product of formula I' or I is designated a "protecting group" or PG, unless the context indicates otherwise. The protection of functional groups by such protecting groups, the protecting groups themselves, and the reactions appropriate for their introduction and removal are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of Organic Chemistry*), Houben Weyl, 4th edition, Volume 15/I, Georg Thieme Verlag, Stuttgart 1974, in H.-D. Jakubke and H. Jeschkeit, "Aminosäuren, Peptide, Proteine" (*Amino acids, Peptides, Proteins*), Verlag Chemie, Weinheim, Deerfield Beach, and Basel 1982, and in Jochen Lehmann, "Chemie der Kohlenhydrate: Monosaccharide und Derivate" (*Chemistry of Carbohydrates: Monosaccharides and Derivatives*), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

Examples of the protecting group or PG, in particular for nitrogen such as the piperidine nitrogen of the compound of formula I' or I are alkoxycarbonyl, sulfonyl and acyl groups. Preferred protecting groups comprise, for example, (i) $C_1$-$C_2$-alkyl that is mono-, di- or trisubstituted by phenyl, such as benzyl, (or) benzhydryl or trityl, wherein the phenyl ring is unsubstituted or substituted by one or more, e.g. two or three, residues e.g. those selected from the group consisting of $C_1$-$C_7$-alkyl, hydroxy, $C_1$-$C_7$-alkoxy, $C_2$-$C_8$-alkanoyl-oxy, halogen, nitro, cyano, and $CF_3$; phenyl-$C_1$-$C_2$-alkoxycarbonyl; and allyl or cinnamyl. Especially preferred are lower (e.g. $C_1$-$C_7$) alkoxycarbonyl, such as tert-butoxycarbonyl or benzyloxycarbonyl; benzyloxycarbonyl (Cbz), 9-fluorenylmethyloxycarbonyl (Fmoc), benzyloxymethyl (BOM), pivaloyl-oxy-methyl (POM), trichloroethxoycarbonyl (Troc), 1-adamantyloxycarbonxyl (Adoc), but can also be benzyl, cumyl, benzhydryl, trityl, allyl, alloc (allyloxycarbonyl). The protecting group can also be silyl, like trialklysilyl, especially trimethylsilyl, tert.-butyl-dimethylsilyl, triethylsilyl, triisopropylsilyl, trimethylsilyethoxymethyl (SEM), and can also be substituted sulfonyl or substituted sulfenyl. Most preferred is lower (e.g. $C_1$-$C_7$) alkoxycarbonyl, such as tert-butoxycarbonyl. The protecting group may also be a sulfonyl group, preferably an aryl sulfonyl group such as a substituted or unsubstituted phenyl sulfonyl group. In this case, phenyl, if substituted, may be mono-, di- or tri-substituted, preferably mono- or di-substituted with a suitable substituent such as $C_1$-$C_7$-alkyl, —O—$C_1$-$C_7$-alkyl, halo-$C_1$-$C_7$-alkyl, —O-halo-$C_1$-$C_7$-alkyl, halo, hydroxy, nitro, cyano, more preferably nitro or methyl. Particularly preferred examples of the sulfonyl protecting group are 2,4-dinitrophenylsulfonyl, 4-nitrophenyl sulfonyl, 2-nitrophenyl sulfonyl and 4-methylphenyl sulfonyl.

All the above-mentioned process steps can be carried out under reaction conditions that are known per se, preferably those mentioned specifically, in the absence or, customarily, in the presence of solvents or diluents, preferably solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., preferably from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofurane or dioxane, liquid aromatic hydrocarbons, such as benzene or toluene, alcohols, such as methanol, ethanol or 1- or 2-propanol, nitriles, such as acetonitrile, halogenated hydrocarbons, e.g. as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, or mixtures of these, for example aqueous solutions, unless otherwise indicated in the description of the processes. Such solvent mixtures may also be used in working up, for example by chromatography or partitioning.

The invention relates also to those forms of the processes in which a compound obtainable as intermediate at any stage of the process is used as starting material and the remaining process steps are carried out, or in which a starting material is formed under the reaction conditions or is used in the form of a derivative, for example in protected form or in the form of a salt, or a compound obtainable by the process according to the invention is produced under the process conditions and processed further in situ. In the processes of the present invention those starting materials are preferably used which result in compounds of formula I' or I described as being preferred. Special preference is given to reaction conditions that are identical or analogous to those mentioned in the Examples. The invention relates also to novel starting compounds and intermediates described herein, especially those leading to novel compounds of the formula I' or I or compounds of the formula I' or I mentioned as preferred herein.

Pharmaceutical Use, Pharmaceutical Preparations and Methods

As described above, the compounds of the formula I' or I are inhibitors of renin activity and, thus, may be of use for the treatment of hypertension, atherosclerosis, unstable coronary syndrome, congestive heart failure, cardiac hypertrophy, cardiac fibrosis, cardiomyopathy postinfarction, unstable coronary syndrome, diastolic dysfunction, chronic kidney disease, hepatic fibrosis, complications resulting from diabetes, such as nephropathy, vasculopathy and neuropathy, diseases of the coronary vessels, restenosis following angioplasty, raised intra-ocular pressure, glaucoma, abnormal vascular growth and/or hyperaldosteronism, and/or further cognitive impairment, alzheimers, dementia, anxiety states and cognitive disorders, and the like. Hypertension, at least as one component of the disease to be treated, is especially preferred, meaning that hypertension alone or in combination with one or more (especially of the mentioned) other diseases may be treated (prophylactically and/or therapeutically).

The present invention further provides pharmaceutical compositions comprising a therapeutically effective amount of a pharmacologically active compound of the formula I' or I, alone or in combination with one or more pharmaceutically acceptable carriers.

The pharmaceutical compositions according to the present invention are those suitable for enteral, such as oral or rectal, transdermal and parenteral administration to mammals, including man, to inhibit renin activity, and for the treatment of conditions associated with (especially inappropriate) renin activity. Such conditions include hypertension, atherosclerosis, unstable coronary syndrome, congestive heart failure, cardiac hypertrophy, cardiac fibrosis, cardiomyopathy postinfarction, unstable coronary syndrome, diastolic dysfunction, chronic kidney disease, hepatic fibrosis, complications resulting from diabetes, such as nephropathy, vasculopathy and neuropathy, diseases of the coronary vessels, restenosis following angioplasty, raised intra-ocular pressure, glaucoma, abnormal vascular growth and/or hyperaldosteronism, and/or further cognitive impairment, alzheimers, dementia, anxiety states and cognitive disorders and the like. Especially preferred is a disease which comprises hypertension, more especially hypertension itself, where treatment with a pharmaceutical composition or the use of a compound of the formula I' or I for its synthesis is useful prophylactically and/or (preferably) therapeutically.

Thus, the pharmacologically active compounds of the formula I' or I may be employed in the manufacture of pharmaceutical compositions comprising an effective amount thereof in conjunction or admixture with excipients or carriers suitable for either enteral or parenteral application. Preferred are tablets and gelatin capsules comprising the active ingredient together with:

a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and or polyvinylpyrrolidone; if desired
d) disintegrants, e.g., starches, agar, alginic acid or its sodium salt, or effervescent mixtures; and/or
e) absorbants, colorants, flavors and sweeteners.

Injectable compositions are preferably aqueous isotonic solutions or suspensions, and suppositories are advantageously prepared from fatty emulsions or suspensions.

Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, preferably about 1-50%, of the active ingredient.

Suitable formulations for transdermal application include a therapeutically effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and pre-determined rate over a prolonged period of time, and means to secure the device to the skin.

Accordingly, the present invention provides pharmaceutical compositions as described above for the treatment of conditions mediated by renin activity, preferably, hypertension, atherosclerosis, unstable coronary syndrome, congestive heart failure, cardiac hypertrophy, cardiac fibrosis, cardiomyopathy postinfarction, unstable coronary syndrome, diastolic dysfunction, chronic kidney disease, hepatic fibrosis, complications resulting from diabetes, such as nephropathy, vasculopathy and neuropathy, diseases of the coronary vessels, restenosis following angioplasty, raised intra-ocular pressure, glaucoma, abnormal vascular growth and/or hyperaldosteronism, and/or further cognitive impairment, alzheimers, dementia, anxiety states and cognitive disorders, as well as methods of their use.

The pharmaceutical compositions may contain a therapeutically effective amount of a compound of the formula I' or I as defined herein, either alone or in a combination with another therapeutic agent, e.g., each at an effective therapeutic dose as reported in the art. Such therapeutic agents include:

a) antidiabetic agents such as insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; peroxisome proliferator-activated receptor (PPAR) ligands; protein tyrosine phosphatase-1B (PTP-1B) inhibitors such as PTP-112; GSK3 (glycogen synthase kinase-3) inhibitors such as SB-517955, SB-4195052, SB-216763, N,N-57-05441 and N,N-57-05445; RXR ligands such as GW-0791 and AGN-194204; sodium-dependent glucose cotransporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; and DPPIV (dipeptidyl peptidase IV) inhibitors such as LAF237;

b) hypolipidemic agents such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin and rivastatin; squalene synthase inhibitors; FXR (farnesoid X receptor) and LXR (liver X receptor) ligands; cholestyramine; fibrates; nicotinic acid and aspirin;

c) anti-obesity agents such as orlistat; and d) anti-hypertensive agents, e.g., loop diuretics such as ethacrynic acid, furosemide and torsemide; angiotensin converting enzyme (ACE) inhibitors such as benazepril, captopril, enalapril, fosinopril, lisinopril, moexipril, perinodopril, quinapril, ramipril and trandolapril; inhibitors of the Na—K-ATPase membrane pump such as digoxin; neutralendopeptidase (NEP) inhibitors; ACE/NEP inhibitors such as omapatrilat, sampatrilat and fasidotril; angiotensin II antagonists such as candesartan, eprosartan, irbesartan, losartan, telmisartan and valsartan, in particular valsartan; β-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amLodipine, bepridil, diltiazem, felodipine, nicardipine, nimodipine, nifedipine, nisoldipine and verapamil; aldosterone receptor antagonists; and aldosterone synthase inhibitors.

Other specific anti-diabetic compounds are described by Patel Mona in *Expert Opin Investig Drugs*, 2003, 12(4), 623-633, in the FIGS. 1 to 7, which are herein incorporated by reference. A compound of the formula I' or I may be administered either simultaneously, before or after the other active ingredient, either separately by the same or different route of administration or together in the same pharmaceutical formulation.

The structure of the therapeutic agents identified by code numbers, generic or trade names may be taken from the actual edition of the standard compendium "The Merck Index" or from databases, e.g., Patents International (e.g. IMS World Publications). The corresponding content thereof is hereby incorporated by reference.

Accordingly, the present invention provides pharmaceutical products or compositions comprising a therapeutically effective amount of a compound of the formula I' or I alone or in combination with a therapeutically effective amount of another therapeutic agent, preferably selected from anti-diabetics, hypolipidemic agents, anti-obesity agents and anti-hypertensive agents, most preferably from antidiabetics, anti-hypertensive agents and hypolipidemic agents as described above.

The present invention further relates to pharmaceutical compositions as described above for use as a medicament.

The present invention further relates to use of pharmaceutical compositions or combinations as described above for the preparation of a medicament for the treatment of conditions mediated by (especially inappropriate) renin activity, preferably, hypertension, atherosclerosis, unstable coronary syndrome, congestive heart failure, cardiac hypertrophy, cardiac fibrosis, cardiomyopathy postinfarction, unstable coronary syndrome, diastolic dysfunction, chronic kidney disease, hepatic fibrosis, complications resulting from diabetes, such as nephropathy, vasculopathy and neuropathy, diseases of the coronary vessels, restenosis following angioplasty, raised intra-ocular pressure, glaucoma, abnormal vascular growth and/or hyperaldosteronism, and/or further cognitive impairment, alzheimers, dementia, anxiety states and cognitive disorders, and the like.

Thus, the present invention also relates to a compound of formula I' or I for use as a medicament, to the use of a compound of formula I' or I for the preparation of a pharmaceutical composition for the prevention and/or treatment of conditions mediated by (especially inappropriate) renin activity, and to a pharmaceutical composition for use in conditions mediated by (especially inappropriate) renin activity comprising a compound of formula I' or I, or a pharmaceutically acceptable salt thereof, in association with a pharmaceutically acceptable diluent or carrier material.

The present invention further provides a method for the prevention and/or treatment of conditions mediated by (especially inappropriate) renin activity, which comprises administering a therapeutically effective amount of a compound of the formula I' or I to a warm-blooded animal, especially a human, in need of such treatment.

A unit dosage for a mammal of about 50-70 kg may contain between about 1 mg and 1000 mg, advantageously between about 5-600 mg of the active ingredient. The therapeutically effective dosage of active compound is dependent on the species of warm-blooded animal (especially mammal, more especially human), the body weight, age and individual condition, on the form of administration, and on the compound involved.

In accordance with the foregoing the present invention also provides a pharmaceutical product comprising a therapeutic combination, e.g., a kit, kit of parts, e.g., for use in any method as defined herein, comprising a compound of formula I' or I, or a pharmaceutically acceptable salt thereof, to be used concomitantly or in sequence with at least one pharmaceutical composition comprising at least another therapeutic agent, preferably selected from anti-diabetic agents, hypolipidemic agents, anti-obesity agents or anti-hypertensive agents. The kit may comprise instructions for its administration.

Similarly, the present invention provides a kit of parts comprising: (i) a pharmaceutical composition comprising a compound of the formula I' or I according to the invention; and (ii) a pharmaceutical composition comprising a compound selected from an anti-diabetic, a hypolipidemic agent, an anti-obesity agent, an anti-hypertensive agent, or a pharmaceutically acceptable salt thereof, in the form of two separate units of the components (i) to (ii).

Likewise, the present invention provides a method as defined above comprising co-administration, e.g., concomitantly or in sequence, of a therapeutically effective amount of a compound of formula I' or I, or a pharmaceutically acceptable salt thereof, and at least a second drug substance, said second drug substance preferably being an anti-diabetic, a hypolipidemic agent, an anti-obesity agent or an anti-hypertensive agent, e.g., as indicated above.

Preferably, a compound of the invention is administered to a mammal in need thereof.

Preferably, a compound of the invention is used for the treatment of a disease which responds to a modulation of (especially inappropriate) renin activity, especially one or more of the specific diseases mentioned above.

Finally, the present invention provides a method or use which comprises administering a compound of formula I' or I in combination with a therapeutically effective amount of an anti-diabetic agent, a hypolipidemic agent, an anti-obesity agent or an anti-hypertensive agent.

Ultimately, the present invention provides a method or use which comprises administering a compound of formula I' or I in the form of a pharmaceutical composition as described herein.

The above-cited properties are demonstrable in vitro and in vivo tests using advantageously mammals, e.g., mice, rats, rabbits, dogs, monkeys or isolated organs, tissues and preparations thereof. Said compounds can be applied in vitro in the form of solutions, e.g., preferably aqueous solutions, and in vivo either enterally, parenterally, advantageously intravenously, e.g., as a suspension or in aqueous solution. The concentration level in vitro may range between about $10^{-3}$ molar and $10^{-10}$ molar concentrations. A therapeutically effective amount in vivo may range depending on the route of administration, between about 0.001 and 500 mg/kg, preferably between about 0.1 and 100 mg/kg.

As described above, the compounds of the present invention have enzyme-inhibiting properties. In particular, they inhibit the action of the natural enzyme renin. Renin passes from the kidneys into the blood where it effects the cleavage of angiotensinogen, releasing the decapeptide angiotensin I which is then cleaved in the lungs, the kidneys and other organs to form the octapeptide angiotensin II. The octapeptide increases blood pressure both directly by arterial vasoconstriction and indirectly by liberating from the adrenal glands the sodium-ion-retaining hormone aldosterone, accompanied by an increase in extracellular fluid volume which increase can be attributed to the action of angiotensin II. Inhibitors of the enzymatic activity of renin lead to a reduction in the formation of angiotensin I, and consequently a smaller amount of angiotensin II is produced. The reduced concentration of that active peptide hormone is a direct cause of the hypotensive effect of renin inhibitors.

The action of renin inhibitors may be demonstrated inter alia experimentally by means of in vitro tests, the reduction in the formation of angiotensin I being measured in various systems (human plasma, purified human renin together with synthetic or natural renin substrate).

Inter alia the following in vitro tests may be used:

Recombinant human renin (expressed in Chinese Hamster Ovary cells and purified using standard methods) at 7.5 nM concentration is incubated with test compound at various concentrations for 1 h at RT in 0.1 M Tris-HCl buffer, pH 7.4, containing 0.05 M NaCl, 0.5 mM EDTA and 0.05% CHAPS. Synthetic peptide substrate Arg-Glu(EDANS)-Ile-His-Pro-Phe-His-Leu-Val-Ile_His_Thr-Lys(DABCYL)-Arg9 is added to a final concentration of 2 µM and increase in fluorescence is recorded at an excitation wave-length of 350 nm and at an emission wave-length of 500 nm in a microplate spectro-fluorimeter. IC50 values are calculated from percentage of inhibition of renin activity as a function of test compound concentration (Fluorescence Resonance Energy Transfer, FRET, assay). Compounds of the formula I' or I, in this assay, preferably can show $IC_{50}$ values in the range from 1 nM to 20 µM.

Alternatively, recombinant human renin (expressed in Chinese Hamster Ovary cells and purified using standard methods) at 0.5 nM concentration is incubated with test compound at various concentrations for 2 h at 37° C. in 0.1 M Tris-HCl buffer, pH 7.4, containing 0.05 M NaCl, 0.5 mM EDTA and 0.05% CHAPS. Synthetic peptide substrate Arg-Glu (EDANS)-Ile-His-Pro-Phe-His-Leu-Val-Ile_His_Thr-Lys (DABCYL)-Arg9 is added to a final concentration of 4 µM and increase in fluorescence is recorded at an excitation wave-length of 340 nm and at an emission wave-length of 485 nm in a microplate spectro-fluorimeter. IC50 values are calculated from percentage of inhibition of renin activity as a function of test compound concentration (Fluorescence Resonance Energy Transfer, FRET, assay). Compounds of the formula I' or I, in this assay, preferably can show $IC_{50}$ values in the range from 1 nM to 20 µM.

In another assay, human plasma spiked with recombinant human renin (expressed in Chinese Hamster Ovary cells and purified using standard methods) at 0.8 nM concentration is incubated with test compound at various concentrations for 2 h at 37° C. in 0.1 M Tris/HCl pH 7.4 containing 0.05 M NaCl, 0.5 mM EDTA and 0.025% (w/v) CHAPS. Synthetic peptide substrate Ac-Ile-His-Pro-Phe-His-Leu-Val-Ile-His-Asn-Lys-[DY-505-X5] is added to a final concentration of 2.5 µM. The enzyme reaction is stopped by adding an excess of a blocking inhibitor. The product of the reaction is separated by capillary electrophoresis and quantified by spectrophotometric measurement at 505 nM wave-length. IC50 values are calculated from percentage of inhibition of renin activity as a function of test compound concentration. Compounds of the formula I' or I, in this assay, preferably can show $IC_{50}$ values in the range from 1 nM to 20 µM.

In another assay, recombinant human renin (expressed in Chinese Hamster Ovary cells and purified using standard methods) at 0.8 nM concentration is incubated with test compound at various concentrations for 2 h at 37° C. in 0.1 M Tris/HCl pH 7.4 containing 0.05 M NaCl, 0.5 mM EDTA and 0.025% (w/v) CHAPS. Synthetic peptide substrate Ac-Ile-His-Pro-Phe-His-Leu-Val-Ile-His-Asn-Lys-[DY-505-X5] is added to a final concentration of 2.5 µM. The enzyme reaction is stopped by adding an excess of a blocking inhibitor. The product of the reaction is separated by capillary electrophoresis and quantified by spectrophotometric measurement at 505 nM wave-length. IC50 values are calculated from percentage of inhibition of renin activity as a function of test compound concentration. Compounds of the formula I' or I, in this assay, preferably show $IC_{50}$ values in the range from 1 nM to 20 µM.

In animals deficient in salt, renin inhibitors bring about a reduction in blood pressure. Human renin may differ from the renin of other species. In order to test inhibitors of human renin, primates, e.g., marmosets (*Callithrix jacchus*) may be used, because human renin and primate renin are substantially homologous in the enzymatically active region. Inter alia the following in vivo tests may be used:

Compounds of the formula I' or I can be tested in vivo in primates as described in the literature (see for example by Schnell C R et al. Measurement of blood pressure and heart rate by telemetry in conscious, unrestrained marmosets. Am J Physiol 264 (Heart Circ Physiol 33). 1993: 1509-1516; or Schnell C R et al. Measurement of blood pressure, heart rate, body temperature, ECG and activity by telemetry in conscious, unrestrained marmosets. Proceedings of the fifth FELASA symposium: Welfare and Science. Eds BRIGHTON. 1993.

EXAMPLES

The following examples serve to illustrate the invention without limiting the scope thereof:

In the following examples the central piperidine ring is displayed in a specific configuration. However, this is intended to include also the compound that is the mirror image with regard to the substituents at this central piperidine ring. In other terms, if not mentioned otherwise a compound of formula I' or I or a precursor thereof is in fact present as a mixture of the shown compound and the mirror image with regard to the substituents bound at the central piperidine ring (where no other chiral centers are present, the examples are thus enantiomeric mixtures, especially racemates). For example, where the central trisubstituted piperidine is represented in the following configuration

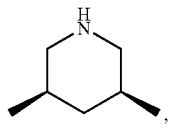

this is also intended to include the mirror image of the formula

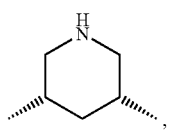

and the like. In other terms, if no other chiral groups are present, a compound of the formula I' or I or a precursor thereof is a racemate. If further chiral groups are present, diastereomeric or enantiomeric mixtures may be present.

The same is also true for intermediates and starting materials, if not indicated otherwise or suggested otherwise by the context.

In any case, however, essentially pure compounds of the formula I' or I wherein the essentially pure compound in the configuration as displayed is present are an especially preferred embodiment of the invention. They can be obtained e.g. according to standard procedures for the separation of enantiomers.

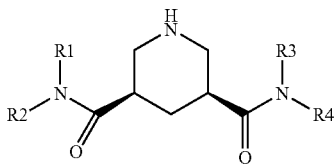

as represented in the following table:

| examples | R1 | R2 | R3 | R4 | Analytical data |
|---|---|---|---|---|---|
| 1 | ▽* | \O\* (with indole-CH2 chain) | H | *\ | MS: $[M+1]^+ =$ 469 HPLC: $_A t_{Ret} = 2.75$ |

-continued

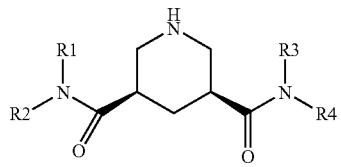

as represented in the following table:

| examples | R1 | R2 | R3 | R4 | Analytical data |
|---|---|---|---|---|---|
| 2 | cyclopropyl-* | 3-(1H-indol-3-yl)methyl, N-propyloxymethyl chain | H | neopentyl-* | MS: $[M+1]^+ =$ 483 HPLC: $^At_{Ret} = 2.88$ |
| 3 | cyclopropyl-* | 3-(1H-indol-3-yl)methyl, N-propyloxymethyl chain | H | isobutyl-* | MS: $[M+1]^+ =$ 483 HPLC: $^At_{Ret} = 2.92$ |
| 4 | cyclopropyl-* | 3-(1H-indol-3-yl)methyl, N-propyloxymethyl chain | H | benzyl-* | MS: $[M+1]^+ =$ 503 HPLC: $^At_{Ret} = 2.85$ |
| 5 | cyclopropyl-* | 3-(1H-indol-3-yl)methyl, N-propyloxymethyl chain | H | pyridin-4-ylmethyl-* | MS: $[M+1]^+ =$ 504 HPLC: $^At_{Ret} = 2.17$ |

-continued

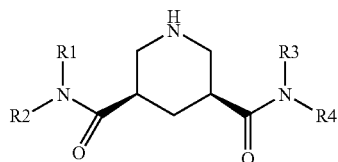

as represented in the following table:

| examples | R1 | R2 | R3 | R4 | Analytical data |
|---|---|---|---|---|---|
| 6 | cyclopropyl-* | 3-(1H-indol-1-yl)propyl methyl ether (indol-3-yl-CH2-*) | H | *-CH2-CH(CH3)-CH2-OH with isobutyl branch | MS: [M + 1]$^+$ = 513 HPLC: $A^t{}_{Ret}$ = 2.75 |
| 7 | cyclopropyl-* | same indole propyl ether | H | *-CH2-CH2-phenyl | MS: [M + 1]$^+$ = 517 HPLC: $A^t{}_{Ret}$ = 2.92 |
| 8 | cyclopropyl-* | same indole propyl ether | Me | *-CH2-phenyl | MS: [M + 1]$^+$ = 517 HPLC: $A^t{}_{Ret}$ = 2.92 |
| 9 | cyclopropyl-* | same indole propyl ether | Me | *-CH2-CH(CH3)2 | MS: [M + 1]$^+$ = 483 HPLC: $A^t{}_{Ret}$ = 2.84 |

-continued

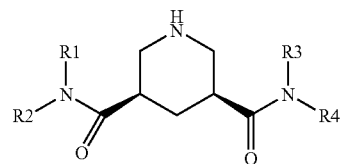

as represented in the following table:

| examples | R1 | R2 | R3 | R4 | Analytical data |
|---|---|---|---|---|---|
| 10 | cyclopropyl* | 3-(1H-indol-3-yl)methyl, N-(3-methoxypropyl) | H | *CH2CH2C(CH3)3 | MS: [M + 1]+ = 497 HPLC: $^C t_{Ret}$ = 3.18 |
| 11 | cyclopropyl* | 3-(1H-indol-3-yl)methyl, N-(3-methoxypropyl) | H | *CH2CH(C2H5)2 | MS: [M + 1]+ = 497 HPLC: $^C t_{Ret}$ = 3.19 |
| 12 | cyclopropyl* | 3-(1H-indol-3-yl)methyl, N-(3-methoxypropyl) | H | *CH2-cyclohexyl | MS: [M + 1]+ = 509 HPLC: $^C t_{Ret}$ = 3.21 |
| 13 | cyclopropyl* | 3-(1H-indol-3-yl)methyl, N-(3-methoxypropyl) | H | *CH(CH2OH)CH2CH(CH3)2 | (chiral) MS: [M + 1]+ = 513 HPLC: $^A t_{Ret}$ = 2.83 |

-continued

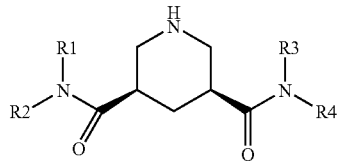

as represented in the following table:

| examples | R1 | R2 | R3 | R4 | Analytical data |
|---|---|---|---|---|---|
| 14 | cyclopropyl-CH2* | 3-(1H-indol-1-yl)propyl-O-methyl (indole linked via 3-CH2*) | H | (S)-4-methyl-2-(hydroxymethyl)pentyl* | (chiral) MS: [M + 1]+ = 513 HPLC: $^A t_{Ret}$ = 2.69 |
| 15 | cyclopropyl-CH2* | 3-(1H-indol-1-yl)propyl-O-methyl (indole linked via 3-CH2*) | H | isopentyl* | (chiral) MS: [M + 1]+ = 483 HPLC: $^A t_{Ret}$ = 3.02 |
| 16 | cyclopropyl-CH2* | 3-(1H-indol-1-yl)propyl-O-methyl (indole linked via 3-CH2*) | H | trans-2-hydroxycyclohexylmethyl* | MS: [M + 1]+ = 525 HPLC: $^C t_{Ret}$ = 2.76 |
| 17 | cyclopropyl-CH2* | 3-(1H-indol-1-yl)propyl-O-methyl (indole linked via 3-CH2*) | H | 2-hydroxy-2-phenylethyl* | MS: [M + 1]+ = 532 HPLC: $^C t_{Ret}$ = 2.75 |

-continued

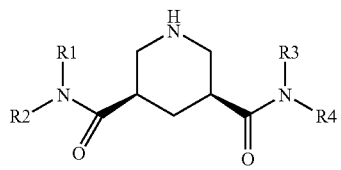

as represented in the following table:

| examples | R1 | R2 | R3 | R4 | Analytical data |
|---|---|---|---|---|---|
| 18 | cyclopropyl-CH2-* | 3-(1H-indol-1-yl)propyl with methoxy (3-methoxypropyl-indol-3-ylmethyl) | H | (1-hydroxycyclohexyl)methyl | MS: [M+1]+ = 525 HPLC: c tRet = 2.80 |
| 19 | cyclopropyl-CH2-* | 4-(3-methoxypropyl)-3-oxo-3,4-dihydro-2H-benzo[b][1,4]oxazin-6-ylmethyl | H | isobutyl (3-methylbutyl) | MS: [M+1]+ = 500 HPLC: c tRet = 2.60 |
| 20 | cyclopropyl-CH2-* | 4-(3-methoxypropyl)-3-oxo-3,4-dihydro-2H-benzo[b][1,4]oxazin-6-ylmethyl | H | 2-phenylethyl | MS: [M+1]+ = 534 HPLC: c tRet = 2.61 |
| 21 | cyclopropyl-CH2-* | 3-(1-(3-methoxypropyl)-1H-indol-3-yl)methyl | H | 1-phenyl-3-hydroxypropyl | MS: [M]+ = 546 HPLC: c tRet = 2.71, 2.84 |

-continued

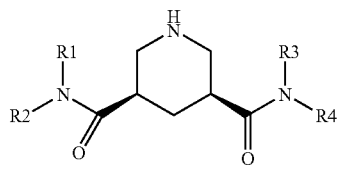

as represented in the following table:

| examples | R1 | R2 | R3 | R4 | Analytical data |
|---|---|---|---|---|---|
| 22 | cyclopropyl-CH2-* | 3-(1H-indol-1-yl)propyl methyl ether (*-CH2-indole-N-(CH2)3-OCH3) | H | *-CH2-CH(OH)-CH2-CH3 | MS: [M]+ = 484 HPLC: c$t_{Ret}$ = 2.51 |
| 23 | cyclopropyl-CH2-* | 3-(1H-indol-1-yl)propyl methyl ether | H | *-CH(Ph)-CH(OH)-CH2OH | MS: [M]+ = 562 HPLC: c$t_{Ret}$ = 2.56 |
| 24 | cyclopropyl-CH2-* | 3-(1H-indol-1-yl)propyl methyl ether | H | *-CH(CH2Ph)-CH2-OH | MS: [M]+ = 546 HPLC: c$t_{Ret}$ = 2.75 |
| 25 | cyclopropyl-CH2-* | 3-(1H-pyrrolo[2,3-b]pyridin-1-yl)propyl methyl ether | H | *-CH(CH3)-CH2-CH(CH3)-CH2OH | MS: [M + 1]+ = 514 HPLC: c$t_{Ret}$ = 2.02, 2.17 |

-continued

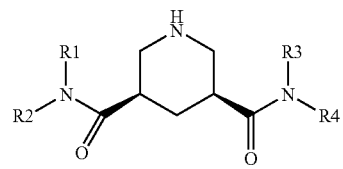

as represented in the following table:

| examples | R1 | R2 | R3 | R4 | Analytical data |
|---|---|---|---|---|---|
| 26 | cyclopropyl | propyl-O-quinoline-4-ylmethyl | H | *CH(CH3)CH2CH(CH3)OH (2-methyl-4-hydroxy branched) | MS: [M + 1]$^+$ = 511 HPLC: $^c$t$_{Ret}$ = 2.78, 2.98 |
| 27 | cyclopropyl | methoxyethyl-O-quinoline-4-ylmethyl | H | *CH(CH3)CH2CH(CH3)OH | MS: [M + 1]$^+$ = 527 HPLC: $^c$t$_{Ret}$ = 2.53, 2.71 |
| 28 | cyclopropyl | methoxypropyl-indol-3-ylmethyl | H | *cyclohexyl-CH2OH | MS: [M + 1]$^+$ = 525 HPLC: $^c$t$_{Ret}$ = 2.70, 2.80 |
| 29 | cyclopropyl | methoxypropyl-indol-3-ylmethyl | H | *CH2-cycloheptyl | MS: [M + 1]$^+$ = 523 HPLC: $^c$t$_{Ret}$ = 3.31 |

-continued

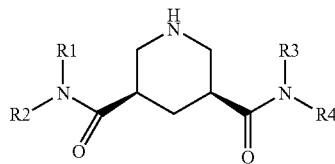

as represented in the following table:

| examples | R1 | R2 | R3 | R4 | Analytical data |
|---|---|---|---|---|---|
| 30 | cyclopropyl | 3-(1H-indol-3-ylmethyl)... methoxypropyl-indolylmethyl | H | tetrahydrofuran-2-ylmethyl | MS: $[M+1]^+ = 497$ HPLC: $^c t_{Ret} = 2.60$ |
| 31 | cyclopropyl | 3-methoxypropyl-indolylmethyl | H | 2-methyl-3-hydroxypropyl | MS: $[M+1]^+ = 499$ HPLC: $^c t_{Ret} = 2.50$ |
| 32 | cyclopropyl | 3-(3-methoxypropoxy)-4,5-dimethylbenzyl | H | 2,4-dimethyl-hydroxypentyl | MS: $[M+1]^+ = 518$ HPLC: $^A t_{Ret} = 2.70, 2.84$ |
| 33 | cyclopropyl | 4-(3-methoxypropyl)-3-oxo-3,4-dihydro-2H-benzo[1,4]oxazin-6-ylmethyl | H | 2,4-dimethyl-hydroxypentyl | MS: $[M+1]^+ = 531$ HPLC: $^c t_{Ret} = 2.30, 2.47$ |

-continued

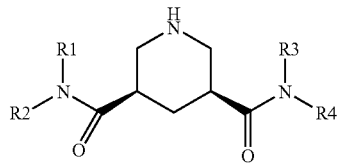

as represented in the following table:

| examples | R1 | R2 | R3 | R4 | Analytical data |
|---|---|---|---|---|---|
| 34 | cyclopropyl | 3-(methoxypropyl)-1H-indol-3-ylmethyl | H | benzylsulfonyl | MS: [M + 1]$^+$ = 567 HPLC: $^c$t$_{Ret}$ = 3.01 |
| 35 | cyclopropyl | 3-(methoxypropyl)-1H-indol-3-ylmethyl | H | (S)-2-hydroxymethyl-4,4-dimethylpentyl | MS: [M + 1]$^+$ = 527 HPLC: $^c$t$_{Ret}$ = 2.81, 2.95 |
| 36 | cyclopropyl | 3-(methoxypropyl)-1H-indol-3-ylmethyl | H | 2-hydroxymethyl-4,4-dimethylpentyl | MS: [M + 1]$^+$ = 527 HPLC: $^c$t$_{Ret}$ = 2.81, 2.94 |
| 37 | cyclopropyl | 3-methoxy-5-(3-methoxypropoxy)benzyl | H | 2-hydroxymethyl-4-methylpentyl | MS: [M + 1]$^+$ = 520 HPLC: $^c$t$_{Ret}$ = 2.62, 2.76 |

-continued

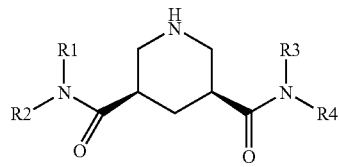

as represented in the following table:

| examples | R1 | R2 | R3 | R4 | Analytical data |
|---|---|---|---|---|---|
| 38 | cyclopropyl* | 3-methoxy-5-(3-methoxypropoxy)benzyl | H | *CH(CH$_2$CH(CH$_3$)$_2$)CH$_2$OH | MS: [M+1]$^+$ = 520 HPLC: c$t_{Ret}$ = 2.56 |
| 39 | cyclopropyl* | 2,3-dimethylbenzyl | H | *CH(CH$_2$CH(CH$_3$)$_2$)CH$_2$OH | MS: [M+1]$^+$ = 430 HPLC: c$t_{Ret}$ = 2.68, 2.87 |
| 40 | cyclopropyl* | 3,5-dimethoxybenzyl | H | *CH(CH$_2$CH(CH$_3$)$_2$)CH$_2$OH | MS: [M+1]$^+$ = 462 HPLC: c$t_{Ret}$ = 2.47, 2.63 |
| 41 | cyclopropyl* | 3-methoxy-5-[(2-methoxyethylamino)methyl]benzyl | H | *CH(CH$_2$CH(CH$_3$)$_2$)CH$_2$OH | MS: [M+1]$^+$ = 519 HPLC: c$t_{Ret}$ = 1.96, 2.06 |
| 42 | cyclopropyl* | 3-methoxy-5-(pentanoylamino)benzyl | H | *CH(CH$_2$CH(CH$_3$)$_2$)CH$_2$OH | MS: [M+1]$^+$ = 531 HPLC: c$t_{Ret}$ = 2.58, 2.86 |

-continued

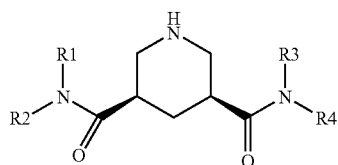

as represented in the following table:

| examples | R1 | R2 | R3 | R4 | Analytical data |
|---|---|---|---|---|---|
| 43 | cyclopropyl-* | 3-methoxy-5-(methoxyethylcarbamoyl)benzyl | H | *-CH(CH2OH)-CH2-CH(CH3)2 | MS: [M + 1]+ = 533 HPLC: c tRet = 2.15, 2.28 |
| 44 | cyclopropyl-* | 3-(3-methoxypropoxy)-5-trifluoromethylbenzyl | H | *-CH(CH2OH)-CH2-CH(CH3)2 | MS: [M + 1]+ = 558 HPLC: c tRet = 2.93, 3.08 |
| 45 | cyclopropyl-* | 1-(3-methoxypropyl)-1H-indol-3-ylmethyl | H | *-CH(CH2OH)-CH2-Ph | (chiral) MS: [M + 1]+ = 547 HPLC: c tRet = 2.75 |
| 46 | cyclopropyl-* | 1-(3-methoxypropyl)-1H-indol-3-ylmethyl | H | *-CH(CH2OH)-CH2-Ph | (chiral) MS: [M + 1]+ = 547 HPLC: c tRet = 2.83 |

-continued

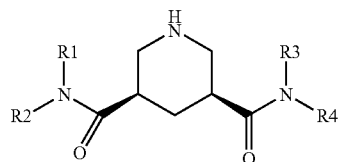

as represented in the following table:

| examples | R1 | R2 | R3 | R4 | Analytical data |
|---|---|---|---|---|---|
| 47 | cyclopropyl-* | 3-methoxypropyl-indol-3-ylmethyl (N-substituted) | H | (R)-1-phenyl-3-hydroxypropyl* | (chiral) MS: $[M+1]^+ = 547$ HPLC: $^c t_{Ret} = 2.83$ |
| 48 | cyclopropyl-* | 3-methoxypropyl-indol-3-ylmethyl | H | (S)-1-phenyl-3-hydroxypropyl* | (chiral) MS: $[M+1]^+ = 547$ HPLC: $^c t_{Ret} = 2.68$ |
| 49 | cyclopropyl-* | 3-methoxypropyl-indol-3-ylmethyl | H | 1-phenyl-2-hydroxyethyl* | MS: $[M+1]^+ = 533$ HPLC: $^c t_{Ret} = 2.67, 2.81$ |
| 50 | cyclopropyl-* | 3-methoxypropyl-indol-3-ylmethyl | H | 2-phenyl-2-hydroxyethyl* | MS: $[M+1]^+ = 533$ HPLC: $^c t_{Ret} = 2.67, 2.81$ |

-continued

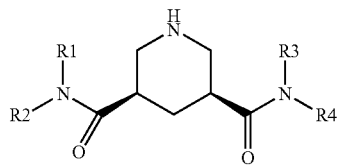

as represented in the following table:

| examples | R1 | R2 | R3 | R4 | Analytical data |
|---|---|---|---|---|---|
| 51 | cyclopropyl | 3-methoxypropyl-indol-1-yl | H | 4-hydroxyphenethyl | MS: [M + 1]$^+$ = 533 HPLC: $_C$t$_{Ret}$ = 2.66 |
| 52 | isopropyl | 3-methoxypropyl-indol-1-yl | H | 2-hydroxymethyl-4-methylpentyl | MS: [M + 1]$^+$ = 515 HPLC: $_C$t$_{Ret}$ = 2.82, 2.89 |
| 53 | cyclopropyl | 3-(3-methoxypropoxy)-5-ethylbenzyl | H | 2-hydroxymethyl-4-methylpentyl | MS: [M + 1]$^+$ = 518 HPLC: $_B$t$_{Ret}$ = 1.63 |
| 54 | cyclopropyl | 4-(3-methoxypropoxy)-6-methoxypyridin-2-ylmethyl | H | 2-hydroxymethyl-4-methylpentyl | MS: [M + 1]$^+$ = 521 HPLC: $_B$t$_{Ret}$ = 1.52 |

-continued

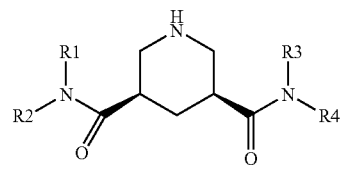

as represented in the following table:

| examples | R1 | R2 | R3 | R4 | Analytical data |
|---|---|---|---|---|---|
| 55 | cyclopropyl | 3-methoxypropyl-indol-3-ylmethyl | H | *CH(iBu)C(O)N(Me)2 | MS: [M + 1]+ = 554 HPLC: $_C t_{Ret}$ = 2.81, 2.93 |
| 56 | cyclopropyl | 1-(3-methoxypropyl)-2-oxo-1,2-dihydropyridin-5-ylmethyl | H | *CH(CH2OH)(iBu) | MS: [M + 1]+ = 491 HPLC: $_B t_{Ret}$ = 1.57 |
| 57 | cyclopropyl | 6-ethyl-2-(3-methoxypropoxy)pyridin-4-ylmethyl | H | *CH(CH2OH)(iBu) | MS: [M + 1]+ = 519 HPLC: $_B t_{Ret}$ = 1.56 |
| 58 | ethyl | 2-methoxy-5-(3-methoxypropoxy)benzyl | H | *CH(CH2OH)(iBu) | MS: [M + 1]+ = 508 HPLC: $_A t_{Ret}$ = 2.25, 2.38 |

-continued

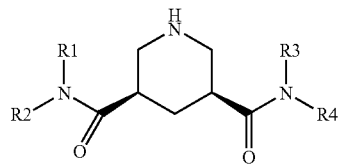

as represented in the following table:

| examples | R1 | R2 | R3 | R4 | Analytical data |
|---|---|---|---|---|---|
| 59 | cyclopropyl | 7-(3-methoxypropyl)-2-oxo-1,2,3,4-tetrahydroquinolin-1-yl methyl | H | 2-hydroxymethyl-4-methylpentyl | MS: $[M+1]^+ =$ 529<br>HPLC: $c_{t_{Ret}} = 2.66, 2.82$ |
| 60 | cyclopropyl | 1-(3-methoxypropyl)-1H-indol-3-ylmethyl | H | (1-hydroxycyclohexyl)methyl | (chiral)<br>MS: $[M+1]^+ =$ 525<br>HPLC: $c_{t_{Ret}} = 2.76$ |
| 61 | cyclopropyl | 3-methoxy-5-(3-methoxypropoxy)benzyl | H | 2-hydroxymethyl-4-methylpentyl | MS: $[M+1]^+ =$ 506<br>HPLC: $c_{t_{Ret}} = 2.41, 2.57$ |
| 62 | cyclopropyl | 3-methoxy-5-(4-methoxybutoxy)benzyl | H | 2-hydroxymethyl-4-methylpentyl | MS: $[M+1]^+ =$ 533<br>HPLC: $c_{t_{Ret}} = 2.66, 2.82$ |

-continued

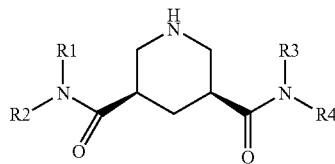

as represented in the following table:

| examples | R1 | R2 | R3 | R4 | Analytical data |
|---|---|---|---|---|---|
| 63 | cyclopropyl* | 3-(1H-indol-1-yl)propyl with methoxy | H | *CH(CH3)CH(OH)CH2CH(CH3)2 type (OH, isobutyl) | MS: [M + 1]+ = 527 HPLC: c tRet = 2.73, 2.87 |
| 64 | cyclopropyl* | methoxypropoxy-2,5-dimethylphenyl* | H | *CH(iBu)CH2OH | MS: [M + 1]+ = 490 HPLC: c tRet = 2.66, 2.83 |
| 65 | cyclopropyl* | 4-(2-methoxyethyl)-3-oxo-3,4-dihydro-2H-benzo[b][1,4]oxazin-6-yl* | H | *CH(iBu)CH2OH | MS: [M + 1]+ = 517 HPLC: c tRet = 2.13, 2.18 |
| 66 | cyclopropyl* | 3-(1H-indol-1-yl)propyl with methoxy | H | trans-2-hydroxycyclohexylmethyl* | (chiral) MS: [M + 1]+ = 525 HPLC: c tRet = 2.71 |

-continued

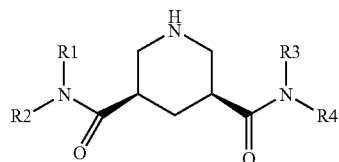

as represented in the following table:

| examples | R1 | R2 | R3 | R4 | Analytical data |
|---|---|---|---|---|---|
| 67 | cyclopropyl-* | 3-(1H-indol-3-ylmethyl)-indol-1-yl propyl methyl ether | H | *-CH(CH2C(CH3)3)-CH2OH (chiral) | (chiral) MS: [M + 1]+ = 527 HPLC: c tRet = 2.76 |
| 68 | cyclopropyl-* | 3-(1H-indol-3-ylmethyl)-indol-1-yl propyl methyl ether | H | *-cyclohexyl-CH2OH | (chiral) MS: [M + 1]+ = 525 HPLC: c tRet = 2.66, 2.78 |
| 69 | cyclopropyl-* | 3-(1H-indol-3-ylmethyl)-indol-1-yl propyl methyl ether | H | *-CH(Ph)-CH2OH | (chiral) MS: [M + 1]+ = 533 HPLC: c tRet = 2.65 |
| 70 | cyclopropyl-* | 3-(1H-indol-3-ylmethyl)-indol-1-yl propyl methyl ether | H | *-CH2CH(CH3)CH2OH | (chiral) MS: [M + 1]+ = 485 HPLC: c tRet = 2.51 |

-continued

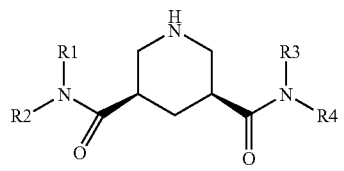

as represented in the following table:

| examples | R1 | R2 | R3 | R4 | Analytical data |
|---|---|---|---|---|---|
| 71 | cyclopropyl-CH2-* | 3-(1H-indol-1-yl)propyl with methoxy | H | (S)-3,3-dimethyl-1-hydroxybutan-2-yl | (chiral) MS: [M + 1]⁺ = 527 HPLC: c$t_{Ret}$ = 2.91 |
| 72 | cyclopropyl-CH2-* | 3-(1H-indol-1-yl)propyl with methoxy | H | (1R,2S)-2-(hydroxymethyl)cyclohexyl | (chiral) MS: [M + 1]⁺ = 525 HPLC: c$t_{Ret}$ = 2.69, 2.79 |
| 73 | cyclopropyl-CH2-* | 3-(1H-indol-1-yl)propyl with methoxy | H | (R)-2-hydroxy-1-phenylethyl | (chiral) MS: [M + 1]⁺ = 533 HPLC: c$t_{Ret}$ = 2.79 |
| 74 | cyclopropyl-CH2-* | 3-(1H-indol-1-yl)propyl with methoxy | H | cycloheptylmethyl | (chiral) MS: [M + 1]⁺ = 523 HPLC: c$t_{Ret}$ = 3.31 |

-continued

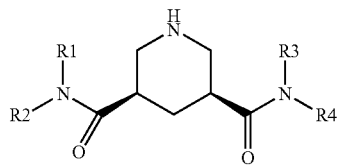

as represented in the following table:

| examples | R1 | R2 | R3 | R4 | Analytical data |
|---|---|---|---|---|---|
| 75 | cyclopropyl | 3-methoxypropyl-indol-3-ylmethyl | H | 2-methyl-4-hydroxybutyl | (chiral) MS: [M + 1]$^+$ = 499 HPLC: $c_{t_{Ret}}$ = 2.50 |
| 76 | cyclopropyl | 3-methoxypropyl-indol-3-ylmethyl | H | 2-(4-hydroxyphenyl)ethyl | (chiral) MS: [M + 1]$^+$ = 533 HPLC: $c_{t_{Ret}}$ = 2.64 |
| 77 | cyclopropyl | 3-methoxypropyl-indol-3-ylmethyl | H | 2,4-dimethylpentyl | MS: [M + 1]$^+$ = 539 HPLC: $c_{t_{Ret}}$ = 3.57 |
| 78 | cyclopropyl | 3-(2-methoxy-4-methylphenoxy)propyl via indole | H | 2-hydroxymethyl-4-methylpentyl | MS: [M + 1]$^+$ = 520 HPLC: $c_{t_{Ret}}$ = 2.40, 2.55 |

-continued

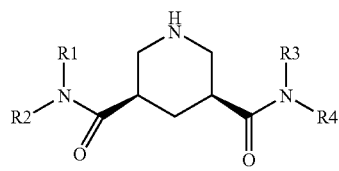

as represented in the following table:

| examples | R1 | R2 | R3 | R4 | Analytical data |
|---|---|---|---|---|---|
| 79 | cyclopropyl | 3-(3-methoxypropyl)-1H-indol-1-yl methylene | H | 2-methyl-1-(isobutyl)propyl with OH | MS: $[M+1]^+ =$ 555  HPLC: $c_{tRet} = 3.02, 3.09, 3.16$ |
| 80 | cyclopropyl | 3-(3-methoxypropyl)-1H-indol-1-yl methylene | H | (tetrahydrofuran-2-yl)methyl | (chiral) MS: $[M+1]^+ =$ 497  HPLC: $c_{tRet} = 2.60$ |
| 81 | cyclopropyl | 3-(3-methoxypropyl)-1H-indol-1-yl methylene | H | 2,5-dihydroxypentyl | (chiral) MS: $[M+1]^+ =$ 515  HPLC: $c_{tRet} = 2.33, 2.42$ |
| 82 | cyclopropyl | 4-(4-methoxybutyl)-3-oxo-3,4-dihydro-2H-benzo[b][1,4]oxazin-6-yl | H | 4-methyl-1-hydroxy-2-pentyl | MS: $[M+1]^+ =$ 545  HPLC: $c_{tRet} = 2.24, 2.30$ |

-continued

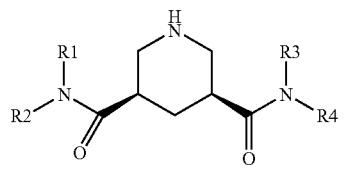

as represented in the following table:

| examples | R1 | R2 | R3 | R4 | Analytical data |
|---|---|---|---|---|---|
| 83 | cyclopropyl* | 3-(indol-1-yl)propyl with OMe (indole-3-CH2*) | H | *C(CH3)2C(O)N(CH3)2 isobutyl | (chiral) MS: [M + 1]+ = 568 HPLC: $^A t_{Ret}$ = 2.89 |
| 84 | cyclopropyl* | 3-(indol-1-yl)propyl with OMe (indole-3-CH2*) | H | *C(CH3)2C(O)N(CH3)2 isobutyl | (chiral) MS: [M + 1]+ = 568 HPLC: $^A t_{Ret}$ = 2.87 |
| 85 | cyclopropyl* | 3-(indol-1-yl)propyl with OMe (indole-3-CH2*) | H | *CH2-tetrahydropyran-4-yl | (chiral) MS: [M + 1]+ = 511 HPLC: $^C t_{Ret}$ = 2.54-chiral |
| 86 | cyclopropyl* | 3-(indol-1-yl)propyl with OMe (indole-3-CH2*) | H | *-cyclohexyl-CH2OH | (chiral) MS: [M + 1]+ = 524 HPLC: $^C t_{Ret}$ = 2.50, 2.64 |

-continued

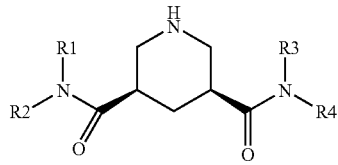

as represented in the following table:

| examples | R1 | R2 | R3 | R4 | Analytical data |
|---|---|---|---|---|---|
| 87 | cyclopropyl* | 4-(3-methoxypropyl)-2,2-dimethyl-3-oxo-3,4-dihydro-2H-benzo[1,4]oxazin-6-ylmethyl* | H | *CH(CH2OH)CH2CH(CH3)2 | MS: [M + 1]+ = 559 HPLC: c tRet = 2.57, 2.73 |
| 88 | cyclopropyl* | 1-(3-methoxypropyl)-1H-indol-3-ylmethyl* | H | (chiral) *CH2..CH(CH2CH(CH3)2)CH2OH | (chiral) MS: [M + 1]+ = 527 HPLC: c tRet = 2.83 |
| 89 | cyclopropyl* | 3-(3-methoxypropoxy)-5-(1-hydroxy-1-methylethyl)benzyl* | H | *CH(CH2OH)CH2CH(CH3)2 | MS: [M + 1]+ = 548 HPLC: c tRet = 2.43, 2.55 |
| 90 | cyclopropyl* | 3-(3-methoxypropoxy)-5-isopropylbenzyl* | H | *CH(CH2OH)CH2CH(CH3)2 | MS: [M + 1]+ = 532 HPLC: c tRet = 3.02, 3.17 |

-continued

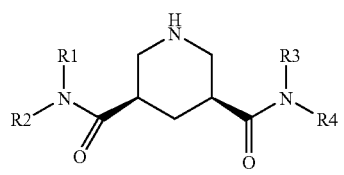

as represented in the following table:

| examples | R1 | R2 | R3 | R4 | Analytical data |
|---|---|---|---|---|---|
| 91 | cyclopropyl* | 3-methoxypropyl-indol-1-yl-methyl* | H | 2-methyl-6-methoxyphenyl* | (chiral) MS: $[M + 1]^+ =$ 533 HPLC: $^C t_{Ret} = 2.92$ |
| 92 | cyclopropyl* | 3-methoxypropoxy-dihydrobenzofuran-6-ylmethyl* | H | 4-methyl-2-(hydroxymethyl)pentyl* | MS: $[M + 1]^+ =$ 532 HPLC: $^C t_{Ret} = 2.65, 2.80$ |
| 93 | cyclopropyl* | 3-methoxypropoxy-quinolin-4-ylmethyl* | H | 4-methyl-2-(hydroxymethyl)pentyl* | MS: $[M + 1]^+ =$ 541 HPLC: $^A t_{Ret} = 2.35, 2.54$ |
| 94 | cyclopropyl* | 3-methoxypropyl-5-ethylthiophen-3-ylmethyl* | H | 4-methyl-2-(hydroxymethyl)pentyl* | MS: $[M + 1]^+ =$ 507 HPLC: $^C t_{Ret} = 2.99, 3.15$ |

-continued

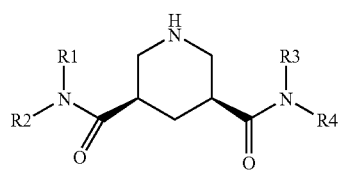

as represented in the following table:

| examples | R1 | R2 | R3 | R4 | Analytical data |
|---|---|---|---|---|---|
| 95 | cyclopropyl | 5-(3-methoxypropoxy)chroman-7-ylmethyl | H | 2-hydroxymethyl-4-methylpentyl | MS: [M + 1]⁺ = 546 HPLC: c$t_{Ret}$ = 3.00, 3.14 |
| 96 | cyclopropyl | 3-methoxy-5-(3-methoxypropoxy)benzyl | H | 3-methylbutyl | MS: [M + 1]⁺ = 490 HPLC: c$t_{Ret}$ = 3.49 Chiral |
| 97 | cyclopropyl | 4-(3-methoxypropyl)-3-oxo-3,4-dihydro-2H-benzo[1,4]oxazin-6-ylmethyl | H | 3-methylbutyl | MS: [M + 1]⁺ = 501 HPLC: c$t_{Ret}$ = 3.23 |
| 98 | sec-butyl | 3-methoxy-5-(3-methoxypropoxy)benzyl | H | 2-hydroxymethyl-4-methylpentyl | MS: [M + 1]⁺ = 536 HPLC: c$t_{Ret}$ = 2.79, 2.94 |

-continued

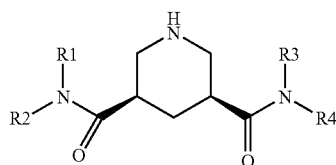

as represented in the following table:

| examples | R1 | R2 | R3 | R4 | Analytical data |
|---|---|---|---|---|---|
| 99 | isobutyl | 3-(3-methoxy-5-methoxyphenoxy)propyl-like (methoxy-propoxy-methoxybenzyl) | H | 2-methyl-1-hydroxymethyl-propyl (HOCH2-CH(*)-CH2-CH(CH3)2) | MS: [M + 1]$^+$ = 536 HPLC: $c_{Ret}^t$ = 2.79, 2.94 |
| 100 | cyclopropyl | 3-(2-tert-butylphenoxy)propyl with methoxy | H | 2-methyl-1-hydroxymethyl-propyl | MS: [M + 1]$^+$ = 546 HPLC: $c_{Ret}^t$ = 3.12, 3.22 |
| 101 | cyclopropyl | 3-(2-methoxyphenoxy)propyl with methoxy | H | 2-methyl-1-hydroxymethyl-propyl | MS: [M + 1]$^+$ = 520 HPLC: $c_{Ret}^t$ = 2.32, 2.43 |
| 102 | cyclopropyl | 3-(2-acetylphenoxy)propyl with methoxy | H | 2-methyl-1-hydroxymethyl-propyl | MS: [M + 1]$^+$ = 517 HPLC: $c_{Ret}^t$ = 2.49, 2.66 |

-continued

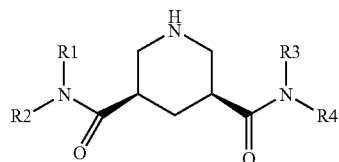

as represented in the following table:

| examples | R1 | R2 | R3 | R4 | Analytical data |
|---|---|---|---|---|---|
| 103 | cyclopropyl | 3-methoxypropyl-indol-1-yl-ethyl | H | 1-phenylcyclopentyl | MS: $[M+1]^+ =$ 557 HPLC: $c_{tRet} = 3.35$ |
| 104 | cyclopropyl | 3-(3-methoxy-5-(oxy))phenylmethyl-propyl | H | 2,4-dimethylpentan-3-yl | (chiral) MS: $[M+1]^+ =$ 546 HPLC: $c_{tRet} = 3.53$ |
| 105 | cyclopropyl | 3-(2,2-dimethyl-3-oxo-benzo[1,4]oxazin-4-yl)propyl with methoxy | H | 2,4-dimethylpentan-3-yl | (chiral) MS: $[M+1]^+ =$ 585 HPLC: $c_{tRet} = 3.46$ |
| 106 | cyclopropyl | 3-(chroman-5-yloxy)propyl with methoxy | H | 2,4-dimethylpentan-3-yl | (chiral) MS: $[M+1]^+ =$ 572 HPLC: $c_{tRet} = 3.60$ |

-continued

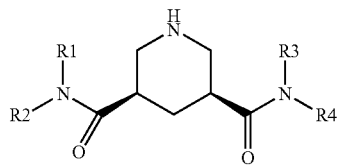

as represented in the following table:

| examples | R1 | R2 | R3 | R4 | Analytical data |
| --- | --- | --- | --- | --- | --- |
| 107 | cyclopropyl | 5-(2-methoxyethoxy)chroman-7-ylmethyl | H | 2-methyl-4-hydroxy-pentyl (chiral position) | MS: [M + 1]⁺ = 532 HPLC: c tRet = 2.65, 2.80 |
| 108 | cyclopropyl | 4-(3-methoxypropyl)-2,2-dimethyl-3-oxo-benzo[1,4]oxazin-6-yl | H | 2-methoxy-6-methylphenyl | (chiral) MS: [M + 1]⁺ = 579 HPLC: c tRet = 2.85 |
| 109 | cyclopropyl | 2-(3-methoxypropoxy)-4-methylphenyl | H | 2,4-dimethylpentyl | (chiral) MS: [M + 1]⁺ = 516 HPLC: c tRet = 3.70 |
| 110 | cyclopropyl | 4-(3-methoxypropyl)-2,2-dimethyl-3-oxo-benzo[1,4]oxazin-6-yl | H | 2-methyl-4-hydroxy-5-methylhexyl | (chiral) MS: [M + 1]⁺ = 601 HPLC: c tRet = 2.96, 3.06 |

-continued

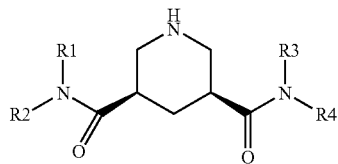

as represented in the following table:

| examples | R1 | R2 | R3 | R4 | Analytical data |
|---|---|---|---|---|---|
| 111 | cyclopropyl-* | 3-methoxy-5-(3-methoxypropoxy)benzyl | H | 2-methoxy-6-methylphenyl-* | (chiral) MS: $[M+1]^+$ = 540 HPLC: $c_{t_{Ret}}$ = 2.90 |
| 112 | cyclopropyl-* | 4-(3-methoxypropyl)-2-(3,5-difluorophenyl)-2-methyl-3-oxo-3,4-dihydro-2H-benzo[1,4]oxazin-6-yl-* (racemate) | H | 2,4-dimethylpentyl-* | (chiral) MS: $[M+1]^+$ = 682 HPLC: $c_{t_{Ret}}$ = 4.04 |
| 113 | cyclopropyl-* | 2-methyl-5-(3-methoxypropoxy)phenyl-* | H | 2-methyl-4-hydroxy-6-methylheptyl-* | (chiral) MS: $[M+1]^+$ = 532 HPLC: $c_{t_{Ret}}$ = 3.11, 3.19 |
| 114 | cyclopropyl-* | 7-(3-methoxypropoxy)chroman-5-yl-methyl-* | H | 2-methoxy-6-methylphenyl-* | (chiral) MS: $[M+1]^+$ = 566 HPLC: $c_{t_{Ret}}$ = 3.08 |

-continued

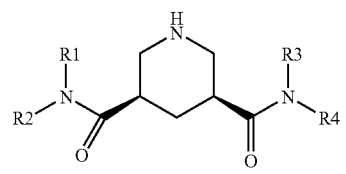

as represented in the following table:

| examples | R1 | R2 | R3 | R4 | Analytical data |
|---|---|---|---|---|---|
| 115 | cyclopropyl* | 3-methoxypropoxy-dihydrobenzofuran-CH2* | H | 2-methoxy-6-methylphenyl* | (chiral) MS: $[M+1]^+ =$ 522 HPLC: $c_{t_{Ret}} = 2.94$ |
| 116 | cyclopropyl* | 2-(3-methoxypropoxy)-5-methylphenyl* | H | 2-methoxy-6-methylphenyl* | (chiral) MS: $[M+1]^+ =$ 510 HPLC: $c_{t_{Ret}} = 2.97$ |
| 117 | cyclopropyl* | 4-(3-methoxypropyl)-2,2-dimethyl-3-oxo-benzoxazine* | H | tetrahydropyran-4-yl-CH2* | (chiral) MS: $[M+1]^+ =$ 557 HPLC: $c_{t_{Ret}} = 2.47$ |
| 118 | cyclopropyl* | 4-(3-methoxypropyl)-2,2-dimethyl-3-oxo-benzoxazine* | H | tetrahydrofuran-2-yl-CH2* | (chiral) MS: $[M+1]^+ =$ 543 HPLC: $c_{t_{Ret}} = 2.51$ |

-continued

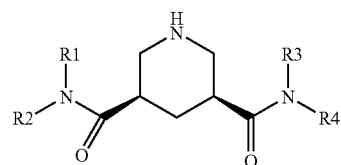

as represented in the following table:

| examples | R1 | R2 | R3 | R4 | Analytical data |
|---|---|---|---|---|---|
| 119 | cyclopropyl-* | 3-(3-methoxypropyl)-2,2-dimethyl-3-oxo-3,4-dihydro-2H-benzo[b][1,4]oxazin-6-yl | H | (S)-2-hydroxy-2,4-dimethylpentan-3-yl* | (chiral) MS: $[M+1]^+ = 586$ HPLC: $c_{t_{Ret}} = 2.70$ |
| 120 | cyclopropyl-* | 3-(3-methoxypropyl)-2,2-dimethyl-3-oxo-3,4-dihydro-2H-benzo[b][1,4]oxazin-6-yl | H | (R)-2-hydroxy-2,4-dimethylpentan-3-yl* | (chiral) MS: $[M+1]^+ = 587$ HPLC: $c_{t_{Ret}} = 2.87$ |
| 121 | cyclopropyl-* | 3-(3-methoxypropyl)-2,2-dimethyl-3-oxo-3,4-dihydro-2H-benzo[b][1,4]oxazin-6-yl | H | 1-(hydroxymethyl)-3-methylbutyl* | MS: $[M+1]^+ = 557$ HPLC: $c_{t_{Ret}} = 2.60, 2.76$ |
| 122 | cyclopropyl-* | 3-(3-methoxypropyl)-2,2-dimethyl-3-oxo-3,4-dihydro-2H-benzo[b][1,4]oxazin-6-yl | H | 1-(pyridin-4-yl)cyclopentyl* | (chiral) MS: $[M+1]^+ = 604$ HPLC: $c_{t_{Ret}} = 2.45$ |

-continued

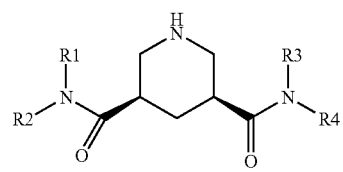

as represented in the following table:

| examples | R1 | R2 | R3 | R4 | Analytical data |
|---|---|---|---|---|---|
| 123 | cyclopropyl* | 4-(3-methoxypropyl)-2,2-dimethyl-3-oxo-3,4-dihydro-2H-benzo[1,4]oxazin-6-yl* | H | 4-fluoro-2-methoxy-6-methylphenyl* | (chiral) MS: $[M+1]^+$ = 596 HPLC: $c_{t_{Ret}}$ = 2.91 |
| 124 | cyclopropyl* | 1-(3-methoxypropyl)-3,3-dimethyl-1,2,3,4-tetrahydroquinolin-7-yl* | H | (2S)-4-methyl-1-hydroxypentan-2-yl* | (chiral) MS: $[M+1]^+$ = 542 HPLC: $c_{t_{Ret}}$ = 3.12 |
| 125 | cyclopropyl* | 4-cyano-3-(3-methoxypropoxy)phenyl* | H | 2,6-dimethylheptan-4-yl* | MS: $[M+1]^+$ = 527 HPLC: $c_{t_{Ret}}$ = 3.44 |
| 126 | cyclopropyl* | 4-cyano-3-(3-methoxypropoxy)phenyl* | H | 2-methoxy-6-methylphenyl* | (chiral) MS: $[M+1]^+$ = 521 HPLC: $c_{t_{Ret}}$ = 2.76 |

-continued

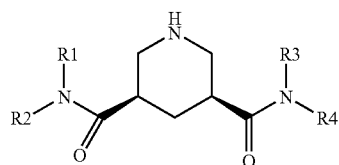

as represented in the following table:

| examples | R1 | R2 | R3 | R4 | Analytical data |
|---|---|---|---|---|---|
| 127 | ethyl | 3-(2,2-dimethyl-3-oxo-2,3-dihydro-4H-benzo[1,4]oxazin-4-yl)propyl, 6-yl attachment | H | 2-methoxy-6-methylphenyl | (chiral) MS: [M + 1]$^+$ = 566 HPLC: c$t_{Ret}$ = 2.80 |
| 128 | cyclopropyl | 3-(2,2-dimethyl-3-oxo-2,3-dihydro-4H-benzo[1,4]oxazin-4-yl)propyl, 6-yl attachment | H | 2-isopropoxyethyl | (chiral) MS: [M + 1]$^+$ = 545 HPLC: c$t_{Ret}$ = 2.64 |
| 129 | cyclopropyl | 3-(2,2-dimethyl-3-oxo-2,3-dihydro-4H-benzo[1,4]oxazin-4-yl)propyl, 6-yl attachment | H | 3-(2-oxopyrrolidin-1-yl)propyl | (chiral) MS: [M + 1]$^+$ = 584 HPLC: c$t_{Ret}$ = 2.37 |
| 130 | cyclopropyl | 3-(2,2-dimethyl-3-oxo-2,3-dihydro-4H-benzo[1,4]oxazin-4-yl)propyl, 6-yl attachment | H | (1-hydroxycyclohexyl)methyl | (chiral) MS: [M + 1]$^+$ = 571 HPLC: c$t_{Ret}$ = 2.68 |

-continued

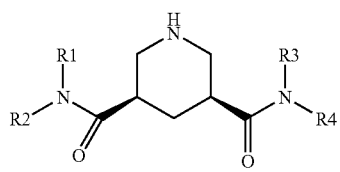

as represented in the following table:

| examples | R1 | R2 | R3 | R4 | Analytical data |
|---|---|---|---|---|---|
| 131 | cyclopropyl | 4-acetyl-3-(3-methoxypropoxy)phenyl | H | 2-methoxy-6-methylphenyl | (chiral) MS: $[M+1]^+ =$ 538 HPLC: $^c t_{Ret} = 2.72$ |
| 132 | cyclopropyl | 4-(3-methoxypropyl)-2,2-dimethyl-3-oxo-3,4-dihydro-2H-benzo[1,4]oxazin-6-yl | H | 2-methylphenyl | (chiral) MS: $[M+1]^+ =$ 549 HPLC: $^c t_{Ret} = 2.84$ |
| 133 | cyclopropyl | 4-(3-methoxypropyl)-2,2-dimethyl-3-oxo-3,4-dihydro-2H-benzo[1,4]oxazin-6-yl | H | 2-methoxyphenyl | (chiral) MS: $[M+1]^+ =$ 565 HPLC: $^c t_{Ret} = 2.88$ |
| 134 | cyclopropyl | 4-(3-methoxypropyl)-2,2-dimethyl-3-oxo-3,4-dihydro-2H-benzo[1,4]oxazin-6-yl | H | 2-methoxy-5-methylphenyl | (chiral) MS: $[M+1]^+ =$ 579 HPLC: $^c t_{Ret} = 3.05$ |

-continued

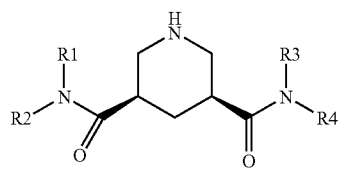

as represented in the following table:

| examples | R1 | R2 | R3 | R4 | Analytical data |
|---|---|---|---|---|---|
| 135 | cyclopropyl | 4-(3-methoxypropyl)-2,2-dimethyl-3-oxo-3,4-dihydro-2H-benzo[b][1,4]oxazin-6-yl | H | 2-methyl-5-methoxyphenyl | (chiral) MS: $[M+1]^+ =$ 579 HPLC: $_C t_{Ret} = 2.91$ |
| 136 | cyclopropyl | 4-(3-methoxypropyl)-2,2-dimethyl-3-oxo-3,4-dihydro-2H-benzo[b][1,4]oxazin-6-yl | H | 2-methoxy-4-methylpyridin-3-yl | (chiral) MS: $[M+1]^+ =$ 580 HPLC: $_C t_{Ret} = 2.60$ |
| 137 | cyclopropyl | 4-(3-methoxypropyl)-2,2-dimethyl-3-oxo-3,4-dihydro-2H-benzo[b][1,4]oxazin-6-yl | H | 3-isobutyl-1-methylpyrrolidin-3-yl | (chiral) MS: $[M+1]^+ =$ 598 HPLC: $_C t_{Ret} = 2.52, 2.67$ |
| 138 | cyclopropyl | 4-(3-methoxypropyl)-2,2-dimethyl-3-oxo-3,4-dihydro-2H-benzo[b][1,4]oxazin-6-yl | H | 3-(dimethylamino)propyl | (chiral) MS: $[M+1]^+ =$ 544 HPLC: $_B t_{Ret} = 1.39$ |

-continued

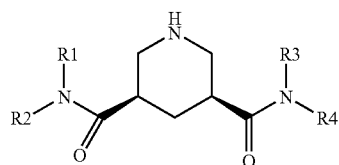

as represented in the following table:

| examples | R1 | R2 | R3 | R4 | Analytical data |
|---|---|---|---|---|---|
| 139 | cyclopropyl | 3-(2,2-dimethyl-3-oxo-2,3-dihydro-4H-benzo[1,4]oxazin-4-yl)propyl, methoxy | H | 4-morpholinobutyl | (chiral) MS: $[M+1]^+ =$ 586 HPLC: $_Bt_{Ret} = 1.41$ |
| 140 | cyclopropyl | 3-(2,2-dimethyl-3-oxo-2,3-dihydro-4H-benzo[1,4]oxazin-4-yl)propyl, methoxy | H | 2-(diethylamino)ethyl | (chiral) MS: $[M+1]^+ =$ 558 HPLC: $_Bt_{Ret} = 1.40$ |
| 141 | cyclopropyl | 3-(2,2-dimethyl-3-oxo-2,3-dihydro-4H-benzo[1,4]oxazin-4-yl)propyl, methoxy | H | 2-morpholinoethyl | (chiral) MS: $[M+1]^+ =$ 572 HPLC: $_Bt_{Ret} = 1.39$ |
| 142 | cyclopropyl | 3-(2,2-dimethyl-3-oxo-2,3-dihydro-4H-benzo[1,4]oxazin-4-yl)propyl, methoxy | H | 1-acetylpiperidin-4-yl | (chiral) MS: $[M+1]^+ =$ 584 HPLC: $_Ct_{Ret} = 2.34$ |

-continued

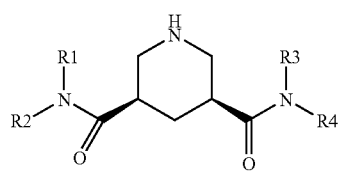

as represented in the following table:

| examples | R1 | R2 | R3 | R4 | Analytical data |
|---|---|---|---|---|---|
| 143 | cyclopropyl-* | 3,3-dimethyl-6-*-4H-benzo[1,4]oxazin-3(2H)-one N-(3-methoxypropyl) | H | *-CH2CH2-(tetrahydropyran-4-yl) | (chiral) MS: [M + 1]+ = 571 HPLC: $c_{t_{Ret}}$ = 2.53 |
| 144 | cyclopropyl-* | 3,3-dimethyl-7-*-3,4-dihydroquinolin-2(1H)-one N-(3-methoxypropyl) | H | *-1-(pyridin-4-yl)cyclopentyl | (chiral) MS: [M + 1]+ = HPLC: $c_{t_{Ret}}$ = |
| 145 | cyclopropyl-* | 4-*-2-(3-methoxypropoxy)benzonitrile | H | *-1-(pyridin-4-yl)cyclopentyl | (chiral) MS: [M + 1]+ = 546 HPLC: $c_{t_{Ret}}$ = 2.38 |
| 146 | cyclopropyl-* | 3,3-dimethyl-7-*-3,4-dihydroquinolin-2(1H)-one N-(3-methoxypropyl) | H | *-CH2-(tetrahydropyran-4-yl) | (chiral) MS: [M + 1]+ = 555 HPLC: $c_{t_{Ret}}$ = 2.46 |

-continued

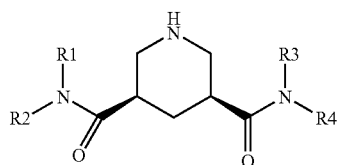

as represented in the following table:

| examples | R1 | R2 | R3 | R4 | Analytical data |
|---|---|---|---|---|---|
| 147 | cyclopropyl | 4-(3-methoxypropyl)-2,2-dimethyl-3-oxo-3,4-dihydro-2H-benzo[1,4]oxazin-6-yl | H | (S)-1-methoxy-3-methylbutan-2-yl | (chiral) MS: [M + 1]⁺ = 573 HPLC: ᶜt_Ret = 2.91 |
| 148 | cyclopropyl | 4-(3-methoxypropyl)-2,2-dimethyl-3-oxo-3,4-dihydro-2H-benzo[1,4]oxazin-6-yl | H | (S)-1-ethoxy-3-methylbutan-2-yl | (chiral) MS: [M + 1]⁺ = 587 HPLC: ᶜt_Ret = 3.05 |
| 149 | cyclopropyl | 4-(3-methoxypropyl)-2,2-dimethyl-3-oxo-3,4-dihydro-2H-benzo[1,4]oxazin-6-yl | H | (S)-1-(dimethylamino)-3-methylbutan-2-yl | (chiral) MS: [M + 1]⁺ = 586 HPLC: ᶜt_Ret = 2.56 |
| 150 | cyclopropyl | 4-(2-ethoxyethyl)-2,2-dimethyl-3-oxo-3,4-dihydro-2H-benzo[1,4]oxazin-6-yl | H | 2,4-dimethylpentan-3-yl | (chiral) MS: [M + 1]⁺ = 585 HPLC: ᴮt_Ret = 1.91 |

Note: R2 and R4 groups are depicted as structural drawings in the original; textual names above are descriptive approximations of the drawn substituents (with * indicating attachment points).

-continued

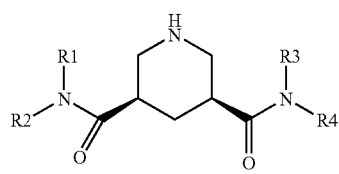

as represented in the following table:

| examples | R1 | R2 | R3 | R4 | Analytical data |
|---|---|---|---|---|---|
| 151 | cyclopropyl* | 4-(3-methoxypropyl)-2,2-dimethyl-3-oxo-3,4-dihydro-2H-benzo[b][1,4]oxazin-6-yl* | H | 1-ethoxycyclohexylmethyl* | (chiral) MS: $[M+1]^+ =$ HPLC: $c_{t_{Ret}} =$ |
| 152 | cyclopropyl* | 4-(3-methoxypropyl)-2,2-dimethyl-3-oxo-3,4-dihydro-2H-benzo[b][1,4]oxazin-6-yl* | H | 1-(tetrahydropyran-4-yl)cyclopropyl* | (chiral) MS: $[M+1]^+ =$ 583 HPLC: $c_{t_{Ret}} = 2.58$ |
| 153 | cyclopropyl* | 2-chloro-5-*-phenyl 3-methoxypropanamide | H | 2-methoxy-6-methylphenyl* | (chiral) MS: $[M+1]^+ =$ 544 HPLC: $c_{t_{Ret}} = 2.40$ |
| 154 | cyclopropyl* | 4-(3-methoxypropyl)-2,2-dimethyl-3-oxo-3,4-dihydro-2H-benzo[b][1,4]oxazin-6-yl* | H | (1S)-2-hydroxy-2-methyl-1-phenylpropyl* | (chiral) MS: $[M+1]^+ =$ 607 HPLC: $c_{t_{Ret}} = 2.76$ |

-continued

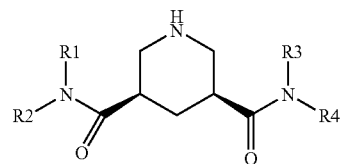

as represented in the following table:

| examples | R1 | R2 | R3 | R4 | Analytical data |
|---|---|---|---|---|---|
| 155 | cyclopropyl | 4-(3-methoxypropyl)-2,2-dimethyl-3-oxo-3,4-dihydro-2H-benzo[1,4]oxazin-6-yl | H | 2-(tetrahydropyran-4-yl)propan-2-yl | (chiral) MS: $[M+1]^+ = 585$ HPLC: $^c t_{Ret} = 2.71$ |
| 156 | cyclopropyl | 4-(3-methoxypropyl)-2,2-dimethyl-3-oxo-3,4-dihydro-2H-benzo[1,4]oxazin-6-yl | H | 2-phenylpropan-2-yl | (chiral) MS: $[M+1]^+ = 577$ HPLC: $^c t_{Ret} = 3.07$ |
| 157 | cyclopropyl | 4-acetyl-3-(3-methoxypropoxy)phenyl | H | 1-(pyridin-4-yl)cyclopentyl | (chiral) MS: $[M+1]^+ = 563$ HPLC: $^c t_{Ret} = 2.30$ |
| 158 | cyclopropyl | 4-(3-methoxypropyl)-2,2-dimethyl-3-oxo-3,4-dihydro-2H-benzo[1,4]oxazin-6-yl | H | (1S)-2-hydroxy-2-methyl-1-phenylpropyl | (chiral) MS: $[M+1]^+ = 607$ HPLC: $^c t_{Ret} = 2.87$ |

-continued

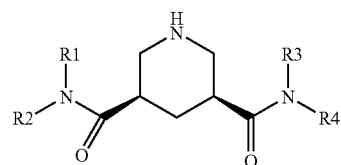

as represented in the following table:

| examples | R1 | R2 | R3 | R4 | Analytical data |
|---|---|---|---|---|---|
| 159 | cyclopropyl | 2,2-dimethyl-3-oxo-4-(3-methoxypropyl)-3,4-dihydro-2H-benzo[b][1,4]oxazin-6-yl | H | (1-methylpiperidin-4-yl)methyl | (chiral) MS: [M + 1]$^+$ = HPLC: c$t_{Ret}$ = |
| 160 | cyclopropyl | 2,2-dimethyl-3-oxo-4-(3-methoxypropyl)-3,4-dihydro-2H-benzo[b][1,4]oxazin-6-yl | H | 4-methyl-2-oxo-1,2-dihydropyridin-3-yl | (chiral) MS: [M + 1]$^+$ = HPLC: c$t_{Ret}$ = |
| 161 | cyclopropyl | 2,2-dimethyl-3-oxo-4-(3-methoxypropyl)-3,4-dihydro-2H-benzo[b][1,4]oxazin-6-yl | H | 1-methyl-4-isobutylpiperidin-4-yl | (chiral) MS: [M + 1]$^+$ = HPLC: c$t_{Ret}$ = |
| 162 | cyclopropyl | 2,2-dimethyl-3-oxo-4-(3-methoxypropyl)-3,4-dihydro-2H-benzo[b][1,4]oxazin-6-yl | H | 1-methyl-4-(2-methylpropyl)piperidin-4-yl | (chiral) MS: [M + 1]$^+$ = 543 HPLC: c$t_{Ret}$ = 2.37 |

-continued

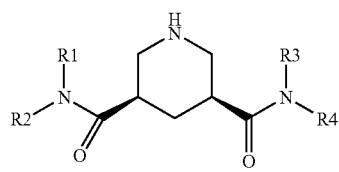

as represented in the following table:

| examples | R1 | R2 | R3 | R4 | Analytical data |
|---|---|---|---|---|---|
| 163 | cyclopropyl* | 3-(2,2-dimethyl-3-oxo-2,3-dihydro-4H-benzo[1,4]oxazin-4-yl)propyl, attached via 6-position* | H | (1R,2S)-2-hydroxycyclohexyl*, racemate | (chiral) MS: $[M+1]^+ =$ 557 HPLC: $^A t_{Ret} = 2.25$ |
| 164 | cyclopropyl* | 3-{[2-(trifluoromethyl)-5-*phenoxy]propoxy}methyl chain | H | 2-methoxy-6-methylphenyl* | (chiral) MS: $[M+1]^+ =$ 564 HPLC: $^A t_{Ret} = 2.95$ |
| 165 | cyclopropyl* | 3-(3-oxo-2,3-dihydro-4H-benzo[1,4]oxazin-4-yl)propyl, attached via 6-position* | H | 1-methyl-4-phenylpiperidin-4-yl* | (chiral) MS: $[M+1]^+ =$ 632 HPLC: $^C t_{Ret} = 2.25$ |
| 166 | cyclopropyl* | 3-(3-oxo-2,3-dihydro-4H-benzo[1,4]oxazin-4-yl)propyl, attached via 6-position* | H | 1-(pyridin-3-yl)cyclopentyl*, racemate | MS: $[M+1]^+ =$ 604 HPLC: $^A t_{Ret} =$ 2.1425 |

-continued

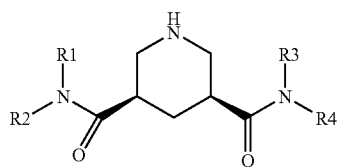

as represented in the following table:

| examples | R1 | R2 | R3 | R4 | Analytical data |
|---|---|---|---|---|---|
| 167 | cyclopropyl-* | 4-(3-methoxypropyl)-3-oxo-3,4-dihydro-2H-benzo[1,4]oxazin-6-yl-* | H | benzyl-* | MS: [M + 1]⁺ = 549 HPLC: $^At_{Ret}$ = 2.62 |
| 168 | cyclopropyl-* | 4-(3-methoxypropyl)-3-oxo-3,4-dihydro-2H-benzo[1,4]oxazin-6-yl-* | H | indan-2-yl-* | MS: [M + 1]⁺ = 575 HPLC: $^At_{Ret}$ = 2.75 |
| 169 | cyclopropyl-* | 5-ethyl-2-(3-methoxypropyl)thiophen-3-ylmethyl-* | H | 1-phenylcyclopentyl-* | MS: [M + 1]⁺ = 522 HPLC: $^Ct_{Ret}$ = 3.29 |
| 170 | cyclopropyl-* | 4-(3-methoxypropyl)-3-oxo-3,4-dihydro-2H-benzo[1,4]oxazin-6-yl-* | H | (R)-1-phenylethyl-* | MS: [M + 1]⁺ = 563 HPLC: $^Ct_{Ret}$ = 2.99 |

-continued

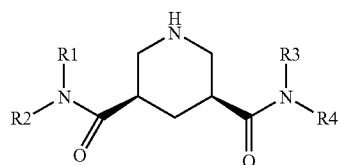

as represented in the following table:

| examples | R1 | R2 | R3 | R4 | Analytical data |
|---|---|---|---|---|---|
| 171 | cyclopropyl-* | 4-(3-methoxypropyl)-3-oxo-3,4-dihydro-2H-benzo[b][1,4]oxazin-6-yl-* | H | (S)-1-phenylethyl-* | MS: [M + 1]⁺ = 563 HPLC: $^C t_{Ret}$ = 2.96 |
| 172 | cyclopropyl-* | 2,2-dimethyl-4-(3-methoxypropyl)-3-oxo-3,4-dihydro-2H-benzo[b][1,4]oxazin-6-yl-* | H | 1-(5-fluoropyridin-3-yl)cyclopentyl-* | MS: [M + 1]⁺ = 622 HPLC: $^C t_{Ret}$ = 2.45 |
| 173 | ethyl-* | 4-(3-methoxypropyl)-3-oxo-3,4-dihydro-2H-benzo[b][1,4]oxazin-6-yl-* | H | 2-phenylpropan-2-yl-* | MS: [M + 1]⁺ = 565 HPLC: $^A t_{Ret}$ = 2.82 |
| 174 | methyl-* | 4-(3-methoxypropyl)-3-oxo-3,4-dihydro-2H-benzo[b][1,4]oxazin-6-yl-* | H | 2-phenylpropan-2-yl-* | MS: [M + 1]⁺ = 551 HPLC: $^A t_{Ret}$ = 2.68 |

-continued

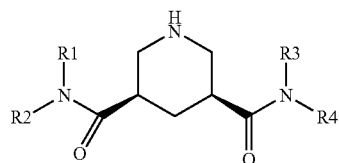

as represented in the following table:

| examples | R1 | R2 | R3 | R4 | Analytical data |
|---|---|---|---|---|---|
| 175 | cyclopropyl | 3-methoxypropyl-(3-oxo-benzo[1,4]oxazin-4-yl) | H | (5-methylpyrazin-2-yl)methyl | MS: [M + 1]⁺ = 565 HPLC: $^At_{Ret}$ = 2.20 |
| 176 | cyclopropyl | (chroman-5-yloxy)propyl methyl ether substituent | H | 1-phenylcyclopentyl | MS: [M + 1]⁺ = 590 HPLC: $^At_{Ret}$ = 3.13 |
| 177 | cyclopropyl | (quinolin-4-yloxy)propyl methyl ether substituent | H | 1-phenylcyclopentyl | MS: [M + 1]⁺ = 585 HPLC: $^At_{Ret}$ = 2.43 |
| 178 | cyclopropyl | (2,5-dimethylphenoxy)propyl methyl ether substituent | H | 2-hydroxy-2-methyl-1-phenylpropyl | MS: [M + 1]⁺ = 538 HPLC: $^Ct_{Ret}$ = 3.0 |

-continued

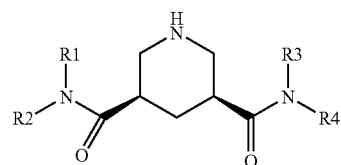

as represented in the following table:

| examples | R1 | R2 | R3 | R4 | Analytical data |
|---|---|---|---|---|---|
| 179 | cyclopropyl | 3-methoxypropoxy-2-methylphenyl | H | 4-(tetrahydropyran-4-yl)propan-2-yl | MS: $[M+1]^+ = 516$ HPLC: $c_{t_{Ret}} = 2.79$ |
| 180 | cyclopropyl | 4-(3-methoxypropyl)-2,2-dimethyl-3-oxo-benzo[1,4]oxazin-6-yl | H | (5-methylisoxazol-3-yl)methyl | MS: $[M+1]^+ = 554$ HPLC: $c_{t_{Ret}} = 2.56$ |
| 181 | cyclopropyl | 4-(3-methoxypropyl)-2,2-dimethyl-3-oxo-benzo[1,4]oxazin-6-yl | H | (1S,2S)-2-hydroxycyclopentyl | MS: $[M+1]^+ = 543$ HPLC: $c_{t_{Ret}} = 2.33$ |
| 182 | cyclopropyl | 4-(3-methoxypropyl)-2,2-dimethyl-3-oxo-benzo[1,4]oxazin-6-yl | H | (1R,2R)-2-hydroxycyclopentyl | MS: $[M+1]^+ = 543$ HPLC: $c_{t_{Ret}} = 2.46$ |

-continued

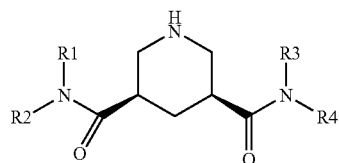

as represented in the following table:

| examples | R1 | R2 | R3 | R4 | Analytical data |
|---|---|---|---|---|---|
| 183 | cyclopropyl* | 3-methoxypropoxy-chroman-7-ylmethyl* | H | 1-methyl-4-phenylpiperidin-4-yl* | MS: [M + 1]⁺ = 619 HPLC: $^C t_{Ret}$ = 2.62 |
| 184 | cyclopropyl* | 4-(3-methoxypropyl)-2,2-dimethyl-3-oxo-benzo[1,4]oxazin-6-yl* | H | 1-phenylcyclopropyl* | MS: [M + 1]⁺ = 575 HPLC: $^C t_{Ret}$ = 2.94 |
| 185 | cyclopropyl* | 4-(3-methoxypropyl)-2,2-dimethyl-3-oxo-benzo[1,4]oxazin-6-yl* | H | 1-phenylcyclopentyl* | MS: [M + 1]⁺ = 603 HPLC: $^C t_{Ret}$ = 2.87 |
| 186 | cyclopropyl* | 3-methoxypropoxy-chroman-7-ylmethyl* | H | 2-(tetrahydropyran-4-yl)propan-2-yl* | MS: [M + 1]⁺ = 572 HPLC: $^A t_{Ret}$ = 2.57 |

-continued

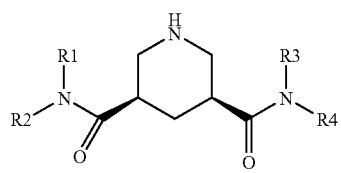

as represented in the following table:

| examples | R1 | R2 | R3 | R4 | Analytical data |
|---|---|---|---|---|---|
| 187 | cyclopropyl | 4-(3-methoxypropyl)-2,2-dimethyl-3-oxo-3,4-dihydro-2H-benzo[1,4]oxazin-6-yl | H | 4-(pent-3-yl)tetrahydropyran-4-yl | MS: [M + 1]$^+$ = 613 HPLC: c$t_{Ret}$ = 3.01 |
| 188 | cyclopropyl | 2-(3-methoxypropoxy)-5-methylphenyl | H | (S)-1-methoxy-3-methylbutan-2-yl | MS: [M + 1]$^+$ = 504 HPLC: c$t_{Ret}$ = 3.26 |
| 189 | cyclopropyl | 4-(3-methoxypropanoyl)-2,2-dimethyl-3,4-dihydro-2H-benzo[1,4]oxazin-6-yl | H | 2-phenylpropan-2-yl | MS: [M + 1]$^+$ = 577 HPLC: c$t_{Ret}$ = 2.99 |
| 190 | cyclopropyl | 2,2-dimethyl-3-oxo-3,4-dihydro-2H-benzo[1,4]oxazin-6-yl | H | 1-phenylcyclopentyl | MS: [M + 1]$^+$ = 531 HPLC: c$t_{Ret}$ = 3.00 |
| 191 | cyclopropyl | 4-(3-methoxypropyl)-2,2-dimethyl-3-oxo-3,4-dihydro-2H-benzo[1,4]oxazin-6-yl | H | tetrahydropyran-3-yl (racemate) | MS: [M + 1]$^+$ = 542 HPLC: c$t_{Ret}$ = 2.53, 2.57 |

-continued

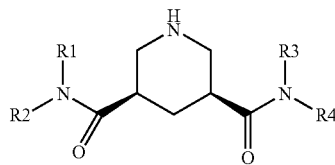

as represented in the following table:

| examples | R1 | R2 | R3 | R4 | Analytical data |
|---|---|---|---|---|---|
| 192 | cyclopropyl* | 3-(2,2-dimethyl-3-oxo-2,3-dihydro-4H-benzo[1,4]oxazin-4-yl)propyl, methoxy substituent* | H | (S)-2-methoxy-2-methyl-1-phenylethyl* | MS: [M + 1]⁺ = 621  HPLC: c$t_{Ret}$ = 3.20 |
| 193 | cyclopropyl* | 3-(chroman-5-yloxy)propyl with 7-methyl substituent* | H | (S)-N,N,4-trimethylpentan-2-yl* | MS: [M + 1]⁺ = 573  HPLC: c$t_{Ret}$ = 2.67 |
| 194 | cyclopropyl* | 3-(2,2-dimethyl-3-oxo-2,3-dihydro-4H-benzo[1,4]oxazin-4-yl)propyl, methoxy substituent* | H | (R)-2-methoxy-2-methyl-1-phenylethyl* | MS: [M + 1]⁺ = 621  HPLC: c$t_{Ret}$ = 3.18 |
| 195 | cyclopropyl* | 3-((5-methylpyrimidin-4-yl)oxy)propyl, 2-methoxy* | H | 2-methyl-1-phenylpropan-2-yl* | MS: [M + 1]⁺ = 510  HPLC: c$t_{Ret}$ = 2.86 |

-continued

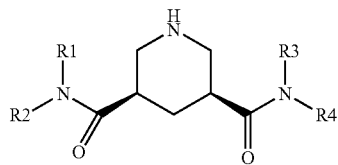

as represented in the following table:

| examples | R1 | R2 | R3 | R4 | Analytical data |
|---|---|---|---|---|---|
| 196 | cyclopropyl* | 3-(2,2-dimethyl-3-oxo-2,3-dihydro-4H-benzo[1,4]oxazin-4-yl)propyl with methoxy | H | *CH(iPr)(Me) (S) | MS: [M + 1]⁺ = 529 HPLC: c$t_{Ret}$ = 2.89 |
| 197 | cyclopropyl* | 3-(2,2-dimethyl-3-oxo-2,3-dihydro-4H-benzo[1,4]oxazin-4-yl)propyl with methoxy | H | *CH(Me)(4-MeO-C₆H₄) | MS: [M + 1]⁺ = 593 HPLC: c$t_{Ret}$ = 2.96 |
| 198 | cyclopropyl* | 3-(2,2-dimethyl-3-oxo-2,3-dihydro-4H-benzo[1,4]oxazin-4-yl)propyl with methoxy | H | *CH(iPr)(Me) (R) | MS: [M + 1]⁺ = 529 HPLC: c$t_{Ret}$ = 2.87 |
| 199 | cyclopropyl* | 3-(2,2-dimethyl-3-oxo-2,3-dihydro-4H-benzo[1,4]oxazin-4-yl)propyl with methoxy | H | *CH(Me)(4-MeO-C₆H₄) | MS: [M + 1]⁺ = 593 HPLC: c$t_{Ret}$ = 2.97 |

-continued

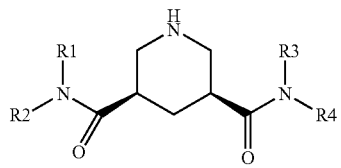

as represented in the following table:

| examples | R1 | R2 | R3 | R4 | Analytical data |
|---|---|---|---|---|---|
| 200 | cyclopropyl | 3-(2,2-dimethyl-3-oxo-2,3-dihydro-4H-benzo[1,4]oxazin-4-yl)propyl, linked at 6-position | H | 1-carbamoylcyclopentyl | MS: [M + 1]$^+$ = 570 HPLC: $c_{t_{Ret}}$ = 2.54 |
| 201 | cyclopropyl | 3-(2-oxo-3,4-dihydro-2H-quinolin-1-yl)propyl with methoxy, linked at 7-position | H | 2-(tetrahydropyran-4-yl)propan-2-yl | MS: [M + 1]$^+$ = 555 HPLC: $c_{t_{Ret}}$ = 2.40 |
| 202 | cyclopropyl | 3-(2-oxo-3,4-dihydro-2H-quinolin-1-yl)propyl with methoxy, linked at 7-position | H | (S)-1-phenylethyl | MS: [M + 1]$^+$ = 533 HPLC: $c_{t_{Ret}}$ = 2.66 |
| 203 | cyclopropyl | (3-methoxy-2-methyl-5-(3-methoxypropoxy)phenyl)methyl | H | 1-phenylcyclopentyl | MS: [M + 1]$^+$ = 578 HPLC: $c_{t_{Ret}}$ = 3.60 |

-continued

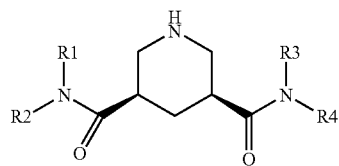

as represented in the following table:

| examples | R1 | R2 | R3 | R4 | Analytical data |
|---|---|---|---|---|---|
| 204 | cyclopropyl | 3-(3-methoxypropoxy)-4-methoxy-5-methylbenzyl (methoxypropoxy methylphenyl) | H | (S)-1-phenylethyl | MS: [M + 1]⁺ = 538 HPLC: c$t_{Ret}$ = 3.28 |
| 205 | cyclopropyl | 2,2-dimethyl-3-oxo-4-(3-methoxypropyl)-3,4-dihydro-2H-benzo[1,4]oxazin-6-ylmethyl | H | 1-acetyl-4-phenylpiperidin-4-yl | MS: [M + 1]⁺ = 660 HPLC: c$t_{Ret}$ = 2.75 |
| 206 | cyclopropyl | 2,2-dimethyl-3-oxo-4-(3-methoxypropyl)-3,4-dihydro-2H-benzo[1,4]oxazin-6-ylmethyl | H | 1-methanesulfonyl-4-phenylpiperidin-4-yl | MS: [M + 1]⁺ = 696 HPLC: c$t_{Ret}$ = 2.99 |
| 207 | isopropyl | 2,2-dimethyl-3-oxo-4-(3-methoxypropyl)-3,4-dihydro-2H-benzo[1,4]oxazin-6-ylmethyl | H | 2-phenylpropan-2-yl | MS: [M + 1]⁺ = 579 HPLC: c$t_{Ret}$ = 3.20 |

-continued

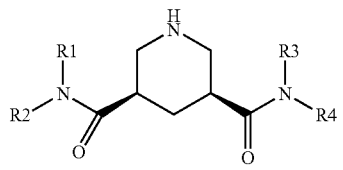

as represented in the following table:

| examples | R1 | R2 | R3 | R4 | Analytical data |
|---|---|---|---|---|---|
| 208 | cyclopropyl | 2,2-dimethyl-4-(2-methoxyethyl)-3-oxo-3,4-dihydro-2H-benzo[1,4]oxazin-6-yl | H | (2S)-1-(dimethylamino)-4-methylpentan-2-yl | MS: [M + 1]⁺ = 586 HPLC: A t_Ret = 2.25 |
| 209 | cyclopropyl | 2,2-dimethyl-4-(3-methoxypropyl)-3-oxo-3,4-dihydro-2H-benzo[1,4]oxazin-6-yl | H | 1-cyclohexylethyl | MS: [M + 1]⁺ = 569 HPLC: C t_Ret = 3.27 |
| 210 | cyclopropyl | 2,2-dimethyl-4-(3-methoxypropyl)-3-oxo-3,4-dihydro-2H-benzo[1,4]oxazin-6-yl | H | cyclopropyl | MS: [M + 1]⁺ = 499 HPLC: C t_Ret = 2.53 |
| 211 | cyclopropyl | 2,2-dimethyl-4-(3-methoxypropyl)-3-oxo-3,4-dihydro-2H-benzo[1,4]oxazin-6-yl | H | 2-phenylcyclopropyl | MS: [M + 1]⁺ = 575 HPLC: C t_Ret = 3.08 |

-continued

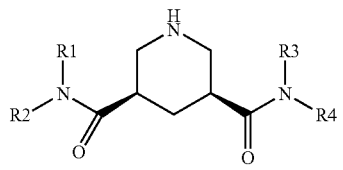

as represented in the following table:

| examples | R1 | R2 | R3 | R4 | Analytical data |
|---|---|---|---|---|---|
| 212 | cyclopropyl | 3-(2,2-dimethyl-3-oxo-2,3-dihydro-4H-benzo[1,4]oxazin-4-yl)propyl with methoxy | H | cyclobutyl | MS: [M + 1]⁺ = 513 HPLC: c$t_{Ret}$ = 2.71 |
| 213 | cyclopropyl | 3-(2,2-dimethyl-3-oxo-2,3-dihydro-4H-benzo[1,4]oxazin-4-yl)propyl with methoxy | H | 1-(methoxymethyl)cyclopropyl | MS: [M + 1]⁺ = 543 HPLC: c$t_{Ret}$ = 2.54 |
| 214 | cyclopropyl | 3-(2,2-dimethyl-3-oxo-2,3-dihydro-4H-benzo[1,4]oxazin-4-yl)propyl with methoxy | H | 2-methoxycyclopentyl | MS: [M + 1]⁺ = 557 HPLC: c$t_{Ret}$ = 2.69 |
| 215 | cyclopropyl | 3-(2,2-dimethyl-3-oxo-2,3-dihydro-4H-benzo[1,4]oxazin-4-yl)propyl with methoxy | H | 1-(tetrahydropyran-4-yl)ethyl racemate | MS: [M + 1]⁺ = 570 HPLC: c$t_{Ret}$ = 2.59, 2.65 |

-continued

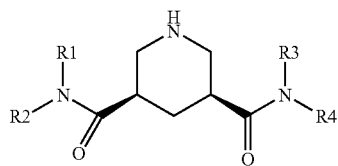

as represented in the following table:

| examples | R1 | R2 | R3 | R4 | Analytical data |
|---|---|---|---|---|---|
| 216 | cyclopropyl* | 3-(3-methoxyphenoxy)propoxy-5-methoxybenzyl* | H | 1-phenylcyclopentyl* | MS: [M + 1]$^+$ = 564 HPLC: c$^t_{Ret}$ = 3.29 |
| 217 | cyclopropyl* | 3-(2,2-dimethyl-3-oxo-2,3-dihydro-4H-benzo[1,4]oxazin-4-yl)propyl with 3-methoxy* | H | 1-cyanocyclopentyl* | MS: [M + 1]$^+$ = 552 HPLC: c$^t_{Ret}$ = 2.79 |
| 218 | cyclopropyl* | 3-(2,2-dimethyl-3-oxo-2,3-dihydro-4H-benzo[1,4]oxazin-4-yl)propyl with 3-methoxy* | H | isopropyl* | MS: [M + 1]$^+$ = 501 HPLC: c$^t_{Ret}$ = 2.63 |
| 219 | cyclopropyl* | 3-(2,2-dimethyl-3-oxo-2,3-dihydro-4H-benzo[1,4]oxazin-4-yl)propyl with 3-methoxy* | H | 2-hydroxyethyl* | MS: [M + 1]$^+$ = 503 HPLC: c$^t_{Ret}$ = 2.30 |

-continued

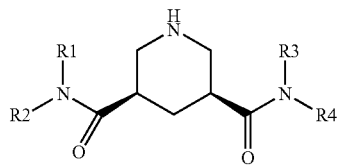

as represented in the following table:

| examples | R1 | R2 | R3 | R4 | Analytical data |
|---|---|---|---|---|---|
| 220 | cyclopropyl* | 3-(2,2-dimethyl-3-oxo-2,3-dihydro-4H-benzo[1,4]oxazin-4-yl)propyl with methoxy | H | 2-ethoxyethyl* | MS: $[M+1]^+$ = 531 HPLC: $c_{t_{Ret}}$ = 2.58 |
| 221 | cyclopropyl* | 3-(2,2-dimethyl-3-oxo-2,3-dihydro-4H-benzo[1,4]oxazin-4-yl)propyl with methoxy | H | trans-2-ethoxycyclopentyl* | MS: $[M+1]^+$ = 571 HPLC: $c_{t_{Ret}}$ = 2.81 |
| 222 | cyclopropyl* | 2-(2,2-dimethyl-3-oxo-2,3-dihydro-4H-benzo[1,4]oxazin-4-yl)ethyl with ethoxy | H | 1-(ethoxymethyl)-3-methylbutyl* | MS: $[M+1]^+$ = 587 HPLC: $c_{t_{Ret}}$ = 3.17 |
| 223 | cyclopropyl* | 3-(2,2-dimethyl-3-oxo-2,3-dihydro-4H-benzo[1,4]oxazin-4-yl)propyl with methoxy | H | 2,6-dimethylcyclohexyl* cis-trans-mix. | MS: $[M+1]^+$ = 569 HPLC: $c_{t_{Ret}}$ = 3.20 |

-continued

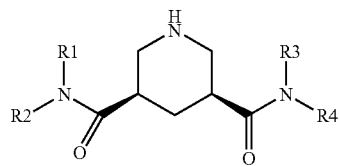

as represented in the following table:

| examples | R1 | R2 | R3 | R4 | Analytical data |
|---|---|---|---|---|---|
| 224 | cyclopropyl | 3-(2,2-dimethyl-3-oxo-2,3-dihydro-4H-benzo[1,4]oxazin-4-yl)propyl with methoxy | H | (S)-1-phenylpropyl | MS: [M + 1]$^+$ = 577 HPLC: c$t_{Ret}$ = 3.13 |
| 225 | cyclopropyl | 3-(2,2-dimethyl-3-oxo-2,3-dihydro-4H-benzo[1,4]oxazin-4-yl)propyl with methoxy | H | (S)-1-phenylpropyl | MS: [M + 1]$^+$ = 577 HPLC: c$t_{Ret}$ = 3.12 |
| 226 | cyclopropyl | 2-(2,2-dimethyl-3-oxo-2,3-dihydro-4H-benzo[1,4]oxazin-4-yl)ethyl with methoxy | H | 1-methoxy-3-methylbutan-2-yl | MS: [M + 1]$^+$ = 573 HPLC: c$t_{Ret}$ = 3.03 |
| 227 | cyclopropyl | 2-(2,2-dimethyl-3-oxo-2,3-dihydro-4H-benzo[1,4]oxazin-4-yl)ethyl with methoxy | H | 1-(tetrahydro-2H-pyran-4-yl)cyclopropyl | MS: [M + 1]$^+$ = 583 HPLC: c$t_{Ret}$ = 2.67 |

-continued

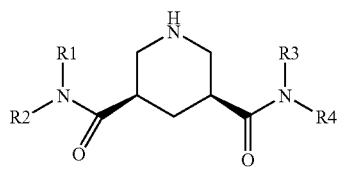

as represented in the following table:

| examples | R1 | R2 | R3 | R4 | Analytical data |
|---|---|---|---|---|---|
| 228 | cyclopropyl | 2-(2,2-dimethyl-3-oxo-2,3-dihydro-4H-benzo[1,4]oxazin-4-yl)ethoxyethyl | H | (S)-1-ethoxymethyl-3-methylbutyl | MS: [M + 1]⁺ = 587 HPLC: $^C t_{Ret} = 2.78$ |
| 229 | cyclopropyl | 3-(2,2-dimethyl-3-oxo-2,3-dihydro-4H-benzo[1,4]oxazin-4-yl)propyl methyl ether | H | 1-(isobutyl)cyclopropylmethyl | MS: [M + 1]⁺ = 555 HPLC: $^C t_{Ret} = 3.04$ |
| 230 | cyclopropyl | 3-(2,2-dimethyl-3-oxo-2,3-dihydro-4H-benzo[1,4]oxazin-4-yl)propyl methyl ether | H | 1-(methoxymethyl)cyclopentyl | MS: [M + 1]⁺ = 571 HPLC: $^A t_{Ret} = 2.50$ |
| 231 | cyclopropyl | 2-(2,2-dimethyl-3-oxo-2,3-dihydro-4H-benzo[1,4]oxazin-4-yl)ethoxyethyl | H | (S)-2-methoxy-2-methyl-1-phenylpropyl | MS: [M + 1]⁺ = 621 HPLC: $^A t_{Ret} = 2.87$ |

-continued

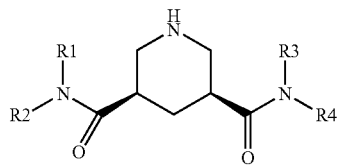

as represented in the following table:

| examples | R1 | R2 | R3 | R4 | Analytical data |
|---|---|---|---|---|---|
| 232 | cyclopropyl | 3-(2,2-dimethyl-3-oxo-2,3-dihydro-benzo[1,4]oxazin-4-yl)propyl with methoxy | H | trans-2-hydroxycyclohexyl | MS: [M + 1]$^+$ = 557 HPLC: $c_{tRet}$ = 2.52 |
| 233 | cyclopropyl | 3-(2,2-dimethyl-3-oxo-2,3-dihydro-benzo[1,4]oxazin-4-yl)propyl with methoxy | H | (1-methoxycyclohexyl)methyl | MS: [M + 1]$^+$ = 585 HPLC: $c_{tRet}$ = 2.85 |
| 234 | cyclopropyl | 3-(2,2-dimethyl-3-oxo-2,3-dihydro-benzo[1,4]oxazin-4-yl)propyl with methoxy | H | 1-cyclohexylethyl | MS: [M + 1]$^+$ = 569 HPLC: $c_{tRet}$ = 3.19 |
| 235 | cyclopropyl | 3-(2,2-dimethyl-3-oxo-2,3-dihydro-benzo[1,4]oxazin-4-yl)propyl with methoxy | H | trans-2-ethoxycyclohexyl | MS: [M + 1]$^+$ = 585 HPLC: $c_{tRet}$ = 2.79 |

-continued

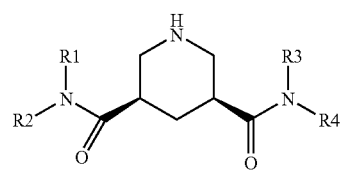

as represented in the following table:

| examples | R1 | R2 | R3 | R4 | Analytical data |
|---|---|---|---|---|---|
| 236 | cyclopropyl | 4-(3-methoxypropyl)-2,2-dimethyl-3-oxo-3,4-dihydro-2H-benzo[1,4]oxazin-6-yl | H | 1-(4-fluorophenyl)cyclopropyl | MS: $[M+1]^+ = 593$ HPLC: $c_{tRet} = 3.04$ |
| 237 | cyclopropyl | 4-(3-methoxypropyl)-2,2-dimethyl-3-oxo-3,4-dihydro-2H-benzo[1,4]oxazin-6-yl | H | 1-(ethoxymethyl)cyclopropyl | MS: $[M+1]^+ = 557$ HPLC: $c_{tRet} = 2.65$ |
| 238 | cyclopropyl | 4-(2-ethoxyethyl)-2,2-dimethyl-3-oxo-3,4-dihydro-2H-benzo[1,4]oxazin-6-yl | H | 1-(methoxymethyl)cyclopropyl | MS: $[M+1]^+ = 543$ HPLC: $c_{tRet} = 2.60$ |
| 239 | cyclopropyl | 4-(3-methoxypropyl)-2,2-dimethyl-3-oxo-3,4-dihydro-2H-benzo[1,4]oxazin-6-yl | H | tert-butyl | MS: $[M+1]^+ = 515$ HPLC: $c_{tRet} = 2.79$ |

-continued

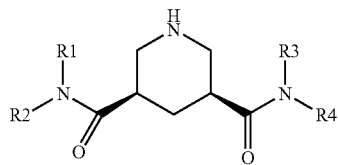

as represented in the following table:

| examples | R1 | R2 | R3 | R4 | Analytical data |
|---|---|---|---|---|---|
| 240 | cyclopropyl-* | 4-(2-ethoxyethyl)-2,2-dimethyl-3-oxo-3,4-dihydro-2H-benzo[1,4]oxazin-6-yl | H | (S)-1-methoxy-3-methylbutan-2-yl | MS: $[M+1]^+ =$ 573 HPLC: $ct_{Ret} = 3.07$ |
| 241 | cyclopropyl-* | 4-(3-methoxypropyl)-2,2-dimethyl-3-oxo-3,4-dihydro-2H-benzo[1,4]oxazin-6-yl | H | (S)-1-ethoxy-3-methylbutan-2-yl | MS: $[M+1]^+ =$ 587 HPLC: $ct_{Ret} = 3.09$ |
| 242 | cyclopropyl-* | 2,2-dimethyl-3-oxo-3,4-dihydro-2H-benzo[1,4]oxazin-6-yl | H | 1-ethoxy-3-methylbutan-2-yl | MS: $[M+1]^+ =$ 515 HPLC: $ct_{Ret} = 2.84$ |
| 243 | cyclopropyl-* | 4-(3-methoxypropyl)-2,2-dimethyl-3-oxo-3,4-dihydro-2H-benzo[1,4]oxazin-6-yl | H | cycloheptyl | MS: $[M+1]^+ =$ 555 HPLC: $ct_{Ret} = 3.06$ |

-continued

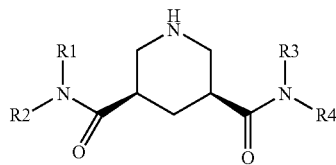

as represented in the following table:

| examples | R1 | R2 | R3 | R4 | Analytical data |
|---|---|---|---|---|---|
| 244 | cyclopropyl | 3-methoxypropyl-dimethyl-benzoxazinone | H | ethoxymethyl-cyclopentyl | MS: [M + 1]+ = 585 HPLC: c$t_{Ret}$ = 3.03 |
| 245 | cyclopropyl | 3-methoxypropyl-dimethyl-benzoxazinone | H | 2,2-dimethyl-3-methoxypropyl | MS: [M + 1]+ = 545 HPLC: c$t_{Ret}$ = 2.73 |
| 246 | cyclopropyl | 3-methoxypropyl-dimethyl-benzoxazinone | H | 2,2-dimethyl-3-ethoxypropyl | MS: [M + 1]+ = 559 HPLC: c$t_{Ret}$ = 2.88 |
| 247 | cyclopropyl | N,2,2-trimethyl-benzoxazinone | H | 1-ethoxymethyl-3-methylbutyl | MS: [M + 1]+ = 529 HPLC: c$t_{Ret}$ = 2.93 |

-continued

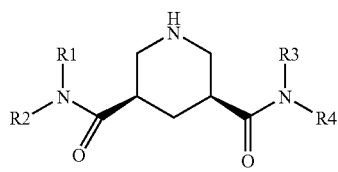

as represented in the following table:

| examples | R1 | R2 | R3 | R4 | Analytical data |
|---|---|---|---|---|---|
| 248 | cyclopropyl | 4-chloro-2-(3-methoxypropoxy)phenyl | H | (R)-1-phenylethyl | MS: [M + 1]⁺ = 514 HPLC: $c_{t_{Ret}} = 3.15$ |
| 249 | cyclopropyl | 4-fluoro-5-methyl-2-(3-methoxypropoxy)phenyl | H | (R)-1-phenylethyl | MS: [M + 1]⁺ = 512 HPLC: $c_{t_{Ret}} = 3.18$ |
| 250 | cyclopropyl | 4-(3-methoxypropyl)-2,2-dimethyl-3-oxo-3,4-dihydro-2H-benzo[1,4]oxazin-6-yl | H | 1-methylcyclohexyl | MS: [M + 1]⁺ = 555 HPLC: $c_{t_{Ret}} = 3.11$ |
| 251 | cyclopropyl | 4-(2-ethoxyethyl)-2,2-dimethyl-3-oxo-3,4-dihydro-2H-benzo[1,4]oxazin-6-yl | H | (1R,2S)-2-ethoxycyclopentyl | MS: [M + 1]⁺ = 571 HPLC: $c_{t_{Ret}} = 2.81$ |

-continued

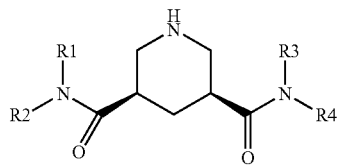

as represented in the following table:

| examples | R1 | R2 | R3 | R4 | Analytical data |
|---|---|---|---|---|---|
| 252 | cyclopropyl-* | 4-(3-methoxypropyl)-2,2-dimethyl-3-oxo-3,4-dihydro-2H-benzo[1,4]oxazin-6-yl-* | H | (S)-1-ethoxymethyl-2-methylpropyl-* | MS: $[M+1]^+$ = 573 HPLC: $c_{t_{Ret}}$ = 2.92 |
| 253 | cyclopropyl-* | 4-(3-methoxypropyl)-2,2-dimethyl-3-oxo-3,4-dihydro-2H-benzo[1,4]oxazin-6-yl-* | H | (S)-1-methoxymethyl-2-methylpropyl-* | MS: $[M+1]^+$ = 559 HPLC: $c_{t_{Ret}}$ = 2.74 |
| 254 | cyclopropyl-* | 4-(3-methoxypropyl)-2,2-dimethyl-3-oxo-3,4-dihydro-2H-benzo[1,4]oxazin-6-yl-* | H | (R)-2-ethoxy-1-phenylethyl-* | MS: $[M+1]^+$ = 607 HPLC: $c_{t_{Ret}}$ = 3.08 |
| 255 | cyclopropyl-* | 4-(3-methoxypropyl)-2,2-dimethyl-3-oxo-3,4-dihydro-2H-benzo[1,4]oxazin-6-yl-* | H | 2-ethoxyindan-1-yl-* | MS: $[M+1]^+$ = 619 HPLC: $c_{t_{Ret}}$ = 3.13 |

-continued

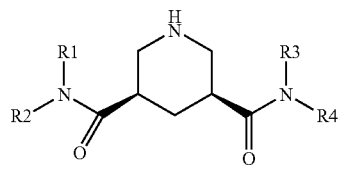

as represented in the following table:

| examples | R1 | R2 | R3 | R4 | Analytical data |
|---|---|---|---|---|---|
| 256 | cyclopropyl | 2-(2,2-dimethyl-3-oxo-2,3-dihydro-4H-benzo[1,4]oxazin-4-yl)ethoxyethyl | H | 2-methyl-2-phenylpropyl | MS: [M + 1]$^+$ = 577 HPLC: c$t_{Ret}$ = 3.14 |
| 257 | cyclopropyl | 3-(2,2-dimethyl-3-oxo-2,3-dihydro-4H-benzo[1,4]oxazin-4-yl)propyl methoxy | H | (1-methoxy-2-phenyl)ethyl | MS: [M + 1]$^+$ = 593 HPLC: c$t_{Ret}$ = 2.94 |
| 258 | cyclopropyl | 3-(2,2-dimethyl-3-oxo-2,3-dihydro-4H-benzo[1,4]oxazin-4-yl)propyl methoxy | H | 2-ethoxy-indanyl | MS: [M + 1]$^+$ = 619 HPLC: c$t_{Ret}$ = 3.20 |
| 259 | cyclopropyl | 3-(2,2-dimethyl-3-oxo-2,3-dihydro-4H-benzo[1,4]oxazin-4-yl)propyl methoxy | H | 2-methyl-1-carbamoyl-propyl | MS: [M + 1]$^+$ = 544 HPLC: c$t_{Ret}$ = 2.38 |

-continued

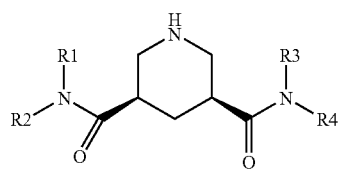

as represented in the following table:

| examples | R1 | R2 | R3 | R4 | Analytical data |
|---|---|---|---|---|---|
| 260 | cyclopropyl | 4-(3-methoxypropyl)-2,2-dimethyl-3-oxo-3,4-dihydro-2H-benzo[1,4]oxazin-6-yl | H | (1S)-2,2-dimethylcyclohexyl | MS: $[M+1]^+ =$ 569 HPLC: $c_{t_{Ret}} = 3.19$ |
| 261 | cyclopropyl | 4-(3-methoxypropyl)-2,2-dimethyl-3-oxo-3,4-dihydro-2H-benzo[1,4]oxazin-6-yl | H | (S)-1-(ethoxymethyl)-2-methylpropyl | MS: $[M+1]^+ =$ 573 HPLC: $c_{t_{Ret}} = 2.97$ |
| 262 | cyclopropyl | 4-(3-methoxypropyl)-2,2-dimethyl-3-oxo-3,4-dihydro-2H-benzo[1,4]oxazin-6-yl | H | (S)-2-ethoxy-1-phenylethyl | MS: $[M+1]^+ =$ 607 HPLC: $c_{t_{Ret}} = 3.06$ |
| 263 | cyclopropyl | 4-(3-methoxypropyl)-2,2-dimethyl-3-oxo-3,4-dihydro-2H-benzo[1,4]oxazin-6-yl | H | (1R)-2,2-dimethylcyclohexyl | MS: $[M+1]^+ =$ 569 HPLC: $c_{t_{Ret}} = 3.19$ |

-continued

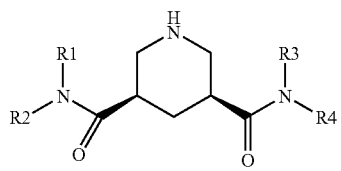

as represented in the following table:

| examples | R1 | R2 | R3 | R4 | Analytical data |
|---|---|---|---|---|---|
| 264 | cyclopropyl* | 3-(2,2-dimethyl-3-oxo-2,3-dihydro-4H-benzo[1,4]oxazin-4-yl)propyl, 6-position* | H | (1S,2R)-2-ethoxy-2,3-dihydro-1H-inden-1-yl* | MS: [M + 1]$^+$ = 619 HPLC: c$t_{Ret}$ = 3.05 |
| 265 | cyclopropyl* | 3-(2,2-dimethyl-3-oxo-2,3-dihydro-4H-benzo[1,4]oxazin-4-yl)propyl* | H | 3-methoxy-2,2-dimethyl-propoxymethyl* | MS: [M + 1]$^+$ = 575 HPLC: c$t_{Ret}$ = 2.73 |
| 266 | cyclopropyl* | 3-(2,2-dimethyl-3-oxo-2,3-dihydro-4H-benzo[1,4]oxazin-4-yl)propyl* | H | (S)-1-methoxypropan-2-yl* | MS: [M + 1]$^+$ = 531 HPLC: c$t_{Ret}$ = 2.54 |
| 267 | cyclopropyl* | 3-(2,2-dimethyl-3-oxo-2,3-dihydro-4H-benzo[1,4]oxazin-4-yl)propyl* | H | (S)-1-ethoxypropan-2-yl* | MS: [M + 1]$^+$ = 545 HPLC: c$t_{Ret}$ = 2.68 |

-continued

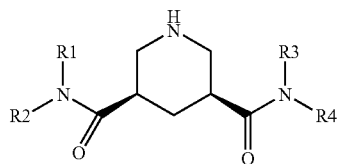

as represented in the following table:

| examples | R1 | R2 | R3 | R4 | Analytical data |
|---|---|---|---|---|---|
| 268 | cyclopropyl | 4-(3-methoxypropyl)-2,2-dimethyl-3-oxo-3,4-dihydro-2H-benzo[1,4]oxazin-6-yl | H | (S)-1-ethoxypropan-2-yl | MS: [M + 1]$^+$ = 545 HPLC: c$t_{Ret}$ = 2.68 |
| 269 | cyclopropyl | 4-(3-methoxypropoxy)-5-isopropylpyridin-2-yl | H | 1-phenylcyclopentyl | MS: [M + 1]$^+$ = 563 HPLC: c$t_{Ret}$ = 3.48 |
| 270 | cyclopropyl | 4-(3-methoxypropyl)-2,2-dimethyl-3-oxo-3,4-dihydro-2H-benzo[1,4]oxazin-6-yl | H | (S)-2-methoxy-1-phenylethyl | MS: [M + 1]$^+$ = 593 HPLC: c$t_{Ret}$ = 2.90 |
| 271 | cyclopropyl | 4-(3-methoxypropyl)-2,2-dimethyl-3-oxo-3,4-dihydro-2H-benzo[1,4]oxazin-6-yl | H | 2-ethoxy-2,3-dihydro-1H-inden-1-yl | MS: [M + 1]$^+$ = 619 HPLC: c$t_{Ret}$ = 2.70 |

-continued

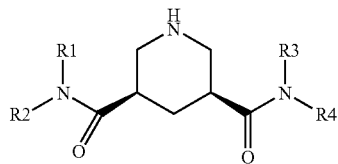

as represented in the following table:

| examples | R1 | R2 | R3 | R4 | Analytical data |
|---|---|---|---|---|---|
| 272 | cyclopropyl | 4-(3-methoxypropyl)-2,2-dimethyl-3-oxo-3,4-dihydro-2H-benzo[1,4]oxazin-6-yl | H | (S)-1-methoxyprop-2-yl | MS: [M + 1]⁺ = 531 HPLC: $^c t_{Ret}$ = 2.58 |
| 273 | cyclopropyl | 4-(3-methoxypropyl)-2,2-dimethyl-3-oxo-3,4-dihydro-2H-benzo[1,4]oxazin-6-yl | H | (S)-1-methoxy-3-methylbut-2-yl | MS: [M + 1]⁺ = 559 HPLC: $^c t_{Ret}$ = 2.80 |
| 274 | cyclopropyl | 4-(3-methoxypropyl)-2,2-dimethyl-3-oxo-3,4-dihydro-2H-benzo[1,4]oxazin-6-yl | H | 2-cyano-2-methylprop-2-yl | MS: [M + 1]⁺ = 526 HPLC: $^c t_{Ret}$ = 2.63 |
| 275 | cyclopropyl | 4-(2-hydroxyethyl)-2,2-dimethyl-3-oxo-3,4-dihydro-2H-benzo[1,4]oxazin-6-yl | H | (S)-1-ethoxy-4-methylpent-2-yl | MS: [M + 1]⁺ = 559 HPLC: $^c t_{Ret}$ = 2.94 |

-continued

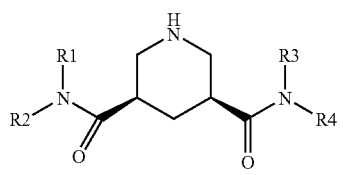

as represented in the following table:

| examples | R1 | R2 | R3 | R4 | Analytical data |
|---|---|---|---|---|---|
| 276 | cyclopropyl | 3-(3-methoxypropoxy)-5-isopropylpyridin-2-yl | H | (S)-1-ethoxy-4-methylpentan-2-yl | MS: [M + 1]$^+$ = 547 HPLC: $c_{t_{Ret}}$ = 2.86 |
| 277 | cyclopropyl | 4-(3-hydroxypropyl)-2,2-dimethyl-3-oxo-3,4-dihydro-2H-benzo[b][1,4]oxazin-6-yl | H | (S)-1-ethoxy-4-methylpentan-2-yl | MS: [M + 1]$^+$ = 573 HPLC: $c_{t_{Ret}}$ = 2.93 |
| 278 | cyclopropyl | 4-fluoro-5-(3-methoxypropoxy)-2-methylphenyl | H | (S)-1-ethoxy-4-methylpentan-2-yl | MS: [M + 1]$^+$ = 536 HPLC: $c_{t_{Ret}}$ = 3.41 |
| 279 | cyclopropyl | 4-fluoro-5-(3-methoxypropoxy)-2-methylphenyl | H | 1-(methoxymethyl)cyclopropyl | MS: [M + 1]$^+$ = 492 HPLC: $c_{t_{Ret}}$ = 2.79 |

-continued

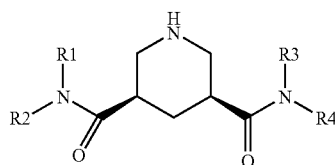

as represented in the following table:

| examples | R1 | R2 | R3 | R4 | Analytical data |
|---|---|---|---|---|---|
| 280 | cyclopropyl | 2-(2,2-dimethyl-3-oxo-2,3-dihydro-4H-benzo[1,4]oxazin-4-yl)ethyl (at 6-position) | H | (S)-1-(ethoxymethyl)-2-methylpropyl | MS: $[M+1]^+$ = 573 HPLC: $c_{t_{Ret}}$ = 3.07 |
| 281 | cyclopropyl | 3-(2,2-dimethyl-3-oxo-2,3-dihydro-4H-benzo[1,4]oxazin-4-yl)propyl (at 6-position) | H | (S)-1-cyclohexyl-2-ethoxyethyl | MS: $[M+1]^+$ = 613 HPLC: $c_{t_{Ret}}$ = 3.34 |
| 282 | cyclopropyl | 3-(2,2-dimethyl-3-oxo-2,3-dihydro-4H-benzo[1,4]oxazin-4-yl)propyl (at 6-position) | H | (R)-1-cyclohexyl-2-ethoxyethyl | MS: $[M+1]^+$ = 613 HPLC: $c_{t_{Ret}}$ = 3.39 |
| 283 | cyclopropyl | 3-(2,2-dimethyl-3-oxo-2,3-dihydro-4H-benzo[1,4]oxazin-4-yl)propyl (at 6-position) | H | (S)-sec-butyl | MS: $[M+1]^+$ = 515 HPLC: $c_{t_{Ret}}$ = 2.79 |

-continued

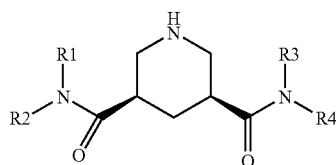

as represented in the following table:

| examples | R1 | R2 | R3 | R4 | Analytical data |
|---|---|---|---|---|---|
| 284 | cyclopropyl | 3-(2,2-dimethyl-3-oxo-2,3-dihydro-4H-benzo[1,4]oxazin-4-yl)propyl attached at 6-position | H | (S)-sec-butyl | MS: $[M+1]^+ =$ 515 HPLC: $c_{tRet} = 2.81$ |
| 285 | cyclopropyl | 2-(2,2-dimethyl-3-oxo-2,3-dihydro-4H-benzo[1,4]oxazin-4-yl)ethyl with 2-ethoxy | H | (S)-1-ethoxy-2-propyl | MS: $[M+1]^+ =$ 545 HPLC: $c_{tRet} = 2.82$ |
| 286 | cyclopropyl | 2-(2,2-dimethyl-3-oxo-2,3-dihydro-4H-benzo[1,4]oxazin-4-yl)ethyl with 2-ethoxy | H | 1-methoxy-3-methyl-2-butyl | MS: $[M+1]^+ =$ 559 HPLC: $c_{tRet} = 2.90$ |
| 287 | cyclopropyl | 3-(2,2-dimethyl-3-oxo-2,3-dihydro-4H-benzo[1,4]oxazin-4-yl)propyl with methoxy | H | (S)-1-methoxy-4-methyl-2-pentyl | MS: $[M+1]^+ =$ 573 HPLC: $c_{tRet} = 3.06$ |

-continued

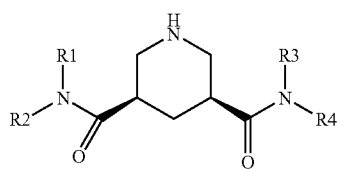

as represented in the following table:

| examples | R1 | R2 | R3 | R4 | Analytical data |
|---|---|---|---|---|---|
| 288 | cyclopropyl | 2-(2-methoxyethyl)-N-(2,2-dimethyl-3-oxo-2,3-dihydro-4H-benzo[b][1,4]oxazin-4-yl) | H | (S)-1-ethoxy-3-methylbutan-2-yl | MS: [M + 1]$^+$ = 572 HPLC: c$^t$$_{Ret}$ = 3.08 |
| 289 | cyclopropyl | 3-methoxypropyl-(2,2-dimethyl-3-oxo-2,3-dihydro-4H-benzo[b][1,4]oxazin-4-yl) | H | (S)-2-cyclohexyl-2-methoxyethyl | MS: [M + 1]$^+$ = 599 HPLC: c$^t$$_{Ret}$ = 3.18 |
| 290 | isopropyl | 3-methoxypropyl-(2,2-dimethyl-3-oxo-2,3-dihydro-4H-benzo[b][1,4]oxazin-4-yl) | H | (S)-1-ethoxy-3-methylbutan-2-yl | MS: [M + 1]$^+$ = 589 HPLC: c$^t$$_{Ret}$ = 3.34 |
| 291 | cyclopropyl | 4-(3-methoxypropoxy)-5-methylpyridin-2-yl | H | (S)-1-ethoxy-3-methylbutan-2-yl | MS: [M + 1]$^+$ = 519 HPLC: c$^t$$_{Ret}$ = 2.64 |
| 292 | cyclopropyl | 2-methoxyethyl-(2,2-dimethyl-3-oxo-2,3-dihydro-4H-benzo[b][1,4]oxazin-4-yl) | H | (S)-1-ethoxy-3-methylbutan-2-yl | MS: [M + 1]$^+$ = 573 HPLC: c$^t$$_{Ret}$ = 3.12 |

-continued

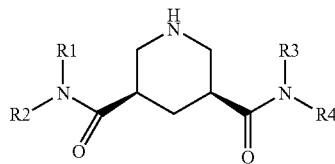

as represented in the following table:

| examples | R1 | R2 | R3 | R4 | Analytical data |
|---|---|---|---|---|---|
| 293 | cyclopropyl | 3-methoxypropoxy-(4-fluoro-2-methylphenyl) | H | (S)-1-ethoxy-2-methylpropyl | MS: [M + 1]⁺ = 494 HPLC: c$t_{Ret}$ = 2.98 |
| 294 | cyclopropyl | 4-(3-methoxypropyl)-2,2-dimethyl-3-oxo-3,4-dihydro-2H-benzo[1,4]oxazin-6-yl | H | (R)-1-ethoxy-3,3-dimethylbutan-2-yl | MS: [M + 1]⁺ = 687 HPLC: c$t_{Ret}$ = 4.26 |
| 295 | cyclopropyl | 4-(3-methoxypropyl)-2,2-dimethyl-3-oxo-3,4-dihydro-2H-benzo[1,4]oxazin-6-yl | H | (R)-1-methoxy-3,3-dimethylbutan-2-yl | MS: [M + 1]⁺ = 573 HPLC: c$t_{Ret}$ = 3.05 |
| 296 | cyclopropyl | 3-isopropyl-6-(3-methoxypropoxy)pyridin-2-yl | H | (S)-1-ethoxy-4-methylpentan-2-yl | MS: [M + 1]⁺ = 547 HPLC: c$t_{Ret}$ = 1.97 |

-continued

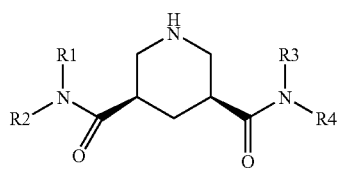

as represented in the following table:

| examples | R1 | R2 | R3 | R4 | Analytical data |
|---|---|---|---|---|---|
| 297 | cyclopropyl | 3-(2,2-dimethyl-3-oxo-2,3-dihydro-4H-benzo[1,4]oxazin-4-yl)propyl with methoxy | H | (S)-1-ethoxy-3,3-dimethylbutan-2-yl | MS: [M + 1]$^+$ = 587 HPLC: $^c t_{Ret}$ = 3.15 |
| 298 | cyclopropyl | 2-(2,2-dimethyl-3-oxo-2,3-dihydro-4H-benzo[1,4]oxazin-4-yl)ethyl with ethoxy | H | (ethoxymethyl)cyclopropyl | MS: [M + 1]$^+$ = 557 HPLC: $^c t_{Ret}$ = 2.82 |
| 299 | isopropyl | 3-(2,2-dimethyl-3-oxo-2,3-dihydro-4H-benzo[1,4]oxazin-4-yl)propyl with methoxy | H | (S)-1-methoxy-4-methylpentan-2-yl | MS: [M + 1]$^+$ = 575 HPLC: $^c t_{Ret}$ = 3.19 |
| 300 | cyclopropyl | 3-(2,2-dimethyl-3-oxo-2,3-dihydro-4H-benzo[1,4]oxazin-4-yl)propyl with methoxy | H | (R)-2-cyclohexyl-1-methoxyethyl | MS: [M + 1]$^+$ = 599 HPLC: $^c t_{Ret}$ = 3.33 |
| 301 | cyclopropyl | 2-(2,2-dimethyl-3-oxo-2,3-dihydro-4H-benzo[1,4]oxazin-4-yl)ethyl with ethoxy | H | (S)-1-methoxy-2-methylpropan-2-yl | MS: [M + 1]$^+$ = 531 HPLC: $^c t_{Ret}$ = 2.71 |

-continued

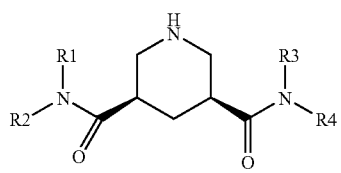

as represented in the following table:

| examples | R1 | R2 | R3 | R4 | Analytical data |
|---|---|---|---|---|---|
| 302 | isopropyl | 3-(2,2-dimethyl-3-oxo-2H-benzo[b][1,4]oxazin-4(3H)-yl)propyl, 6-yl attachment | H | (S)-1-ethoxy-3-methylbutan-2-yl | MS: [M + 1]$^+$ = 575<br>HPLC: $^c t_{Ret}$ = 3.20 |
| 303 | isopropyl | 3-(2,2-dimethyl-3-oxo-2H-benzo[b][1,4]oxazin-4(3H)-yl)propyl, 6-yl attachment | H | (S)-1-ethoxypropan-2-yl | MS: [M + 1]$^+$ = 547<br>HPLC: $^c t_{Ret}$ = 2.96 |
| 304 | cyclopropyl | 3-(2,2-dimethyl-3-oxo-2H-benzo[b][1,4]oxazin-4(3H)-yl)propyl, 6-yl attachment | H | (S)-1-cyclohexyl-3-ethoxypropan-2-yl | MS: [M + 1]$^+$ = 627<br>HPLC: $^c t_{Ret}$ = 3.61 |
| 305 | cyclopropyl | 3-(2,2-dimethyl-3-oxo-2H-benzo[b][1,4]oxazin-4(3H)-yl)propyl, 6-yl attachment | H | (S)-1-cyclohexyl-3-methoxypropan-2-yl | MS: [M + 1]$^+$ = 613<br>HPLC: $^c t_{Ret}$ = 3.43 |

-continued

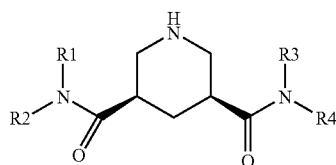

as represented in the following table:

| examples | R1 | R2 | R3 | R4 | Analytical data |
|---|---|---|---|---|---|
| 306 | cyclopropyl-* | 2,2-dimethyl-4-(3-methoxypropyl)-3-oxo-3,4-dihydro-2H-benzo[1,4]oxazin-6-yl-* | H | (S)-indan-1-yl-* | MS: [M + 1]⁺ = 575 HPLC: c$t_{Ret}$ = 3.13 |
| 307 | cyclopropyl-* | 2,2-dimethyl-4-(3-methoxypropyl)-3-oxo-3,4-dihydro-2H-benzo[1,4]oxazin-6-yl-* | H | (R)-indan-1-yl-* | MS: [M + 1]⁺ = 575 HPLC: c$t_{Ret}$ = 3.10 |
| 308 | cyclopropyl-* | 4-ethyl-5-fluoro-2-(3-methoxypropoxy)-phenyl-* | H | (S)-1-ethoxy-prop-2-yl-* | MS: [M + 1]⁺ = 508 HPLC: c$t_{Ret}$ = 3.21 |
| 309 | cyclopropyl-* | 4-ethyl-5-fluoro-2-(3-methoxypropoxy)-phenyl-* | H | 1-methyl-cyclohexyl-* | MS: [M + 1]⁺ = 518 HPLC: c$t_{Ret}$ = 3.65 |

-continued

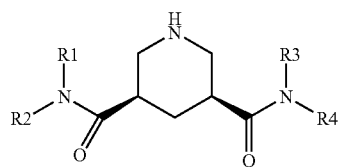

as represented in the following table:

| examples | R1 | R2 | R3 | R4 | Analytical data |
|---|---|---|---|---|---|
| 310 | cyclopropyl | 4-fluoro-2-(3-methoxypropoxy)-5-isopropylphenyl | H | (S)-1-(ethoxymethyl)ethyl | MS: [M + 1]$^+$ = 522 HPLC: $c^tRet$ = 3.39 |
| 311 | cyclopropyl | 4-(3-methoxypropyl)-2,2-dimethyl-3-oxo-3,4-dihydro-2H-benzo[1,4]oxazin-6-yl | H | (S)-1-(methoxymethyl)-2,2-dimethylpropyl | MS: [M + 1]$^+$ = 573 HPLC: $c^tRet$ = 3.01 |
| 312 | isopropyl | 4-(3-methoxypropyl)-2,2-dimethyl-3-oxo-3,4-dihydro-2H-benzo[1,4]oxazin-6-yl | H | trans-2-ethoxycyclopentyl | MS: [M + 1]$^+$ = 573 HPLC: $c^tRet$ = 3.11 |
| 313 | cyclopropyl | 4-(3-methoxypropyl)-2,2-dimethyl-3-oxo-3,4-dihydro-2H-benzo[1,4]oxazin-6-yl | H | 1-(isopropoxymethyl)cyclopropyl | MS: [M + 1]$^+$ = 571 HPLC: $c^tRet$ = 2.89 |

-continued

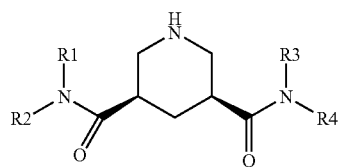

as represented in the following table:

| examples | R1 | R2 | R3 | R4 | Analytical data |
|---|---|---|---|---|---|
| 314 | cyclopropyl | 4-(3-methoxypropyl)-2,2-dimethyl-3-oxo-3,4-dihydro-2H-benzo[1,4]oxazin-6-yl | H | (S)-1-ethoxymethyl-2-phenyl-ethyl | MS: $[M+1]^+ =$ 621 HPLC: $ct_{Ret} = 3.31$ |
| 315 | cyclopropyl | 4-(3-methoxypropyl)-2,2-dimethyl-3-oxo-3,4-dihydro-2H-benzo[1,4]oxazin-6-yl | H | (S)-1-methoxymethyl-2-phenyl-ethyl | MS: $[M+1]^+ =$ 607 HPLC: $ct_{Ret} = 3.19$ |
| 316 | cyclopropyl | 4-ethyl-5-fluoro-2-(3-methoxypropoxy)-phenyl | H | 1-ethoxymethyl-3-methyl-butyl | MS: $[M+1]^+ =$ 550 HPLC: $ct_{Ret} = 3.64$ |
| 317 | cyclopropyl | 5-fluoro-4-isopropyl-2-(3-methoxypropoxy)-phenyl | H | 1-ethoxymethyl-3-methyl-butyl | MS: $[M+1]^+ =$ 564 HPLC: $ct_{Ret} = 3.78$ |

-continued

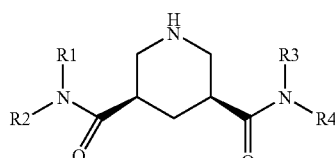

as represented in the following table:

| examples | R1 | R2 | R3 | R4 | Analytical data |
|---|---|---|---|---|---|
| 318 | cyclopropyl* | 3-(2,2-dimethyl-3-oxo-2,3-dihydro-4H-benzo[1,4]oxazin-4-yl)propoxymethyl-benzoxazinyl* | H | (S)-1-ethoxy-3-phenylpropan-2-yl* | MS: [M + 1]⁺ = 621 HPLC: $^c t_{Ret}$ = 3.29 |
| 319 | cyclopropyl* | 3-(2,2-dimethyl-3-oxo-2,3-dihydro-4H-benzo[1,4]oxazin-4-yl)propoxymethyl* | H | (S)-3-cyclohexyl-1-ethoxypropan-2-yl* | MS: [M + 1]⁺ = 627 HPLC: $^c t_{Ret}$ = 3.07 |
| 320 | cyclopropyl* | 3-(2,2-dimethyl-3-oxo-2,3-dihydro-4H-benzo[1,4]oxazin-4-yl)propoxymethyl* | H | (S)-3-cyclohexyl-1-methoxypropan-2-yl* | MS: [M + 1]⁺ = 613 HPLC: $^c t_{Ret}$ = 3.43 |
| 321 | cyclopropyl* | 2-(2,2-dimethyl-3-oxo-2,3-dihydro-4H-benzo[1,4]oxazin-4-yl)ethoxyisopropyl* | H | (S)-1-ethoxy-4-methylpentan-2-yl* | MS: [M + 1]⁺ = 601 HPLC: $^c t_{Ret}$ = 3.46 |
| 322 | cyclopropyl* | 3-(2,2-dimethyl-3-oxo-2,3-dihydro-4H-benzo[1,4]oxazin-4-yl)propoxymethyl* | H | (S)-1-methoxy-3-phenylpropan-2-yl* | MS: [M + 1]⁺ = 607 HPLC: $^c t_{Ret}$ = 3.20 |

-continued

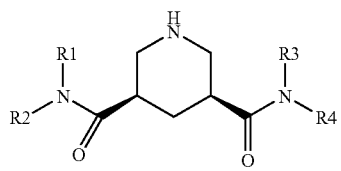

as represented in the following table:

| examples | R1 | R2 | R3 | R4 | Analytical data |
|---|---|---|---|---|---|
| 323 | cyclopropyl | 3-(2,2-dimethyl-3-oxo-2,3-dihydro-4H-benzo[1,4]oxazin-4-yl)propyl with 6-methoxy link | H | (R)-1-phenyl-2-methoxyethyl | MS: [M + 1]$^+$ = 607 HPLC: c$t_{Ret}$ = 3.21 |
| 324 | cyclopropyl | 3-(2,2-dimethyl-3-oxo-2,3-dihydro-4H-benzo[1,4]oxazin-4-yl)propyl with 6-methoxy link | H | (R)-1-phenyl-2-ethoxyethyl | MS: [M + 1]$^+$ = 621 HPLC: c$t_{Ret}$ = 3.33 |
| 325 | cyclopropyl | pentyl-benzo[1,4]oxazinone linker | H | 2-ethoxy-1-isobutyl | MS: [M + 1]$^+$ = 585 HPLC: c$t_{Ret}$ = 3.77 |
| 326 | cyclopropyl | 3-(2,2-dimethyl-3-oxo-2,3-dihydro-4H-benzo[1,4]oxazin-4-yl)propyl with 6-methoxy link | H | (S)-1-phenyl-3-ethoxypropyl | MS: [M + 1]$^+$ = 621 HPLC: c$t_{Ret}$ = 3.29 |

-continued

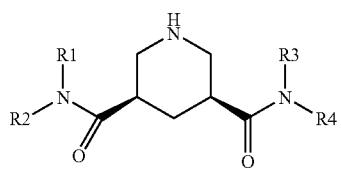

as represented in the following table:

| examples | R1 | R2 | R3 | R4 | Analytical data |
|---|---|---|---|---|---|
| 327 | cyclopropyl | 4-(3-methoxypropoxy)-2-ethyl-5-fluorophenyl | H | (1S,2R)-2-hydroxycyclohexyl | MS: [M + 1]⁺ = 520 HPLC: ctRet = 3.09 |
| 328 | cyclopropyl | 2,2-dimethyl-3-oxo-4-(3-methoxypropyl)-3,4-dihydro-2H-benzo[1,4]oxazin-6-yl | H | (S)-1-phenyl-3-methoxypropyl | MS: [M + 1]⁺ = 607 HPLC: ctRet = 3.17 |
| 329 | cyclopropyl | 4-(3-methoxypropoxy)-2-ethyl-5-fluorophenyl | H | 3-oxoazepan-4-yl racemate | MS: [M + 1]⁺ = 533 HPLC: ctRet = 2.95, 3.09 |
| 330 | cyclopropyl | 2,2-dimethyl-3-oxo-4-(2-ethoxyethyl)-3,4-dihydro-2H-benzo[1,4]oxazin-6-yl | H | (S)-1-phenyl-2-methoxyethyl | MS: [M + 1]⁺ = 593 HPLC: ctRet = 3.17 |
| 331 | cyclopropyl | 2,2-dimethyl-3-oxo-4-(3-methoxypropyl)-3,4-dihydro-2H-benzo[1,4]oxazin-6-yl | H | (R)-1-methoxy-4-methylpentan-2-yl | MS: [M + 1]⁺ = 587 HPLC: ctRet = 3.32 |

-continued

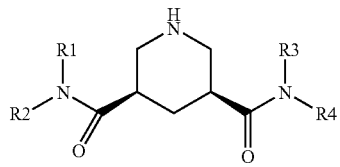

as represented in the following table:

| examples | R1 | R2 | R3 | R4 | Analytical data |
|---|---|---|---|---|---|
| 332 | cyclopropyl* | 3-(2,2-dimethyl-3-oxo-2,3-dihydro-4H-benzo[1,4]oxazin-4-yl)propyl with 6-* and methoxy | H | (S)-1-(ethoxymethyl)-3-methylbutyl* | MS: [M + 1]$^+$ = 601 HPLC: $c_t{}_{Ret}$ = 3.51 |
| 333 | cyclopropyl* | 2-(2,2-dimethyl-3-oxo-2,3-dihydro-4H-benzo[1,4]oxazin-4-yl)ethyl with 6-* and ethoxy | H | (1S,2S)-2-ethoxy-1-methylindanyl* | MS: [M + 1]$^+$ = 619 HPLC: $c_t{}_{Ret}$ = 3.57 |
| 334 | cyclopropyl* | 2-(2,2-dimethyl-3-oxo-2,3-dihydro-4H-benzo[1,4]oxazin-4-yl)ethyl with 6-* and ethoxy | H | 1-(isopropoxymethyl)cyclopropyl* | MS: [M + 1]$^+$ = 571 HPLC: $c_t{}_{Ret}$ = 3.20 |
| 335 | cyclopropyl* | 3-(2,2-dimethyl-3-oxo-2,3-dihydro-4H-benzo[1,4]oxazin-4-yl)propyl with NH$_2$ and 6-* | H | (S)-1-(ethoxymethyl)-3-methylbutyl* | MS: [M + 1]$^+$ = 572 HPLC: $c_t{}_{Ret}$ = 2.96 |

-continued

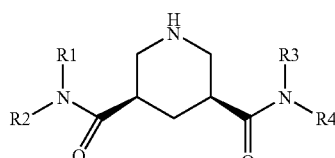

as represented in the following table:

| examples | R1 | R2 | R3 | R4 | Analytical data |
|---|---|---|---|---|---|
| 336 | cyclopropyl | 4-(2,2-dimethyl-3-oxo-2,3-dihydro-4H-benzo[1,4]oxazin-4-yl)butyl with methoxy | H | (S)-1-ethoxymethyl-3-methylbutyl | MS: $[M+1]^+ = 601$ HPLC: $^C t_{Ret} = 3.53$ |
| 337 | cyclopropyl | 3-(2,2-dimethyl-3-oxo-2,3-dihydro-4H-benzo[1,4]oxazin-4-yl)propyl with methoxy | H | 2-methoxy-2,4-dimethylpentyl | MS: $[M+1]^+ = 601$ HPLC: $^A t_{Ret} = 2.77$ |
| 338 | cyclopropyl | 3-(2,2-dimethyl-3-oxo-2,3-dihydro-4H-benzo[1,4]oxazin-4-yl)propyl with methoxy | H | (S)-1-(2-ethoxyethyl)-3-methylbutyl | MS: $[M+1]^+ = 601$ HPLC: $^C t_{Ret} = 3.14$ |
| 339 | cyclopropyl | 3-(2,2-dimethyl-3-oxo-2,3-dihydro-4H-benzo[1,4]oxazin-4-yl)propyl with methoxy | H | (S)-1-(2-methoxyethyl)-3-methylbutyl | MS: $[M+1]^+ = 587$ HPLC: $^C t_{Ret} = 2.49$ |
| 340 | cyclopropyl | 3-(2,2-dimethyl-3-oxo-2,3-dihydro-4H-benzo[1,4]oxazin-4-yl)propyl with F | H | (S)-1-ethoxymethyl-3-methylbutyl | MS: $[M+1]^+ = 575$ HPLC: $^C t_{Ret} = 3.15$ |

-continued

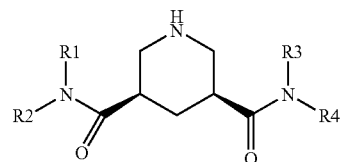

as represented in the following table:

| examples | R1 | R2 | R3 | R4 | Analytical data |
|---|---|---|---|---|---|
| 341 | cyclopropyl | 2-(2-propoxyethyl)-2,2-dimethyl-benzo[1,4]oxazin-3-one | H | (S)-1-ethoxy-2-methylpentyl | MS: [M + 1]⁺ = 601 HPLC: ᶜt_Ret = 3.38 |
| 342 | cyclopropyl | 2-(3-methoxypropyl)-2,2-dimethyl-benzo[1,4]oxazin-3-one | H | (R)-1-methoxy-1,3-dimethylbutyl | MS: [M + 1]⁺ = 601 HPLC: ᶜt_Ret = 3.38 |
| 343 | cyclopropyl | 2-(3-dimethylaminopropyl)-2,2-dimethyl-benzo[1,4]oxazin-3-one | H | (S)-1-ethoxy-2-methylpentyl | MS: [M + 1]⁺ = 660 HPLC: ᶜt_Ret = 2.60 |
| 369 | cyclopropyl | 4-(3-methoxypropoxy)-2-ethyl-5-fluorophenyl | H | 4-methyltetrahydropyran-4-yl | MS: [M + 1]⁺ = 520 HPLC: ᶜt_Ret = 3.17 |

-continued

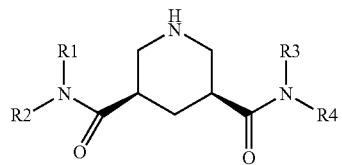

as represented in the following table:

| examples | R1 | R2 | R3 | R4 | Analytical data |
|---|---|---|---|---|---|
| 370 | cyclopropyl | 4-(2,2-dimethyl-3-oxo-2,3-dihydro-4H-benzo[1,4]oxazin-4-yl)propyl | H | 4-methyltetrahydro-2H-pyran-4-yl | MS: [M + 1]$^+$ = 557 HPLC: $^C$t$_{Ret}$ = 2.77 |
| 371 | ethyl | 4-(2,2-dimethyl-3-oxo-2,3-dihydro-4H-benzo[1,4]oxazin-4-yl)propyl | H | (S)-1-ethoxy-4-methylpentan-2-yl | MS: [M + 1]$^+$ = 575 HPLC: $^A$t$_{Ret}$ = 3.33 |
| 372 | isopropyl | 4-(2,2-dimethyl-3-oxo-2,3-dihydro-4H-benzo[1,4]oxazin-4-yl)propyl | H | 1-ethoxy-2,2-dimethylpropyl | MS: [M + 1]$^+$ = 561 HPLC: $^C$t$_{Ret}$ = 3.28 |

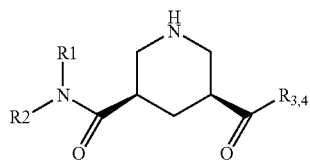
| examples | R1 | R2 | R3,4 | |
|---|---|---|---|---|
| 344 | 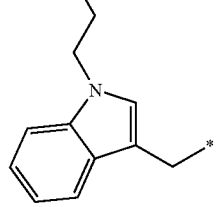 |  | | MS: [M + 1]⁺ = 481 HPLC: $c^t{}_{Ret}$ = 2.72 |
| 345 | 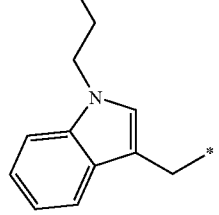 |  | | MS: [M + 1]⁺ = 509 HPLC: $c^t{}_{Ret}$ = 2.97 |
| 346 | 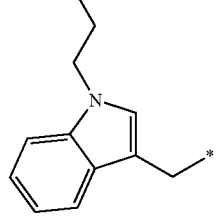 |  | | MS: [M + 1]⁺ = 497 HPLC: $c^t{}_{Ret}$ = 2.49 |
| 347 | 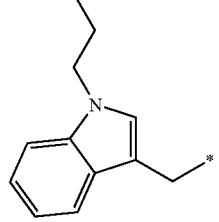 |  | | MS: [M + 1]⁺ = 483 HPLC: $c^t{}_{Ret}$ = 2.41 |

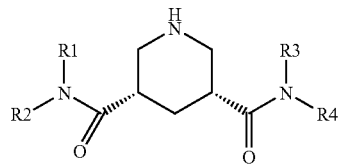
| example | R1 | R2 | R3 | R4 | |
|---|---|---|---|---|---|
| 348 | 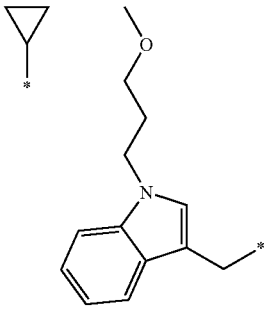 | | H | 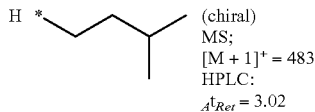 | (chiral) MS: [M + 1]$^+$ = 483 HPLC: $A^{t}{}_{Ret}$ = 3.02 |
| 349 | 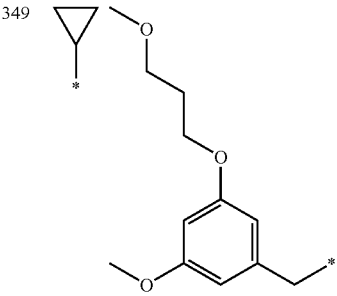 | | H | 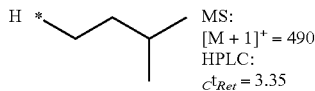 | MS: [M + 1]$^+$ = 490 HPLC: $C^{t}{}_{Ret}$ = 3.35 |
| 350 | 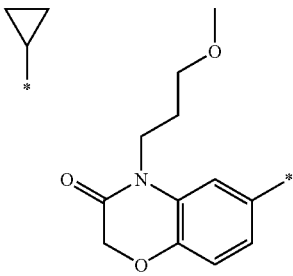 | | H | 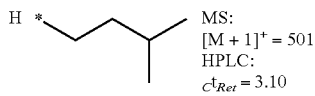 | MS: [M + 1]$^+$ = 501 HPLC: $C^{t}{}_{Ret}$ = 3.10 |

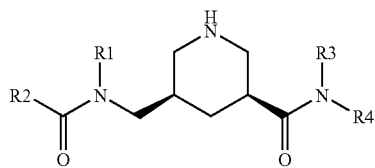
| example | R1 | R2 | R3 | R4 | |
|---|---|---|---|---|---|
| 351 | cyclopropyl-* | 3-methoxypropyl-indole | H | *-CH2CH2CH(CH3)2 | (chiral) MS: [M + 1]+ = 482 HPLC: C tRet = 2.88 |
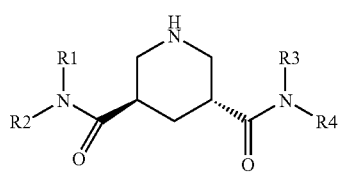
| examples | R1 | R2 | R3 | R4 | |
|---|---|---|---|---|---|
| 352 | cyclopropyl-* | 3-(3-methoxy-5-oxypropoxy)benzyl | H | *-CH2CH2CH(CH3)2 | MS: [M + 1]+ = 490 HPLC: A tRet = 2.88 |
| 353 | cyclopropyl-* | 3-methoxypropyl-indole | H | *-CH2CH2CH(CH3)2 | MS: [M + 1]+ = 483 HPLC: A tRet = 2.97 |

-continued
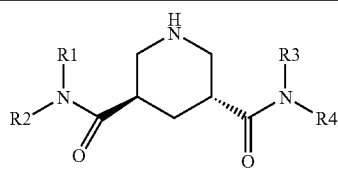
| examples | R1 | R2 | R3 | R4 | |
|---|---|---|---|---|---|
| 354 | 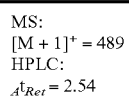 | 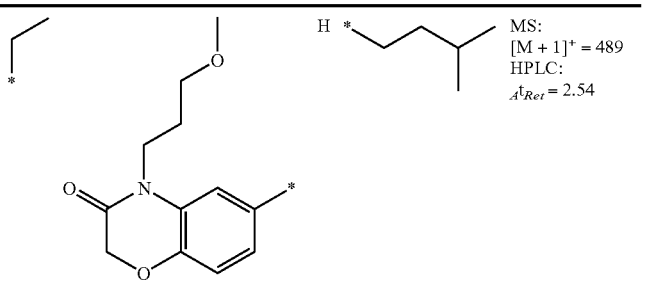 | H | * | MS: [M + 1]⁺ = 489<br>HPLC:<br>$A^t{}_{Ret}$ = 2.54 |
| 355 | 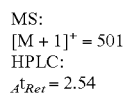 | 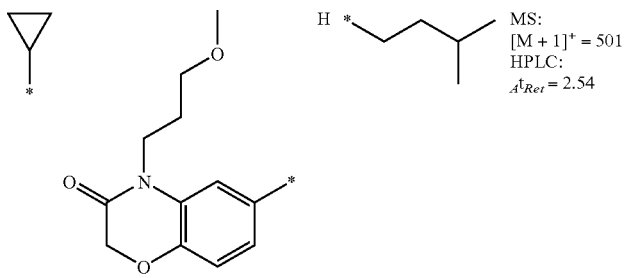 | H | * | MS: [M + 1]⁺ = 501<br>HPLC:<br>$A^t{}_{Ret}$ = 2.54 |
| 356 | 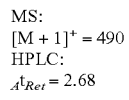 | 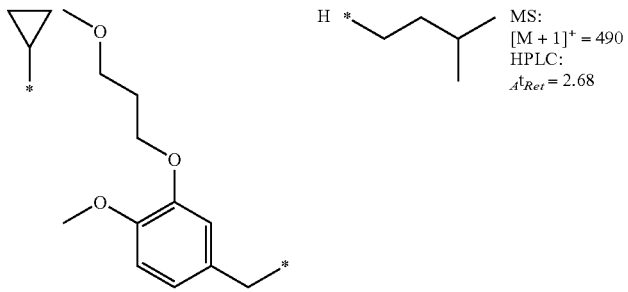 | H | * | MS: [M + 1]⁺ = 490<br>HPLC:<br>$A^t{}_{Ret}$ = 2.68 |
| 357 | 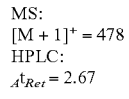 | 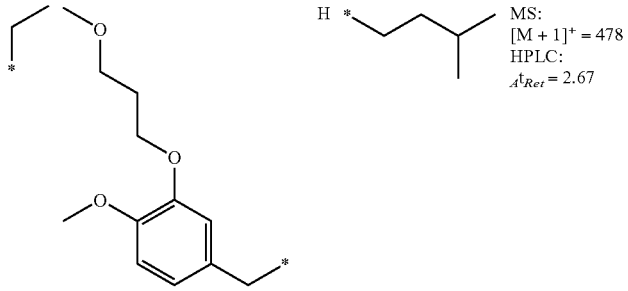 | H | * | MS: [M + 1]⁺ = 478<br>HPLC:<br>$A^t{}_{Ret}$ = 2.67 |

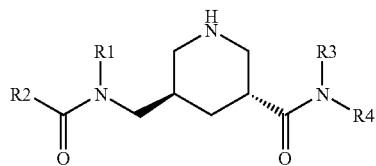
| example | R1 | R2 | R3 | R4 | |
|---|---|---|---|---|---|
| 358 |  | 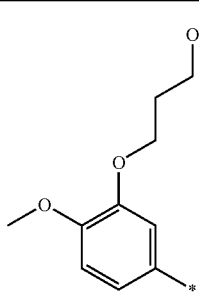 | H | 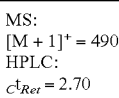 | MS: [M + 1]⁺ = 490 HPLC: $c^t{}_{Ret}$ = 2.70 |
| 359 |  | 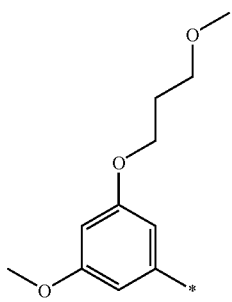 | H | 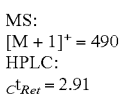 | MS: [M + 1]⁺ = 490 HPLC: $c^t{}_{Ret}$ = 2.91 |
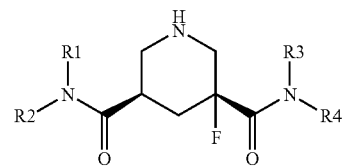
| example | R1 | R2 | R3 | R4 | |
|---|---|---|---|---|---|
| 360 |  | 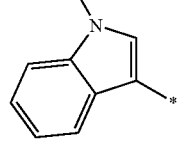 | H | 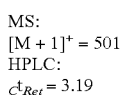 | MS: [M + 1]⁺ = 501 HPLC: $c^t{}_{Ret}$ = 3.19 |

| example | R1 | R2 | R3 | R4 | |
|---|---|---|---|---|---|
| 361 | cyclopropyl | 3-(indol-1-yl)propyl-O-methyl | H | isopentyl | MS: [M + 1]⁺ = 501 HPLC: $^c t_{Ret}$ = 3.00 |
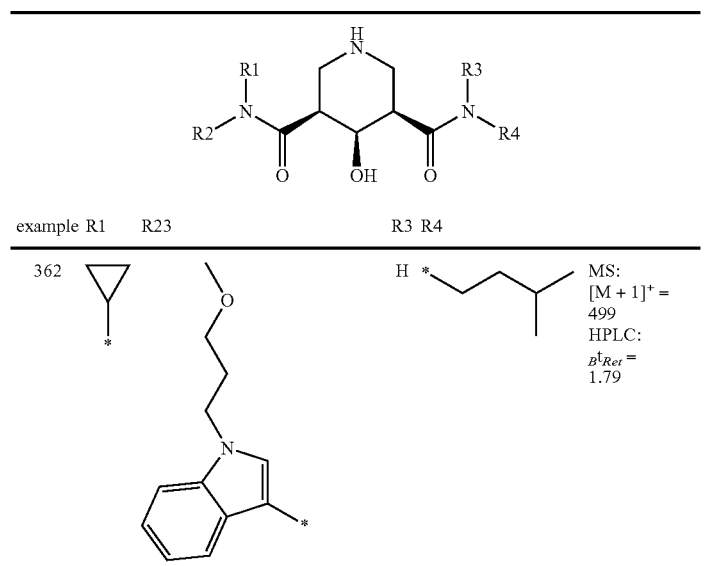
| example | R1 | R23 | R3 | R4 | |
|---|---|---|---|---|---|
| 362 | cyclopropyl | 3-(indol-1-yl)propyl-O-methyl | H | isopentyl | MS: [M + 1]⁺ = 499 HPLC: $^B t_{Ret}$ = 1.79 |
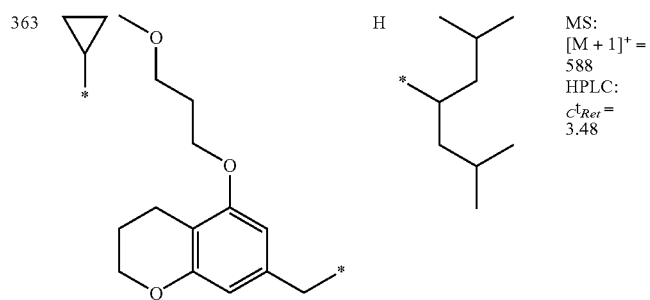
| 363 | cyclopropylmethoxy-propyl-chroman | | H | 2,4-dimethylpentyl | MS: [M + 1]⁺ = 588 HPLC: $^c t_{Ret}$ = 3.48 |

-continued

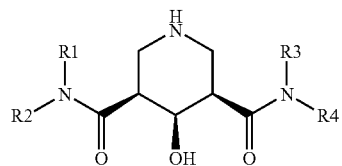

| example | R1 | R23 | R3 | R4 | |
|---|---|---|---|---|---|
| 364 | cyclopropyl | 5-(3-oxypropoxy)chroman-7-ylmethyl | H | 4-tert-butyl-tetrahydropyran-4-yl | MS: [M + 1]$^+$ = 588 HPLC: $c^t{}_{Ret}$ = 2.99 |
| 365 | cyclopropyl | 5-(3-oxypropoxy)chroman-7-ylmethyl | H | (S)-1-ethoxy-3-methylbutan-2-yl | MS: [M + 1]$^+$ = 590 HPLC: $c^t{}_{Ret}$ = 3.35 |
| 366 | cyclopropyl | 4-(3-methoxypropyl)-2,2-dimethyl-3-oxo-benzo[1,4]oxazin-6-yl | H | (S)-1-ethoxy-3-methylbutan-2-yl | MS: [M + 1]$^+$ = 603 HPLC: $c^t{}_{Ret}$ = 3.15 |
| 367 | cyclopropyl | 4-(3-methoxypropyl)-2,2-dimethyl-3-oxo-benzo[1,4]oxazin-6-yl | H | 3-methylbutan-2-yl | MS: [M + 1]$^+$ = 545 HPLC: $c^t{}_{Ret}$ = 2.87 |
| 368 | cyclopropyl | 4-(3-methoxypropyl)-2,2-dimethyl-3-oxo-benzo[1,4]oxazin-6-yl | H | (S)-1-ethoxy-3-methylbutan-2-yl | MS: [M + 1]$^+$ = 603 HPLC: $c^t{}_{Ret}$ = 3.22 |

-continued

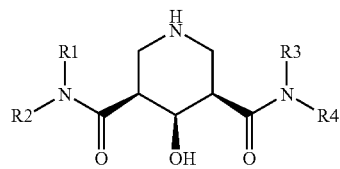

| example | R1 | R2 | R3 | R4 |
|---------|----|----|----|----| or a (preferably pharmaceutically acceptable) salt thereof, respectively.

Abbreviations

| | |
|---|---|
| Ac | acetyl |
| BINAP | 2,2'-bis(diphenylphosphino)-1,1'-binaphthyl |
| Boc | tert-butoxycarbonyl |
| (Boc)$_2$O | di-tert-butyl dicarbonate |
| Celite | Celite ® is a filtering aid based on diatomaceous earth (trademark of The Celite Corporation) |
| Cbz, Z | Benzyloxycarbonyl |
| DCM | dichloromethane |
| dba | dibenzylideneacetone |
| DEAD | diethylazodicarboxylate |
| Dess-Martin periodinane | 1,1,1-tris(acetyloxy)-1,1-dihydro-1,2-benziodoxol-3-(1H)-one |
| DIBAL | diisobutylaluminum hydride |
| DIPEA | N-ethyldiisopropylamine |
| DMA | N,N-dimethylacetamide |
| DMAP | 4-(N,N-dimethylamino)-pyridine |
| DMF | N,N-dimethylformamide |
| DPPA | diphenylphosphoryl azide |
| EDCl·HCl | 1-[3-(dimethylamino)propyl]-3-ethylcarbodiimide hydrochloride |
| Et | ethyl |
| Fmoc | 9-fluorenylmethoxycarbonyl |
| h | hour(s) |
| HATU | O-(7-azabenzotriazol-1-yl)-N,N,N',N'-tetramethyluronium hexafluorophosphate |
| HCTU | O-(1H-6-chlorobenzotriazole-1-yl)-1,1,3,3-tetramethyluronium hexafluorophosphate |
| HOAT | 1-hydroxy-7-azabenzotriazole |
| HM-N isolute | isolute sorbent from International Sorbent Technology Ltd. |
| LAH | lithium aluminum hydride |
| LDA | lithium diisopropylamide |
| mL | milliliter |
| Me | methyl |
| Ms | methanesulfonyl |
| MS | mass spectrometry |
| NBS | N-bromosuccinimide |
| NMP | N-methylpyrrolidinone |
| Ph | phenyl |
| i-Pr | isopropyl |
| PS | polystyrene resin |
| RT | room temperature |
| TBAF | tetra-butylammonium fluoride |
| TFA | trifluoroacetic acid |
| THF | tetrahydrofuran |
| TLC | thin layer chromatography |
| TMSOTf | trimethylsilyl trifluoromethanesulfonate |
| Tosyl | para-toluenesulfonyl |
| t$_R$ | retention time |

Temperatures are measured in degrees Celsius. Unless otherwise indicated, the reactions take place at RT. Unless otherwise indicated, the hydrogenation reactions in the presence of H$_2$ take place at atmospheric pressure. The microwave irradiation is performed by using a "Biotage Initiator 60" machine.

HPLC Condition-A:

Column: CombiScreen ODS-AM, 50×4.6 mm.

Flow rate: 2.0 mL/min

Mobile phase: A) TFA/water (0.1/100, v/v), B) TFA/acetonitrile (0.1/100, v/v)

Gradient: linear gradient from 5% B to 100% B in 5 min then 100% B in 2 min

Detection: UV at 215 nm

HPLC Condition-B:

Column: ACQUITY UPLC™ BEH C$_{18}$ 1.7 µm, 50×2.1 mm.

Flow rate: 0.5 mL/min

Mobile phase: A) TFA/water (0.1/100, v/v), B) TFA/acetonitrile (0.1/100, v/v)

Gradient: linear gradient from 5% B to 100% B in 2 min then 100% B in 1 min

Detection: UV at 215 nm

HPLC Condition-C:

Column: ACQUITY UPLC™ BEH C$_{18}$ 1.7 µm, 50×2.1 mm.

Flow rate: 0.5 mL/min

Mobile phase: A) TFA/water (0.1/100, v/v), B) TFA/acetonitrile (0.1/100, v/v)

Gradient: 5% B in 0.5 min then linear gradient from 5% B to 100% B in 5.0 min then 100% B in 1.5 min Detection: UV at 215 nm TLC conditions: R$_f$ values for TLC are measured on 5×10 cm TLC plates, silica gel F$_{254}$, Merck, Darmstadt, Germany.

Methods for preparing compounds of formula I are described in detail below. It should be noted that the brief description on each of the arrows for each conversion has been added for illustration purposes only and should not be regarded as limiting with respect to the sequence or each individual step.

Scheme 1
(for racemic-cis-scaffold)

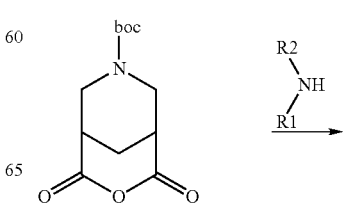

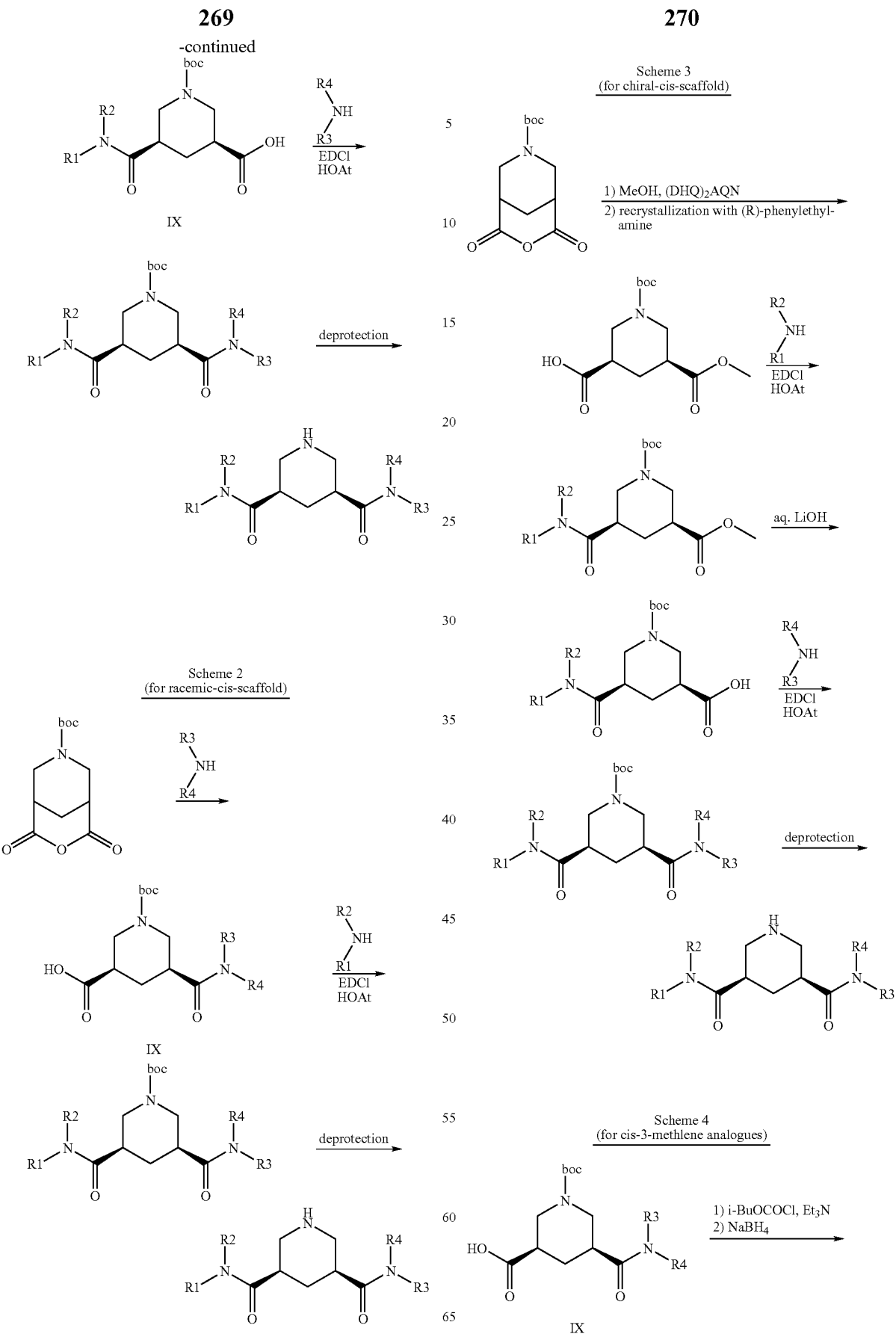

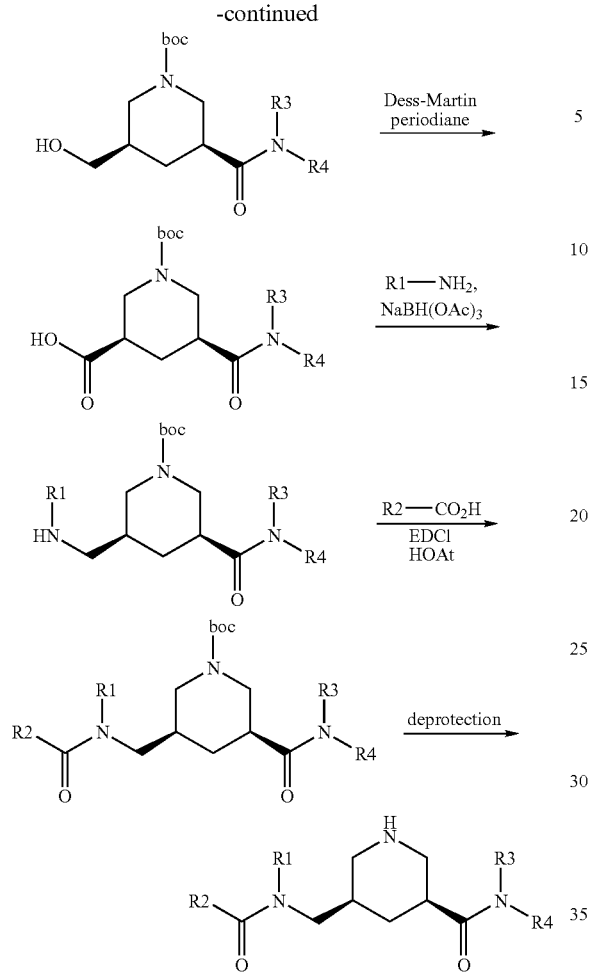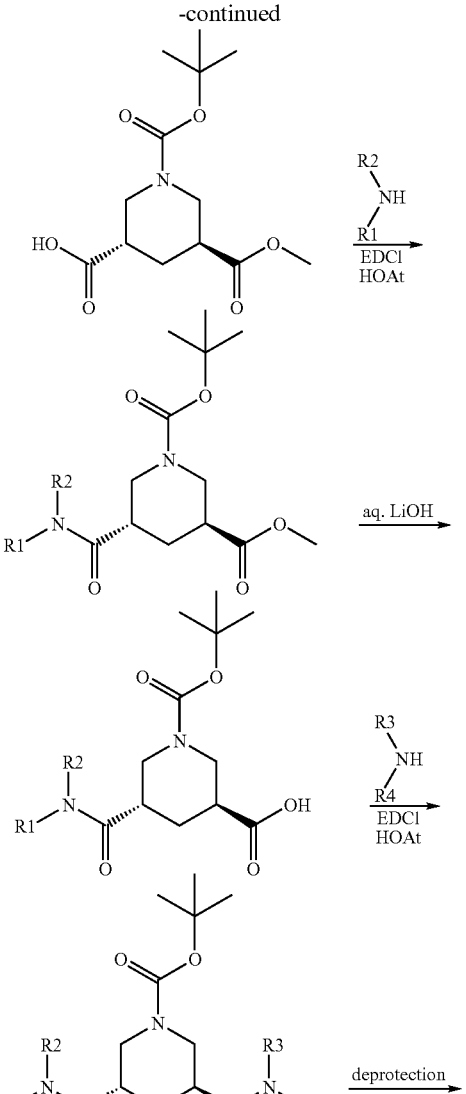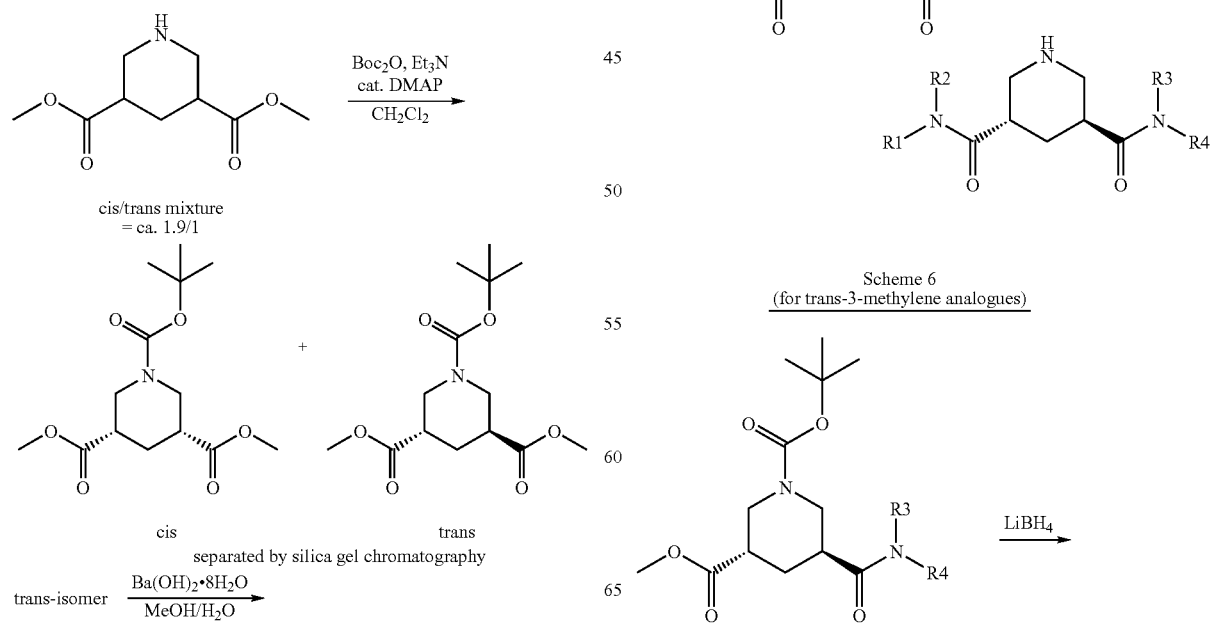

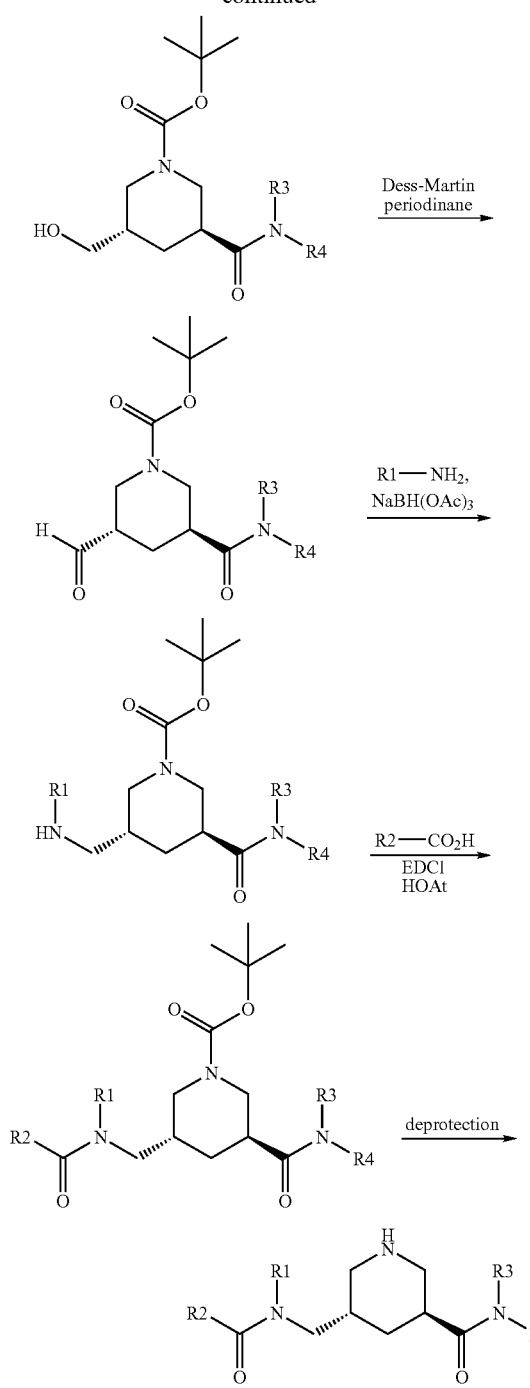
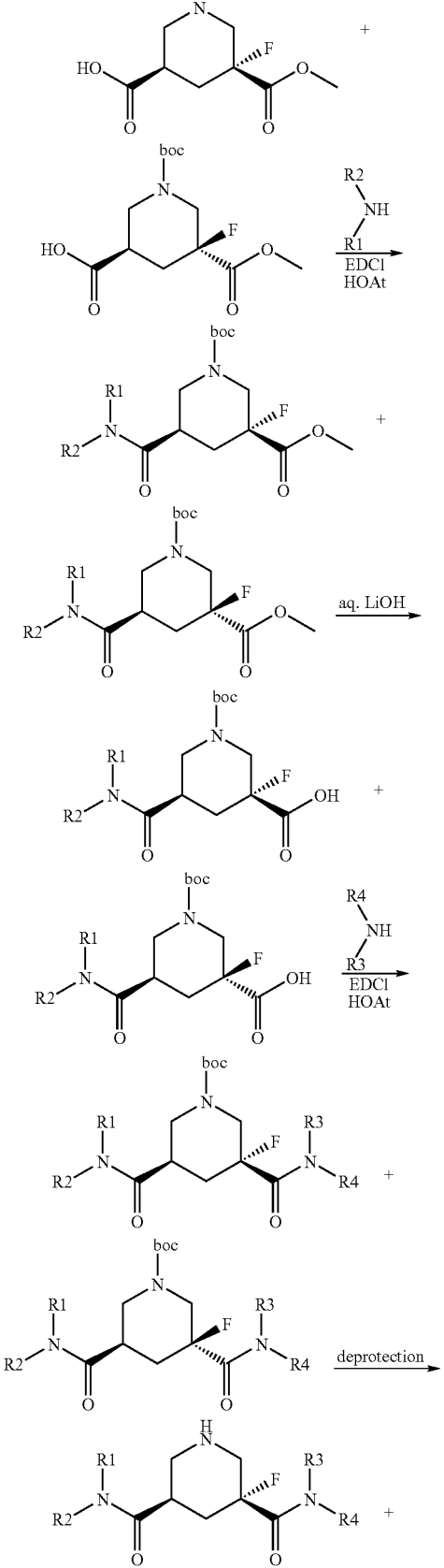
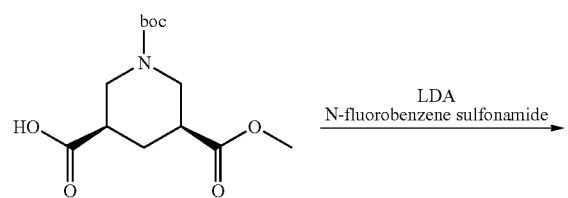
Scheme 7
(for 5-fluoro analogues)

275
-continued

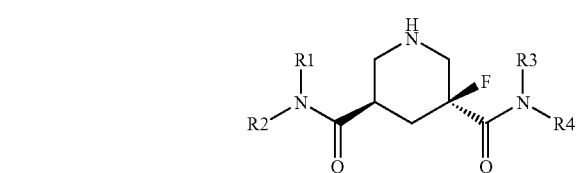

Scheme 8
(for 4-hydroxy analogues)

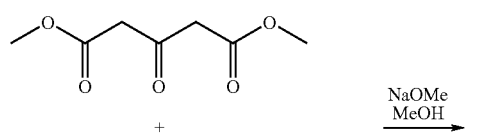

NaOMe
MeOH
→

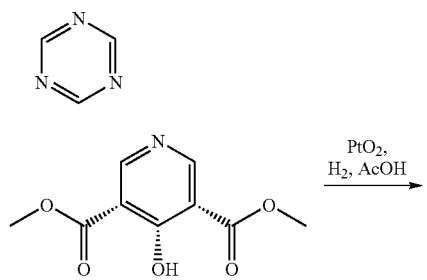

PtO₂,
H₂, AcOH
→

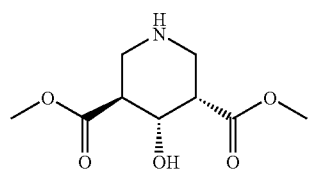

(3:4)

Separation
by silica-gel
chromatography
→

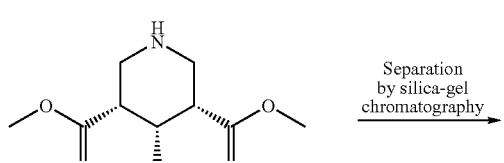

Boc₂O
NEt₃
CH₂Cl₂
→

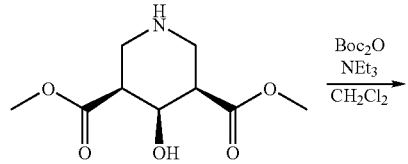

Lipase M
(Murcor javanicus)
→

276
-continued

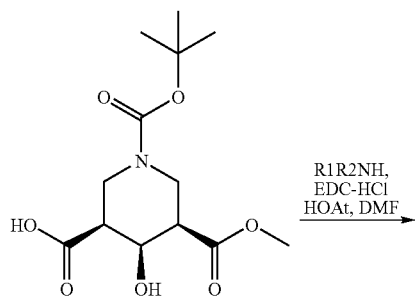

98% ee

R1R2NH,
EDC-HCl
HOAt, DMF
→

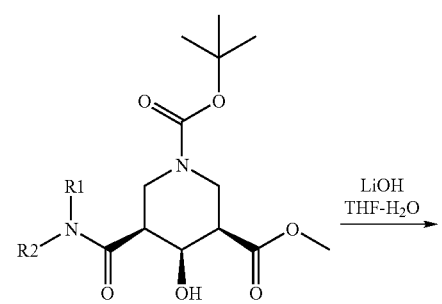

LiOH
THF-H₂O
→

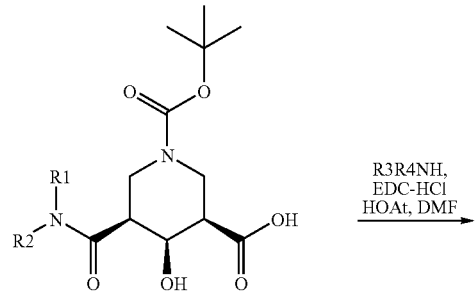

R3R4NH,
EDC-HCl
HOAt, DMF
→

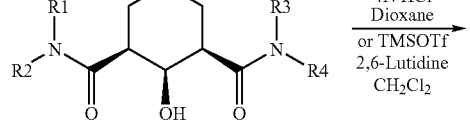

4N HCl
Dioxane
or TMSOTf
2,6-Lutidine
CH₂Cl₂
→

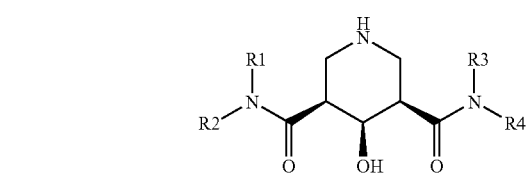

The starting material is prepared as follows:

Preparation of cyclic anhydride shown as intermediate in Scheme 1, 2, 3 and the piperidine-3,5-dicarboxylic acid dimethyl ester starting material for trans-scaffold in Scheme 4:

Scheme 9

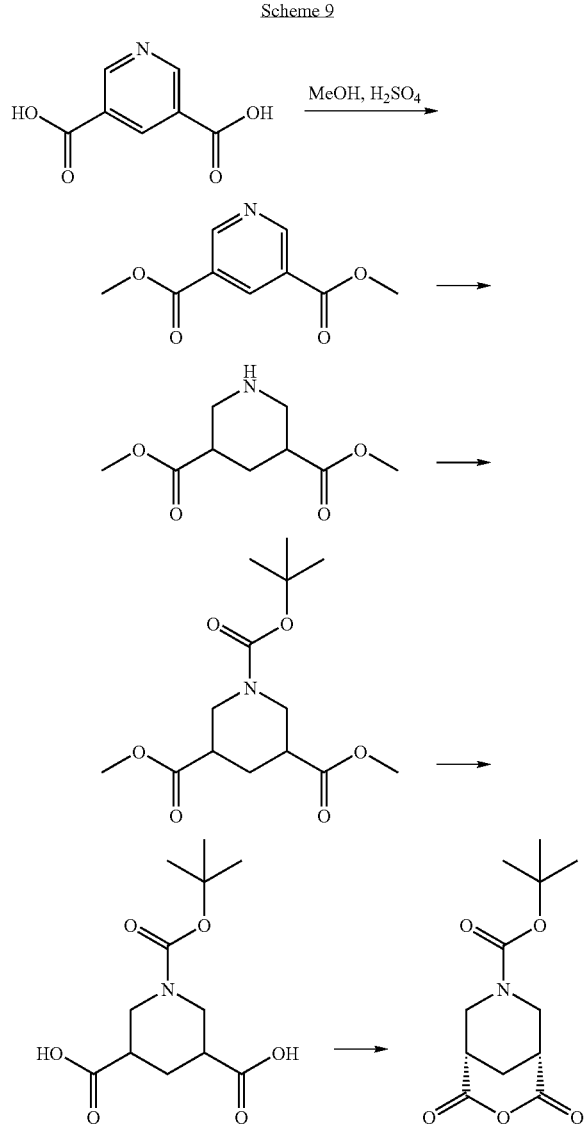

A: Pyridine-3,5-dicarboxylic acid dimethyl ester

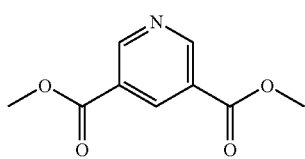

3,5-Pyridinedicarboxylic acid (1.5 g, 63 mmol) and conc. $H_2SO_4$ (0.9 mL) in MeOH (15 mL) are heated in a microwave oven at 120° C. for 2 h. The solvent is evaporated to give a residue with is partitioned between ethyl acetate and sat. aq. $NaHCO_3$. The organic phase is washed with brine, dried over Na2SO4, filtered and evaporated to give a light yellow solid. MS (LC-MS): 196 [M+H]$^+$ TLC, Rf (ethyl acetate/hexane 1:1)=0.56.

B: Piperidine-3,5-dicarboxylic acid dimethyl ester

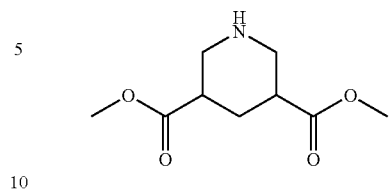

Pyridine-3,5-dicarboxylic acid dimethyl ester (5.3 g, 27 mmol) and Rh/PtO$_2$ (0.5 g) in MeOH (200 mL) are stirred under hydrogen overnight. The resulting mixture is filtered and the solvents are evaporated to leave a brown oil. MS (LC-MS): 202 [M+H]$^+$ C: Piperidine-1,3,5-tricarboxylic acid 1-tert-butyl ester 3,5-dimethyl ester

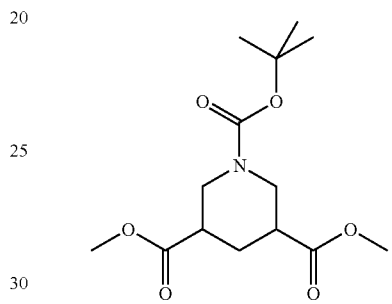

A solution of piperidine-3,5-dicarboxylic acid dimethyl ester (5.4 g, 26.8 mmol) in CH$_2$Cl$_2$ (55 mL) is treated with Boc$_2$O (6.4 g, 29.5 mmol) and the reaction is stirred at rt overnight. The reaction is quenched with 0.1N aq. HCl and the organic phase is washed with 0.1N aq HCl. The combined aqueous phases are extracted 2 times with CH$_2$Cl$_2$/MeOH (9/1) before the combined organic phases are dried over Na$_2$SO$_4$, filtered and evaporated. The resulting residue is purified by flash chromatography on silica gel (eluent: CH$_2$Cl$_2$/MeOH 95:5) to give the title compound as a yellow solid. MS (LC-MS): 302 [M+H]$^+$ TLC, Rf (CH$_2$Cl$_2$/MeOH 95:5)=0.5.

D: Piperidine-1,3,5-tricarboxylic acid 1-tert-butyl ester

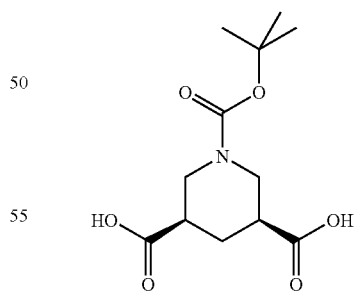

To a solution of piperidine-1,3,5-tricarboxylic acid 1-tert-butyl ester 3,5-dimethyl ester (6.8 g, 22.5 mmol) in MeOH/water (4:1, 120 mL), K$_2$CO$_3$ (9.4 g, 68 mmol) is added. The reaction is stirred at reflux overnight. The MeOH is evaporated and the residue is extracted with dicholoromethane and 1N aq. HCl. The organic phase is dried over Na$_2$SO$_4$, filtered and evaporated to give a light yellow solid. MS (LC-MS): 274 [M+H]$^+$.

E: 2,4-Dioxo-3-oxa-7-aza-bicyclo[3.3.1]nonane-7-carboxylic acid tert-butyl ester

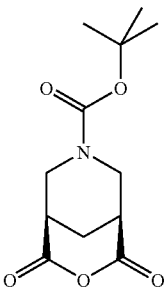

A suspension of piperidine-1,3,5-tricarboxylic acid 1-tert-butyl ester (1 g, 3.6 mmol) in acetic anhydride (20 mL) is heated at reflux for 2 h. The reaction mixture is evaporated three times with toluene before it is dried under high vacuum at rt overnight to give a yellow solid. MS (LC-MS): 278 [M+Na]$^+$.

(3S,5R)-Starting material-F

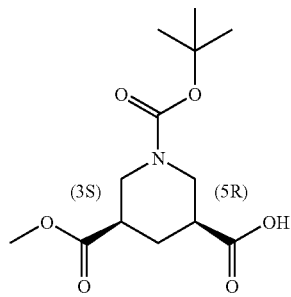

To the solution of starting material-E (401.5 mg, 1.57 mmol, XXIII) and commercially available (DHQD)$_2$AQN (423.6 mg, 0.47 mmol, 95% purity)$^a$ dissolved in Et$_2$O (60 mL) and THF (20 mL) under N$_2$, MeOH (0.64 mL, 15.67 mmol) is added at −40° C. After stirring at that temperature for 24 h, sat. citric acid aq. is added. The reaction mixture is extracted with EA. Organic phase is washed with brine, dried over Na$_2$SO$_4$ and subjected to silica chromatography to give (3S,5R)-starting material-F in 98% ee. White amorphous material ES-MS: M+H-tBu=232; HPLC: $_Ct_{Ret}$=2.73 min. chiral HPLC (column: CHIRALPAH AD-H (0.46 cm×25 cm), eluent: hexane/i-PrOH=95/5, flow rate: 0.5 mL/min, detection: UV 210 nm, temperature: rt) $t_R$=33.25 min for (3R,5S)-starting material-F, 35.56 min for (3S,5R)-starting material-F, $^a$ Chen, Y.; Tian, S-K.; Deng, Li. *J. Am. Chem. Soc.* 2000, 122, 9542-9543.

(3R,5S)-Starting material-F

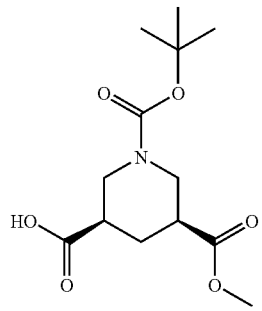

To a solution of (3R,5S)-starting material-F (72% ee) (4.2 g, 14.6 mmol) in hot EtOH (20 mL) is added (R)-1-phenylethylamine (1.79 g, 14.76 mmol) at 70° C. The solution is cooled to rt and allowed to stand for 1 h, which results in the precipitation of a salt. The salt is collected by filtration. After repeating the same recrystallization procedure three times, the resulting salt was dissolved in water, acidified with 1M HClaq and extracted five times with ether. The combined organic phases are washed with brine, dried with MgSO$_4$. Concentration under reduced pressure gives (3R,5S)-starting material-F: colorless crystal; ES-MS: M+H=288; $_Bt_{Ret}$=2.67 min. chiral HPLC: AD-H, 5% i-PrOH/Hexane, flow 0.5 mL/min, 210 nm, $t_{Ret}$=33 (major), 36 (minor).

(3R,5S)-starting material-F (72% ee)

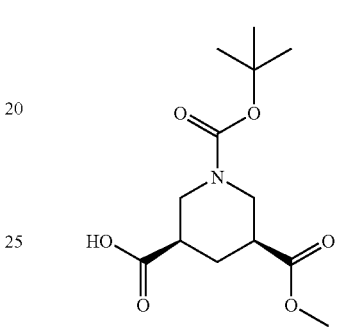

To a solution of starting material-E (200 mg, 0.78 mmol) in THF (10 mL) and ether (30 mL) is added (DHQ)2AQN (67 mg, 0.08 mmol) and MeOH (0.32 mL) at 0° C. under N$_2$. The resulting mixture is stirred for 5 h at 0° C. After adding 1M HCl aq, the mixture is extracted with EtOAc, the organic phases are washed with brine and dried with MgSO$_4$. Concentration under reduced pressure and silica gel flash chromatography give (3R,5S)-starting material-F: ES-MS: M+H=288; $_Ct_{Ret}$=2.67 min. chiral HPLC: 72% ee, AD-H, 5% i-PrOH/Hexane, flow 0.5 mL/min, 210 nm, $t_{Ret}$=33 (major), 36 (minor).

Example 1

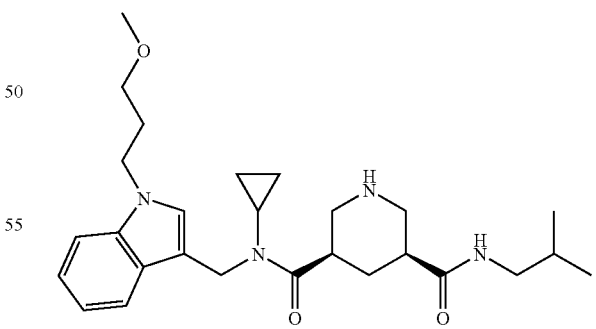

To a solution of Intermediate 1.1 (1 eq) in DCM is added 2,6-lutidine (3 eq) and TMSOTf (3 eq) at rt and stirred for 30 min. After adding a drop of MeOH and AcOH, the reaction mixture is concentrated under reduced pressure and purified with RP-HPLC to give example 1: ES-MS: M+H= 469: $_Ct_{Ret}$=2.75 min.

Intermediate 1.1

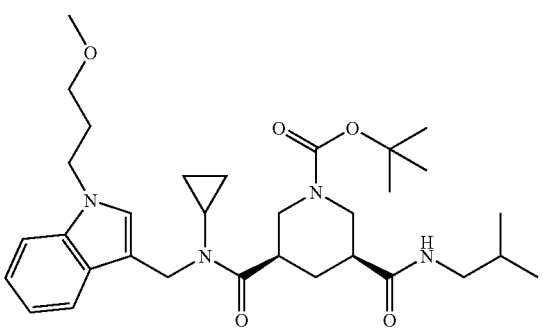

To a solution of Intermediate 1.2 (50 mg, 0.10 mmol) in DMF (1 mL) are added EDCI HCl (29 mg, 0.15 mmol), HOAt (4 mg, 0.03 mmol) and isobutylamine (7.8 mg, 0.11 mmol) at room temperature. After stirring for 7 h at room temperature, the reaction mixture is quenched with $H_2O$ (10 mL) and extracted with $EtOAc/Et_2O$ twice (c.a. 1:1, 40 mL). The organic layer is successively washed with 5% $KHSO_4$aq (twice), 5% $NaHCO_3$aq, $H_2O$, and brine, then dried over $Na_2SO_4$ and concentrated in reduced pressure to afford Intermediate 1.1 as a white amorphous material; ES-MS: M=569; HPLC: $_At_{Ret}$=3.95 min.

Intermediate 1.2

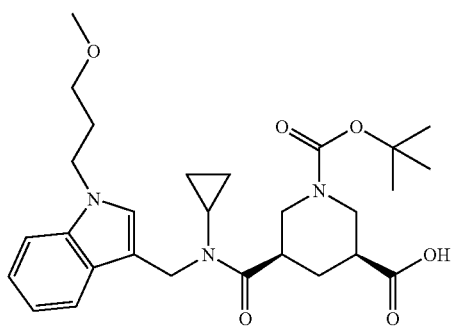

To a solution of starting material-E (511 mg, 2 mmol) in THF are added $Et_3N$ and intermediate 1.3 (516 mg, 2 mmol) at 0° C. After stirring for 1 h at 60° C., the reaction mixture is quenched with saturated aqueous $NaHCO_3$ (10 mL) and water (30 mL), and washed with $Et_2O$ (twice). To the aqueous layer is then added 5% aqueous $KHSO_4$ (10 mL), and extracted with EtOAc (twice). The combined organic layer is washed with $H_2O$, and brine, then dried over $Na_2SO_4$ and concentrated in reduced pressure to afford Intermediate 1.2 as a white amorphous material; ES-MS: M=514; HPLC: $_At_{Ret}$=3.65 min.

Intermediate 1.3

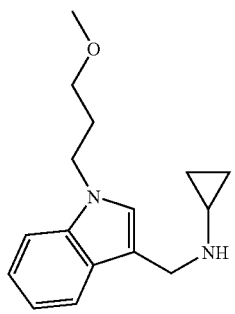

A mixture of Intermediate 1.4 (780 mg, 3.6 mmol), cyclopropylamine (410 mg, 7.2 mmol), AcOH (0.5 mL) and NaBH(OAc)$_3$ (1.1 g, 5.4 mmol) in DCM (3 mL) and MeOH (1 mL) is stirred under $N_2$ at 0° C. After stirring at RT for 1 hour, the reaction mixture is quenched with saturated aqueous $NaHCO_3$ and extracted with DCM. The combined organic phases are washed with $H_2O$, brine and dried ($Na_2SO_4$). Concentration under reduced pressure and silica gel flash chromatography give Intermediate 1.3 as a yellow oil; ES-MS: [M+H]$^+$=202; HPLC: $_At_{Ret}$=2.67 min Intermediate 1.4

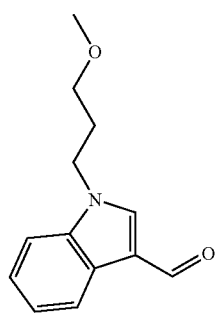

To a mixture of indole-3-carboxaldehyde (1.0 g, 6.9 mmol), toluene-4-sulfonic acid 3-methoxy-propyl ester (2.1 g, 9.0 mmol) and KI (1.1 g, 7.0 mmol) in DMF (15 mL), NaH (320 mg, 7.5 mmol) is added under $N_2$ at 0° C. After stirring at 50° C. for 4 h, the reaction mixture is supplemented with $H_2O$ and extracted with EtOAc. The combined organic phases are washed with $H_2O$, brine and dried ($Na_2SO_4$). Concentration under reduced pressure and silica gel flash chromatography give Intermediate 1.4 as a colorless oil; ES-MS: [M+H]$^+$=218, HPLC: $_At_{Ret}$=3.18 min.

Examples 2-12, 16-18, 21-24, 28-31, 35-36, 49-51, and 344-347 are synthesized by condensation and deprotection from intermediate 1.2 analogously to the preparation of example 1.

Example 13

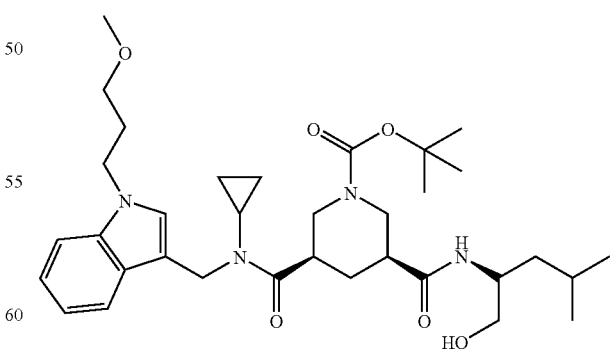

Example 13 is synthesized by deprotection of Intermediate 13.1 analogously to the preparation of example 1: ES-MS: M+H=513: $_At_{Ret}$=2.83 min.

Intermediate 13.1

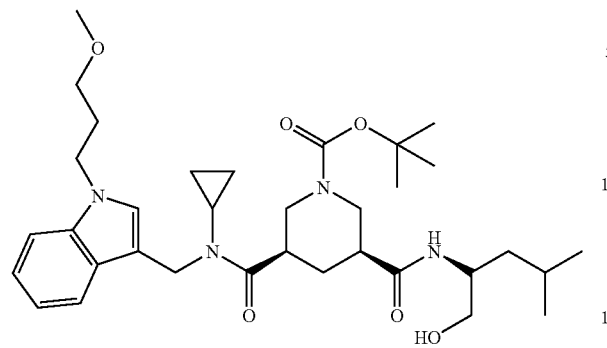

To a solution of Intermediate 13.2 (240 mg, 0.64 mmol) in DMF (1.5 mL) are added EDCI HCl (184 mg, 0.96 mmol), HOAt (26 mg, 0.2 mmol) and intermediate 1.3 (248 mg, 0.96 mmol) at room temperature. After stirring for 2.5 h at room temperature, the reaction mixture is quenched with H$_2$O (10 mL) and extracted with EtOAc/Et$_2$O twice (c.a. 1:1, 40 mL). The organic layer is successively washed with 5% KHSO$_4$aq (twice), 5% NaHCO$_3$aq, H$_2$O, and brine, then dried over Na$_2$SO$_4$ and concentrated under reduced pressure to afford Intermediate 13.1 as a white amorphous material; ES-MS: [M+H]$^+$=613; HPLC: $_C$t$_{Ret}$=3.76 min.

Intermediate 13.2

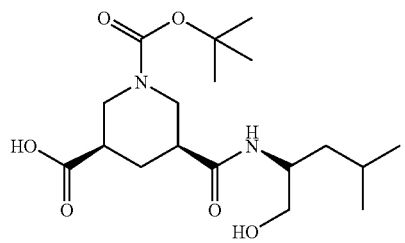

To a solution of Intermediate 13.3 (250 mg, 0.65 mmol) in THF (5 mL) are added H$_2$O (2.5 mL) and LiOH.H$_2$O (55 mg, 1.3 mmol) at 0° C. After stirring for 3 h at 0° C., the reaction mixture is quenched with 5% aqueous KHSO$_4$ (5 mL) and extracted with EtOAc (20 mL). The organic layer is successively washed with H$_2$O and brine, then dried over Na$_2$SO$_4$ and concentrated in reduced pressure to afford Intermediate 13.2 as a white amorphous material; ES-MS: [M]+=372; HPLC: $_C$t$_{Ret}$=2.50 min.

Intermediate 13.3

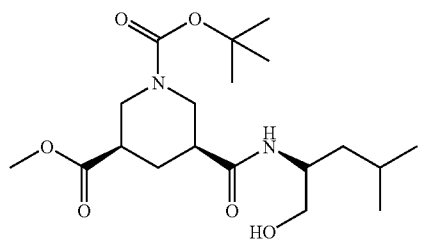

To a solution of (3S,5R)-Starting material-F (200 mg, 0.70 mmol) in DMF (1 mL) are added EDCI HCl (200 mg, 1.04 mmol), HOAt (29 mg, 0.21 mmol) and S-(+)-leucinol (122 mg, 1.04 mmol) at room temperature. After stirring for 3 h at room temperature, the reaction mixture is quenched with H$_2$O (10 mL) and extracted with EtOAc/Et$_2$O twice (c.a. 1:1, 20 mL). The organic layer is successively washed with 5% KHSO$_4$aq (twice), 5% NaHCO$_3$aq, H$_2$O, and brine, then dried over Na$_2$SO$_4$ and concentrated in reduced pressure to afford Intermediate 13.3 as a white amorphous material; ES-MS: [M]$^+$=387; HPLC: $_C$t$_{Ret}$=2.93 min.

Example 14

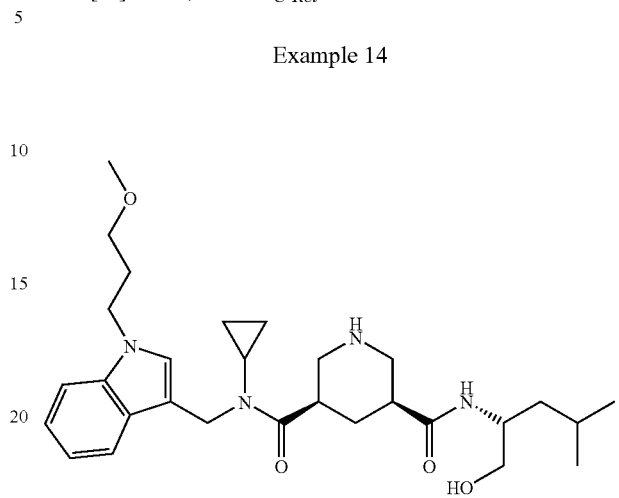

Example 14 is synthesized by deprotection of Intermediate 14.1 analogously to the preparation of example 1: ES-MS: M+H=513: $_A$t$_{Ret}$=2.69 min.

Intermediate 14.1

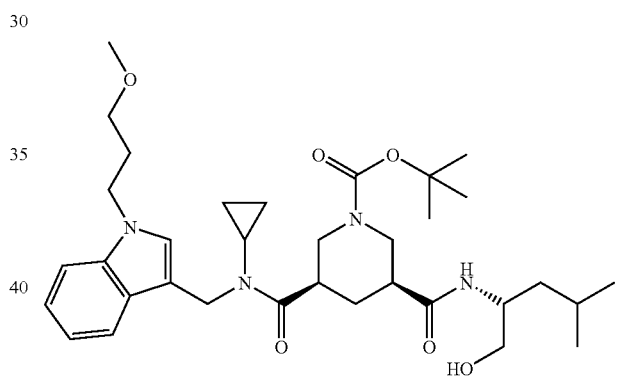

Intermediate 14.1 is synthesized by condensation of Intermediate 14.2 (240 mg, 0.64 mmol) with intermediate 1.3 (248 mg, 0.96 mmol) analogously to the preparation of Intermediate 13.1. White amorphous material; ES-MS: [M+H]$^+$=613; HPLC: $_C$t$_{Ret}$=3.76 min.

Intermediate 14.2

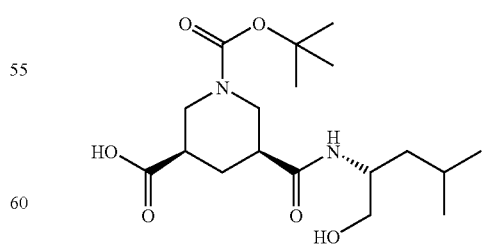

Intermediate 14.2 is synthesized by hydrolysis of Intermediate 14.3 (250 mg, 0.65 mmol) analogously to the preparation of Intermediate 13.2. White amorphous material; ES-MS: [M+H]$^+$=373; HPLC: $_C$t$_{Ret}$=2.68 min.

Intermediate 14.3

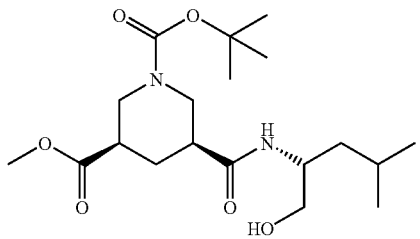

Intermediate 14.3 is synthesized by condensation of (3S, 5R)-Starting material-F (200 mg, 0.70 mmol) with R(–)-leucinol (122 mg, 1.04 mmol) analogously to the preparation of Intermediate 13.3. White amorphous material; ES-MS: [M]$^+$=387; HPLC: $_C t_{Ret}$=3.00 min.

Example 15

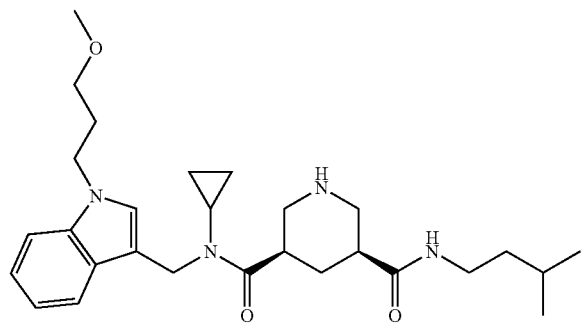

Example 15 is synthesized by deprotection of Intermediate 15.1 analogously to the preparation of example 1: ES-MS: M+H=483: $_A t_{Ret}$=3.02 min.

Intermediate 15.1

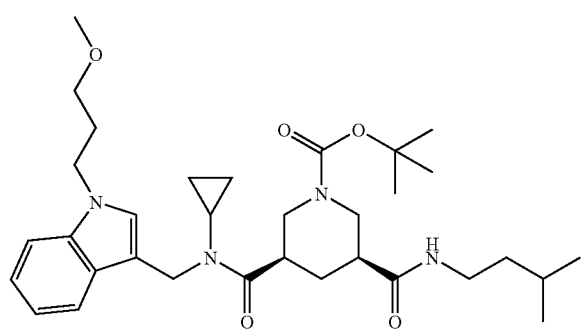

Intermediate 15.1 is synthesized by condensation of Intermediate 15.2 (220 mg, 0.64 mmol) with intermediate 1.3 (199 mg, 0.77 mmol) analogously to the preparation of Intermediate 13.1. White amorphous material; ES-MS: [M+H]$^+$= 583; HPLC: $_C t_{Ret}$=4.14 min.

Intermediate 15.2

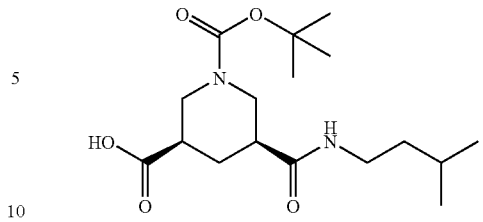

Intermediate 15.2 is synthesized by hydrolysis of Intermediate 15.3 (240 mg, 0.67 mmol) analogously to the preparation of Intermediate 13.2. White amorphous material; ES-MS: [M]$^+$=342; HPLC: $_C t_{Ret}$=3.02 min.

Intermediate 15.3

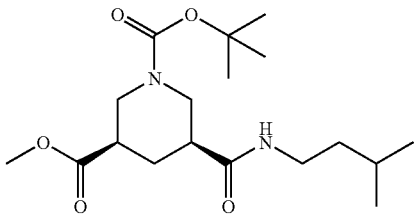

Intermediate 15.3 is synthesized by condensation of (3S, 5R)-Starting material-F (200 mg, 0.70 mmol) with isoamylamine (91 mg, 1.04 mmol) analogously to the preparation of Intermediate 13.3. White amorphous material; ES-MS: [M]$^+$=356; HPLC: $_C t_{Ret}$=3.43 min.

Examples 96-97 are synthesized by condensation and deprotection from intermediate 15.2 analogously to the preparation of example 1.

Example 19

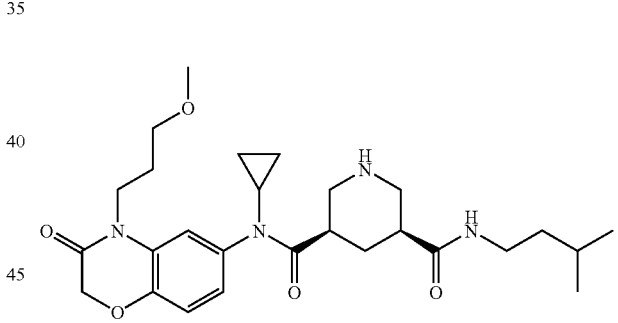

Example 19 is synthesized by deprotection of Intermediate 19.1 analogously to the preparation of example 1. Alternatively deprotection of Intermediate 19.1 is performed by treatment with 4 N—HCl followed by concentration.: ES-MS: M+H=500: $_C t_{Ret}$=2.60 min.

Intermediate 19.1

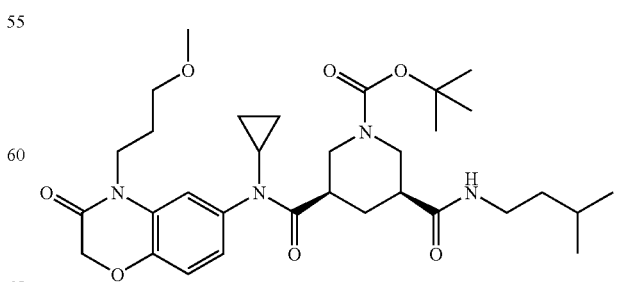

To a solution of Intermediate 19.2 (90 mg, 0.26 mmol) in THF (2 mL) are added Et$_3$N (29 mg, 0.29 mmol) and Isobutyl chloroformate (43 mg, 0.31 mmol) at 0° C. After stirring for 1 h at 0° C., the white precipitate is filtered off through celite pad and the filtrate is concentrated under reduced pressure.

To a solution of the residue in THF (2 mL) are added Intermediate 19.3 (108 mg, 0.39 mmol) and MgBr$_2$OEt$_2$ (100 mg, 0.39 mmol) at room temperature. After stirring for 3 days at room temperature, the reaction mixture is quenched with H$_2$O (10 mL) and extracted with EtOAc/Et$_2$O twice (c.a. 1:1, 40 mL). The organic layer is successively washed with 5% KHSO$_4$aq (twice), 5% NaHCO$_3$aq, H$_2$O, and brine, dried over Na$_2$SO$_4$ and concentrated under reduced pressure. RP-HPLC purification affords Intermediate 19.1 as white amorphous material; ES-MS: [M+H]$^+$=601; HPLC: $_A$t$_{Ret}$=3.60 min.

Intermediate 19.2

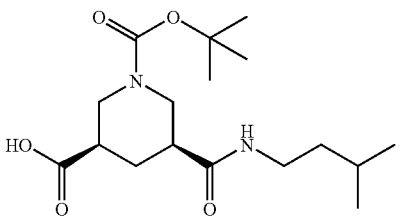

Intermediate 19.2 is synthesized by the ring opening of starting material-E (70 mg, 0.27 mmol) with isoamylamine (36 mg, 0.41 mmol) analogously to the preparation of Intermediate 1.2. White amorphous material; ES-MS: [M]$^+$=342; HPLC: $_A$t$_{Ret}$=3.02 min.

Intermediate 19.3

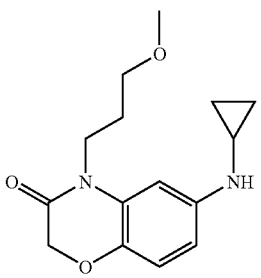

To a suspension of Intermediate 19.4 (5 g, 24.5 mmol), toluene-4-sulfonic acid 3-methoxy-propyl ester (7.18 g, 29.4 mmol) and KI (816 mg, 4.9 mmol) in DMF (125 mL) is added NaH (60% in oil, 1.18 g, 29.4 mmol) at 0° C. The reaction mixture is stirred at 60° C. for 3 h. After adding water, the reaction mixture is extracted with EtOAc, the organic layer is washed with water, brine and dried (MgSO$_4$). Concentration under reduced pressure and silica gel flash chromatography gives Intermediate 19.3: Yellow crystal; ES-MS: M+H=277: $_A$t$_{Ret}$=2.60 min.

Intermediate 19.4

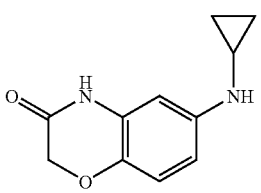

To a suspension of Fe (5.24 g, 93.9 mmol) in 6M HClaq (15.65 mL) is added Intermediate 19.5 (5 g, 18.8 mmol) in EtOH (100 mL) at rt. The reaction mixture is stirred at 60° C. for 3 h. After adding 1M NaOHaq (94 mL), the reaction mixture is filtered on a celite pad. The celite cake is washed with EtOH. Concentration under reduced pressure gives Intermediate 19.4: white powder; ES-MS: M+H=205: $_A$t$_{Ret}$=1.95 min.

Intermediate 19.5

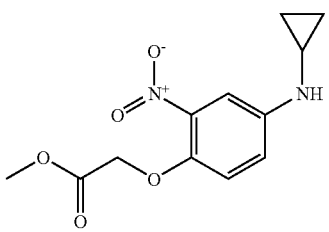

To a suspension of NaBH$_4$ (7.47 g, 197 mmol) in THF (290 mL) is added BF$_3$-Et$_2$O (28 g, 197 mmol) at 0° C. The resulting mixture is stirred for 30 min. A solution of Intermediate 19.6 (39 g, 131.6 mmol) in THF (290 mL) is added to the reaction mixture. The reaction mixture is stirred at 0° C. for 2 h. The mixture is poured into ice-water and extracted with EtOAc, washed with brine and dried (MgSO$_4$). Concentration under reduced pressure and silica gel flash chromatography gives Intermediate 19.5: Yellow crystal; ES-MS: M+H=267: $_A$t$_{Ret}$=3.52 min.

Intermediate 19.6

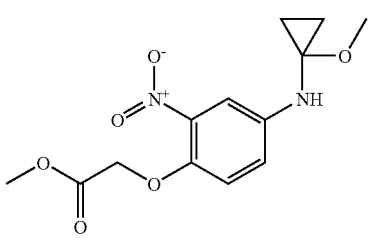

To a solution of Intermediate 19.7 (11 g, 49.1 mmol) and methyl bromoacetate (11.3 g, 73.7 mmol) in acetonitrile (132 mL) is added potassium carbonate (11.5 g, 83.5 mmol) at rt. The reaction mixture is stirred overnight. After adding water, the reaction mixture is extracted with EtOAc, washed with brine and dried (MgSO$_4$). Concentration under reduced pressure and silica gel flash chromatography gives Intermediate 19.6: orange oil; ES-MS: M+H=297: $_A$t$_{Ret}$=3.37 min.

Intermediate 19.7

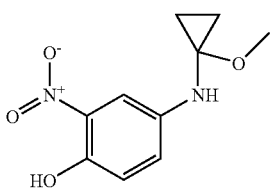

To a solution of 4-amino-2-nitrophenol (20 g, 116 mmol) in MeOH (160 mL) is added AcOH (40 mL) and [(1-ethoxy-cyclopropyl)-oxy]trimethylsilane (22.1 g, 127 mmol) at rt. The reaction mixture is stirred under reflux for 4 h. The reaction mixture is diluted with EtOAc, washed with 2% K2CO3aq, brine and dried (MgSO$_4$). Concentration under reduced pressure gives Intermediate 19.7: red crystal; ES-MS: M+H=225: $_A$t$_{Ret}$=3.38 min.

Alternative synthesis of intermediate 19.3

Intermediate 19.3 is synthesized by the following alternative procedure.

At 0° C., a solution of 2-amino-4-nitrophenol (6.24 g, 40.5 mmol) in DMF (62 mL) is treated with K$_2$CO$_3$ (8.44 g, 61.1 mmol) and chloroacetyl chloride (X. Huang, C. Chan, Synthesis 1984, 31, 851.) (3.5 mL, 44.0 mmol), stirred at the same temperature for 40 min, warmed to 60° C., and stirred for 23 h, cooled to 0° C., and treated with KI (1.32 g, 7.95 mmol) and a solution of 1-methoxy-3-(p-toluenesulfonyloxy)propane (12.1 g, 49.5 mmol) in DMF (24 mL). After adding 60% of NaH (2.00 g, 50.0 mmol) over 10 min, the mixture is stirred at 0° C. for 1 h, warmed to 60° C., stirred for 24 h, and treated with H₂O (650 mL). After extraction of the mixture with EtOAc (3×80 mL) and Et₂O (3×80 mL), the combined org. layer is washed with H₂O (2×50 mL), dried (Na₂SO₄), and evaporated. A SiO₂ flash chromatography (300 g, hexane/ EtOAc 5:4) gives 4-(3-methoxypropyl)-6-nitro-4H-benzo[1,4]oxazin-3-one as yellow solid.

At room temperature, an ethanolic solution (1100 mL) of 4-(3-methoxypropyl)-6-nitro-4H-benzo[1,4]oxazin-3-one (91.0 g, 0.34 mol) is treated with 6N HCl (170 mL, 1.02 mol of HCl) and powdered Fe (57.0 g, 1.02 mol), heated to 70° C., stirred for 15 h, cooled to 0° C., treated with 6N NaOH (250 mL), and filtered on a celite pad. The filtrate is diluted with CH₂Cl₂ (1000 mL), and the aq. layer is separated. The org. layer is washed with brine (2×300 mL), dried (Na₂SO₄), and evaporated to give 6-amino-4-(3-methoxypropyl)-4H-benzo[1,4]oxazin-3-one as light brown solid.

At room temperature, a methanolic solution (20 mL) of 6-amino-4-(3-methoxypropyl)-4H-benzo[1,4]oxazin-3-one (2.49 g, 10.5 mmol) is treated with AcOH (5.0 mL) and [(1-ethoxycycopropyl)-oxy]trimethylsilane (2.1 mL, 10.5 mmol), stirred at 70° C. under reflux for 1.5 h. At the same temperature, to this mixture is added dropwise a methanolic solution (3.7 mL) of NaBH₃CN (0.73 g, 11.6 mmol) over 5 min, and the resulting mixture is stirred at 70° C. under reflux for 2 h, and evaporated. After co-evaporation with PhMe for several times until the smell of AcOH disappeared, the residue is dissolved in EtOAc (200 mL), and the solution is washed with sat. aqueous solution of NaHCO₃ (40 mL) and brine (40 mL), dried (Na₂SO₄), and evaporated. A SiO₂ flash chromatography (100 g, CH₂Cl₂/EtOAc 1:1) gives Intermediate 19.3 as white solid.

Example 20

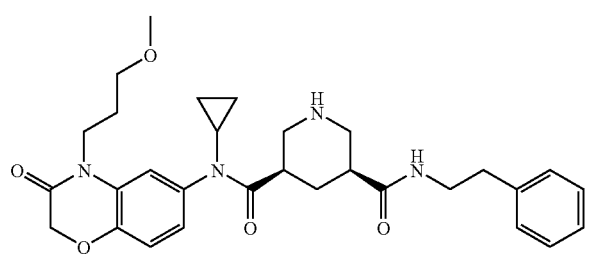

Example 20 is synthesized by deprotection of Intermediate 20.1 analogously to the preparation of example 1: ES-MS: M+H=534: $_c t_{Ret}$=2.61 min.

Intermediate 20.1

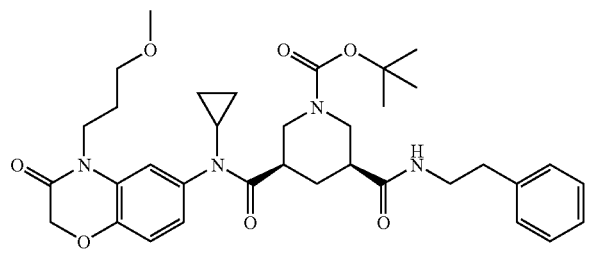

Intermediate 20.1 is synthesized by the condensation of Intermediate 20.2 (90 mg, 0.24 mmol) with Intermediate 19.3 (108 mg, 0.39 mmol) analogously to the preparation of Intermediate 19.1. White amorphous material; ES-MS: [M+H]⁺=635; HPLC: $_A t_{Ret}$=3.59 min.

Intermediate 20.2

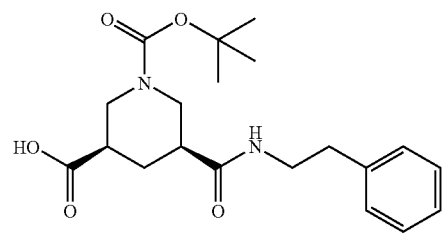

Intermediate 20.2 is synthesized by the ring opening of starting material-E (70 mg, 0.27 mmol) with 2-phenetylamine (50 mg, 0.41 mmol) analogously to the preparation of Intermediate 1.2. White amorphous material; ES-MS: [M]⁺=376; HPLC: $_c t_{Ret}$=3.01 min.

Example 25

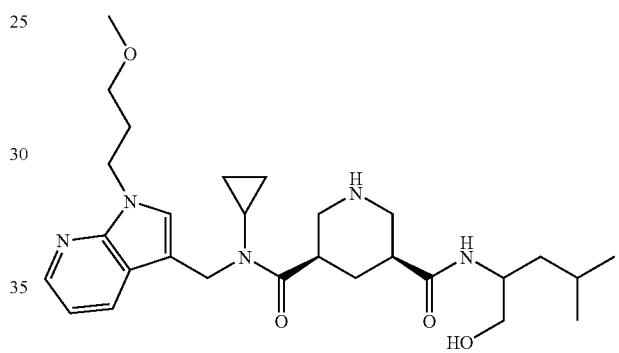

Example 25 is synthesized by deprotection of Intermediate 25.1 analogously to the preparation of example 1: ES-MS: M+H=514: $_c t_{Ret}$=2.02, 2.17 min.

Intermediate 25.1

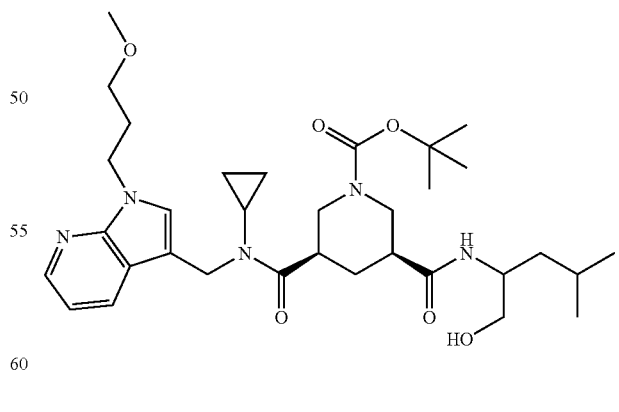

Intermediate 25.1 is synthesized by condensation of Intermediate 33.2 (50 mg, 0.13 mmol) with Intermediate 25.2 (49 mg, 0.19 mmol) analogously to the preparation of Intermediate 1.1. White amorphous material; ES-MS: [M-ᵗBu+H]⁺=557; HPLC: $_c t_{Ret}$=2.86, 2.96 min.

Intermediate 25.2

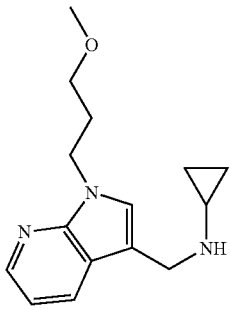

Intermediate 25.2 (184 mg, 0.843 mmol) and cyclopropylamine (114 mg, 2 mmol) are dissolved in CH$_2$Cl$_2$, the solution is stirred for 15 min at room temperature followed by addition of sodium cyanoborohydride (530 mg, 2.5 mmol). The reaction mixture is stirred for 40 h at room temperature. The reaction mixture is partitioned between AcOEt (100 mL) and 1M NaHCO$_3$. The organic layer is washed with 1 M aqueous NaHCO$_3$ (2×20 mL), brine (1×5 mL), dried over MgSO$_4$, filtered and concentrated under reduced pressure to give Intermediate 25.3 as a yellow oil; ES-MS: [M]$^+$=259; HPLC: $_c$t$_{Ret}$=1.55 min.

Intermediate 25.3

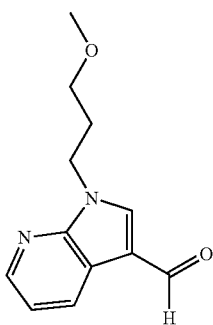

7-azaindole is suspended in DMF (4 mL), Potassium tert-butoxide (135 mg, 1.2 mmol) is added and the reaction mixture is stirred for 20 min at 80° C. 3-Tosyloxy-1-methoxypropane (415 mg, 1.7 mmol) dissolved in DMF (2 mL) is added and stirring is continued for 21 h. The reaction mixture is partitioned between AcOEt and 1M NaHCO$_3$ (10 mL). The organic layer is washed with 1M NaHCO$_3$ (2×20 mL), brine (1×5 mL), dried over MgSO$_4$, filtered and concentrated under reduced pressure.

The residue is dissolved in DMF (3 mL) and then treated with a solution of POCl$_3$ (175 mg, 1.1 mmol) in DMF (1.5 mL) (15 min preactivation). The solution is stirred for 1 h at room temperature and for further 16 h at 60° C. The reaction mixture is poured into water which is basified with 1M NaHCO$_3$, and extracted with AcOEt (3×50 mL). The combined organic layer is washed with brine (1×10 mL), dried over MgSO$_4$, filtered and concentrated under reduced pressure to give Intermediate 25.3 as a yellow oil; ES-MS: [M]$^+$= 259; HPLC: $_c$t$_{Ret}$=1.55 min.

Example 26

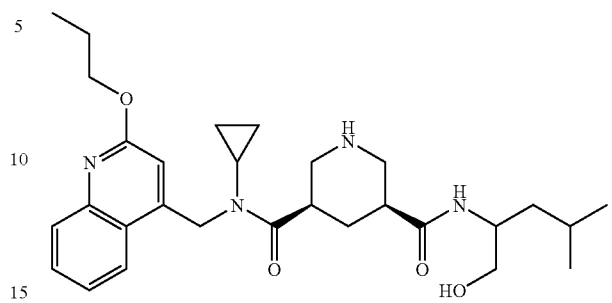

Example 26 is synthesized by deprotection of Intermediate 26.1 analogously to the preparation of example 1: ES-MS: M+H=511: $_c$t$_{Ret}$=2.78, 2.98 min.

Intermediate 26.1

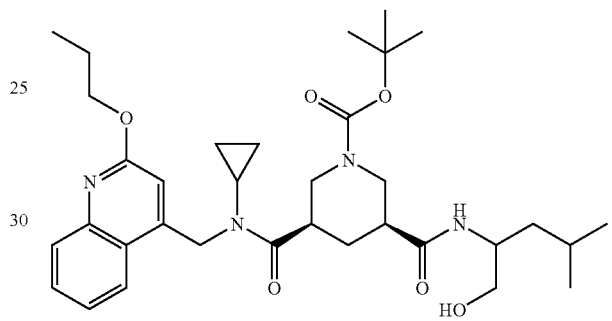

Intermediate 26.1 is synthesized by condensation of Intermediate 33.2 (50 mg, 0.13 mmol) with Intermediate 26.2 (48 mg, 0.19 mmol) analogously to the preparation of Intermediate 1.1. White amorphous material; ES-MS: [M-$^t$Bu+H]$^+$= 611; HPLC: $_c$t$_{Ret}$=3.86 min.

Intermediate 26.2

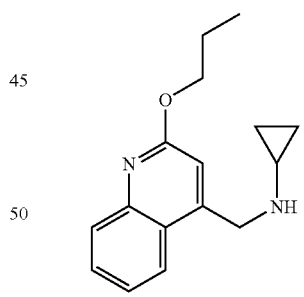

To a suspension of NaH (97 mg, 60% dispersion in mineral oil, 2.4 mmol) and 1-propanol (303 µL, 4.1 mmol) in NMP (3 mL) is added Intermediate 26.3 (200 mg, 0.81 mmol). After stirring for 3 h at 70° C., the mixture is partitioned between AcOEt (50 mL) and 1M NaHCO$_3$ (10 mL). The organic layer is washed with 1 M aqueous NaHCO$_3$ (2×10 mL), brine (1×5 mL), dried over MgSO$_4$, filtered and concentrated under reduced pressure. The mixture of the residue and BH$_3$ solution (1M in THF, 5 mmol) is stirred at room temperature. After stirring for 36 h at rt, MeOH is added to the reaction mixture and the mixture is stirred for 3.5 h at 50° C. The reaction mixture is partitioned between AcOEt (50 mL) and 1 M NaHCO$_3$ The organic layer is washed with 1 M aqueous NaHCO$_3$ (2×10 mL), brine (1×5 mL), dried over MgSO$_4$, filtered and concentrated under reduced pressure to give Intermediate 26.2 as a colorless oil; ES-MS: [M+H]⁺=257; HPLC: $c_{t_{Ret}}$=2.47 min.

Intermediate 26.3

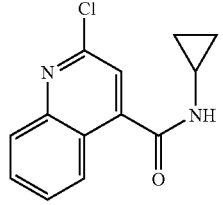

A mixture of 2-Chloroquinoline 4-carboxylic acid (1 g, 4.8 mmol), oxalyl chloride (4 mL) and DMF (20 μL) in CH₂Cl₂ (20 mL) is stirred at room temperature. After stirring for 2.5 h at room temperature, the reaction mixture is concentrated under reduced pressure.

To a suspension of the residue in CH₂Cl₂ (10 mL) are added ethyl diisopropylamine (1.65 mL, 9.6 mmol) and cyclopropylamine (668 μL, 9.6 mmol) at room temperature. After stirring for 1 h at room temperature, the reaction mixture is partitioned between AcOEt (300 mL) and 1M NaHCO₃ (50 mL). The organic layer is washed with 1M NaHCO₃ (2×30 mL), brine (1×10 mL), dried over MgSO₄, filtered and concentrated under reduced pressure to give Intermediate 26.3 as a white powder; ES-MS: [M]⁺=246; HPLC: $c_{t_{Ret}}$=2.50 min.

Example 27

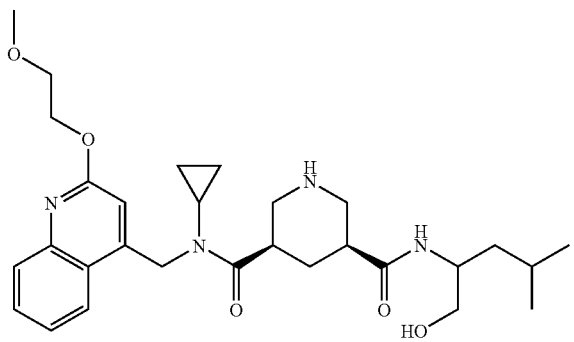

Example 27 is synthesized by deprotection of Intermediate 27.1 analogously to the preparation of example 1: ES-MS: M+H=527: $c_{t_{Ret}}$=2.53, 2.71 min.

Intermediate 27.1

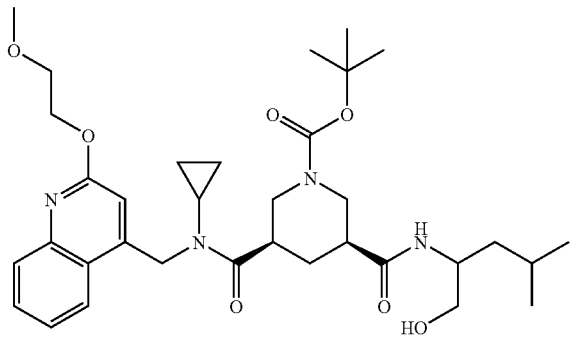

Intermediate 27.1 is synthesized by condensation of Intermediate 33.2 (50 mg, 0.13 mmol) with Intermediate 27.2 (51.2 mg, 0.19 mmol) analogously to the preparation of Intermediate 1.1. White amorphous material; ES-MS: [M-ᵗBu+H]⁺=627; HPLC: $c_{t_{Ret}}$=3.56 min.

Intermediate 27.2

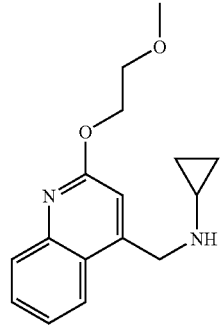

Intermediate 27.2 is synthesized by etherification followed by reduction of Intermediate (200 mg, 0.81 mmol) analogously to the preparation of Intermediate 27.2. White colorless oil; ES-MS: [M+H]⁺=273; HPLC: $c_{t_{Ret}}$=2.05 min.

Example 32

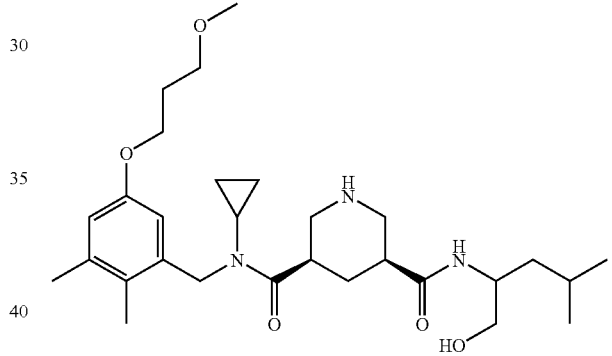

Example 32 is synthesized by deprotection of Intermediate 32.1 analogously to the preparation of example 1: ES-MS: M+H=518: $c_{t_{Ret}}$=2.70, 2.84 min.

Intermediate 32.1

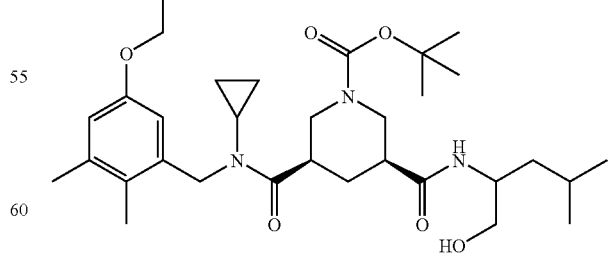

Intermediate 32.1 is synthesized by condensation of Intermediate 33.2 (50 mg, 0.134 mmol) with Intermediate 32.2 (55 mg, 0.21 mmol) analogously to the preparation of Intermediate 1.1. White amorphous material; ES-MS: [M+H]⁺=618; HPLC: $c_{t_{Ret}}$=3.93 min.

Intermediate 32.2

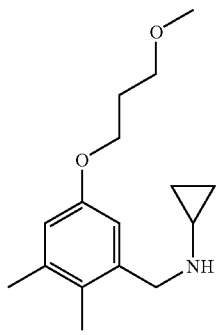

A mixture of Intermediate 32.3 (190 mg, 0.68 mmol) and BH$_3$ (1M in THF, 4 mL, 4 mmol) is stirred at 50° C. After stirring for 80 h at 50° C., the reaction mixture is cooled down at 0° C., 1 mL of MeOH is added. After stirring for 2 h at 50° C., the reaction mixture is cooled down to room temperature, then diluted with 1N NaOH aq. and extracted with CH$_2$Cl$_2$. The organic layers are extracted with 1 M aqueous HCl, then the HCl layer is acidified with 1N NaOH aq. (pH>12). The aqueous layer is extracted with CH$_2$Cl$_2$. The combined organic extracts are washed with H$_2$O and brine, dried over Na$_2$SO$_4$ and concentrated under reduced pressure to afford Intermediate 32.2 as a colorless oil; ES-MS: [M+H]$^+$=264; HPLC: $_c t_{Ret}$=2.37 min.

Intermediate 32.3

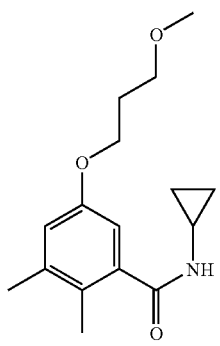

To a solution of Intermediate 32.4 (400 mg, 2.4 mmol) and cyclopropylamine (200 µL, 2.9 mmol) in DMF (5 mL) are added EDCI.HCl (690 mg, 3.6 mmol) and HOAt (98 mg, 0.72 mmol). After stirring for 2 h, the reaction is quenched with H$_2$O (10 mL) and 5% aqueous KHSO$_4$ (10 mL) and extracted with EtOAc twice (30 mL). The combined organic layers are washed is H$_2$O and brine, then dried over Na$_2$SO$_4$ and concentrated under reduced pressure. The residue is purified by silica gel column chromatography to afford the desired amide. To a solution of the amide and toluene-4-sulfonic acid 3-methoxypropyl ester (1.2 g, 4.8 mmol) in DMF (10 mL) are added K$_2$CO$_3$ (663 mg, 4.8 mmol) and KI (100 mg, 0.6 mmol). After stirring for 2 h at 80° C., the reaction is quenched with H$_2$O (5 mL) and extracted with EtOAc (20 mL). The organic layer is successively washed with 5% aqueous KHSO$_4$aq, 5% aqueous NaHCO$_3$, H$_2$O, and brine, then dried over Na$_2$SO$_4$ and concentrated under reduced pressure. The residue is purified by silica gel column chromatography to afford Intermediate 32.3. as a colorless oil; ES-MS: [M+H]$^+$=278; HPLC: $_c t_{Ret}$=2.78 min.

Intermediate 32.4

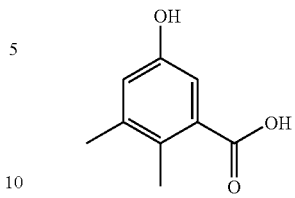

To a solution of Intermediate 32.5 (1.2 g, 7.3 mmol) and H$_2$SO$_4$ (464 µL, 8.7 mmol) in H$_2$O (25 mL) is added aqueous NaNO$_2$ (601 mg in 10 mL, 8.7 mmol) After stirring for 2 h at 80° C., the reaction mixture is cooled down to room temperature and is poured into ice/5% aqueous NaHCO$_3$ (100 g/50 mL). After stirring for 10 min, the reaction mixture is acidified with 5% aqueous KHSO$_4$ (pH<3), then extracted with EtOAc twice. The combined organic layers are washed with H$_2$O and brine, dried over Na$_2$SO$_4$. and concentrated under reduced pressure to afford Intermediate 32.4. as a light yellow amorphous; ES-MS: [M+H]$^+$=166; HPLC: $_c t_{Ret}$=2.06 min.

Intermediate 32.5

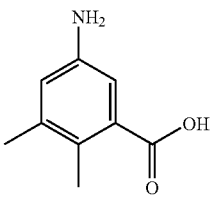

To a solution of Intermediate 32.6 (1.5 g, 7.7 mmol) in MeOH (60 mL) is added Pd(en)cat (60 mg), then the mixture is stirred under H$_2$ atmosphere. After stirring for 2 h, the catalyst is removed by filtration through a celite pad and the celite cake is washed with MeOH. Concentration of the filtrate affords Intermediate 32.5. as a brown solid; ES-MS: [M+H]$^+$=165; HPLC: $_c t_{Ret}$=1.25 min.

Intermediate 32.6

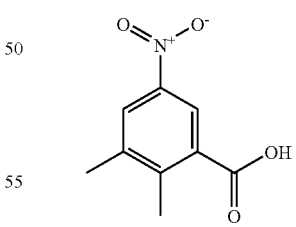

To a solution of 2,3-dimethylbenzoic acid (3 g, 20 mmol) in conc. H$_2$SO$_4$ (40 mL) is added KNO$_3$ (2.02 g, 22 mmol) at 0° C. After stirring for 5 h at 0° C., the reaction mixture is poured into ice, then the white precipitate is collected by filtration. The collected precipitate is triturated with CH$_3$CN (10 mL) and H$_2$O (20 mL) and the solids are collected by filtration to give Intermediate 32.6 as a white solid material; ES-MS: [M+H]$^+$=195; HPLC: $_c t_{Ret}$=2.73 min.

Example 33

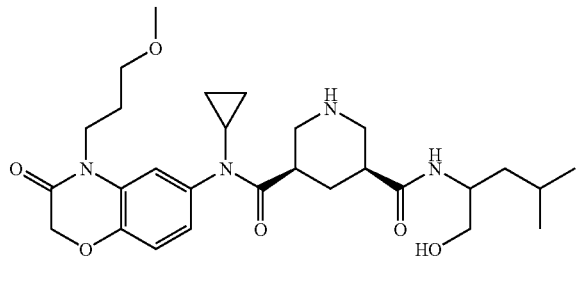

Example 33 is synthesized by deprotection of Intermediate 33.1 analogously to the preparation of example 1: ES-MS: M+H=531; $_C t_{Ret}$=2.30, 2.47 min.

Intermediate 33.1

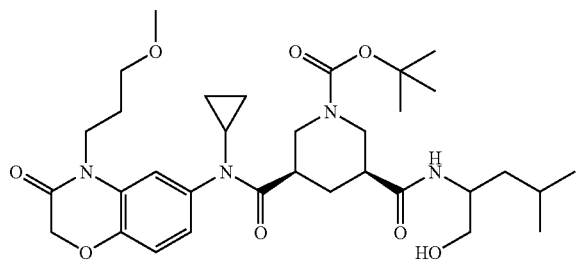

Intermediate 33.1 is synthesized by the condensation of Intermediate 33.2 (90 mg, 0.24 mmol) with Intermediate 19.3 (108 mg, 0.39 mmol) analogously to the preparation of Intermediate 19.1. White amorphous material; ES-MS: [M+H]$^+$= 631; HPLC: $_A t_{Ret}$=3.22, 3.29 min.

Intermediate 33.2

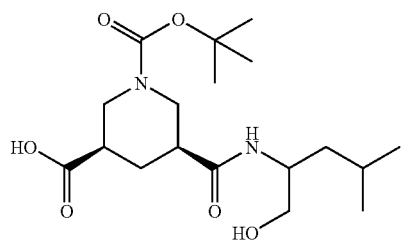

Intermediate 33.2 is synthesized by the ring opening of starting material-E (70 mg, 0.27 mmol) with DL-leucinol (49 mg, 0.41 mmol) analogously to the preparation of Intermediate 1.2. White amorphous material; ES-MS: [M]$^+$=372; HPLC: $_C t_{Ret}$=2.50, 2.74 min.

Example 34

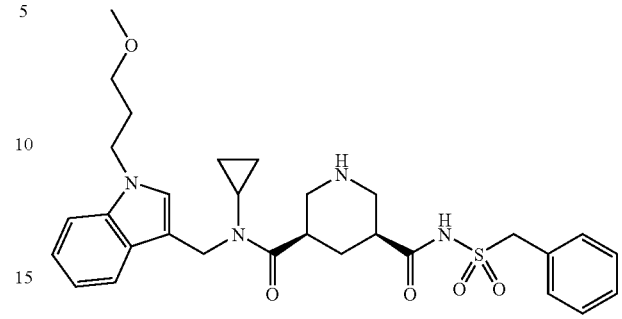

Example 34 is synthesized by deprotection of Intermediate 34.1 analogously to the preparation of example 1: ES-MS: M+H=567; $_C t_{Ret}$=3.01 min.

Intermediate 34.1

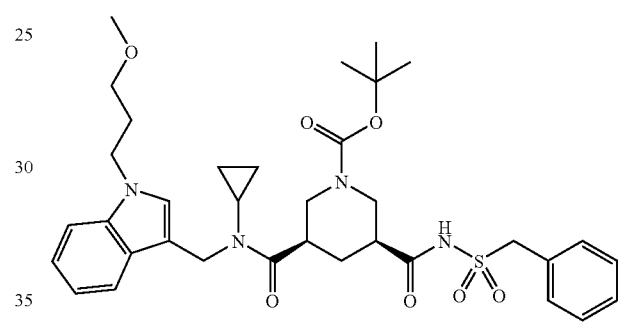

To a solution of Intermediate 1.2 (50 mg, 0.1 mmol) and phenyl methanesulfonamide (26 mg, 0.15 mmol) in DMF were added EDCI.HCl (29 mg, 0.15 mmol) and DMAP (6 mg, 0.05 mmol) at room temperature. After stirring for 64 h, the reaction mixture is quenched with H$_2$O (10 mL) and extracted with EtOAc (20 mL). The organic layer is successively washed with 5% KHSO$_4$aq, 5% NaHCO$_3$aq, H$_2$O, and brine, then dried over Na$_2$SO$_4$ and concentrated under reduced pressure to afford Intermediate 34.1 as a yellow solid; ES-MS: [M+H]$^+$=667; HPLC: $_C t_{Ret}$=4.06 min.

Example 37

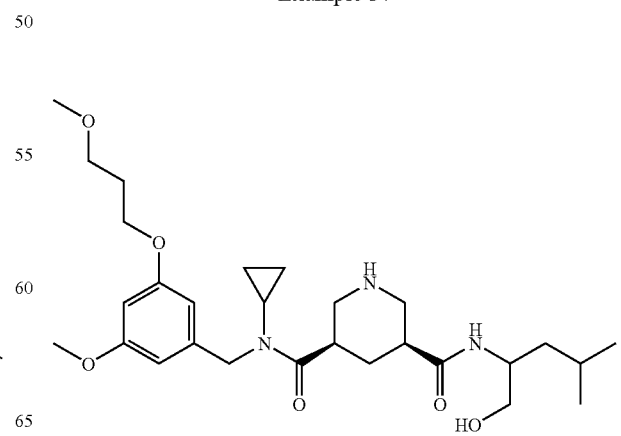

Example 37 is synthesized by deprotection of Intermediate 37.1 analogously to the preparation of example 1: ES-MS: M+H=520: $_C t_{Ret}$=2.62, 2.76 min.

Intermediate 37.1

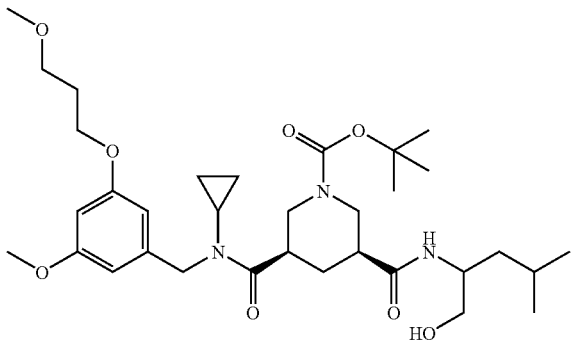

Intermediate 37.1 is synthesized by condensation of Intermediate 37.2 (50 mg, 0.13 mmol) with Intermediate 33.2 (41 mg, 0.16 mmol) analogously to the preparation of Intermediate 1.1. White amorphous material; ES-MS: [M+H]$^+$=620; HPLC: $_C t_{Ret}$=3.65 min.

Intermediate 37.2

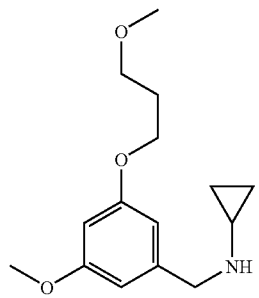

Intermediate 37.2 is synthesized by condensation of Intermediate 37.3 (2.50 g, 11.1 mmol) and cyclopropylamine (855 mg, 15.0 mmol) analogously to the preparation of Intermediate 1.3. Yellow oil; ES-MS: M+H=266; HPLC: $_A t_{Ret}$=2.48 min.

Intermediate 37.3

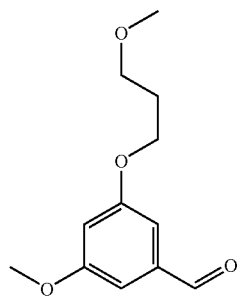

Intermediate 37.3 is synthesized by MnO$_2$ oxidation of Intermediate 37.4 (4.20 g, 18.6 mmol) in toluene at RT for 12 h. Yellow oil; ES-MS: M+H=225; HPLC: $_A t_{Ret}$=3.59 min.

Intermediate 37.4

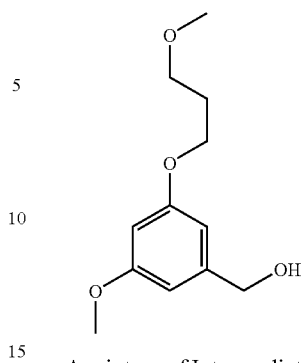

A mixture of Intermediate 37.5 (5 g, 19.7 mmol) and LAH (528 mg, 20 mmol) in THF (110 mL) is stirred under N$_2$ at 0° C. for 3 h. After adding H$_2$O, the reaction mixture is extracted with EtOAc. The combined organic phases are washed with H$_2$O, brine and dried (Na$_2$SO$_4$). Concentration under reduced pressure and silica gel flash chromatography give Intermediate 37.4 as a colorless oil; ES-MS: M+H=227; HPLC: $_A t_{Ret}$=2.85 min.

Intermediate 37.5

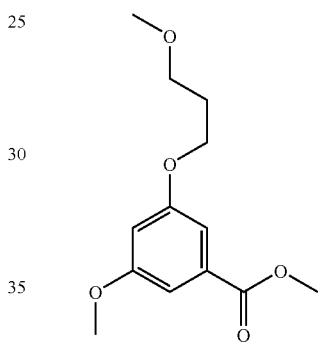

To a mixture of 3-methoxy-5-hydroxybenzoic acid methyl ester (23.2 g, 127 mmol), toluene-4-sulfonic acid 3-methoxypropyl ester (40.7 g, 167 mmol) and KI (2.23 g, 13.4 mmol) in DMF (350 mL), K$_2$CO$_3$ (53.1 g, 384 mmol) is added under N$_2$. After stirring at 60° C. for 17 h, the reaction mixture is supplemented with H$_2$O and extracted with Et$_2$O. The combined organic phases are washed with H$_2$O and dried (Na$_2$SO$_4$). Concentration under reduced pressure and silica gel flash chromatography give Intermediate 37.5 as a colorless oil; ES-MS: M+H=255, HPLC: $_A t_{Ret}$=3.80 min.

Example 38

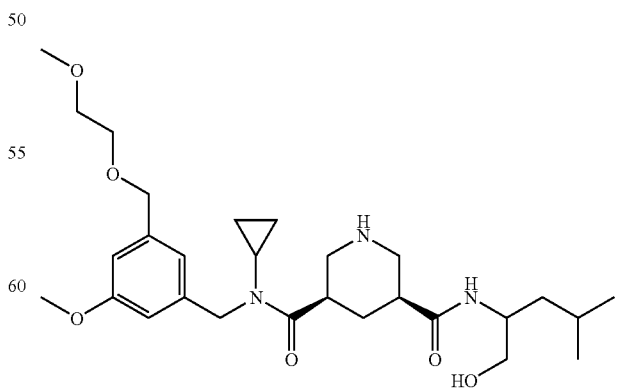

Example 38 is synthesized by deprotection of Intermediate 38.1 analogously to the preparation of example 1: ES-MS: M+H=520: $_C t_{Ret}$=2.56 min.

Intermediate 38.1

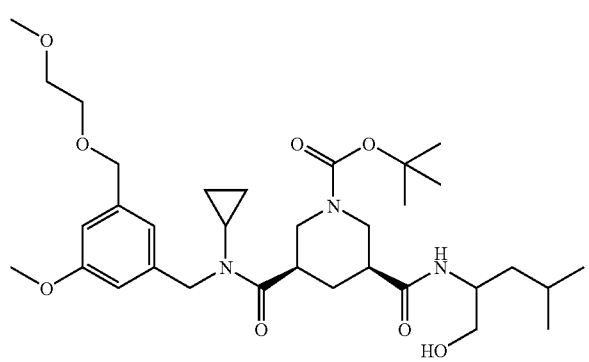

Intermediate 38.1 is synthesized by condensation of Intermediate 38.2 (50 mg, 0.13 mmol) with Intermediate 33.2 (41 mg, 0.16 mmol) analogously to the preparation of Intermediate 1.1. White amorphous material; ES-MS: [M+H]$^+$=620; HPLC: $_C t_{Ret}$=3.43, 3.49 min.

Intermediate 38.2

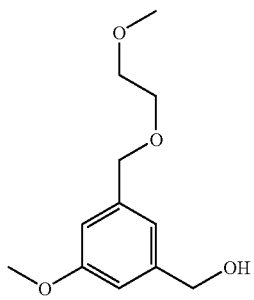

Intermediate 38.2 is synthesized by reduction of Intermediate 38.3 (824 mg, 3.3 mmol) analogously to the preparation of Intermediate 37.4. White powder; HPLC: $_A t_{Ret}$=2.52 min; Rf=0.21 (EtOAc:n-Hex=1:1)

Intermediate 38.3

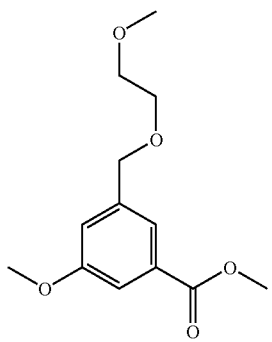

Intermediate 38.3 is synthesized by alkylation of 3-(hydroxymethyl)-5-methoxy-benzoic acid methylester (1.85 g, 9.4 mmol) (see e.g. *Synthetic Communications*, 2001, 31, 1921-1926) analogously to the preparation of Intermediate 37.5. White amorphous material; ES-MS: M+H=255; HPLC: $_A t_{Ret}$=3.44 min Example 39

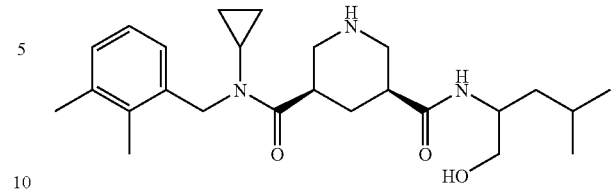

Example 39 is synthesized by deprotection of Intermediate 39.1 analogously to the preparation of example 1: ES-MS: M+H=430: $_C t_{Ret}$=2.68, 2.87 min.

Intermediate 39.1

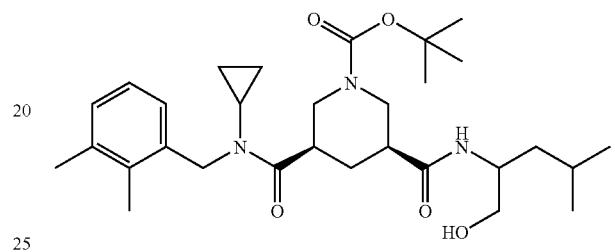

To a solution of Intermediate 33.2 (50 mg, 0.13 mmol) in DMF (1 mL) are added EDCI HCl (40 mg, 0.20 mmol), HOAt (5.5 mg, 0.04 mmol) and cyclopropyl-(2,3-dimethylbenzyl)amine (34 mg, 0.16 mmol) and Et$_3$N (16 mg, 0.16 mmol) at room temperature. After stirring for 48 h at room temperature, the reaction mixture is quenched with H$_2$O (10 mL) and extracted with EtOAc. The organic layer is successively washed with 5% KHSO$_4$aq, 5% NaHCO$_3$aq, H$_2$O, and brine, then dried over Na$_2$SO$_4$ and concentrated under reduced pressure to afford Intermediate 39.1 as white amorphous material; ES-MS: [M+H]$^+$=530; HPLC: $_C t_{Ret}$=3.85 min.

Example 40

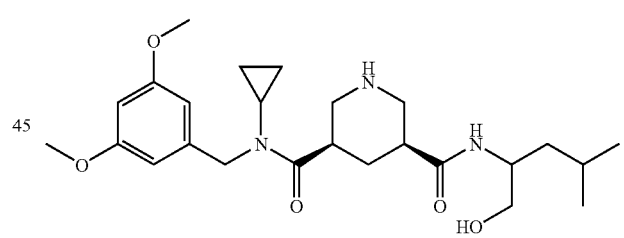

Example 40 is synthesized by deprotection of Intermediate 40.1 analogously to the preparation of example 1: ES-MS: M+H=462: $_C t_{Ret}$=2.47, 2.63 min.

Intermediate 40.1

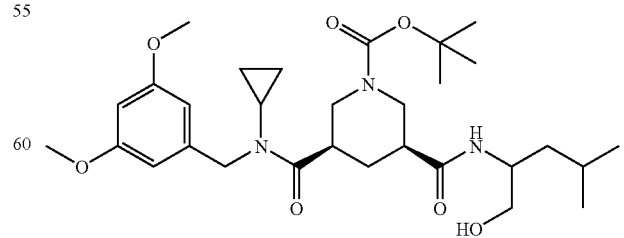

Intermediate 40.1 is synthesized by condensation of cyclopropyl-(3,5-dimethoxybenzyl)amine (50 mg, 0.13 mmol) with Intermediate 33.2 (39 mg, 0.16 mmol) analogously to the preparation of Intermediate 40.1. White amorphous material; ES-MS: [M+H]⁺=562; HPLC: $_C t_{Ret}$=3.53 min.

Example 41

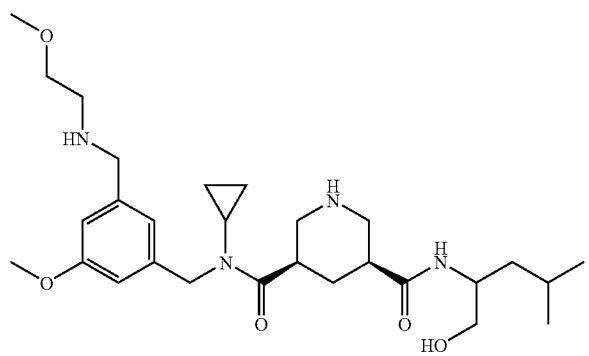

Example 41 is synthesized by deprotection of Intermediate 41.1 analogously to the preparation of example 1: ES-MS: M+H=519: $_C t_{Ret}$=1.96, 2.06 min.

Intermediate 41.1

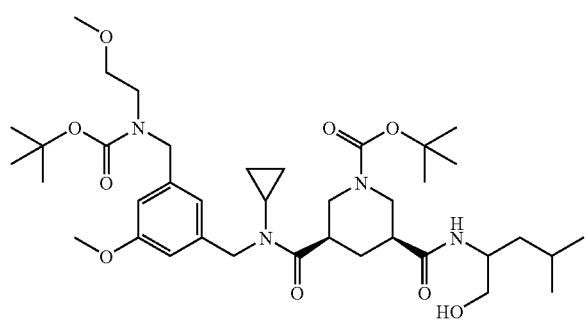

Intermediate 41.1 is synthesized by condensation of Intermediate 33.2 (50 mg, 0.13 mmol) with Intermediate 41.2 (58 mg, 0.16 mmol) analogously to the preparation of Intermediate 1.1. White amorphous material; ES-MS: [M+H]⁺=719; HPLC: $_C t_{Ret}$=3.95 min.

Intermediate 41.2

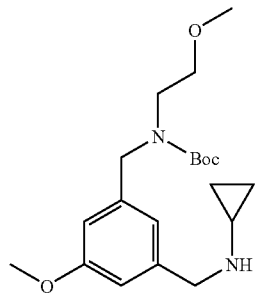

Intermediate 41.2 is synthesized by amination of Intermediate 41.3 (770 mg, 1.98 mmol) and cyclopropylamine (1.4 mL, 19.8 mmol) analogously to the preparation of Intermediate 42.2. Colorless oil; ES-MS: M+H=365; HPLC: $_B t_{Ret}$=1.56 min.

Intermediate 41.3

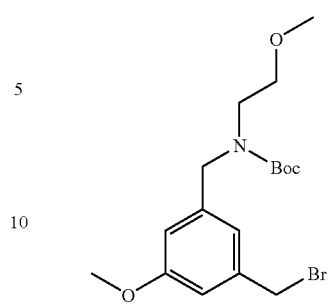

Intermediate 41.3 is synthesized by bromination of Intermediate 41.4 (800 mg, 2.46 mmol) analogously to the preparation of Intermediate 42.3. Colorless oil; ES-MS: M+H=389, 391; HPLC: $_B t_{Ret}$=2.1 min.

Intermediate 41.4

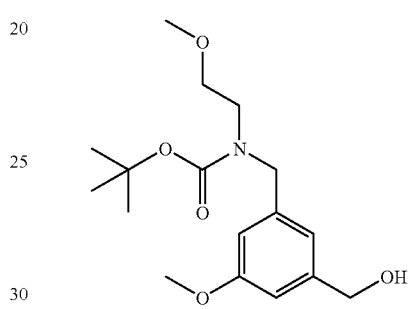

A mixture of Intermediate 41.5 (2 g, 7.5 mmol) and LAH (1.4 g, 37.4 mmol) in THF (70 mL) is stirred under N₂ at 0° C. After stirring for 6 h at 70° C., the reaction mixture is cooled down at 0° C., and sodium sulfate decahydrate is added to the mixture. The resulted gray materials is removed by filtration through celite pad, then the filtrate is concentrated under reduced pressure to give the crude.

To a solution of the crude in CH₂Cl₂ are added Et₃N and Boc₂O at room temperature. After stirring for 18 h at room temperature, the reaction mixture is acidified with a 1N KHSO₄ solution and extracted with CH₂Cl₂. The organic layer is washed with brine, dried over Na₂SO₄, and concentrated. Silica gel flash chromatography gives Intermediate 41.4 as a white amorphous; ES-MS: M+H=240; HPLC: $_A t_{Ret}$=1.72 min.

Intermediate 41.5

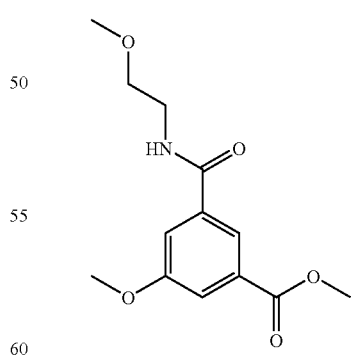

To a solution of 5-methoxyisophthalic acid monomethyl ester (2 g, 9.5 mmol) in DMF (20 mL) are added EDCI HCl (2.7 g, 14.3 mmol), HOAt (0.97 g, 7.1 mmol) and 2-methoxyethylamine (786 mg, 10.5 mmol) at room temperature. After stirring for 4 h at room temperature, the reaction mixture is quenched with H₂O (10 mL) and extracted with EtOAc. The organic layer is successively washed with H₂O twice and brine, then dried over Na$_2$SO$_4$. Concentration under reduced pressure affords Intermediate 41.5 as a white solid material; ES-MS: M+H=268; HPLC: $_A$t$_{Ret}$=2.38 min.

Synthesis of Example 42

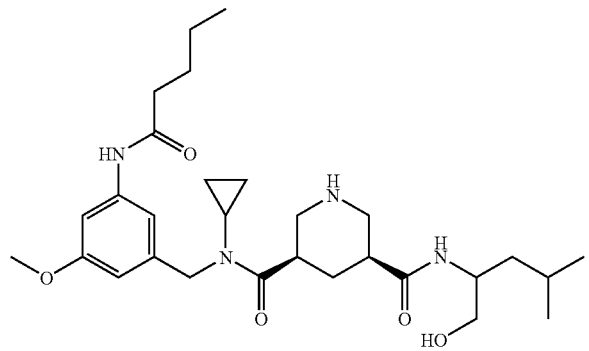

To a solution of Intermediate 42.1 (1 eq) in DCM is added 2,6-lutidine (3 eq) and TMSOTf (3 eq) at rt and stirred for 30 min. After adding a drop of MeOH and AcOH, the reaction mixture is concentrated under reduced pressure and purified with RP-HPLC to give example 42: ES-MS: M+H=531: $_C$t$_{Ret}$=2.58, 2.86 min.

Intermediate 42.1

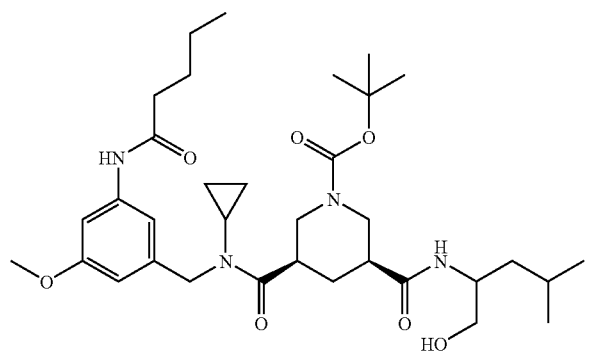

Intermediate 42.1 is synthesized by condensation of intermediate 33.2 (81 mg, 0.22 mmol) and Intermediate 42.2 (60 mg, 0.22 mmol) analogously to the preparation of Intermediate 1.1. White amorphous material; ES-MS: M+H=631; HPLC: $_B$t$_{Ret}$=1.89 min.

Intermediate 42.2

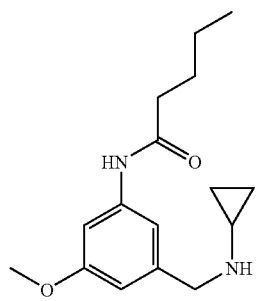

To a solution of cyclopropylamine (1.1 mL) in DMF (5 mL) is added K$_2$CO$_3$ (663 mg, 4.8 mmol) and a solution of Intermediate 42.3 (480 mg, 1.6 mmol) in DMF at 60° C. After stirring for 30 min, the reaction mixture is diluted with EtOAc, washed with water, brine and dried (MgSO$_4$). Concentration under reduced pressure and silica gel flash chromatography give intermediate 42.2: ES-MS: M+H=277: $_B$t$_{Ret}$=1.42 min.

Intermediate 42.3

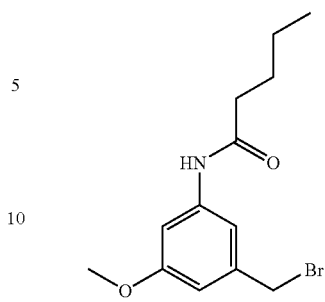

To a solution of Intermediate 42.4 (324 mg, 1.37 mmol) in CH$_2$Cl$_2$ (15 mL) is added PPh$_3$ (430 mg, 1.64 mmol) and NBS (292 mg, 1.64 mmol) at rt After stirring for 3 h, the mixture is concentration under reduced pressure and silica gel flash chromatography to give intermediate 42.3: ES-MS: M+H=300, 302: $_B$t$_{Ret}$=1.89 min.

Intermediate 42.4

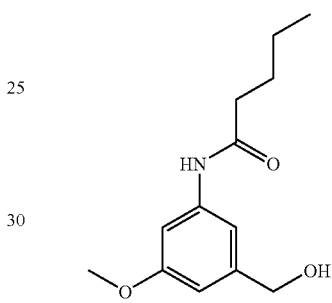

A solution of Intermediate 42.5 (400 mg, 1.58 mmol) in 4M HCl/dioxane (5 mL) is stirred at rt for 1 h. The mixture is concentrated under reduced pressure. To a solution of the evaporated residue in CH$_2$Cl$_2$ (10 mL) is added N-ethyldiisopropylamine (0.95 mL) and n-valeroyl chloride (0.4 mL) at rt After stirring for 2 h, the reaction mixture is diluted with EtOAc, the organic layer is washed with 1M HClaq, sat NaHCO$_3$aq and brine. Upon concentration under reduced pressure, the evaporated residue is dissolved in MeOH. Sodium methoxide is added and the solution is stirred at rt overnight. After adding NH$_4$Cl, the solution is concentrated under vacuum and purified on a silica gel column to give Intermediate 42.4: ES-MS: M+H=238: $_B$t$_{Ret}$=1.53 min Intermediate 42.5

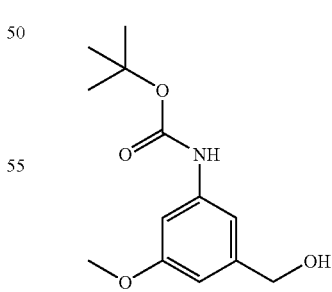

To a solution of Intermediate 42.6 (1.9 g, 6.75 mmol) in THF (100 mL) is added LAH (513 mg, 13.5 mmol) at 0° C. The reaction mixture is warmed to rt After stirring for 1 h, the mixture is quenched with 5 g of Na$_2$SO$_4$-10H$_2$O, and filtered on a celite pad. Concentration under reduced pressure and silica gel flash chromatography give Intermediate 42.5: ES-MS: M+H=253: $_B$t$_{Ret}$=1.65 min.

Intermediate 42.6

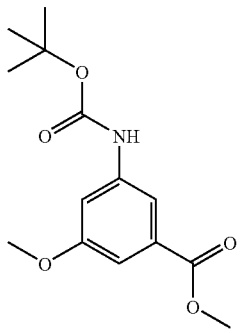

To a solution of 5-methoxyisophthalic acid monomethyl ester (5 g, 23.8 mmol) in t-BuOH (20 mL) and dioxane (20 mL) is added triethylamine (3.8 mL, 28.6 mmol) and DPPA (6.15 mL, 28.6 mmol) at 0° C. The reaction mixture is warmed to 80° C. After stirring for 4 h, the mixture is diluted with EtOAc, the organic layer is washed with 1 M HClaq, water, sat. NaHCO$_3$ aq and brine. Concentration under reduced pressure and silica gel flash chromatography give Intermediate 42.6: ES-MS: M (-t-Bu)=255: $_B t_{Ret}$=1.94 min.

Synthesis of Example 43

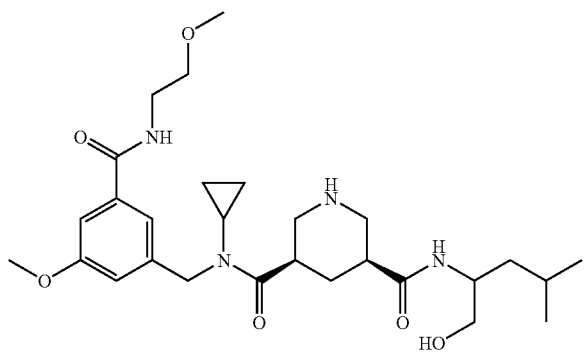

Example 43 is synthesized by deprotection of Intermediate 43.1 analogously to the preparation of example 42: ES-MS: M+H=533: $_C t_{Ret}$=2.15, 2.28 min.

Intermediate 43.1

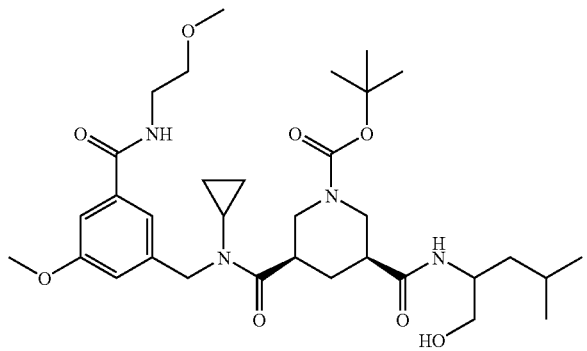

Intermediate 43.1 is synthesized by condensation of intermediate 33.2 (67 mg, 0.18 mmol) and Intermediate 43.2 (50 mg, 0.18 mmol) analogously to the preparation of Intermediate 1.1. White amorphous material; ES-MS: M+H=633; HPLC: $_B t_{Ret}$=1.73 min.

Intermediate 43.2

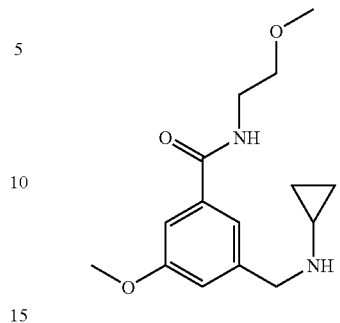

Intermediate 43.2 is synthesized by amination of Intermediate 43.3 (320 mg, 1.06 mmol) and cyclopropylamine (1.1 mL, 15.9 mmol) analogously to the preparation of Intermediate 42.2. Colorless oil; ES-MS: M+H=279; HPLC: $_B t_{Ret}$=1.22 min.

Intermediate 43.3

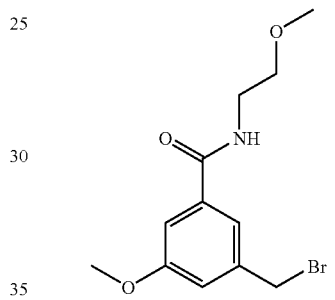

Intermediate 43.3 is synthesized by bromination of 3-hydroxymethyl-5-methoxy-N-(2-methoxyethyl)-benzamide (250 mg, 1.05 mmol) analogously to the preparation of Intermediate 42.3. Colorless oil; ES-MS: M+H=301, 303; HPLC: $_B t_{Ret}$=1.61 min.

Example 44

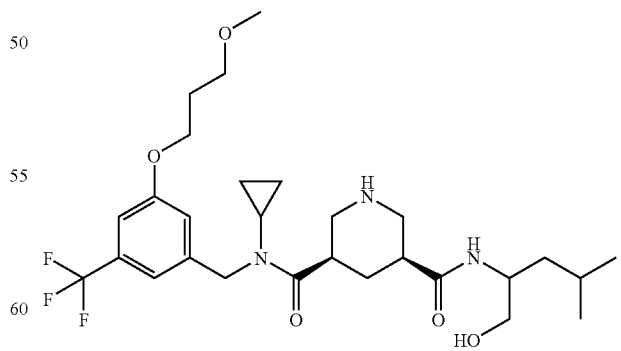

Example 44 is synthesized by deprotection of Intermediate 44.1 analogously to the preparation of 42. White amorphous material; ES-MS: M+H=558; HPLC: $_C t_{Ret}$=2.93, 3.08 min.

Intermediate 44.1

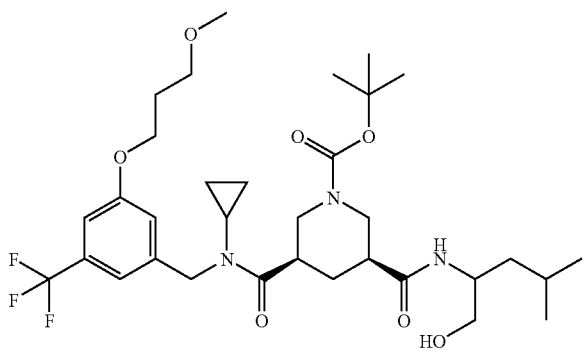

Intermediate 44.1 is synthesized by condensation of intermediate 33.2 (67 mg, 0.18 mmol) and Intermediate 44.2 (50 mg, 0.18 mmol) analogously to the preparation of Intermediate 1.1. White amorphous material; ES-MS: M+H=658; HPLC: $_B t_{Ret}$=2.06 min.

Intermediate 44.2

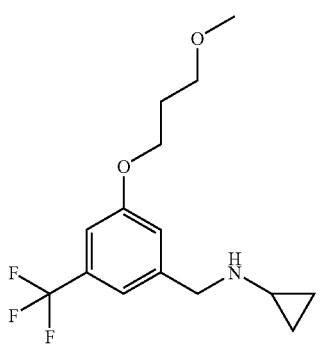

A mixture of 3-fluoro-5-(trifluoromethyl)benzylbromide (1.00 g, 3.9 mmol), potassium carbonate (1.62 g, 11.7 mmol), cyclopropylamine (223 mg, 39 mmol) in DMF (15 mL) is stirred at 60° C. for 1 h. The mixture is filtered, and the filtrate is added to a suspension of 60% NaH (312 mg, 7.8 mmol) and 3-methoxy-1-propanol (417 mg, 4.68 mmol) in DMF (30 mL) at 0° C. over 10 min. The reaction mixture is stirred for 5 h at 60° C. After adding H$_2$O, the reaction mixture is extracted with EtOAc. The combined organic phases are washed with water and brine and dried (MgSO$_4$). Concentration under reduced pressure and silica gel flash chromatography give Intermediate 44.2: yellow oil; ES-MS: M+H=304: $_A t_{Ret}$=2.47 min.

Example 45

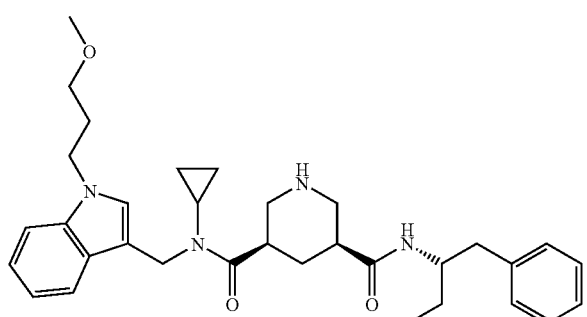

Example 45 is synthesized by deprotection of Intermediate 45.1 analogously to the preparation of example 1: ES-MS: M+H=547: $_C t_{Ret}$=2.75 min.

Intermediate 45.1

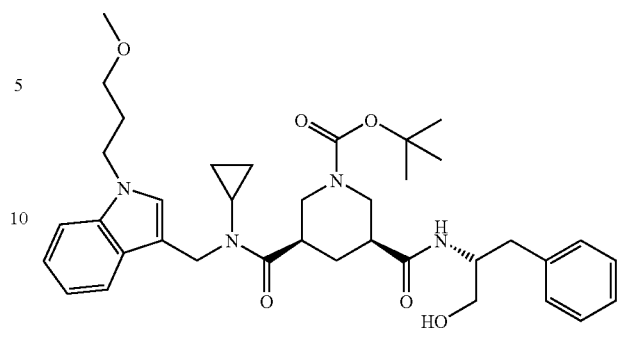

Intermediate 45.1 is synthesized by condensation of Intermediate 45.2 (195 mg, 0.48 mmol) with Intermediate 1.3 (190 mg, 0.72 mmol) analogously to the preparation of Intermediate 1.1. White amorphous material; ES-MS: [M+H]$^+$=647; HPLC: $_C t_{Ret}$=3.79 min.

Intermediate 45.2

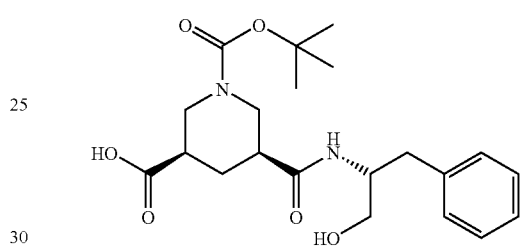

Intermediate 45.2 is synthesized by hydrolysis of Intermediate 45.3 (210 mg, 0.5 mmol) analogously to the preparation of Intermediate 13.2. White amorphous material; ES-MS: [M+H]$^+$=407; HPLC: $_C t_{Ret}$=2.74 min.

Intermediate 45.3

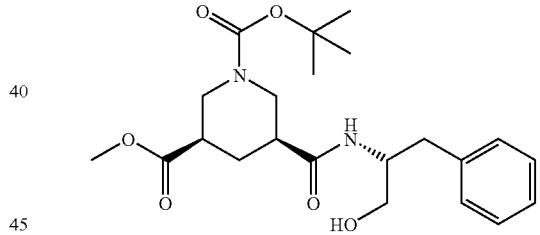

Intermediate 45.3 is synthesized by condensation of (3S, 5R)-Starting material-F (150 mg, 0.70 mmol) with D(+)-phenylalaminol (118 mg, 0.783 mmol) analogously to the preparation of Intermediate 13.3. White amorphous material; ES-MS: [M+H]$^+$=421; HPLC: $_C t_{Ret}$=3.03 min.

Example 46

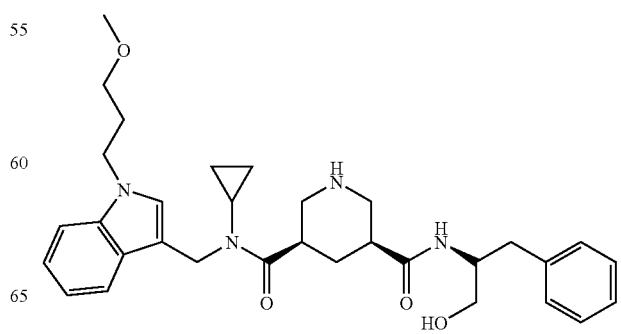

Example 46 is synthesized by deprotection of Intermediate 46.1 analogously to the preparation of example 1: ES-MS: M+H=547: $_ct_{Ret}$=2.83 min.

Intermediate 46.1

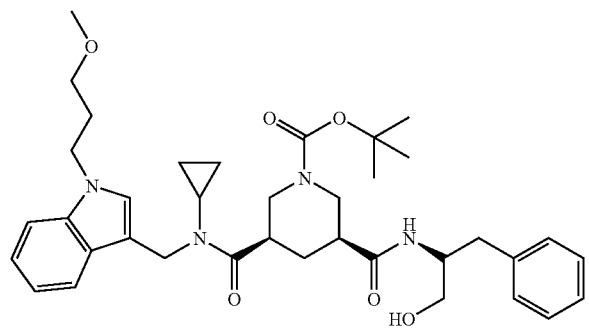

Intermediate 46.1 is synthesized by condensation of Intermediate 46.2 (195 mg, 0.48 mmol) with Intermediate 1.3 (190 mg, 0.72 mmol) analogously to the preparation of Intermediate 1.1. White amorphous material; ES-MS: [M+H]⁺=647; HPLC: $_ct_{Ret}$=3.73 min.

Intermediate 46.2

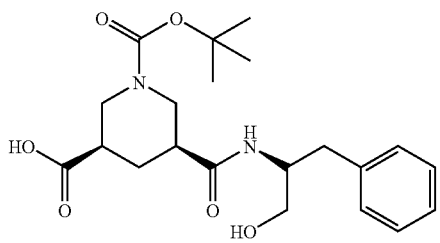

Intermediate 46.2 is synthesized by hydrolysis of Intermediate 46.3 (205 mg, 0.49 mmol) analogously to the preparation of Intermediate 13.2. White amorphous material; ES-MS: [M+H]⁺=407; HPLC: $_ct_{Ret}$=2.54 min.

Intermediate 46.3

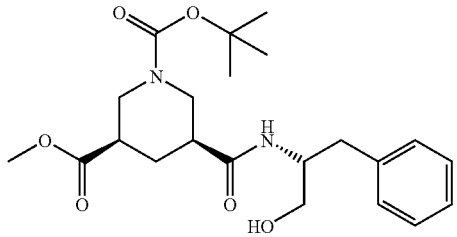

Intermediate 46.3 is synthesized by condensation of (3S, 5R)-Starting material-F (150 mg, 0.70 mmol) with L-(−)-phenylalaminol (118 mg, 0.783 mmol) analogously to the preparation of Intermediate 13.3. White amorphous material; ES-MS: [M+H]⁺=421; HPLC: $_ct_{Ret}$=2.97 min.

Example 47

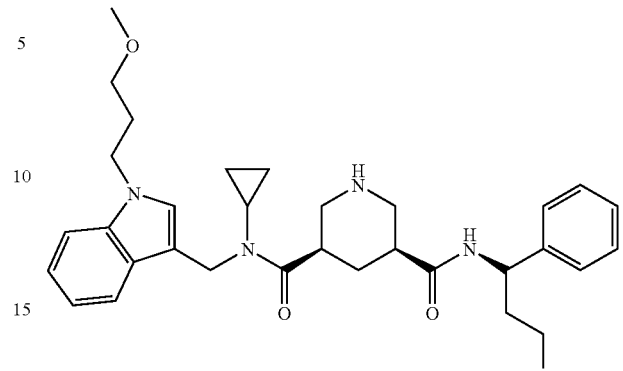

Example 47 is synthesized by deprotection of Intermediate 47.1 analogously to the preparation of example 1: ES-MS: M+H=547: $_ct_{Ret}$=2.83 min.

Intermediate 47.1

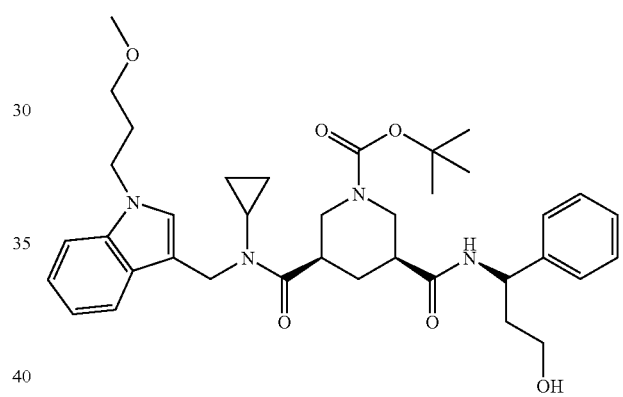

Intermediate 47.1 is synthesized by condensation of Intermediate 47.2 (195 mg, 0.48 mmol) with Intermediate 1.3 (190 mg, 0.72 mmol) analogously to the preparation of Intermediate 1.1. White amorphous material; ES-MS: [M+H]⁺=647; HPLC: $_ct_{Ret}$=3.74 min.

Intermediate 47.2

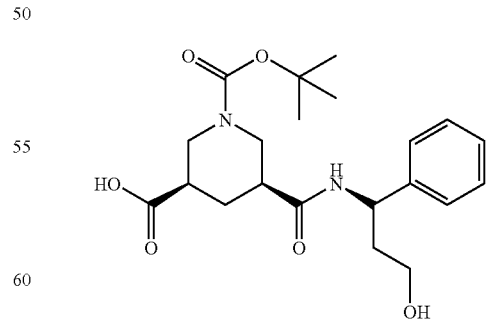

Intermediate 47.2 is synthesized by hydrolysis of Intermediate 47.3 (205 mg, 0.49 mmol) analogously to the preparation of Intermediate 13.2. White amorphous material; ES-MS: [M+H]⁺=407; HPLC: $_ct_{Ret}$=2.52 min.

Intermediate 47.3

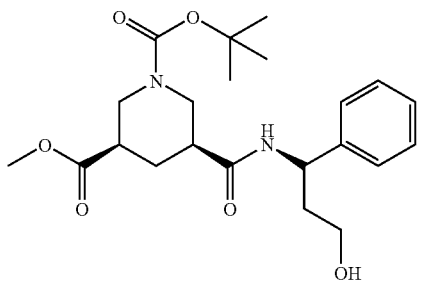

Intermediate 47.3 is synthesized by condensation of (3S, 5R)-Starting material-F (150 mg, 0.70 mmol) with (R)-3-amino-phenylalanine-1-ol (118 mg, 0.783 mmol) analogously to the preparation of Intermediate 13.3. White amorphous material; ES-MS: [M+H]$^+$=421; HPLC: $_c t_{Ret}$=2.95 min.

Example 48

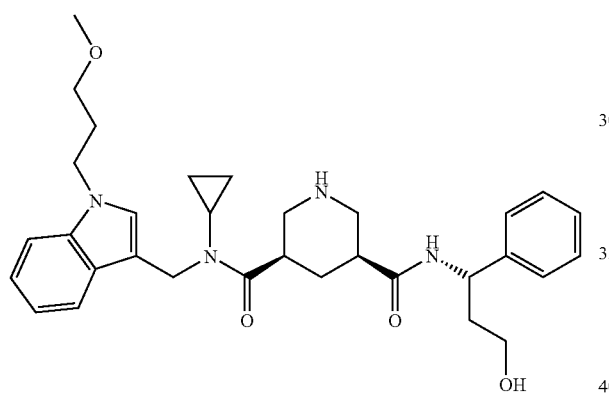

Example 48 is synthesized by deprotection of Intermediate 48.1 analogously to the preparation of example 1: ES-MS: M+H=547: $_c t_{Ret}$=2.68 min.

Intermediate 48.1

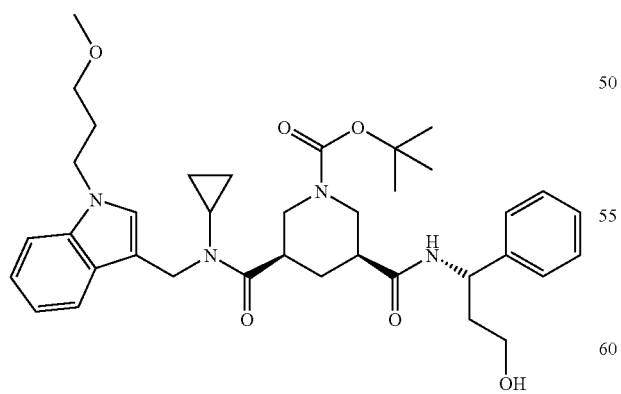

Intermediate 48.1 is synthesized by condensation of Intermediate 48.2 (195 mg, 0.48 mmol) with Intermediate 1.3 (190 mg, 0.72 mmol) analogously to the preparation of Intermediate 1.1. White amorphous material; ES-MS: [M+H]$^+$=647; HPLC: $_c t_{Ret}$=3.77 min.

Intermediate 48.2

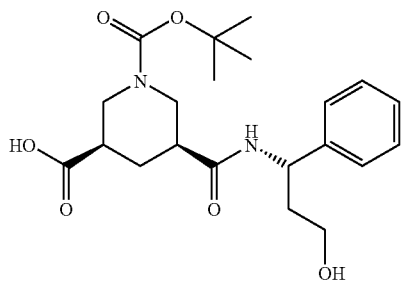

Intermediate 48.2 is synthesized by hydrolysis of Intermediate 48.3 (200 mg, 0.48 mmol) analogously to the preparation of Intermediate 13.2. White amorphous material; ES-MS: [M+H]$^+$=407; HPLC: $_c t_{Ret}$=2.72 min.

Intermediate 48.3

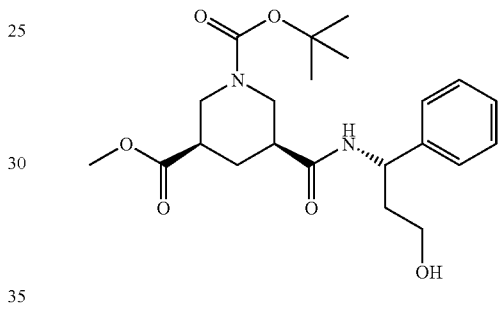

Intermediate 48.3 is synthesized by condensation of (3S, 5R)-Starting material-F (150 mg, mmol) with S-3-amino-phenylalanine-1-ol (118 mg, 0.783 mmol) analogously to the preparation of Intermediate 13.3. White amorphous material; ES-MS: [M+H]$^+$=421; HPLC: $_c t_{Ret}$=3.01 min.

Example 52

Example 52 is synthesized by deprotection of Intermediate 52.1 analogously to the preparation of example 1: ES-MS: M+H=515: $_c t_{Ret}$=2.82, 2.98 min.

Intermediate 52.1

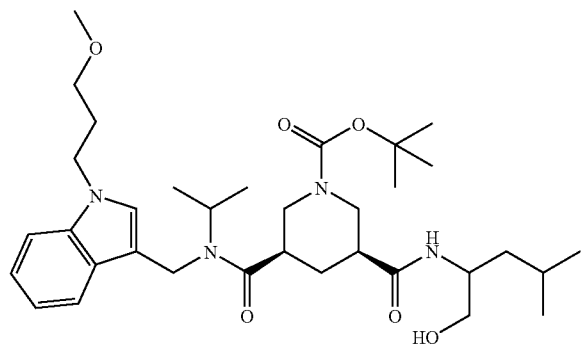

Intermediate 52.1 is synthesized by condensation of Intermediate 33.2 (76 mg, 0.20 mmol) with Intermediate 52.2 (80 mg, 0.31 mmol) analogously to the preparation of Intermediate 1.1. White amorphous material; ES-MS: $[M+H]^+=615$; HPLC: $_Ct_{Ret}=3.90$ min.

Intermediate 52.2

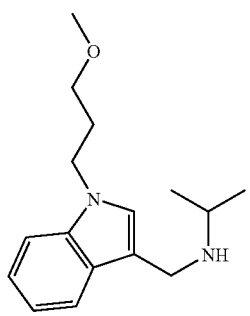

To a solution of 1-(3-Methoxypropyl)-1H-indole-3-carbaldehyde (350 mg, 1.61 mmol) in $CH_2Cl_2$/MeOH are added isopropylamine (115 mg, 1.93 mmol), AcOH (192 mg, 3.2 mmol) and sodium cyanoborohydride (1.02 g, 4.83 mmol) at room temperature. After stirring for 20 h at room temperature, the reaction mixture is quenched with 5% aqueous $NaHCO_3$ (10 mL) and water (40 mL), and extracted with $CH_2Cl_2$ (twice). The combined organic layer is washed with $H_2O$ and brine, then dried over $Na_2SO_4$ and concentrated under reduced pressure. $SiO_2$ chromatography purification affords Intermediate 52.2 as a brown oil; ES-MS: $[M+H]^+=261$; HPLC: $_Ct_{Ret}=2.25$ min.

Example 53

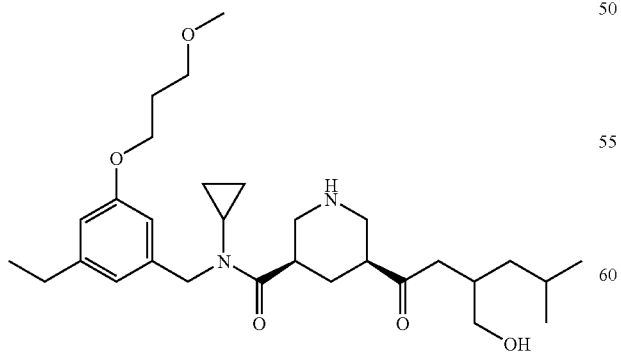

Example 53 is synthesized by deprotection of Intermediate 53.1 analogously to the preparation of example 42. White amorphous material; ES-MS: M+H=518; HPLC: $_Bt_{Ret}=1.63$ min.

Intermediate 53.1

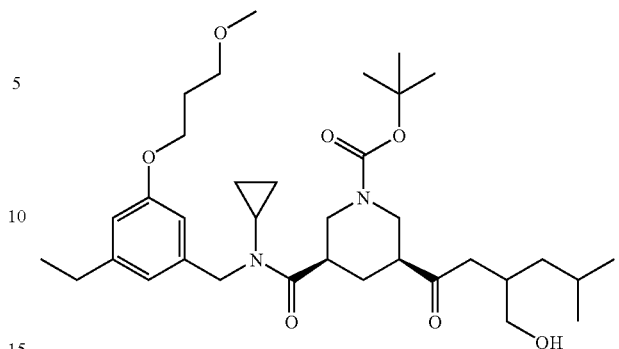

Intermediate 53.1 is synthesized by condensation of intermediate 33.2 (100 mg, 0.27 mmol) and Intermediate 53.2 (106 mg, 0.40 mmol) analogously to the preparation of Intermediate 42.1; ES-MS: M+H=618; HPLC: $_Bt_{Ret}=2.04$ min.

Intermediate 53.2

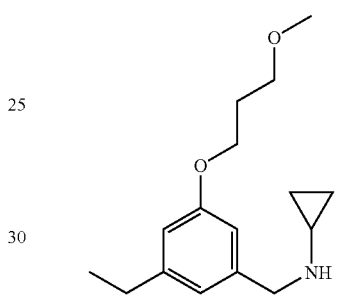

Intermediate 53.3 (537 mg, 2.13 mmol) in MeOH (4 mL) is treated with 5 N aqueous NaOH. After stirring at 75° C. for 2 h, the reaction mixture is cooled to rt and acidified with 1 N HCl. The mixture is diluted with AcOEt, washed with brine, dried ($MgSO_4$) and concentrated. The residue is dissolved in DMF (2 mL) and treated with cyclopropylamine (0.30 mL, 4.29 mmol), EDCI (615 mg, 3.21 mmol) and HOAt (291 mg, 2.13 mmol). After stirring for 2 h, the reaction mixture is diluted with AcOEt, washed with brine, dried ($MgSO_4$) and concentrated. To a solution of the residue in THF (3 mL) is added $BH_3$.THF complex (1.0 M, 2.7 mL). After stirring at 60° C. for 2 h, the mixture is cooled to rt and $H_2O$ and MeOH are added. The mixture is extracted with AcOEt, washed with brine, dried ($MgSO_4$) and concentrated. The residue is purified by silica gel column chromatography to give Intermediate 53.2; ES-MS: M+H=264; HPLC: $_Bt_{Ret}=1.50$ min.

Intermediate 53.3

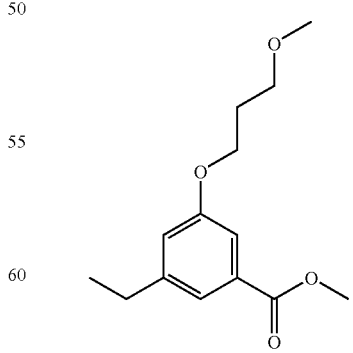

To a solution of Intermediate 53.4 (482 mg, 2.67 mmol) in DMF is added NaH (128 mg, 3.2 mmol) at rt. Toluene-4-sulfonic acid 3-methoxypropyl ester (784 mg, 3.2 mmol) and KI (44 mg, 0.27 mmol) are added and the mixture is heated to 65° C. After stirring for 3 h, H₂O is added. The mixture is extracted with AcOEt, washed with brine, dried (MgSO₄) and concentrated. The residue is purified by silica gel column chromatography to give Intermediate 53.3; ES-MS: M+H=221; HPLC: $_Bt_{Ret}$=2.03 min.

Intermediate 53.4

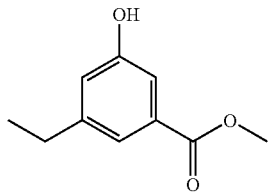

To a solution of Intermediate 53.5 (1.89 g, 7.10 mmol) in EtOH (75 mL) is added 10% Pd/C (0.19 g, 0.07 mmol). The reaction mixture is stirred under H₂ at rt for 20 h then stirred at 40° C. for 2 h. After cooling to rt, the mixture is filtered and the filtrate is concentrated in vacuo to give Intermediate 53.4; ES-MS: M+H=181; HPLC: $_Bt_{Ret}$=2.08 min.

Intermediate 53.5

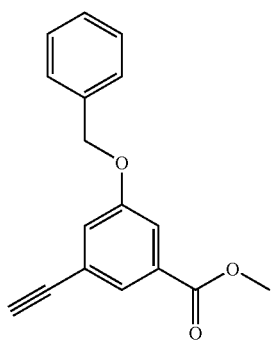

Intermediate 53.6 (8.5 g, 21.8 mmol), trimethylsilylacetylene (9.23 mL, 43.6 mmol), Pd(PPh₃)₄ (1.2 g, 1.04 mmol), CuI (0.21 g, 1.04 mmol) and diisopropylethylamine (11 mL, 43.6 mmol) in dichloromethane (100 mL) are stirred at rt for 12 h. After adding H₂O, the organic layer is separated and concentrated. The residue is purified by silica gel column chromatography. The product is dissolved in THF (20 mL) and treated with TBAF in THF (1.0 M, 22.1 mL) at −78° C. After stirring for 0.5 h, H₂O is added and the mixture is extracted with AcOEt, washed with brine, dried (MgSO₄) and concentrated. The residue is purified by silica gel column chromatography to give Intermediate 53.5; Rf=0.5 (20% AcOEt in n-Hexane) ¹H-NMR (CDCl3) 7.77 (1H, s), 7.64 (1H, s), 7.4 (5H, m), 7.27 (1H, s), 5.10 (2H, s), 3.91 (3H, s), 3.09 (1H, s).

Intermediate 53.6

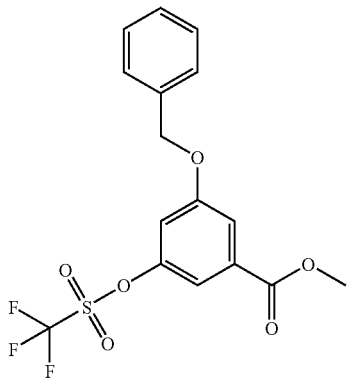

To a solution of Intermediate 53.7 (2.47 g, 9.56 mmol) and diisopropylethylamine (4.12 mL, 23.9 mmol) in dichloromethane (30 mL) is added Tf₂O (1.93 mL, 11.5 mmol) at −78° C. After stirring for 4 h, the reaction is quenched with H₂O and warmed to rt. The organic layer is separated, concentrate and purified by silica gel column chromatography to give Intermediate 53.6; ES-MS: M+=390; HPLC: $_Bt_{Ret}$=2.23 min.

Intermediate 53.7

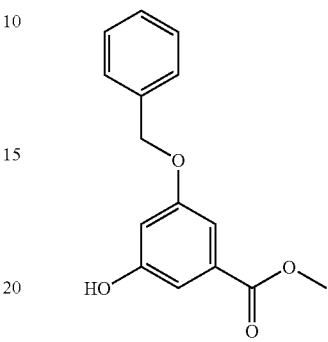

To a solution of 3,5-dihydroxy benzoic acid methyl ester (5.22 g, 31.0 mmol) and K₂CO₃ (6.4 g, 46.3 mmol) in acetone (75 mL) is added benzyl bromide (4.06 mL, 34.1 mmol). After stirring at 55° C. for 15 h, the mixture is cooled to rt and the resulting precipitate is removed by filtration. The filtrate is concentrated, diluted with Et₂O and washed with brine. The organic layer is dried (MgSO₄), concentrated and purified by silica gel column chromatography to give Intermediate 53.7; ES-MS: M+H=259; HPLC: $_Bt_{Ret}$=1.84 min.

Example 54

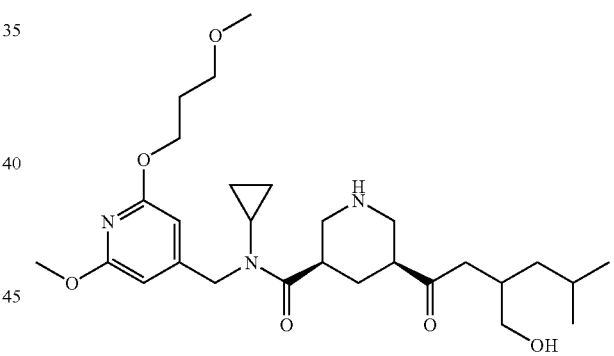

Example 54 is synthesized by deprotection of Intermediate 54.1 analogously to the preparation of example 42. White amorphous material; ES-MS: M+H=521; HPLC: $_Bt_{Ret}$=1.52 min.

Intermediate 54.1

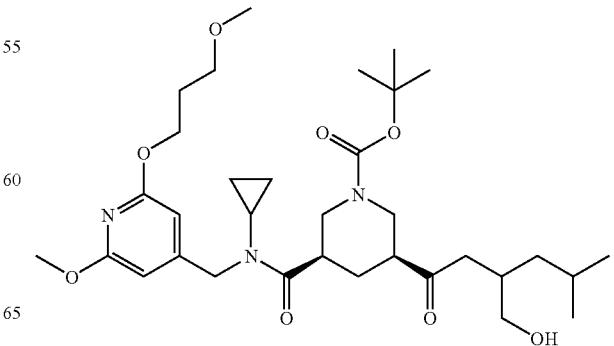

Intermediate 54.1 is synthesized by condensation of intermediate 33.2 (100 mg, 0.27 mmol) and Intermediate 54.2 (230 mg, 0.86 mmol) analogously to the preparation of Intermediate 42.1; ES-MS: M+H=621; HPLC: $_B t_{Ret}$=1.93 min.

Intermediate 54.2

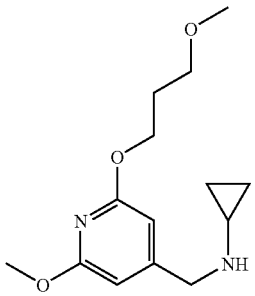

To a solution of Intermediate 54.3 (199 mg, 0.88 mmol) and Et$_3$N (0.081 mL, 1.04 mmol) in dichloromethane (3 mL) is added MsCl (0.081 mL, 1.05 mmol). After stirring at rt for 1 h, H$_2$O is added and the mixture is extracted with dichloromethane. The organic layer is concentrated. The residue is dissolved in DMF (3 mL) and treated with K$_2$CO$_3$ (242 mg, 1.75 mmol) and cyclopropylamine (0.12 mL, 1.75 mmol). After stirring at rt for 5 h, the mixture is diluted with AcOEt, washed with H$_2$O and brine. The organic layer is dried (MgSO$_4$), concentrated and purified by silica gel column chromatography to give Intermediate 54.2; ES-MS: M+H=267; HPLC: $_B t_{Ret}$=1.37 min.

Intermediate 54.3

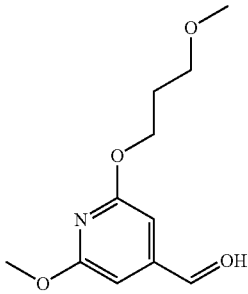

To a solution of Intermediate 54.4 (290 mg, 1.21 mmol) and Et$_3$N (1.57 mmol) in THF (4 mL) is added chloro ethylformate (0.15 mL, 1.56 mmol) at 0° C. After stirring for 0.5 h, the resulting precipitate is removed by filtration, and the filtrate is concentrated in vacuo. The residue is dissolved in EtOH (3 mL) and treated with NaBH$_4$ (59 mg, 1.56 mmol) at rt. The reaction is quenched with H$_2$O, and the mixture is extracted with AcOEt. The organic layer is washed with brine, dried (MgSO$_4$), concentrated and purified by silica gel column chromatography to give Intermediate 54.3; ES-MS: M+H=228; HPLC: $_B t_{Ret}$=1.50 min.

Intermediate 54.4

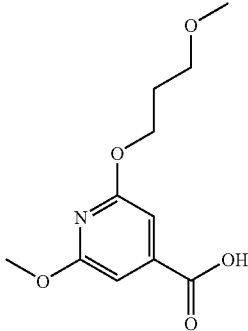

1-Methoxypropanol (3 mL) is treated with NaH (0.42 g, 10.4 mmol) at rt. After stirring for 15 min, a solution of 2,6-dichloroisonicotinic acid (1 g, 5.2 mmol) in DMF (7 mL) is added. The reaction mixture is heated to 80° C. and stirred for 7 h. After cooling to rt, H$_2$O and 0.5 N HCl are added and the mixture is extracted with AcOEt. The organic layer is dried (MgSO$_4$) and concentrated in vacuo. The residue is dissolved in DMF (5 mL) and treated with NaOMe (2.25 g, 25 wt % in MeOH). After stirring at 100° C. for 5 h, 0.5 N HCl is added and the reaction mixture is extracted with AcOEt, dried (MgSO$_4$) and concentrated. The residue is purified by RP-HPLC to give Intermediate 54.4; ES-MS: M+H=242; HPLC: $_B t_{Ret}$=1.63 min.

Example 55


Example 55 is synthesized by deprotection of Intermediate 55.1 analogously to the preparation of example 1: ES-MS: M+H=554: $_C t_{Ret}$=2.81 min.

Intermediate 55.1


Intermediate 55.1 is synthesized by condensation of Intermediate 55.2 (100 mg, 0.20 mmol) with 2-(R)-amino-4-methylpentanoic acid dimethylamide hydrochloride (56 mg, 0.29 mmol) analogously to the preparation of Intermediate 39.1. White amorphous material; ES-MS: [M+H]$^+$=654; HPLC: $_C t_{Ret}$=3.93 min.

Intermediate 55.2

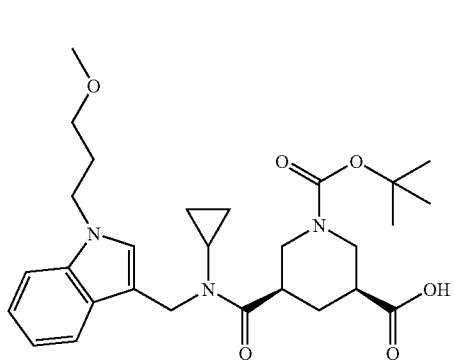

Intermediate 55.2 is synthesized by hydrolysis of Intermediate 55.3 (900 mg, 1.71 mmol) analogously to the preparation of Intermediate 13.2. White amorphous material; ES-MS: [M+H]$^+$=514; HPLC: $_C t_{Ret}$=3.67 min.

Intermediate 55.3

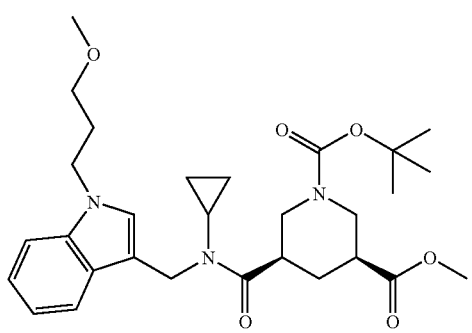

Intermediate 55.3 is synthesized by condensation of (3R, 5S)-Starting material-F (500 mg, 1.74 mmol) with Intermediate 1.3 (675 mg, 2.61 mmol) analogously to the preparation of Intermediate 13.3. White amorphous material; ES-MS: [M]$^+$=528; HPLC: $_C t_{Ret}$=4.09 min.

Example 56

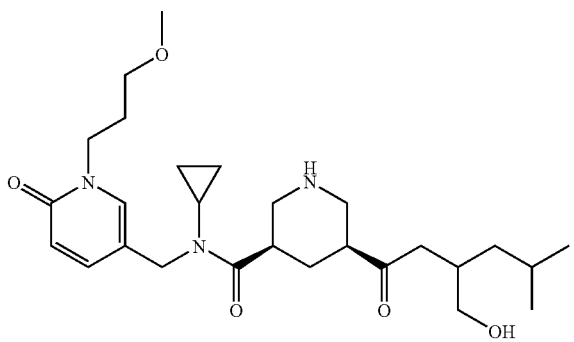

Example 56 is synthesized by deprotection of Intermediate 56.1 analogously to the preparation of example 42. White amorphous material; ES-MS: M+H=491; HPLC: $_B t_{Ret}$=1.57 min.

Intermediate 56.1

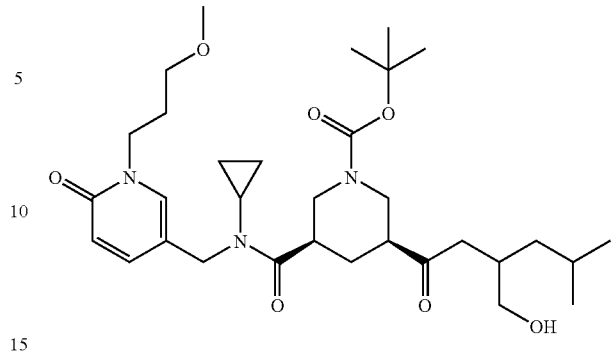

Intermediate 56.1 is synthesized by condensation of intermediate 33.2 (100 mg, 0.27 mmol) and Intermediate 56.2 (110 mg, 0.47 mmol) analogously to the preparation of Intermediate 42.1; ES-MS: M+H=591; HPLC: $_B t_{Ret}$=1.64 min.

Intermediate 56.2

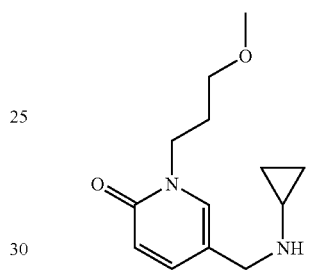

Intermediate 56.2 is synthesized by reaction of Intermediate 56.3 (235 mg, 1.91 mmol) analogously to the preparation of Intermediate 54.2; ES-MS: M+H=237; HPLC: $_B t_{Ret}$=1.08 min.

Intermediate 56.3

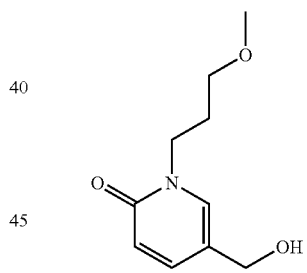

Intermediate 56.3 is synthesized by reaction of Intermediate 56.4 (235 mg, 1.91 mmol) analogously to the preparation of Intermediate 54.3; ES-MS: M+H=198; HPLC: $_B t_{Ret}$=1.09 min.

Intermediate 56.4

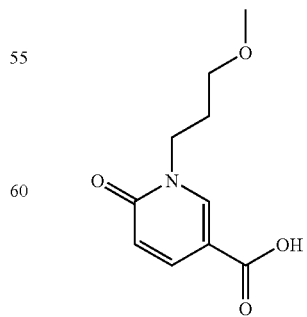

To a solution of 2-piperidone-3-carboxylic acid (2.14 g, 15.4 mmol) in DMF (20 mL) is added NaH (1.54 g, 38.5 mmol). After stirring for 1 h, toluene-4-sulfonic acid 3-methoxypropyl ester (9.4 g, 38.5 mmol) and KI (0.26 g, 1.54 mmol) are added. After heating at 110° C., the mixture is treated with H₂O and extracted with AcOEt. The organic layer is dried (MgSO₄), concentrated and purified by silica gel column chromatography. The obtained ester is treated with 5 N aqueous NaOH (5 mL) in EtOH (5 mL) and stirred at 70° C. for 2 h. The mixture is cooled to rt, acidified with 1 N HCl and extracted with AcOEt. The organic layer is dried (MgSO₄) and concentrated to give Intermediate 56.4; ES-MS: M+H=212; HPLC: $_Bt_{Ret}$=1.18 min.

Example 57

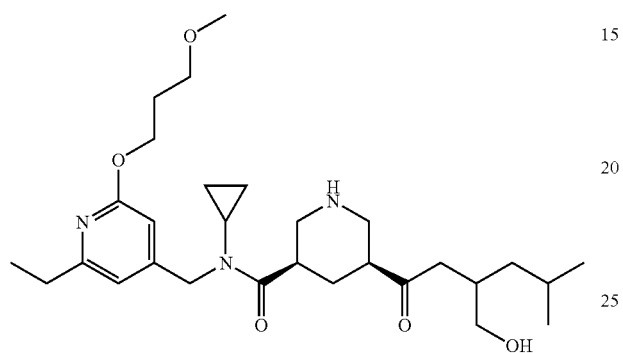

Example 57 is synthesized by deprotection of Intermediate 57.1 analogously to the preparation of example 42. White amorphous material; ES-MS: M+H=519; HPLC: $_Bt_{Ret}$=1.56 min.

Intermediate 57.1

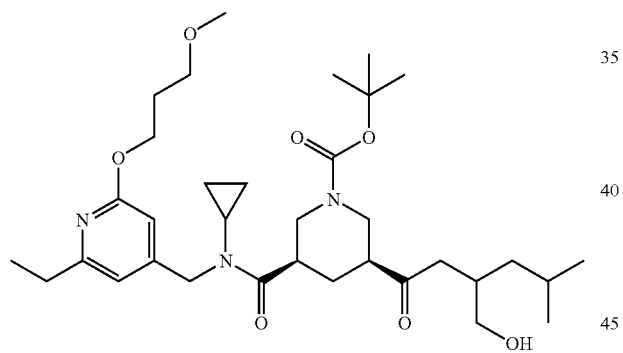

Intermediate 57.1 is synthesized by condensation of intermediate 33.2 (85 mg, 0.23 mmol) and Intermediate 57.2 (60 mg, 0.23 mmol) analogously to the preparation of Intermediate 42.1; ES-MS: M+H=619; HPLC: $_Bt_{Ret}$=1.77 min.

Intermediate 57.2

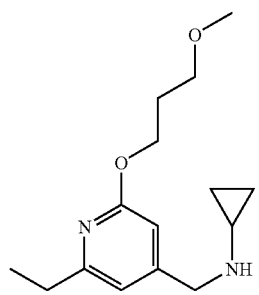

Intermediate 57.2 is synthesized by reaction of Intermediate 57.3 (178 mg, 0.79 mmol) analogously to the preparation of Intermediate 54.2; ES-MS: M+H=265; HPLC: $_Bt_{Ret}$=1.36 min.

Intermediate 57.3

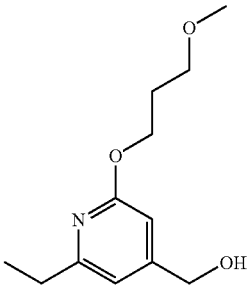

Intermediate 57.3 is synthesized by reaction of Intermediate 57.4 (190 mg, 0.79 mmol) analogously to the preparation of Intermediate 54.3; ES-MS: M+H=226; HPLC: $_Bt_{Ret}$=1.48 min.

Intermediate 57.4

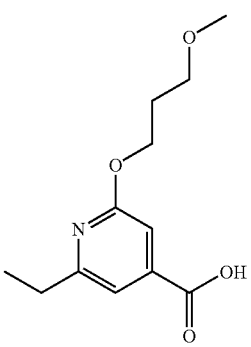

1-Methoxypropanol (1.5 mL) is treated with NaH (0.17 g, 4.3 mmol) at rt. After stirring for 15 min, a solution of Intermediate 57.5 (400 mg, 2.16 mmol) in DMF (3 mL) is added. The reaction mixture is heated to 100° C. and stirred for 3 h. After cooling to rt, H₂O and 0.5 N HCl are added and the mixture is extracted with AcOEt. The organic layer is dried (MgSO₄) and concentrated in vacuo to give Intermediate 57.4; ES-MS: M+H=240; HPLC: $_Bt_{Ret}$=1.60 min.

Intermediate 57.5

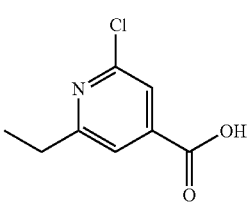

6-Ethyl-2-oxo-1,2-dihydro-pyridine-4-carboxylic acid (590 mg, 3.53 mmol) is treated with POCl₃ (5 mL) and heated at 100° C. for 1 h. After cooling to rt, the mixture is concentrated and the residue is poured into ice water. The mixture is extracted with dichloromethane, and the organic layer is concentrated to give Intermediate 57.5; ES-MS: M+=185; HPLC: $_Bt_{Ret}$=1.59 min.

Example 58

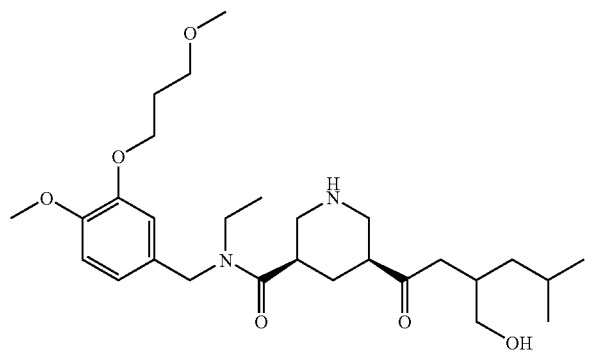

Example 58 is synthesized by deprotection of Intermediate 58.1 analogously to the preparation of example 42. White amorphous material; ES-MS: M+H=508; HPLC: $_c t_{Ret}$=2.25, 2.38 min.

Intermediate 58.1


Intermediate 58.1 is synthesized by condensation of intermediate 33.2 (54 mg, 0.145 mmol) and Intermediate 58.2 (54 mg, 0.22 mmol) analogously to the preparation of Intermediate 42.1; ES-MS: M+H=608; HPLC: $_c t_{Ret}$=3.35 min.

Intermediate 58.2

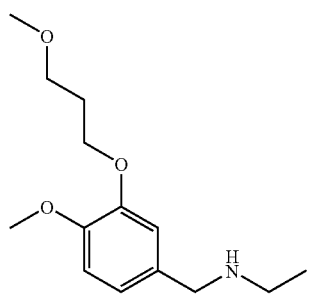

Intermediate 58.2 is synthesized by reduction of Intermediate 58.3 (102 mg, 0.38 mmol) analogously to the preparation of Intermediate 78.2. Yellow oil; ES-MS: [M+H]⁺=254; HPLC: $_A t_{Ret}$=1.80 min.

Intermediate 58.3

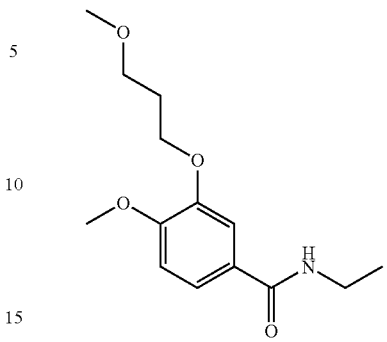

Intermediate 58.3 is synthesized by condensation of Intermediate 58.4 (200 mg, 0.83 mmol) with ethyl amine analogously to the preparation of Intermediate 1.1. Yellow oil; ES-MS: [M+H]⁺=267; HPLC: $_c t_{Ret}$=3.88 min.

Intermediate 58.4

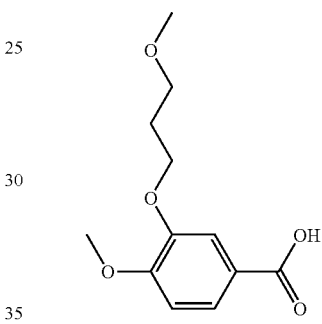

A solution of 4-methoxy-3-(3-methoxy-propoxy)-benzoic acid methyl ester (140 g, 0.55 mol) and NaOH (1 N, 825 mL, 0.825 mol) in MeOH (840 mL) is stirred at rt for 18 h. After completion the solvent is removed under reduced pressure, the residue is diluted with water (200 mL) and extracted twice with EtOAc (250 mL). The aqueous layer is acidified with addition of aq. HCl (2N, 470 mL) and extracted 3 times with EtOAc (1 L). the combined organic extracts are washed with brine, dried over Na₂SO₄, filtered and concentrated. The crude material is purified by cristalization in EtOAc to give the title compound.

MS (LC-MS): 239.1 [M−H]⁻

$t_R$ (HPLC, CC 70/4 nucleosil 3 C18HD column, 20 to 100% CH₃CN in H₂O in 2, then 4 min with 100% CH₃CN, CH₃CN and H₂O with 0.1% TFA, flow: 1.5 mL/min): 2.43 min.

Intermediate 58.5

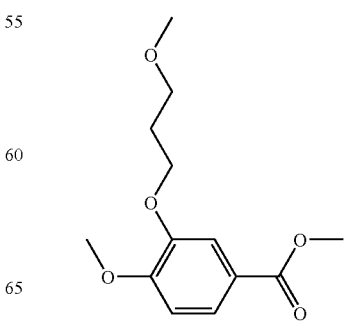

A solution of methyl-3-hydroxy-4-methoxybenzoate (89.3 g, 0.49 mol), K$_2$CO$_3$ (100.5 g, 0.727 mol) and 1-bromo-3-methoxy-propane (80 g, 0.523 mol) in CH$_3$CN (1100 mL) is refluxed for 6 h. After completion of the reaction, the mixture is cooled to rt and concentrated under reduced pressure. The residue is taken up into EtOAc (500 mL) and washed with water. The aqueous layer is back-extracted twice with EtOAc and the combined organic extracts are dried over MgSO$_4$, filtered and concentrated to afford the title compound which is further used without purification in the next step.

$t_R$ (HPLC, CC 70/4 nucleosil 3 C18HD column, 20 to 100% CH$_3$CN in H$_2$O in 2, then 4 min with 100% CH$_3$CN, CH$_3$CN and H$_2$O with 0.1% TFA, flow: 1.5 mL/min): 3.07 min.

Example 59

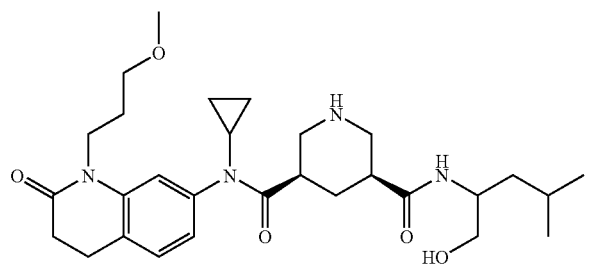

Example 59 is synthesized by deprotection of Intermediate 59.1 analogously to the preparation of example 42. White amorphous material; ES-MS: M+H=529; HPLC: $_Ct_{Ret}$=2.66, 2.82 min.

Intermediate 59.1

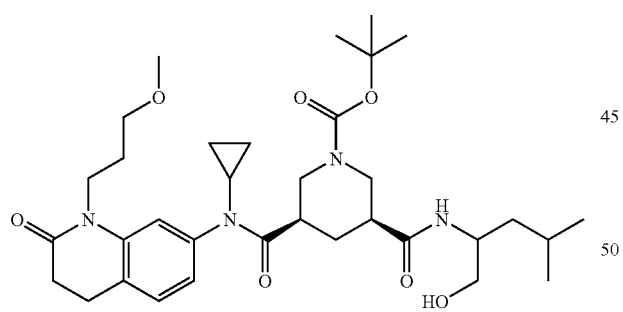

To a solution of Intermediate 33.2 (80 mg, 0.22 mmol) in THF (3 mL), Et$_3$N (0.114 mL, 0.86 mmol) and Isobutyl chloroformate (0.113 mL, 0.86 mmol) are added at 0° C. After stirring for 0.5 h at same temperature, the resulting precipitate is filtered off and the filtrate is concentrated. The residue is dissolved in THF (3 mL), Intermediate 59.2 (59 mg, 0.22 mmol) and MgBr$_2$-OEt$_2$ (51 mg, 0.2 mmol) are added at room temperature. After stirring for 12 h, the reaction is quenched with H$_2$O and the resulting mixture is extracted with AcOEt, washed with 1 N HCl solution and brine. The organic layer is dried (MgSO$_4$), concentrated and purified by silica gel column chromatography to afford Intermediate 59.1. White amorphous material; ES-MS: M+H=629; HPLC: $_Ct_{Ret}$=3.16, 3.23 min.

Intermediate 59.2

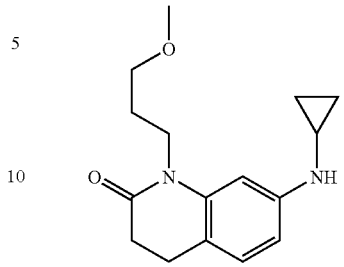

Intermediate 59.2 is synthesized by alkylation of Intermediate 59.3 (85 mg, 0.42 mmol) and toluene-4-sulfonic acid 3-methoxy-propyl ester (100 µL, 0.46 mmol) analogously to a known method (see e.g. *European Journal of Medicinal Chemistry* 1998, 33, 957-967. or EP 432893). Yellow oil; ES-MS: M+H=275; HPLC: $_At_{Ret}$=2.52 min.

Intermediate 59.3

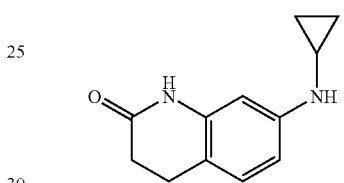

A mixture of (E)-3-(4-cyclopropylamino-2-nitrophenyl)-acrylic acid methylester (130 mg, 0.50 mmol) and NiCl$_2$-6H$_2$O (120 mg, 0.50 mmol) in MeOH (5 mL) is cooled to 0° C. and NaBH$_4$ (113 mg, 3.0 mmol) is added portionwise. The resulting solution is stirred at 0° C. for 2 h, then at 60° C. for 21 h. The reaction mixture is diluted with H$_2$O and extracted with EtOAc. The combined organic phases are washed with H$_2$O and dried over Na$_2$SO$_4$. Concentration under reduced pressure and silica gel flash chromatography give Intermediate 59.3 as brown powder; Rf=0.2 (EtOAc:n-Hex=1:1); $^1$H NMR (CDCl$_3$), δ: 0.48-0.52 (2H, m), 0.71-0.75 (2H, m), 2.37-2.42 (1H, m), 2.60 (1H, t), 2.86 (2H, t), 4.15 (1H, s), 6.18 (1H, d), 6.38-6.41 (1H, m), 6.95 (1H, d), 7.31 (1H, s).

Example 60

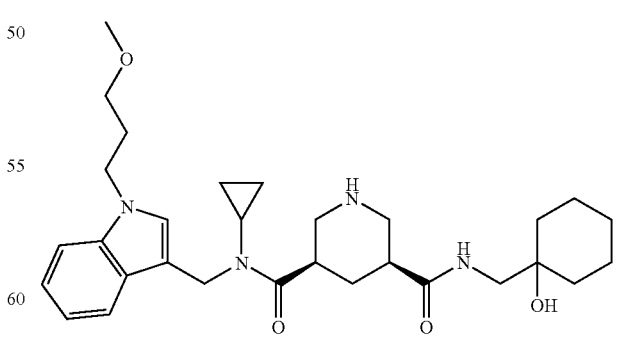

Example 60 is synthesized by deprotection of Intermediate 60.1 analogously to the preparation of example 1: ES-MS: M+H=525: $_Ct_{Ret}$=2.76 min.

Intermediate 60.1

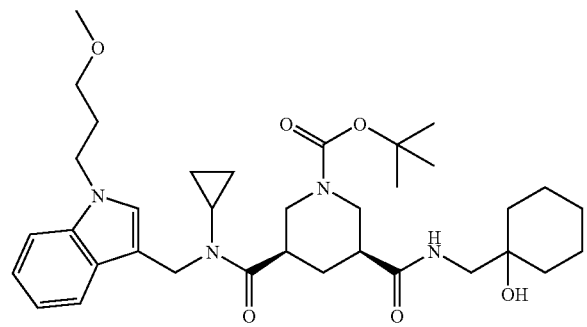

Example 60.1 is synthesized by condensation of Intermediate 60.2 with the corresponding amine analogously to the preparation of example 1.1: ES-MS: M+H=625: $_c t_{Ret}$=3.73 min.

Intermediate 60.2

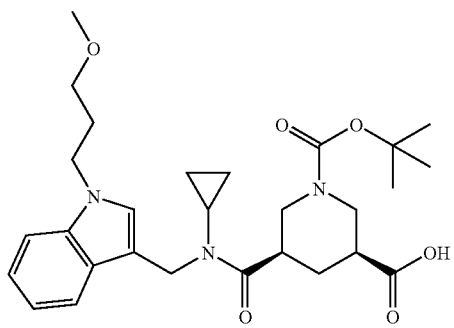

Intermediate 60.2 is synthesized by hydrolysis of Intermediate 60.3 analogously to the preparation of Intermediate 13.2. White amorphous material; ES-MS: [M+H]$^+$=514; HPLC: $_c t_{Ret}$=3.75 min.

Intermediate 60.3

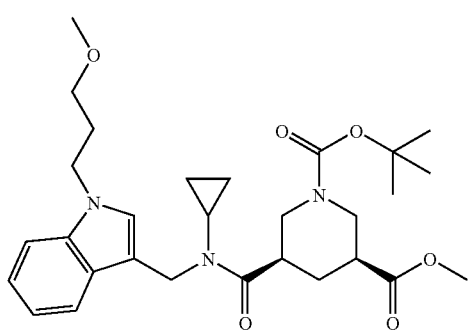

Example 60.3 is synthesized by condensation of (3R,5S)-Starting material-F with intermediate 1.3 analogously to the preparation of example 1.1: ES-MS: M+H=528: $_A t_{Ret}$=4.14 min.

Examples 66-76, 80-81, 85-86, 91 are synthesized by condensation of intermediate 60.2 with corresponding amines followed by deprotection analogously to the preparation of example 1.

Example 61

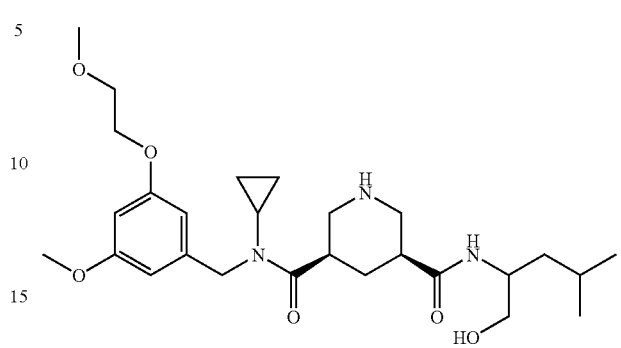

Example 61 is synthesized by deprotection of Intermediate 61.1 analogously to the preparation of example 1: ES-MS: M+H=506: $_c t_{Ret}$=2.41, 2.57 min.

Intermediate 61.1

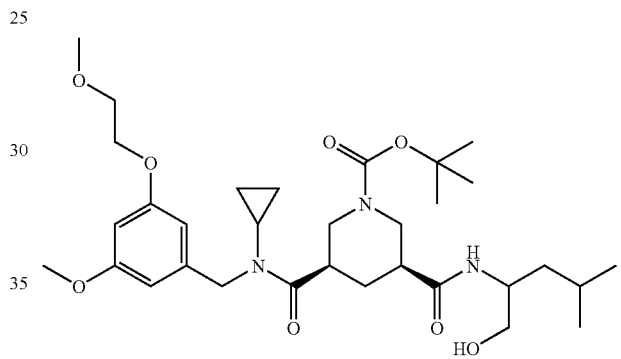

Intermediate 61.1 is synthesized by condensation of Intermediate 61.2 (40 mg, 0.16 mmol) with Intermediate 33.2 (59 mg, 0.16 mmol) analogously to the preparation of Intermediate 1.1. White amorphous material; ES-MS: [M+H]$^+$=606; HPLC: $_c t_{Ret}$=3.44, 3.50 min.

Intermediate 61.2

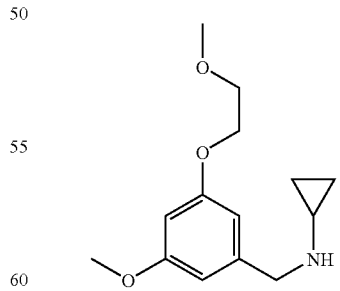

Intermediate 61.2 is synthesized by reduction of Intermediate 61.3 (426 mg, 1.61 mmol) analogously to the preparation of Intermediate 78.2. Yellow oil; ES-MS: M+H=252; HPLC: $_c t_{Ret}$=1.86 min.

Intermediate 61.3

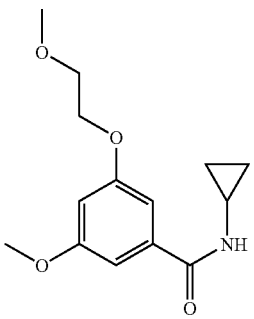

Intermediate 61.3 is synthesized by condensation of Intermediate 61.4 (565.9 mg, 2.5 mmol) with cyclopropylamine (0.17 mL, 2.5 mmol) analogously to the preparation of Intermediate 1.1. Yellow oil; ES-MS: M+H=267; HPLC: $_c t_{Ret}$=2.42 min.

Intermediate 61.4

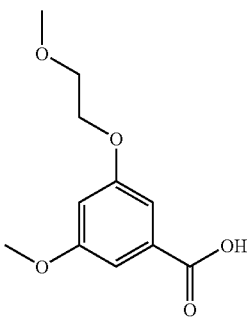

Intermediate 61.4 is synthesized by hydrolysis of Intermediate 61.5 (857.8 mg, 3.79 mmol) analogously to the preparation of Intermediate 58.4. White material; ES-MS: M+H=227; HPLC: $_c t_{Ret}$=2.34 min.

Intermediate 61.5

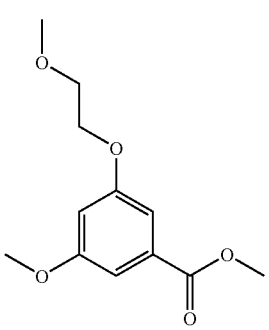

Intermediate 61.5 is synthesized by alkylation of 3-methoxy-5-hydroxybenzoic acid methyl ester (1 g, 5.48 mmol) with Bromo-2-methoxy-ethane (0.514 mL, 5.48 mmol) analogously to the preparation of Intermediate 37.5. White material; ES-MS: M+H=241 HPLC: $_c t_{Ret}$=2.93 min.

Example 62

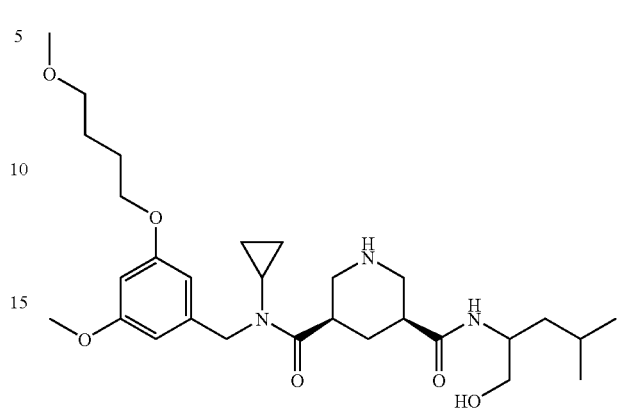

Example 62 is synthesized by deprotection of Intermediate 62.1 analogously to the preparation of example 1: ES-MS: M+H=533: $_c t_{Ret}$=2.66, 2.82 min.

Intermediate 62.1

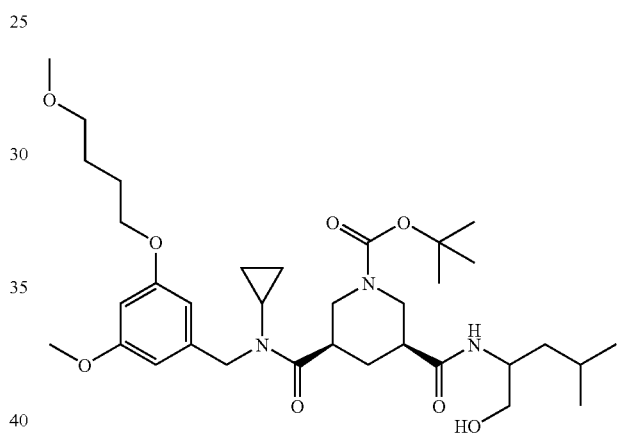

Intermediate 62.1 is synthesized by condensation of Intermediate 62.2 (109 mg, 0.269 mmol) with Intermediate 33.2 (100 mg, 0.269 mmol) analogously to the preparation of Intermediate 1.1. White amorphous material; ES-MS: [M+H]$^+$=606; HPLC: $_c t_{Ret}$=3.44, 3.50 min.

Intermediate 62.2

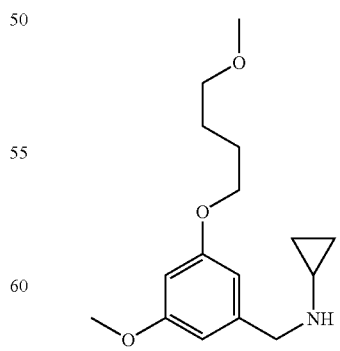

Intermediate 62.2 is synthesized by reduction of Intermediate 62.3 (825 g, 2.81 mmol) analogously to the preparation of Intermediate 78.2. Yellow oil; ES-MS: M+H=280; HPLC: $_c t_{Ret}$=2.27 min.

Intermediate 62.3

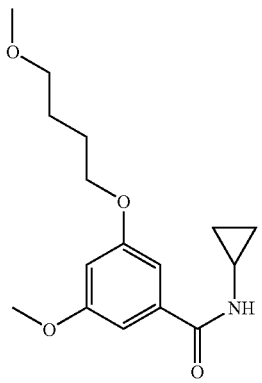

Intermediate 62.3 is synthesized by condensation of Intermediate 62.4 (965.8 mg, 3.78 mmol) with cyclopropylamine (0.26 mL, 3.78 mmol) analogously to the preparation of Intermediate 1.1. Yellow oil; ES-MS: M+H=294; HPLC: $_C t_{Ret}$=2.82 min.

Intermediate 62.4

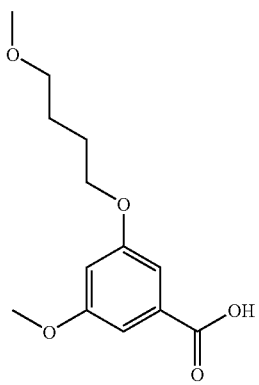

Intermediate 62.4 is synthesized by hydrolysis of Intermediate 62.5 (1.20 g, 4.47 mmol) analogously to the preparation of Intermediate 58.4. White material; ES-MS: M+H=255; HPLC: $_C t_{Ret}$=2.84 min.

Intermediate 62.5

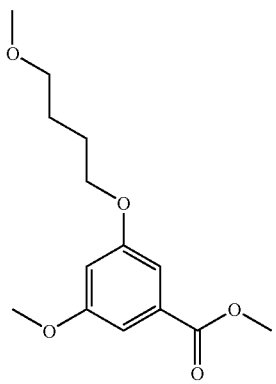

To a solution of 3-methoxy-5-hydroxybenzoic acid methyl ester (1 g, 5.48 mmol) in THF (10 mL) under $N_2$ at rt are added PPh$_3$ (1.43 g, 5.45 mmol), DEAD (2.48 mL in 40% toluene, 5.48 mmol), 4-Methoxy-butan-1-ol (770 mg, 7.39 mmol). After stirring at rt for 7 hours, the reaction mixture is concentrated under reduced pressure and subjected to chromatography to give Intermediate 62.5. White material; ES-MS: M+H=269 HPLC: $_A t_{Ret}$=3.65 min.

Example 63

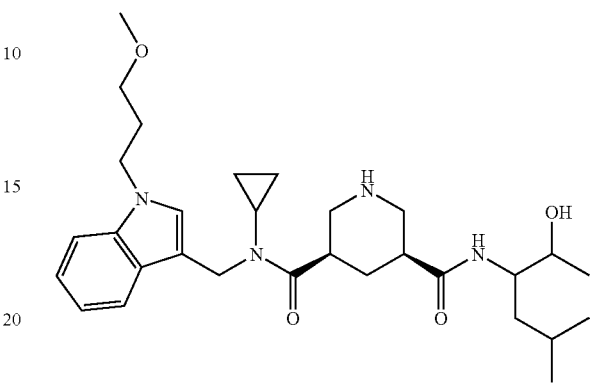

Example 63 is synthesized by deprotection of Intermediate 63.1 analogously to the preparation of example 1: ES-MS: M+H=527: $_C t_{Ret}$=2.73, 2.87 min.

Intermediate 63.1

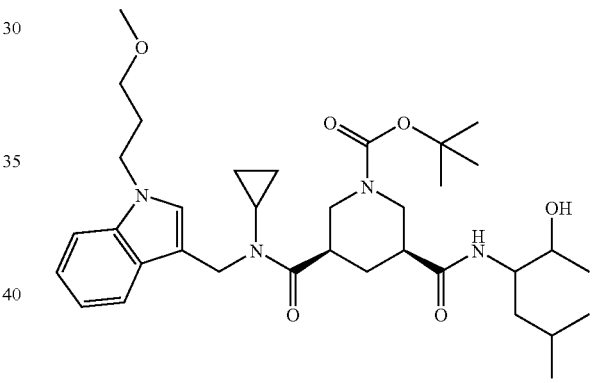

Example 63.1 is synthesized by condensation of Intermediate 60.2 (103 mg, 0.2 mmol) with 3-amino-5-methylhexan-2-ol (*Angewandte Chemie* 1987, 99, 1186.) (26 mg, 0.2 mmol) analogously to the preparation of example 1.1: ES-MS: M+H=627: $_C t_{Ret}$=3.79, 3.86 min.

Example 64

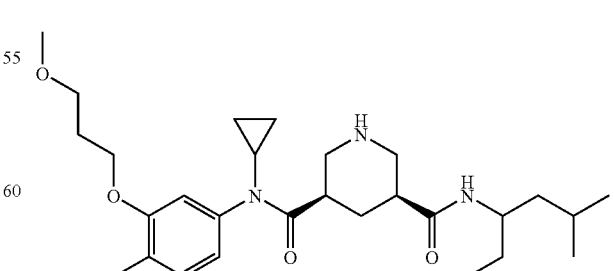

Example 64 is synthesized by deprotection of Intermediate 64.1 analogously to the preparation of example 1: ES-MS: M+H=490: $_C t_{Ret}$=2.73, 2.83 min.

Intermediate 64.1

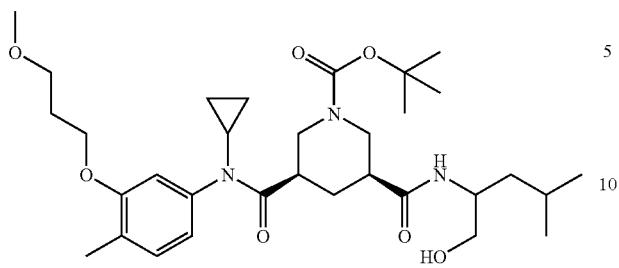

Intermediate 64.1 is synthesized by condensation of Intermediate 33.2 (80 mg, 0.22 mmol) and Intermediate 64.2 (51 mg, 0.22 mmol) analogously to the preparation of Example 19.1: ES-MS: M+H=490: $_C t_{Ret}$=2.66, 2.83 min.

Intermediate 64.2

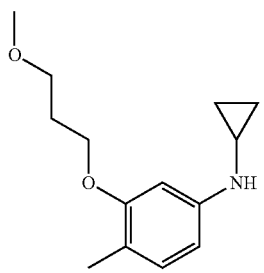

Intermediate 64.2 is synthesized by cyclopropanation of intermediate 64.3 (800 mg, 4.1 mmol) analogously to the preparation of Intermediate 19.5, 19.6. Yellow oil; ES-MS: M+H=236; HPLC: $_A t_{Ret}$=2.98 min.

Intermediate 64.3

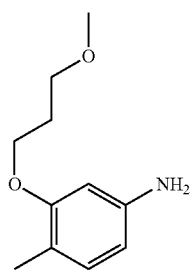

Intermediate 64.3 is synthesized by reduction of Intermediate 64.4 (266 mg, 1.00 mmol) analogously to the preparation of Intermediate 87.3. Brown solid; ES-MS: M+H=197; HPLC: $_A t_{Ret}$=2.19 min.

Intermediate 64.4

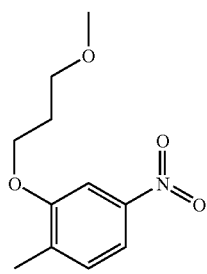

Intermediate 64.4 is synthesized by alkylation of 5-methyl-2-nitro-phenol (5.0 g, 32.6 mmol) analogously to the preparation of Intermediate 37.5. red solid; ES-MS: M+H=226; HPLC: $_A t_{Ret}$=4.06 min.

Example 65

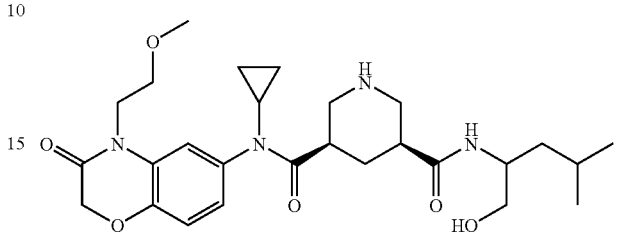

Example 65 is synthesized by deprotection of Intermediate 65.1 analogously to the preparation of example 1: ES-MS: M+H=517: $_C t_{Ret}$=2.13, 2.18 min.

Intermediate 65.1

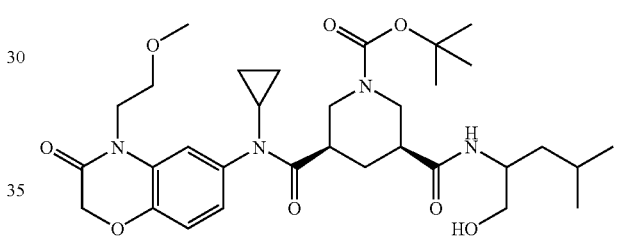

Intermediate 65.1 is synthesized by condensation of Intermediate 33.2 (81 mg, 0.22 mmol) and Intermediate 65.2 (56 mg, 0.22 mmol) analogously to the preparation of Example 19.1: ES-MS: M+H=517: $_C t_{Ret}$=2.13, 2.18 min.

Intermediate 65.2

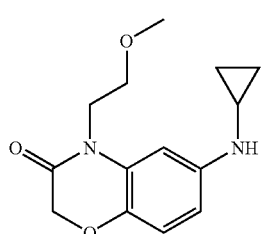

Intermediate 65.2 is synthesized by alkylation of Intermediate 19.4 (204 mg, 1 mmol) analogously to the preparation of Intermediate 19.3. White amorphous material; ES-MS: M+H=263; HPLC: $_B t_{Ret}$=1.44 min.

Example 77

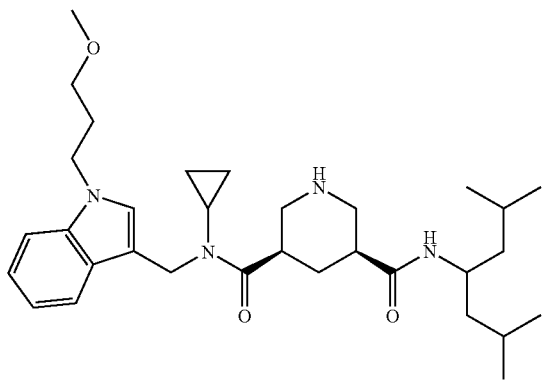

Example 77 is synthesized by deprotection of Intermediate 77.1 analogously to the preparation of example 1: ES-MS: M+H=539: $c_{t_{Ret}}$=3.57 min.

Intermediate 77.1

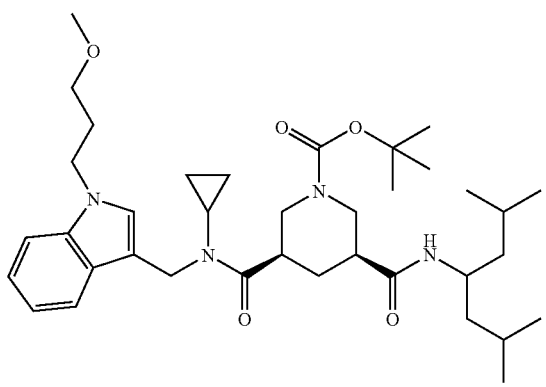

Example 77.1 is synthesized by condensation of Intermediate 60.2 with 1-Isobutyl-3-methylbutylamine (J. Am. Chem. Soc. 1944, 66, 1516.) analogously to the preparation of example 1.1: ES-MS: M+H=639: $c_{t_{Ret}}$=4.72 min.

Example 78

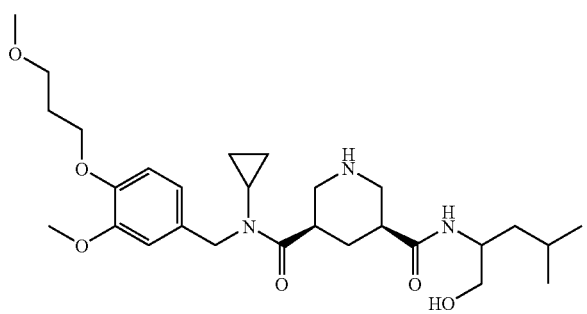

Example 78 is synthesized by deprotection of Intermediate 78.1 analogously to the preparation of example 1: ES-MS: M+H=520: $c_{t_{Ret}}$=2.43 min.

Intermediate 78.1

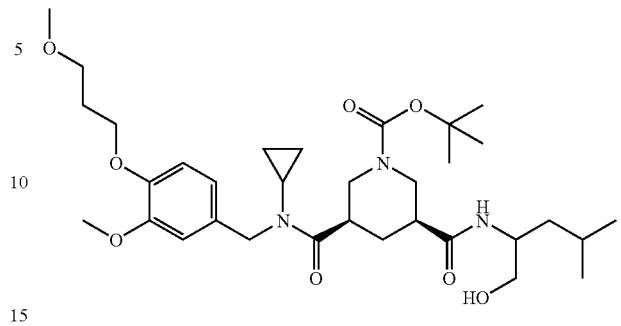

Intermediate 78.1 is synthesized by condensation of Intermediate 78.2 (46 mg, 0.172 mmol) with Intermediate 33.2 (54 mg, 0.145 mmol) analogously to the preparation of Intermediate 1.1. White amorphous material; ES-MS: [M+H]$^+$=620; HPLC: $c_{t_{Ret}}$=3.48 min.

Intermediate 78.2

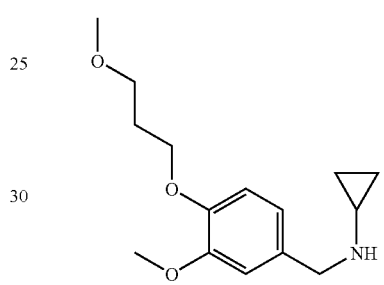

A mixture of Intermediate 78.3 (300 mg, 1.07 mmol) and BH$_3$ (1M in THF, 9 mL, 9 mmol) is stirred at 50° C. for 16 h. The reaction is quenched with MeOH (2 mL) and 2N NaOH aq. then stirred at 100° C. After stirring for 15 h, the reaction is quenched with H$_2$O (5 mL) and extracted with CH$_2$Cl$_2$ twice (30 mL). The combined organic layers are successively washed with 5% aqueous NaHCO$_3$aq, H$_2$O, and brine, then dried over Na$_2$SO$_4$ and concentrated under reduced pressure. RP-HPLC purification affords Intermediate 78.2. Colorless oil; ES-MS: [M+H]$^+$=266; HPLC: $c_{t_{Ret}}$=1.85 min.

Intermediate 78.3

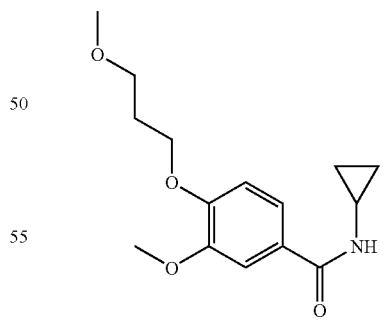

To a solution of Intermediate 78.4 (300 mg, 1.25 mmol) and cyclopropylamine (130 µL, 1.87 mmol) in CH$_2$Cl$_2$ (10 mL) are added EDCI HCl (358 mg, 1.87 mmol) and HOAt (255 mg, 1.87 mmol), then the mixture is stirred at room temperature for 1 h. The reaction is quenched with H$_2$O (5 mL) and extracted with EtOAc (50 mL, twice). The combined organic layers are successively washed with 5% aqueous KHSO$_4$, 5% aqueous NaHCO$_3$, H$_2$O, and brine, then dried over Na$_2$SO$_4$ and concentrated under reduced pressure. SiO$_2$ column chromatography affords the Intermediate 78.3. White amorphous material: ES-MS: [M+H]⁺=280: HPLC: $_ct_{Ret}$=2.27 min.

Intermediate 78.4

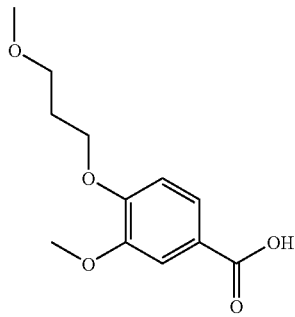

Intermediate 78.4 is synthesized by alkylation of 4-hydroxy-3-methoxybenzoic acid (2 g, 11.9 mmol) with toluene-4-sulfonic acid 3-methoxypropyl ester (4.4 g, 17.8 mmol) analogously to the preparation of Intermediate 1.4. White amorphous material; ES-MS: [M+H]⁺=241; HPLC: $_ct_{Ret}$=2.27 min.

Example 79

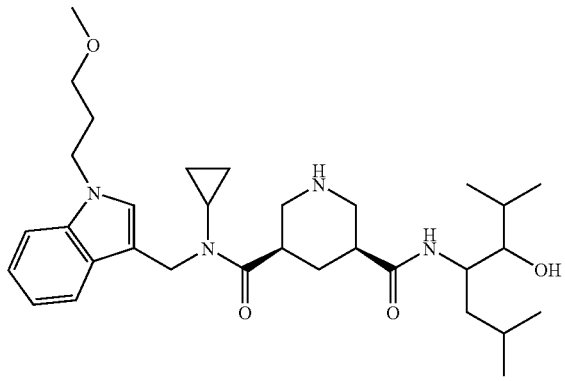

Example 79 is synthesized by deprotection of Intermediate 79.1 analogously to the preparation of example 1: ES-MS: M+H=555: $_ct_{Ret}$=3.02, 3.09, 3.16 min.

Intermediate 79.1

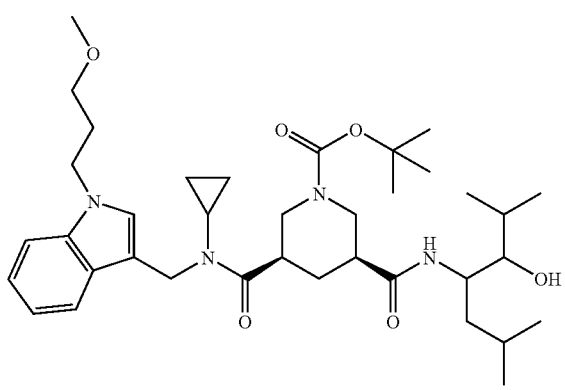

Example 79.1 is synthesized by condensation of Intermediate 60.2 (98 mg, 0.19 mmol) with 4-Amino-2,6-dimethyl-heptan-3-ol (47 mg, 0.18 mmol) analogously to the preparation of example 1.1: ES-MS: M+H=655: $_ct_{Ret}$=4.17, 4.22 min.

Example 82

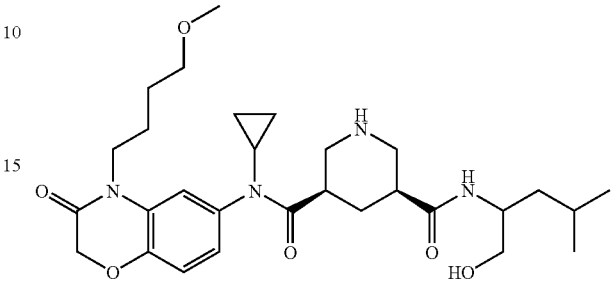

Example 82 is synthesized by deprotection of Intermediate 82.1 analogously to the preparation of example 1: ES-MS: M+H=545: $_ct_{Ret}$=2.24, 2.30 min.

Intermediate 82.1

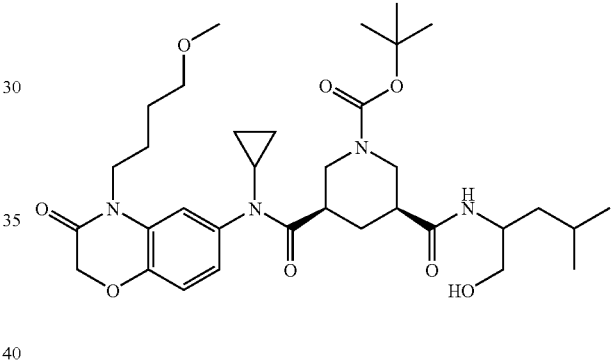

Intermediate 82.1 is synthesized by condensation of Intermediate 33.2 (81 mg, 0.22 mmol) and Intermediate 82.2 (62 mg, 0.22 mmol) analogously to the preparation of 19.1: ES-MS: M+H=545: $_ct_{Ret}$=2.24, 2.30 min.

Intermediate 82.2

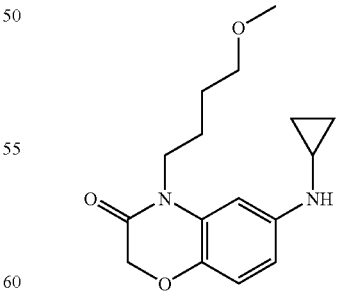

Intermediate 82.2 is synthesized by alkylation of Intermediate 19.4 (200 mg, 1 mmol) analogously to the preparation of Intermediate 19.3. White amorphous material; ES-MS: M+H=291; HPLC: $_Bt_{Ret}$=1.56 min.

Example 83

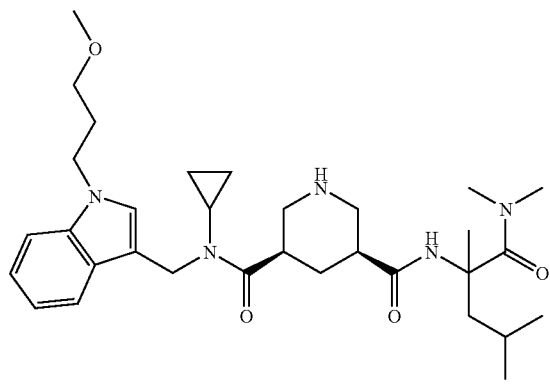

Example 83 is synthesized by deprotection of Intermediate 83.1 analogously to the preparation of example 1: ES-MS: M+H=568: $_A t_{Ret}$=2.89 min.

Example 84

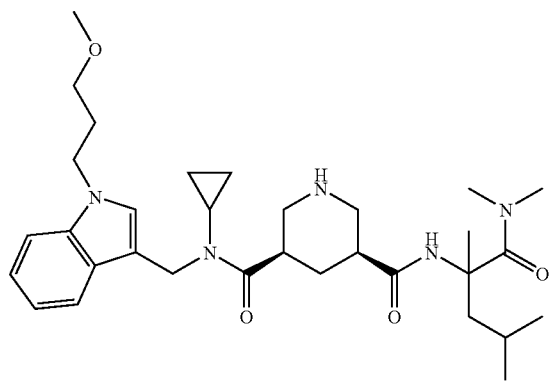

Example 84 is synthesized by deprotection of Intermediate 84.1 analogously to the preparation of example 1: ES-MS: M+H=568: $_A t_{Ret}$=2.87 min.

Intermediate 83.1 & 84.1

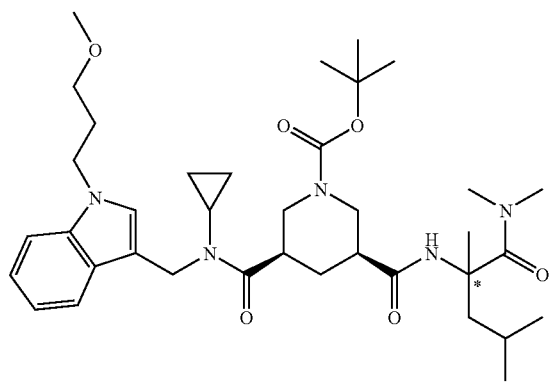

Condensation of Intermediate 60.2 with Intermediate 83.2 is performed analogously to the preparation of example 1.1. The resulting diastereomixture is separated by preparative HPLC (Chiralpak AD-H, Flow; 10 mL/min, 15% iPrOH in n-Hexane) to give Intermediate 83.1 and 84.1 (Stereochemistry of the quarternary center is not determined):

Intermediate 83.1: ES-MS: M+H=668: $_C t_{Ret}$=3.89 min.
Intermediate 84.1: ES-MS: M+H=668: $_C t_{Ret}$=3.89 min.

Intermediate 83.2

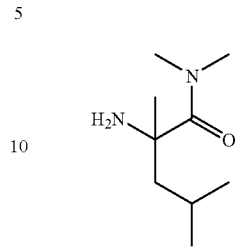

A mixture of Intermediate 83.3 (420 mg, 1.54 mmol) in HCl in dioxane (4N, 5 mL) is stirred at room temperature for 2 h. Concentration under reduced pressure gives Intermediate 83.2. White amorphous material; ES-MS: [M+H]$^+$=173; HPLC: $_C t_{Ret}$=1.35 min.

Intermediate 83.3

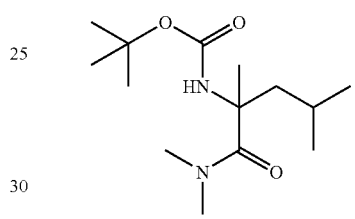

To a solution of 2-tert-butoxycarbonylamino-2,4-dimethylpentanoic acid (400 mg, 1.63 mmol) and dimethylamine hydrochloride (200 mg, 2.5 mmol) in CH$_2$Cl$_2$ (8 mL) are added EDCI HCl (480 mg, 2.5 mmol), HOAt (340 mg, 2.5 mmol) and Et$_3$N (349 µL, 2.5 mmol) at room temperature. After stirring for 20 h, the reaction is quenched with H$_2$O (20 mL) and extracted with EtOAc (50 mL). The organic layer is successively washed with 5% aqueous KHSO$_4$, 5% aqueous NaHCO$_3$, H$_2$O, and brine, then dried over Na$_2$SO$_4$ Concentration under reduced pressure gives Intermediate 83.3. White amorphous material: ES-MS: [M+H]$^+$=273: HPLC: $_C t_{Ret}$=2.96 min.

Example 87

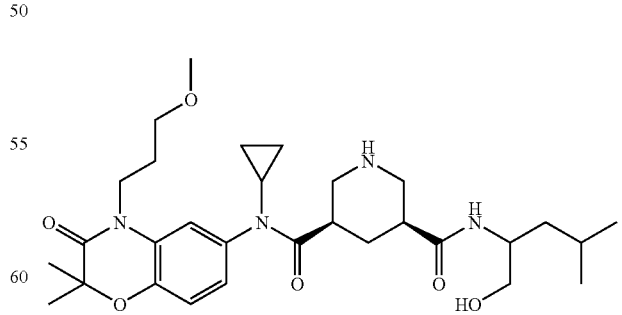

Example 87 is synthesized by deprotection of Intermediate 87.1 analogously to the preparation of example 1: ES-MS: M+H=559: $_C t_{Ret}$=2.57, 2.73 min.

Intermediate 87.1

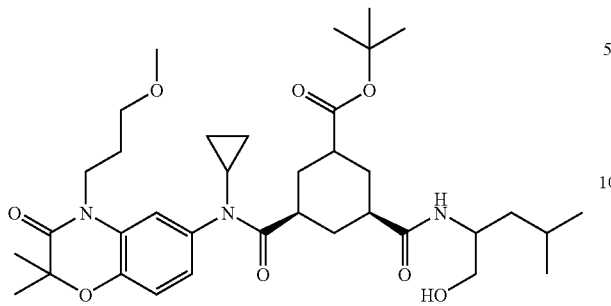

Intermediate 87.1 is synthesized by condensation of Intermediate 33.2 (41 mg, 0.11 mmol) and Intermediate 87.2 (28 mg, 0.09 mmol) analogously to the preparation of Example 19. 1: ES-MS: M+H=559: $_C t_{Ret}$=2.57, 2.73 min.

Intermediate 87.2

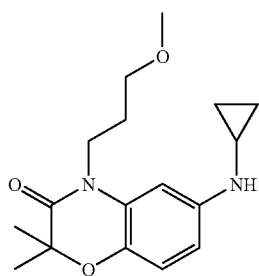

At room temperature, a methanolic solution (3.2 mL) of Intermediate 87.3 (400 mg, 1.5 mmol) is treated with AcOH (0.8 mL) and [(1-ethoxycycopropyl)-oxy]trimethylsilane (0.58 mL, 2.66 mmol), stirred at 70° C. under reflux for 1.5 h. At the same temperature, to this mixture is added dropwise a methanolic solution (3 mL) of NaBH$_3$CN (0.17 g, 2.7 mmol) over 5 min, and the resulting mixture is stirred at 70° C. under reflux for 2 h, and evaporated. After coevaporation with PhMe for several times until the smell of AcOH disappeared, the residue is dissolved in EtOAc and the solution is washed with sat. aqueous solution of NaHCO$_3$ and brine dried (MgSO$_4$), the reaction mixture is concentrated under reduced pressure and purified with Silica gel column chromatography to give Intermediate 87.2: ES-MS: M+H=305: $_B t_{Ret}$=1.66 min.

Intermediate 87.3

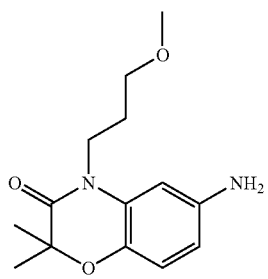

To a solution of Intermediate 87.4 (500 mg, 1.7 mmol) in EtOH (2 mL) is added NH$_4$Cl (182 mg, 3.4 mmol), water (2 mL) and Zn (555 mg, 8.5 mmol). The mixture is stirred at 80° C. for 1 h. After filtration on a celite pad, the solution is diluted with EtOAc, washed with sat NaHCO$_3$aq, brine and dried (MgSO$_4$). Concentration under reduced pressure gives Intermediate 87.3: ES-MS: M+H=265: $_B t_{Ret}$=1.32 min.

Intermediate 87.4

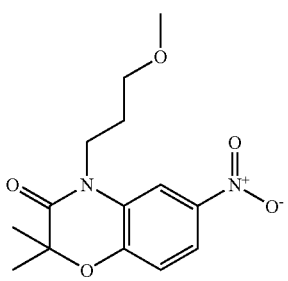

Intermediate 87.4 is synthesized by alkylation of 2,2-dimethyl-6-nitro-4H-benzo[1,4]oxazin-3-one (835 mg, 3.76 mmol, Bioorganic & Medicinal Chemistry 2002, 10, 2663-2669.) analogously to the preparation of Intermediate 19.3. Yellow crystal; ES-MS: M+H=295; HPLC: $_B t_{Ret}$=1.89 min.

Example 88

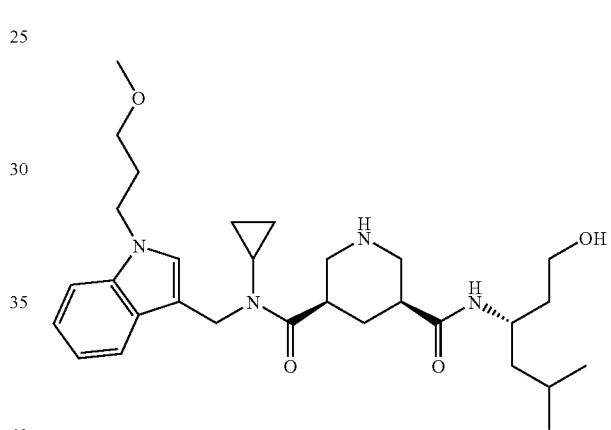

Example 88 is synthesized by deprotection of Intermediate 88.1 analogously to the preparation of example 1: ES-MS: M+H=527: $_C t_{Ret}$=2.83 min.

Intermediate 88.1

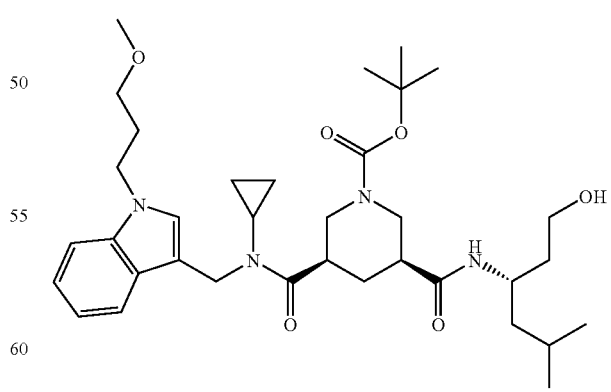

Example 88.1 is synthesized by condensation of Intermediate 60.2 with (S)-3-Amino-5-methylhexan-1-ol analogously to the preparation of example 1.1: ES-MS: M+H=627: $_C t_{Ret}$=3.83 min.

Example 89

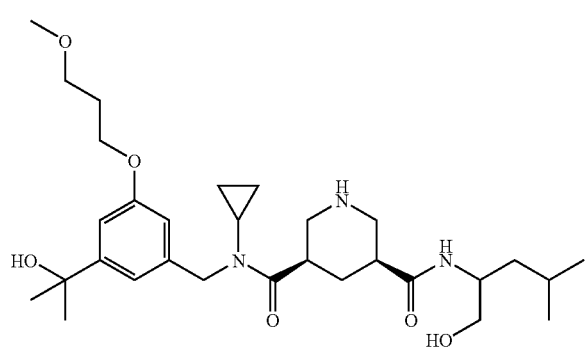

Example 89 is synthesized by deprotection of Intermediate 89.1 analogously to the preparation of example 1: ES-MS: M+H=548: $_c t_{Ret}$=2.43, 2.55 min.

Intermediate 89.1

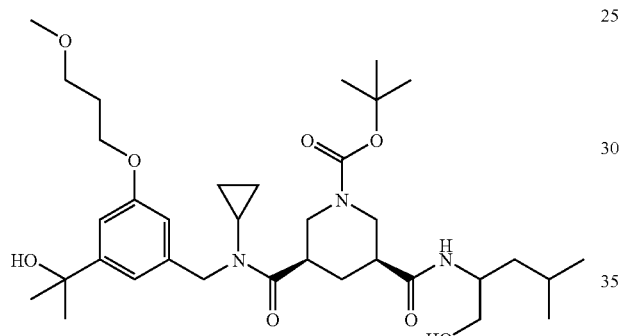

Intermediate 89.1 is synthesized by condensation of Intermediate 89.2 (94 mg, 0.32 mmol) with Intermediate 33.2 (100 mg, 0.27 mmol) analogously to the preparation of Intermediate 1.1. White amorphous material; ES-MS: [M+H]$^+$=648; HPLC: $_c t_{Ret}$=3.43 min.

Intermediate 89.2

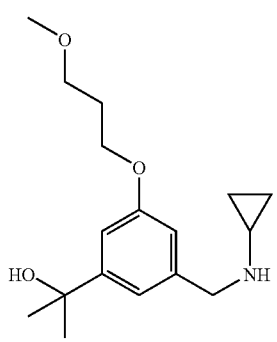

Intermediate 89.2 is synthesized by reduction of Intermediate 89.3 (94 mg, 0.32 mmol) analogously to the preparation of Intermediate 78.2. Colorless oil; ES-MS: [M+H]$^+$=294; HPLC: $_c t_{Ret}$=1.92 min.

Intermediate 89.3

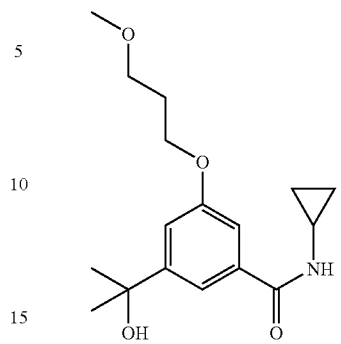

To a solution of Intermediate 89.4 (400 mg, 1.3 mmol) in THF (20 mL) is added MeMgBr in THF (3 M in THF, 1.7 mL, 5.2 mmol) at −78° C. After stirring at −78° C. for 2 h, additional MeMgBr (3 M in THF, 1.7 mL, 5.2 mmol) is added to the mixture, then the mixture is stirred at 0° C. for 4 h. The reaction is quenched with saturated aqueous NH$_4$Cl (100 mL) and extracted with EtOAc. The organic layer is successively washed with 5% aqueous KHSO$_4$, 5% aqueous NaHCO$_3$, H$_2$O, and brine, then dried over Na$_2$SO$_4$. Concentration under reduced pressure gives Intermediate 89.3. Colorless oil; ES-MS: [M+H]$^+$=308; HPLC: $_c t_{Ret}$=2.36 min.

Intermediate 89.4

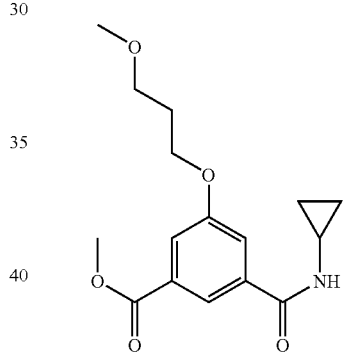

Intermediate 89.4 is synthesized by condensation of Intermediate 89.5 with cyclopropylamine analogously to the preparation of Intermediate 1.1. White amorphous material; ES-MS: [M+H]$^+$=308; HPLC: $_c t_{Ret}$=2.71 min.

Intermediate 89.5

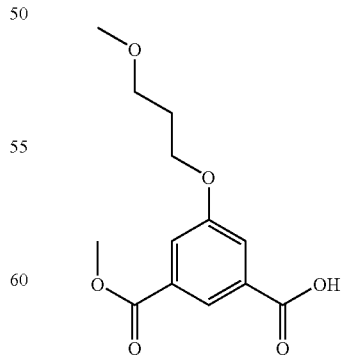

To a solution of Intermediate 89.6 (5 g, 18 mmol) in THF (100 mL) is added LiOH (957 mg, 22.8 mmol) in H$_2$O (50 mL) at 0° C. After stirring at 0° C. for 3 h, the reaction mixture is acidified with 5% aqueous KHSO$_4$ and extracted with EtOAc twice. The combined organic layers are successively washed with 5% aqueous $KHSO_4$, $H_2O$, and brine, then dried over $Na_2SO_4$ and concentrated under reduced pressure. $SiO_2$ column chromatography affords Intermediate 89.5. White amorphous material; ES-MS: $[M+H]^+=269$; HPLC: $_Bt_{Ret}=2.70$ min.
Intermediate 89.6

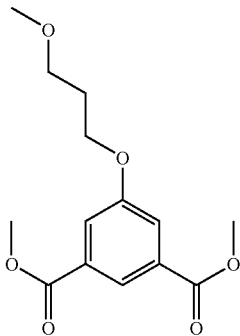

Intermediate 89.6 is synthesized by condensation of 5-hydroxyisophthalic acid dimethyl ester (4 g, 19 mmol) with toluene-4-sulfonic acid 3-methoxypropyl ester (9.3 g, 38 mmol) analogously to the preparation of Intermediate 1.4. White solid material; ES-MS: $[M+H]^+=283$; HPLC: $_Ct_{Ret}=3.35$ min.

Example 90

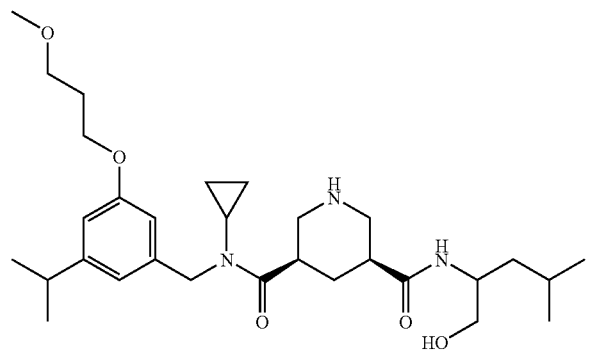

Example 90 is synthesized by deprotection of Intermediate 90.1 analogously to the preparation of example 1: ES-MS: M+H=532: $_Ct_{Ret}=3.02, 3.17$ min.
Intermediate 90.1

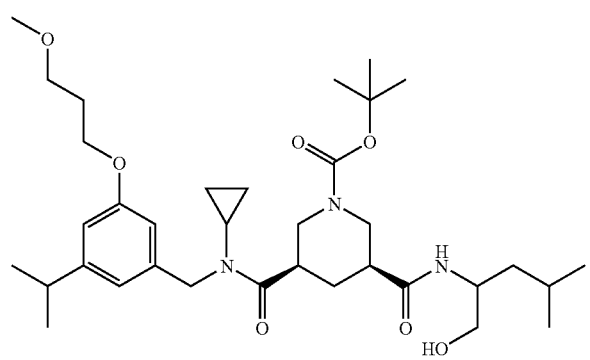

Intermediate 90.1 is synthesized by condensation of Intermediate 90.2 (50 mg, 0.322 mmol) with Intermediate 33.2 (100 mg, 0.27 mmol) analogously to the preparation of Intermediate 1.1. White amorphous material; ES-MS: $[M+H]^+=632$; HPLC: $_Ct_{Ret}=4.14$ min.
Intermediate 90.2

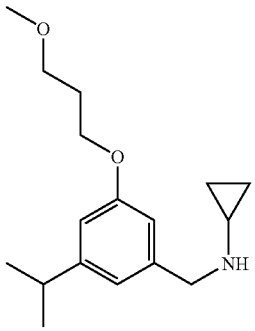

Intermediate 90.2 is synthesized by reduction of Intermediate 90.3 (360 mg, 1.24 mmol) analogously to the preparation of Intermediate 78.2. Colorless oil; ES-MS: $[M+H]^+=278$; HPLC: $_Ct_{Ret}=2.63$ min.
Intermediate 90.3

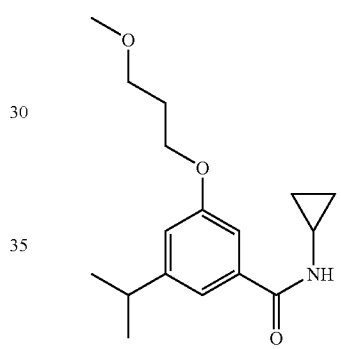

To a solution of Intermediate 89.4 (400 mg, 1.3 mmol) in $CH_2Cl_2$ (18 mL) are added $Et_3SiH$ (1.04 mL, 6.5 mmol) and TFA (2 mL) at room temperature. After stirring for 25 h, the reaction is quenched with $H_2O$ (50 mL) and extracted with $CH_2Cl_2$. The organic layer is successively washed with 5% aqueous $KHSO_4$, 5% aqueous $NaHCO_3$, $H_2O$, and brine, then dried over $Na_2SO_4$ and concentrated under reduced pressure. $SiO_2$ column chromatography gives Intermediate 90.3. Colorless oil; ES-MS: $[M+H]^+=292$; HPLC: $_Ct_{Ret}=3.28$ min.

Example 92

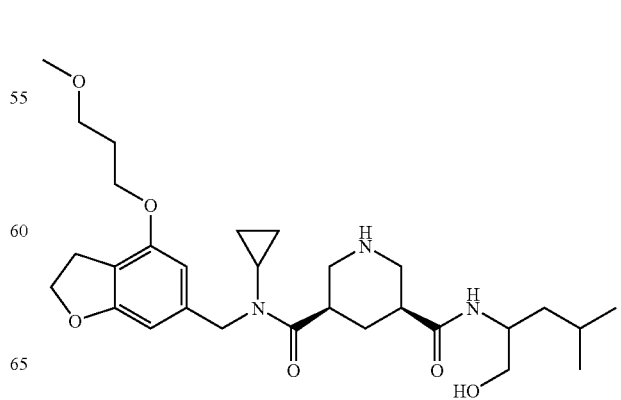

Example 92 is synthesized by deprotection of Intermediate 92.1 analogously to the preparation of example 1: ES-MS: M+H=532: $_c t_{Ret}$=2.65, 2.80 min.

Intermediate 92.1

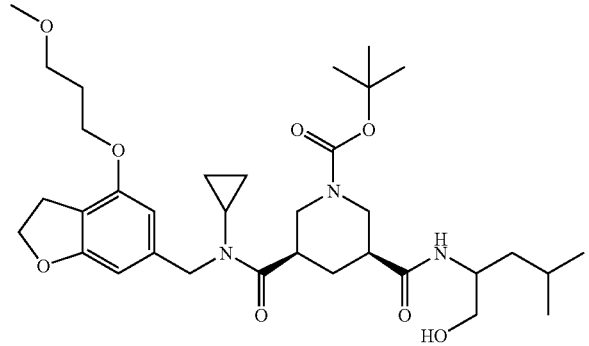

Intermediate 92.1 is synthesized by condensation of Intermediate 92.2 (34 mg, 0.12 mmol) with Intermediate 33.2 (48 mg, 0.076 mmol) analogously to the preparation of Intermediate 1.1. White amorphous material; ES-MS: [M+H]$^+$=632; HPLC: $_c t_{Ret}$=3.70 min.

Intermediate 92.2

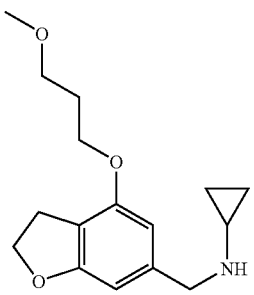

Intermediate 92.2 is synthesized by reduction of Intermediate 92.3 (72.9 mg, 0.25 mmol) analogously to the preparation of Intermediate 78.2. Yellow oil; ES-MS: [M+H]$^+$=278; HPLC: $_c t_{Ret}$=2.16 min.

Intermediate 92.3

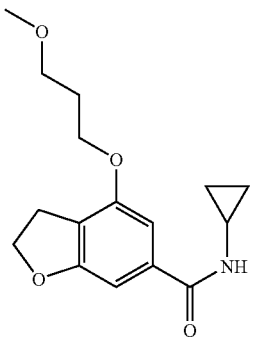

Intermediate 92.3 is synthesized by condensation of Intermediate 92.4 (75.6 mg, 0.3 mmol) with cyclopropylamine (0.041 mL, 0.6 mmol) analogously to the preparation of Intermediate 1.1. Yellow oil; ES-MS: M+H=292; HPLC: $_c t_{Ret}$=2.65 min.

Intermediate 92.4

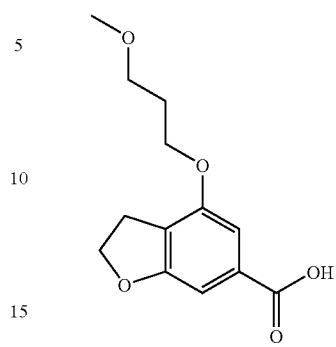

Intermediate 92.4 is synthesized by hydrolysis of Intermediate 92.5 (84.3 mg, 0.3 mmol) analogously to the preparation of Intermediate 58.4. White material; ES-MS: M+H=253; HPLC: $_c t_{Ret}$=2.66 min.

Intermediate 92.5

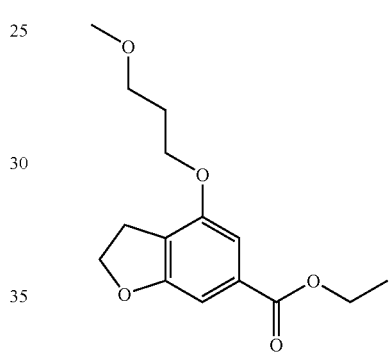

Intermediate 92.5 is synthesized by alkylation of 4-Hydroxy-2,3-dihydro-benzofuran-6-carboxylic acid ethyl ester (J. Org. Chem. 1994, 59, 2043.) (89.8 mg, 0.43 mmol) with 3-Methoxy-propan-1-ol (0.05 mL, 0.52 mmol) analogously to the preparation of Intermediate 62.5. White material; ES-MS: M+H=281, HPLC: $_A t_{Ret}$=3.60 min.

Example 93

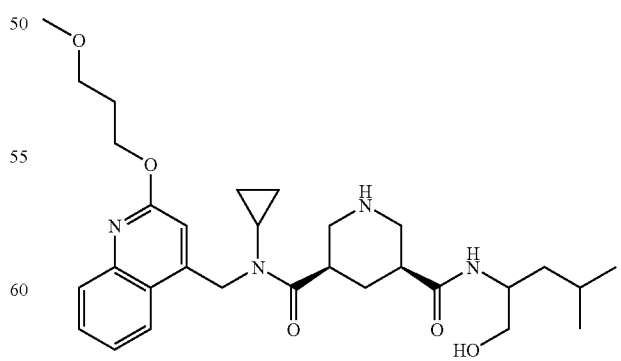

Example 93 is synthesized by deprotection of Intermediate 93.1 analogously to the preparation of example 1: ES-MS: M+H=541: $_A t_{Ret}$=2.35, 2.54 min.

Intermediate 93.1

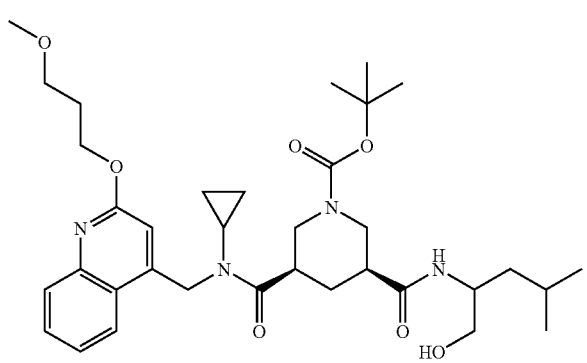

Intermediate 93.1 is synthesized by condensation of Intermediate 33.2 (33 mg, 0.115 mmol) with Intermediate 93.2 (68 mg, 0.18 mmol) analogously to the preparation of Intermediate 1.1. White amorphous material; ES-MS: $[M+H]^+=641$; HPLC: $_B t_{Ret}$=1.83, 1.88 min.

Intermediate 93.2

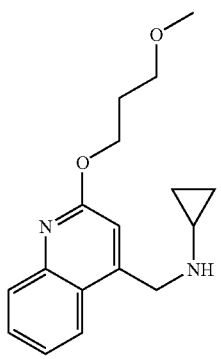

Intermediate 93.2 is synthesized by etherification followed by reduction of Intermediate (119 mg, 0.48 mmol) analogously to the preparation of Intermediate 27.2. White colorless oil; ES-MS: $[M+H]^+=287$; HPLC: $_B t_{Ret}$=1.43 min.

Example 94

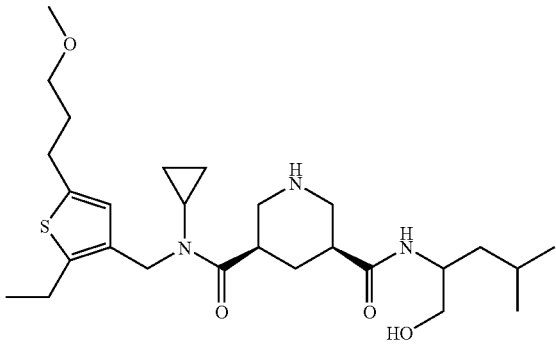

Example 94 is synthesized by deprotection of Intermediate 94.1 analogously to the preparation of example 1: ES-MS: M+H=507; $_C t_{Ret}$=2.99, 3.15 min.

Intermediate 94.1

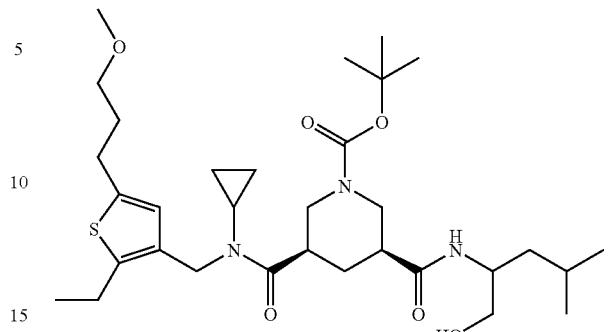

Intermediate 94.1 is synthesized by condensation of Intermediate 33.2 (79 mg, 0.21 mmol) with Intermediate 94.2 (60 mg, 0.24 mmol) analogously to the preparation of Intermediate 1.1. White amorphous material; ES-MS: M+H=607; HPLC: $_C t_{Ret}$=4.12 min.

Intermediate 94.2

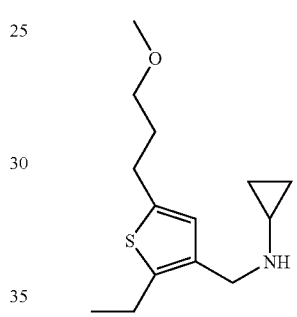

Intermediate 94.2 is synthesized by reductive alkylation of Intermediate 94.3 (289 mg, 1.36 mmol) with cyclopropylamine (0.14 mL, 2.02 mmol) analogously to the preparation of Intermediate 1.3. Colorless oil; ES-MS: $[M+H]^+=253$; HPLC: $_B t_{Ret}$=1.52 min.

Intermediate 94.3

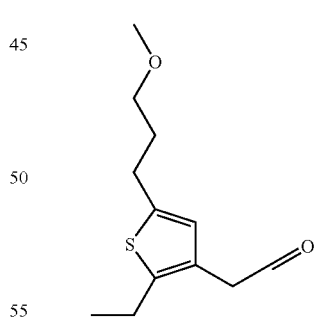

To a solution of intermediate 94.4 (405 mg, 1.54 mmol) in $Et_2O$ (4 mL) cooled to −78° C. is added tert-BuLi (1.47 M, 2.3 mL, 3.38 mmol) dropwise. After the addition is completed, the reaction is stirred at −78° C. for an additional 10 min. A solution of DMF (0.24 mL, 3.12 mmol) in $Et_2O$ (2 mL) is added via syringe to the reaction mixture. The reaction is allowed to slowly warmed to room temperature and then quenched with water. The mixture is transferred to a separatory funnel and the aqueous layer extracted with EtOAc/n-hexane (1:1). The combined organic layers are washed with water and brine and then dried over $Na_2SO_4$. The solution is filtered and the solvent is evaporated in vacuo. The residue is purified by silica gel column chromatography to give intermediate 94.3. Colorless oil; ES-MS: [M+H]$^+$=212; HPLC: $_Bt_{Ret}$=1.90 min.

Intermediate 94.4

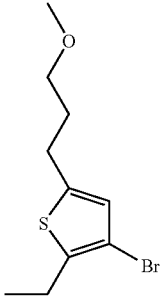

To a solution of intermediate 94.5 (1.88 g, 6.52 mmol) in THF (20 mL) cooled to 0° C. is added NaH (60%, 392 mg, 9.8 mmol). After 10 min, MeI (0.61 mL, 9.8 mmol) is added to the reaction mixture. The reaction is allowed to warmed to room temperature for 1 h. NaH (60%, 100 mg, 2.5 mmol) and MeI (0.2 mL, 3.2 mmol) are added, and the mixture is stirred for 40 min. The reaction is quenched with aq. KHSO$_4$, and the resulting mixture is extracted with EtOAc. The combined organic extracts are washed with water and brine and then dried over Na$_2$SO$_4$. The solution is filtered and the solvent is evaporated in vacuo. The residue is purified by silica gel column chromatography to give intermediate 94.4. Colorless oil; ES-MS: [M+H]$^+$=262; HPLC: $_Bt_{Ret}$=2.30 min.

Intermediate 94.5

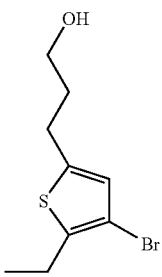

To a solution of intermediate 94.6 (1.88 g, 6.85 mmol) in THF-MeOH (8-20 mL) at 0° C. is added NiCl$_2$ (90 mg, 0.69 mmol). To this suspension is added NaBH$_4$ (280 mg, 7.4 mmol) portionwise. After the addition is completed, the mixture is stirred at 0° C. for 30 min. The reaction is quenched with aq. KHSO$_4$, and the resulting mixture is extracted with EtOAc. The combined organic extracts are washed with water and brine and then dried over Na$_2$SO$_4$. The solution is filtered and the solvent is evaporated in vacuo. The residue is directly used for the next reaction without further purification.

To a solution of the residue in CH$_2$Cl$_2$ is added DIBAL (1.0 M, 14.3 mL, 14.3 mmol) at −78° C. After stirring at −78° C. for 30 min, the reaction is quenched with aq. KHSO$_4$, and the resulting mixture is extracted with CH$_2$Cl$_2$. The combined organic extracts are washed with water, sat. aq. NaHCO$_3$, water and brine and then dried over Na$_2$SO$_4$. The solution is filtered and the solvent is evaporated in vacuo. The residue is directly used for the next reaction without further purification.

To a solution of the residue in MeOH (20 mL) is added NaBH4 (240 mg, 6.34 mmol) at 0° C. After stirring at room temperature for 1 h, the reaction is quenched with aq. KHSO$_4$, and the resulting mixture is extracted with EtOAc. The combined organic extracts are washed with water and brine and then dried over Na$_2$SO$_4$. The solution is filtered and the solvent is evaporated in vacuo. The residue is purified by silica gel column chromatography to give intermediate 94.5. Colorless oil; ES-MS: [M+H]$^+$=248; HPLC: $_Bt_{Ret}$=1.94 min.

Intermediate 94.6

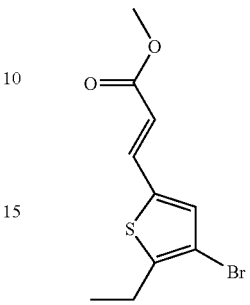

To a solution of 4-Bromo-5-ethylthiophene-2-carbaldehyde (4.13 g, 18.8 mmol) in toluene (30 mL) is added Ph$_3$P=CHCO$_2$Me (9.4 g, 28.1 mmol). The reaction mixture is stirred at 80° C. for 40 min, then diluted with n-hexane/Et$_2$O. The resulting precipitate is filtered through a pad of silica, and the filtrate is evaporated in vacuo. The residue is purified by silica gel column chromatography to give intermediate 94.6. Colorless oil; ES-MS: [M+H]$^+$=274; HPLC: $_Bt_{Ret}$=2.21 min.

Example 95

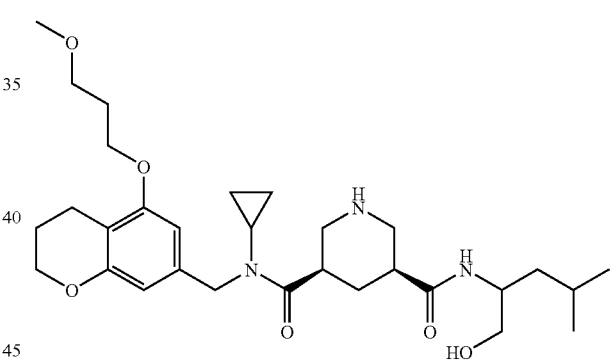

Example 95 is synthesized by deprotection of Intermediate 95.1 analogously to the preparation of example 1: ES-MS: M+H=546: $_Ct_{Ret}$=3.00, 3.14 min.

Intermediate 95.1

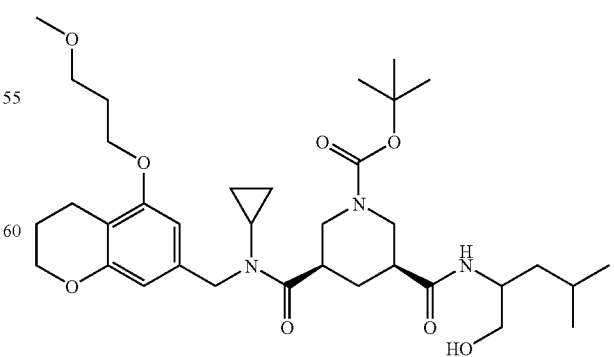

Intermediate 95.1 is synthesized by condensation of Intermediate 95.2 (115 mg, 0.31 mmol) with Intermediate 33.2

(114 mg, 0.31 mmol) analogously to the preparation of Intermediate 1.1. White amorphous material; ES-MS: [M+H]$^+$=646; HPLC: $_C t_{Ret}$=4.02 min.

Intermediate 95.2

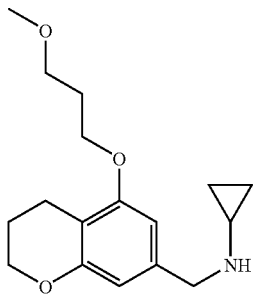

Intermediate 95.2 is synthesized by alkylation of Intermediate 95.3 (468.4 mg, 1.486 mmol) with cyclopropylamine (0.12 mL, 1.78 mmol) analogously to the preparation of Intermediate 98.2. White material; ES-MS: [M+H]$^+$=292; HPLC: $_B t_{Ret}$=1.55 min.

Intermediate 95.3

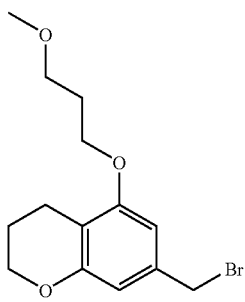

Intermediate 95.3 is synthesized by bromination of Intermediate 95.4 (465.5 mg, 1.84 mmol) analogously to the preparation of Intermediate 98.3. White material; ES-MS: [M+H]$^+$=316; HPLC: $_B t_{Ret}$=2.12 min.

Intermediate 95.4

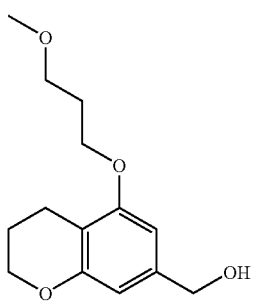

Intermediate 95.4 is synthesized by reduction of Intermediate 95.5 (440.8 mg, 1.50 mmol) analogously to the preparation of Intermediate 37.4. White material; ES-MS: [M+H]$^+$=253; HPLC: $_B t_{Ret}$=1.67 min.

Intermediate 95.5

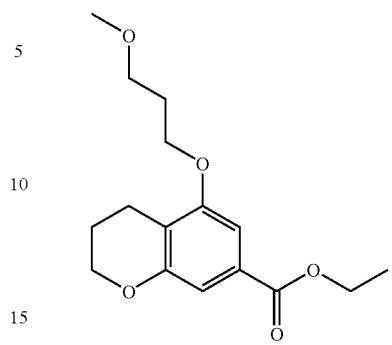

Intermediate 95.5 is synthesized by alkylation of 5-hydroxy-chroman-7-carboxylic acid ethyl ester (*J. Org. Chem.* 1994, 59, 2043.) (1.4 g, 6.3 mmol) with 3-Methoxy-propan-1-ol (0.91 mL, 9.5 mmol) analogously to the preparation of Intermediate 62.5. White material; ES-MS: M+H=295, HPLC: $_C t_{Ret}$=3.96 min.

Example 98

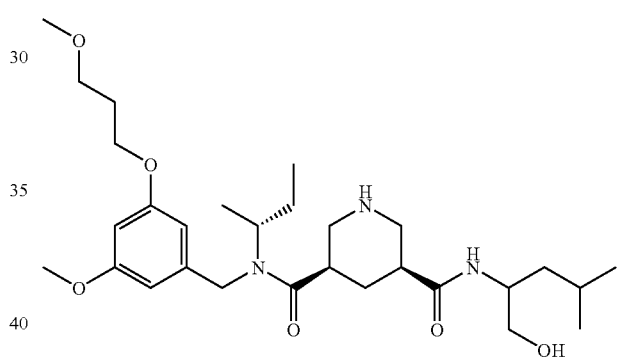

Example 98 is synthesized by deprotection of Intermediate 98.1 analogously to the preparation of example 1: ES-MS: M+H=536: $_C t_{Ret}$=2.79, 2.94 min.

Intermediate 98.1

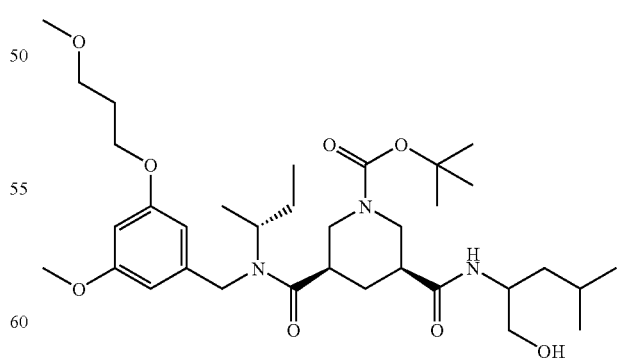

Intermediate 98.1 is synthesized by condensation of Intermediate 98.2 (126 mg, 0.449 mmol) with Intermediate 33.2 (110 mg, 0.299 mmol) analogously to the preparation of Intermediate 1.1. White amorphous material; ES-MS: [M+H]$^+$=636; HPLC: $_C t_{Ret}$=3.85 min.

Intermediate 98.2

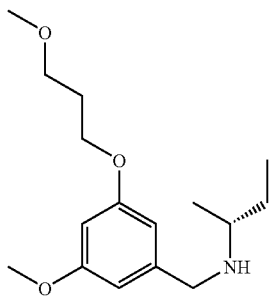

To a solution of intermediate 98.3 (150 mg, 0.52 mmol) in DMF (1 mL) are added K$_2$CO$_3$ (350 mg, 2.6 mmol) and (R)-isobutylamine (190 mg, 2.6 mmol) at room temperature, then the mixture is stirred at 80° C. After stirring at 80° C. for 2 h, the reaction is quenched with H$_2$O (50 mL) and extracted with EtOAc/Et$_2$O (c.a. 1/1, 50 mL). The organic layer is successively washed with 5% aqueous NaHCO$_3$, H$_2$O, and brine, then dried over Na$_2$SO$_4$ Concentration under reduced pressure gives Intermediate 98.2. Colorless oil; ES-MS: [M+H]$^+$=282; HPLC: $_C$t$_{Ret}$=2.32 min.

Intermediate 98.3

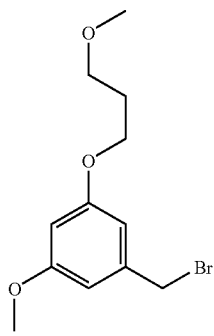

A mixture of Intermediate 37.4 (11.1 g, 49.0 mmol), PPh$_3$ (21.9 g, 83.5 mmol) and NBS (13.2 g, 74.2 mmol) in DCM (170 mL) is stirred under N$_2$ at RT. After stirring 14 h, the reaction mixture is concentrated under reduced pressure and purified by silica gel flash chromatography to give Intermediate 98.3 as a colorless oil; ES-MS: M$^+$=291; HPLC: $_A$t$_{Ret}$=4.09 min.

Example 99

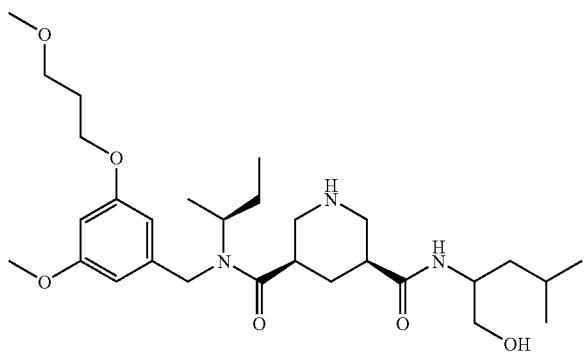

Example 99 is synthesized by deprotection of Intermediate 99.1 analogously to the preparation of example 1: ES-MS: M+H=536: $_C$t$_{Ret}$=2.79, 2.94 min.

Intermediate 99.1

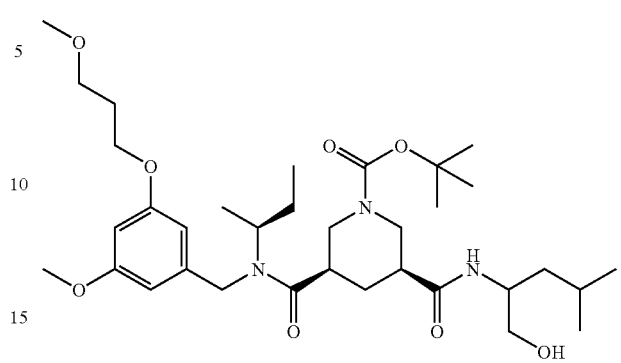

Intermediate 99.1 is synthesized by condensation of Intermediate 99.2 (126 mg, 0.449 mmol) with Intermediate 33.2 (110 mg, 0.299 mmol) analogously to the preparation of Intermediate 1.1. White amorphous material; ES-MS: [M+H]$^+$=636; HPLC: $_C$t$_{Ret}$=3.85 min.

Intermediate 99.2

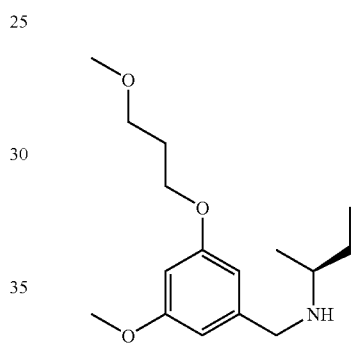

Intermediate 99.2 is synthesized by alkylation (S)-isobutylamine (190 mg, 2.6 mmol) with intermediate 98.3 (150 mg, 0.52 mmol) analogously to the preparation of Intermediate 98.2. Colorless oil; ES-MS: [M+H]$^+$=282; HPLC: $_C$t$_{Ret}$=2.31 min.

Example 100

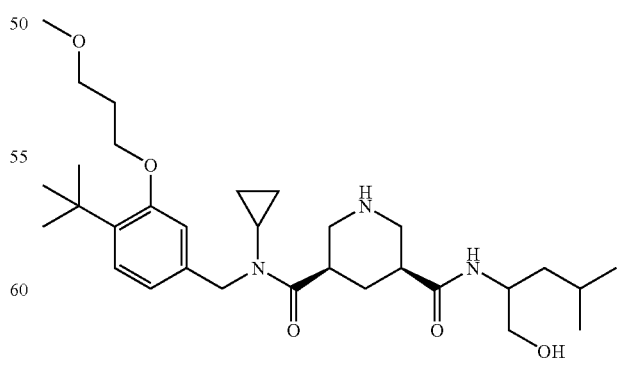

Example 100 is synthesized by deprotection of Intermediate 100.1 analogously to the preparation of example 1: ES-MS: M+H=546: $_C$t$_{Ret}$=3.12, 3.22 min.

Intermediate 100.1

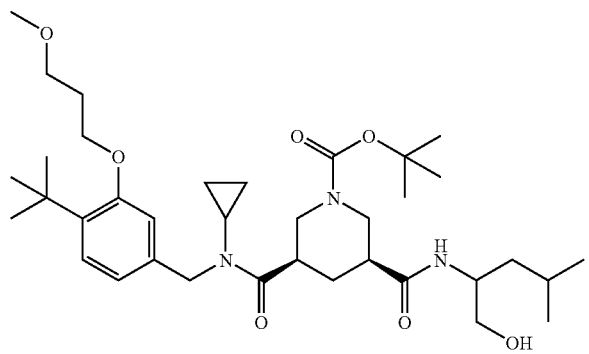

Intermediate 100.1 is synthesized by condensation of Intermediate 100.2 (50 mg, 0.172 mmol) with Intermediate 33.2 (54 mg, 0.145 mmol) analogously to the preparation of Intermediate 1.1. White amorphous material; ES-MS: [M+H]$^+$= 646; HPLC: $_c t_{Ret}$=4.52 min.

Intermediate 100.2

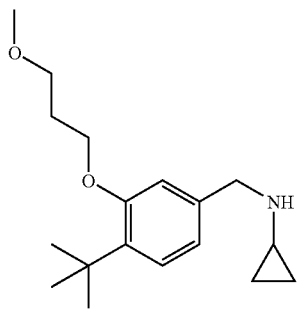

Intermediate 100.2 is synthesized by reduction of Intermediate 100.3 (125 mg, 0.41 mmol) analogously to the preparation of Intermediate 78.2. colorless oil; ES-MS: [M+H]$^+$= 292; HPLC: $_c t_{Ret}$=2.92 min.

Intermediate 100.3

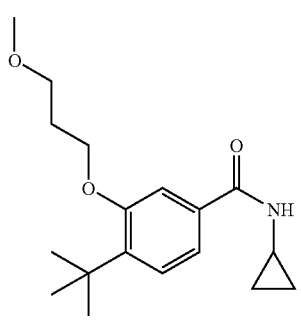

Intermediate 100.3 is synthesized by condensation of 4-tert-Butyl-3-(3-methoxy-propoxy)-benzoic acid (112 mg, 0.42 mmol) with cyclopropylamine (44 µL, 0.63 mmol) analogously to the preparation of Intermediate 1.1. White amorphous material; ES-MS: [M+H]$^+$=306; HPLC: $_c t_{Ret}$=3.88 min.

Example 101

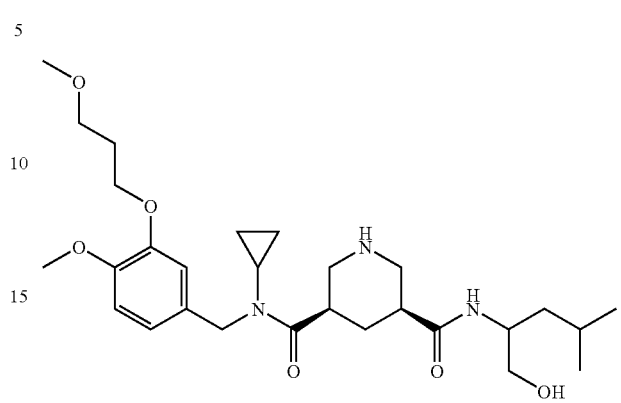

Example 101 is synthesized by deprotection of Intermediate 101.1 analogously to the preparation of example 1: ES-MS: M+H=520: $_c t_{Ret}$=2.32, 2.43 min.

Intermediate 101.1

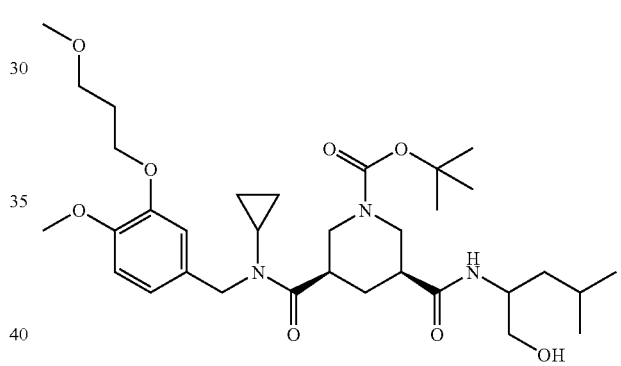

Intermediate 101.1 is synthesized by condensation of Intermediate 101.2 (46 mg, 0.172 mmol) with Intermediate 33.2 (54 mg, 0.145 mmol) analogously to the preparation of Intermediate 1.1. White amorphous material; ES-MS: [M+H]$^+$= 620; HPLC: $_c t_{Ret}$=3.43 min.

Intermediate 101.2

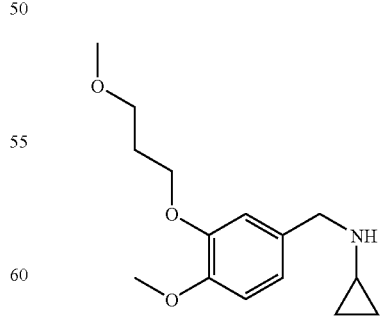

Intermediate 101.2 is synthesized by reduction of Intermediate 101.3 (115 mg, 0.42 mmol) analogously to the preparation of Intermediate 78.2. colorless oil; ES-MS: [M+H]$^+$= 266; HPLC: $_c t_{Ret}$=1.87 min.

Intermediate 101.3

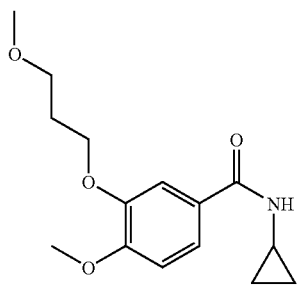

Intermediate 101.3 is synthesized by condensation of intermediate 78.4 (100 mg, 0.42 mmol) with cyclopropylamine (44 µL, 0.63 mmol) analogously to the preparation of Intermediate 1.1. White amorphous material; ES-MS: [M+H]$^+$= 280; HPLC: $_C t_{Ret}$=2.82 min.

Example 102

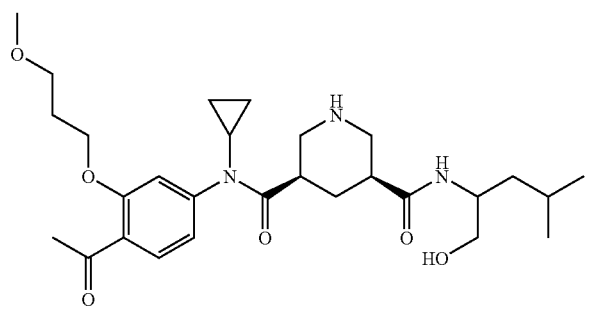

Example 102 is synthesized by condensation of Intermediate 33.2 (112 mg, 0.3 mmol) and Intermediate 102.1 (79 mg, 0.3 mmol) followed by deprotection analogously to the preparation of Example 19. ES-MS: M+H=517: $_C t_{Ret}$=2.49, 2.66 min.

Intermediate 102.1

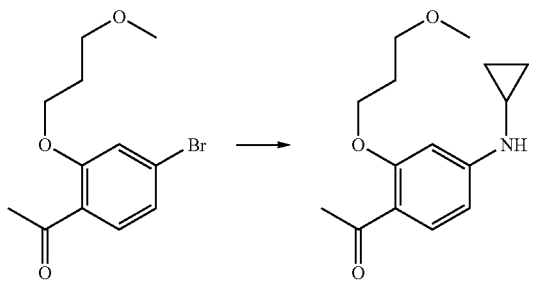

Intermediate 102.2 (540 mg, 1.88 mmol), cyclopropylamine (322 mg, 5.64 mmol), Pd$_2$(dba)$_3$ (191 mg, 0.2 mmol), rac-BINAP (392 mg, 0.62 mmol) and sodium tert-butoxide (303 mg, 3.2 mmol) in toluene (10 mL) is stirred at 80° C. for 1.5 h. After adding water, the reaction mixture is extracted with EtOAc. The organic phases are washed with sat. NaHCO$_3$aq, brine and dried (MgSO$_4$). Concentration under reduced pressure and purified with Silica gel column chromatography gives Intermediate 102.1: colorless oil, ES-MS: M+H=397: $_B t_{Ret}$=1.97 min.

Intermediate 102.2

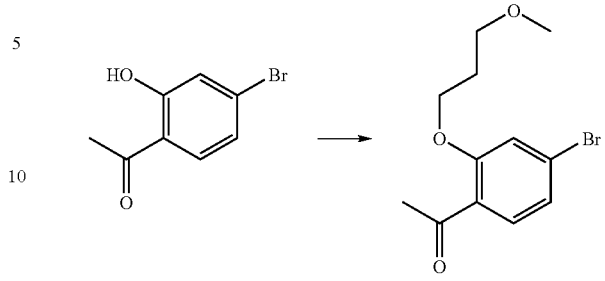

To a solution of 4-bromo-2-hydroxyacetophenone (2.3 g, 10.7 mmol) in DMF are added K$_2$CO$_3$ (4.4 g, 32 mmol), toluene-4-sulfonic acid 3-methoxy-propyl ester (3.1 g, 12.84 mmol) and KI (355 mg, 2.14 mmol). The reaction mixture is stirred at 60° C. for 5 h. After adding water, the mixture is extracted with EtOAc. The combined organic phases are washed with water and brine and dried (MgSO$_4$). Concentration under reduced pressure and purification by Silica gel column chromatography gives Intermediate 102.2: pale yellow crystal, ES-MS: M+H=288: $_A t_{Ret}$=3.65 min.

Example 103

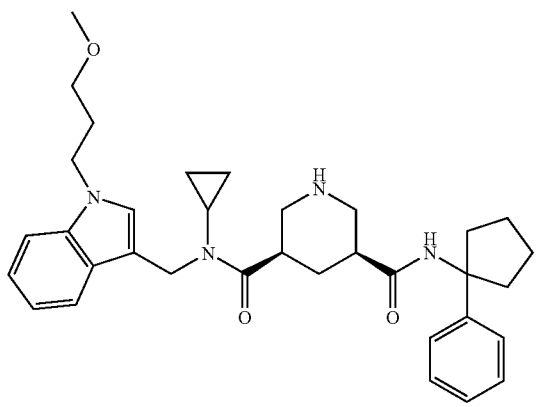

Example 103 is synthesized by deprotection of intermediate 103.1 analogously to the preparation of Example 19: ES-MS: M+H=557: $_C t_{Ret}$=3.35 min.

Intermediate 103.1

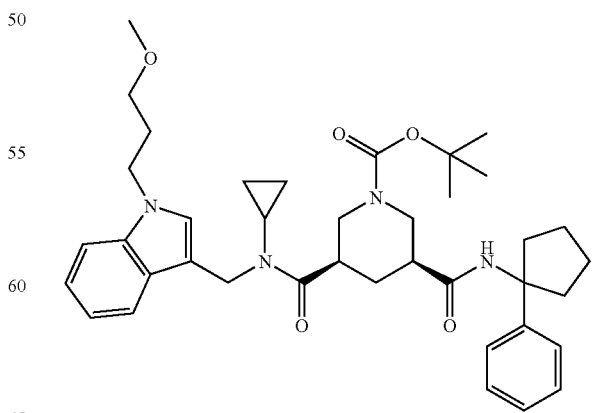

Intermediate 103.1 is synthesized by condensation of Intermediate 55.2 (100 mg, 0.195 mmol) and Intermediate 103.2

(58 mg, 0.293 mmol) analogously to the preparation of Intermediate 39.1. ES-MS: M+H=657: $c t_{Ret}$=4.45 min.

Intermediate 103.2

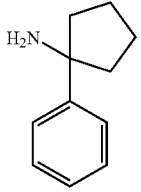

Intermediate 103.2 is synthesized by deprotection of Intermediate 103.3 (490 mg, 1.9 mmol) analogously to the preparation of Example 19: ES-MS=167: $c t_{Ret}$=1.86 min.

Intermediate 103.3

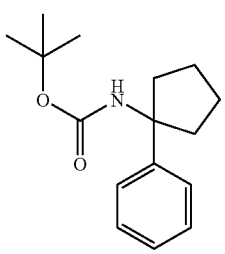

A mixture of Intermediate 103.4 (1 g, 5.3 mmol) and [Bis(trifluoroacetoxy)iodo]benzene (3.4 g, 8 mmol) in $^t$BuOH (12 mL) is stirred at 90° C. After 2 h, pyridine is added to the mixture and the mixture is stirred at the same temperature. After additional 6 h, the reaction mixture is cooled down at room temperature and diluted with H$_2$O (50 mL) and extracted with EtOAc (100 mL). The organic phase is successively washed with 5% aqueous KHSO$_4$, 5% aqueous NaHCO$_3$, H$_2$O, and brine, then dried over Na$_2$SO$_4$ and concentrated in vacuo. Purification by SiO$_2$ column chromatography gives Intermediate 103.3: White solid material: ES-MS=262: $c t_{Ret}$=4.10 min.

Intermediate 103.4

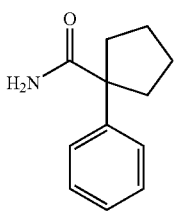

A mixture of 1-phenylcyclopentanecarbonitrile (CAS 77-57-6, 3 9, 18 mmol) and aqueous KOH (8M in H$_2$O, 20 mL) in EtOH (20 mL) is stirred under reflux. After 8 h, the reaction mixture is cooled down to room temperature and poured into ice/5% aqueous KHSO$_4$ (ca. 1:1 v/v) and extracted with Et$_2$O (200 mL). The organic phase is successively washed with 5% aqueous KHSO$_4$, H$_2$O, and brine, then dried over Na$_2$SO$_4$ and concentrated in vacuo. The residue is suspended in hexane/Et$_2$O, and the resulting solid material is collected by filtration to give Intermediate 103.4: White solid material: ES-MS=262: $c t_{Ret}$=190 min.

Example 104

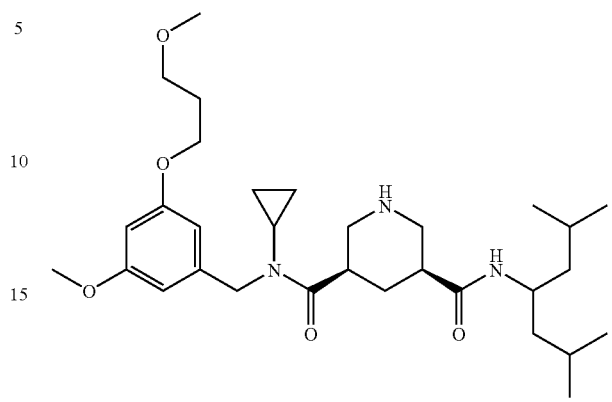

Example 104 is synthesized by deprotection of intermediate 104.1 analogously to the preparation of Example 19: ES-MS: M+H=546: $c t_{Ret}$=3.53 min.

Intermediate 104.1

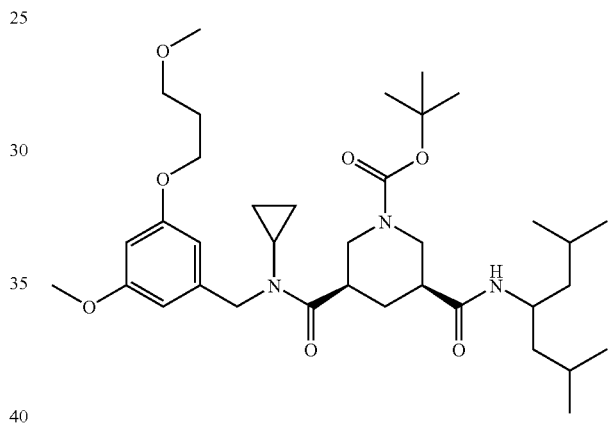

Intermediate 104.1 is synthesized by condensation of Intermediate 104.2 (80 mg, 20 mmol) and Intermediate 62.2 (80 mg, 30 mmol) analogously to the preparation of Intermediate 39.1: ES-MS: M+H=646: $c t_{Ret}$=4.67 min.

Intermediate 104.2

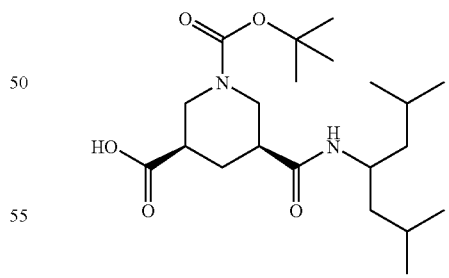

To a solution of LiOH.H$_2$O (101 mg, 2.4 mmol) in H$_2$O (5 mL) is added a solution of Intermediate 104.3 (470 mg, 1.14 mmol) in THF (5 mL) at 0° C., then the mixture is stirred at 0° C. After 1.5 h, the reaction mixture is quenched with 5% aqueous KHSO$_4$ (30 mL), and extracted with EtOAc. The organic phase is washed with 5% KHSO$_4$aq, H$_2$O, and brine, then dried over Na$_2$SO$_4$. The solution is filtered and the filtrate is evaporated in vacuo to give intermediate 104.2. White amorphous material; ES-MS: [M+H]$^+$=3.86; HPLC: $c t_{Ret}$=399 min.

Intermediate 104.3

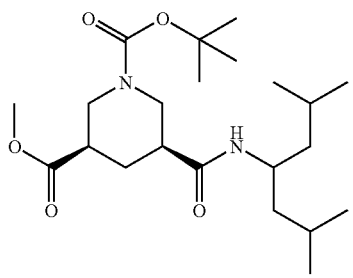

To a solution of (3S,5R)-starting material-F (400 mg, 1.4 mmol) and 1-isobutyl-3-methylbutylamine hydrochloride (CAS No. 65530-92-9, *JACS* 1944, 66, 1516-1520.) in $CH_2Cl_2$ (5 mL) are added EDCI.HCl (400 mg, 2.1 mmol), HOAt (286 mg, 2.1 mmol) and $Et_3N$ (253 uL, 1.8 mmol), then the mixture is stirred at room temperature. After 1 h, the reaction mixture is quenched with $H_2O$ (50 mL) and extracted with EtOAc (100 mL). The combined organic phase is successively washed with 5% aqueous $KHSO_4$, 5% aqueous $NaHCO_3$, $H_2O$, and brine, then dried over $Na_2SO_4$ and concentrated under reduced pressure. The residue is purified by silica gel column chromatography to give intermediate 104.3. White amorphous material; ES-MS: $[M+H]^+=413$; HPLC: $_ct_{Ret}$=4.29 min.

Example 105

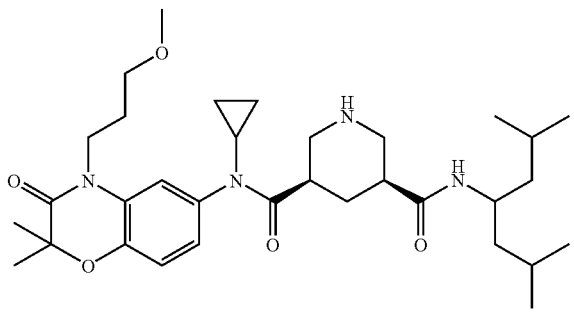

Example 105 is synthesized by deprotection of intermediate 105.1 analogously to the preparation of Example 19: ES-MS: M+H=585: $_ct_{Ret}$=3.46 min.

Intermediate 105.1

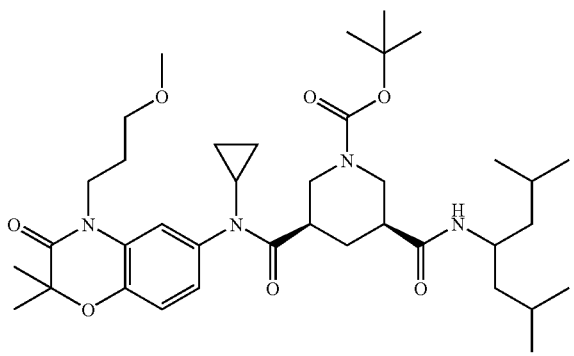

Intermediate 105.1 is synthesized by condensation of intermediate 105.2 (80 mg, 0.2 mmol) and Intermediate 87.2 (61 mg, 0.2 mmol) analogously to the preparation of Example 19.1: ES-MS: M+H=685: $_ct_{Ret}$=2.28 min.

Example 106

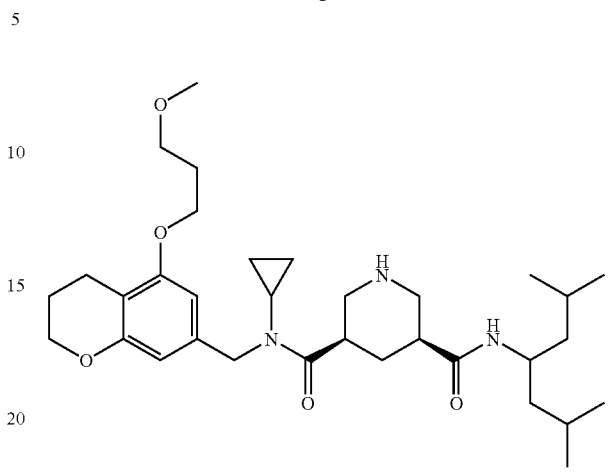

Example 106 is synthesized by deprotection of intermediate 106.1 analogously to the preparation of Example 19: ES-MS: M+H=572: $_ct_{Ret}$=3.60 min.

Intermediate 106.1

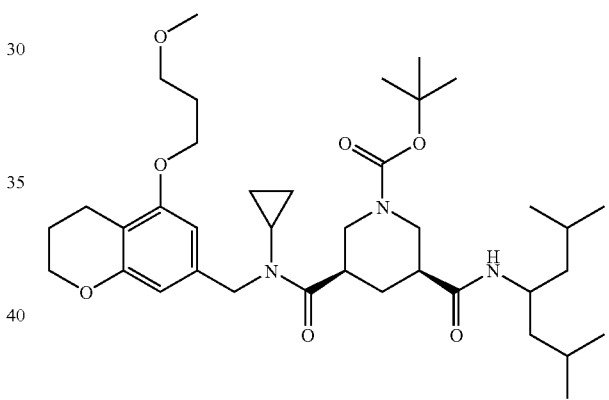

Intermediate 106.1 is synthesized by condensation of Intermediate 106.2 (103.0 mg, 0.26 mmol) and Intermediate 95.2 (97.6 mg, 0.33 mmol) analogously to the preparation of Intermediate 39.1: ES-MS: M+H=672: $_Bt_{Ret}$=2.36 min.

Example 107

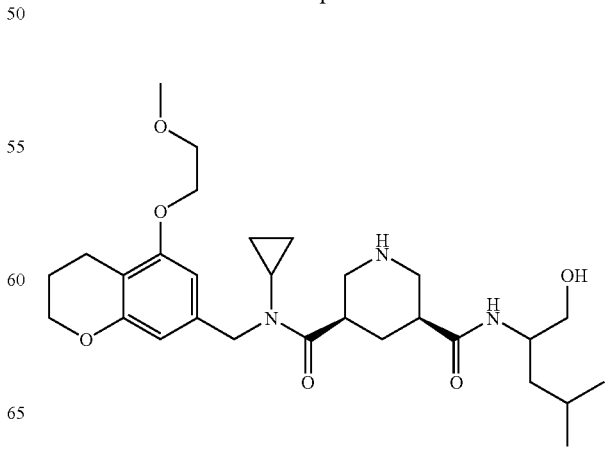

Example 107 is synthesized by deprotection of intermediate 107.1 analogously to the preparation of Example 1: ES-MS: M+H=532: $_C t_{Ret}$=2.65, 2.80 min.

Intermediate 107.1

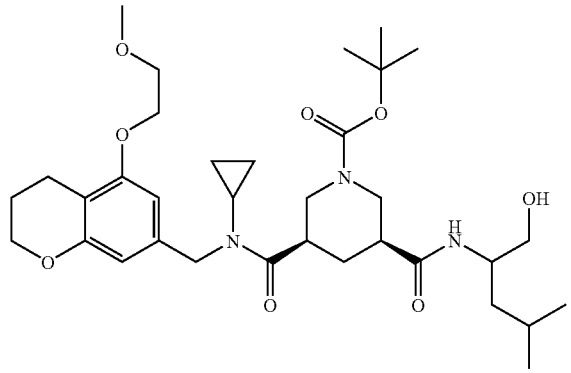

Intermediate 107.1 is synthesized by condensation of Intermediate 33.2 (145.4 mg, 0.39 mmol) and Intermediate 107.2 (42.2 mg, 0.39 mmol) analogously to the preparation of Intermediate 39.1: ES-MS: M+H=632: $_B t_{Ret}$=1.94 min.

Intermediate 107.2

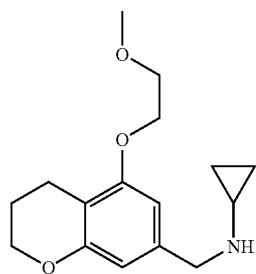

Intermediate 107.2 is synthesized by alkylation of Intermediate 107.3 (117.8 mg, 0.39 mmol) with cyclopropylamine (0.05 mL, 0.72 mmol) analogously to the preparation of Intermediate 42.2: white material; ES-MS: [M+H]$^+$=278; HPLC: $_B t_{Ret}$=1.43 min.

Intermediate 107.3

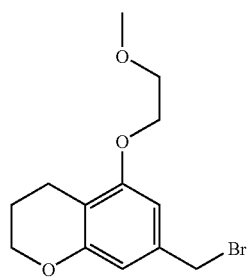

Intermediate 107.3 is synthesized by bromination of Intermediate 107.4 (128.6 mg, 0.54 mmol) analogously to the preparation of Intermediate 42.3: white material; ES-MS: [M+H]$^+$=301; HPLC: $_B t_{Ret}$=1.98 min.

Intermediate 107.4

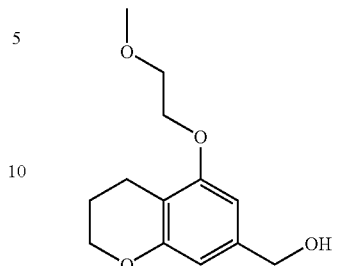

Intermediate 107.4 is synthesized by reduction of Intermediate 107.5 (473.3 mg, 1.68 mmol) analogously to the preparation of Intermediate 42.5: white material; ES-MS: [M+H—H$_2$O]$^+$=221; HPLC: $_B t_{Ret}$=1.47 min.

Intermediate 107.5

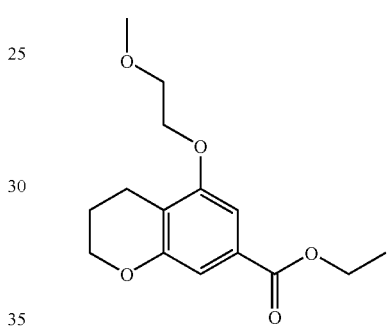

Intermediate 107.5 is synthesized by alkylation of 5-hydroxy-chroman-7-carboxylic acid ethyl ester (612.1 mg, 2.75 mmol) with 2-Methoxy-ethanol (0.26 mL, 3.3 mmol) analogously to the preparation of Intermediate 62.5: white material; ES-MS: M+H=281, HPLC: $_B t_{Ret}$=1.97 min.

Example 108

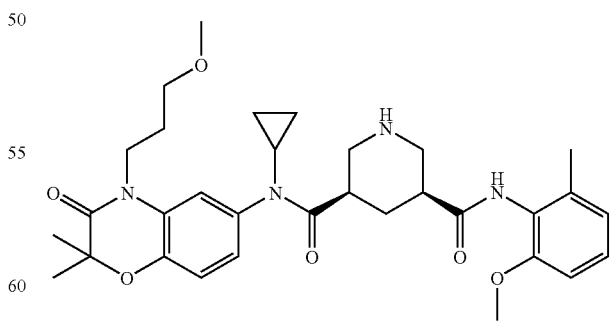

Example 108 is synthesized by deprotection of Intermediate 108.1 analogously to the preparation of Example 19: ES-MS: M+H=579: $_C t_{Ret}$=2.85 min.

Intermediate 108.1

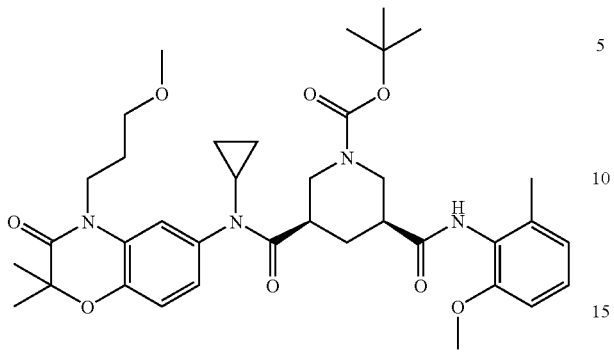

Intermediate 108.1 is synthesized by condensation of Intermediate 108.2 (100 mg, 0.179 mmol) and 2-methoxy-5-methylaniline (24.5 mg, 0.179 mmol) analogously to the preparation of Example 19.1: ES-MS: M+H=679: $_B t_{Ret}$=2.01 min.

Intermediate 108.2

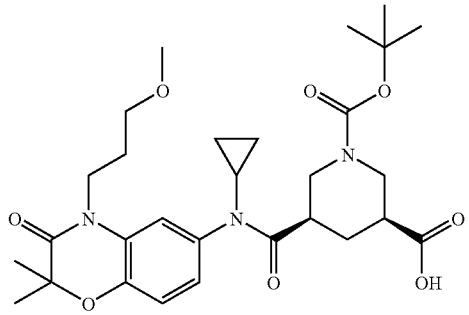

Intermediate 108.2 is synthesized by condensation of Intermediate 87.2 (609 mg, 2 mmol) and (3R,5S)-Starting material-F (24.5 mg, 0.179 mmol) analogously to the preparation of Example 19.1, followed by hydrolysis with 1N NaOHaq. ES-MS: M+H=560: $_B t_{Ret}$=1.87 min.

Example 109

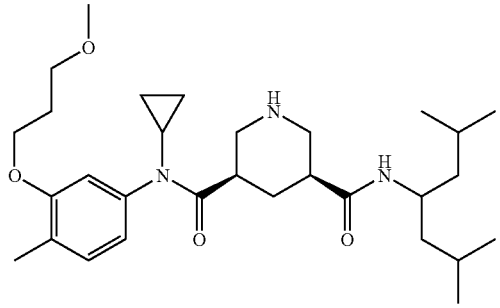

Example 109 is synthesized by deprotection of Intermediate 109.1 analogously to the preparation of Example 19: ES-MS: M+H=516: $_C t_{Ret}$=3.70 min.

Intermediate 109.1

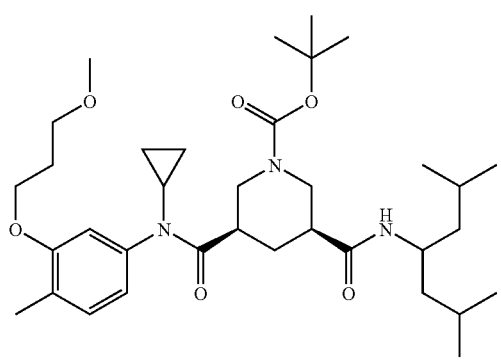

Intermediate 109.1 is synthesized by condensation of Intermediate 104.2 (72 mg, 0.181 mmol) and Intermediate 64.2 (72 mg, 0.3 mmol) analogously to the preparation of Example 19.1: ES-MS: M+H=616: $_C t_{Ret}$=2.36 min.

Example 110

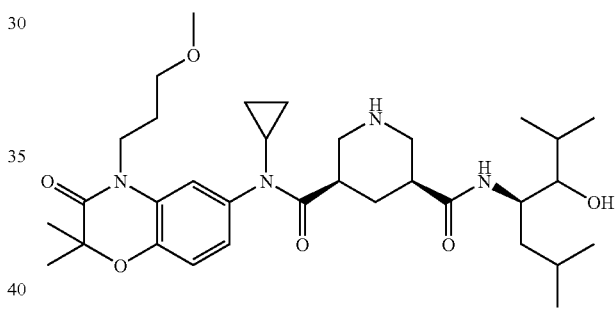

Example 110 is synthesized by deprotection of intermediate 110.1 analogously to the preparation of Example 1: ES-MS: M+H=601: $_C t_{Ret}$=2.96, 3.06 min.

Intermediate 110.1

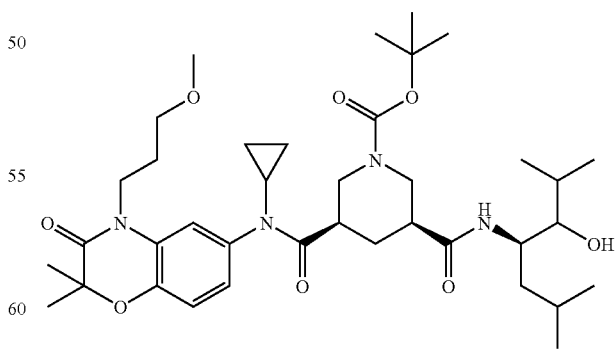

Intermediate 110.1 is synthesized by condensation of Intermediate 108.2 (156.6 mg, 0.28 mmol) and Intermediate 110.2 (56.4 mg, 0.288 mmol) analogously to the preparation of Example 39.1: ES-MS: M+H=701: $_C t_{Ret}$=4.01, 4.06 min.

Intermediate 110.2

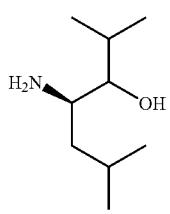

Intermediate 110.2 is synthesized by deprotection of intermediate 110.3 analogously to the preparation of Example 19: major isomer ES-MS: M+H=160: $_c t_{Ret}$=1.81 min. minor isomer ES-MS: M+H=160: $_c t_{Ret}$=1.87 min.

Intermediate 110.3

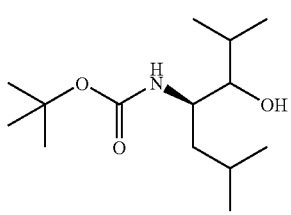

To the solution of (R)-2-tert-Butoxycarbonylamino-4-methyl-pentanoic acid methyl ester (1.762 g, 7.2 mmol, CAS 133467-01-3) in toluene (30 mL) under $N_2$ at −78° C., DIBAL (16.8 mL of 0.94 M in hexane, 15.8 mmol) is slowly added over a period of 1 h. The reaction mixture is stirred at that temperature for 30 min. MeOH (2.0 mL) is added to the reaction solution at −78° C. The resulting solution is warmed to rt. A solution of Roschelle salt (7.4 g, 26.3 mmol) in $H_2O$ (30 mL) is added. The reaction mixture is stirred at rt for 15 min and filtered through celites and extracted with $Et_2O$. The organic phase is dried over $MgSO_4$. concentareted under the reduced pressure to give the crude aldehyde (cCAS 116662-96-5).

To a solution of the crude aldehyde in toluene (30 mL) under $N_2$ at −78° C., i-PrLi (33 mL of 0.7 M in pentane, 23.1 mmol) is added. The temperature is allowed to rise to rt. The reaction mixture is stirred at rt for a few min. Then sat. $NH_4Cl$ aq. is added to the solution and extracted with EtOAc. The organic phase is dried over $Na_2SO_4$, concentareted under the reduced pressure to give the crude product. The crude product is purified by silica gel chromatography to give the desired alcohol (diastereomeric ratio=1.25/1). The two diastereomers can be separated by silica gel chromatography.

major isomer ES-MS: M+H-$^t$Bu=204: $_c t_{Ret}$=3.66 min.
minor isomer ES-MS: M+H-$^t$Bu=204: $_c t_{Ret}$=3.81 min.

Example 111

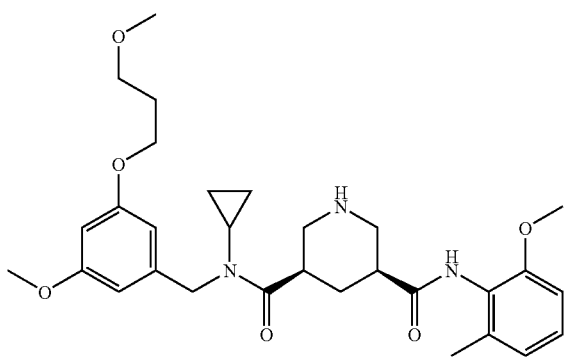

Example 111 is synthesized by deprotection of intermediate 111.1 analogously to the preparation of Example 19: ES-MS: M+H=540: $_c t_{Ret}$=2.90 min.

Intermediate 111.1

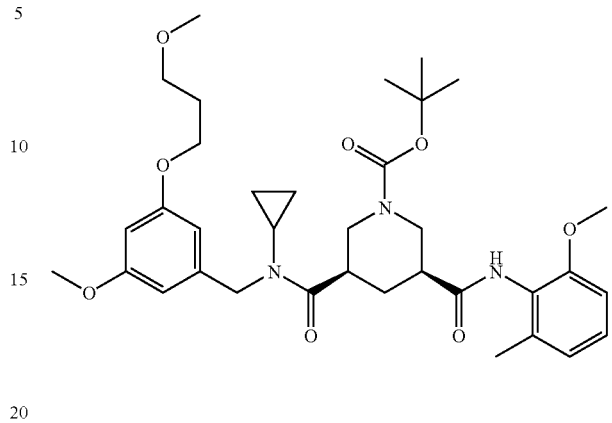

Intermediate 111.1 is synthesized by condensation of Intermediate 111.2 (60 mg, 0.15 mmol) and Intermediate 62.2 (61 mg, 0.23 mmol) analogously to the preparation of Intermediate 39.1: ES-MS: M+H=640: $_c t_{Ret}$=3.94 min.

Intermediate 111.2

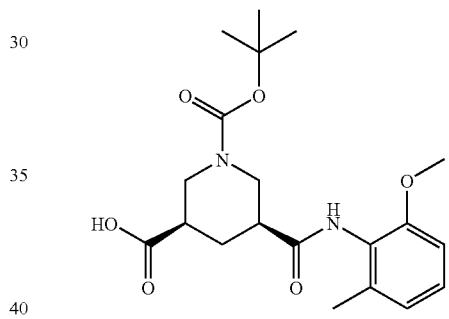

Intermediate 111.2 is synthesized by saponification of Intermediate 111.3 analogously to the preparation of Intermediate 13.2: white amorphous material; ES-MS: [M+H]$^+$=393; HPLC: $_c t_{Ret}$=2.93 min.

Intermediate 111.3

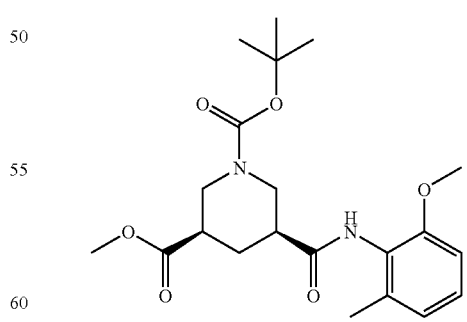

Intermediate 111.3 is synthesized by condensation of (3S, 5R)— starting material-F and 2-methoxy-5-methylaniline analogously to the preparation of Intermediate 13.3: white amorphous material; ES-MS: [M+H]$^+$=407; HPLC: $_c t_{Ret}$=3.34 min.

Example 112

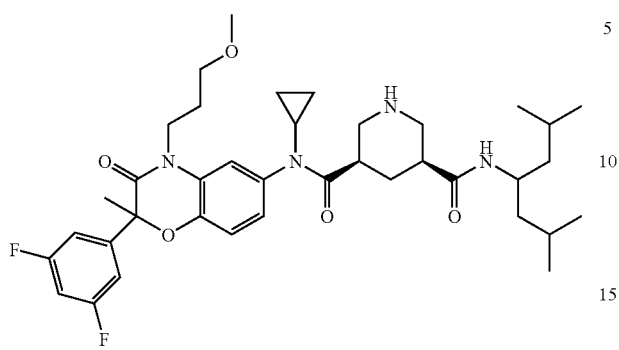

Example 112 is synthesized by deprotection of intermediate 112.1 analogously to the preparation of Example 19: ES-MS: M+H=682: $_C t_{Ret}$=4.04 min.

Intermediate 112.1

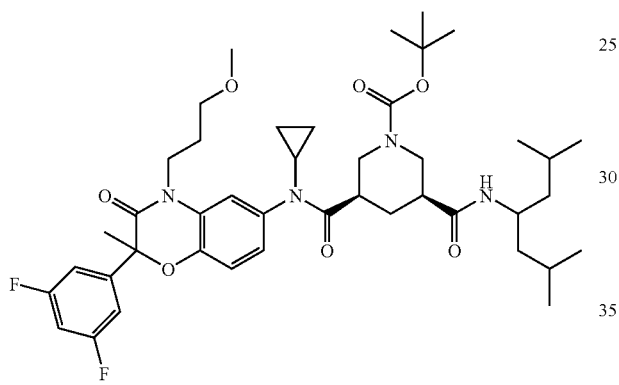

Intermediate 112.1 is synthesized by condensation of Intermediate 105.1 (22 mg, 0.055 mmol) and Intermediate 112.2 (22 mg, 0.055 mmol) analogously to the preparation of Example 19.1: ES-MS: M+H=782: $_B t_{Ret}$=2.40 min.

Intermediate 112.2

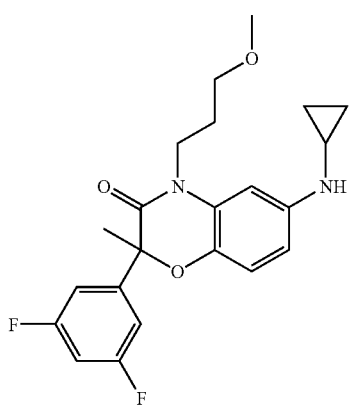

A mixture of 6-bromo-2-(3,5-difluorophenyl)-4-(3-methoxypropyl)-2-methyl-4H-benzo[1,4]oxazin-3-one (144 mg, 0.338 mmol), cyclopropylamine (38 mg, 0.666 mmol), Pd$_2$(dba)$_3$ (15 mg, 0.016 mmol), NaO$^t$Bu (39 mg, 0.406 mmol), and biphenyl-2-yl-di-tert-butylphosphane mg, 0.0503 mmol) in toluene (1.6 mL) is heated under N$_2$ at 80° C. for 3.5 h. After filtration through a celite pad, the filtrate is concentrated. The residue is purified by silica gel column chromatography to afford intermediate 112.2: ES-MS: M+H=402: $_B t_{Ret}$=2.08 min.

Example 113

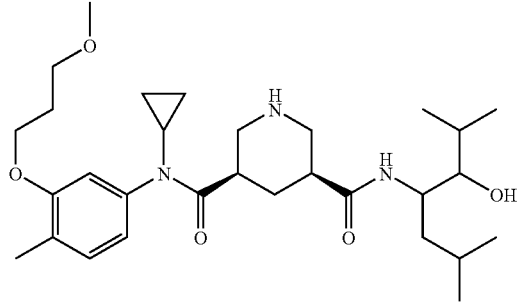

Example 113 is synthesized by deprotection of Intermediate 113.1 analogously to the preparation of Example 1: ES-MS: M+H=532: $_C t_{Ret}$=3.11, 3.19 min.

Intermediate 113.1

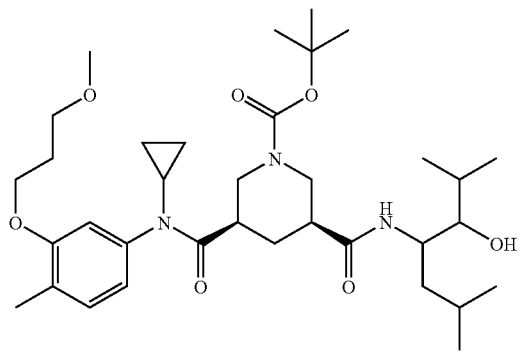

Intermediate 113.1 is synthesized by condensation of Intermediate 113.2 (117 mg, 0.237 mmol) and Intermediate 110.2 (116 mg, 0.594 mmol) analogously to the preparation of Example 39.1: ES-MS: M+H=632: $_B t_{Ret}$=2.14 min.

Intermediate 113.2

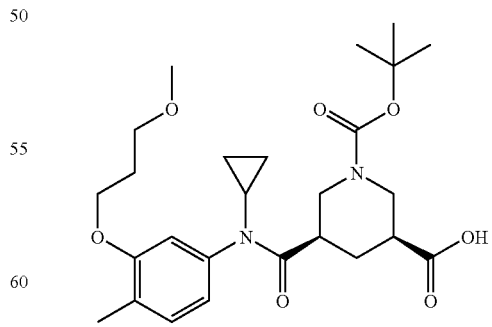

Intermediate 113.2 is synthesized by saponification of Intermediate 113.3 analogously to the preparation of Intermediate 13.2: white amorphous material; ES-MS: [M+H]$^+$=491; HPLC: $_B t_{Ret}$=1.95 min.

Intermediate 113.3

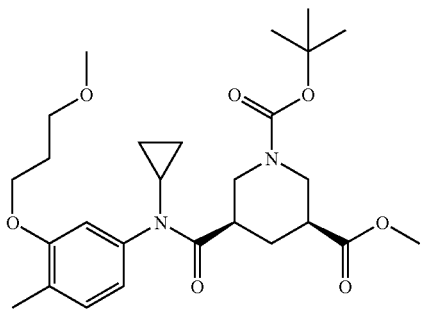

Intermediate 113.3 is synthesized by condensation of Intermediate 64.2 (234 mg, 0.993 mmol) and (3R,5S)-Starting material-F (200 mg, 0.696 mmol) analogously to the preparation of Example 19.1: ES-MS: M+H=505: $_B t_{Ret}$=2.13 min.

Example 114

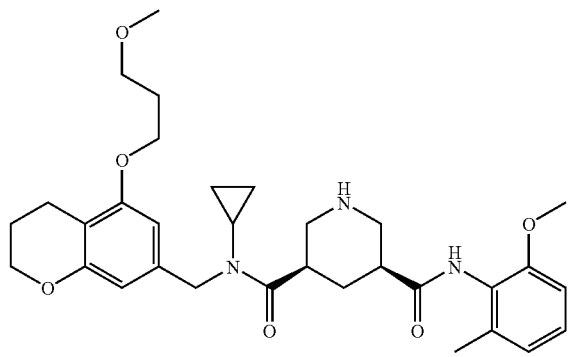

Example 114 is synthesized by deprotection of intermediate 114.1 analogously to the preparation of Example 19: ES-MS: M+H=566: $_C t_{Ret}$=3.08 min.

Intermediate 114.1

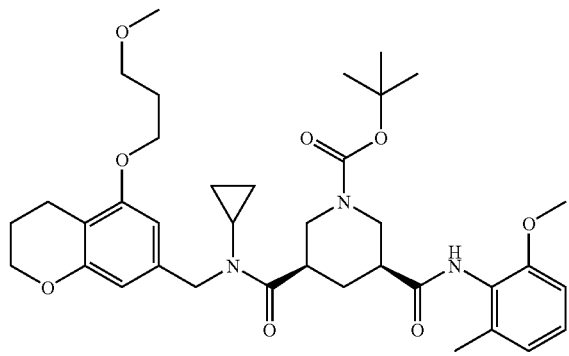

Intermediate 114.1 is synthesized by condensation of Intermediate 114.2 (150 mg, 0.38 mmol) and Intermediate 95.2 (160 mg, 0.55 mmol) analogously to the preparation of Intermediate 39.1: ES-MS: M+H=606: $_C t_{Ret}$=4.16 min.

Example 115

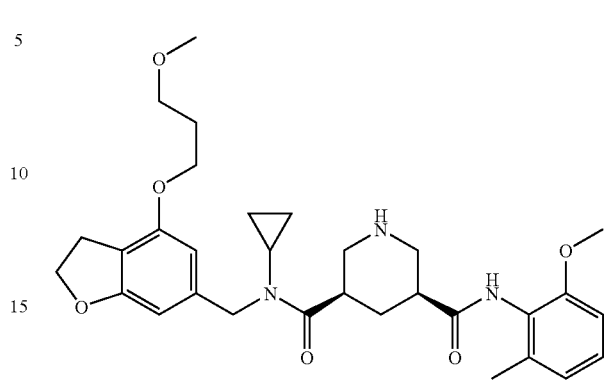

Example 115 is synthesized by deprotection of intermediate 115.1 analogously to the preparation of Example 19: ES-MS: M+H=552: $_C t_{Ret}$=2.94 min.

Intermediate 115.1

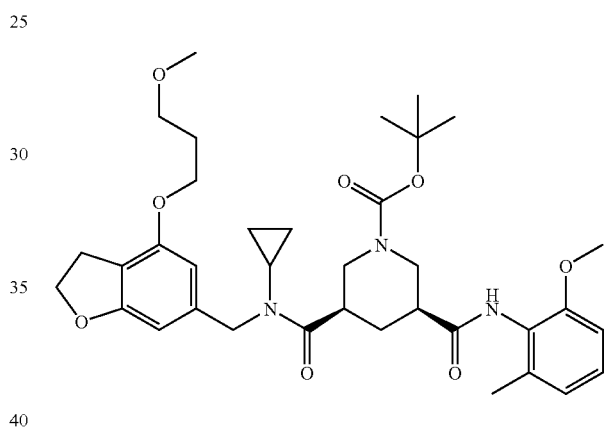

Intermediate 115.1 is synthesized by condensation of Intermediate 111.2 (85 mg, 0.22 mmol) and Intermediate 92.2 (63 mg, 0.226 mmol) analogously to the preparation of Intermediate 39.1: ES-MS: M+H=652: $_C t_{Ret}$=3.97 min.

Example 116

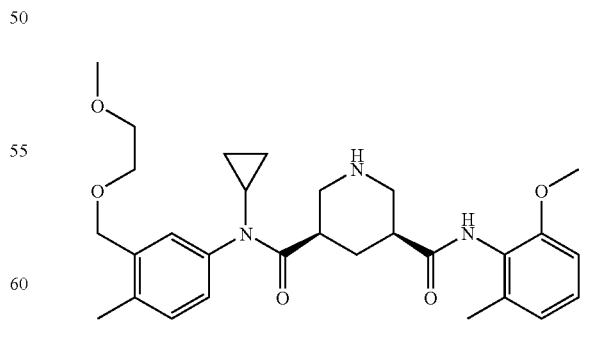

Example 116 is synthesized by deprotection of intermediate 116.1 analogously to the preparation of Example 19: ES-MS: M+H=510: $_C t_{Ret}$=2.97 min.

Intermediate 116.1

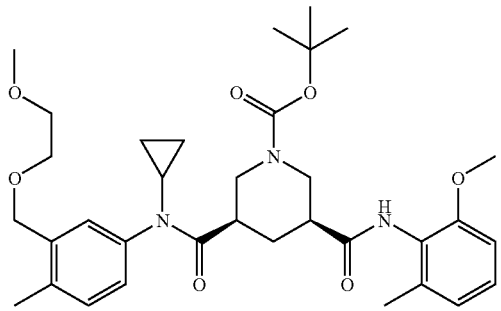

Intermediate 116.1 is synthesized by condensation of Intermediate 111.2 (78 mg, 0.197 mmol) and Intermediate 64.2 (118 mg, 0.50 mmol) analogously to the preparation of Intermediate 19.1: ES-MS: M+H=610: $c t_{Ret}$=4.11 min.

Example 117

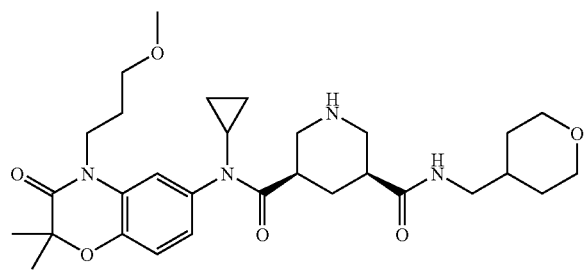

Example 117 is synthesized by deprotection of intermediate 117.1 analogously to the preparation of Example 19: ES-MS: M+H=557: $c t_{Ret}$=2.47 min.

Intermediate 117.1

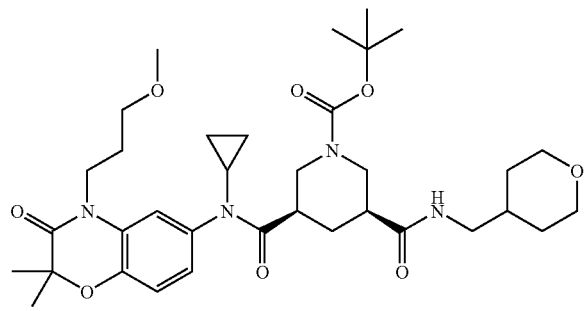

Intermediate 117.1 is synthesized by condensation of Intermediate 108.2 (50 mg, 0.09 mmol) with 4-Aminomethyltetrahydropyran (21 mg, 0.18 mmol) analogously to the preparation of intermediate 32.3: white amorphous material, ES-MS: M+H=657: $c t_{Ret}$=3.43 min.

Example 118

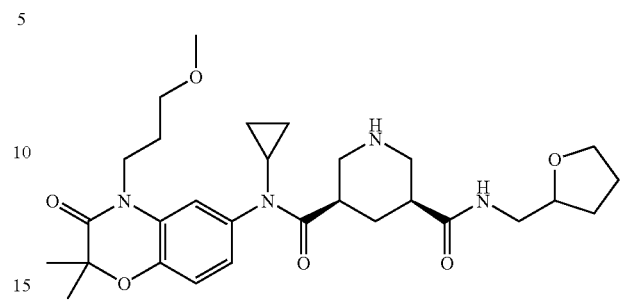

Intermediate 108.2 (50 mg, 0.09 mmol) is coupled with 4-Aminomethyltetrahydropyran (21 mg, 0.18 mmol) analogously to the preparation of intermediate 32.3. The resulting coupling product is treated with 4N HCl-1,4-dioxane followed by concentration to afford the title compound. ES-MS: M+H=543: $c t_{Ret}$=2.51 min.

Example 119

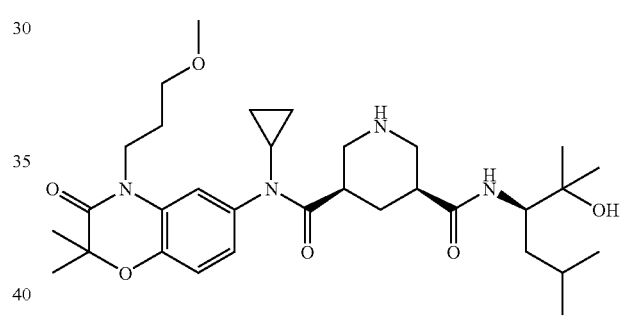

Example 119 is synthesized by deprotection of intermediate 119.1 analogously to the preparation of Example 1: ES-MS: M+H=586: $c t_{Ret}$=2.70 min.

Intermediate 119.1

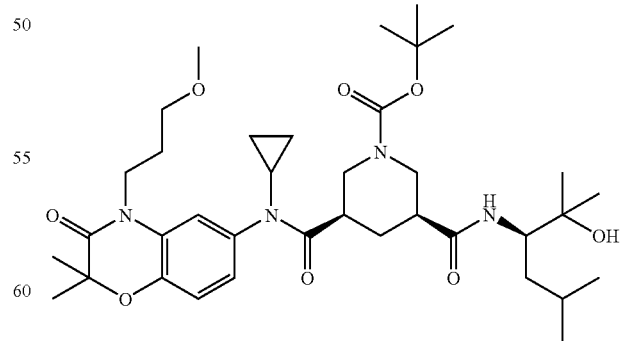

Intermediate 119.1 is synthesized by condensation of Intermediate 108.2 (100 mg, 0.178 mmol) with Intermediate 119.2 (32 mg, 0.178 mmol) analogously to the preparation of intermediate 32.3. White amorphous material, ES-MS: M+H=687: $c t_{Ret}$=3.79 min.

Intermediate 119.2

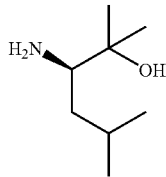

Intermediate 119.2 is synthesized by saponification of intermediate 119.3 analogously to the preparation of Intermediate 13.2: ES-MS: M+H=146: $_Bt_{Ret}$=1.20 min.

Intermediate 119.3

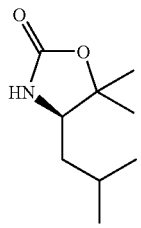

To a solution of (R)-2-tert-Butoxycarbonylamino-4-methyl-pentanoic acid methyl ester (1.762 g, 7.2 mmol, CAS 133467-01-3) in THF (20 mL) under $N_2$ at −78° C., MeLi (4.3 mL of 3.0 M in diethoxyethane, 13.04 mmol) is added. After stirring at rt for 30 min. sat. $NH_4Cl$ aq. is added. The reaction mixture is extracted with EtOAc. The organic phase is dried over $Na_2SO_4$. and concentared under the reduced pressure to afford the crude product. The crude product is purified by silica gel chromatography to give Intermediate 119.3 (699.6 mg). ES-MS: M+H=172: $_Bt_{Ret}$=1.55 min.

Example 120

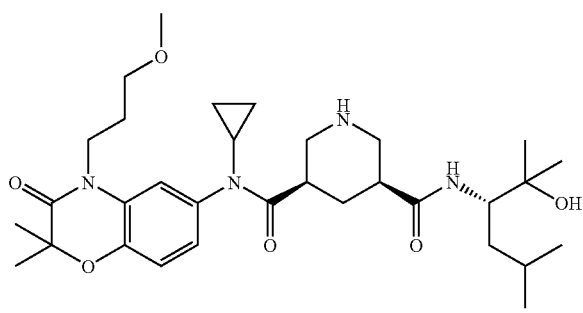

Example 120 is synthesized by deprotection of intermediate 120.1 analogously to the preparation of Example 1: ES-MS: M+H=587: $_Ct_{Ret}$=2.87 min.

Intermediate 120.1

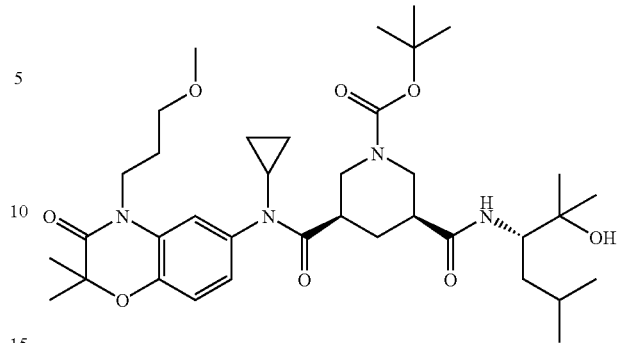

Intermediate 120.1 is synthesized by condensation of Intermediate 108.2 (100 mg, 0.178 mmol) with Intermediate 120.2 (46 mg, 0.253 mmol) analogously to the preparation of intermediate 32.3: White amorphous materials, ES-MS: M+H=687: $_Ct_{Ret}$=3.74 min.

Intermediate 120.2

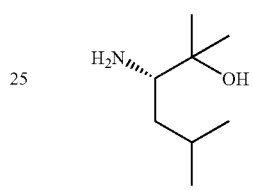

Intermediate 120.2 is synthesized by saponification of intermediate 120.3 analogously to the preparation of Intermediate 13.2: ES-MS: M+H=146: $_Bt_{Ret}$=1.23 min.

Intermediate 120.3

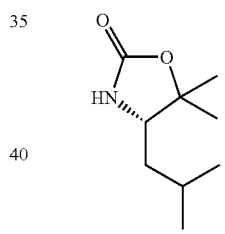

To a solution of (S)-2-tert-Butoxycarbonylamino-4-methyl-pentanoic acid methyl ester (543.0 mg, 2.213 mmol, CAS 63096-02-6) in THF (15 mL) under $N_2$ at −78° C., MeLi (4.3 mL of 3.0 M in diethoxyethane, 13.04 mmol) is added. After stirring at rt overnight, sat.$NH_4Cl$aq. is added. The reaction mixture is extracted with EtOAc. The organic phase is dried over $Na_2SO_4$. and concentared under the reduced pressure to afford the crude product. The crude product is purified by silica gel chromatography to give intermediate 120.3 (243.6 mg). ES-MS: M+H=172: $_Bt_{Ret}$=1.55 min.

Example 121

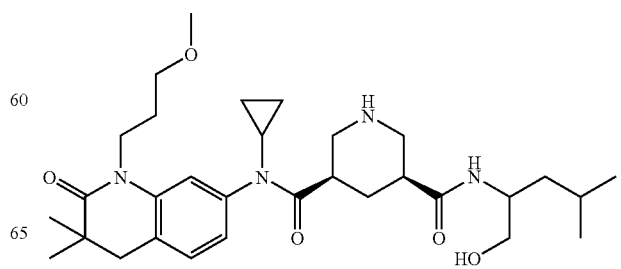

Example 121 is synthesized by deprotection of intermediate 121.1 analogously to the preparation of Example 1: ES-MS: M+H=557: $_Ct_{Ret}$=2.60, 2.76 min.

Intermediate 121.1

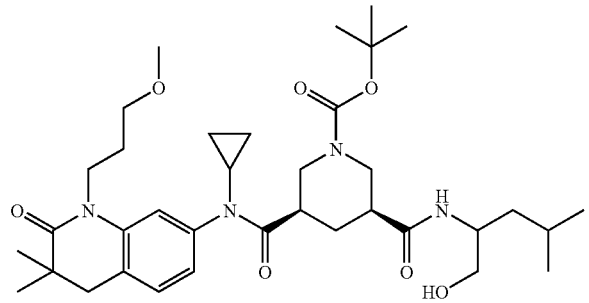

Intermediate 121.1 is synthesized by condensation of Intermediate 33.2 (112 mg, 0.3 mmol) and Intermediate 121.2 (91 mg, 0.3 mmol) analogously to the preparation of Example 19.1: ES-MS: M+H=657: $_Bt_{Ret}$=1.90 min Intermediate 121.2

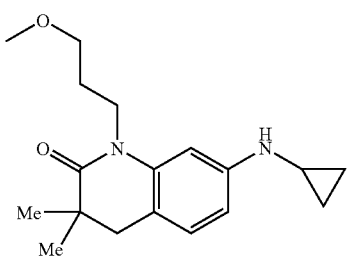

At 0° C., a solution of Intermediate 121.3 (2.62 g, 11.4 mmol) and 1-methoxy-3-(p-toluenesulfonyloxy)propane (3.31 g, 13.5 mmol) in DMF (40 mL) is treated with KI (0.57 g, 3.43 mmol). After adding 60% of NaH (0.55 g, 13.5 mmol) over 5 min, the mixture is stirred at 0° C. for 30 min, warmed to 60° C., stirred for 13 h, and treated with H₂O (200 mL). After extraction of the mixture with EtOAc (2×30 mL) and Et₂O (2×30 mL), the combined org. layer is washed with H₂O (2×25 mL), dried (Na₂SO₄), and evaporated. SiO₂ flash chromatography (120 g, hexane/EtOAc 3:2) gives Intermediate 121.2 as a light yellow solid. R$_f$ (hexane/EtOAc 3:2) 0.47. ¹H-NMR (400 MHz, CDCl₃) 0.49-0.53 (m, 2 H), 0.70-0.76 (m, 2 H), 1.12 (s), 1.86-1.95 (m, 2 H), 2.38-2.44 (m, 1 H), 2.61 (s), 3.32 (s), 3.44 (t, J=6.0), 3.93 (t, J=9.0), 4.17 (br. s), 6.45 (dd, J=9.0, 0.4), 6.52 (d, J=0.4), 6.92 (d, J=9.0). ¹³C-NMR (100 MHz, CDCl₃) 175.6 (s), 148.2 (s), 140.0 (s), 128.9 (d), 114.4 (s), 107.1 (d), 100.0 (d), 70.5 (t), 58.6 (q), 40.3 (t), 39.5 (t), 37.5 (s), 27.7 (t), 25.4 (d), 24.5 (2q), 7.4 (2t).

Intermediate 121.3

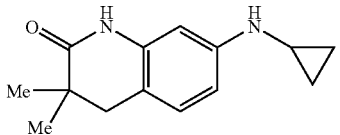

At room temperature, a methanolic suspension (23 mL) of 3,3,7-triamino-3,4-dihydro-1H-quinolin-2-one (Y. Matsumoto, R. Tsuzuki, A. Matsuhisa, T. Yoden, Y. Yamagiwa, I. Yanagisawa, T. Shibanuma, H. Nohira, *Bioorg. Med. Chem.* 2000, 8, 393.) (2.85 g, 15.0 mmol) is treated with AcOH (6.0 mL) and [(1-ethoxycycopropyl)-oxy]trimethylsilane (3.0 mL, 15.0 mmol), warmed to 70° C. and stirred for 2 h under reflux (observing that the mixture changed from a suspension to a homogeneous solution). At the same temperature, to this solution is added dropwise a methanolic solution (5.0 mL) of NaBH₃CN (1.02 g, 16.2 mmol) over 5 min, and the resulting mixture is stirred at 70° C. under reflux for 2 h, and treated with CH₂Cl₂ (100 mL) and 5 N NaOH (50 mL). After separation of the both layers, the aq. layer is extracted with CH₂Cl₂ (3×30 mL). The combined org. layer is washed with brine (40 mL), dried (Na₂SO₄), and evaporated. SiO₂ flash chromatography (130 g, hexane/EtOAc 1:1) gives Intermediate 121.3 as light yellow solid. R$_f$ (hexane/EtOAc 1:1) 0.48. ¹H-NMR (400 MHz, CDCl₃) 0.47-0.52 (m, 2 H), 0.69-0.75 (m, 2 H), 1.20 (s), 2.38-2.43 (m, 1 H), 2.66 (s), 4.14 (br. s), 6.19 (d, J=0.4), 6.40 (dd, J=9.0, 0.4), 6.91 (d, J=9.0), 7.71 (br. s). ¹³C-NMR (100 MHz, CDCl₃) 176.9 (s), 148.3 (s), 137.6 (s), 129.0 (d), 112.4 (s), 107.9 (d), 99.4 (d), 39.6 (t), 37.7 (s), 25.3 (d), 24.5 (2q), 7.4 (2t).

Example 122

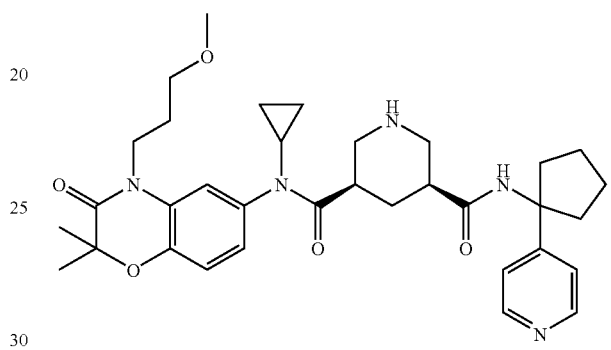

Example 122 is synthesized by deprotection of intermediate 122.1 analogously to the preparation of Example 19: ES-MS: M+H=604: $_Ct_{Ret}$=2.45 min.

Intermediate 122.1

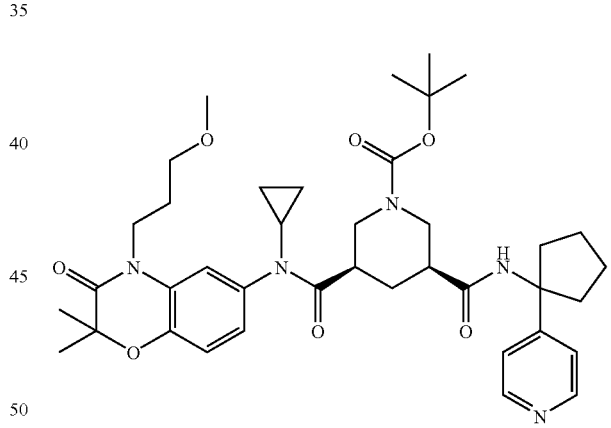

Intermediate 122.1 is synthesized by condensation of Intermediate 108.2 (50 mg, 0.089 mmol) with Intermediate 122.2 (32 mg, 0.14 mmol) analogously to the preparation of intermediate 32.3. White amorphous material, ES-MS: M+H=704: $_Ct_{Ret}$=3.21 min.

Intermediate 122.2

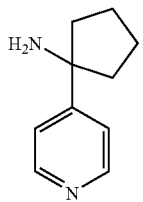

Intermediate 122.2 is synthesized by deprotection of Intermediate 122.3 (580 mg, 2.21 mmol) analogously to the preparation of Intermediate 103.2: ES-MS: M+H=163: $_c t_{Ret}$=0.43 min.

Intermediate 122.3

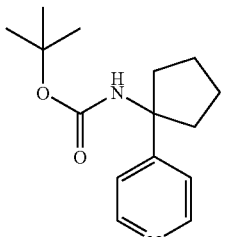

Intermediate 122.3 is synthesized by rearrangement of Intermediate 122.4 (600 mg, 3.15 mmol) analogously to the preparation of Intermediate 103.3: ES-MS: M+H=263: $_c t_{Ret}$=2.14 min.

Intermediate 122.4

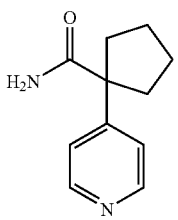

A mixture of Intermediate 122.5 (900 mg, 5.23 mmol) and potassium trimethylsilanolate (1.5 g, 10.4 mmol) in toluene (50 mL) is stirred at 100° C. After 16 h, the reaction mixture is cooled down at room temperature and diluted with H$_2$O (100 mL), and extracted with EtOAc (200 mL). The organic phase is successively washed with H$_2$O and brine, then dried over Na$_2$SO$_4$. The solution is filtered and the solvent is evaporated in vacuo to give Intermediate 122.4: White solid material: ES-MS=191: $_c t_{Ret}$=1.15 min.

Intermediate 122.5

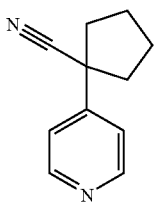

A mixture of cyclopentanecarbonitrile (800 mg, 8.4 mmol), 4-chloropyridine hydrochloride (1.9 g, 12.6 mmol) and KHMDS (5 g, 25 mmol) in THF (20 mL) is stirred at 70° C. After 16 h, the reaction mixture is cooled down to room temperature and poured into H$_2$O and extracted with Et$_2$O (500 mL). The organic extracts are successively washed with 5% aqueous NaHCO$_3$, H$_2$O, and brine, then dried over Na$_2$SO$_4$ and concentrated in vacuo. The residue is purified by SiO$_2$ column chromatography to give Intermediate 122.5: Colorless oil: ES-MS=173: $_c t_{Ret}$=1.45 min.

Example 123

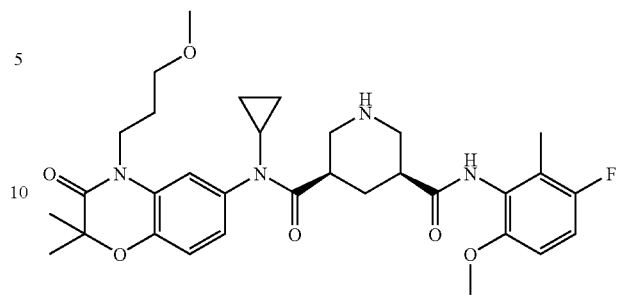

A mixture of Intermediate 123.1 (40 mg, 0.058 mmol) in 4N HCl-1,4-dioxane (1 mL) is stirred at room temperature for 1 h, and concentrated to afford example 123: ES-MS: M+H=596: $_c t_{Ret}$=2.91 min.

Intermediate 123.1

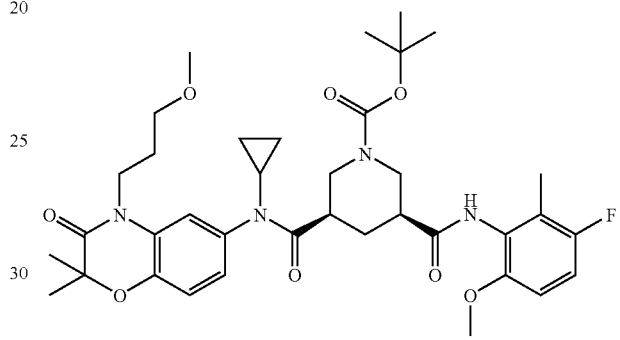

Intermediate 123.1 is synthesized by condensation of intermediate 108.2 (35 mg, 0.063 mmol) and intermediate 123.2 (13 mg, 0.068 mmol) analogously to the preparation of Example 19.1: ES-MS: M+H=696: $_c t_{Ret}$=3.95 min.

Intermediate 123.2

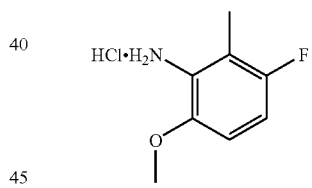

A mixture of (2-(N-tert-butoxycarbonylamino)-4-fluoro-3-methylanisole (1.442 g, EP0409484A2) in 4 N HCl-1,4-dioxane is stirred at room temperature for 1 h, and filtered to afford Intermediate 123.2 as a white solid.

Example 124

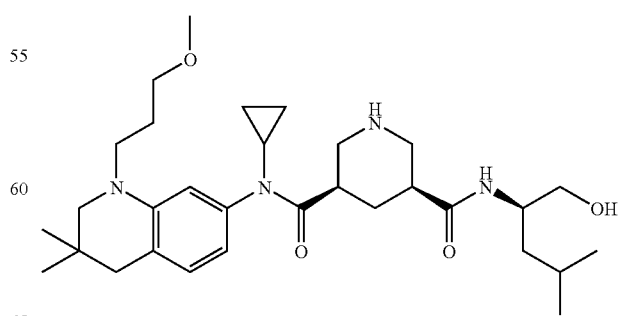

To a mixture of intermediate 124.1 (72 mg, 0.132 mmol) and (R)-(−)-leucinol (17 mg, 0.145 mmol) in DMF (1 mL) are added EDCI.HCl (28 mg, 0.146 mmol) and HOAt (20 mg, 0.146 mmol). After stirring at room temperature for 1.5 h, the mixture is diluted with EtOAc, washed with aq. KHSO₄, water, sat. aq. NaHCO₃, water, and brine. The mixture is dried over Na₂SO₄, filtered, and concentrated. The residue is purified by silica gel column chromatography to afford the Boc protected titled compound (107 mg, 0.167 mmol), which is treated with TMSOTf and 2,6-lutidine for deprotection of the Boc analogously to the preparation of Example 1: ES-MS: M+H=542: $_C t_{Ret}$=3.12 min.

Intermediate 124.1

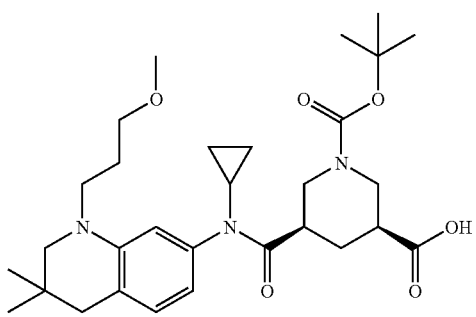

Intermediate 124.1 is synthesized by condensation of intermediate 124.2 (85 mg, 0.295 mmol) and (3R,5S)-starting material-F (85 mg, 0.295 mmol) analogously to the preparation of Example 19.1, followed by hydrolysis analogously to the preparation of Example 13.2: ES-MS: M+H= - - -: $_C t_{Ret}$= - - - min.

Intermediate 124.2

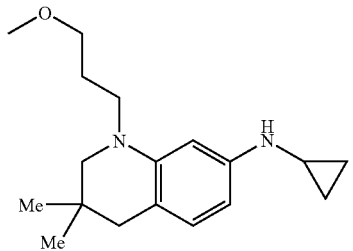

At room temperature, a solution of Intermediate 121.2 (412.0 mg, 1.36 mmol) in THF (4.1 mL) is treated with 1 M BH₃-THF solution (13.6 mL, 13.6 mmol), heated to 60° C. and stirred for 6 h under reflux. After cooling to room temperature, the mixture is treated with MeOH (16 mL), stirred for 30 min at the same temperature, and evaporated. After pouring the residue into H₂O (50 mL), the aqueous phase is treated with 5 N NaOH to adjust its pH 9~10, and extracted with EtOAc (4×15 mL). The combined org. layer is washed with brine (10 mL), dried (Na₂SO₄), and evaporated. SiO₂ flash chromatography (25 g, CH₂Cl₂/EtOAc 15:1) gives Intermediate 124.2 as a light yellow oil. $R_f$(CH₂Cl₂/EtOAc 15:1) 0.67. ¹H-NMR (400 MHz, CDCl₃) 0.47-0.51 (m, 2 H), 0.63-0.69 (m, 2 H), 0.96 (s), 1.81-1.89 (m, 2 H), 2.38-2.44 (m, 1 H), 2.39 (s), 2.85 (s), 3.35 (t, J=6.0), 3.37 (s), 3.46 (t, J=9.0), 4.00 (br. s), 6.07-6.10 (m, 2 H), 6.74 (d, J=9.0). ¹³C-NMR (100 MHz, CDCl₃) 148.1 (s), 144.7 (s), 130.1 (d), 111.4 (s), 101.1 (d), 95.3 (d), 70.4 (t), 61.3 (t), 58.6 (q), 48.3 (t), 41.3 (t), 28.4 (s), 27.1 (t), 26.6 (2q), 25.5 (d), 7.3 (2t).

Example 125

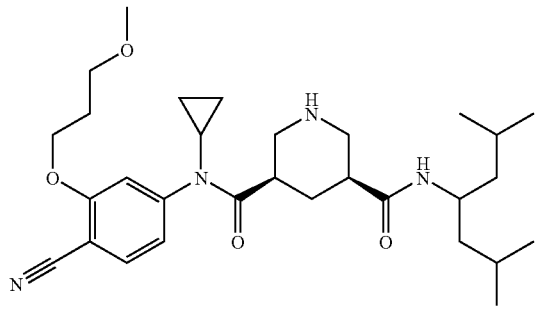

To a solution of intermediate 125.3 (50 mg, 0.125 mmol) in THF (1.0 mL), Et₃N (0.02 mL, 0.138 mmol) and 2,2,2-trichloro-1,1-dimethylethyl chloroformate (33 mg, 0.138 mmol) are added at 0° C. After stirring for 1 h at the same temperature, the resulting precipitate is filtered off and the filtrate is concentrated. The residue is dissolved in THF (1 mL), intermediate 125.1 (31 mg, 0.125 mmol) and MgBr₂ (36 mg, 0.138 mmol) are added at room temperature. After stirring for 16 h, the reaction is quenched with H₂O and resulting mixture is extracted with AcOEt, washed with sat.KHSO₄aq and brine. The organic layer is dried (MgSO₄), concentrated and purified by RP-HPLC followed by deprotection of the Boc group with 4 N HCl in dioxane to afford example 125: white amorphous material, ES-MS: M+H=527; HPLC: $_C t_{Ret}$=3.44 min.

Intermediate 125.1

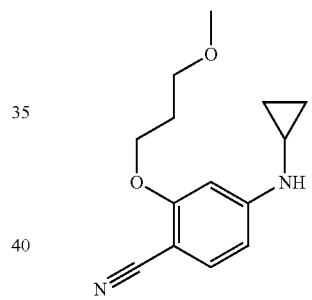

A mixture of Intermediate 125.2 (4.20 g, 15.5 mmol), cyclopropylamine (639 mg, 11.1 mmol), Pd₂(dba)₃ (91 mg, 0.10 mmol), NaOtBu (528 mg, 5.5 mmol) and racemic BINAP (186 mg, 0.30 mmol) in toluene (3 mL) is heated under N₂ at 90° C. for 6 h. After adding H₂O at RT, the reaction mixture is extracted with EtOAc. The combined organic phases are washed with H₂O and dried (MgSO₄). Concentration under reduced pressure and silica gel flash chromatography give Intermediate 152.1: White amorphous material; ES-MS: M+H=247; HPLC: $_A t_{Ret}$=3.57 min.

Intermediate 125.2

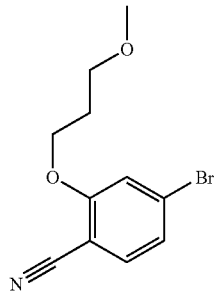

A mixture of 4-bromo-2-fluorobenzonitrile (5.00 g, 25.0 mmol), 3-methoxypropan-1-ol (3.30 g, 38.0 mmol) and K₂CO₃ (3.50 g, 38 mmol) in DMF (30 mL) is heated at 80° C. for 24 h. After adding H₂O at rt, the reaction mixture is extracted with EtOAc. The combined organic phases are washed twice with H₂O, and dried (MgSO₄). Concentration under reduced pressure and silica gel flash chromatography give Intermediate 125.2. White solids; ES-MS: M+H=270; HPLC: $_A t_{Ret}$=2.40 min.

Intermediate 125.3

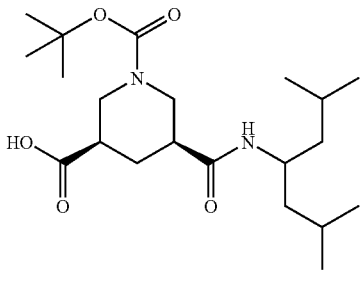

recemic

To a solution of 1-Isobutyl-3-methyl-butylamine hydrochloride (1.08 g, 6 mmol) and triethylamine (1.73 mL, 12 mmol) in THF (50 mL) is added 2,4-Dioxo-3-oxa-7-azabicyclo[3.3.1]nonane-7-carboxylic acid tert-butyl ester (1.02 g, 4 mmol) at 0° C. and the mixture is stirred for 1.5 h. The mixture is diluted with EtOAc, washed with 1 N HClaq, water and brine. The organic layer is dried over MgSO₄ and concentrated under vacuum to give Intermediate 125.3: white amorphous material, ES-MS: M+H=399: $_B t_{Ret}$=2.01 min.

Example 126

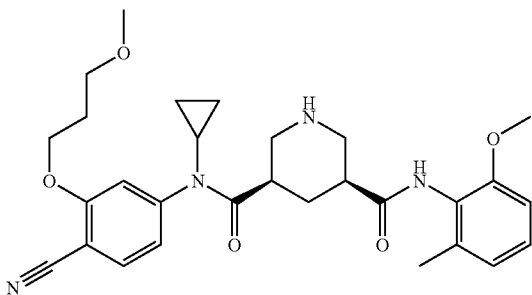

Example 126 is synthesized by condensation of and intermediate 111.2 (64 mg, 0.163 mmol) and intermediate 125.1 (40 mg, 0.163 mmol) analogously to the preparation of example 125: white amorphous material, ES-MS: M+H=521: $_C t_{Ret}$=2.76 min.

Example 127

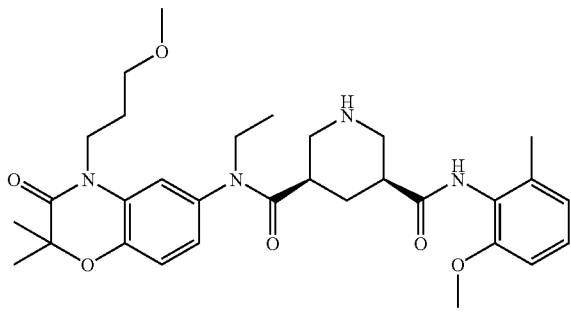

A mixture of Intermediate 127.1 (81 mg, 0.058 mmol) in 4 N HCl-1,4-dioxane (1 mL) is stirred at room temperature for 1 h, and concentrated to afford example 127: ES-MS: M+H=566: $_C t_{Ret}$=2.80 min.

Intermediate 127.1

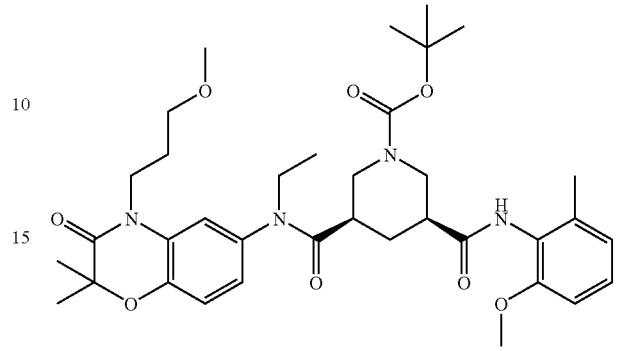

Intermediate 127.1 is synthesized by condensation of intermediate 111.2 (58 mg, 0.148 mmol) and intermediate 127.2 (44 mg, 0.15 mmol) analogously to the preparation of Example 19.1: ES-MS: M+H=666: $_C t_{Ret}$=3.89 min.

Intermediate 127.2

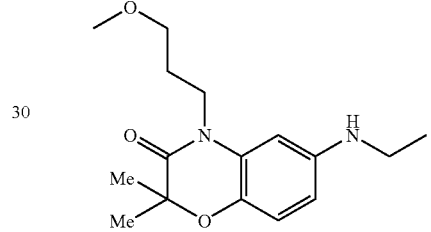

At room temperature, a methanolic solution (20 mL) of Intermediate 127.3 (0.95 g, 2.23 mmol) is treated with 10% Pd/C (0.10 g), stirred for 2 h under H₂, treated with N₂ stream, and filtered on a celite pad. After washing the cake with MeOH for several times, the combined filtrate is evaporated to give Intermediate 127.2 as brown solid. R$_f$(hexane/EtOAc 1:1) 0.56. ¹H-NMR (270 MHz, CDCl₃) 1.26 (t, J=9.0), 1.45 (s), 1.88-1.95 (m, 2 H), 3.13 (q, J=9.0), 3.34 (s), 3.45 (t, J=6.0), 3.94 (t, J=6.0), 6.24 (dd, J=9.0, 0.4), 6.35 (d, J=0.4), 6.78 (d, J=9.0). ¹³C-NMR (67.5 MHz, CDCl₃) 169.0 (s), 144.0 (s), 135.0 (s), 129.6 (s), 118.0 (d), 107.5 (d), 99.7 (d), 77.5 (s), 69.9 (t), 58.7 (q), 39.2 (t), 39.1 (t), 27.7 (t), 23.6 (2q), 15.0 (q).

Intermediate 127.3

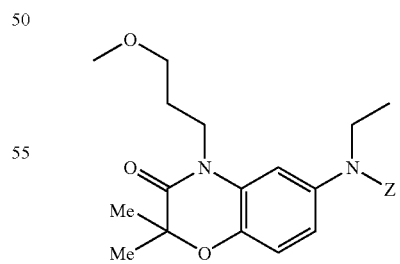

At 0° C., a solution of Intermediate 127.4 (1.06 g, 2.67 mmol) and iodoethane (1.1 mL, 13.8 mmol) in DMF (15 mL) is treated with 60% of NaH (0.13 g, 3.25 mmol) over 5 min. The mixture is stirred at 0° C. for 20 min, warmed to room temperature, stirred for 14 h, and poured into H₂O (100 mL). After extraction of the mixture with EtOAc (2×15 mL) and Et₂O (2×15 mL), the combined org. layer is washed with H₂O (20 mL), dried (Na₂SO₄), and evaporated. SiO₂ flash chromatography (30 g, hexane/EtOAc 4:3) gives Intermediate 127.3 as a yellow oil. $R_f$(hexane/EtOAc 3:2) 0.38. $^1$H-NMR (400 MHz, CDCl$_3$) 1.17 (t, J=9.0), 1.48 (s), 1.82-1.90 (m, 2 H), 3.27 (s), 3.38 (t, J=3.5), 3.69 (q, J=9.0), 3.94 (t, J=3.5), 5.15 (s), 6.76-6.90 (m, 3 H), 7.16-7.35 (m, 5 H).
Intermediate 127.4

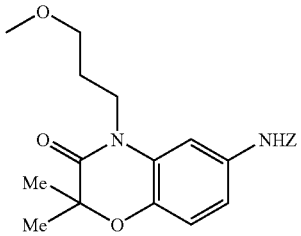

At room temperature, a solution of 2,2-dimethyl-6-nitro-4H-benzo[1,4]oxazin-3-one (*Bioorganic & Medicinal Chemistry* 2002, 10, 2663-2669.) (2.01 g, 6.83 mmol) in EtOAc (20 mL) is treated with tin(II) chloride dihydrate (5.48 g, 24.3 mmol), heated to 80° C., stirred for 6 h under reflux, cooled to room temperature, and treated with 5 N NaOH (12 mL). After filtration to remove off the resulting precipitate, the cake is washed with small amount of EtOAc. At ambient temperature, the combined filtrate is treated benzyloxycarbonyl chloride (1.5 mL, 10.5 mmol), heated to 60° C., stirred for 14 h at the same temperature, and cooled to room temperature. After separation of the both layers, the aqueous layer is extracted with EtOAc (2×5 mL), and the combined org. layer is washed with sat. aq. NaHCO$_3$ solution (2×5 mL), dried (Na$_2$SO$_4$), and evaporated. The residue is suspended in 15 mL of Et$_2$O, and the resulting precipitate is collected by filtration, and washed with Et$_2$O for several times to give Intermediate 127.4 as a white solid. $R_f$(hexane/EtOAc 3:2) 0.38. $^1$H-NMR (400 MHz, CDCl$_3$) 1.46 (s), 1.88-1.96 (m, 2 H), 3.30 (s), 3.40 (t, J=6.0), 3.96 (t, J=6.0), 5.19 (s), 6.64 (br. s), 6.83-6.89 (m, 2 H), 7.20-7.26 (m, 1 H), 7.31-7.42 (m, 5 H).

Example 128

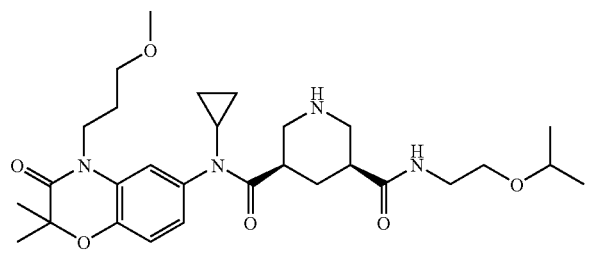

Example 128 is synthesized by deprotection of intermediate 128.1 analogously to the preparation of Example 19: ES-MS: M+H=545: $ct_{Ret}$=2.64 min.
Intermediate 128.1

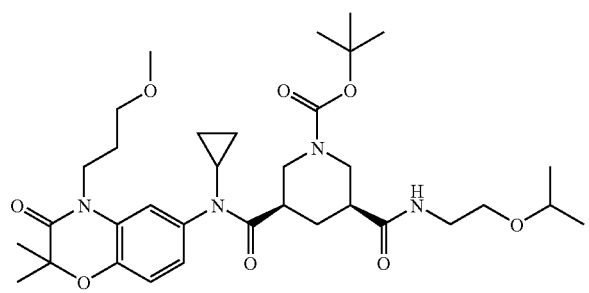

Intermediate 128.1 is synthesized by condensation of Intermediate 108.2 (128 mg, 0.23 mmol) with 2-Isopropoxy-ethylamine (31 µL, 0.25 mmol) analogously to the preparation of intermediate 32.3. White amorphous material, ES-MS: M+H=645: $ct_{Ret}$=3.67 min.

Example 129

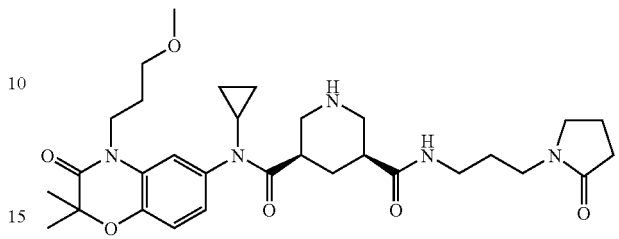

Example 129 is synthesized by deprotection of intermediate 129.1 analogously to the preparation of Example 19: ES-MS: M+H=584: $ct_{Ret}$=2.37 min.
Intermediate 129.1

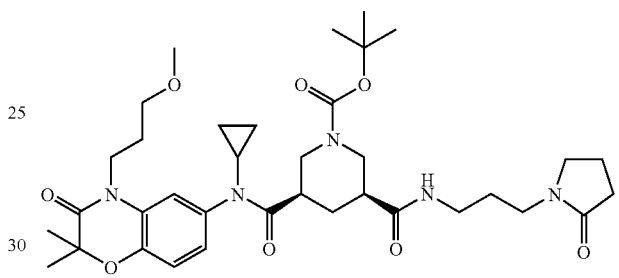

Intermediate 129.1 is synthesized by condensation of Intermediate 108.2 (104 mg, 0.19 mmol) with 1-(3-Amino-propyl)-pyrrolidin-2-one (29 µL, 0.20 mmol) analogously to the preparation of intermediate 32.3: White amorphous material, ES-MS: M+H=684: $ct_{Ret}$=3.26 min.

Example 130

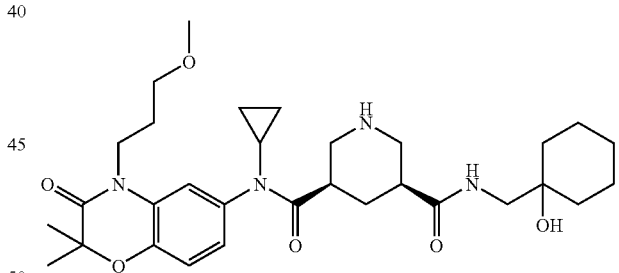

Example 130 is synthesized by deprotection of intermediate 130.1 analogously to the preparation of Example 19: ES-MS: M+H=571: $ct_{Ret}$=2.68 min.
Intermediate 130.1

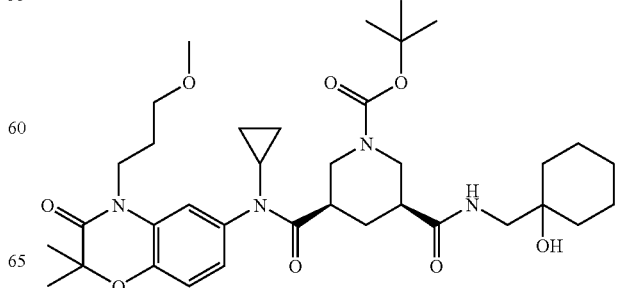

Intermediate 130.1 is synthesized by condensation of Intermediate 108.2 (104 mg, 0.18 mmol) with 1-Aminomethyl-cyclohexanol (34 mg, 0.20 mmol) analogously to the preparation of intermediate 32.3: White amorphous material, ES-MS: M+H=671: $c_{t_{Ret}}$=3.61 min.

Example 131

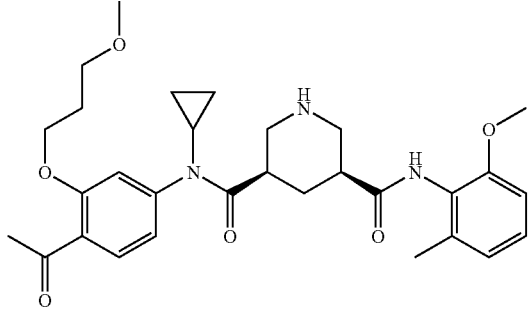

Example 131 is synthesized by deprotection of intermediate 131.1 analogously to the preparation of Example 19: ES-MS: M+H=538: $c_{t_{Ret}}$=2.72 min.

Intermediate 131.1

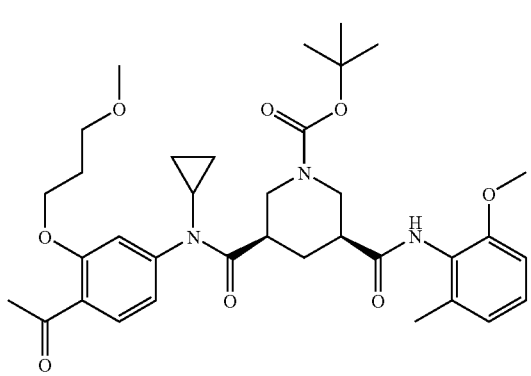

Intermediate 131.1 is synthesized by condensation of intermediate 111.2 (64 mg, 0.163 mmol) and Intermediate 102.1 (64 mg, 0.163 mmol) analogously to the preparation of example 125: White amorphous material, ES-MS: M+H=638: $c_{t_{Ret}}$=3.74 min.

Example 132

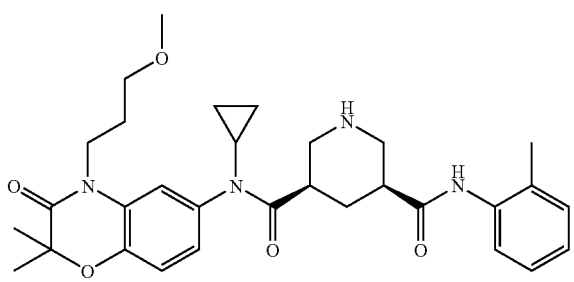

Example 132 is synthesized by deprotection of intermediate 132.1 analogously to the preparation of Example 19: ES-MS: M+H=549: $c_{t_{Ret}}$=2.84 min.

Intermediate 132.1

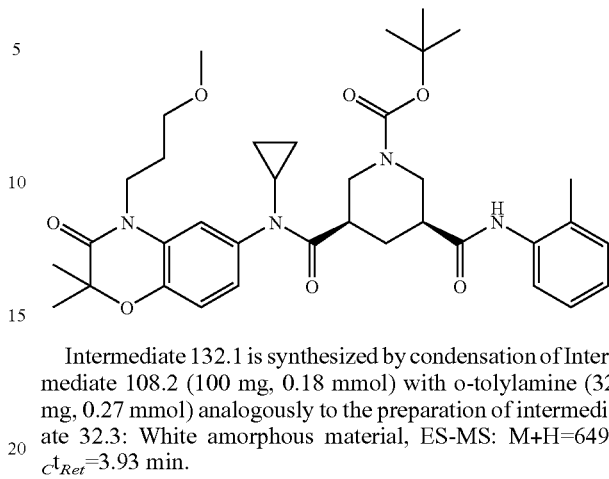

Intermediate 132.1 is synthesized by condensation of Intermediate 108.2 (100 mg, 0.18 mmol) with o-tolylamine (32 mg, 0.27 mmol) analogously to the preparation of intermediate 32.3: White amorphous material, ES-MS: M+H=649: $c_{t_{Ret}}$=3.93 min.

Example 133

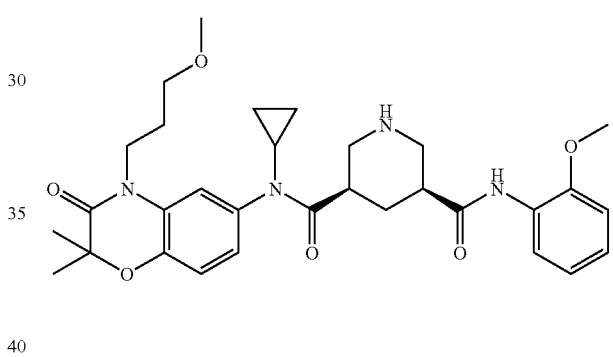

Example 133 is synthesized by deprotection of intermediate 133.1 analogously to the preparation of Example 19: ES-MS: M+H=565: $c_{t_{Ret}}$=2.88 min.

Intermediate 133.1


Intermediate 133.1 is synthesized by condensation of Intermediate 108.2 (100 mg, 0.18 mmol) with 2-Methoxy-phenylamine (33 mg, 0.27 mmol) analogously to the preparation of intermediate 32.3: White amorphous material, ES-MS: M+H=665: $c_{t_{Ret}}$=4.00 min.

Example 134

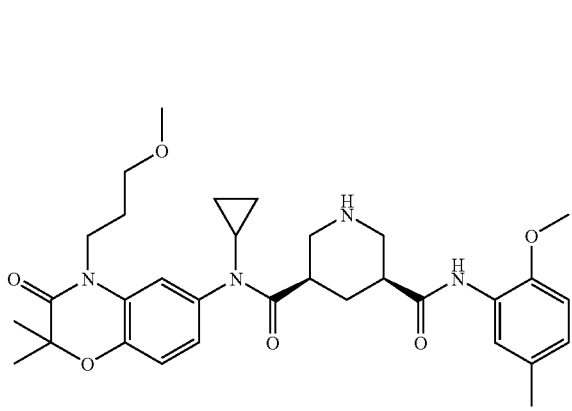

Example 134 is synthesized by deprotection of intermediate 134.1 analogously to the preparation of Example 19: ES-MS: M+H=579: $_c t_{Ret}$=3.05 min.

Intermediate 134.1

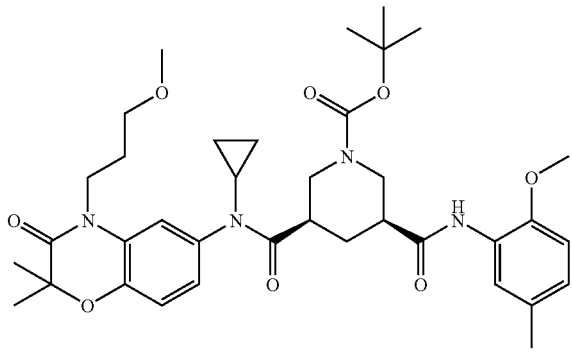

Intermediate 134.1 is synthesized by condensation of Intermediate 108.2 (100 mg, 0.18 mmol) with 2-Methoxy-5-methyl-phenylamine (37 mg, 0.27 mmol) analogously to the preparation of intermediate 32.3: White amorphous material, ES-MS: M+H=679: $_c t_{Ret}$=4.16 min.

Example 135

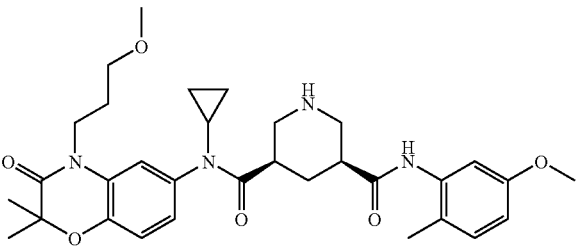

Example 135 is synthesized by deprotection of intermediate 135.1 analogously to the preparation of Example 19: ES-MS: M+H=579: $_c t_{Ret}$=2.91 min.

Intermediate 135.1

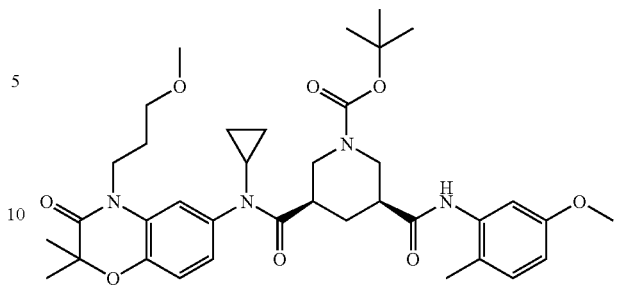

Intermediate 135.1 is synthesized by condensation of Intermediate 108.2 (100 mg, 0.18 mmol) with 5-Methoxy-2-methyl-phenylamine (37 mg, 0.27 mmol) analogously to the preparation of intermediate 32.3: White amorphous material, ES-MS: M+H=679: $_c t_{Ret}$=3.95 min.

Example 136

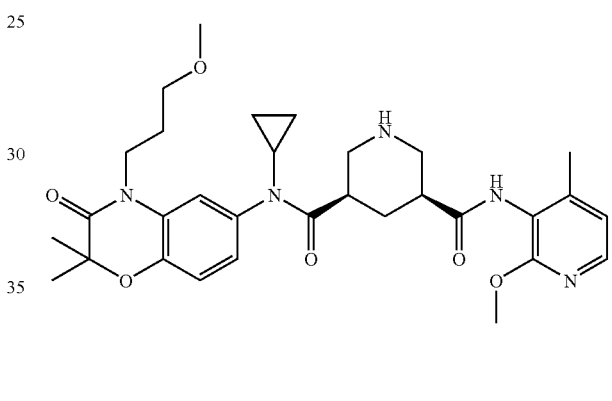

Example 136 is synthesized by deprotection of intermediate 136.1 analogously to the preparation of Example 19: ES-MS: M+H=580: $_c t_{Ret}$=2.60 min.

Intermediate 136.1

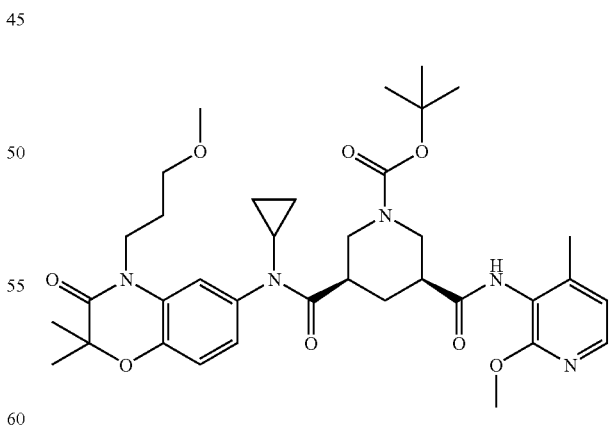

Intermediate 136.1 is synthesized by condensation of Intermediate 108.2 (100 mg, 0.18 mmol) with 2-methoxy-4-methylpyridin-3-ylamine (48 mg, 0.20 mmol) analogously to the preparation of intermediate 32.3: White amorphous material, ES-MS: M+H=680: $_c t_{Ret}$=3.62 min.

Example 137

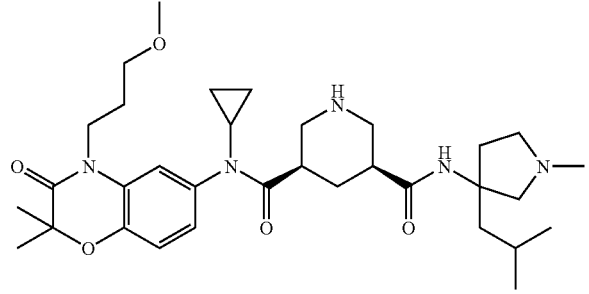

Example 137 is synthesized by deprotection of intermediate 137.1 analogously to the preparation of Example 19: ES-MS: M+H=598: $ct_{Ret}$=2.52, 2.67 min.

Intermediate 137.1

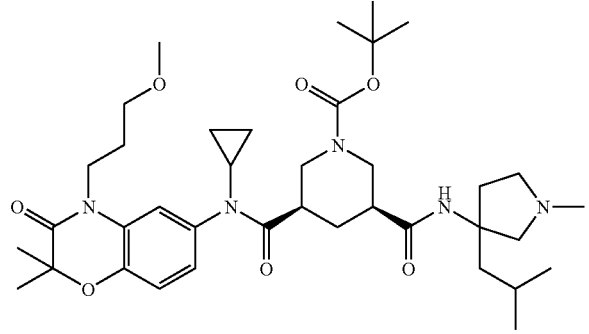

Intermediate 137.1 is synthesized by condensation of Intermediate 108.2 (80 mg, 0.14 mmol) with Intermediate 137.2 (39 mg, 0.172 mmol) analogously to the preparation of intermediate 32.3: White amorphous material, ES-MS: M+H=698: $ct_{Ret}$=3.20, 3.33 min.

Intermediate 137.2

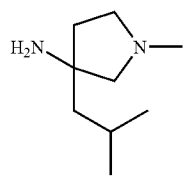

A mixture of Intermediate 137.3 (200 mg, 0.83 mmol) and LiAlH$_4$ (96 mg, 2.48 mmol) in THF (8 mL) is stirred at 60° C. After 2 h, the reaction mixture is cooled down to 0° C., then Na$_2$SO$_4$ 10H$_2$O is added to the reaction mixture and stirred for 0.5 h. The suspension is filtered, HCl in MeOH is added to the solution, then the solvent is evaporated in vacuo to give Intermediate 137.2: Colorless oil: ES-MS=157: $ct_{Ret}$=0.62 min.

Intermediate 137.3

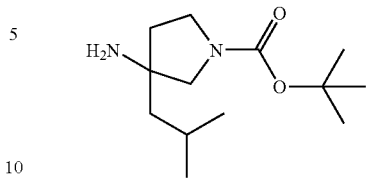

A mixture of Intermediate 137.4 (1.3 g, 3.36 mmol) and TBAF (1 M in THF, 6.7 mmol) in THF (6 mL) is stirred at 60° C. After 4 h, the reaction mixture is cooled down to room temperature, and quenched with H$_2$O (100 mL) and extracted with EtOAc (100 mL) twice. The combined organic phase is successively washed with 5% aqueous NaHCO$_3$, H$_2$O, and brine, then dried over Na$_2$SO$_4$ and concentrated under reduced pressure. Purification by SiO$_2$ column chromatography affords Intermediate 137.3: Colorless oil: ES-MS=243: $ct_{Ret}$=2.29 min.

Intermediate 137.4

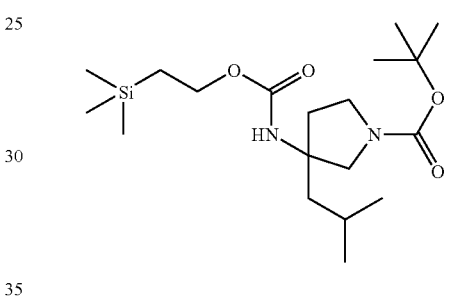

A mixture of Intermediate 137.5 (1 g, 3.7 mmol) and [Bis(trifluoroacetoxy)iodo]benzene (2.4 g, 5.6 mmol) in 2-trimethylsilyl ethanol (10 mL) is stirred at 90° C. After 0.5 h, pyridine (1 mL) is added to the mixture and the mixture is stirred at the same temperature. After additional 1.5 h, the reaction-mixture is cooled down to room temperature and diluted with H$_2$O (50 mL) and extracted with EtOAc (100 mL). The organic phase is successively washed with 5% aqueous KHSO$_4$, 5% aqueous NaHCO$_3$, H$_2$O, and brine, then dried over Na$_2$SO$_4$ and concentrated in vacuo. Purification by SiO$_2$ column chromatography gives Intermediate 137.4: Colorless oil: ES-MS=387: $ct_{Ret}$=4.79 min.

Intermediate 137.5

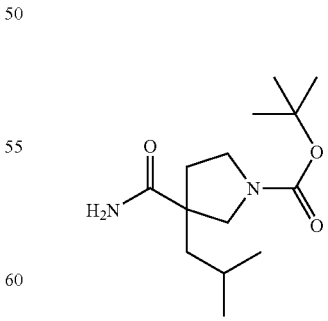

Intermediate 137.5 is synthesized by the reaction of intermediate 137.6 with KOH analogously to the preparation of Intermediate 103.4: ES-MS: M+H=271: $ct_{Ret}$=2.91 min.

Intermediate 137.6

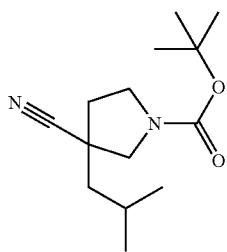

To a solution of 3-cyanopyrrolidine-1-carboxylic acid tert-butyl ester (1 g, 5.1 mmol) in THF (25 mL) is added LDA solution (2M in THF, 3.8 mmol) at −78° C. After stirring for 1 h at −78° C., to the solution is added isobutyl iodide (1.8 g, 10 mmol) at −78° C., then the mixture is stirred at the same temperature. After 2 h, the reaction mixture is quenched with 5% aqueous $KHSO_4$ (50 mL) and extracted with $Et_2O$ (100 mL). The organic phase is successively washed with 5% $KHSO_4$aq, 5% $NaHCO_3$aq, $H_2O$, and brine, then dried over $Na_2SO_4$ and concentrated under reduced pressure. Purification by $SiO_2$ column chromatography affords Intermediate 137.6: Colorless oil: ES-MS: M+H=253: $_Ct_{Ret}$=3.75 min.

Example 138

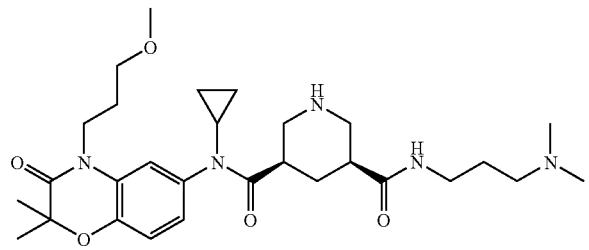

Example 138 is synthesized by deprotection of intermediate 138.1 analogously to the preparation of Example 19: ES-MS: M+H=544: $_Bt_{Ret}$=1.39 min.

Intermediate 138.1

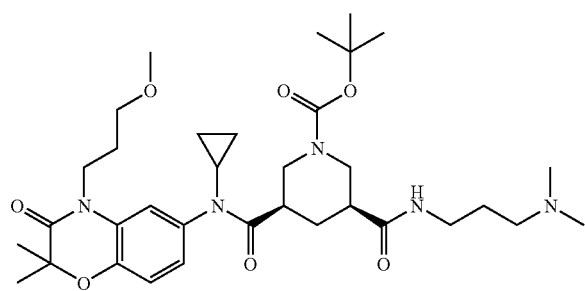

Intermediate 138.1 is synthesized by condensation of Intermediate 108.2 (100 mg, 0.179 mmol) with N*1*,N*1*-Dimethyl-propane-1,3-diamine (22 mg, 0.214 mmol) analogously to the preparation of intermediate 32.3: White amorphous material, ES-MS: M+H=644: $_Bt_{Ret}$=1.65 min.

Example 139

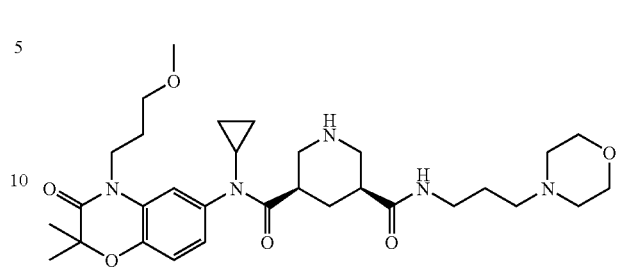

Example 139 is synthesized by deprotection of intermediate 139.1 analogously to the preparation of Example 19: ES-MS: M+H=586: $_Bt_{Ret}$=1.41 min.

Intermediate 139.1

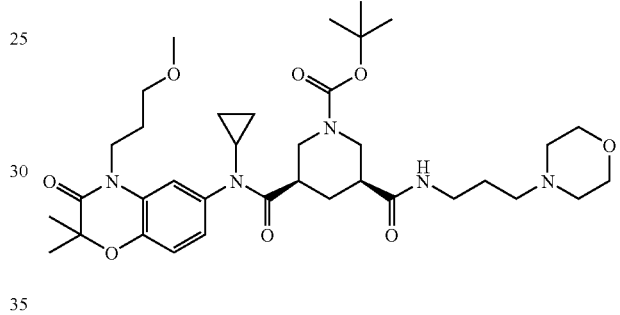

Intermediate 139.1 is synthesized by condensation of Intermediate 108.2 (100 mg, 0.179 mmol) with 3-Morpholin-4-yl-propylamine (31 mg, 0.214 mmol) analogously to the preparation of intermediate 32.3: White amorphous material, ES-MS: M+H=686: $_Bt_{Ret}$=1.86 min.

Example 140

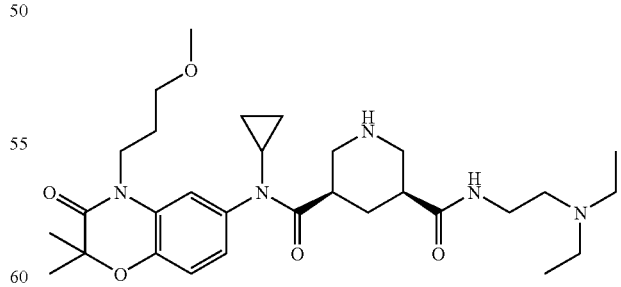

Example 140 is synthesized by deprotection of intermediate 140.1 analogously to the preparation of Example 19: ES-MS: M+H=558: $_Bt_{Ret}$=1.40 min.

Intermediate 140.1

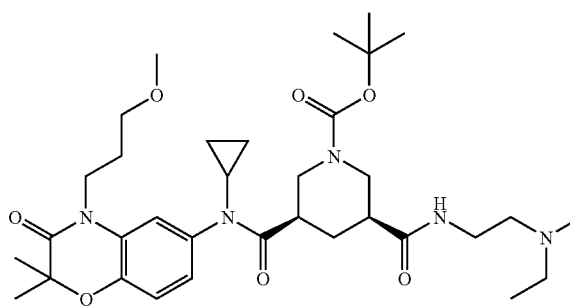

Intermediate 140.1 is synthesized by condensation of Intermediate 108.2 (100 mg, 0.179 mmol) with N*1*,N*1*-Diethyl-ethane-1,2-diamine (25 mg, 0.214 mmol) analogously to the preparation of intermediate 32.3: White amorphous material, ES-MS: M+H=658: $_B t_{Ret}$=1.68 min.

Example 141

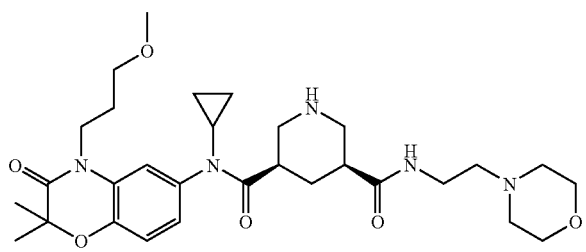

Example 141 is synthesized by deprotection of intermediate 141.1 analogously to the preparation of Example 19: ES-MS: M+H=572: $_B t_{Ret}$=1.39 min.

Intermediate 141.1

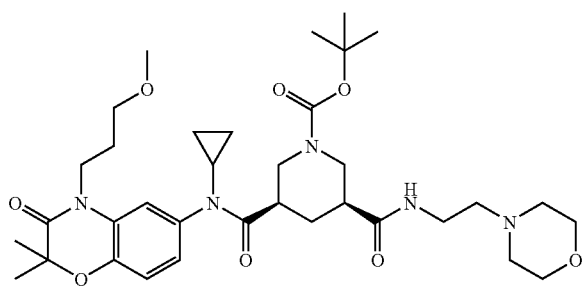

Intermediate 141.1 is synthesized by condensation of Intermediate 108.2 (100 mg, 0.179 mmol) with 2-Morpholin-4-yl-ethylamine (28 mg, 0.214 mmol) analogously to the preparation of intermediate 32.3: White amorphous material, ES-MS: M+H=672: $_B t_{Ret}$=1.66 min.

Example 142

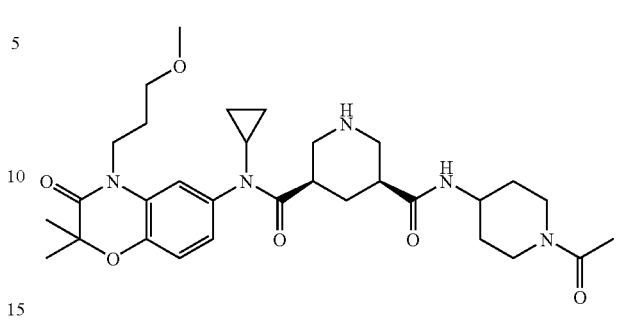

Example 142 is synthesized by deprotection of intermediate 142.1 analogously to the preparation of Example 19: ES-MS: M+H=584: $_C t_{Ret}$=2.34 min.

Intermediate 142.1

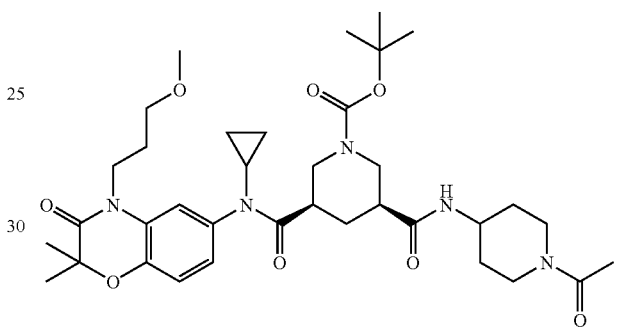

Intermediate 142.1 is synthesized by condensation of Intermediate 108.2 (78 mg, 0.14 mmol) with intermediate 142.2 (27 mg, 0.15 mmol) analogously to the preparation of intermediate 32.3: White amorphous material, ES-MS: M+H=684: $_C t_{Ret}$=3.23 min.

Intermediate 142.2

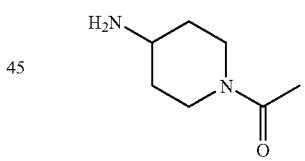

Intermediate 142.2 is synthesized by deprotection of Intermediate 142.3 analogously to the preparation of example 19.

Intermediate 142.3

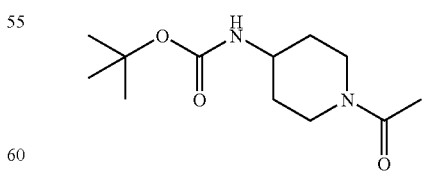

To a solution of 4-(N-Boc-amino)-piperidine (524.4 mg, 2.62 mmol) in pyridine (3 mL) under N₂ at rt, acetyl chloride (279 µL, 3.93 mmol) is added at 0° C. The reaction mixture is stirred at room temperature for 1 h. After adding 1N HCl at 0° C., the mixture is extracted with EtOAc. The combined organic phases are washed with 1 N HCl and brine and dried over Na₂SO₄. Concentrated under reduced pressure affords Intermediate 142.3: White amorphous material, ES-MS: M+H=243: $_B$t$_{Ret}$=1.46 min.

Example 143

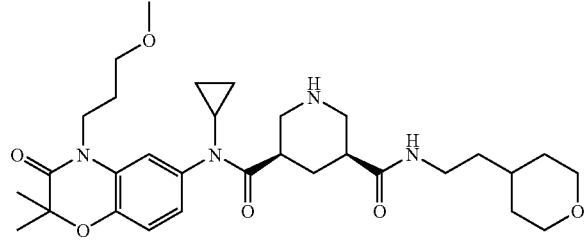

Example 143 is synthesized by deprotection of intermediate 143.1 analogously to the preparation of Example 19: ES-MS: M+H=571: $_C$t$_{Ret}$=2.57 min.

Intermediate 143.1

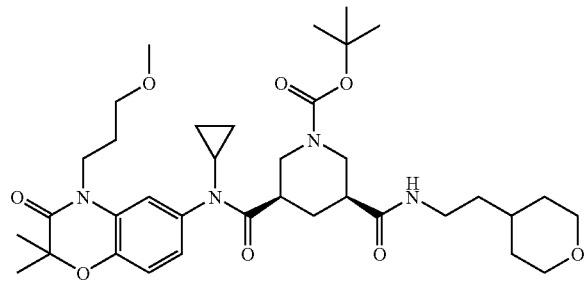

Intermediate 143.1 is synthesized by condensation of Intermediate 108.2 (123 mg, 0.22 mmol) with 2-(Tetrahydro-pyran-4-yl)-ethylamine (31 mg, 0.24 mmol) analogously to the preparation of intermediate 32.3: White amorphous material, ES-MS: M+H=671: $_C$t$_{Ret}$=3.53 min.

Example 144

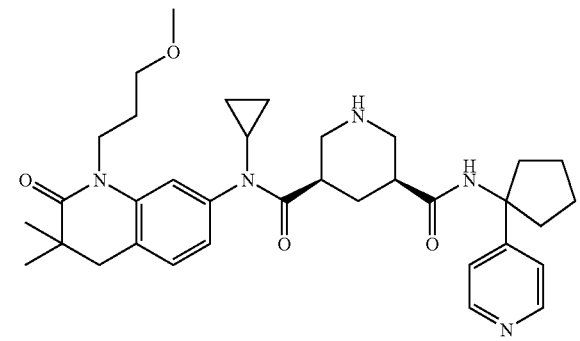

Example 144 is synthesized by deprotection of intermediate 144.1 analogously to the preparation of Example 19: ES-MS: M+H=602: $_C$t$_{Ret}$=2.48 min.

Intermediate 144.1

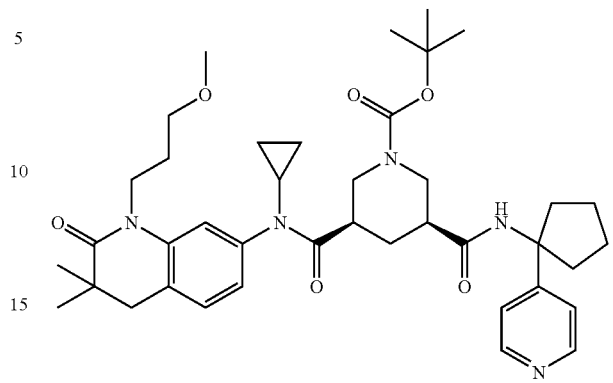

Intermediate 144.1 is synthesized by condensation of Intermediate 144.2 (100 mg, 0.17 mmol) with intermediate 122.2 (63 mg, 0.27 mmol) analogously to the preparation of intermediate 32.3: ES-MS: M+H=702: $_C$t$_{Ret}$=3.19 min.

Intermediate 144.2

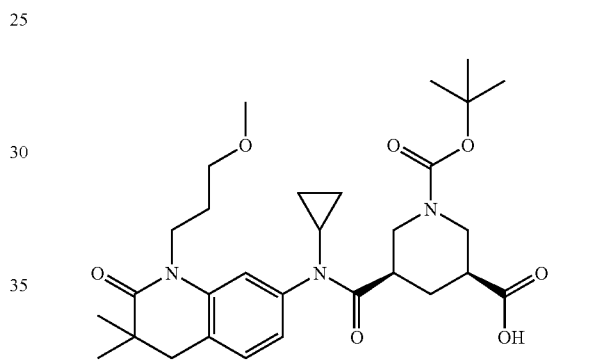

Intermediate 144.2 is synthesized by condensation of Intermediate 138.2 (1 g, 3.3 mmol) and (3R,5S)-Starting material-F (862 mg, 3 mmol) analogously to the preparation of Example 19.1, followed by hydrolysis with 1 N LiOHaq. ES-MS: M+H=558: $_C$t$_{Ret}$=3.44 min.

Example 145

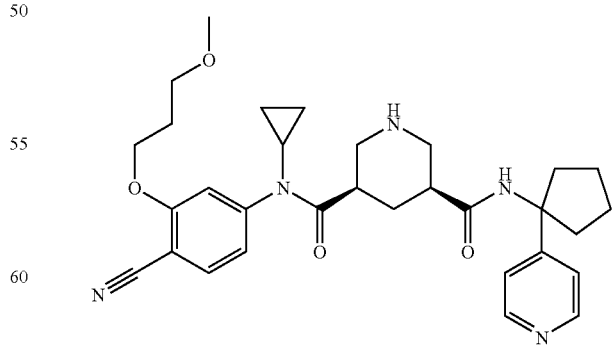

Example 145 is synthesized by deprotection of intermediate 145.1 analogously to the preparation of Example 19: ES-MS: M+H=546: $_C$t$_{Ret}$=2.38 min.

Intermediate 145.1

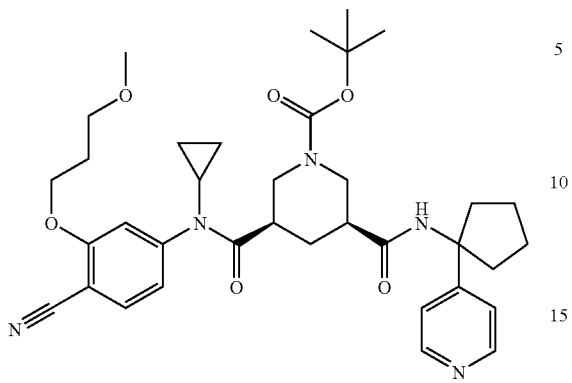

Intermediate 145.1 is synthesized by condensation of Intermediate 145.2 (75 mg, 0.15 mmol) with intermediate 122.2 (54 mg, 0.23 mmol) analogously to the preparation of intermediate 32.3. Colorless oil: ES-MS: M+H=646: $_B t_{Ret}$=1.70 min.

Intermediate 145.2

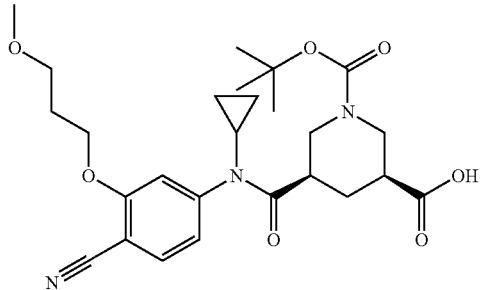

Intermediate 145.2 is synthesized by saponification of Intermediate 145.3 analogously to the preparation of Intermediate 13.2. White amorphous material; ES-MS: M+H=502: $_B t_{Ret}$=1.81 min.

Intermediate 145.3

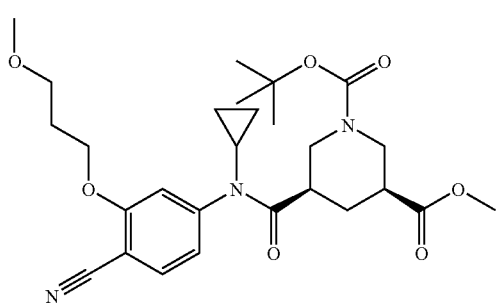

Intermediate 145.3 is synthesized by condensation of Intermediate 125.1 (500 mg, 2.03 mmol) and (3R,5S)-Starting material-F (612 mg, 2.13 mmol) analogously to the preparation of example 125: Yellow oil; ES-MS: M+H=546: $_B t_{Ret}$=1.96 min.

Example 146

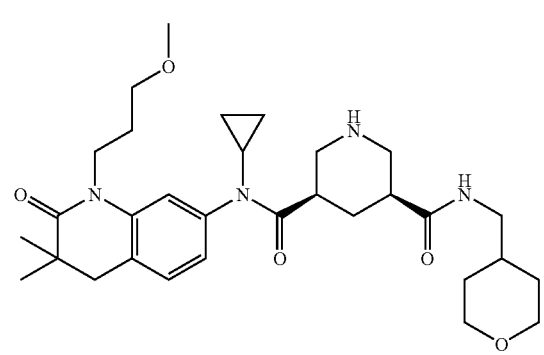

Example 146 is synthesized by deprotection of intermediate 146.1 analogously to the preparation of Example 19: ES-MS: M+H=555: $_C t_{Ret}$=2.46 min.

Intermediate 146.1

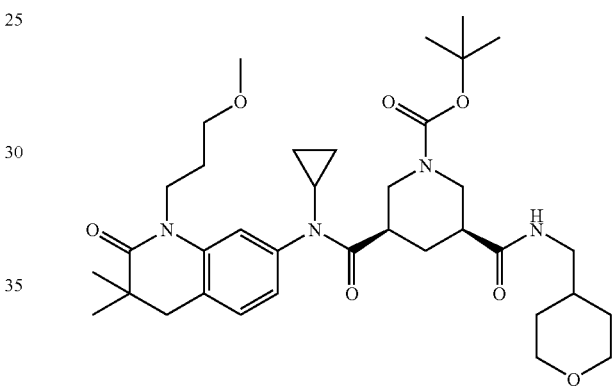

Intermediate 146.1 is synthesized by condensation of Intermediate 144.2 (75 mg, 0.15 mmol) with 4-Aminomethyltetrahydropyran (26 mg, 0.23 mmol) analogously to the preparation of intermediate 32.3: Colorless oil, ES-MS: M+H=655: $_B t_{Ret}$=1.84 min.

Example 147

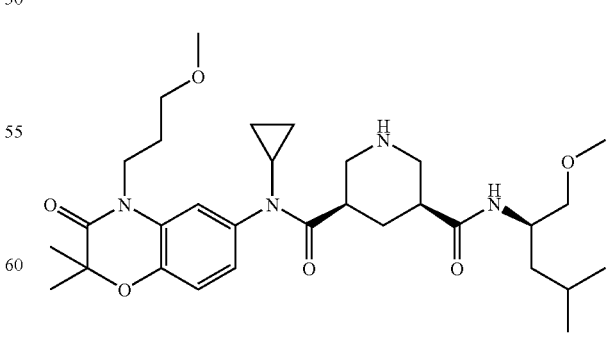

Example 147 is synthesized by deprotection of intermediate 147.1 analogously to the preparation of Example 19: ES-MS: M+H=573: $_C t_{Ret}$=2.91 min.

Intermediate 147.1

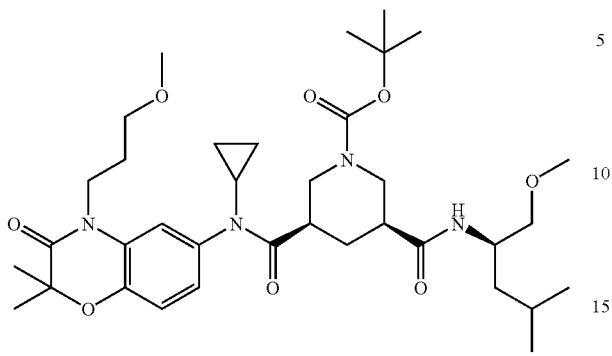

Intermediate 147.1 is synthesized by condensation of Intermediate 108.2 (100 mg, 0.178 mmol) with (R)-1-methoxymethyl-3-methylbutylamine hydrochloride (*Org. Lett.* 2001, 3, 1241.) (139.6 mg, 0.83 mmol) analogously to the preparation of intermediate 32.3: White amorphous material, ES-MS: M+H=673: $_C t_{Ret}$=4.01 min.

Example 148

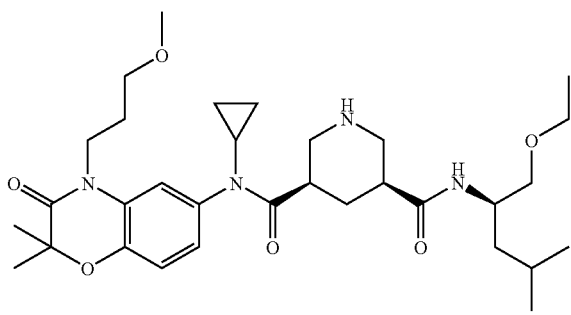

Example 148 is synthesized by deprotection of intermediate 148.1 analogously to the preparation of Example 19: ES-MS: M+H=587: $_C t_{Ret}$=3.05 min.

Intermediate 148.1

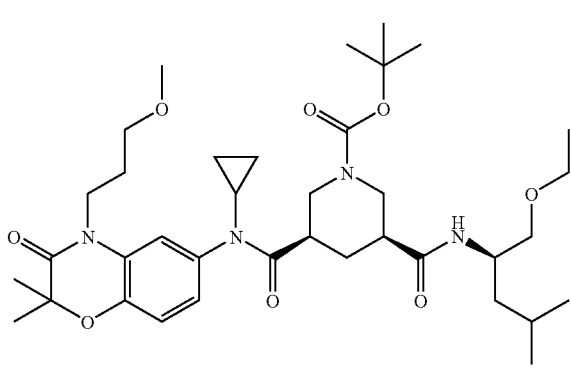

Intermediate 148.1 is synthesized by condensation of Intermediate 108.2 (100 mg, 0.178 mmol) with Intermediate 148.2 hydrochloride (44 mg, 0.24 mmol) analogously to the preparation of intermediate 32.3: White amorphous material, ES-MS: M+H=687: $_C t_{Ret}$=4.22 min.

Intermediate 148.2

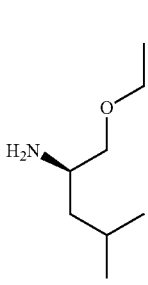

Intermediate 148.2 is synthesized by deprotection of intermediate 148.3 analogously to the preparation of Example 19: ES-MS: M+H=146: $_B t_{Ret}$=1.32 min.

Intermediate 148.3

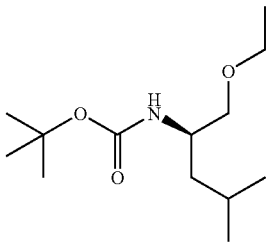

To a solution of Boc-D-Leucinol (277.9 mg, 1.278 mmol) in THF (5 mL) under N$_2$ at 0° C., is added NaH (80.3 mg of 60 wt % in mineral oil, 2.00 mmol). After stirring at the same temperature for a few min, EtI (0.122 mL, 1.53 mmol) is added. The resulting solution is stirred at rt for 2 h. The reaction is quenched with H$_2$O and the mixture is extracted with EtOAc, dried over Na$_2$SO$_4$. Concentration under reduced pressure gives the crude product. The crude product is purified by silica gel chromatography to afford Intermediate 148.3 (55.3 mg): ES-MS: M+H-Boc=146: $_B t_{Ret}$=2.11 min.

Example 149

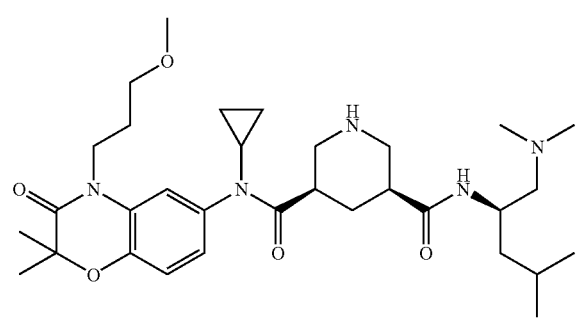

Example 149 is synthesized by deprotection of intermediate 149.1 analogously to the preparation of Example 19: ES-MS: M+H=586: $_C t_{Ret}$=2.56 min.

Intermediate 149.1

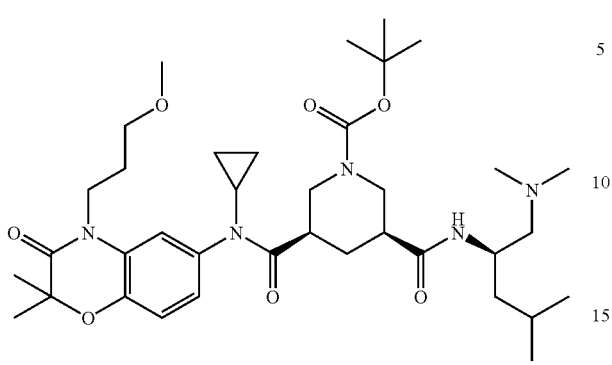

Intermediate 149.1 is synthesized by condensation of Intermediate 108.2 (100 mg, 0.178 mmol) with (R)-4,N*1*,N*1*-trimethylpentane-1,2-diamine hydrochloride (WO2006009869) (63.1 mg, 0.29 mmol) analogously to the preparation of intermediate 32.3: White amorphous material, ES-MS: M+H=686: $_ct_{Ret}$=3.36 min.

Example 150

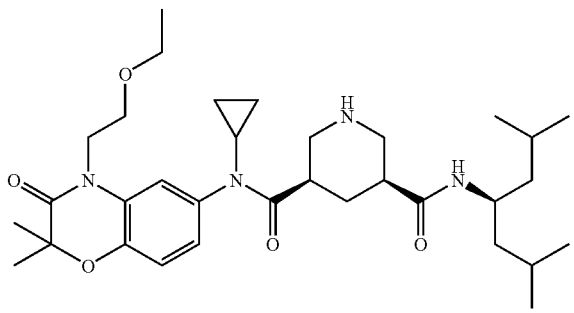

Example 150 is synthesized by deprotection of intermediate 150.1 analogously to the preparation of Example 19: ES-MS: M+H=585: $_Bt_{Ret}$=1.91 min.

Intermediate 150.1

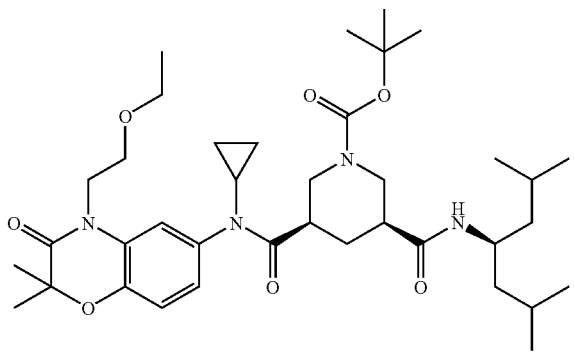

Intermediate 150.1 is synthesized by condensation of intermediate 104.2 (200 mg, 0.502 mmol) and Intermediate 150.2 (168 mg, 0.552 mmol) analogously to the preparation of Example 19.1: ES-MS: M+H=685: $_ct_{Ret}$=4.68 min.

Intermediate 150.2

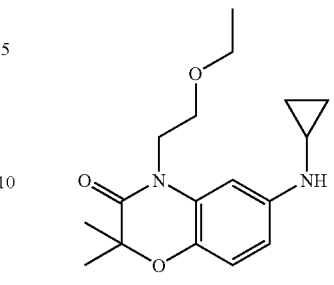

To a suspension of sodium hydride (56.8 mg, 2.37 mmol) in DMF (10.0 mL) is added 6-cyclopropylamino-2,2-dimethyl-4H-benzo[1,4]oxazin-3-one (500 mg, 2.15 mmol) in DMF (5.0 mL) at 0° C. After stirring for 15 min at the same temperature, 2-bromoethyl ethyl ether (362 mg, 2.37 mmol) and potassium iodide (5.0 mg, 0.03 mmol) are added. The mixture is stirred for 2 hours at 50° C., and H$_2$O is added. The resulting mixture is extracted with EtOAc, and the organic layer is dried over Na$_2$SO$_4$ and concentrated under reduced pressure. The obtained residue is purified by silica gel column chromatography to give Intermediate 150.2: ES-MS: M+H=305: $_Bt_{Ret}$=1.74 min.

Example 151

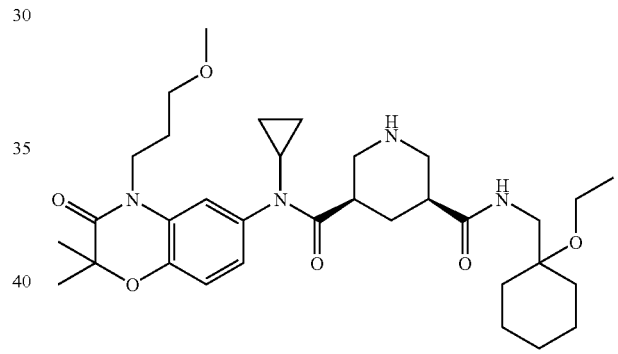

Example 151 is synthesized by deprotection of intermediate 151.1 analogously to the preparation of Example 19: ES-MS: M+H=599: $_ct_{Ret}$=3.17 min.

Intermediate 151.1

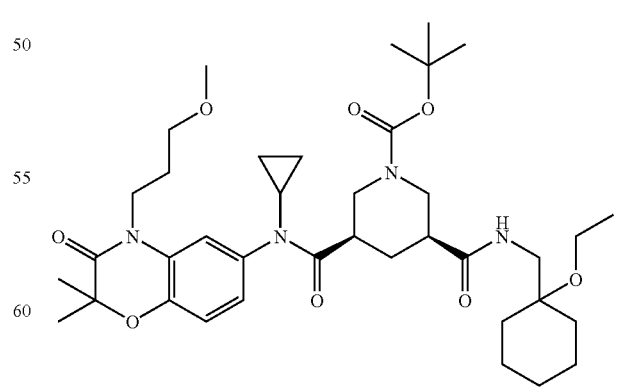

Intermediate 151.1 is synthesized by condensation of Intermediate 108.2 (56 mg, 0.10 mmol) with intermediate 151.2 analogously to the preparation of intermediate 32.3: White amorphous material, ES-MS: M+H=699: $_ct_{Ret}$=4.27 min.

Intermediate 151.2

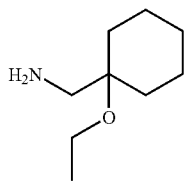

Intermediate 151.2 is synthesized by deprotection of Intermediate 151.3 analogously to the preparation of example 19. The resulting amine hydrochloride is directly used for the next reaction.

Intermediate 151.3

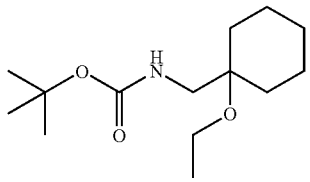

To a solution of Intermediate 151.4 (202.6 mg, 0.88 mmol) in DMF (2 mL) under $N_2$ at rt are added NaH (42.4 mg, 1.06 mmol) and EtI (76.9 µL, 0.97 mmol) at 0° C. The reaction mixture is stirred at rt overnight. Then, $H_2O$ is added to the resulting solution. The aqueous phase is extracted with EtOAc. The combined organic phases are washed with brine and dried over $Na_2SO_4$. Concentration under reduced pressure and purification by Silica gel column chromatography give Intermediate 151.3: White amorphous material, ES-MS: M+H=258: $_Bt_{Ret}$=2.15 min.

Intermediate 151.4

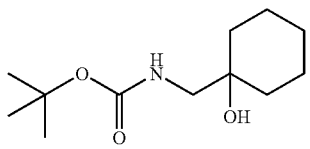

To the solution of 1-Aminomethyl-1-cyclohexanol hydrochloride (709.0 mg, 4.28 mmol) in dioxane (8.6 mL) and $H_2O$ (4.3 mL) under $N_2$ at RT, 1N NaOH (8.6 mL, 8.56 mmol) and $(Boc)_2O$ (1.03 mg, 4.71 mmol) are added at 0° C. The reaction mixture is stirred at rt overnight. After the bulk of solvent is concentrated under reduced pressure, sat critic acid aq is added to the resulting solution. The aqueous phase is extracted with $Et_2O$. The combined organic phases are dried over $Na_2SO_4$, concentrated under reduced pressure to afford Intermediate 151.4: White amorphous material, ES-MS: M+H=230: $_Bt_{Ret}$=1.72.

Example 152

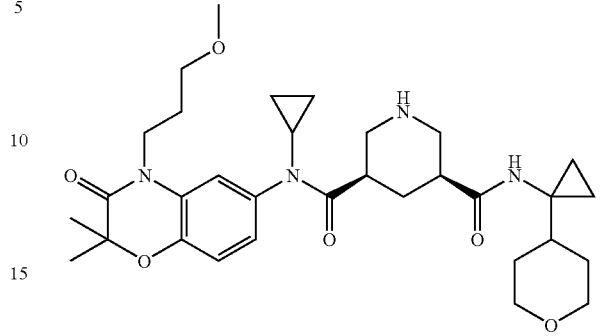

Example 152 is synthesized by deprotection of intermediate 152.1 analogously to the preparation of Example 19: ES-MS: M+H=583: $_Ct_{Ret}$=2.58 min.

Intermediate 152.1

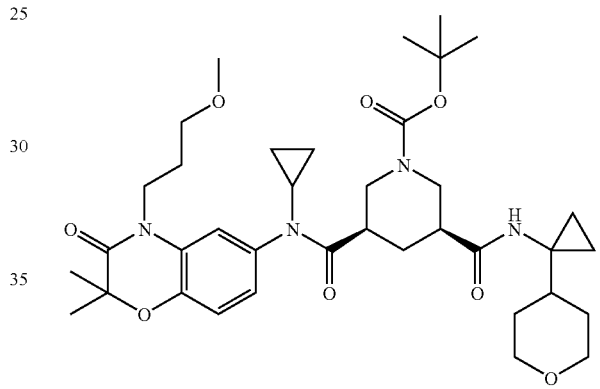

Intermediate 152.1 is synthesized by condensation of Intermediate 108.2 (50 mg, 0.09 mmol) with intermediate 152.2 (23 mg, 0.1 mmol) analogously to the preparation of intermediate 32.3: White amorphous material, ES-MS: M+H=683: $_Ct_{Ret}$=3.57 min.

Intermediate 152.2

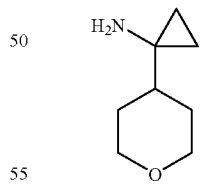

EtMgBr (9.1 mL, 9.1 mmol, 1 M in THF) is added under argon at −78° C. to a solution of 4-Cyanotetrahydro-4H-pyran (4.1 mmol) and Ti(O$^i$Pr)$_4$ (1.33 mL, 4.56 mmol) in $Et_2O$ (42 mL). The solution is slowly warmed to room temperature during 1 h, and then it is stirred at rt for 30 min. At this stage, $BF_3.OEt_2$ (1.16 mL, 8.3 mmol) is added and stirring is continued for 2 h. Water (10 mL) is added, followed by 10% aq. HCl (10 mL) and $Et_2O$ (20 mL). A 10% aq. NaOH solution is added to the resulting clear mixture until the pH become basic. The product is extracted with $Et_2O$ (2×30 mL). The combined organic extracts is dried with $Na_2SO_4$. After evaporation of the solvent, the product is used for next reaction without purification: yellow oil. ES-MS: M+H=142: $_B t_{Ret}$=0.73 min Example 153

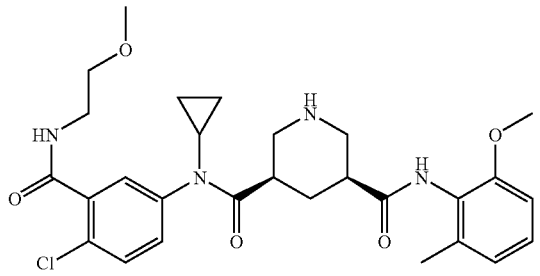

Example 153 is synthesized by deprotection of Intermediate 153.1 (74 mg, 0.12 mmol) analogously to the preparation of Example 19: ES-MS: M+H=544: $_C t_{Ret}$=2.40 min.

Intermediate 153.1

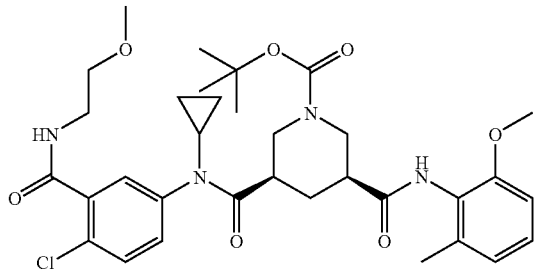

Intermediate 153.1 is synthesized by condensation of Intermediate 153.2 (56 mg, 0.209 mmol) and Intermediate 111.2 (75 mg, 0.19 mmol) analogously to the preparation of example 125: colorless oil; ES-MS: M+H=644: $_C t_{Ret}$=3.37 min.

Intermediate 153.2

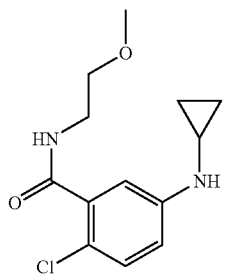

Intermediate 153.2 is synthesized by condensation of Intermediate 153.3 (550 mg, 2.6 mmol) with 2-methoxyethylamine (233 mg, 3.1 mmol) analogously to the preparation of Intermediate 32.3. White solid; ES-MS: M+H=282; HPLC: $_A t_{Ret}$=2.95 min.

Intermediate 153.3

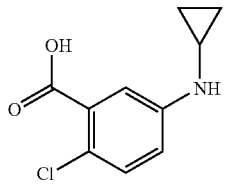

Intermediate 153.3 is synthesized by hydrolysis of Intermediate 153.4 (1.5 g, 6.6 mmol) analogously to the preparation of Intermediate 13.2. White solid; ES-MS: M+H=211; HPLC: $_A t_{Ret}$=3.05 min.

Intermediate 153.4

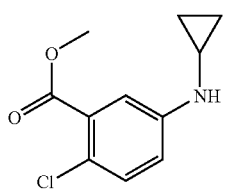

Intermediate 153.4 is synthesized by cyclopropanation of 5-amino-2-chlorobenzoic acid methyl ester (2 g, 10.8 mmol) analogously to the preparation of Intermediates 19.5 and 19.6. White solid; ES-MS: M+H=225; HPLC: $_A t_{Ret}$=3.84 min.

Example 154

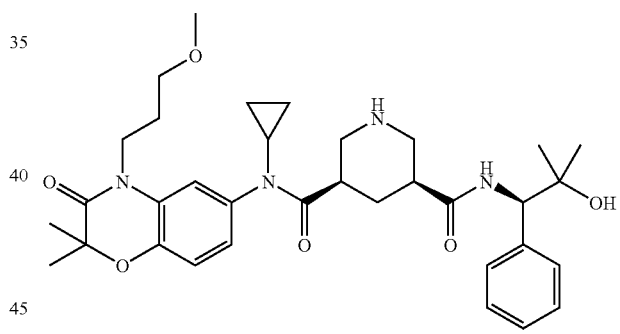

Example 154 is synthesized by deprotection of intermediate 154.1 analogously to the preparation of Example 19: ES-MS: M+H=607: $_C t_{Ret}$=2.76 min.

Intermediate 154.1

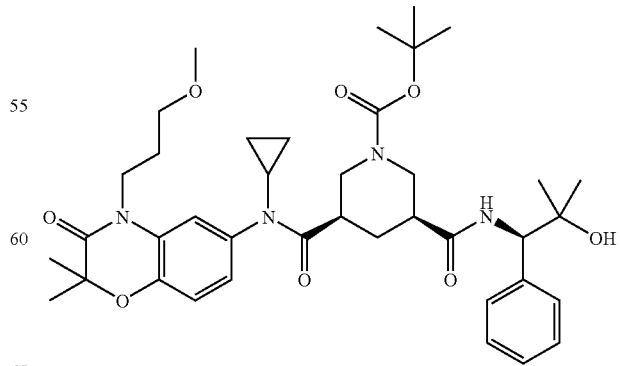

Intermediate 154.1 is synthesized by condensation of Intermediate 108.2 (120 mg, 0.21 mmol) with (R)-1-amino-2- methyl-1-phenylpropan-2-ol hydrochloride (CAS 110480-87-0) (75.8 mg, 0.376 mmol) analogously to the preparation of intermediate 32.3: White amorphous material, ES-MS: M+H=707: $_c t_{Ret}$=3.75 min.

Example 155

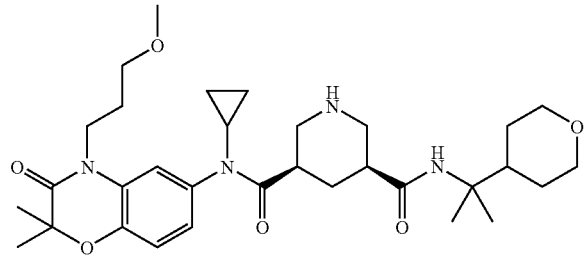

Example 155 is synthesized by deprotection of intermediate 155.1 analogously to the preparation of Example 19: ES-MS: M+H=585: $_c t_{Ret}$=2.71 min.

Intermediate 155.1

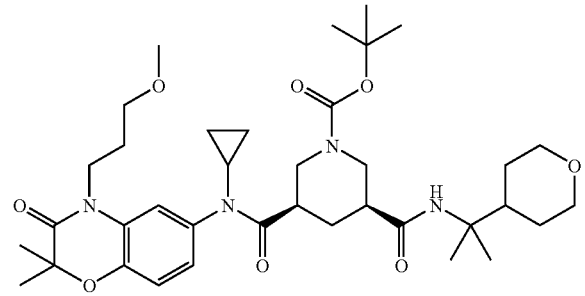

Intermediate 155.1 is synthesized by condensation of Intermediate 108.2 (100 mg, 0.178 mmol) with 1-methyl-1-(tetrahydropyran-4-yl)-ethylamine hydrochloride (*J. Med. Chem.* 1996, 39, 2795.) (48 mg, 0.266 mmol) analogously to the preparation of intermediate 32.3: White amorphous material, ES-MS: M+H=685: $_c t_{Ret}$=3.71 min.

Example 156

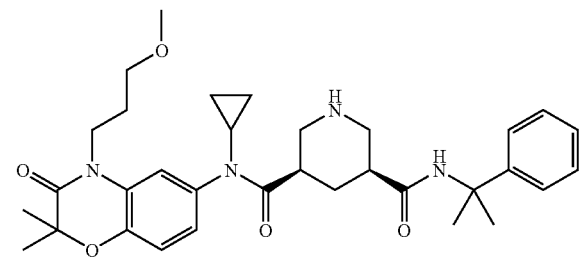

Example 156 is synthesized by deprotection of intermediate 156.1 analogously to the preparation of Example 19: ES-MS: M+H=577: $_c t_{Ret}$=3.07 min.

Intermediate 156.1

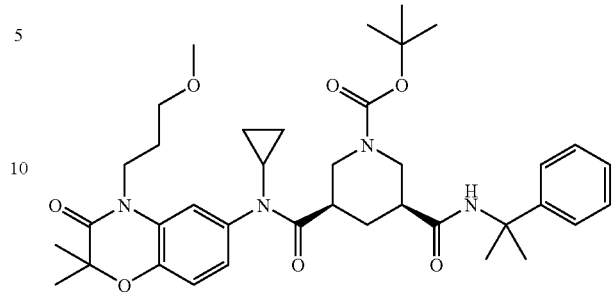

Intermediate 156.1 is synthesized by condensation of Intermediate 108.2 (120 mg, 0.21 mmol) with 1-Methyl-1-phenyl-ethylamine (0.045 mL, 0.315 mmol) analogously to the preparation of intermediate 32.3: White amorphous material, ES-MS: M+H=677: $_c t_{Ret}$=4.09 min.

Example 157

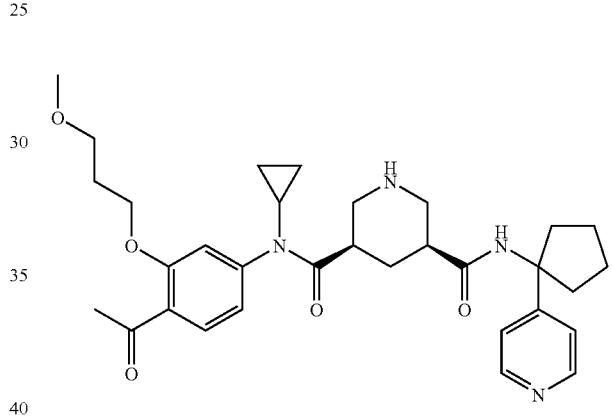

Example 157 is synthesized by condensation of Intermediate 157.1 (130 mg, 0.25 mmol) and Intermediate 122.2 (77 mg, 0.33 mmol) analogously to the preparation of Intermediate 39.1 followed by deprotection analogously to the preparation of Example 19: ES-MS: M+H=563: $_c t_{Ret}$=2.30 min.

Intermediate 157.1

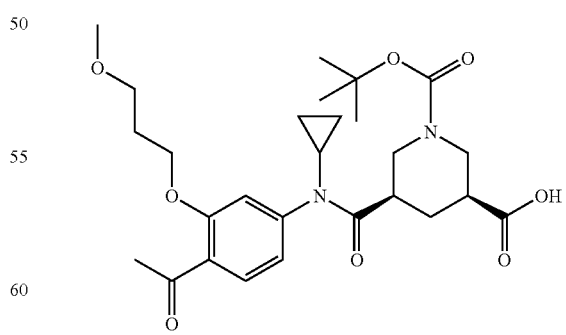

Intermediate 157.1 is synthesized by saponification of Intermediate 157.2 analogously to the preparation of Intermediate 13.2. White amorphous material; ES-MS: M+H=519: $_c t_{Ret}$=3.31 min.

Intermediate 157.2

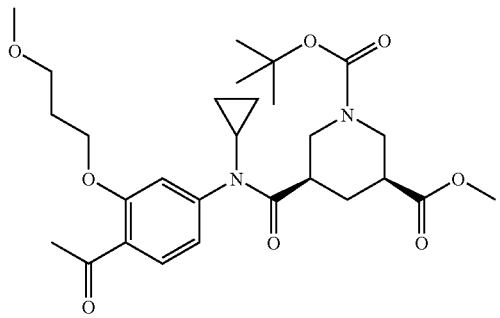

Intermediate 157.2 is synthesized by condensation of Intermediate 102.1 (100 mg, 0.38 mmol) and (3R,5S)-Starting material-F (120 mg, 0.42 mmol) analogously to the preparation of example 125: Yellow oil; ES-MS: M+H=533: $_B t_{Ret}$=1.96 min.

Example 158

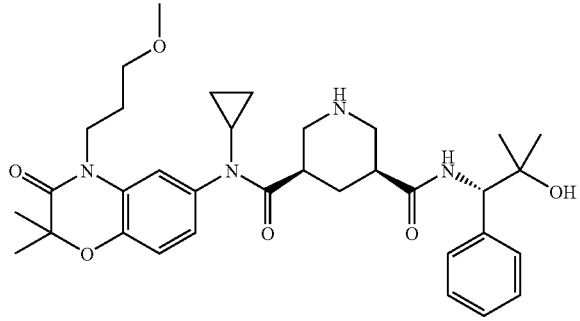

Example 158 is synthesized by deprotection of intermediate 158.1 analogously to the preparation of Example 19: ES-MS: M+H=607: $_C t_{Ret}$=2.87 min.

Intermediate 158.1

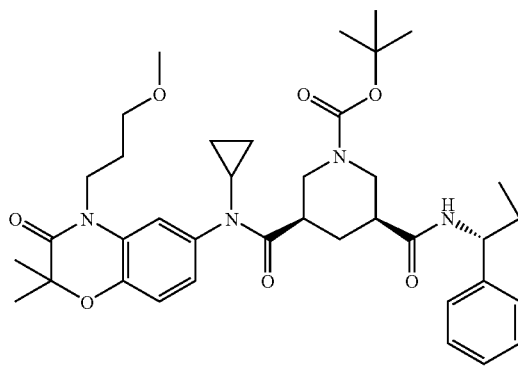

Intermediate 158.1 is synthesized by condensation of Intermediate 108.2 (150 mg, 0.268 mmol) with (S)-1-amino-2-methyl-1-phenylpropan-2-ol hydrochloride (*Synthesis* 2004, 909.) (100 mg, 0.47 mmol) analogously to the preparation of intermediate 32.3: White amorphous material, ES-MS: M+H=707: $_C t_{Ret}$=3.73 min.

Example 159

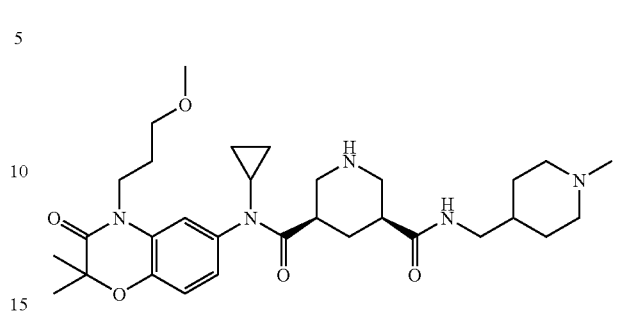

Example 159 is synthesized by deprotection of intermediate 159.1 analogously to the preparation of Example 19: ES-MS: M+H=570: $_C t_{Ret}$=2.22 min.

Intermediate 159.1

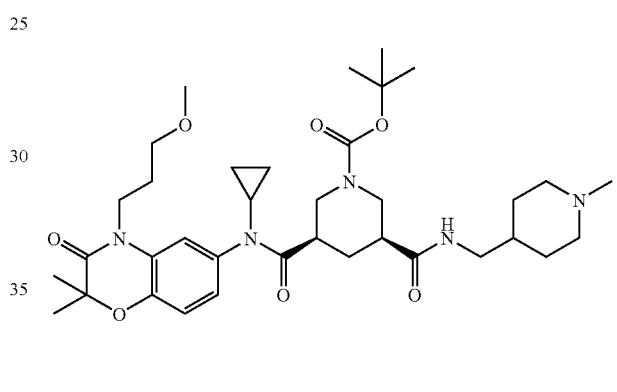

Intermediate 159.1 is synthesized by condensation of Intermediate 108.2 (80 mg, 0.14 mmol) with C-(1-methylpiperidin-4-yl)-methylamine (22 mg, 0.17 mmol) analogously to the preparation of intermediate 32.3: White amorphous material, ES-MS: M+H=670: $_C t_{Ret}$=3.01 min.

Example 160

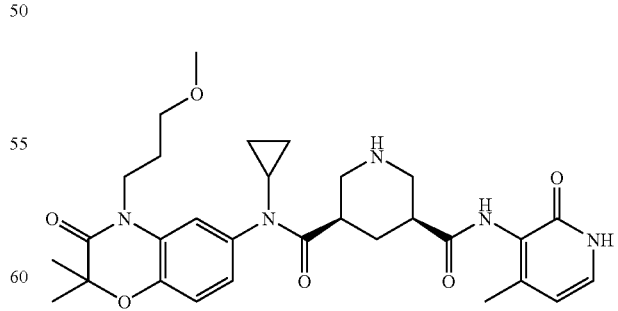

Example 160 is synthesized by deprotection of intermediate 160.1 analogously to the preparation of Example 19: ES-MS: M+H=566: $_C t_{Ret}$=2.37 min.

Intermediate 160.1

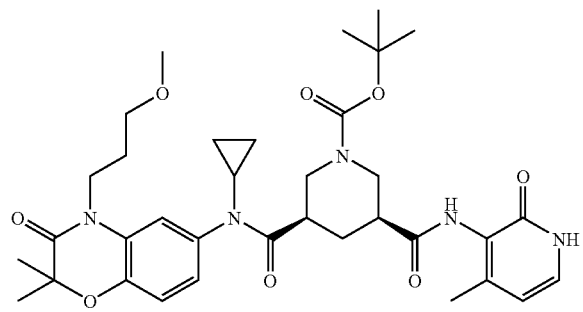

Intermediate 160.1 is synthesized by condensation of Intermediate 108.2 (80 mg, 0.143 mmol) with 3-Amino-4-methyl-1H-pyridin-2-one (WO 2004063155) (28 mg, 0.172 mmol) analogously to the preparation of intermediate 32.3: White amorphous material, ES-MS: M+H=666: $_c t_{Ret}$=3.17 min.

Example 161

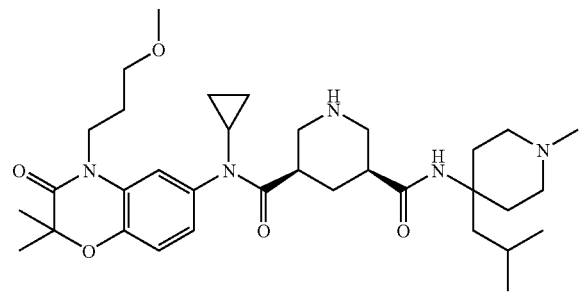

Example 161 is synthesized by deprotection of intermediate 161.1 analogously to the preparation of Example 19: ES-MS: M+H=612: $_c t_{Ret}$=2.57 min.

Intermediate 161.1

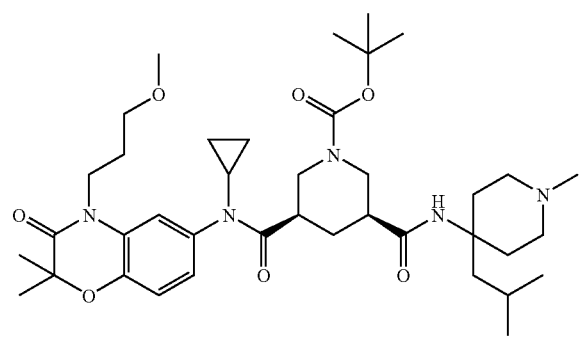

Intermediate 161.1 is synthesized by condensation of Intermediate 108.2 (80 mg, 0.143 mmol) with Intermediate 161.2 (29 mg, 0.172 mmol) analogously to the preparation of intermediate 32.3: White amorphous material, ES-MS: M+H=712: $_c t_{Ret}$=3.22 min.

Intermediate 161.2

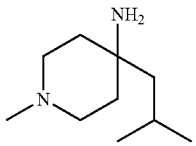

Intermediate 161.2 is synthesized by reduction of Intermediate 161.3 (100 mg, 0.39 mmol) analogously to the preparation of intermediate 137.2: colorless oil, ES-MS: M+H=171: $_c t_{Ret}$=0.67 min.

Intermediate 161.3

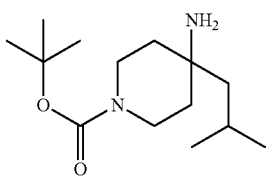

Intermediate 161.3 is synthesized by deprotection of Intermediate 161.4 (300 mg, 0.75 mmol) analogously to the preparation of intermediate 137.3: colorless oil, ES-MS: M+H=257: $_c t_{Ret}$=2.47 min.

Intermediate 161.4

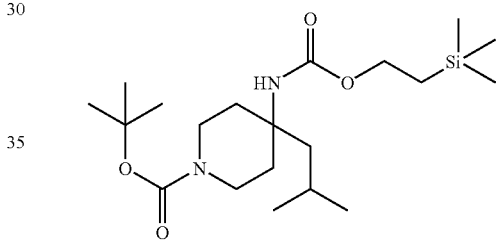

To a solution of Intermediate 161.5 (700 mg, 2.45 mmol) in toluene (20 mL) are added Et₃N (3 mL, 9.8 mmol), 2-(trimethylsilyl)ethanol (580 mg, 4.9 mmol) and DPPA (1.06 mL, 4.9 mmol), then the mixture is stirred at 100° C. After 2 h, CuCl₂ (100 mg, 0.74 mmol) is added to the mixture, then the mixture is stirred at 100° C. After 4 h, the reaction mixture is cooled to room temperature and quenched with H₂O (50 mL) and extracted with EtOAc (200 mL). The organic phase is successively washed with 5% aqueous NH₄Cl twice, 5% aqueous NaHCO₃, H₂O and brine, then dried over Na₂SO₄ and concentrated in vacuo. The residue is purified by SiO₂ column chromatography to afford Intermediate 161.4: Colorless oil, ES-MS: M+H=401: $_c t_{Ret}$=4.99 min.

Intermediate 161.5

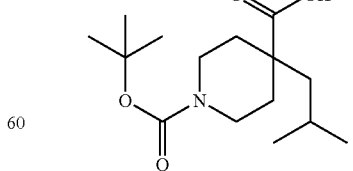

A mixture of Intermediate 161.6 (2.3 g, 7.7 mmol) and KOHaq (8 M in H₂O, 20 mL) in ethyleneglycol (60 mL) is stirred at 120° C. After 15 h, the reaction mixture is cooled down to room temperature and quenched with 5% aqueous KHSO₄ by pH <4, then extracted with Et₂O twice (300 mL×2). The combined organic phase is successively washed with H₂O twice, and brine, then dried over Na₂SO₄. The mixture is filtered, and the filtrate is evaporated in vacuo to give Intermediate 161.5: White solid material: ES-MS=286: $_C t_{Ret}$=3.63 min.

Intermediate 161.6

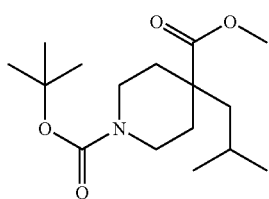

To a solution of piperidine-1,4-dicarboxylic acid 1-tert-butyl ester 4-methyl ester (2 g, 8.2 mmol) in THF (80 mL) is added LDA (2M solution, 6 mmol) at −78° C. After stirring for 0.5 h, to the solution is added isobutyl iodide (1.3 mL, 16 mmol) at −78° C. Then the mixture is warmed up to room temperature. After stirring for 2 h, the reaction mixture is quenched with 5% aqueous KHSO₄ (200 mL) and extracted with Et₂O (500 mL). The organic phase is successively washed with H₂O twice, and brine, then dried over Na₂SO₄ and concentrated in vacuo. The residue is purified by SiO₂ column chromatography to give Intermediate 161.6: colorless oil: ES-MS=299: $_C t_{Ret}$=4.37 min.

Example 162

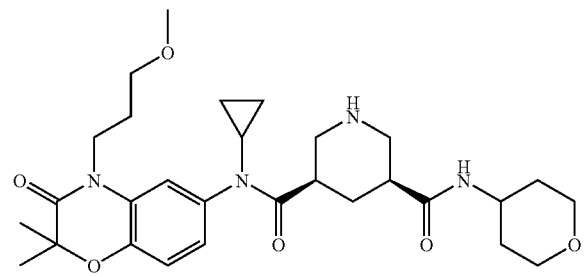

Example 162 is synthesized by deprotection of intermediate 162.1 analogously to the preparation of Example 19: ES-MS: M+H=543: $_C t_{Ret}$=2.37 min.

Intermediate 162.1

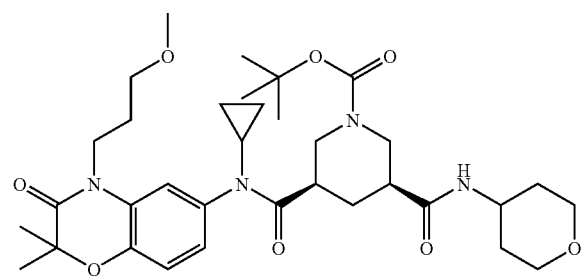

Intermediate 162.1 is synthesized by condensation of Intermediate 108.2 (100 mg, 0.18 mmol) with 4-Aminotetrahydropyran (27 mg, 0.27 mmol) analogously to the preparation of intermediate 32.3: Colorless oil, ES-MS: M+H=643, $_B t_{Ret}$=1.83 min.

Example 163

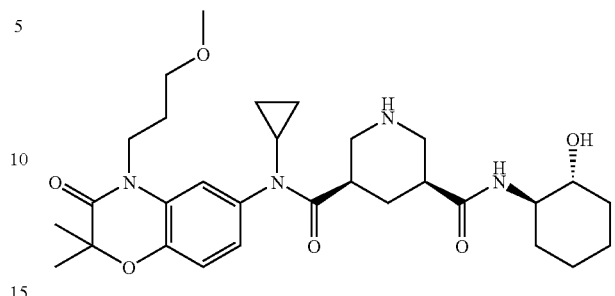

Example 163 is synthesized by deprotection of intermediate 163.1 analogously to the preparation of Example 19: ES-MS: M+H=557: $_A t_{Ret}$=2.25 min.

Intermediate 163.1

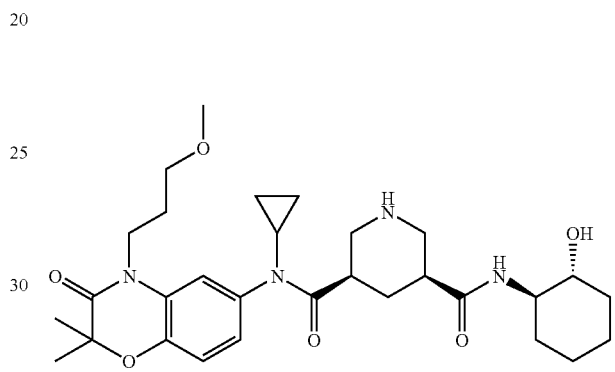

Intermediate 163.1 is synthesized by condensation of Intermediate 108.2 (99.6 mg, 0.18 mmol) with (rac)-trans-4-aminocyclohexanol (22.5 mg, 0.20 mmol) analogously to the preparation of intermediate 32.3: White amorphous material, ES-MS: M+H=657: $_B t_{Ret}$=1.78 min.

Example 164

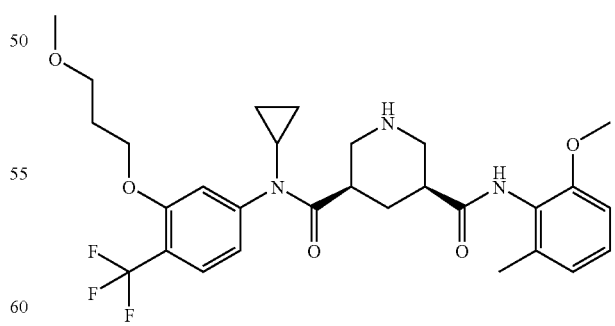

Example 164 is synthesized by deprotection of intermediate 164.1 analogously to the preparation of Example 19: ES-MS: M+H=564: $_A t_{Ret}$=2.95 min.

Intermediate 164.1

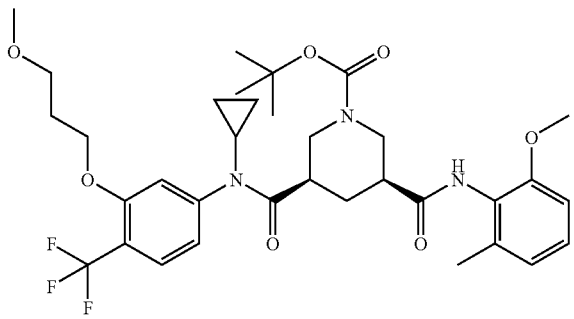

Intermediate 164.1 is synthesized by condensation of intermediate 164.2 (40 mg, 0.163 mmol) with Intermediate 111.2 (64 mg, 0.163 mmol) analogously to the preparation of intermediate 32.3: Colorless oil, ES-MS: M+H=664, $_c t_{Ret}$=4.24 min.

Intermediate 164.2

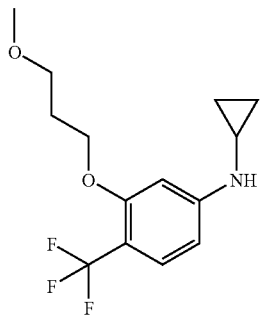

Intermediate 164.2 is synthesized by condensation of Intermediate 164.3 (626 mg, 2.00 mmol) and cyclopropylamine (343 mg, 6.00 mmol) analogously to the preparation of Intermediate 112.2. Yellow oil; ES-MS: M+H=290; HPLC: $_A t_{Ret}$=4.12 min.

Intermediate 164.3

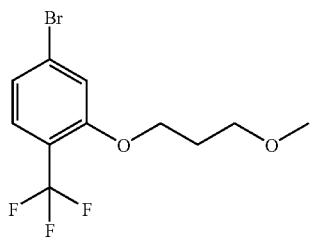

A mixture of 3-fluoro-4-(trifluoromethyl)bromobenzene (3.00 g, 12.35 mmol), 60% NaH (1.48 g, 37.05 mmol) and 3-methoxy-1-propanol (1.67 g, 18.5 mmol) in DMF (80 mL) is stirred at 0° C. for 30 min. The reaction mixture is stirred at 60° C. for 30 min. After adding H$_2$O, the reaction mixture is extracted with EtOAc. The combined organic phases are washed with brine and dried (MgSO$_4$). Concentration under reduced pressure and silica gel flash chromatography give Intermediate 164.3: Yellow oil; ES-MS: M+H=292: $_A t_{Ret}$=4.39 min.

Example 165

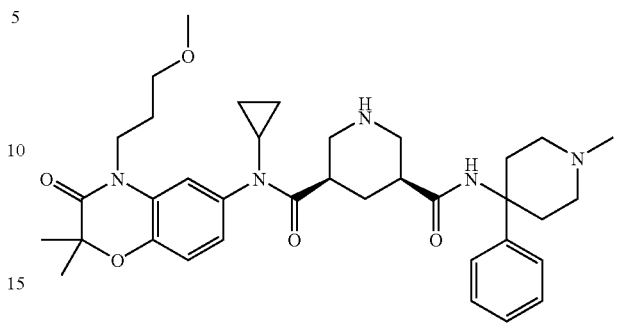

Example 165 is synthesized by a deprotection of Intermediate 165.1 (95 mg, 0.13 mmol) analogously to the preparation of intermediate 103.2: White amorphous material, ES-MS: M+H=632: $_c t_{Ret}$=2.25 min.

Intermediate 165.1

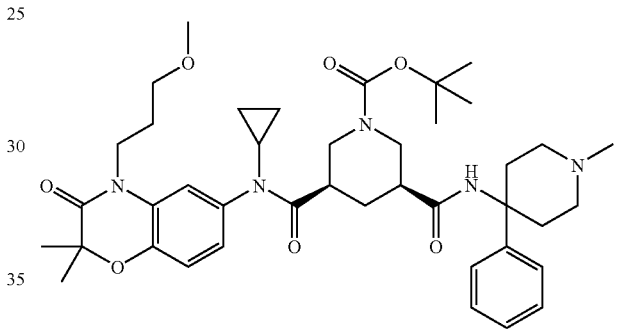

Intermediate 165.2 is synthesized by a condensation of 1-methyl-4-phenylpiperidin-4-ylamine (CASNo, 100316-65-2, 45 mg, 0.17 mmol) with Intermediate 108.2 (80 mg, 0.14 mmol) analogously to the preparation of intermediate 1.1: Colorless oil, ES-MS: M+H=732: $_c t_{Ret}$=3.00 min.

Example 166

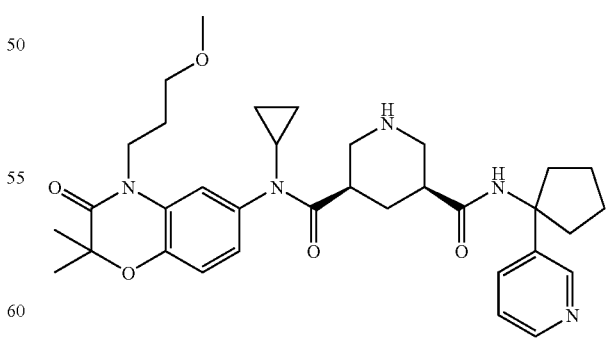

Example 166 is synthesized by condensation of Intermediate 108.2 (100 mg, 0.18 mmol) and Intermediate 166.1 (55 mg, 0.23 mmol) analogously to the preparation of Intermediate 1.1 followed by deprotection of the Boc group with 4N HCl/dioxane. ES-MS: M+H=604: $_A t_{Ret}$=2.14 min.

Intermediate 166.1

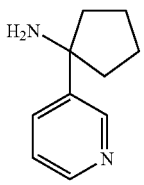

Intermediate 166.2 (300 mg, 1.58 mmol) and bis(trifluoroacetoxy)iodobenzene (1 g, 2.37 mmol) is dissolved in t-BuOH (3 mL) and stirred at 70° C. for 5 h. The mixture is diluted with AcOEt, washed with sat. NaHCO₃aq. The organic layer is extracted with 2 N HClaq. The aqueous layer is washed with AcOEt then basified with 5 N NaOHaq. The aqueous layer is extracted again with AcOEt and the extracts are washed with brine. Concentration under vacuum and deprotection of the Boc group with 4N HCl in dioxane and EtOH gives Intermediate 166.1 as white crystals. ES-MS: M+H=263, $_A t_{Ret}$=1.97 min.

Intermediate 166.2

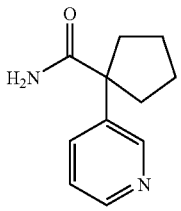

Intermediate 166.2 is synthesized by hydrolysis of 1-Pyridin-3-yl-cyclopentanecarbonitrile (630 mg, 3.66 mmol) with KOTMS (939 mg, 7.32 mmol) in toluene at 100° C. for 8 h. Intermediate 166.2: white crystals; ES-MS: M+H=191: $_B t_{Ret}$=1.05 min.

Example 167

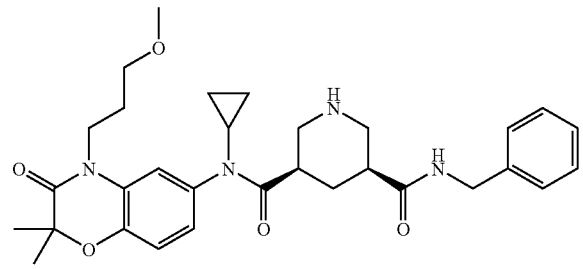

Example 167 is synthesized by condensation of Intermediate 108.2 (100 mg, 0.18 mmol) and benzylamine (38 mg, 0.358 mmol) analogously to the preparation of intermediate 1.1 followed by deprotection of the Boc group with 4 N HCl/dioxane. ES-MS: M+H=549: $_A t_{Ret}$=2.62 min.

Example 168

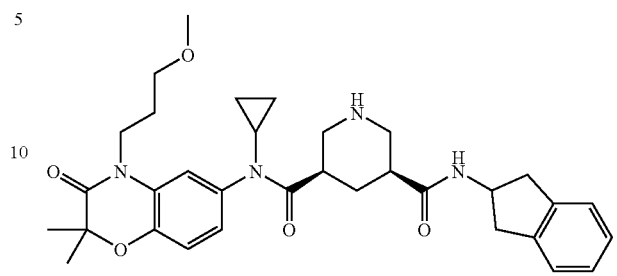

Example 168 is synthesized by deprotection of Intermediate 168.1 (80 mg, 0.12 mmol) analogously to the preparation of Example 123. White amorphous material, ES-MS: M+H=575: $_A t_{Ret}$=2.75 min.

Intermediate 168.1

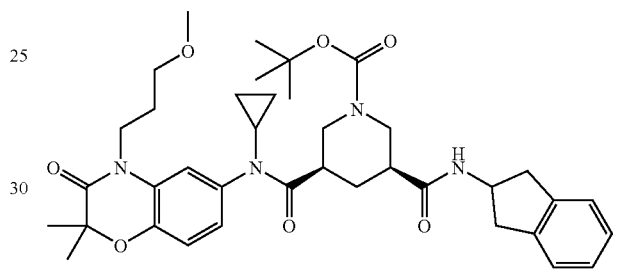

Intermediate 168.1 is synthesized by condensation of Intermediate 108.2 (100 mg, 0.18 mmol) and 2-Aminoindan (31 mg, 0.23 mmol) analogously to the preparation of Intermediate 1.1. Colorless oil, ES-MS: M+H=675: $_A t_{Ret}$=3.95 min.

Example 169

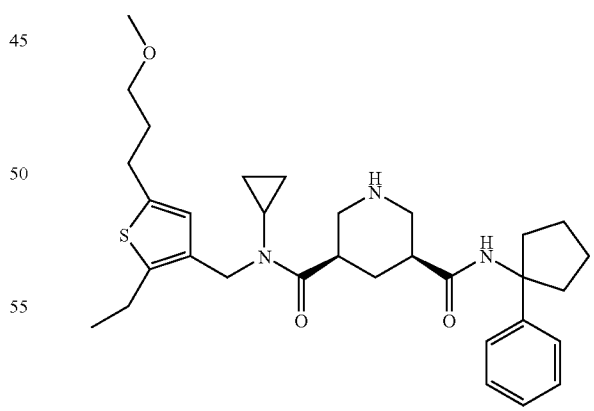

Example 169 is synthesized by a deprotection of Intermediate 169.1 (75 mg, 0.12 mmol) analogously to the preparation of Example 1. White amorphous material, ES-MS: M+H=622: $_C t_{Ret}$=2.45 min.

Intermediate 169.1

Intermediate 169.1 is synthesized by condensation of Intermediate 169.2 (50 mg, 0.120

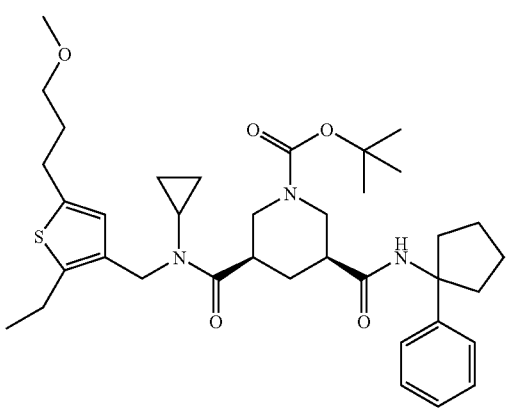

mmol) with Intermediate 94.2 (37 mg, 0.144 mmol) analogously to the preparation of intermediate 13.1. White amorphous material, ES-MS: M+H=652: $c_{tRet}$=4.64 min.

Intermediate 169.2

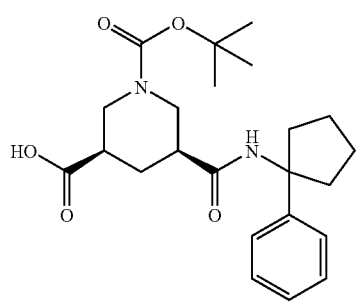

Intermediate 169.2 is synthesized by hydrolysis of Intermediate 169.3 (700 mg, 1.63 mmol) analogously to the preparation of intermediate 13.2. White amorphous material, ES-MS: M+H=417: $c_{tRet}$=3.35 min.

Intermediate 169.3

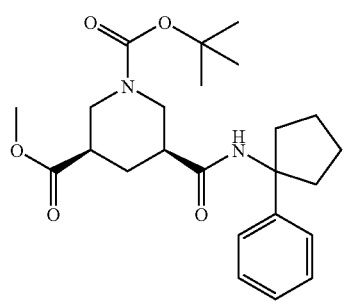

Intermediate 169.3 is synthesized by condensation of Intermediate 103.2 (400 mg, 2 mmol) with (3S,5R)-Starting material-F (575 mg, 2 mmol) analogously to the preparation of intermediate 13.3. White amorphous material, ES-MS: M+H=431: $c_{tRet}$=3.80 min.

Example 170

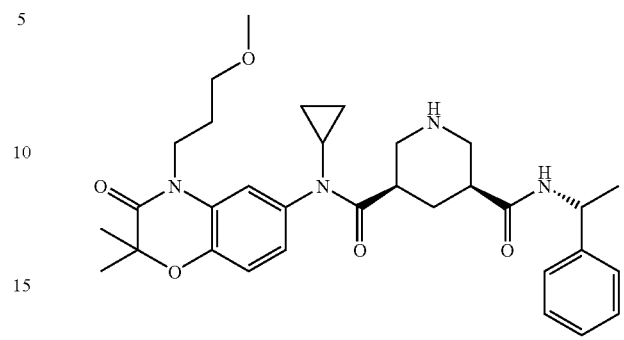

Example 170 is synthesized by deprotection of intermediate 170.1 analogously to the preparation of Example 19: ES-MS: M+H=563: $c_{tRet}$=2.99 min.

Intermediate 170.1

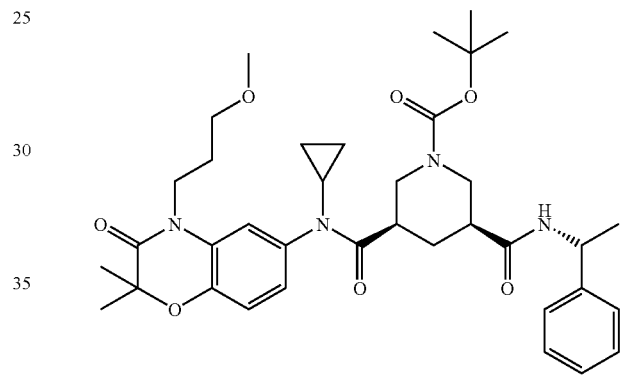

Intermediate 170.1 is synthesized by condensation of Intermediate 108.2 (103 mg, 0.18 mmol) with (R)-(+)-phenylethylamine (26 μL, 0.20 mmol) analogously to the preparation of intermediate 32.3: ES-MS: M+H=663: $c_{tRet}$=3.87 min.

Example 171

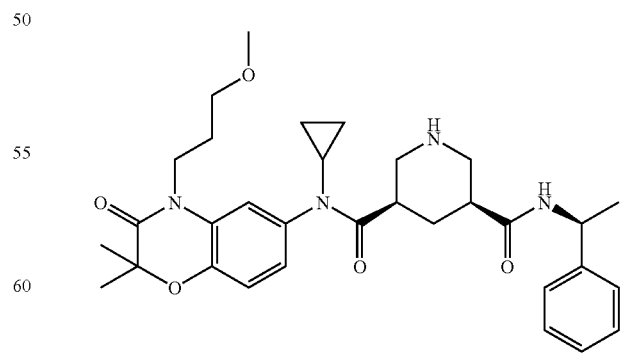

Example 171 is synthesized by deprotection of intermediate 171.1 analogously to the preparation of Example 19: ES-MS: M+H=563: $c_{tRet}$=2.96 min.

Intermediate 171.1

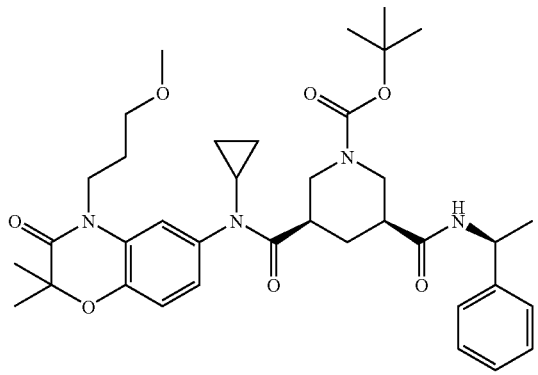

Intermediate 171.1 is synthesized by condensation of Intermediate 108.2 (109 mg, 0.19 mmol) with (S)-(−)-phenylethylamine (27 μL, 0.21 mmol) analogously to the preparation of intermediate 32.3: ES-MS: M+H=663: $_c t_{Ret}$=4.01 min.

Example 172

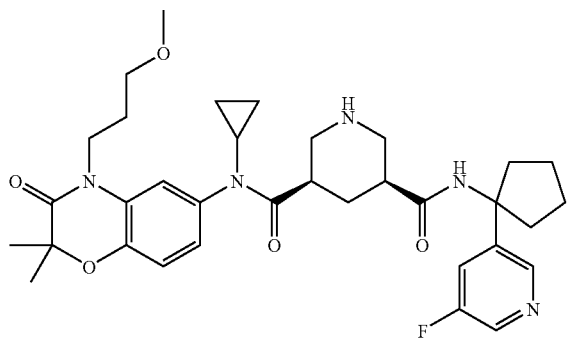

Example 172 is synthesized by a deprotection of Intermediate 172.1 (95 mg, 0.12 mmol) analogously to the preparation of intermediate 103.2. White amorphous material, ES-MS: M+H=622: $_c t_{Ret}$=2.45 min.

Intermediate 172.1

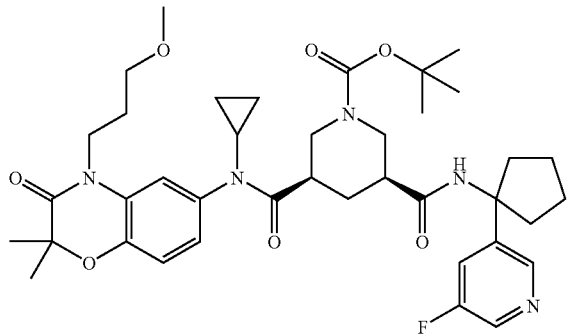

Intermediate 172.1 is synthesized by condensation of Intermediate 172.2 (44 mg, 0.172 mmol) with Intermediate 108.2 (80 mg, 0.143 mmol) analogously to the preparation of intermediate 1.1. White amorphous material, ES-MS: M+H=722: $_c t_{Ret}$=3.38 min.

Intermediate 172.2

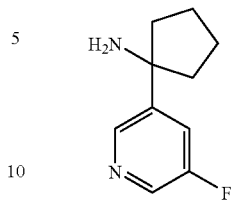

Intermediate 172.2 is synthesized by deprotection of Intermediate 172.3 (200 mg, 0.71 mmol) analogously to the preparation of intermediate 103.2. White amorphous material, ES-MS: M+H=181: $_c t_{Ret}$=1.42 min.

Intermediate 172.3

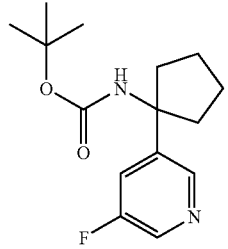

Intermediate 172.3 is synthesized by rearrangement reaction of Intermediate 172.4 (300 mg, 1.44 mmol) analogously to the preparation of intermediate 103.3. White amorphous material, ES-MS: M+H=281: $_c t_{Ret}$=2.63 min.

Intermediate 172.4

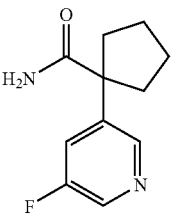

Intermediate 172.4 is synthesized by a reaction of Intermediate 172.5 (400 mg, 2.1 mmol) with potassium trimethylsilanolate (600 mg, 90% purity, 4.2 mmol) analogously to the preparation of intermediate 122.4: White solid, ES-MS: M+H=209: $_c t_{Ret}$=1.60 min.

Intermediate 172.5

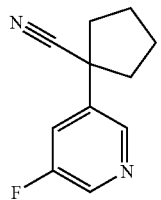

Intermediate 172.5 is synthesized by a reaction of 3,5-difluoropyridine (1.9 g, 12.6 mmol) with cyclopentanecarbonitrile (1 g, 10.5 mmol) analogously to the preparation of intermediate 122.5. Colorless oil, ES-MS: M+H=279: $_c t_{Ret}$=3.05 min.

Example 173

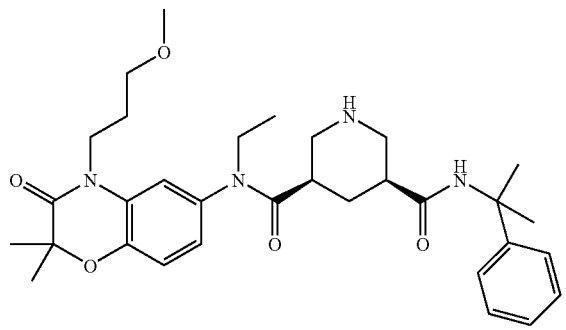

Example 173 is synthesized by deprotection of Intermediate 173.1 (153 mg, 0.23 mmol) analogously to the preparation of Example 123. White amorphous material, ES-MS: M+H=565: $_At_{Ret}$=2.82 min.

Intermediate 173.1

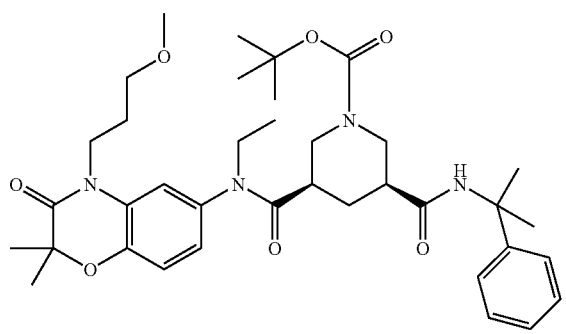

Intermediate 173.1 is synthesized by condensation of intermediate 173.2 (150 mg, 0.38 mmol) and intermediate 127.2 (117 mg, 0.4 mmol) analogously to the preparation of intermediate 19.1. Colorless oil, ES-MS: M+H=665: $_At_{Ret}$=4.03 min.

Intermediate 173.2

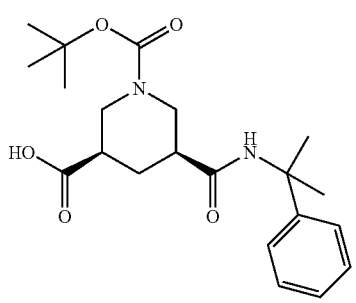

Intermediate 173.2 is synthesized by hydrolysis of Intermediate 173.3 (474 mg, 1.17 mmol) analogously to the preparation of Intermediate 13.2. Colorless crystal, ES-MS: M+H=391: $_At_{Ret}$=3.10 min.

Intermediate 173.3

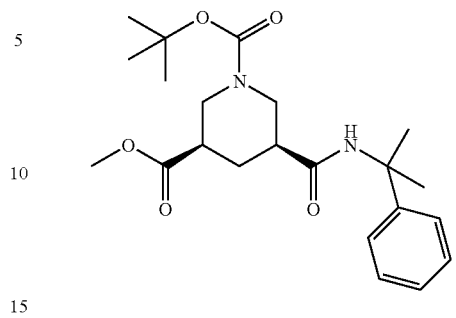

Intermediate 173.2 is synthesized by condensation of (3S, 5R)-Starting material-F (431 mg, 1.5 mmol) with Cumylamine (264 mg, 1.95 mmol) analogously to the preparation of Intermediate 13.3. Colorless oil, ES-MS: M+H=405: $_At_{Ret}$=3.54 min.

Example 174

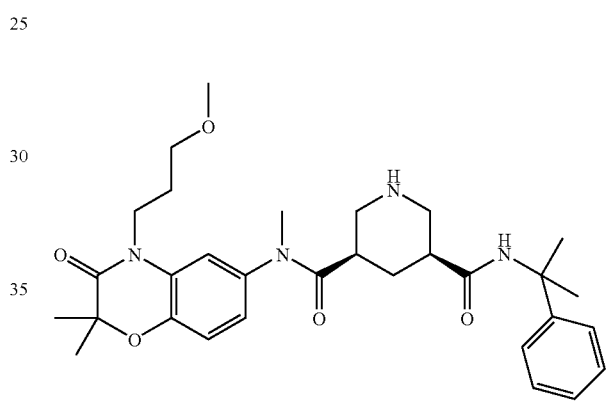

Example 174 is synthesized by deprotection of Intermediate 174.1 (157 mg, 0.24 mmol) analogously to the preparation of Example 1. White amorphous material, ES-MS: M+H=551: $_At_{Ret}$=2.68 min.

Intermediate 174.1

Intermediate 174.1 is synthesized by condensation of Intermediate 173.2 (150 mg, 0.38 mmol) and Intermediate 174.2 (112 mg, 0.4 mmol) analogously to the preparation of Intermediate 19.1. Colorless oil, ES-MS: M+H=651: $_At_{Ret}$=3.85 min.

Intermediate 174.2

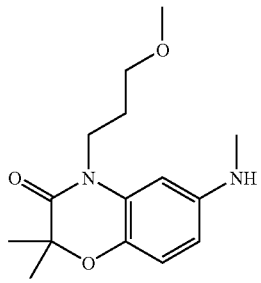

At room temperature, a methanolic solution (37 mL) of Intermediate 174.3 (1.84 g, 4.46 mmol) is treated with 10% Pd/C (0.18 g), stirred for 2 h under bubbling of a continuous flow of $H_2$, treated with $N_2$ stream, and filtered on a celite pad. After washing the cake with MeOH for several times, the combined filtrate is evaporated to give the desired compound as light yellow crystalline material. $R_f$ (hexane/EtOAc 1:1) 0.33. $^1$H-NMR (270 MHz, CDCl$_3$) 1.45 (s), 1.90-1.95 (m, 2 H), 2.82 (s), 3.34 (s), 3.43 (br. s), 3.45 (t, J=6.0), 3.96(t, J=6.0), 6.25 (dd, J=9.0, 0.4), 6.36 (d, J=0.4), 6.80 (d, J=9.0). $^{13}$C-NMR (67.5 MHz, CDCl$_3$) 169.1 (s), 144.9 (s), 135.0 (s), 129.6 (s), 118.0 (d), 107.0 (d), 99.3 (d), 77.5 (s), 69.9 (t), 58.7 (q), 39.2 (t), 31.3 (q), 27.7 (t), 23.6 (2q).

Intermediate 174.3

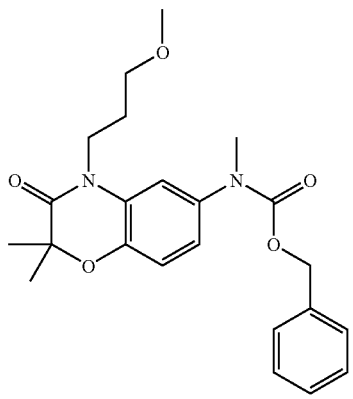

At 0° C., a solution of Intermediate 127.4 (1.811 g, 4.54 mmol) and iodomethane (1.4 mL, 22.5 mmol) in DMF (18 mL) is treated with 60% of NaH (0.228 g, 5.70 mmol) over 5 min, the mixture is stirred at 0° C. for 40 min, warmed to room temperature, stirred for 14 h, and poured into $H_2O$ (120 mL). After the extraction of the mixture with EtOAc (2×15 mL) and Et$_2$O (2×15 mL), the combined organic layer is washed with $H_2O$ (25 mL), dried (Na$_2$SO$_4$), and evaporated. SiO$_2$ flash chromatography (70 g, hexane/EtOAc 4:3) gives the desired compound as a colorless oil. $R_f$ (hexane/EtOAc 3:2) 0.42. $^1$H-NMR (400 MHz, CDCl$_3$) 1.50 (s), 1.81-1.90 (m, 2 H), 3.29 (s), 3.30 (s), 3.38 (t, J=3.5), 3.92 (t, J=3.5), 5.16 (s), 6.80-6.96 (m, 3 H), 7.20-7.33 (m, 5 H).

Example 175

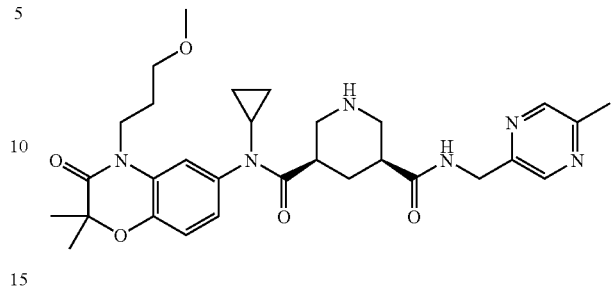

Example 175 is synthesized by deprotection of Intermediate 175.1 (75 mg, 0.11 mmol) analogously to the preparation of Example 1. White amorphous material, ES-MS: M+H=565: $_At_{Ret}$=2.20 min.

Intermediate 175.1

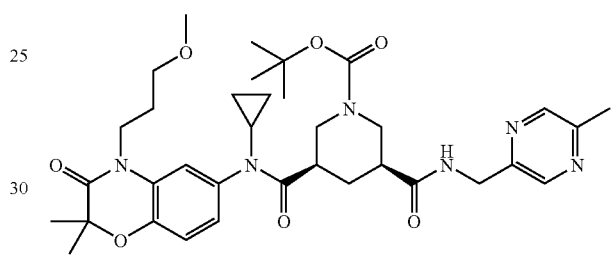

Intermediate 175.1 is synthesized by condensation of Intermediate 108.2 (100 mg, 0.18 mmol) and C-(5-Methylpyrazin-2-yl)methylamine (29 mg, 0.24 mmol) analogously to the preparation of Intermediate 1.1. Colorless oil, ES-MS: M+H=665: $_Bt_{Ret}$=1.81 min.

Example 176

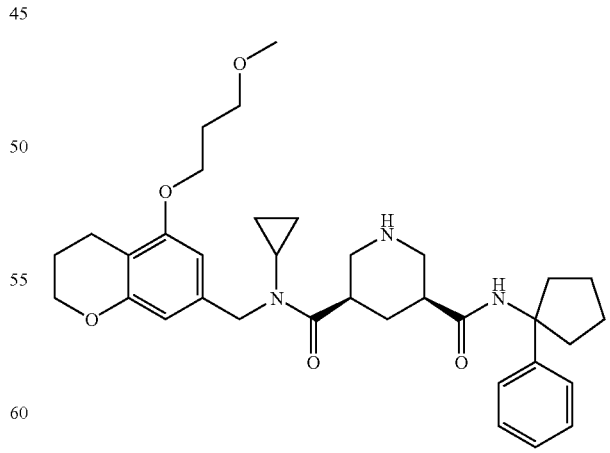

Example 176 is synthesized by deprotection of Intermediate 176.1 analogously to the preparation of example 19: ES-MS: M+H=590: $_Ct_{Ret}$=3.13 min.

Intermediate 176.1

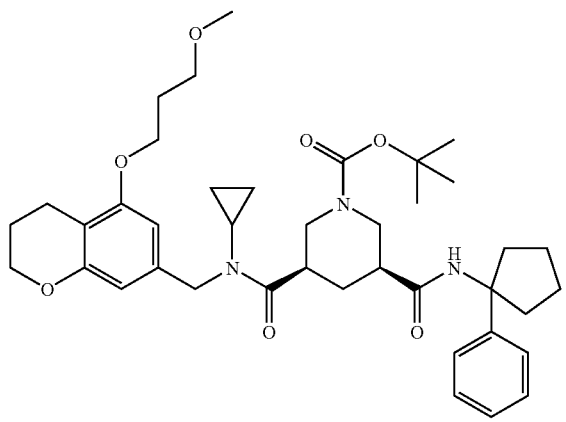

Intermediate 176.1 is synthesized by condensation of Intermediate 169.2 (79.9 mg, 0.19 mmol) and intermediate 107.2 (55.9 mg, 0.19 mmol) analogously to the preparation of Intermediate 32.3: ES-MS: M+H=690: $_C t_{Ret}$=4.50 min.

Example 177

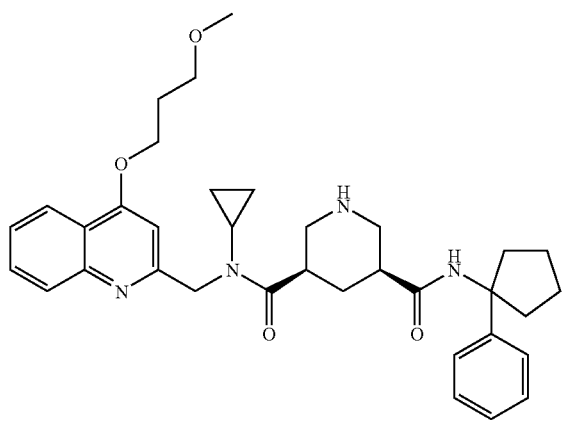

Example 177 is synthesized by deprotection of Intermediate 177.1 analogously to the preparation of example 19. ES-MS: M+H=585: $_A t_{Ret}$=2.43 min.

Intermediate 177.1

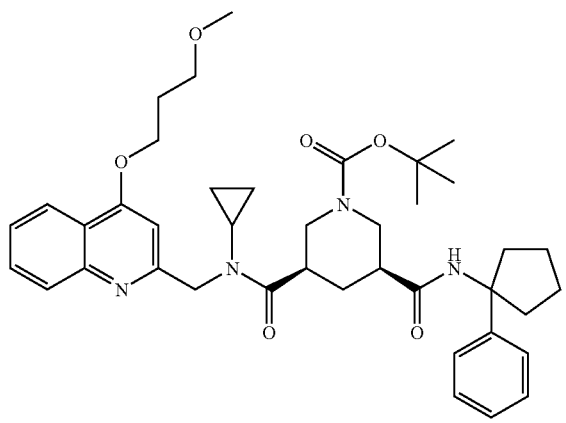

Intermediate 177.1 is synthesized by condensation of Intermediate 169.2 (107.3 mg, 0.26 mmol) and intermediate 177.2 (79.21 mg, 0.28 mmol) analogously to the preparation of Intermediate 39.1: ES-MS: M+H=585: $_A t_{Ret}$=2.43 min.

Intermediate 177.2

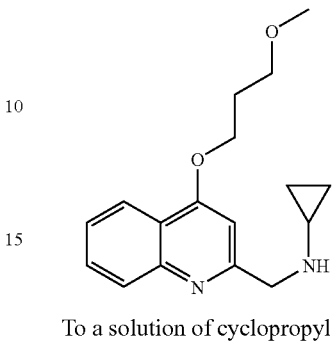

To a solution of cyclopropyl amine (2.5 mL, 35.52 mmol) in DMF (1 mL) under N$_2$ at 0° C., intermediate 177.3 hydrochloride salt (396.5 mg, 1.31 mmol) dissolved in DMF (3 mL) is slowly added. The resulting mixture is stirred at rt for 1 hour. The reaction is quenched with H$_2$O and extracted with EtOAc, washed with H$_2$O, dried over Na$_2$SO$_4$. Concentration under reduced pressure gives intermediate 177.2 (336.8 mg): ES-MS: M+H=585: $_A t_{Ret}$=2.43 min.

Intermediate 177.3

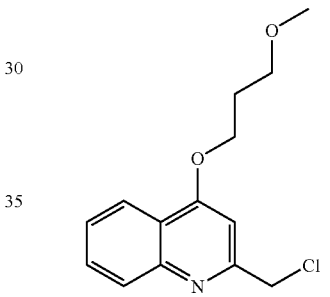

To the solution of intermediate 177.4 (293 mg, 1.184 mmol) in CH$_2$Cl$_2$ (5 mL) under N$_2$ at 0° C., SOCl$_2$ (0.43 mL, 5.92 mmol) is added. The reaction solution is stirred at rt overnight. Concentration under reduced pressure gives intermediate 177.3 hydrocholride salt. ES-MS: M+H=265.96: $_A t_{Ret}$=2.05 min.

Intermediate 177.4

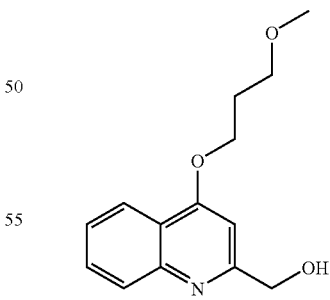

To a solution of intermediate 177.5 (624 mg, 2.26 mmol) in MeOH (50 mL) under N$_2$ at 0° C., NaBH$_4$ (112 mg, 2.96 mmol) is added. The reaction mixture is stirred at rt overnight. Then, excess NaBH$_4$ (624.5 mg, 16.54 mmol) is added to the reaction solution. The resulting solution is stirred at rt for 2 h. After concentration under reduced pressure, NaHCO$_3$ aq. is added and the resulting mixture is extracted with CH$_2$Cl$_2$, dried over Na$_2$SO$_4$. Concentration under the reduced pressure gives the crude product. The crude product is purified by silica gel chromatography to give the desired intermediate 177.4. ES-MS: M+H=248, $_A t_{Ret}$=1.82 min.

Intermediate 177.5

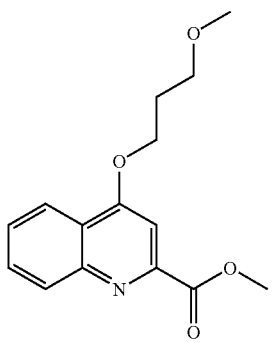

Intermediate 177.5 is synthesized by alkyaltion of methyl 4-oxo-1,4-dihydro-2-quinolinecarboxylate (*Bioorganic & Medicinal Chemistry* 20, 5453-5463, 2004) (78.4 mg, 0.38 mmol) with 3-Methoxy-propan-1-ol (0.037 mL, 0.39 mmol) analogously to the preparation of Intermediate 62.5. ES-MS: M+H=276, $_A t_{Ret}$=2.17 min.

Example 178

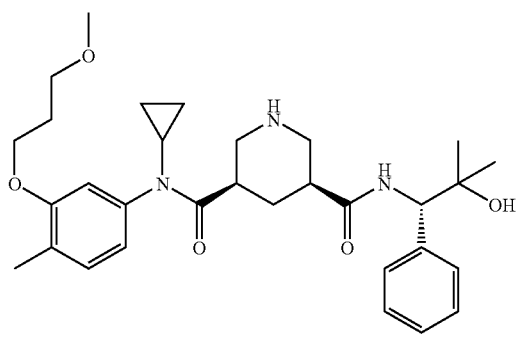

Example 178 is synthesized by condensation of Intermediate 113.2 (120 mg, 0.24 mmol) and (S)-1-Amino-2-methyl-1-phenylpropan-2-ol (65 mg, 0.32 mmol) analogously to the preparation of Intermediate 1.1 followed by deprotection of the Boc group with TMSOTf and 2,6-lutidine. ES-MS: M+H=538: $_C t_{Ret}$=3.0 min.

Example 179

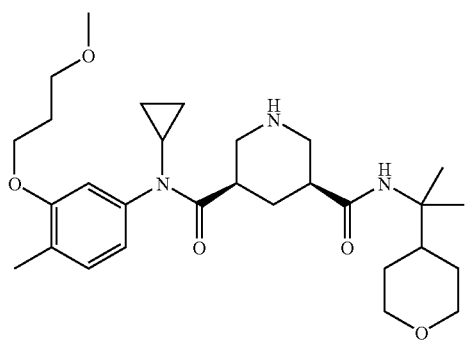

Example 179 is synthesized by deprotection of Intermediate 179.1 (93 mg, 0.15 mmol) analogously to the preparation of Example 1. White amorphous material, ES-MS: M+H=516: $_C t_{Ret}$=2.79 min.

Intermediate 179.1

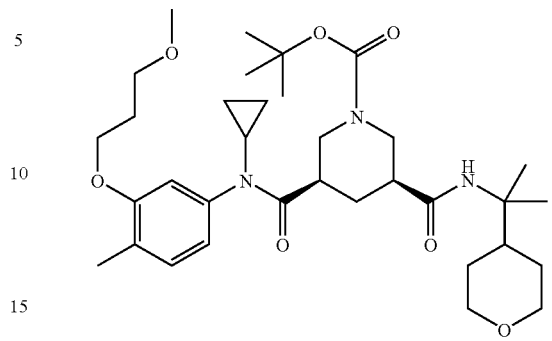

Intermediate 179.1 is synthesized by condensation of Intermediate 113.2 (120 mg, 0.25 mmol) and 1-methyl-1-(tetrahydropyran-4-yl)-ethylamine hydrochloride (*J. Med. Chem.* 1996, 39, 2795.) (88 mg, 0.49 mmol) analogously to the preparation of Intermediate 1.1. Colorless oil, ES-MS: M+H=616: $_B t_{Ret}$=2.04 min.

Example 180

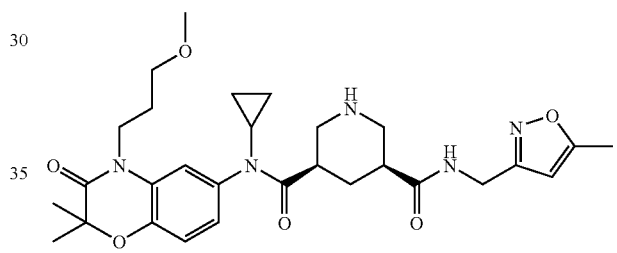

Example 180 is synthesized by condensation of Intermediate 108.2 (100 mg, 0.18 mmol) and C-(5-Methylisoxazol-3-yl)methylamine (40 mg, 0.36 mmol) analogously to the preparation of Intermediate 1.1 followed by deprotection of the Boc group with 4N HCl/dioxane. ES-MS: M+H=554: $_C t_{Ret}$=2.56 min.

Example 181

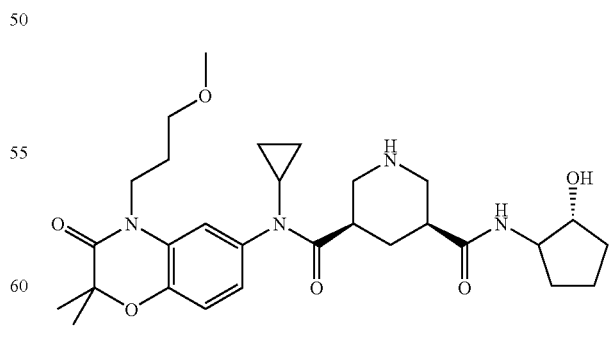

Example 181 is synthesized by deprotection of intermediate 181.1 analogously to the preparation of example 1. Diastereomers can be separated by reverse preparative HPLC M+H=543, $_C t_{Ret}$=2.33 min.

Intermediate 181.1

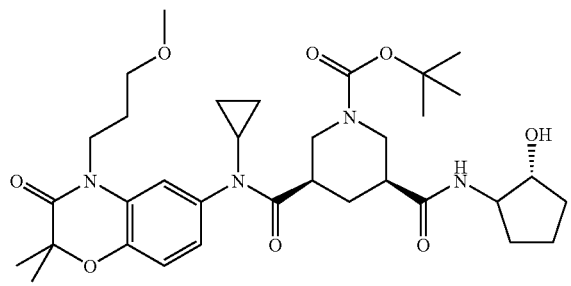

Intermediate 181.1 is synthesized by condensation of Intermediate 108.2 (150 mg, 0.268 mmol) and racemic trans-2-amino cyclopentanol (36.8 mg, 0.268 mmol) analogously to the preparation of Intermediate 32.3: ES-MS: M+H=643: $_c t_{Ret}$=3.35 min.

Example 182

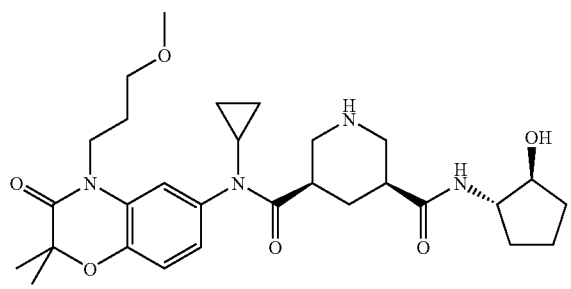

Example 182 is synthesized by deprotection of intermediate 182.1 analogously to the preparation of example 1. M+H=543, $_c t_{Ret}$=2.51 min.

Intermediate 182.1

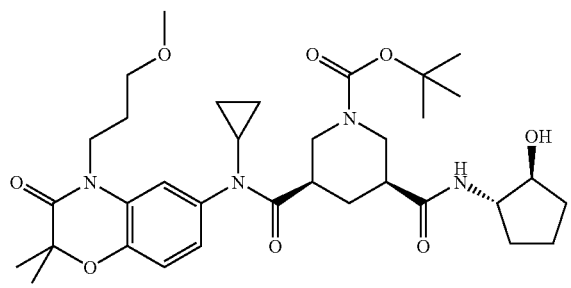

Intermediate 182.1 is synthesized by condensation of Intermediate 108.2 (150 mg, 0.268 mmol) and (1S,2S)-trans-2-amino cyclopentanol (36.8 mg, 0.268 mmol) analogously to the preparation of Intermediate 32.3: ES-MS: M+H=643: $_c t_{Ret}$=3.43 min.

Example 183

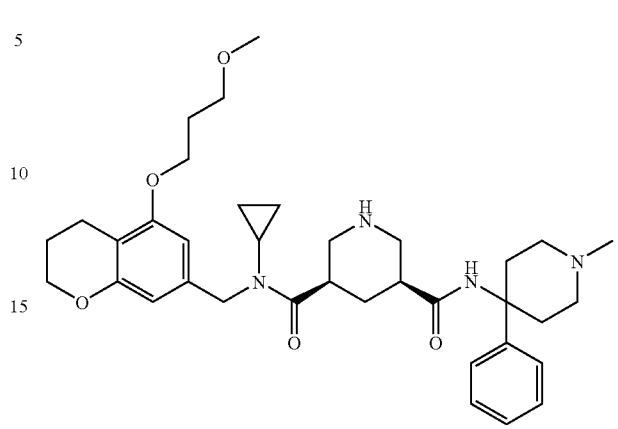

Example 183 is synthesized by deprotection of intermediate 183.1 analogously to the preparation of example 19. M+H=619, $_c t_{Ret}$=2.62 min.

Intermediate 183.1

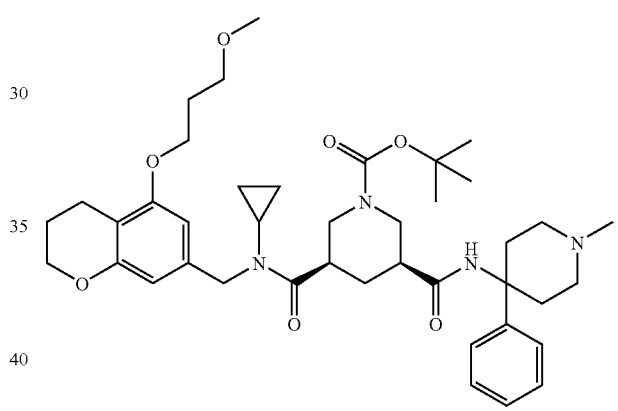

Intermediate 183.1 is synthesized by condensation of Intermediate 183.2 (62.3 mg, 0.114 mmol) and intermediate 103.2 (30 mg, 0.113 mmol) analogously to the preparation of Intermediate 32.3: ES-MS: M+H=719: $_c t_{Ret}$=3.51 min.

Intermediate 183.2

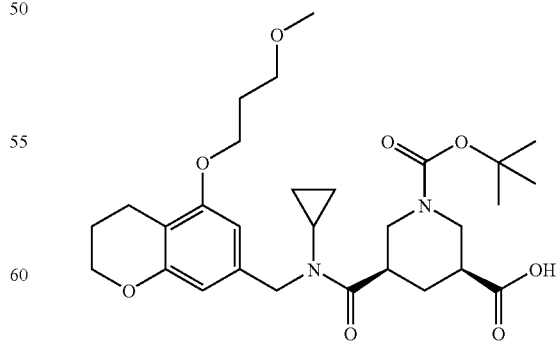

Intermediate 183.2 is synthesized by hydrolysis of Intermediate 183.3 analogously to the preparation of Intermediate 13.2: ES-MS: M+H=546: $_B t_{Ret}$=1.97 min.

Intermediate 183.3

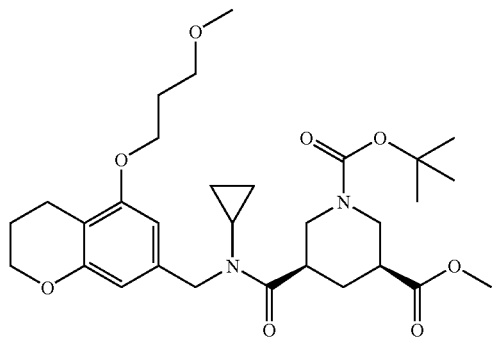

Intermediate 183.3 is synthesized by condensation of (3R, 5R)-starting material F (150 mg, 0.52 mmol) with Intermediate 95.2 (152 mg, 0.52 mmol) analogously to the preparation of Intermediate 1.3: ES-MS: M+H=561: $_B t_{Ret}$=2.14 min.

Example 184

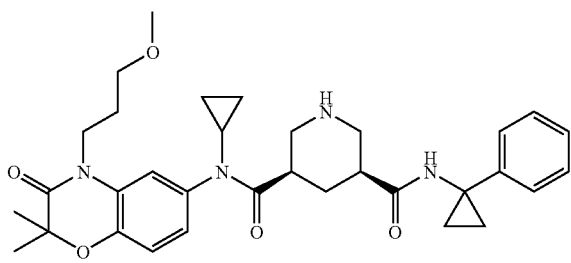

Example 184 is synthesized by deprotection of intermediate 184.1 analogously to the preparation of Example 19: ES-MS: M+H=575: $_C t_{Ret}$=2.94 min.

Intermediate 184.1

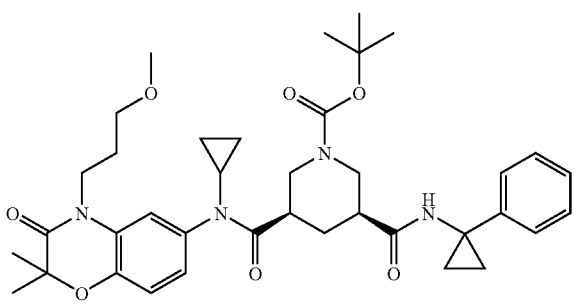

Intermediate 184.1 is synthesized by condensation of Intermediate 108.2 (112 mg, 0.2 mmol) and 1-phenyl-cyclopropylamine (32 mg, 0.24 mmol) analogously to the preparation of Intermediate 32.3. ES-MS: [M+H]⁺=675; HPLC: $_C t_{Ret}$=3.95 min.

Example 185

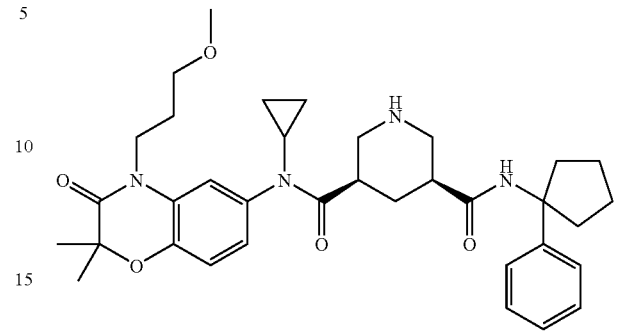

Example 185 is synthesized by a deprotection of Intermediate 185.1 (38 mg, 0.06 mmol) analogously to the preparation of intermediate 103.2: White amorphous material, ES-MS: M+H=603: $_C t_{Ret}$=2.87 min.

Intermediate 185.1

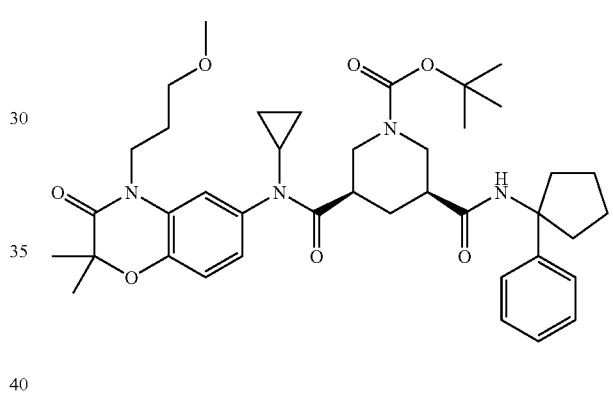

Intermediate 185.1 is synthesized by condensation of Intermediate 103.2 (21 mg, 0.11 mmol) with Intermediate 108.2 (50 mg, 0.09 mmol) analogously to the preparation of intermediate 1.1: White amorphous material, ES-MS: M+H=703: $_C t_{Ret}$=4.28 min.

Example 186

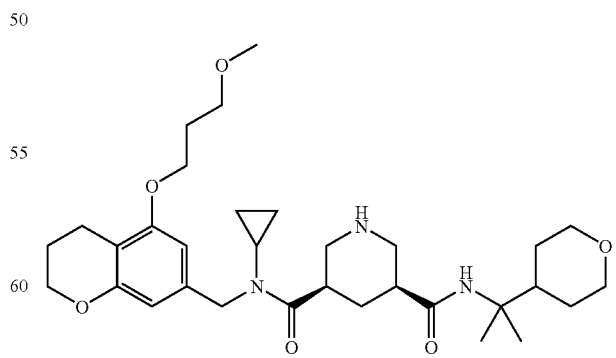

Example 186 is synthesized by deprotection of intermediate 186.1 analogously to the preparation of example 19. White material: M+H=572, $_A t_{Ret}$=2.57 min.

Intermediate 186.1

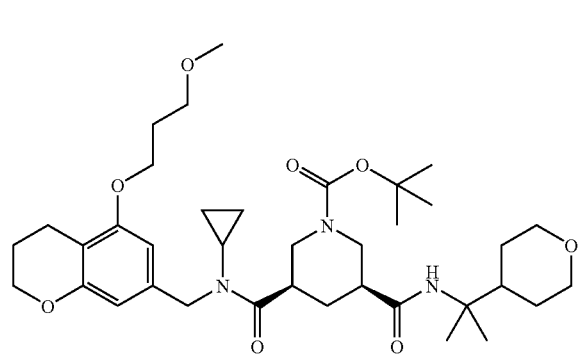

Intermediate 186.1 is synthesized by condensation of Intermediate 181.2 (46.7 mg, 0.085 mmol) and 1-methyl-1-(tetrahydropyran-4-yl)-ethylamine hydrocholoride (*J. Med. Chem.* 1996, 39, 2795.) (23 mg, 0.128 mmol) analogously to the preparation of Intermediate 32.3: ES-MS: M+H=672: $_A t_{Ret}$=3.79 min.

Example 187

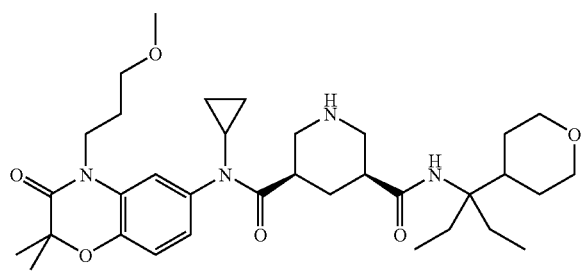

Example 187 is synthesized by deprotection of intermediate 187.1 analogously to the preparation of example 19: M+H=613, $_c t_{Ret}$=3.01 min.

Intermediate 187.1

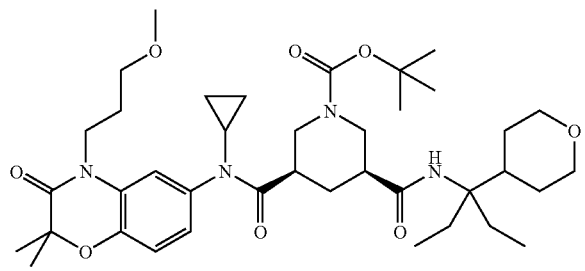

Intermediate 187.1 is synthesized by condensation of Intermediate 108.2 (150 mg, 0.268 mmol) and Intermediate 187.2 hydrochloride (105 mg, 0.51 mmol) analogously to the preparation of Intermediate 32.3: ES-MS: M+H=713: $_c t_{Ret}$=4.05 min.

Intermediate 187.2

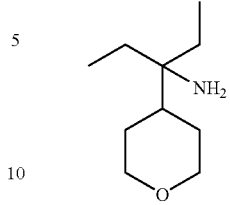

Intermediate 187.2 is synthesized by deprotection of Intermediate 187.3 analogously to the preparation of example 19: M+H=172, $_A t_{Ret}$=1.20 min.

Intermediate 187.3

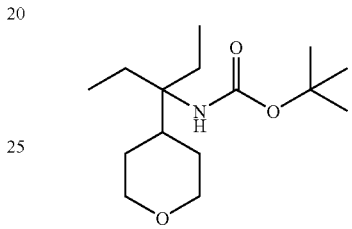

To a solution of Intermediate 187.4 (1.1565 g, 4.66 mmol) in EtOH (10 mL)/AcOH (2 mL) under $N_2$ at rt, thiourea (426 mg, 5.6 mmol) is added. The reaction mixture is stirred at 80° C. for 9 h. Concentration under reduced pressure gives the desired amine.

To a solution of crude product in $CH_2Cl_2$ (20 mL) under $N_2$ at RT, triethyl amine (2.25 mL, 23.3 mmol) and $Boc_2O$ (2.5 g, 11.65 mmol) are added. The reaction mixture is stirred at rt for 1.5 h. Concentration under reduced pressure gives the crude product. The crude product is purified by silica gel chromatography to afford the desired Intermediate 187.3. M+H-Boc=172, $_A t_{Ret}$=3.55 min.

Intermediate 187.4

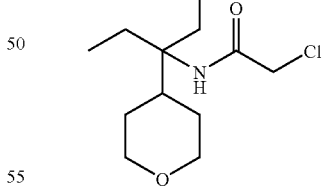

To a solution of 3-(Tetrahydro-pyran-4-yl)-pentanol (Collection of Czechoslovak Chemical Communications (1938), 10 399-410.) (991.1 mg, 5.75 mmol) and Chloroacetonitrile (0.44 mL) in AcOH (0.88 mL) under $N_2$ at 0° C., c. $H_2SO_4$ (0.88 mL) is slowly added. Then, the reaction solution is warmed to rt and stirred at rt overnight. The reaction is quenched with sat. $NaHCO_3$ aq. and extracted with EtOAc, dried over $MgSO_4$. Concentration under the reduced pressure gives intermediate 187.4 (1.16 g). M+H=248, $_A t_{Ret}$=2.57 min.

Example 188

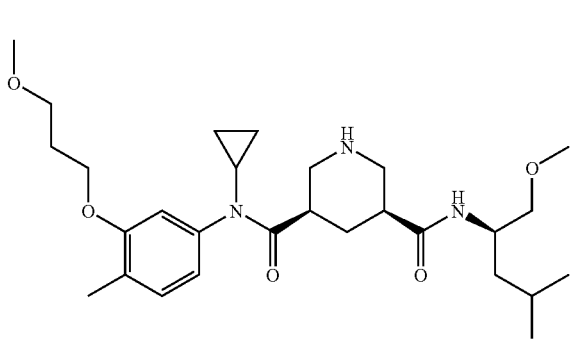

Example 188 is synthesized by deprotection of intermediate 188.1 analogously to the preparation of example 19. White material: M+H=504, $_c t_{Ret}$=3.06 min.

Intermediate 188.1

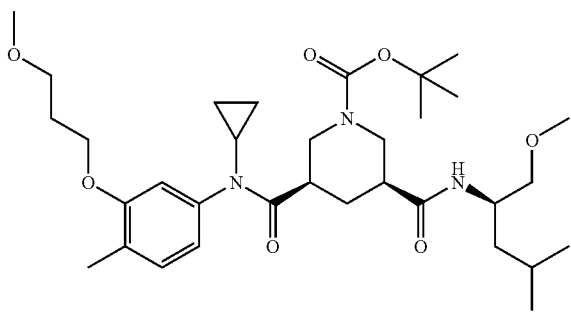

Intermediate 188.1 is synthesized by condensation of Intermediate 113.2 (72.8 mg, 0.148 mmol) and (R)-1-methoxymethyl-3-methylbutylamine hydrochloride (*Org. Lett.* 2001, 3, 1241) (105 mg, 0.51 mmol) analogously to the preparation of Intermediate 32.3: White material. ES-MS: M+H=604: $_c t_{Ret}$=4.30 min.

Example 189

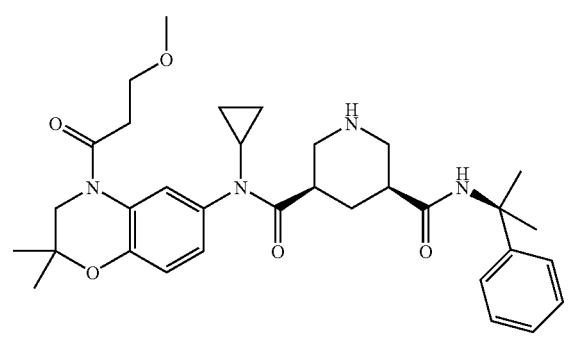

Example 189 is synthesized by deprotection of Intermediate 189.1 (175 mg, 0.26 mmol) analogously to the preparation of Example 1. White amorphous material, ES-MS: M+H=577: $_c t_{Ret}$=2.99 min.

Intermediate 189.1

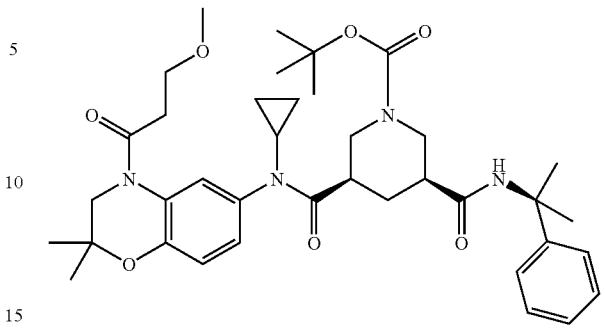

Intermediate 189.1 is synthesized by condensation of Intermediate 173.2 (160 mg, 0.41 mmol) and Intermediate 189.2 (125 mg, 0.41 mmol) analogously to the preparation of Intermediate 19.1. Colorless oil, ES-MS: M+H=677: $_B t_{Ret}$=2.1 min.

Intermediate 189.2

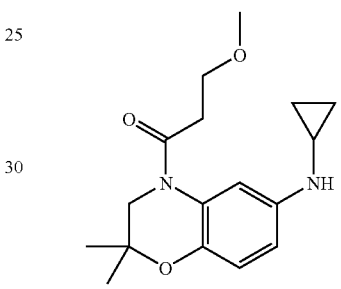

At room temperature, a methanolic solution (7.5 mL) of Intermediate 189.3 (941 mg, 3.56 mmol) is treated with AcOH (1.9 mL) and [(1-ethoxycycopropyl)-oxy]trimethylsilane (0.71 mL, 3.56 mmol), warmed to 60° C., stirred for 1 h under reflux. At the same temperature, to this mixture is added dropwise a methanolic solution (1.3 mL) of NaBH$_3$CN (0.255 g, 4.06 mmol) over 5 min, and the resulting mixture is stirred at 60° C. under reflux for 2 h, and treated with CH$_2$Cl$_2$ (50 mL) and 5 N NaOH (10 mL). After separating both layers, the aqueous layer is extracted with CH$_2$Cl$_2$ (3×10 mL). The combined organic layer is washed with brine (15 mL), dried (Na$_2$SO$_4$), and evaporated. SiO$_2$ flash chromatography (30 g, hexane/EtOAc 1:1) gives the desired compound as a yellow solid. R$_f$ (hexane/EtOAc 1:1) 0.48. $^1$H-NMR (400 MHz, CDCl$_3$) 0.48-0.53 (m, 2 H), 0.68-0.73 (m, 2 H), 1.30 (s), 2.34-2.41 (m, 1 H), 2.95 (br. s), 3.32 (s), 3.74 (br. s), 3.76 (t, J=6.0), 3.96 (br. s), 6. 54 (dd, J=9.0, 0.4), 6.60-6.81 (m, 1 H), 6.68 (d, J=9.0).

Intermediate 189.3

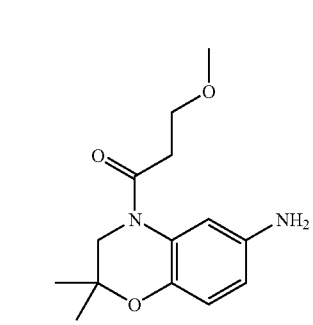

At room temperature, a solution of Intermediate 189.4 (1.178 g, 4.00 mmol) in EtOAc (18 mL) is treated with tin(II) chloride dihydrate (3.15 g, 14.0 mmol), heated to 80° C., stirred for 6 h under reflux, cooled to 0° C., and treated with 5 N NaOH (20 mL). The resulting precipitate is removed off by filtration, and washed with EtOAc for several times. After separating the both layers of the combined filtrate, the organic layer is washed with brine (20 mL), dried (Na$_2$SO$_4$), and evaporated to give the desired compound as a brown oil. R$_f$ (CH$_2$Cl$_2$/EtOAc 1:1) 0.30. $^1$H-NMR (400 MHz, CDCl$_3$) 1.32 (s), 2.91 (br. s), 3.34 (s), 3.42 (br. s), 3.71 (br. s), 3.78 (t, J=6.0), 6.46 (dd, J=9.0, 0.4), 6.46-6.68 (m, 1H), 6.68 (d, J=9.0).

Intermediate 189.4

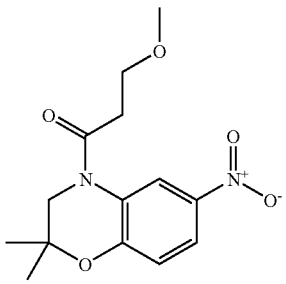

At 0° C., a solution of Intermediate 189.5 (1.090 g, 5.23 mmol) in DMF (11 mL) is treated with K$_2$CO$_3$ (2.39 g, 17.3 mmol) and 3-methoxypropionic chloride (0.85 mL, 7.83 mmol), stirred at the same temperature for 30 min, warmed to room temperature, stirred for 20 h, and treated with furthermore acid chloride (0.85 mL, 7.83 mmol). After stirring for 3 h, the mixture is treated with additional acid chloride (4.0 mL, 36.9 mmol), stirred at the ambient temperature for 1 h, treated with 1 N NaOH (30 mL), and extracted with EtOAc (3×20 mL) and Et$_2$O (3×20 mL). The combined organic layer is washed with 1 N NaOH (15 mL), 5 N NaOH (15 mL), and H$_2$O (2×20 mL), dried (Na$_2$SO$_4$), and evaporated. SiO$_2$ flash chromatography (60 g, hexane/EtOAc 3:4) gives the desired compound as yellow crystalline. R$_f$ (hexane/EtOAc 1:1) 0.40. $^1$H-NMR (400 MHz, CDCl$_3$) 1.37 (s), 2.84-2.93 (m, 2 H), 3.38 (s), 3.72-3.84 (m, 2 H), 3.81 (t, J=6.0), 6.95 (d, J=9.0), 7.94 (dd, J=9.0, 0.4), 7.94-8.93 (m, 1H). $^{13}$C-NMR (100 MHz, CDCl$_3$) 170.1 (s), 140.4 (s), 121.7 (s), 120.3 (d), 117.8 (s and 2d), 77.2 (s), 68.7 (t), 59.0 (q), 34.4 (t), 24.6 (2q).

Intermediate 189.5

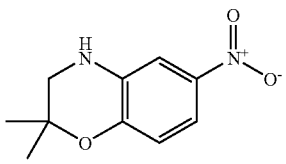

At 0° C., solid state of 2,2-dimethyl-6-nitro-4H-benzo[1,4]oxazin-3-one (5.763 g, 25.9 mmol) is added to 1.0 M BH$_3$-THF solution (65 mL, 65.0 mmol). The mixture is stirred at the same temperature for 15 min, warmed to 80° C., stirred for 3 h under reflux, cooled to 0° C., and slowly treated with MeOH (8 mL). After stirring at 80° C. for 1 h under reflux, the solution is cooled to 0° C. again, treated with 12 N HCl (8 mL), warmed to 80° C., stirred for 1 h under reflux, and evaporated. After washing the residue with Et$_2$O for several times, the solid is treated with 280 mL of 0.2 N NaOH. The resulting precipitate is collected by filtration, and washed with H$_2$O several times to give the desired compound as a yellow solid. R$_f$ (hexane/EtOAc 2:1) 0.50. $^1$H-NMR (400 MHz, CDCl$_3$) 1.38 (s), 3.12 (s), 4.11 (br. s), 6.78 (d, J=9.0), 7.49 (d, J=0.4), 7.58 (dd, J=9.0, 0.4).

Example 190

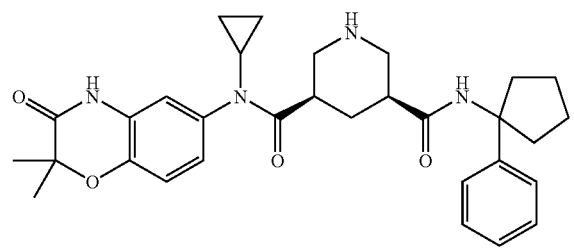

Example 190 is synthesized by deprotection of Intermediate 190.1 (70 mg, 0.11 mmol) analogously to the preparation of intermediate 103.2: White amorphous material, ES-MS: M+H=531: $ct_{Ret}$=3.00 min.

Intermediate 190.1

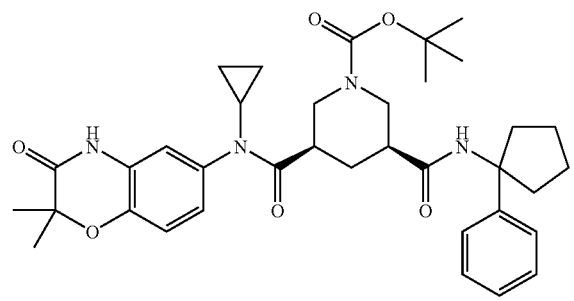

Intermediate 190.1 is synthesized by condensation of Intermediate 169.2 (50 mg, 0.12 mmol) with Intermediate 190.2 (45 mg, 0.18 mmol) analogously to the preparation of intermediate 19.1.: White amorphous material, ES-MS: M+H=631: $ct_{Ret}$=3.95 min.

Intermediate 190.2

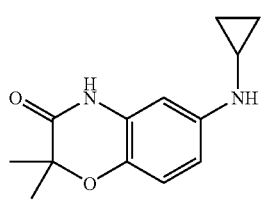

At room temperature, a methanolic solution (240 mL) of Intermediate 190.3 (28.2 g, 0.147 mol) is treated with AcOH (60 mL) and [(1-ethoxycycopropyl)-oxy]trimethylsilane (29 mL, 0.147 mol, Aldrich), warmed to 70° C., stirred for 2 h under reflux. At the same temperature, to this mixture is added dropwise a methanolic solution (50 mL) of NaBH$_3$CN (10.1 g, 0.161 mol) over 5 min, and the resulting mixture is stirred at 70° C. under reflux for 2 h, and treated with CH$_2$Cl$_2$ (800 mL) and 5 N NaOH (400 mL). After separation of the both layers, the aqueous layer is extracted with CH$_2$Cl$_2$ (3×200 mL). The combined organic layer is washed with brine (300 mL), dried (Na$_2$SO$_4$), and evaporated. SiO$_2$ flash chromatography (1000 g, hexane/EtOAc 5:4) gives the desired product as a white solid. R$_f$ (hexane/EtOAc 5:4) 0.48. $^1$H-NMR (400 MHz, CDCl$_3$) 0.46-0.53 (m, 2 H), 0.64-0.73 (m, 2 H), 1.50 (s), 2.36-2.43 (m, 1 H), 4.06 (br. s), 6.25 (d, J=0.4), 6.39 (dd, J=9.0, 0.4), 6.79 (d, J=9.0). $^{13}$C-NMR (100 MHz, CDCl₃) 170.7 (s), 144.3 (s), 134.5 (s), 127.2 (s), 118.0 (d), 108.6 (d), 99.9 (d), 77.8 (s), 25.7 (d), 23.4 (2q), 7.3 (2t).

Intermediate 190.4

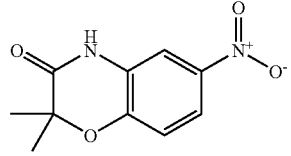

At room temperature, a solution of 2-amino-4-nitrophenol (82.5 g, 0.54 mol, Tokyo Chemical Industry) in DMF (660 mL) is treated with ethyl 2-bromoisobutyrate (160 mL, 1.07 mol) and KF (124.7 g, 2.15 mol), stirred at the same temperature for 1 h, warmed to 60° C., and stirred for 48 h. After pouring the mixture into H₂O (3500 mL), the resulting precipitate is collected by filtration, and washed with H₂O and Et₂O for several times to give the desired product as a yellow solid. $R_f$ (hexane/EtOAc 2:1) 0.42. ¹H-NMR (400 MHz, DMSO-d6) 1.48 (s), 7.16 (d, J=9.0), 6.42 (d, J=0.4), 8.00 (dd, J=9.0, 0.4). ¹³C-NMR (100 MHz, DMSO-d6) 167.7 (s), 147.5 (s), 142.0 (s), 128.0 (s), 119.2 (d), 117.3 (d), 110.3 (d), 78.9 (s), 23.7 (2q).

Example 191

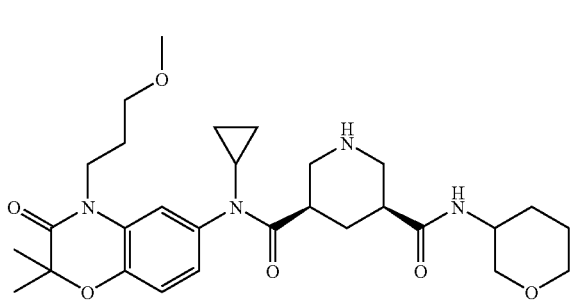

Example 191 is synthesized by deprotection of intermediate 191.1 analogously to the preparation of Example 19: ES-MS: M+H=542: $_c t_{Ret}$=2.53, 2.57 min.

Intermediate 191.1

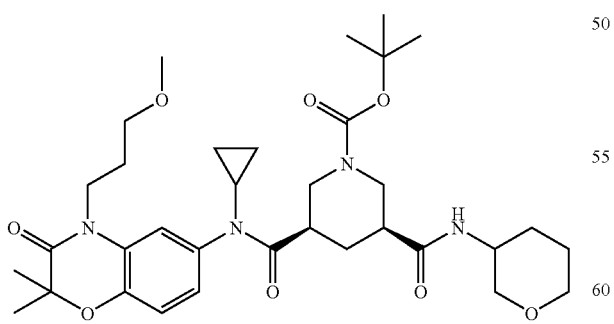

Intermediate 191.1 is synthesized by condensation of Intermediate 108.2 (70 mg, 0.125 mmol) with tetrahydropyran-3-yl-amine (25 mg, 0.182 mmol, CAS-675112-58-0) analogously to the preparation of intermediate 32.3: ES-MS: M+H=642: $_B t_{Ret}$=1.93 min.

Example 192

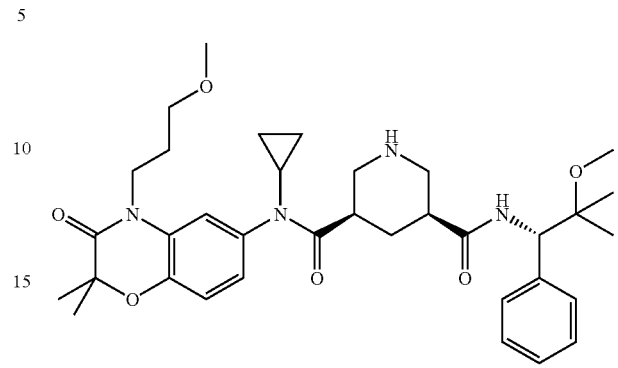

Example 192 is synthesized by deprotection of intermediate 192.1 analogously to the preparation of example 19. White material: M+H=621 $_c t_{Ret}$=3.20 min.

Intermediate 192.1

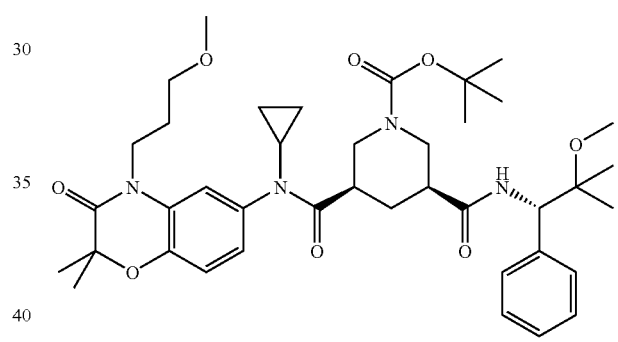

Intermediate 192.1 is synthesized by condensation of Intermediate 108.2 (32.9 mg, 0.058 mmol) and Intermediate 192.2 hydrochloride (12.7 mg, 0.058 mmol) analogously to the preparation of Intermediate 32.3: ES-MS: M+H=721: $_c t_{Ret}$=4.24 min.

Intermediate 192.2

Intermediate 192.2 is synthesized by deprotection of intermediate 192.3 analogously to the preparation of example 19. White material (for hydrochloride salt): M+H=180 $_c t_{Ret}$=1.90 min.

Intermediate 192.3

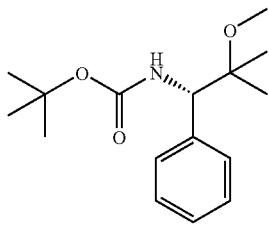

To a solution of ((S)-2-Hydroxy-2-methyl-1-phenyl-propyl)-carbamic acid tert-butyl seter (*Synthesis*, 2004, 909) (112.1 mg, 0.422 mmol) in DMF (3 mL) under $N_2$ at 0° C., NaH (71 mg of 60 wt % in mineral oil, 1.78 mmol) is added. After stirring at rt for 10 min, the solution cooled down at 0° C. Then, methyl iodine (26.27 µL, 0.422 mmol) is added to the reaction mixture. The reaction solution is stirred at rt for 1.25 h. The reaction is quenched with sat. $KHSO_4$ aq. and extracted with EtOAc, washed with $H_2O$, dried over $MgSO_4$. Concentration under reduced pressure gives the crude product. The crude product is purified on silica gel to give the desired intermediate 192.3. M+H-tBu=224 $_ct_{Ret}$=3.97 min.

Example 193

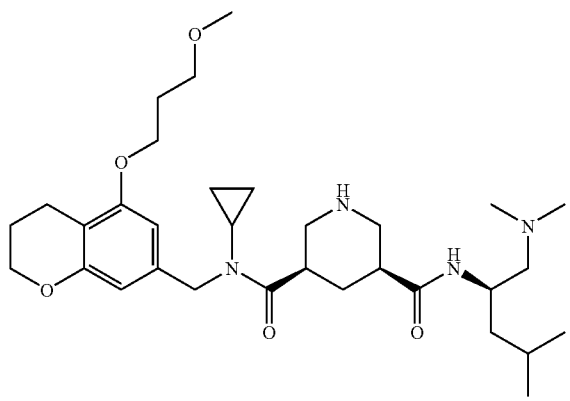

Example 193 is synthesized by deprotection of intermediate 193.1 analogously to the preparation of example 19. White material: M+H=573 $_ct_{Ret}$=2.67 min.

Intermediate 193.1

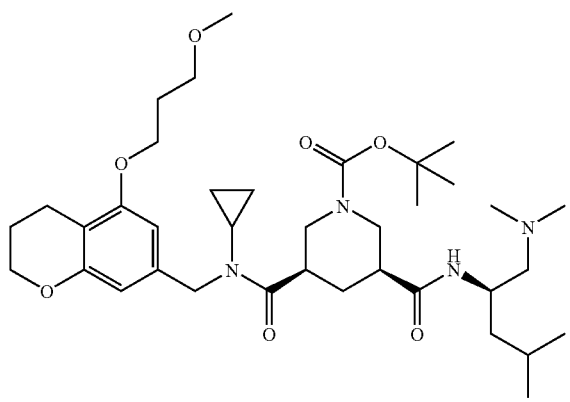

Intermediate 193.1 is synthesized by condensation of Intermediate 183.2 (38.2 mg, 0.0698 mmol) and (R)-4,N*1*,N*1*-trimethylpentane-1,2-diamine hydrochloride (WO2006009869) mg, 0.0698 mmol) analogously to the preparation of Intermediate 32.3: ES-MS: M+H=673: $_ct_{Ret}$=3.65 min.

Example 194

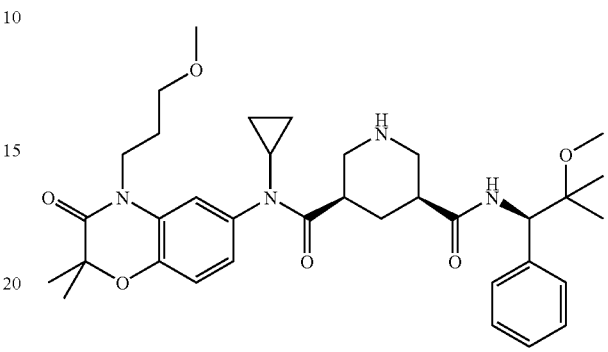

Example 194 is synthesized by deprotection of intermediate 194.1 analogously to the preparation of example 19. White material: M+H=621 $_ct_{Ret}$=3.18 min.

Intermediate 194.1

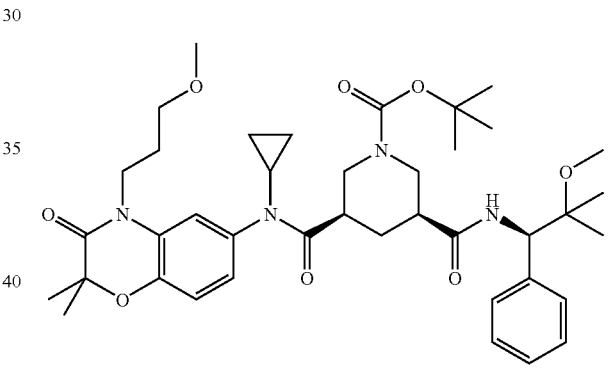

Intermediate 194.1 is synthesized by condensation of Intermediate 108.2 (21.26 mg, 0.038 mmol) and Intermediate 194.2 hydrochloride (13.7 mg, 0.063 mmol) analogously to the preparation of Intermediate 32.3: ES-MS: M+H=721: $_ct_{Ret}$=4.25 min.

Intermediate 194.2

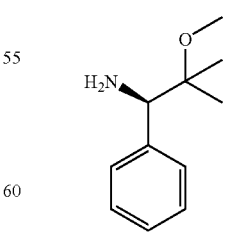

Intermediate 194.2 is synthesized by deprotection of intermediate 194.3 analogously to the preparation of example 19. White material (for hydrochloride salt): M+H=180 $_ct_{Ret}$=1.89 min.

Intermediate 194.3

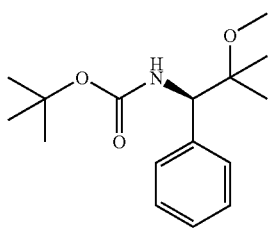

Intermediate 194.3 is synthesized by alkylation of ((R)-2-Hydroxy-2-methyl-1-phenylpropyl)-carbamic acid tert-butyl seter (Journal of the Chemical Society, Perkin Transactions 1: Organic and Bio-Organic Chemistry (1999), (4), 387-398.) analogously to the preparation of intermediate 192.3: M+H-Bu=224 $_ct_{Ret}$=3.96 min.

Example 195

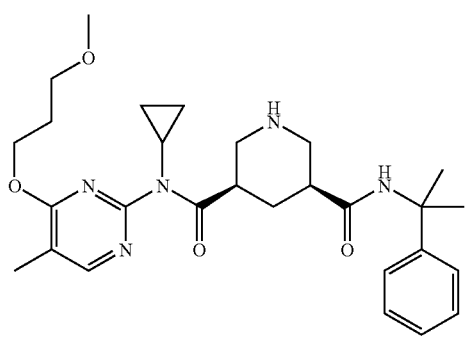

Example 195 is synthesized by deprotection of intermediate 195.1 analogously to the preparation of Example 19: ES-MS: M+H=509: $_ct_{Ret}$=2.86 min.

Intermediate 195.1

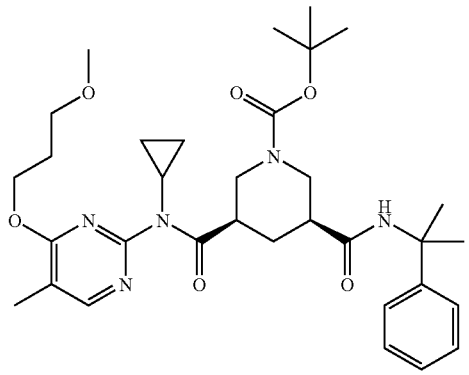

Intermediate 195.1 is synthesized by condensation of Intermediate 195.2 (34 mg, 0.143 mmol) and intermediate 173.2 (46 mg, 0.118 mmol) analogously to the preparation of example 125: colorless oil; ES-MS: M+H=609: $_ct_{Ret}$=3.83 min.

Intermediate 195.2

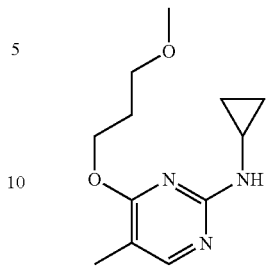

A mixture of intermediate 195.3 (260 mg, 1.2 mmol) and cyclopropylamine (210 mg, 3.7 mmol) in THF (4 mL) is stirred in sealed tube at 100° C. for 10 h, then it is irradiated by microwave at 180° C. for 30 min. After dilution with EtOAc, the mixture is washed with water and brine, dried over Mg$_2$SO$_4$, filtered, and concentrated in vacuo. The residue is purified by silica gel column chromatography to afford intermediate 195.2: pale yellow oil; $^1$H-NMR (CDCl$_3$, 400 MHz): δ 0.51 (2H, m), 0.78 (2H, m), 1.98 (3H, s), 2.03 (2H, quint.), 2.71 (1H, m), 3.35 (3H, s), 3.52 (2H, t), 4.37 (2H, t), 5.03 (1H, br), 7.87 (1H, s).

Intermediate 195.3

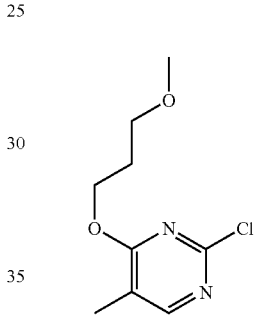

To a solution of 3-methoxy-propan-1-ol (1.4 g, 15.5 mmol) in THF (20 mL) is added NaH (60%, 440 mg, 11 mmol) at 0° C. After stirring for 30 min, the resulting solution is transferred into a solution of 2,4-dichloro-5-methylpyrimidine (2 g, 12.3 mmol) at −8° C. The mixture is stirred for 50 min, then the reaction is quenched with the addition of aq. KHSO$_4$. The mixture is extracted with ether, and the extracts are washed with water and brine. The organic layer is dried over Mg$_2$SO$_4$, filtered, and concentrated in vacuo. The residue is purified by silica gel column chromatography to afford intermediate 195.3: colorless oil; $^1$H-NMR (CDCl$_3$, 400 MHz): δ 2.05 (2H, quint.), 2.13 (3H, s), 3.37 (3H, s), 3.53 (2H, t), 4.48 (2H, t), 8.81 (1H, s).

Example 196

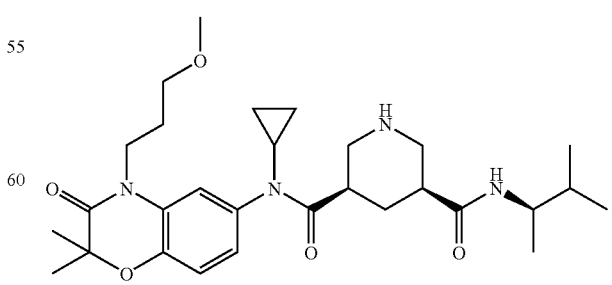

Example 196 is synthesized by deprotection of intermediate 196.1 analogously to the preparation of Example 19: ES-MS: M+H=529: $_ct_{Ret}$=2.89 min.

Intermediate 196.1

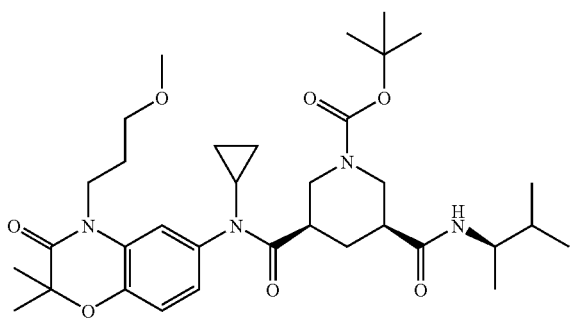

Intermediate 196.1 is synthesized by condensation of Intermediate 108.2 (102 mg, 0.18 mmol) with (R)-(−)-2-amino-3-methylbutane (23 μL, 0.20 mmol) analogously to the preparation of intermediate 32.3: ES-MS: M+H=629: $_ct_{Ret}$=3.93 min.

Example 197

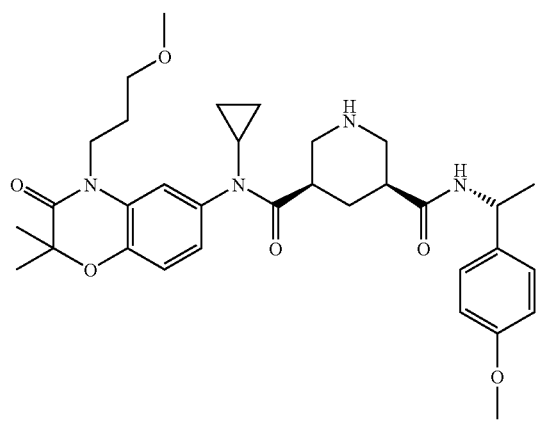

Example 197 is synthesized by deprotection of intermediate 197.1 analogously to the preparation of Example 19: ES-MS: M+H=593: $_ct_{Ret}$=2.96 min.
Intermediate 197.1

Intermediate 197.1 is synthesized by condensation of Intermediate 108.2 (101 mg, 0.18 mmol) with (R)-(+)-4-methoxy-α-methylbenzylamine (29 μL, 0.20 mmol) analogously to the preparation of intermediate 32.3: ES-MS: M+H=693: $_ct_{Ret}$=3.97 min.

Example 198

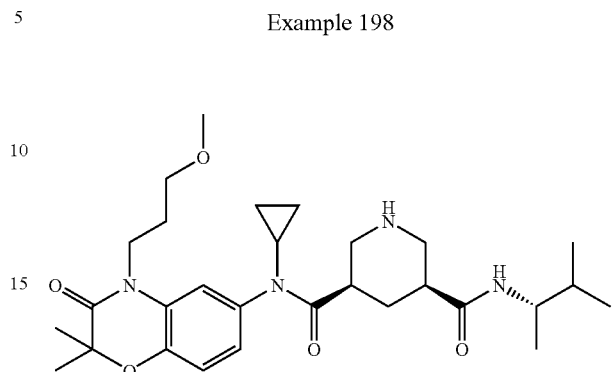

Example 198 is synthesized by deprotection of intermediate 198.1 analogously to the preparation of Example 19: ES-MS: M+H=529: $_ct_{Ret}$=2.87 min.
Intermediate 198.1

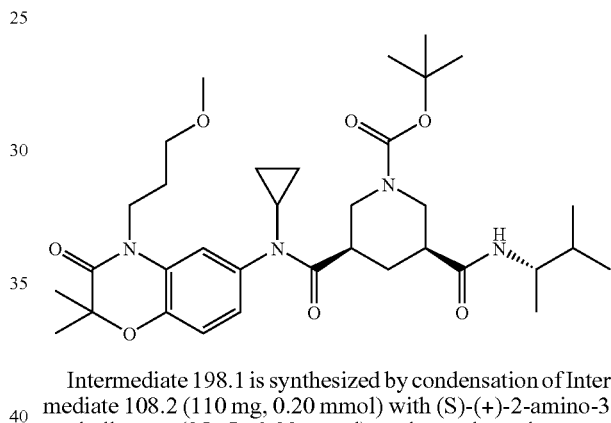

Intermediate 198.1 is synthesized by condensation of Intermediate 108.2 (110 mg, 0.20 mmol) with (S)-(+)-2-amino-3-methylbutane (25 μL, 0.22 mmol) analogously to the preparation of intermediate 32.3: ES-MS: M+H=629: $_ct_{Ret}$=3.96 min.

Example 199

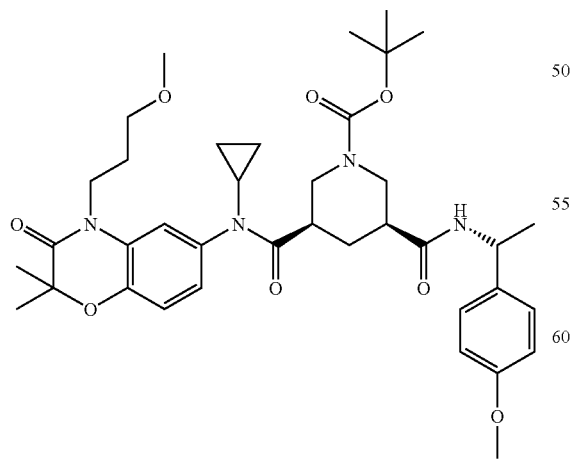

Example 199 is synthesized by deprotection of intermediate 199.1 analogously to the preparation of Example 19: ES-MS: M+H=593: $_ct_{Ret}$=2.97 min.

Intermediate 199.1

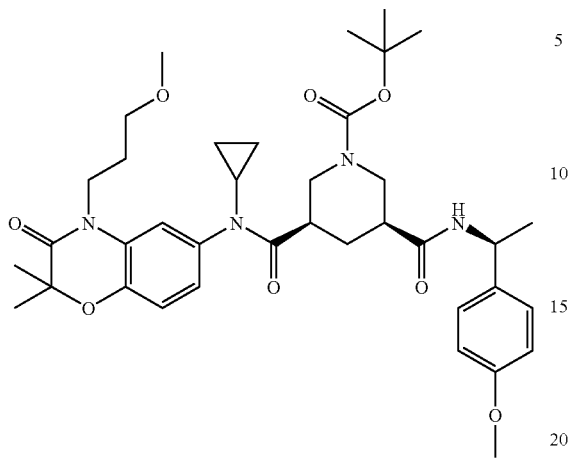

Intermediate 199.1 is synthesized by condensation of Intermediate 108.2 (103 mg, 0.18 mmol) with (S)-(−)-4-methoxy-α-methylbenzylamine (30 µL, 0.20 mmol) analogously to the preparation of intermediate 32.3: ES-MS: M+H=693: $_Ct_{Ret}$=3.98 min.

Example 200

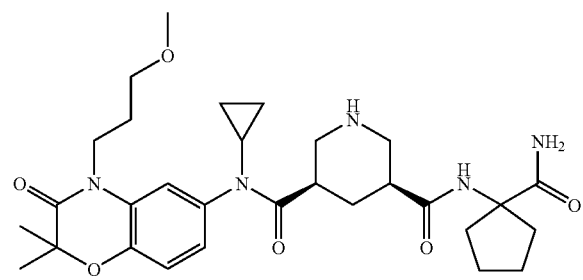

Example 200 is synthesized by deprotection of intermediate 200.1 (100 mg, 0.15 mmol) analogously to the preparation of intermediate 103.2. White amorphous material, ES-MS: M+H=570: $_Ct_{Ret}$=2.54 min.

Intermediate 200.1

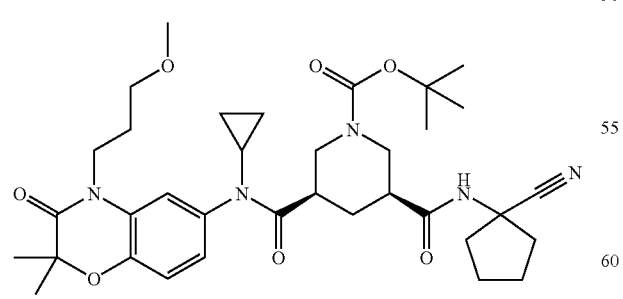

Intermediate 200.1 is synthesized by condensation of 1-aminocyclopentanecarbonitrile hydrochloride (32 mg, 0.216 mmol) with Intermediate 108.2 (100 mg, 0.18 mmol) analogously to the preparation of intermediate 1.1: white amorphous material, ES-MS: M+H=652: $_Ct_{Ret}$=3.81 min.

Example 201

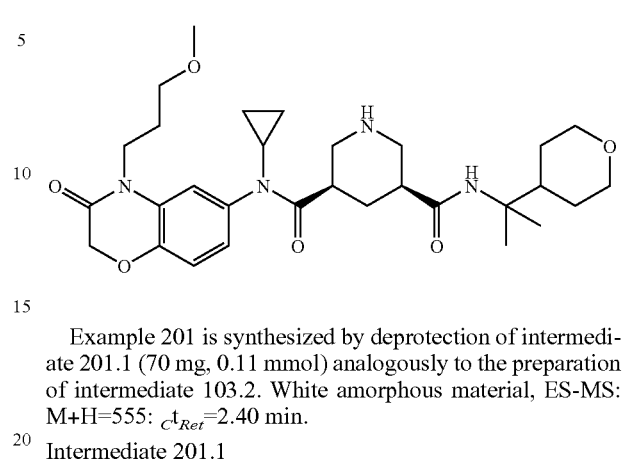

Example 201 is synthesized by deprotection of intermediate 201.1 (70 mg, 0.11 mmol) analogously to the preparation of intermediate 103.2. White amorphous material, ES-MS: M+H=555: $_Ct_{Ret}$=2.40 min.

Intermediate 201.1

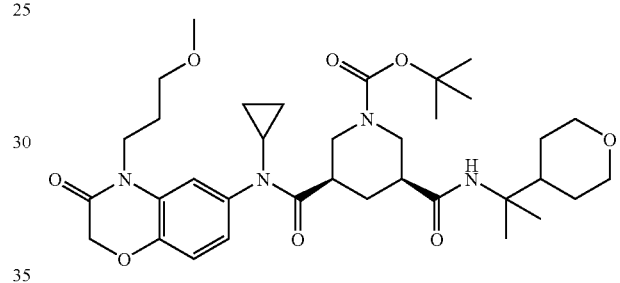

Intermediate 201.1 is synthesized by condensation of intermediate 201.2 (100 mg, 0.19 mmol) with 1-methyl-1-(tetrahydro-pyran-4-yl)ethylamine (28 mg, 0.22 mmol) analogously to the preparation of intermediate 1.1: white amorphous material, ES-MS: M+H=655: $_Ct_{Ret}$=3.32 min.

Intermediate 201.2

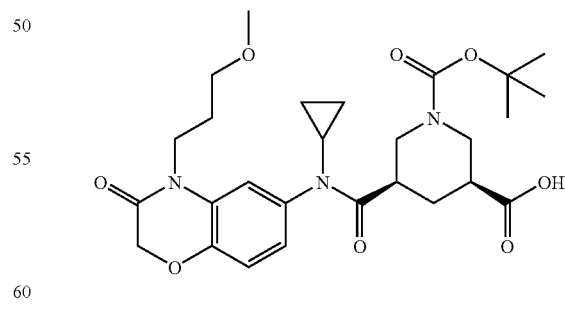

Intermediate 201.2 is synthesized by hydrolysis of Intermediate 201.3 (400 mg, 0.74 mmol) analogously to the preparation of intermediate 13.2. White amorphous material, ES-MS: M+H=530: $_Ct_{Ret}$=3.05 min.

Intermediate 201.3

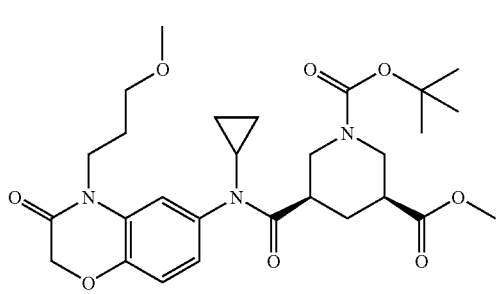

Intermediate 201.3 is synthesized by condensation of intermediate 19.3 (303 mg, 1.04 mmol) with (3R,5S)-Starting material-F (250 mg, 0.87 mmol) analogously to the preparation of intermediate 19.1. White amorphous material, ES-MS: M+H=544: $c_{t_{Ret}}$=3.42 min.

Example 202

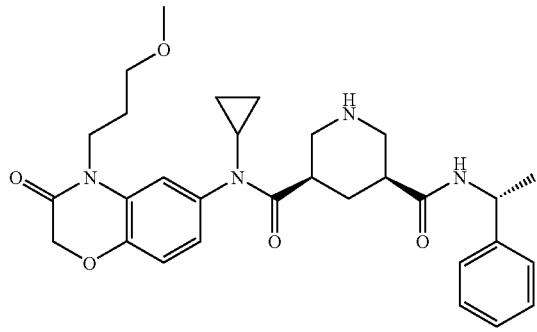

Example 202 is synthesized by deprotection of intermediate 202.1 (80 mg, 0.13 mmol) analogously to the preparation of intermediate 103.2. White amorphous material, ES-MS: M+H=633: $c_{t_{Ret}}$=2.66 min.

Intermediate 202.1

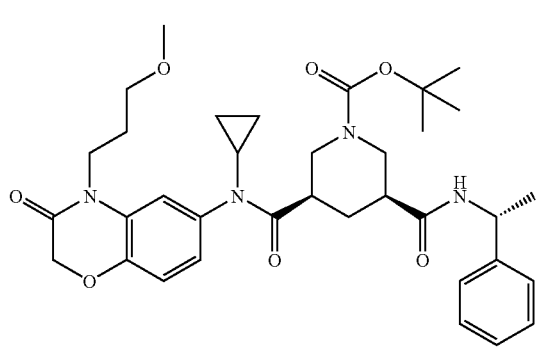

Intermediate 202.1 is synthesized by condensation of Intermediate 201.2 (100 mg, 0.19 mmol) with (R)-1-phenethylamine (28 mg, 0.22 mmol) analogously to the preparation of intermediate 1.1: white amorphous material, ES-MS: M+H=633: $c_{t_{Ret}}$=3.57 min.

Example 203

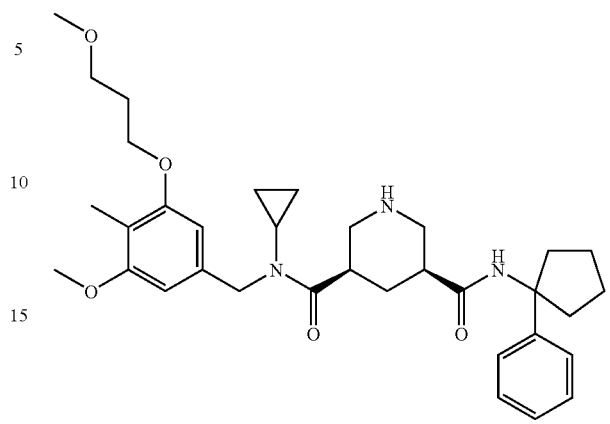

Example 203 is synthesized by deprotection of intermediate 203.1 (30 mg, 0.04 mmol) analogously to the preparation of intermediate 103.2. White amorphous material, ES-MS: M+H=578: $c_{t_{Ret}}$=3.60 min.

Intermediate 203.1

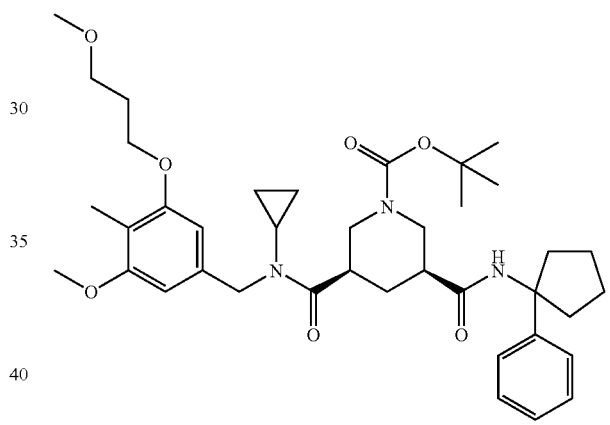

Intermediate 203.1 is synthesized by condensation of intermediate 203.2 (50 mg, 0.09 mmol) with Intermediate 103.2 (22 mg, 0.11 mmol) analogously to the preparation of intermediate 1.1: white amorphous material, ES-MS: M+H=678: $c_{t_{Ret}}$=4.62 min.

Intermediate 203.2

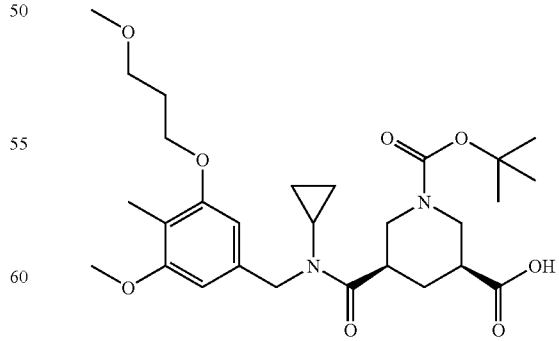

Intermediate 203.2 is synthesized by hydrolysis of intermediate 203.3 (250 mg, 0.46 mmol) analogously to the preparation of intermediate 13.2. White amorphous material, ES-MS: M+H=535: $c_{t_{Ret}}$=3.88 min.

Intermediate 203.3

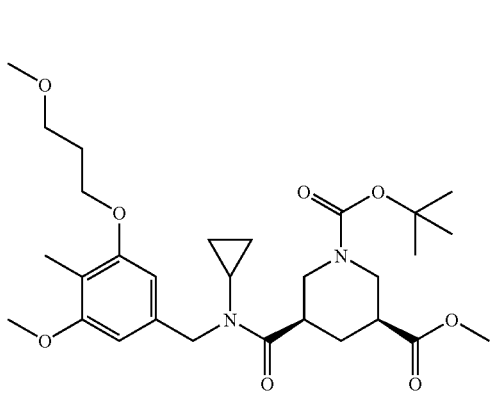

Intermediate 203.3 is synthesized by condensation of intermediate 203.4 (160 mg, 573 mmol) with (3R,5S)-Starting material-F (137 mg, 0.48 mmol) analogously to the preparation of intermediate 1.1: white amorphous material, ES-MS: M+H=549: $_c t_{Ret}$=4.31 min.

Intermediate 203.4

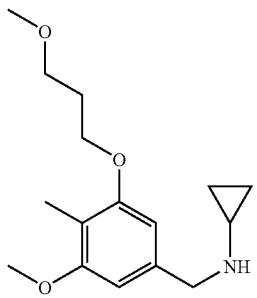

Intermediate 203.4 is synthesized by reaction of intermediate 203.5 (350 mg, 1.2 mmol) with cyclopropylamine (685 mg, 12 mmol) analogously to the preparation of intermediate 41.2: yellow oil, ES-MS: M+H=280: $_c t_{Ret}$=2.52 min.

Intermediate 203.5

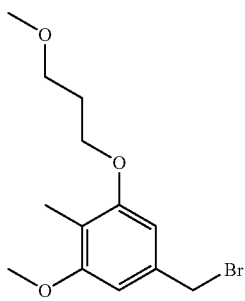

Intermediate 203.5 is synthesized by reaction of intermediate 203.6 (650 mg, 2.7 mmol) with N-bromosuccinimide (730 mg, 4.1 mmol) analogously to the preparation of intermediate 42.3: yellow oil, ES-MS: M+H=303, 305: $_c t_{Ret}$=4.06 min.

Intermediate 203.6

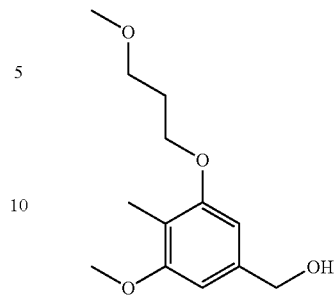

Intermediate 203.6 is synthesized by Mitsunobu reduction of 3-hydroxy-5-methoxy-4-methylbenzoic acid (CASNo. 72922-62-4, 1 g, 5.5 mmol) with 3-methoxypropanol followed by reduction with analogously to the preparations of intermediate 42.5 and intermediate 62.5: yellow oil, ES-MS: M+H=241: $_c t_{Ret}$=2.87 min.

Example 204

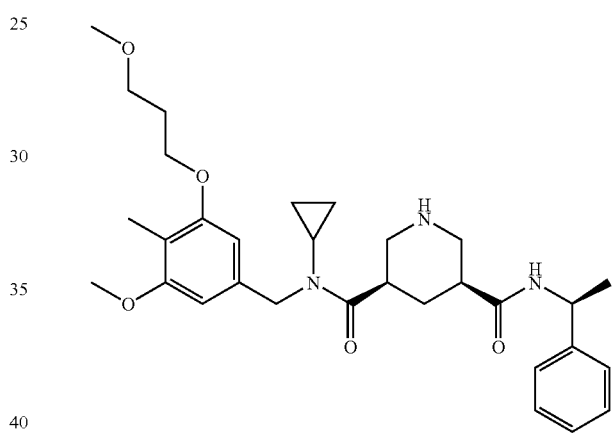

Example 204 is synthesized by deprotection of intermediate 204.1 (40 mg, 0.06 mmol) analogously to the preparation of intermediate 103.2. White amorphous material, ES-MS: M+H=538: $_c t_{Ret}$=3.28 min.

Intermediate 204.1

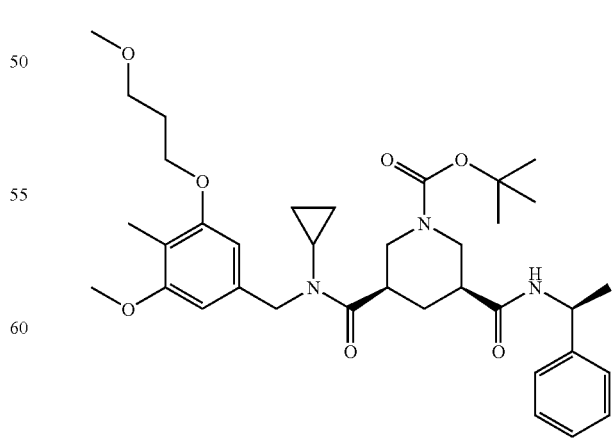

Intermediate 204.1 is synthesized by condensation of intermediate 203.2 (50 mg, 0.09 mmol) with (R)-1-phenetylamine (14 mg, 0.11 mmol) analogously to the preparation of intermediate 1.1: white amorphous material, ES-MS: M+H=638: $_ct_{Ret}$=4.31 min.

Example 205

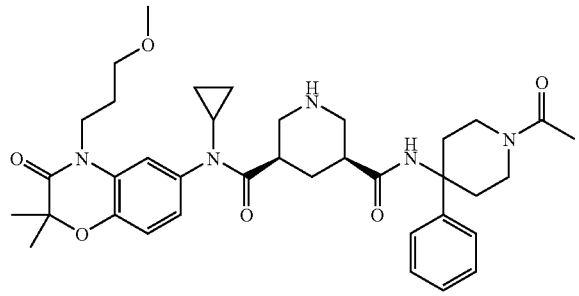

Example 205 is synthesized by deprotection of intermediate 205.1 (60 mg, 0.08 mmol) analogously to the preparation of intermediate 103.2. White amorphous material, ES-MS: M+H=660: $_ct_{Ret}$=2.75 min.

Intermediate 205.1

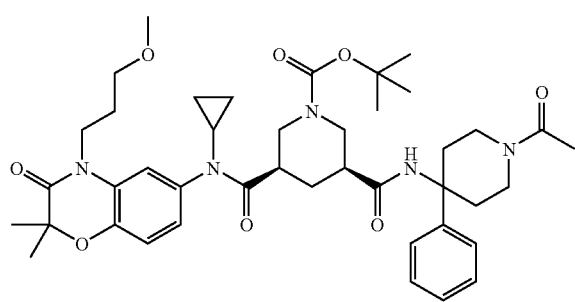

To a solution of intermediate 205.2 (150 mg, 0.21 mmol) in aqueous CH$_2$Cl$_2$ are added 5% aqueous NaHCO$_3$ (1 mL) and acetic anhydride (103 mg, 1 mmol) at room temperature. After stirring for 30 h at room temperature, the reaction mixture is diluted with CH$_2$Cl$_2$ (20 mL) and washed with 5% aqueous NaHCO$_3$, H$_2$O, and brine, then dried over Na$_2$SO$_4$ and concentrated in vacuo. RP-HPLC purification affords intermediate 205.1: white amorphous material, ES-MS: M+H=760: $_ct_{Ret}$=3.65 min.

Intermediate 205.2

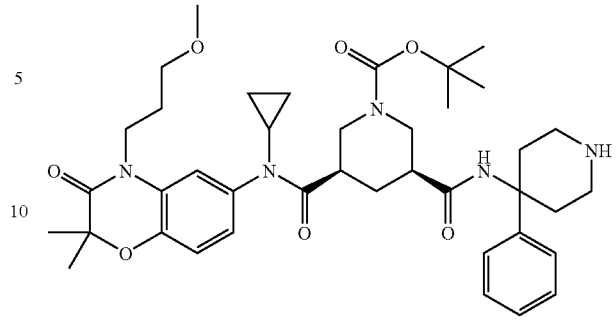

To a solution of intermediate 205.3 (655 mg, 0.77 mmol) in CH$_2$Cl$_2$ (10 mL) are added triethylsilane (600 mg, 5.2 mmol), triethylamine (155 mg, 1.54 mmol) and PdCl$_2$ (89 mg, 0.5 mmol) at room temperature. After stirring for 4 h at room temperature, the reaction mixture is quenched with H$_2$O (50 mL) and extracted with EtOAc (100 mL). The organic phase is successively washed with 5% NaHCO$_3$aq, H$_2$O, and brine, then dried over Na$_2$SO$_4$ and concentrated in vacuo. SiO$_2$ column chromatography purification affords intermediate 205.2: white amorphous material, ES-MS: M+H=718: $_ct_{Ret}$=3.29 min.

Intermediate 205.3

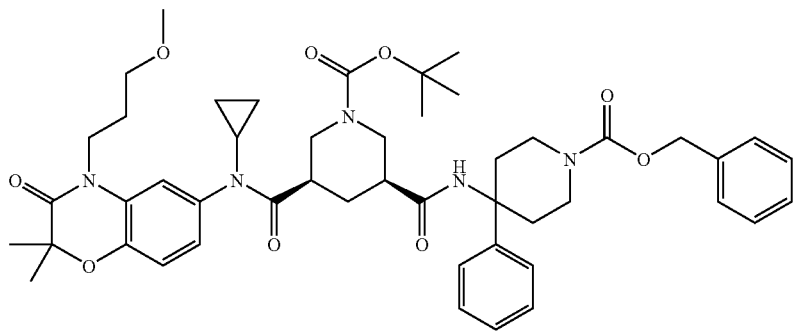

Intermediate 205.3 is synthesized by condensation of 4-amino-4-phenyl-piperidine-1-carboxylic acid benzyl ester (CASNo, 619295-93-1, 310 mg, 1 mmol) with Intermediate 108.2 (467 mg, 0.83 mmol) analogously to the preparation of intermediate 1.1: colorless oil, ES-MS: M+H=852: $_ct_{Ret}$=4.43 min.

Example 206

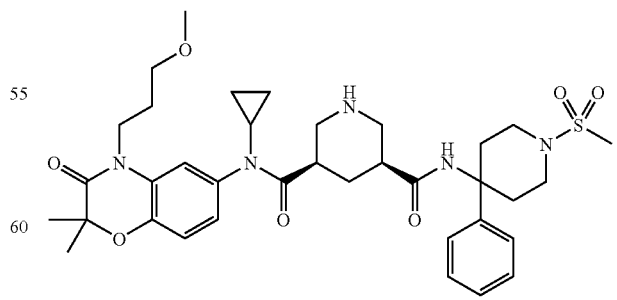

Example 206 is synthesized by a deprotection of intermediate 206.1 (55 mg, 0.07 mmol) analogously to the preparation of intermediate 103.2. White amorphous material, ES-MS: M+H=696: $_ct_{Ret}$=2.99 min.

Intermediate 206.1

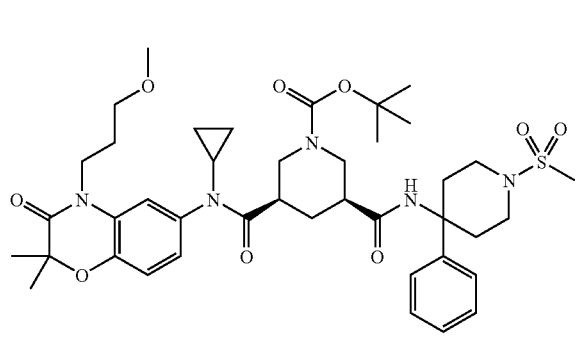

Intermediate 206.1 is synthesized by sulfonylation of intermediate 205.2 (150 mg, 0.21 mmol) with methanesulfonyl chloride (114 mg, 1 mmol) analogously to the preparation of intermediate 205.1: white amorphous material, ES-MS: M+H=796: $_C t_{Ret}$=3.88 min.

Example 207

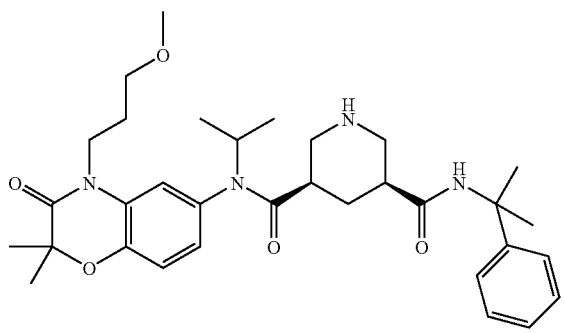

Example 207 is synthesized by deprotection of intermediate 207.1 (57 mg, 0.08 mmol) analogously to the preparation of Example 1. White amorphous material, ES-MS: M+H=579: $_C t_{Ret}$=3.20 min.

Intermediate 207.1

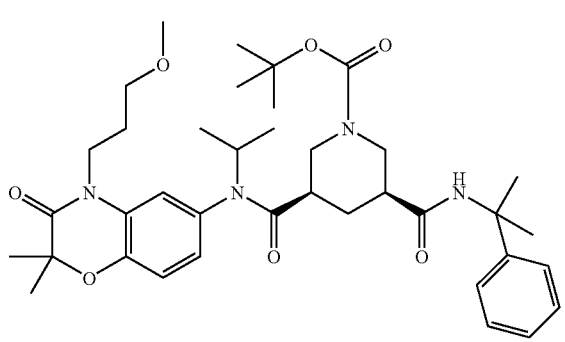

Intermediate 207.1 is synthesized by condensation of intermediate 173.2 (50 mg, 0.128 mmol) and intermediate 207.2 (39 mg, 0.128 mmol) analogously to the preparation of intermediate 19.1. Colorless oil, ES-MS: M+H=679: $_B t_{Ret}$=2.21 min.

Intermediate 207.2

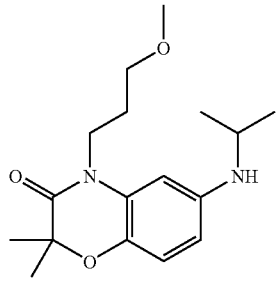

At room temperature, a solution of intermediate 87.4 (1.530 g, 5.20 mmol) in EtOAc (15 mL) is treated with tin(II) chloride dihydrate (4.17 g, 18.5 mmol), heated to 80° C., stirred for 6 h under reflux, cooled to room temperature, and treated with 5 N NaOH (10 mL). After filtration to remove off the resulting precipitate, the cake is washed with a small amount of EtOAc. At ambient temperature, the combined filtrate is treated with 2-iodopropane (3.1 mL, 31.0 mmol), heated to 70° C., stirred for 18 h at the same temperature under reflux, and cooled to room temperature. After separation of the both layers, the aqueous layer is extracted with EtOAc (3×6 mL), and the combined organic layer is washed with brine (10 mL), dried (Na$_2$SO$_4$), and evaporated. A SiO$_2$ flash chromatography (70 g, hexane/EtOAc 11:8) to give the desired product as a light yellow solid. R$_f$(hexane/EtOAc 3:2) 0.45. $^1$H-NMR (400 MHz, CDCl$_3$) 1.21 (d, J=6.2), 1.45 (s), 1.90-1.95 (m, 2 H), 3.34 (s), 3.40 (br. s), 3.43 (t, J=6.0), 3.55 (sep., J=6.2), 3.94 (t, J=6.0), 6.24 (dd, J=9.0, 0.4), 6.32 (d, J=0.4), 6.77 (d, J=9.0).

Example 208

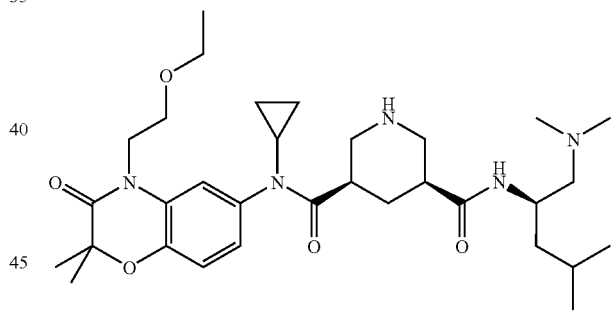

Example 208 is synthesized by deprotection of intermediate 208.1 analogously to the preparation of example 19. White material: M+H=586 $_A t_{Ret}$=2.25 min.

Intermediate 208.1

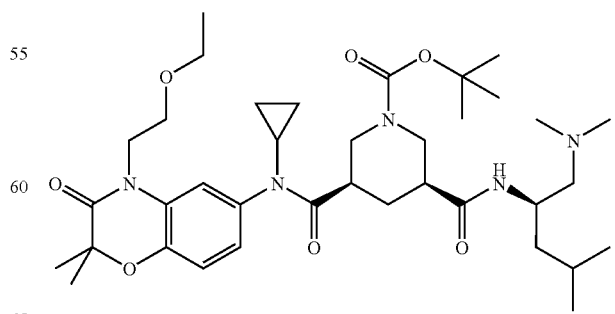

Intermediate 208.1 is synthesized by condensation of intermediate 208.2 (121.8 mg, 0.22 mmol) and (R)-4,N*1*,N*1*- trimethylpentane-1,2-diamine hydrochloride (WO2006009869) (47.2 mg, 0.22 mmol) analogously to the preparation of Intermediate 32.3: ES-MS: M+H=686: $_A t_{Ret}$=3.15 min.

Intermediate 208.2

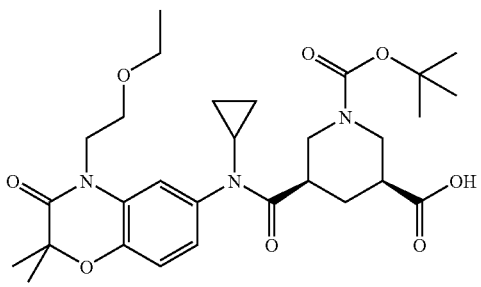

Intermediate 208.2 is synthesized by hydrolysis of intermediate 208.3 analogously to the preparation of intermediate 13.2: ES-MS: M+H=560: $_C t_{Ret}$=3.38 min.

Intermediate 208.3

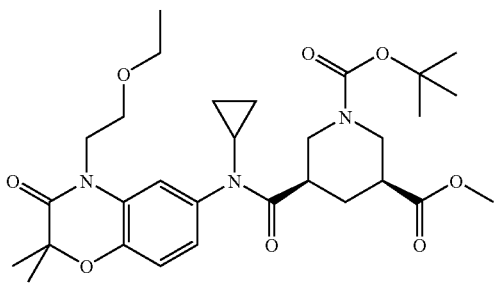

Intermediate 208.3 is synthesized by condensation of (3R, 5R)-starting material F (139.6 mg, 0.486 mmol) and Intermediate 150.2 (148 mg, 0.486 mmol) analogously to the preparation of Intermediate 32.3: ES-MS: M+H=574: $_A t_{Ret}$=3.80 min.

Example 209

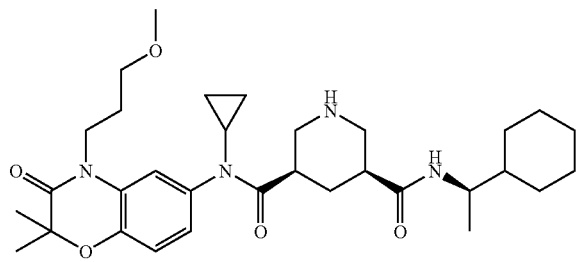

Example 209 is synthesized by deprotection of intermediate 209.1 analogously to the preparation of Example 19: ES-MS: M+H=569: $_C t_{Ret}$=3.27 min.

Intermediate 209.1

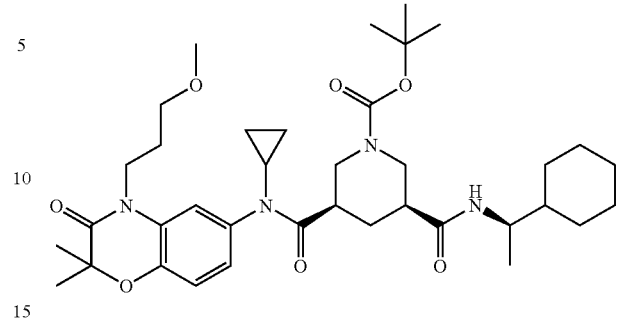

Intermediate 209.1 is synthesized by condensation of intermediate 108.2 (99 mg, 0.18 mmol) with (R)-(−)-1-cyclohexylethylamine (28 μL, 0.19 mmol) analogously to the preparation of intermediate 32.3: ES-MS: M+H=669: $_C t_{Ret}$=4.20 min.

Example 210

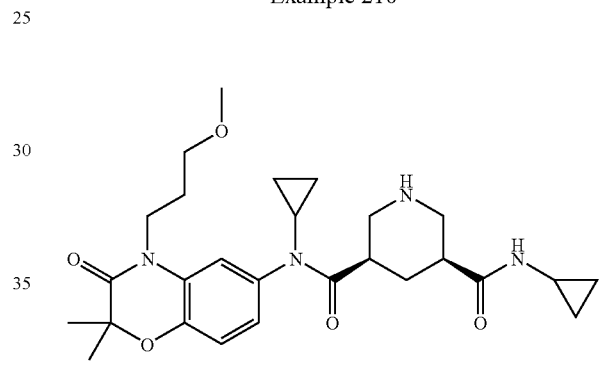

Example 210 is synthesized by deprotection of intermediate 210.1 analogously to the preparation of Example 19: ES-MS: M+H=2.53: $_C t_{Ret}$=499 min.

Intermediate 210.1

Intermediate 210.1 is synthesized by condensation of intermediate 108.2 (56 mg, 0.1 mmol) and cyclopropylamine (8 μL, 0.12 mmol) analogously to the preparation of intermediate 32.3. ES-MS: M+H=599: $_C t_{Ret}$=3.53 min.

Example 211

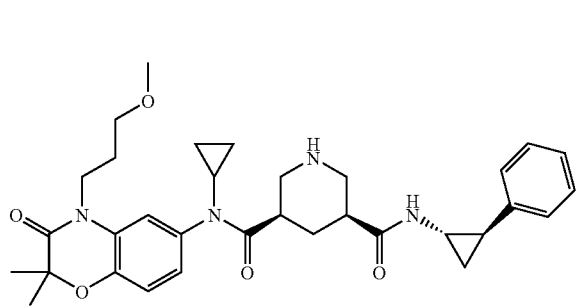

Example 211 is synthesized by deprotection of intermediate 211.1 analogously to the preparation of Example 19: ES-MS: M+H=3.08: $ct_{Ret}$=575 min.

Intermediate 211.1

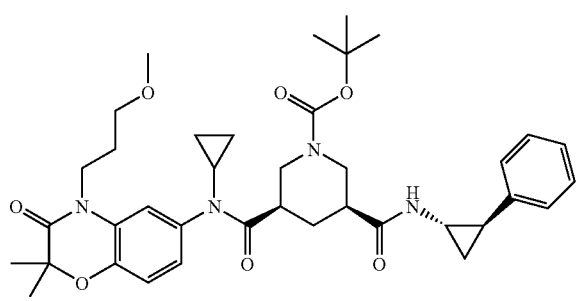

Intermediate 211.1 is synthesized by condensation of intermediate 108.2 (100 mg, 0.18 mmol) and trans-2-phenylcyclopropylamine hydrochloride (37 mg, 0.22 mmol) analogously to the preparation of intermediate 32.3 in the presence of Et$_3$N (33 µL, 0.23 mmol). ES-MS: M+H=675: $ct_{Ret}$=4.07 min.

Example 212

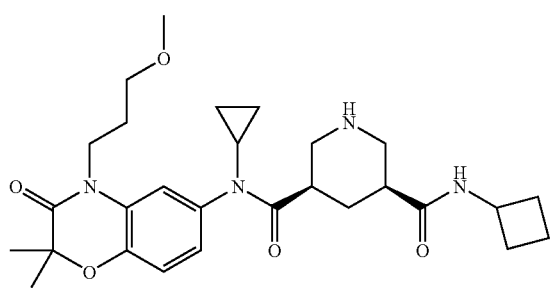

Example 212 is synthesized by deprotection of intermediate 212.1 analogously to the preparation of Example 19: ES-MS: M+H=2.71: $ct_{Ret}$=513 min.

Intermediate 212.1

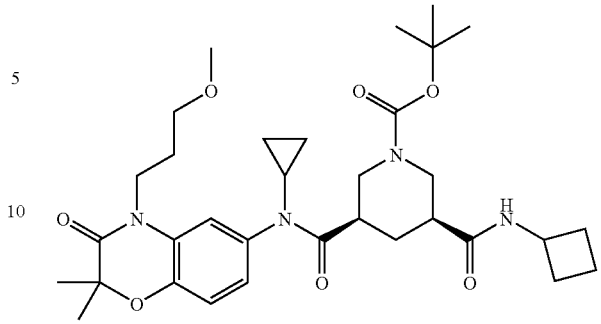

Intermediate 212.1 is synthesized by condensation of intermediate 108.2 (56 mg, 0.1 mmol) and cyclobutylamine (10 µL, 0.12 mmol) analogously to the preparation of intermediate 32.3. ES-MS: M+H=613: $ct_{Ret}$=3.74 min.

Example 213

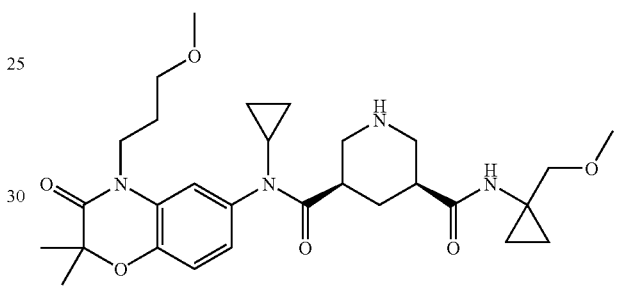

Example 213 is synthesized by deprotection of intermediate 213.1 analogously to the preparation of Example 19: ES-MS: M+H=2.54: $ct_{Ret}$=543 min.

Intermediate 213.1

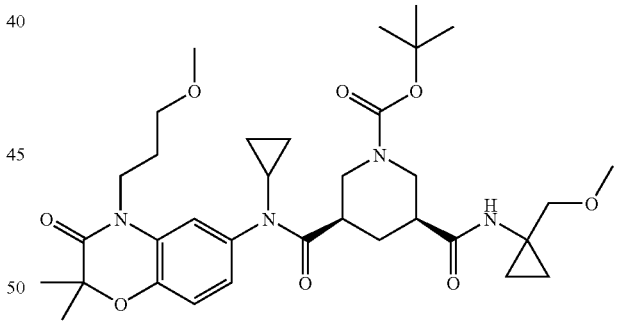

Intermediate 213.1 is synthesized by condensation of intermediate 108.2 (100 mg, 0.18 mmol) and intermediate 213.2 (30 mg, 0.22 mmol) analogously to the preparation of intermediate 32.3 in the presence of Et$_3$N (33 µL, 0.22 mmol). ES-MS: M+H=643: $ct_{Ret}$=3.53 min.

Intermediate 213.2

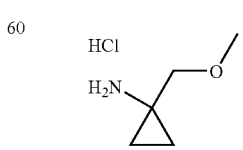

Intermediate 213.2 is synthesized by deprotection of intermediate 213.3 analogously to the preparation of Example 19.

The material is used in next step without further purification.

Intermediate 213.3

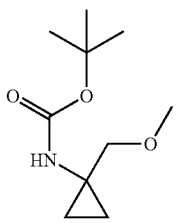

Intermediate 213.3 is synthesized by methylation of 1-(hydroxymethyl)cyclopropyl carbamic acid tert-butyl ester (*J. Med. Chem.* 1988, 31, 2004-2008) analogously to the preparation of Intermediate 151.3: $^1$H NMR (CDCl$_3$) δ 0.73-0.90 (m, 4 H), 1.44 (s, 9 H), 3.37 (s, 3 H), 3.39 (s, 3 H), 5.00 (br s, 1 H): Rf=0.38 (AcOEt:n-Hexane=1:1).

Example 214

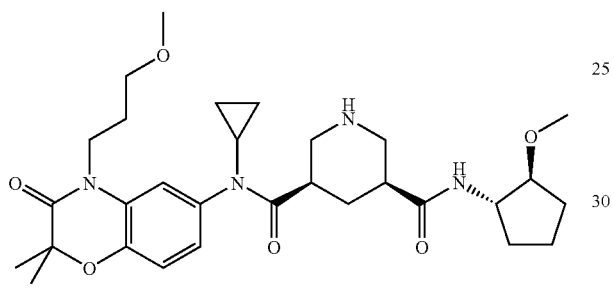

Example 214 is synthesized by deprotection of intermediate 214.1 analogously to the preparation of example 19. White material: M+H=557 $_c$t$_{Ret}$=2.69 min.

Intermediate 214.1

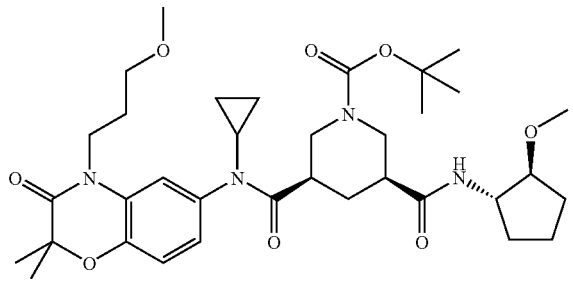

Intermediate 214.1 is synthesized by condensation of intermediate 108.2 (150 mg, 0.268 mmol) and intermediate 214.2 hydrochloride (40.6 mg, 0.268 mmol) analogously to the preparation of Intermediate 32.3: ES-MS: M+H=657: $_c$t$_{Ret}$=3.69 min.

Intermediate 214.2

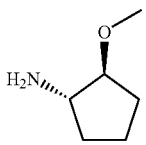

Intermediate 214.2 is synthesized by deprotection of intermediate 214.3 analogously to the preparation of example 19. White material for hydrochloride salt: ES-MS: M+H=116 $_B$t$_{Ret}$=0.71 min.

Intermediate 214.3

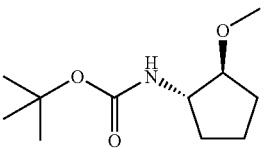

To a solution of ((1S,2S)-2-Hydroxy-cyclopentyl)-carbamic acid tert-butyl ester (Journal of Organic Chemistry (2004), 69(17), 5725-5734.) (261.0 mg, 1.29 mmol) in THF (10 mL) under N$_2$ at 0° C., NaH (114 mg of 60 wt % in mineral oil, 2.85 mmol) is added. After stirring at that temperature for 5 min, methyl iodine (80.3 μL, 1.29 mmol) is added. The resulting solution is stirred at rt for 45 min. The reaction is quenched with H$_2$O and extracted with EtOAc, dried over Na$_2$SO$_4$. Concentration under the reduced pressure affords the crude product. The crude product is purified by silica gel chromatography to give the desired intermediate 214.3. ES-MS: M+H-tBu=160: $_A$t$_{Ret}$=2.90 min.

Example 215

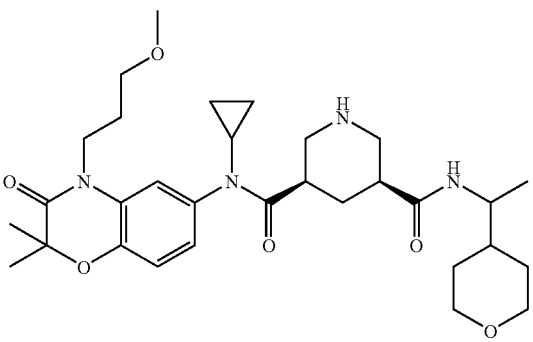

Example 215 is synthesized by deprotection of intermediate 215.1 analogously to the preparation of Example 19: ES-MS: M+H=570: $_c$t$_{Ret}$=2.59, 2.65 min.

Intermediate 215.1

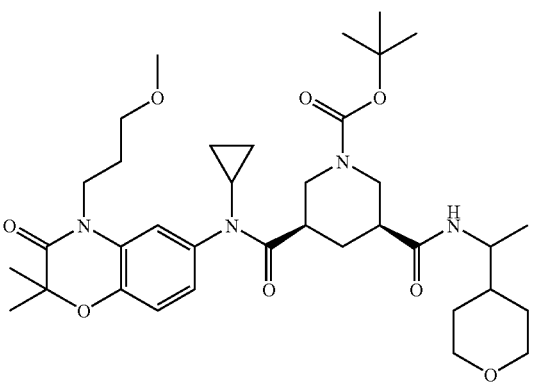

Intermediate 215.1 is synthesized by condensation of intermediate 108.2 (98 mg, 0.175 mmol) with 1-(tetrahydropyran-4-yl)-ethylamine (28 mg, 0.217 mmol, CAS-854697-78-2) analogously to the preparation of intermediate 32.3: ES-MS: M+H=671: $_c$t$_{Ret}$=3.45 min.

Example 216

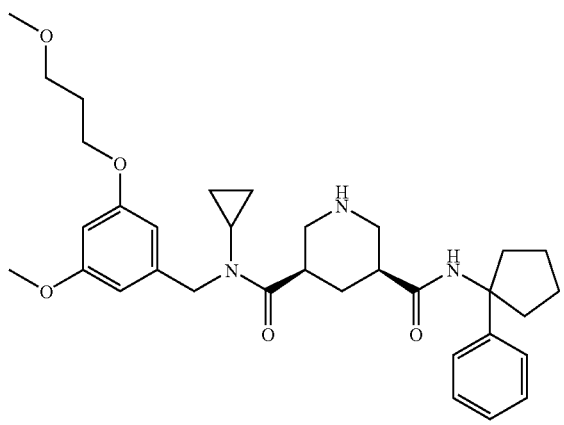

Example 216 is synthesized by deprotection of intermediate 216.1 (65 mg, 0.1 mmol) analogously to the preparation of intermediate 103.2. White amorphous material, ES-MS: M+H=564: $_c t_{Ret}$=3.29 min.

Intermediate 216.1

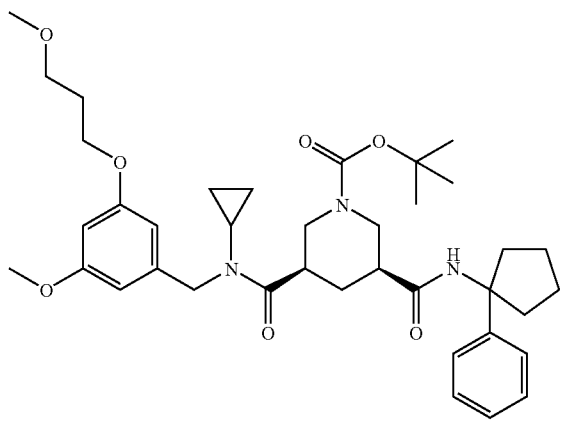

Intermediate 216.1 is synthesized by condensation of intermediate 37.2 (48 mg, 0.18 mmol) with intermediate 169.2 (50 mg, 0.12 mmol) analogously to the preparation of intermediate 1.1: white amorphous material, ES-MS: M+H=664: $_c t_{Ret}$=4.37 min.

Example 217

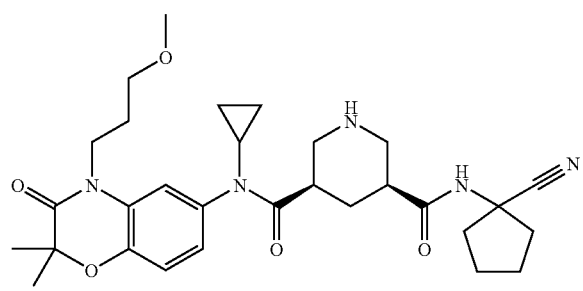

Example 217 is synthesized by deprotection of intermediate 217.1 (100 mg, 0.15 mmol) analogously to the preparation of Example 1. White amorphous material, ES-MS: M+H=552: $_c t_{Ret}$=2.79 min.

Example 218

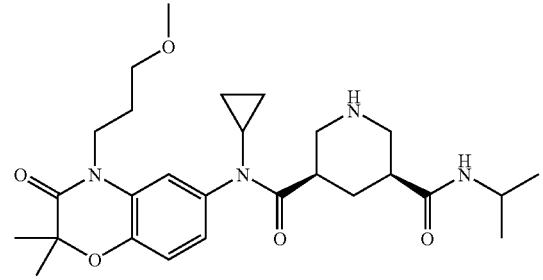

Example 218 is synthesized by deprotection of intermediate 218.1 (45 mg, 0.08 mmol) analogously to the preparation of intermediate 103.2. White amorphous material, ES-MS: M+H=501: $_c t_{Ret}$=2.63 min.

Intermediate 218.1

Intermediate 218.1 is synthesized by condensation of isopropylamine (8.3 mg, 0.135 mmol) with intermediate 108.2 (50 mg, 0.09 mmol) analogously to the preparation of intermediate 1.1: white amorphous material, ES-MS: M+H=601: $_c t_{Ret}$=3.66 min.

Example 219

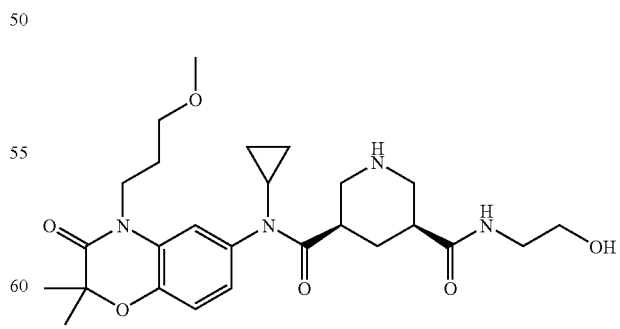

Example 219 is synthesized by deprotection of intermediate 219.1 (10 mg, 0.02 mmol) analogously to the preparation of intermediate 103.2. White amorphous material, ES-MS: M+H=503: $_c t_{Ret}$=2.30 min.

Intermediate 219.1

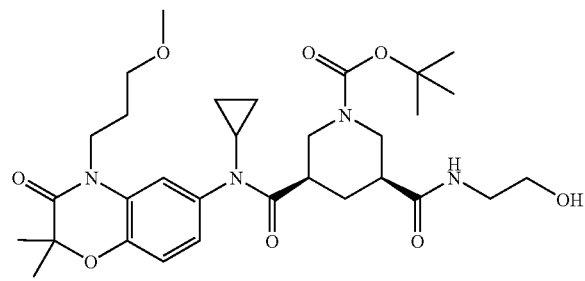

Intermediate 219.1 is synthesized by condensation of 2-aminopropanol (8.3 mg, 0.135 mmol) with Intermediate 108.2 (50 mg, 0.09 mmol) analogously to the preparation of intermediate 1.1: white amorphous material, ES-MS: M+H=603: $c_{t_{Ret}}$=3.18 min.

Example 220

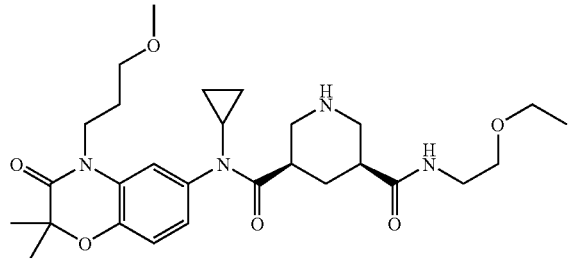

Example 220 is synthesized by deprotection of intermediate 220.1 (50 mg, 0.08 mmol) analogously to the preparation of intermediate 103.2. White amorphous material, ES-MS: M+H=531: $c_{t_{Ret}}$=2.58 min.

Intermediate 220.1

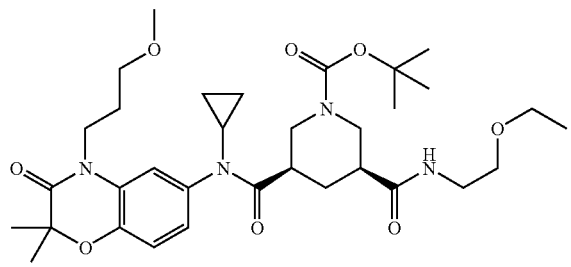

Intermediate 220.1 is synthesized by condensation of 2-ethoxyethylamine (12 mg, 0.135 mmol) with Intermediate 108.2 (50 mg, 0.09 mmol) analogously to the preparation of intermediate 1.1: white amorphous material, ES-MS: M+H=631: $c_{t_{Ret}}$=3.58 min.

Example 221

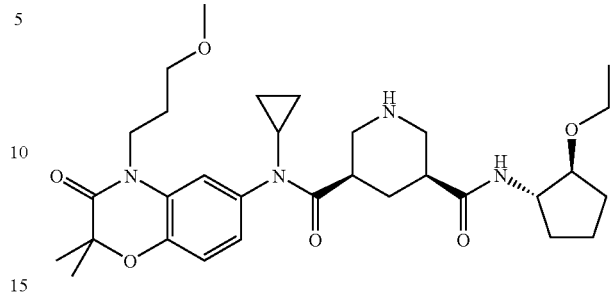

Example 221 is synthesized by deprotection of intermediate 221.1 analogously to the preparation of example 19. White material: M+H=571 $c_{t_{Ret}}$=2.81 min.

Intermediate 221.1

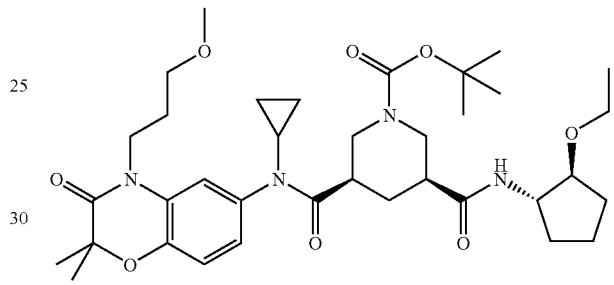

Intermediate 221.1 is synthesized by condensation of intermediate 108.2 (148.1 mg, 0.265 mmol) and intermediate 221.2 hydrochloride (60.5 mg, 0.365 mmol) analogously to the preparation of Intermediate 32.3: ES-MS: M+H=671: $c_{t_{Ret}}$=3.84 min.

Intermediate 221.2

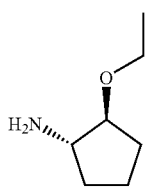

Intermediate 221.2 is synthesized by deprotection of intermediate 221.3 analogously to the preparation of example 19. White material (for hydrochloride salt): ES-MS: M+H=130 $c_{t_{Ret}}$=1.03 min.

Intermediate 221.3

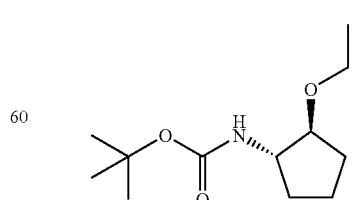

Intermediate 221.3 is synthesized by alkylation of ((1S, 2S)-2-Hydroxy-cyclopentyl)-carbamic acid tert-butyl ester (Journal of Organic Chemistry (2004), 69(17), 5725-5734.)

analogously to the preparation of intermediate 214.3. White colorless oil: ES-MS: M+H-tBu=174 $c^tRet$=3.22 min.

Example 222

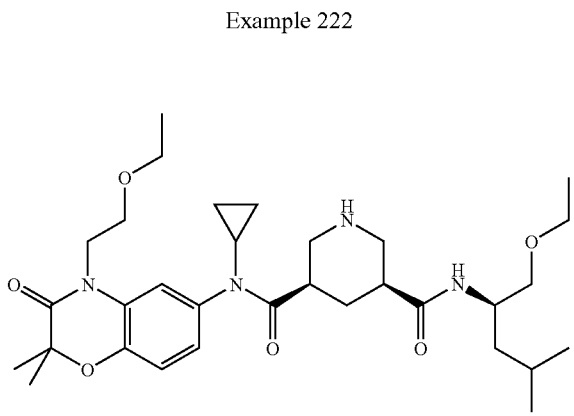

Example 222 is synthesized by deprotection of intermediate 222.1 analogously to the preparation of example 19. White material: M+H=587 $c^tRet$=3.17 min.

Intermediate 222.1

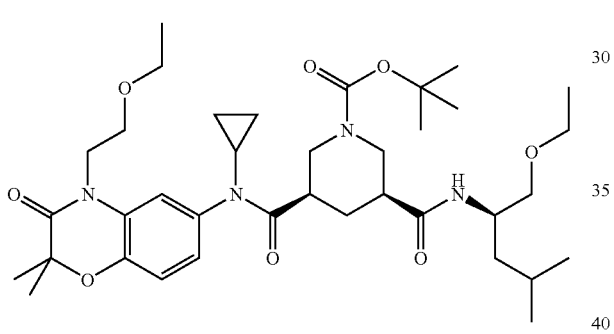

Intermediate 222.1 is synthesized by condensation of intermediate 104.2 (119.2 mg, 0.21 mmol) and intermediate 148.2 hydrochloride (68 mg, 0.37 mmol) analogously to the preparation of intermediate 32.3: ES-MS: M+H=687: $c^tRet$=4.30 min.

Example 223

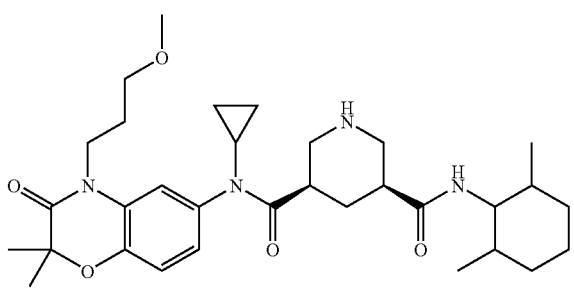

Example 223 is synthesized by deprotection of intermediate 223.1 (35 mg, 0.05 mmol) analogously to the preparation of example 1. White amorphous material, ES-MS: M+H=569: $c^tRet$=3.20 min.

Intermediate 223.1

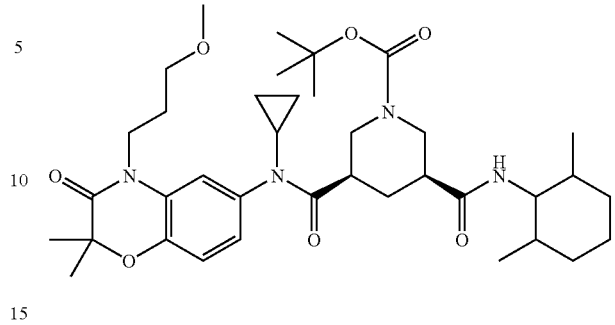

Intermediate 223.1 is synthesized by condensation of intermediate 108.2 (100 mg, 0.18 mmol) and 2,5-dimethylcyclohexylamine (60 mg) analogously to the preparation of intermediate 39.1: colorless oil, ES-MS: M+H=669: $c^tRet$=4.29 min.

Example 224

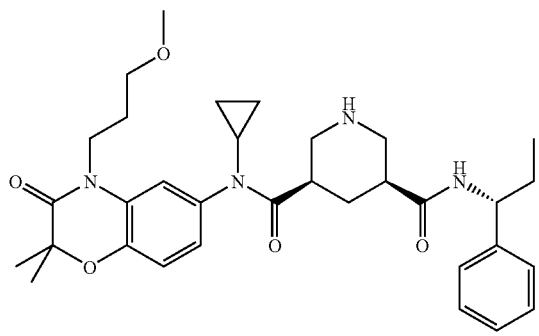

Example 224 is synthesized by deprotection of intermediate 224.1 analogously to the preparation of example 19. White material: M+H=577 $c^tRet$=3.13 min Intermediate 224.1

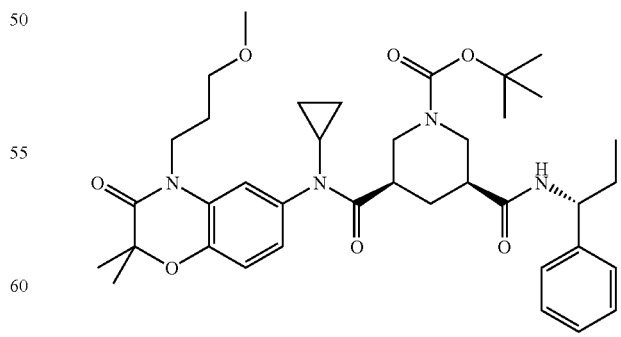

Intermediate 224.1 is synthesized by condensation of intermediate 108.2 (150 mg, 0.268 mmol) and (R)-ethyl benzylamine (0.0385 mL, 0.268 mmol) analogously to the preparation of Intermediate 32.3: ES-MS: M+H=677: $c^tRet$=4.15 min.

Example 225

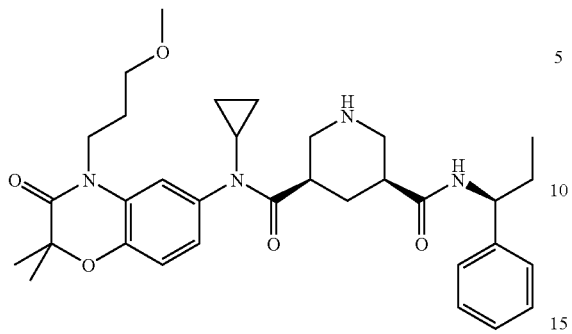

Example 225 is synthesized by deprotection of intermediate 225.1 analogously to the preparation of example 19. White material: M+H=577 $c_tRet$=3.12 min Intermediate 225.1

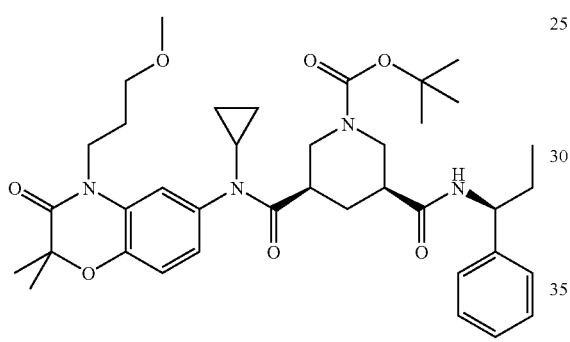

Intermediate 225.1 is synthesized by condensation of intermediate 108.2 (150 mg, 0.268 mmol) and (S)-ethyl benzylamine (0.0385 mL, 0.268 mmol) analogously to the preparation of Intermediate 32.3: ES-MS: M+H=677: $c_tRet$=4.14 min.

Example 226

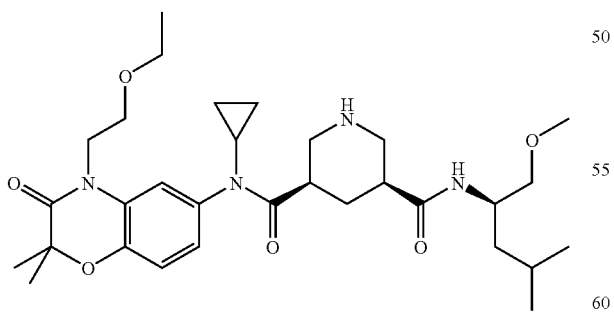

Example 226 is synthesized by deprotection of intermediate 226.1 analogously to the preparation of example 19. White material: M+H=573: $c_tRet$=3.03 min Intermediate 226.1

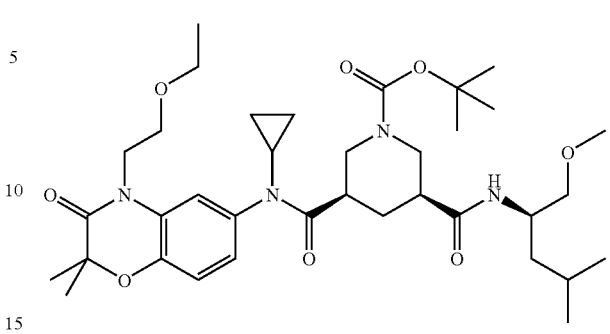

Intermediate 226.1 is synthesized by condensation of intermediate 104.2 (155.6 mg, 0.278 mmol) and (R)-1-methoxymethyl-3-methylbutylamine hydrochloride (*Org. Lett.* 2001, 3, 1241) (56 mg, 0.33 mmol) analogously to the preparation of Intermediate 32.3: ES-MS: M+H=673: $c_tRet$=4.14 min.

Example 227

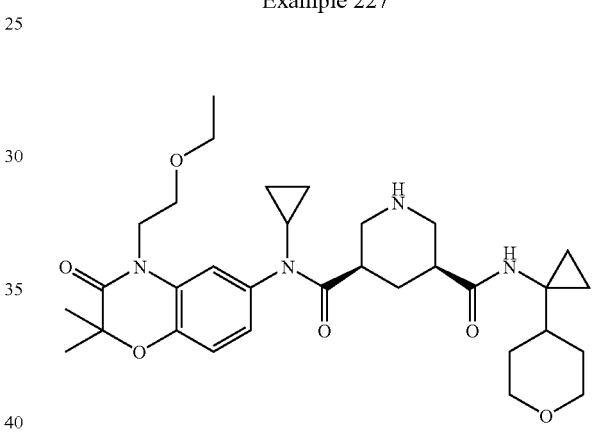

Example 227 is synthesized by deprotection of intermediate 227.1 analogously to the preparation of Example 19: ES-MS: M+H=583: $c_tRet$=2.67 min.

Intermediate 227.1

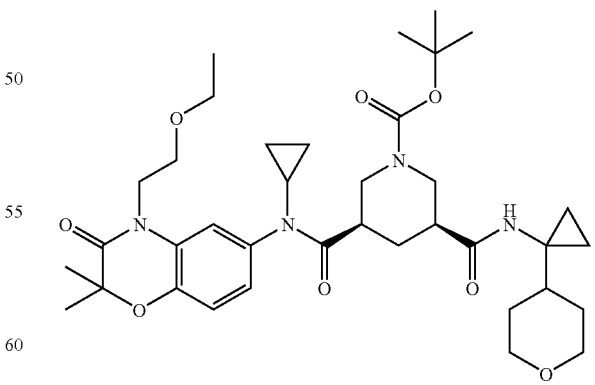

Intermediate 227.1 is synthesized by condensation of intermediate 208.2 (150 mg, 0.27 mmol) with intermediate 152.2 (76 mg, 0.40 mmol) analogously to the preparation of intermediate 32.3: white amorphous material, ES-MS: M+H=683: $c_tRet$=3.71 min.

Example 228

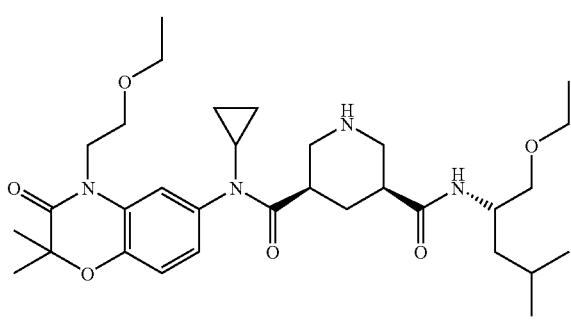

Example 228 is synthesized by deprotection of intermediate 228.1 analogously to the preparation of Example 19: ES-MS: M+H=587: $_c t_{Ret}$=2.78 min.

Intermediate 228.1

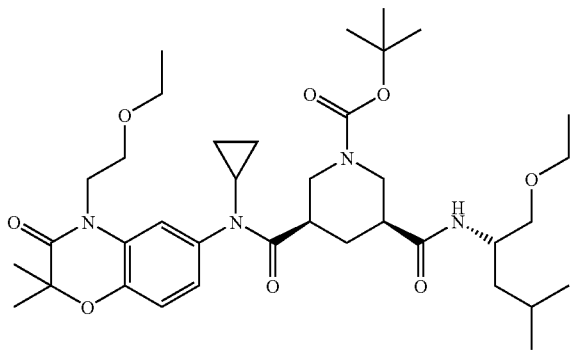

Intermediate 228.1 is synthesized by condensation of intermediate 208.2 (150 mg, 0.27 mmol) with (S)-1-Ethoxymethyl-3-methylbutylamine hydrochloride (WO9315047, 54 mg, 0.30 mmol) analogously to the preparation of intermediate 32.3: white amorphous material, ES-MS: M+H=687: $_c t_{Ret}$=4.27 min.

Example 229

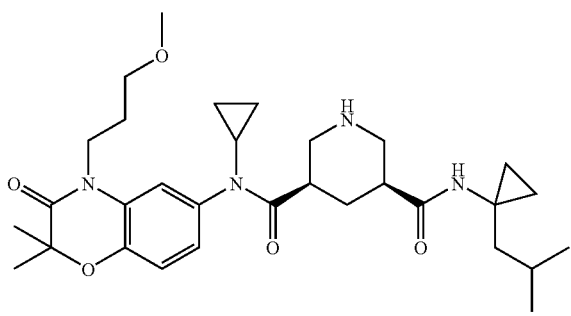

Example 229 is synthesized by deprotection of intermediate 229.1 analogously to the preparation of example 19: ES-MS: M+H=555: $_c t_{Ret}$=3.04 min Intermediate 229.1

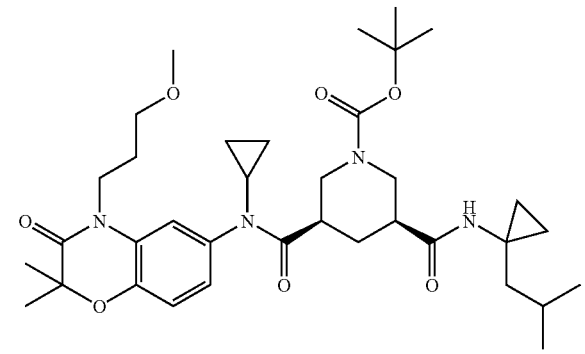

Intermediate 229.1 is synthesized by condensation of intermediate 108.2 (100 mg, 0.18 mmol) with intermediate 229.2 (29.4 mg, 0.20 mmol) analogously to the preparation of intermediate 32.3: white amorphous material, ES-MS: M+H=655: $_c t_{Ret}$=4.14 min.

Intermediate 229.2

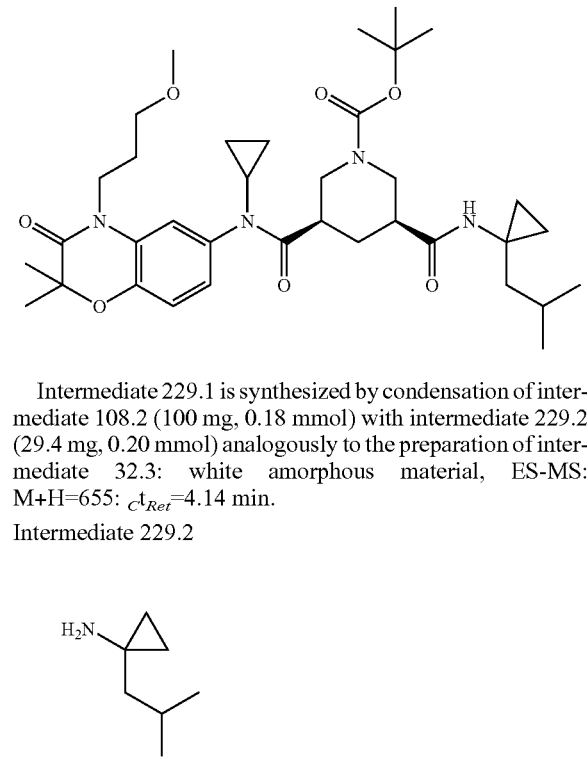

EtMgBr (13.2 mL, 13.2 mmol, 1 M in THF) is added under argon at −78° C. to a solution of 4-cyanotetrahydro-4H-pyran (500 mg, 6.01 mmol) and Ti(O$^i$Pr)$_4$ (1.94 mL, 6.60 mmol) in Et$_2$O (60 mL). The solution is slowly warmed to room temperature during 1 h, it is then stirred at rt for 30 min. At this stage, BF$_3$.OEt$_2$ (1.69 mL, 12.02 mmol) is added and stirring is continued for 2 h. Water (10 mL) is added, followed by 10% aq. HCl (10 mL) and Et$_2$O (20 mL). A 10% NaOHaq. solution is added to the resulting clear mixture until the pH becomes basic. The product is extracted with Et$_2$O (2×30 mL). The combined organic extracts are dried with Na$_2$SO$_4$. After evaporation of the solvent, the product is used for next reaction without purification: yellow oil. ES-MS: M+H=114: $_B t_{Ret}$=1.25 min.

Example 230

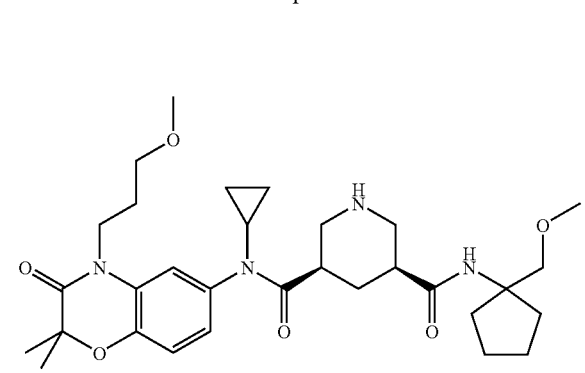

Example 230 is synthesized by deprotection of intermediate 230.1 analogously to the preparation of example 19. White material: M+H=671: $_A t_{Ret}$=3.68 min Intermediate 230.1

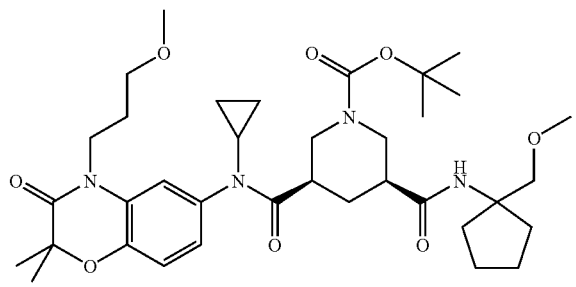

Intermediate 230.1 is synthesized by condensation of intermediate 108.2 (100 mg, 0.1786 mmol) and 1-Methoxymethyl-cyclopentylamine hydrochloride (Journal of Medicinal Chemistry (2006), 49(11), 3068-3076.) (40.5 mg, 0.187 mmol) analogously to the preparation of intermediate 32.3: ES-MS: M+H=571: $_A t_{Ret}$=2.50 min.

Example 231

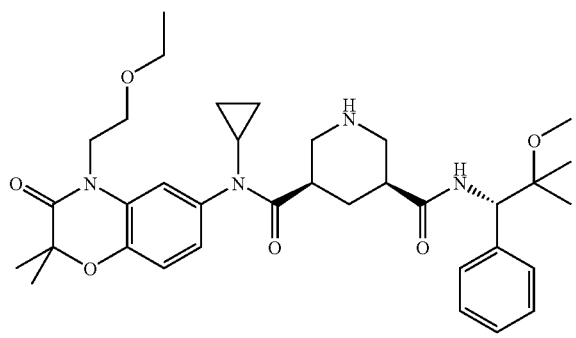

Example 231 is synthesized by deprotection of intermediate 231.1 analogously to the preparation of example 19. White material: M+H=621: $_A t_{Ret}$=2.87 min.

Intermediate 231.1

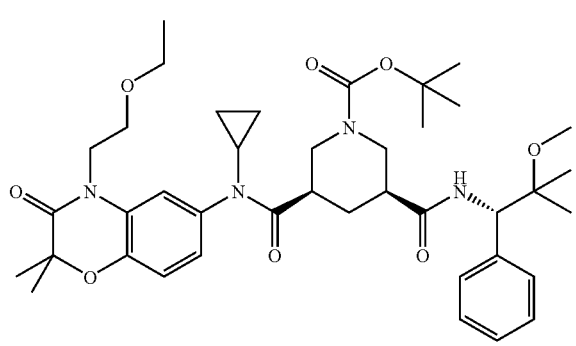

Intermediate 231.1 is synthesized by condensation of intermediate 208.2 (100 mg, 0.1786 mmol) and intermediate 192.2 hydrochloride (40.5 mg, 0.187 mmol) analogously to the preparation of Intermediate 32.3: ES-MS: M+H=721: $_A t_{Ret}$=4.09 min.

Example 232

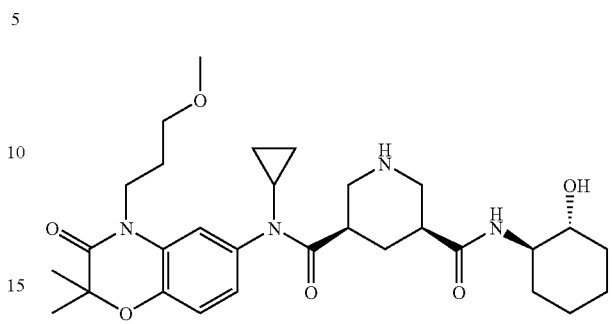

Example 232 is synthesized by deprotection of intermediate 232.1 analogously to the preparation of example 19: ES-MS: M+H=557: $_C t_{Ret}$=2.52 min.

Intermediate 232.1

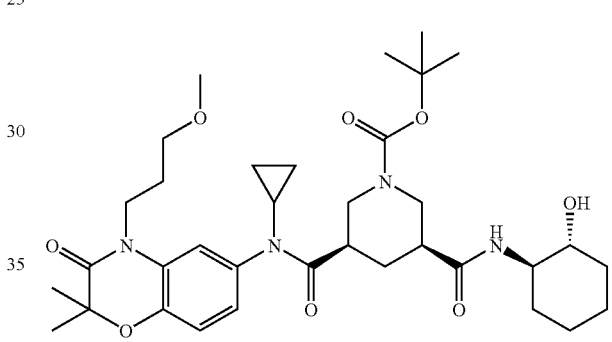

Intermediate 232.1 is synthesized by condensation of intermediate 108.2 (102 mg, 0.18 mmol) with (1R,2R)-2-aminocyclohexanol hydrochloride (31 mg, 0.20 mmol, CAS-13374-31-7) analogously to the preparation of intermediate 32.3: ES-MS: M+H=657: $_C t_{Ret}$=3.37 min.

Example 233

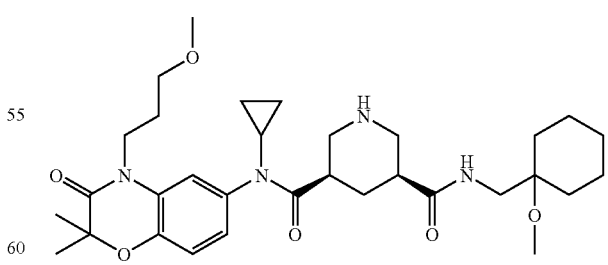

Example 233 is synthesized by deprotection of intermediate 233.1 analogously to the preparation of Example 19: ES-MS: M+H=585: $_C t_{Ret}$=2.85 min.

Intermediate 233.1

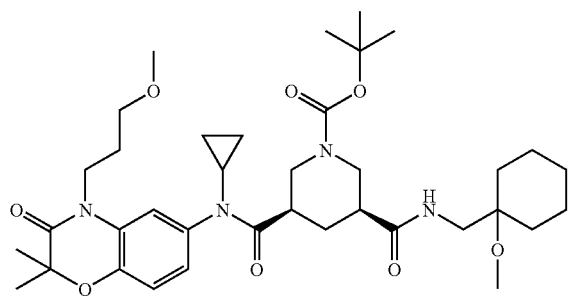

Intermediate 233.1 is synthesized by condensation of intermediate 108.2 (105 mg, 0.19 mmol) with 1-methoxy-cyclohexanemethanamine hydrochloride (51 mg, 0.28 mmol) analogously to the preparation of intermediate 32.3: ES-MS: M+H=685: $_Ct_{Ret}$=3.70 min.

Example 234

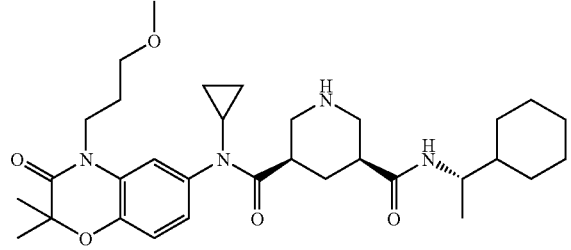

Example 234 is synthesized by deprotection of intermediate 234.1 analogously to the preparation of example 19: ES-MS: M+H=569: $_Ct_{Ret}$=3.19 min.
Intermediate 234.1

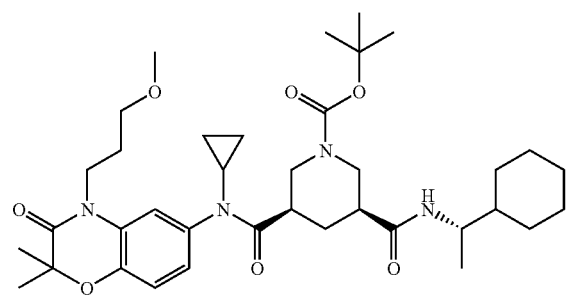

Intermediate 234.1 is synthesized by condensation of intermediate 108.2 (118 mg, 0.21 mmol) with (S)-(+)-1-cyclohexylethylamine (34 μL, 0.23 mmol) analogously to the preparation of intermediate 32.3: ES-MS: M+H=669: $_Bt_{Ret}$=4.36 min.

Example 235

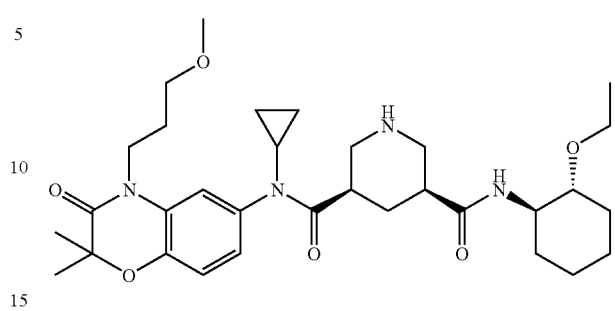

Example 235 is synthesized by deprotection of intermediate 235.1 analogously to the preparation of example 19: ES-MS: M+H=585: $_Ct_{Ret}$=2.79 min.
Intermediate 235.1

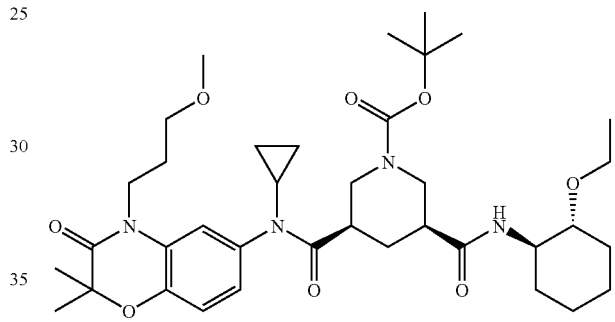

Intermediate 235.1 is synthesized by condensation of intermediate 108.2 (133 mg, 0.24 mmol) with trans-2-ethoxy-cyclohexanamine hydrochloride (47 mg, 0.26 mmol, CAS-56251-94-6) analogously to the preparation of intermediate 32.3: ES-MS: M+H=685: $_Ct_{Ret}$=3.83 min.

Example 236

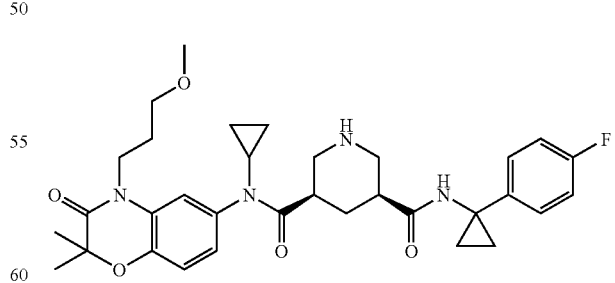

Example 236 is synthesized by deprotection of intermediate 236.1 analogously to the preparation of example 19: ES-MS: M+H=3.04: $_Ct_{Ret}$=593 min.

Intermediate 236.1

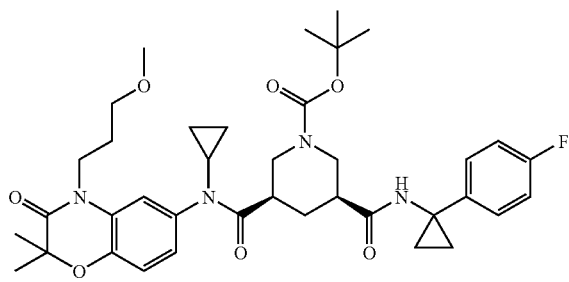

Intermediate 236.1 is synthesized by condensation of intermediate 108.2 (100 mg, 0.18 mmol) and 1-(4-fluorophenyl)cyclopropylamine (J. Org. Chem. 2003, 68, 7133-7136, 41 mg, 0.27 mmol) analogously to the preparation of intermediate 32.3. ES-MS: M+H=693: $_ct_{Ret}$=4.05 min.

Example 237

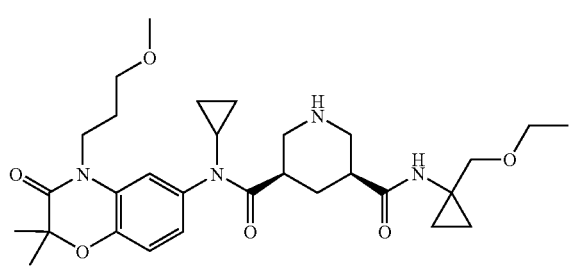

Example 237 is synthesized by deprotection of intermediate 237.1 analogously to the preparation of example 19: ES-MS: M+H=2.65: $_ct_{Ret}$=557 min.

Intermediate 237.1

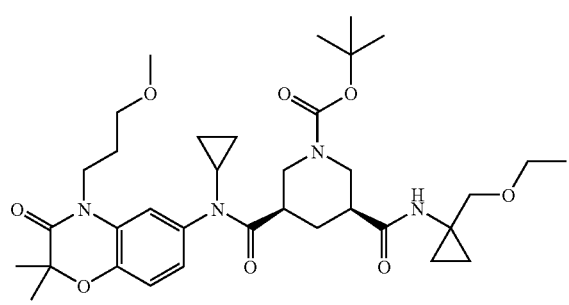

Intermediate 237.1 is synthesized by condensation of intermediate 108.2 (123 mg, 0.2 mmol) and intermediate 237.2 (50 mg, 0.33 mmol) analogously to the preparation of intermediate 32.3 in the presence of Et$_3$N (46 µL, 0.33 mmol). ES-MS: M+H=657: $_ct_{Ret}$=3.66 min.

Intermediate 237.2

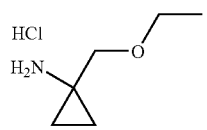

Intermediate 237.2 is synthesized by deprotection of intermediate 237.3 analogously to the preparation of example 19. The material is used in next step without further purification.

Intermediate 237.3

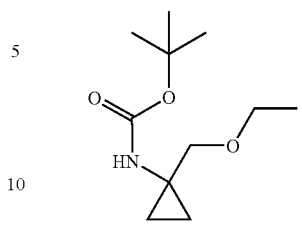

Intermediate 237.3 is synthesized by ethylation of 1-(hydroxymethyl)cyclopropyl carbamic acid tert-butyl ester (J. Med. Chem. 1988, 31, 2004-2008) analogously to the preparation of intermediate 151.3. ES-MS: M+H=215: $_ct_{Ret}$=2.92 min.

Example 238

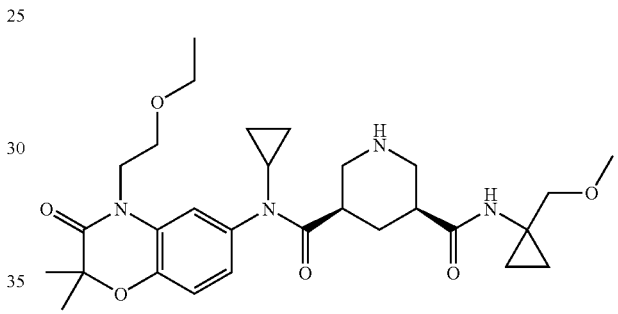

Example 238 is synthesized by deprotection of intermediate 238.1 analogously to the preparation of example 19: ES-MS: M+H=2.60: $_ct_{Ret}$=543 min.

Intermediate 238.1

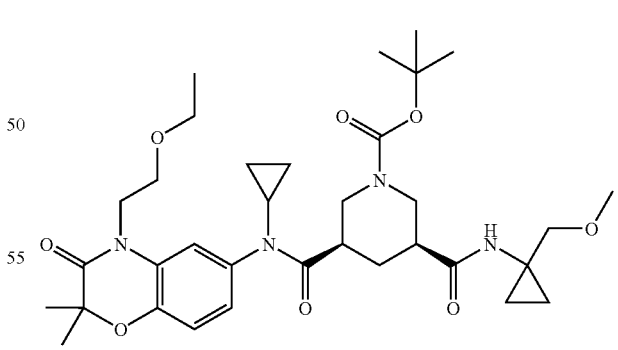

Intermediate 238.1 is synthesized by condensation of intermediate 208.2 (94 mg, 0.17 mmol) and intermediate 213.2 (23 mg, 0.17 mmol) analogously to the preparation of intermediate 32.3 in the presence of Et$_3$N (26 µL, 0.18 mmol). ES-MS: M+H=643: $_ct_{Ret}$=3.61 min.

Example 239

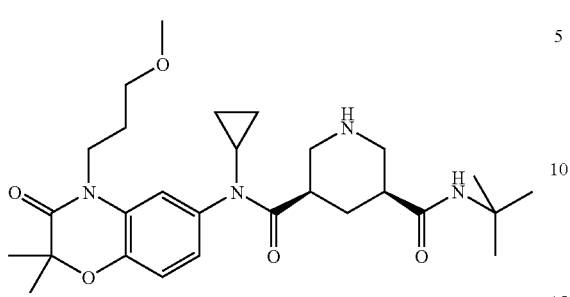

Example 239 is synthesized by deprotection of intermediate 239.1 analogously to the preparation of example 19: ES-MS: M+H=2.79: $ct_{Ret}$=515 min.

Intermediate 239.1

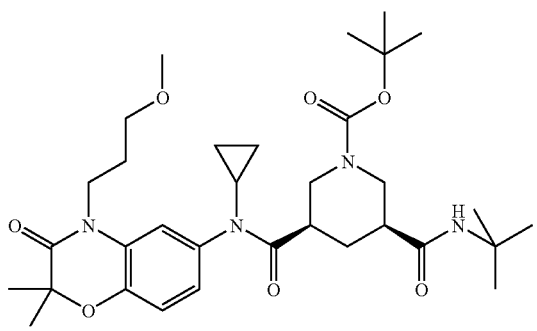

Intermediate 239.1 is synthesized by condensation of intermediate 108.2 (94 mg, 0.17 mmol) and tert-butylamine (23 mg, 0.17 mmol) analogously to the preparation of intermediate 32.3. ES-MS: M+H=615: $ct_{Ret}$=3.88 min.

Example 240

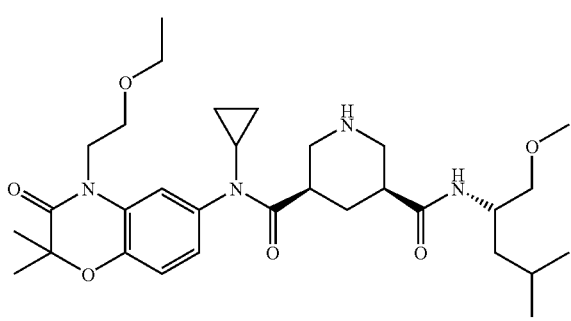

Example 240 is synthesized by deprotection of intermediate 240.1 analogously to the preparation of example 19: ES-MS: M+H=573: $ct_{Ret}$=3.07 min.

Intermediate 240.1

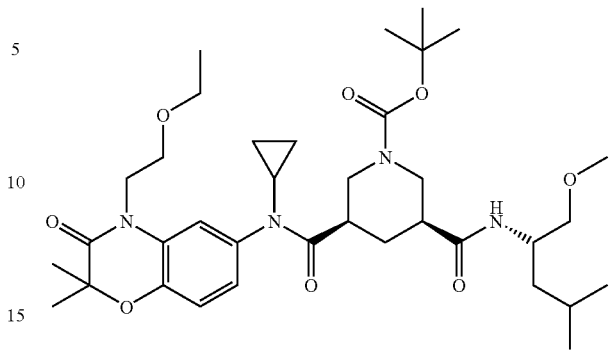

Intermediate 240.1 is synthesized by condensation of intermediate 208.2 (100 mg, 0.18 mmol) with (S)-1-Methoxymethyl-3-methylbutylamine hydrochloride (J. Org. Chem. 1978, 43, 892. 36.4 mg, 0.20 mmol) analogously to the preparation of intermediate 32.3: white amorphous material, ES-MS: M+H=673: $ct_{Ret}$=4.12 min.

Example 241

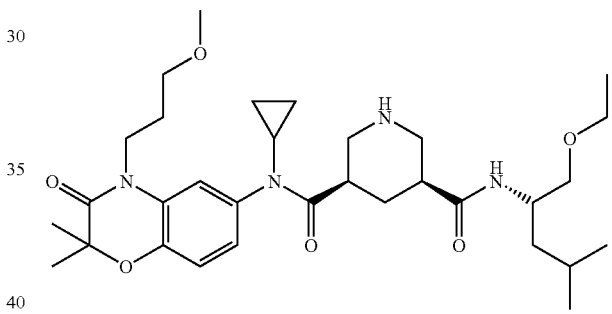

Example 241 is synthesized by deprotection of intermediate 241.1 analogously to the preparation of example 19: ES-MS: M+H=587: $ct_{Ret}$=3.09 min.

Intermediate 241.1

Intermediate 241.1 is synthesized by condensation of intermediate 108.2 (100 mg, 0.18 mmol) with (S)-1-ethoxymethyl-3-methylbutylamine hydrochloride (WO9315047, 36.4 mg, 0.20 mmol) analogously to the preparation of intermediate 32.3: white amorphous material, ES-MS: M+H=687: $ct_{Ret}$=4.21 min.

Example 242

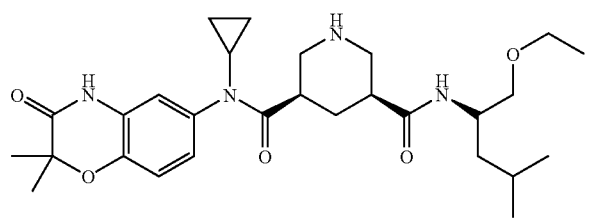

Example 242 is synthesized by a deprotection of intermediate 242.1 (120 mg, 0.20 mmol) analogously to the preparation of example 19: white amorphous material, ES-MS: M+H=515: $_ct_{Ret}$=2.84 min.

Intermediate 242.1

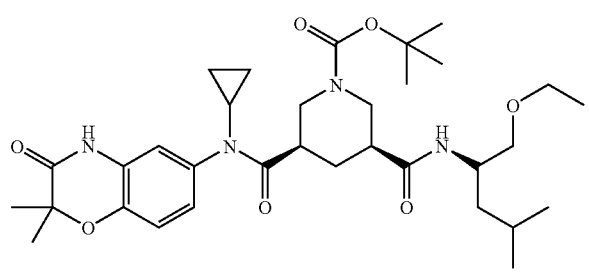

Intermediate 242.1 is synthesized by condensation of intermediate 148.2 (49 mg, 0.27 mmol) with intermediate 242.2 (110 mg, 0.23 mmol) analogously to the preparation of intermediate 1.1: white amorphous material, ES-MS: M+H=615: $_ct_{Ret}$=3.85 min.

Intermediate 242.2

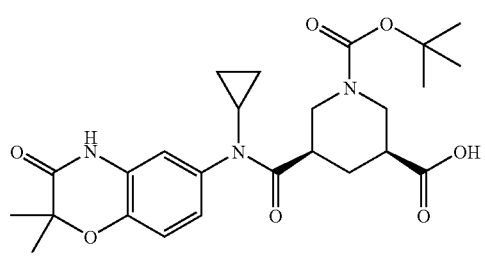

Intermediate 242.2 is synthesized by hydrolysis of intermediate 242.3 (120 mg, 0.24 mmol) analogously to the preparation of intermediate 13.2: white amorphous material, ES-MS: M+H=488: $_ct_{Ret}$=3.13 min.

Intermediate 242.3

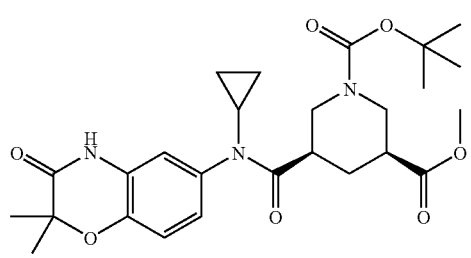

Intermediate 242.3 is synthesized by condensation of intermediate 190.2 (311 mg, 1.25 mmol) with (3R,5S)-Starting material-F (300 mg, 1 mmol) analogously to the preparation of intermediate 19.1: white amorphous material, ES-MS: M+H=502: $_ct_{Ret}$=3.48 min.

Example 243

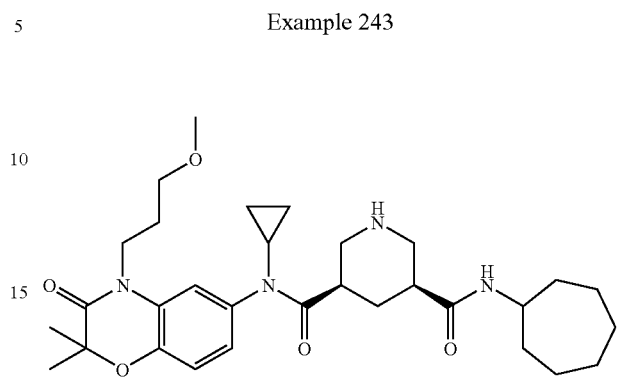

Example 243 is synthesized by deprotection of intermediate 243.1 analogously to the preparation of example 19: ES-MS: M+H=555: $_ct_{Ret}$=3.06 min.

Intermediate 243.1

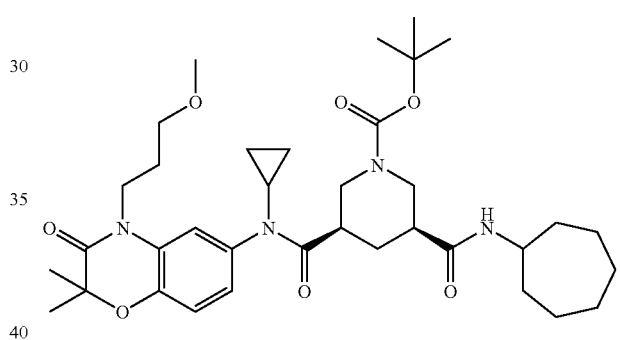

Intermediate 243.1 is synthesized by condensation of intermediate 108.2 (100 mg, 0.18 mmol) with cycloheptylamine (41.0 mg, 0.36 mmol) analogously to the preparation of intermediate 32.3: white amorphous material, ES-MS: M+H=655: $_ct_{Ret}$=3.91 min.

Example 244

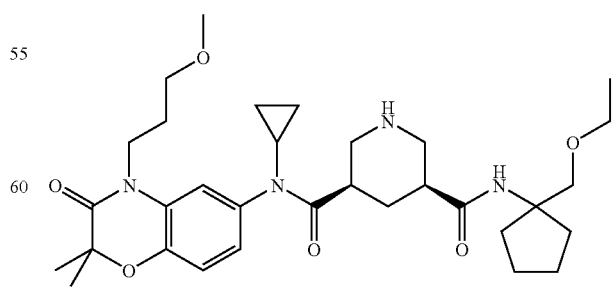

Example 244 is synthesized by deprotection of intermediate 244.1 analogously to the preparation of example 19. White material: M+H=585: $_ct_{Ret}$=3.03 min.

Intermediate 244.1

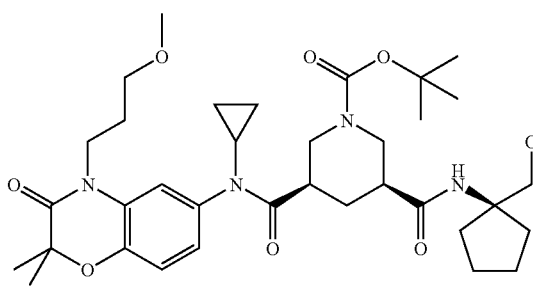

Intermediate 244.1 is synthesized by condensation of intermediate 108.2 (102.4 mg, 0.183 mmol) and 1-ethoxymethyl-cyclopentylamine hydrochloride (Journal of Medicinal Chemistry (2006), 49(11), 3068-3076.) (32.8 mg, 0.183 mmol) analogously to the preparation of Intermediate 32.3: ES-MS: M+H=685: $_A t_{Ret}$=3.90 min.

Example 245

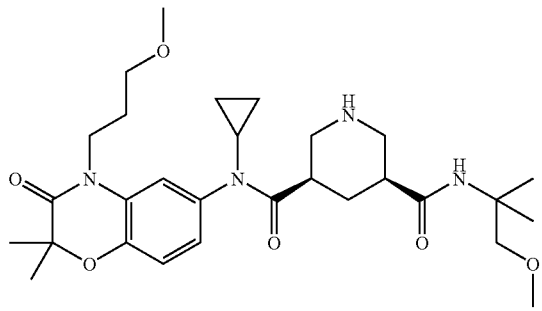

Example 245 is synthesized by deprotection of intermediate 245.1 analogously to the preparation of example 19: ES-MS: M+H=2.73: $_C t_{Ret}$=545 min.

Intermediate 245.1

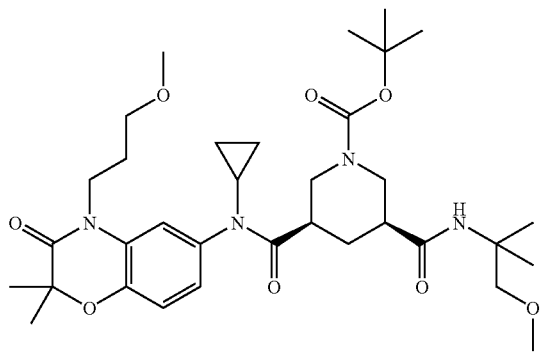

Intermediate 245.1 is synthesized by condensation of intermediate 108.2 (100 mg, 0.18 mmol) and 2-methoxy-1,1-dimethyl-ethylamine (25 mg, 0.18 mmol) analogously to the preparation of intermediate 32.3. ES-MS: M+H=645: $_C t_{Ret}$=3.81 min.

Example 249

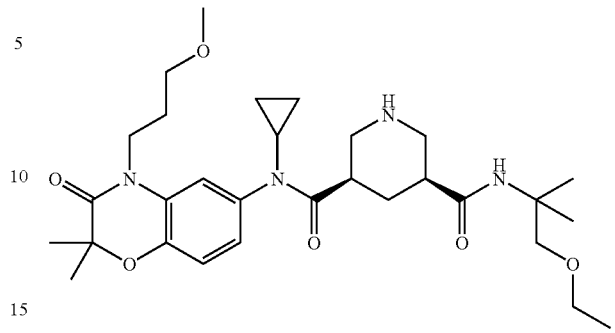

Example 249 is synthesized by deprotection of intermediate 249.1 analogously to the preparation of example 19: ES-MS: M+H=2.88: $_C t_{Ret}$=559 min.

Intermediate 246.1

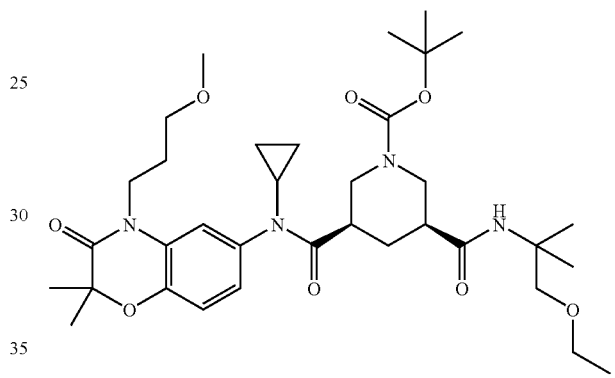

Intermediate 246.1 is synthesized by condensation of intermediate 108.2 (100 mg, 0.18 mmol) and intermediate 246.2 (28 mg, 0.18 mmol) analogously to the preparation of Intermediate 32.3. ES-MS: M+H=659: $_C t_{Ret}$=4.00 min.

Intermediate 246.2

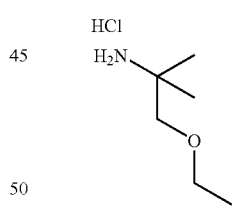

Intermediate 246.2 is synthesized by deprotection of intermediate 246.3 analogously to the preparation of example 19. The material is used in next step without further purification.

Intermediate 246.3

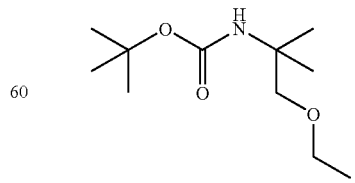

Intermediate 246.3 is synthesized by ethylation of (2-hydroxy-1,1-dimethyl-ethyl) carbamic acid tert-butyl ester (J. Org. Chem. 2003, 68, 743-746) analogously to the preparation of Intermediate 151.3: $^1$H NMR (CDCl$_3$) δ 1.19 (t, 3 H), 1.29 (s, 6 H), 1.43 (s, 9 H), 3.33 (s, 2 H), 3.51 (q, 2 H), 4.78 (br s, 1 H).

Example 247

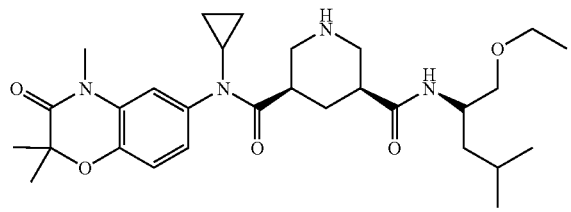

Example 247 is synthesized by deprotection of intermediate 247.1 (45 mg, 0.07 mmol) analogously to the preparation of example 19: white amorphous material, ES-MS: M+H=529: $_C t_{Ret}$=2.93 min.

Intermediate 247.1

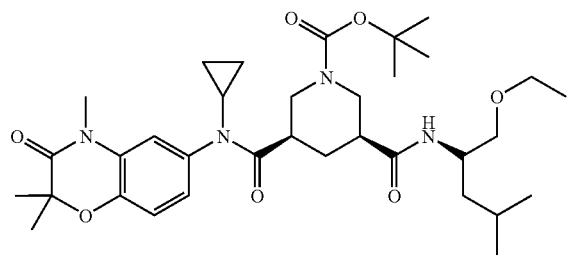

Intermediate 247.1 is synthesized by condensation of intermediate 148.2 (18 mg, 0.1 mmol) with intermediate 247.2 (43 mg, 0.085 mmol) analogously to the preparation of intermediate 1.1: white amorphous material, ES-MS: M+H=629: $_C t_{Ret}$=4.08 min.

Intermediate 247.2

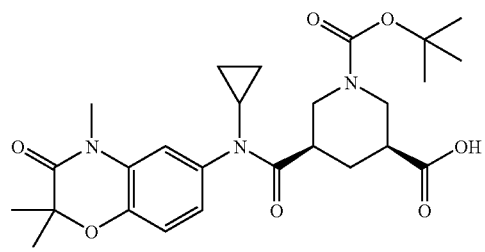

Intermediate 247.2 is synthesized by hydrolysis of intermediate 247.3 (45 mg, 0.087 mmol) analogously to the preparation of intermediate 13.2. White amorphous material, ES-MS: M+H=502: $_C t_{Ret}$=3.37 min.

Intermediate 247.3

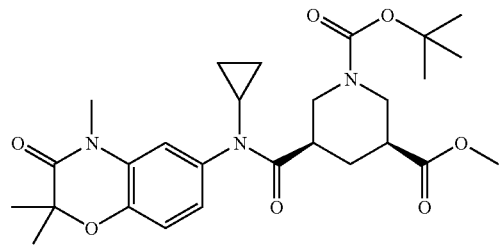

To a solution of intermediate 242.3 (50 mg, 0.1 mmol) in DMF are added K$_2$CO$_3$ (17 mg, 0.12 mmol) and methyl iodide (20 mg, 0.2 mmol). The reaction mixture is stirred at room temperature for 30 h. After adding 5% aqueous KHSO$_4$, the mixture is extracted with EtOAc. The combined organic phases are washed with water and brine and dried (Na$_2$SO$_4$). Concentration under reduced pressure and purification by RP-HPLC gives intermediate 247.3: white amorphous material, ES-MS: M+H=516: $_C t_{Ret}$=3.76.

Example 248

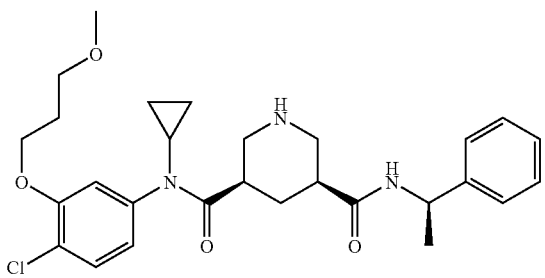

Example 248 is synthesized by deprotection of intermediate 248.1 (80 mg, 0.13 mmol) analogously to the preparation of example 1. white amorphous material, ES-MS: M+H=514: $_C t_{Ret}$=3.15 min.

Intermediate 248.1

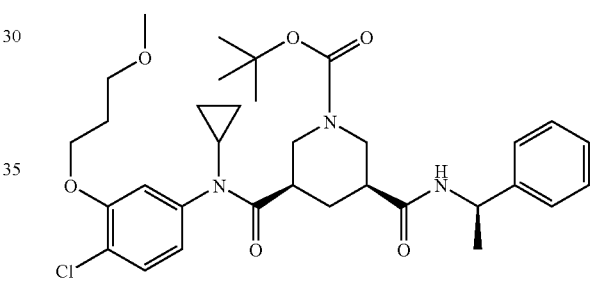

Intermediate 248.1 is synthesized by condensation of intermediate 248.4 (83 mg, 0.22 mmol) and intermediate 248.2 (56 mg, 0.22 mmol) analogously to the preparation of example 125. Colorless oil, ES-MS: M+H=614: $_B t_{Ret}$=2.18 min.

Intermediate 248.2

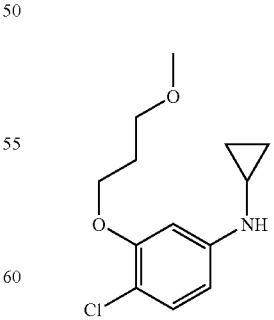

Intermediate 248.2 is synthesized by condensation of intermediate 248.3 (500 mg, 1.79 mmol) and cyclopropylamine (305 mg, 5.30 mmol) analogously to the preparation of intermediate 112.2. White amorphous material; ES-MS: M+H=256; HPLC: $_A t_{Ret}$=4.07 min.

Intermediate 248.3

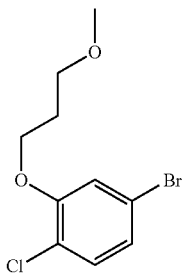

Intermediate 248.3 is synthesized by condensation of 5-bromo-2-chlorophenol (1.50 g, 7.20 mmol) and toluene-4-sulfonicacid 3-methoxypropyl ester (1.95 g, 8.00 mmol) analogously to the preparation of intermediate 37.5. Colorless oil; ES-MS: M+H=280; HPLC: $_A t_{Ret}$=4.59 min.

Intermediate 248.4

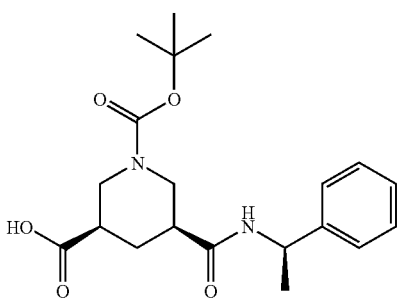

Intermediate 248.4 is synthesized by hydrolysis of intermediate 248.5 (920 mg, 2.36 mmol) analogously to the preparation of Intermediate 13.2. White amorphous material; ES-MS: [M+H]$^+$=377; HPLC: $_B t_{Ret}$=1.78 min.

Intermediate 248.5

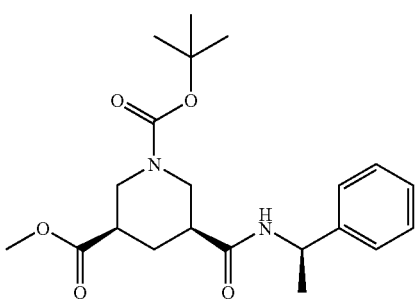

Intermediate 248.5 is synthesized by condensation of (3S,5R)-Starting material-F (765 mg, 2.66 mmol) with (R)-1-Phenyl-ethylamine (0.88 mL, 2.92 mmol) analogously to the preparation of intermediate 32.3: white amorphous material, ES-MS: M+H=391: $_B t_{Ret}$=1.93 min.

Example 249

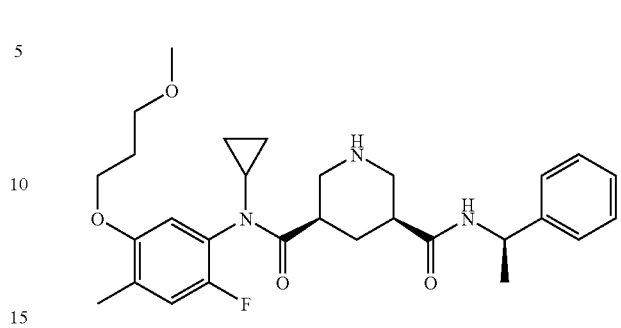

Example 249 is synthesized by deprotection of intermediate 249.1 (60 mg, 0.1 mmol) analogously to the preparation of example 1. White amorphous material, ES-MS: M+H=512: $_C t_{Ret}$=3.18 min.

Intermediate 249.1

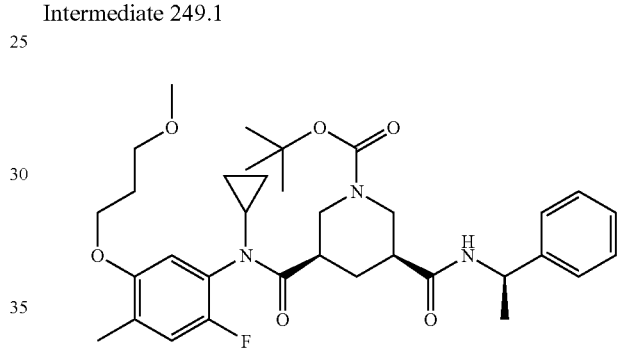

Intermediate 249.1 is synthesized by condensation of intermediate 248.4 (83 mg, 0.22 mmol) and intermediate 249.2 (56 mg, 0.22 mmol) analogously to the preparation of example 125. Colorless oil, ES-MS: M+H=612: $_B t_{Ret}$=2.20 min.

Intermediate 249.2

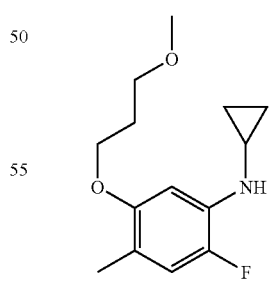

Intermediate 249.2 is prepared by cyclopropylation with intermediate 249.3 (340 mg, 1.6 mmol) analogously to the preparation of intermediate 87.2. White solid, ES-MS: M+H=254: $_B t_{Ret}$=2.14 min.

Intermediate 249.3

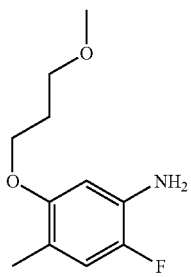

To a solution of intermediate 249.4 (555 mg, 2.28 mmol) in EtOH (3 mL) is added ammonium chloride (244 mg, 4.56 mmol), water (3 mL) and Zn (746 mg, 11.4 mmol). The mixture is stirred at 80° C. for 30 min and then filtered on celites. The filtrate is concentrated under vacuum and purified by silica gel column chromatography to give intermediate 249.3 as a colorless oil. ES-MS: M+H=214: $_B t_{Ret}$=1.54 min.

Intermediate 249.4

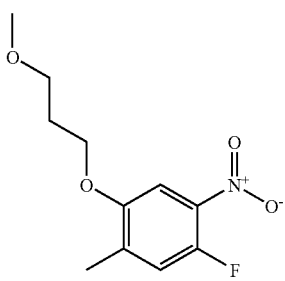

Intermediate 249.4 is synthesized by alkylation of 4-fluoro-2-methyl-5-nitrophenol (171 mg, mmol) analogously to the preparation of Intermediate 37.5. Colorless oil, ES-MS: M+H=244: $_B t_{Ret}$=2.02 min.

Example 250

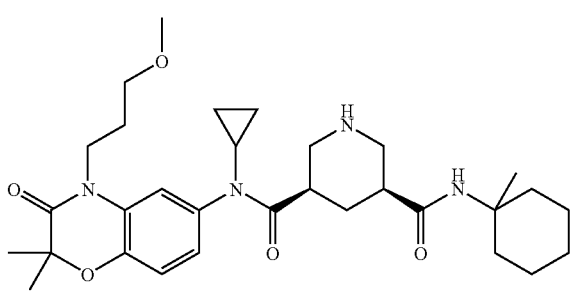

Example 250 is synthesized by deprotection of intermediate 250.1 (35 mg, 0.05 mmol) analogously to the preparation of example 123. White amorphous material, ES-MS: M+H=555: $_C t_{Ret}$=3.11 min.

Intermediate 250.1

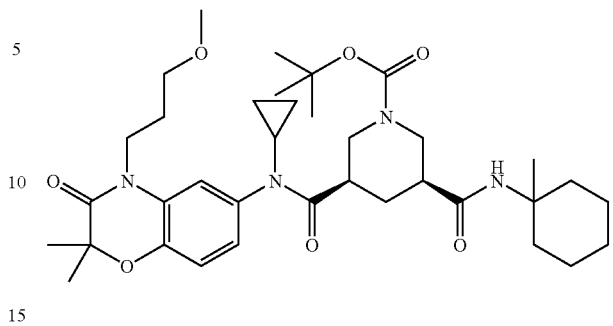

Intermediate 250.1 is synthesized by condensation of intermediate 108.2 (100 mg, 0.18 mmol) and 1-amino-1-methyl-cyclohexane analogously to the preparation of intermediate 1.1. Colorless oil, ES-MS: M+H=655: $_B t_{Ret}$=2.19 min.

Example 251

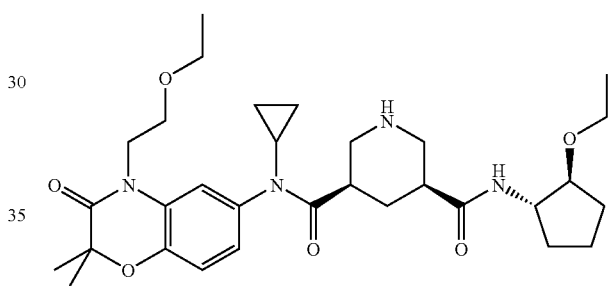

Example 251 is synthesized by deprotection of intermediate 251.1 analogously to the preparation of example 19. White material: M+H=571: $_C t_{Ret}$=2.81 min.

Intermediate 251.1

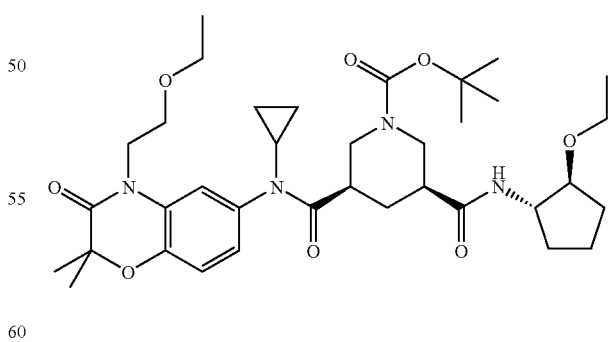

Intermediate 251.1 is synthesized by condensation of intermediate 104.2 (118.2 mg, 0.21 mmol) and intermediate 221.2 hydrochloride (46.9 mg, 0.28 mmol) analogously to the preparation of Intermediate 32.3: ES-MS: M+H=671: $_C t_{Ret}$=3.92 min.

Example 252

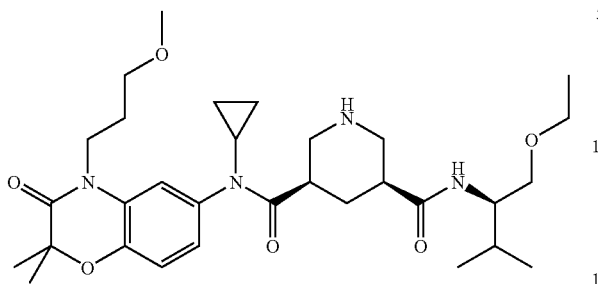

Example 252 is synthesized by deprotection of intermediate 252.1 analogously to the preparation of example 19. White material: M+H=573: $_c t_{Ret}$=2.92 min.

Intermediate 252.1

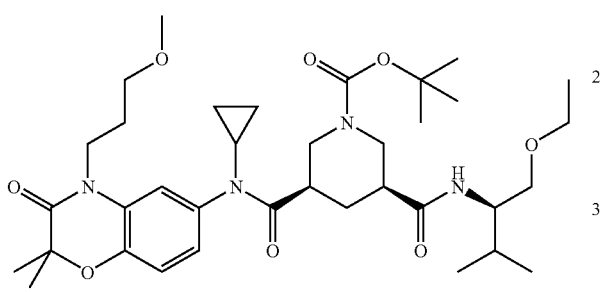

Intermediate 252.1 is synthesized by condensation of intermediate 108.2 (100 mg, 0.1786 mmol) and intermediate 252.2 hydrochloride (34 mg, 0.20 mmol) analogously to the preparation of Intermediate 32.3: ES-MS: M+H=673: $_c t_{Ret}$=4.04 min.

Intermediate 252.2

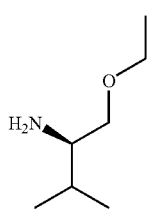

Intermediate 252.2 is synthesized by deprotection of intermediate 252.3 analogously to the preparation of example 19. ES-MS: M+H=132: $_B t_{Ret}$=1.17 min.

Intermediate 252.3

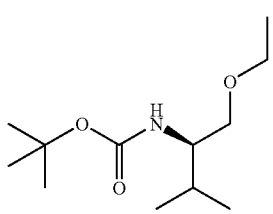

Intermediate 252.3 is synthesized by alkylation of Boc-D-valinol (Journal of Organic Chemistry (2000), 65(16), 5037-5042.) analogously to the preparation of intermediate 151.3. ES-MS: M+H-Boc=132: $_B t_{Ret}$=2.03 min Example 253

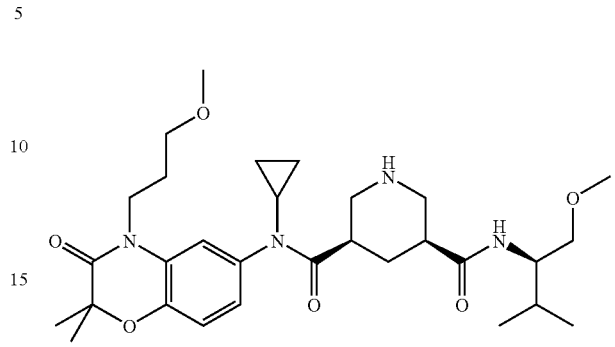

Example 253 is synthesized by deprotection of intermediate 253.1 analogously to the preparation of example 19. White material: M+H=559: $_c t_{Ret}$=2.74 min.

Intermediate 253.1

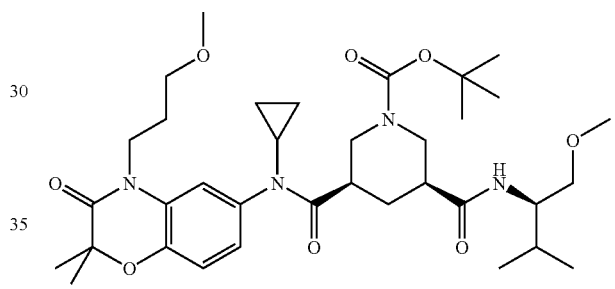

Intermediate 253.1 is synthesized by condensation of intermediate 108.2 (100 mg, 0.178 mmol) and (R)-1-methoxymethyl-2-methyl-propylamine (WO9507257) (27.3 mg, 0.178 mmol) analogously to the preparation of intermediate 32.3: ES-MS: M+H=659: $_c t_{Ret}$=3.87 min.

Example 254

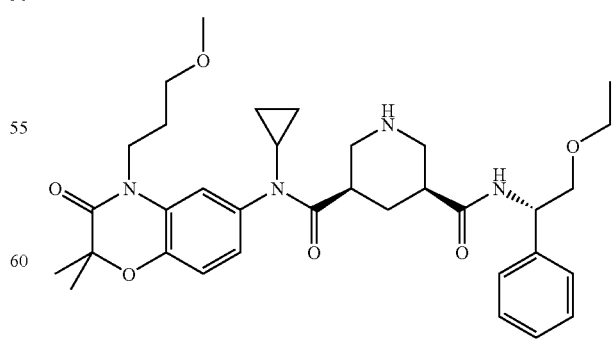

Example 254 is synthesized by deprotection of intermediate 254.1 analogously to the preparation of example 19. White material: M+H=607: $_c t_{Ret}$=3.08 min.

Intermediate 254.1

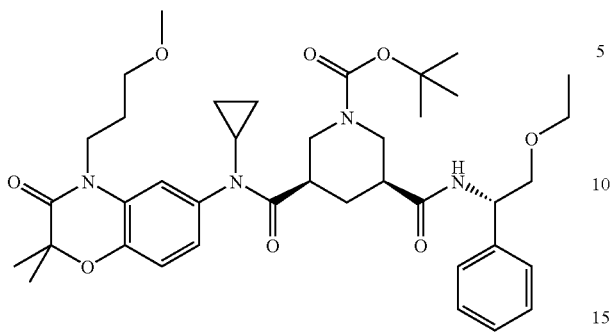

Intermediate 254.1 is synthesized by condensation of intermediate 108.2 (100 mg, 0.178 mmol) and (S)-2-ethoxy-1-phenyl-ethylamine (WO2005080373) (35.9 mg, 0.178 mmol) analogously to the preparation of intermediate 32.3: ES-MS: M+H=707: $_C t_{Ret}$=4.09. min.

Example 255

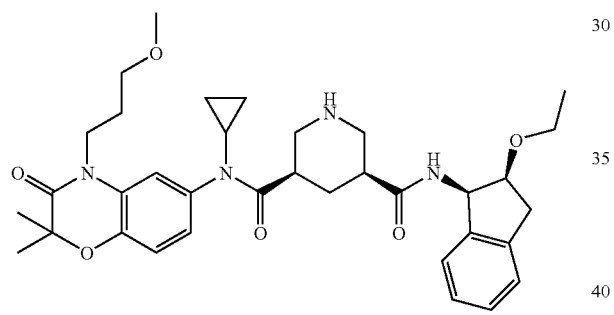

Example 255 is synthesized by deprotection of Intermediate 255.1 analogously to the preparation of example 19: ES-MS: M+H=619: $_C t_{Ret}$=3.13 min.

Intermediate 255.1

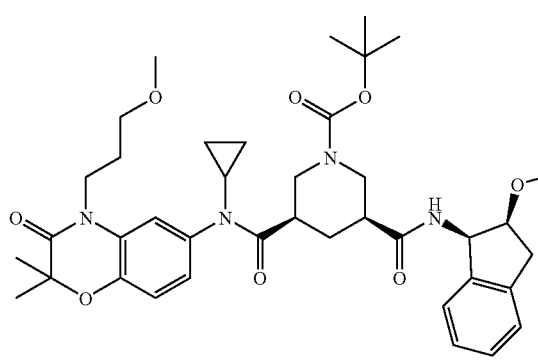

Intermediate 255.1 is synthesized by condensation of intermediate 108.2 (100 mg, 0.18 mmol) with intermediate 255.2 (46.2 mg, 0.22 mmol) analogously to the preparation of intermediate 32.3: white amorphous material, ES-MS: M+H=718: $_B t_{Ret}$=2.18 min.

Intermediate 255.2

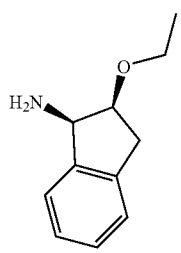

Intermediate 255.2 is synthesized by deprotection of intermediate 255.3 analogously to the preparation of example 19: ES-MS: M+H=178: $_B t_{Ret}$=1.32 min.

Intermediate 255.3

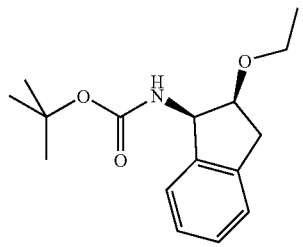

To a solution of ((1R,2S)-2-hydroxy-indan-1-yl)-carbamic acid tert-butyl ester (300 mg, 1.20 mmol) in DMF (3 mL) under $N_2$ at 0° C., is added NaH (104 mg of 60 wt % in mineral oil, 2.60 mmol). After stirring at the same temperature for a few min, EtI (0.10 mL, 1.20 mmol) is added. The resulting solution is stirred at rt for 2 h. The reaction is quenched with $H_2O$ and the mixture is extracted with EtOAc and dried over $Na_2SO_4$. Concentration under reduced pressure gives the crude product. The crude product is purified by silica gel chromatography to afford intermediate 255.3: ES-MS: M+H-$^t$Bu=222: $_B t_{Ret}$=2.14 min.

Example 256

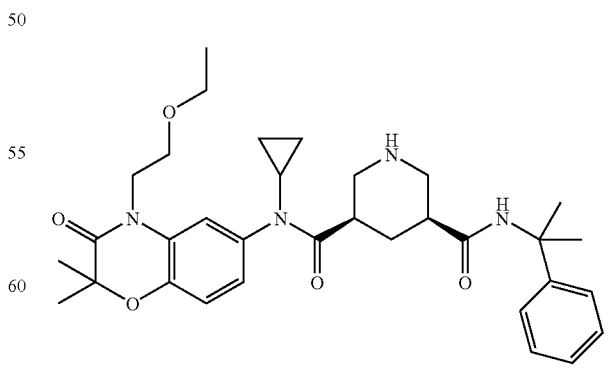

Example 256 is synthesized by deprotection of intermediate 256.1 analogously to the preparation of example 19: ES-MS: M+H=577: $_C t_{Ret}$=3.14 min.

Intermediate 256.1

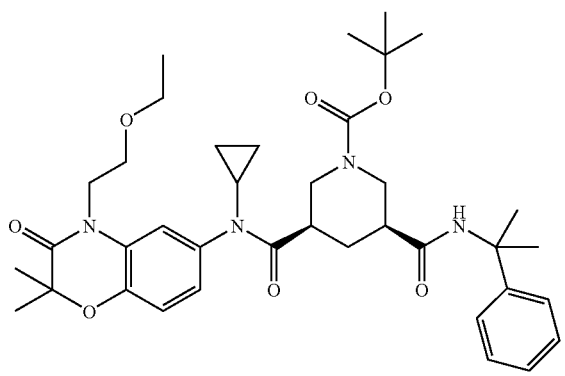

Intermediate 256.1 is synthesized by condensation of intermediate 208.2 (150 mg, 0.27 mmol) with 1-methyl-1-phenyl-ethylamine (54.0 mg, 0.40 mmol) analogously to the preparation of intermediate 32.3: white amorphous material, ES-MS: M+H=677: $_B t_{Ret}$=2.17 min.

Example 257

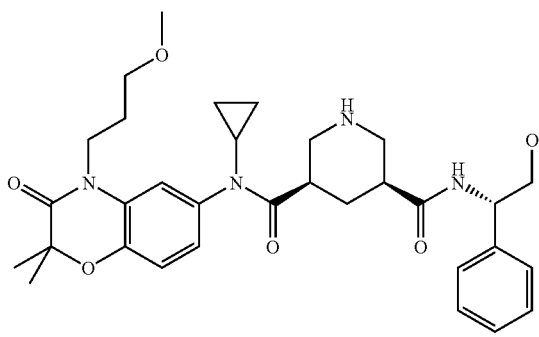

Example 257 is synthesized by deprotection of intermediate 257.1 analogously to the preparation of example 19. White material: M+H=593: $_C t_{Ret}$=2.94 min.
Intermediate 257.1

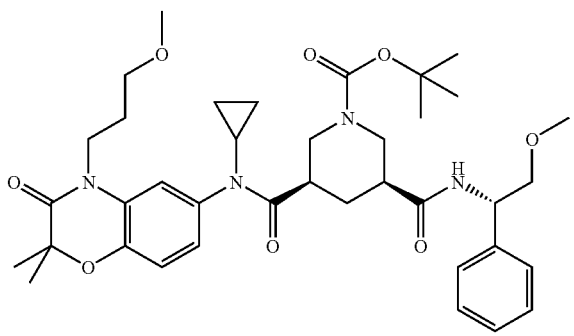

Intermediate 257.1 is synthesized by condensation of intermediate 108.2 (120 mg, 0.2136 mmol) and (S)-2-methoxy-1-phenyl-ethylamine (Tetrahedron: Asymmetry (2003), 14(5), 525-528.) (40.08 mg, 0.2136 mmol) analogously to the preparation of intermediate 32.3: ES-MS: M+H=693: $_C t_{Ret}$=3.93 min.

Example 258

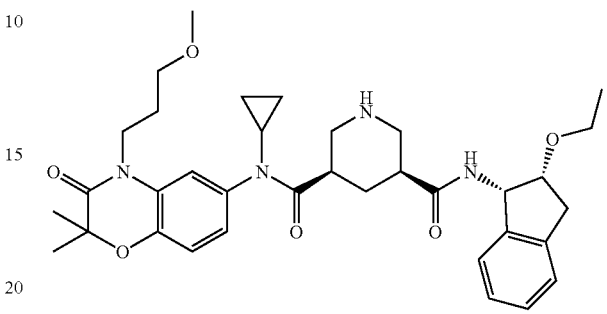

Example 258 is synthesized by deprotection of intermediate 258.1 analogously to the preparation of example 19: ES-MS: M+H=619: $_C t_{Ret}$=3.20 min.
Intermediate 258.1

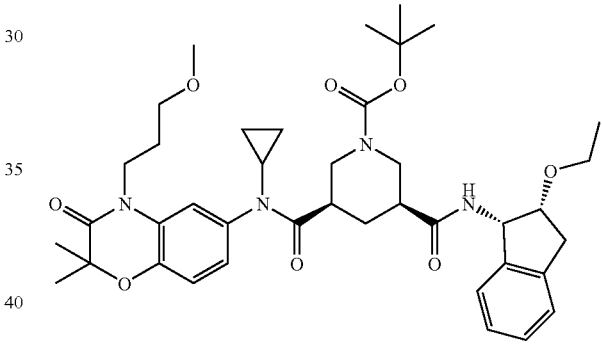

Intermediate 258.1 is synthesized by condensation of intermediate 108.2 (100 mg, 0.18 mmol) with intermediate 258.2 (46.2 mg, 0.22 mmol) analogously to the preparation of intermediate 32.3: white amorphous material, ES-MS: M+H=718: $_B t_{Ret}$=2.18 min.
Intermediate 258.2

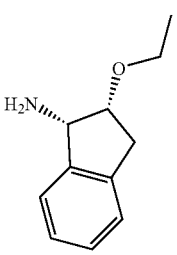

Intermediate 258.2 is synthesized by deprotection of intermediate 258.3 analogously to the preparation of example 19: ES-MS: M+H=178: $_B t_{Ret}$=1.32 min.

Intermediate 258.3

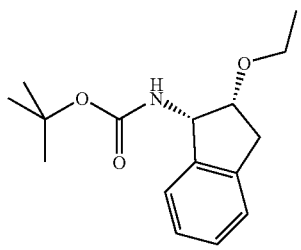

Intermediate 258.3 is synthesized by alkylation of ((1S, 2R)-2-hydroxy-indan-1-yl)-carbamic acid tert-butyl ester (300 mg, 1.20 mmol) with NaH (104 mg of 60 wt % in mineral oil, 2.60 mmol) and EtI (0.10 mL, 1.20 mmol) analogously to the preparation of intermediate 148.3. White amorphous material, ES-MS: M+H-$^t$Bu=222: $_c$t$_{Ret}$=4.07 min.

Example 259

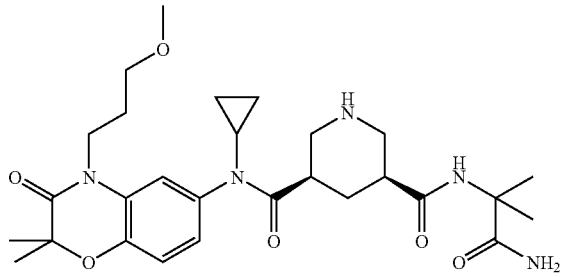

Example 259 is synthesized by deprotection of intermediate 259.1 analogously to the preparation of example 19: ES-MS: M+H=2.38: $_c$t$_{Ret}$=544 min.

Intermediate 259.1

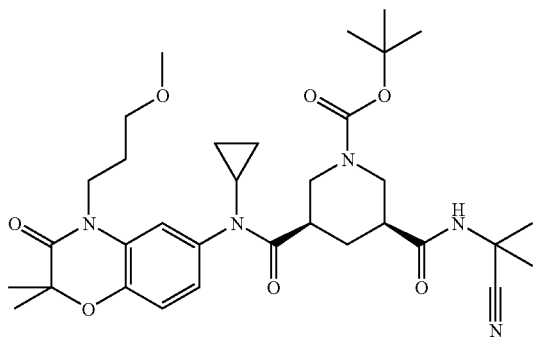

Intermediate 259.1 is synthesized by condensation of intermediate 108.2 (100 mg, 0.18 mmol) and 2-amino-2-methyl-propionitrile (23 mg, 0.27 mmol) analogously to the preparation of intermediate 32.3. ES-MS: M+H=626: $_c$t$_{Ret}$=3.65 min.

Example 260

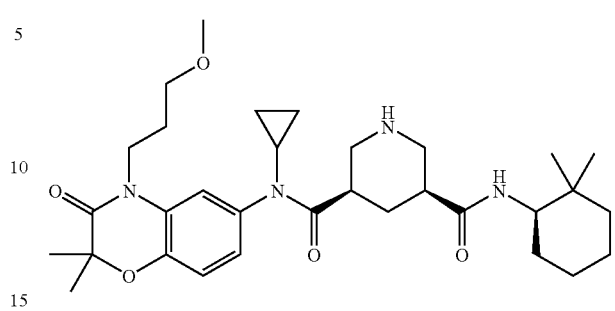

Example 260 is synthesized by deprotection of intermediate 260.1 (72 mg, 0.1 mmol) analogously to the preparation of example 123. White amorphous material, ES-MS: M+H=569: $_c$t$_{Ret}$=3.19 min.

Intermediate 260.1

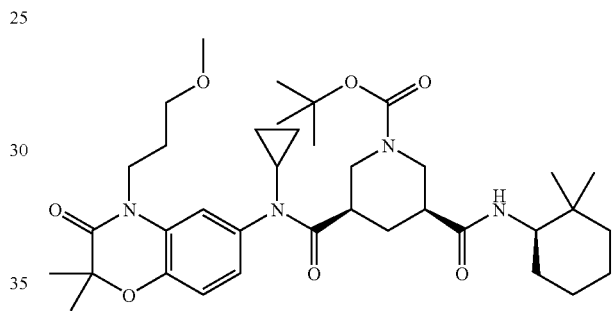

Intermediate 260.1 is synthesized by condensation of intermediate 108.2 (100 mg, 0.18 mmol) and (R)-2,2-dimethyl-cyclohexylamine (44 mg, 0.27 mmol) analogously to the preparation of Intermediate 1.1. Colorless oil, ES-MS: M+H=669: $_B$t$_{Ret}$=2.20 min.

Example 261

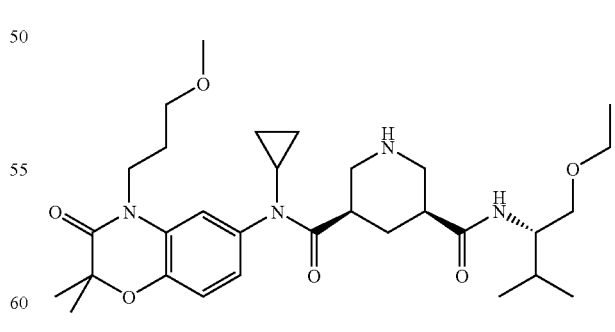

Example 261 is synthesized by deprotection of intermediate 261.1 analogously to the preparation of example 19. White material: M+H=573: $_c$t$_{Ret}$=2.97 min.

Intermediate 261.1

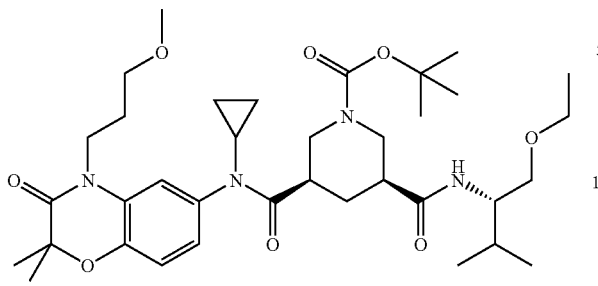

Intermediate 261.1 is synthesized by condensation of intermediate 108.2 (100 mg, 0.178 mmol) and intermediate 261.2 hydrochloride (42.8 mg, 0.26 mmol) analogously to the preparation of intermediate 32.3: ES-MS: M+H=673: $_C t_{Ret}$=4.01 min.

Intermediate 261.2

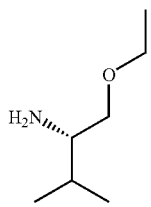

Intermediate 261.2 is synthesized by deprotection of intermediate 261.3 analogously to the preparation of example 19. White material: M+H=132: $_B t_{Ret}$=1.20 min.

Intermediate 261.3

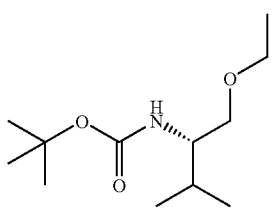

Intermediate 261.3 is synthesized by alkylation of Boc-L-valinol (Journal of the American Chemical Society (2004), 126(37), 11440-11441.) analogously to the preparation of intermediate 151.3: M+H-Boc=132: $_B t_{Ret}$=2.17 min.

Example 262

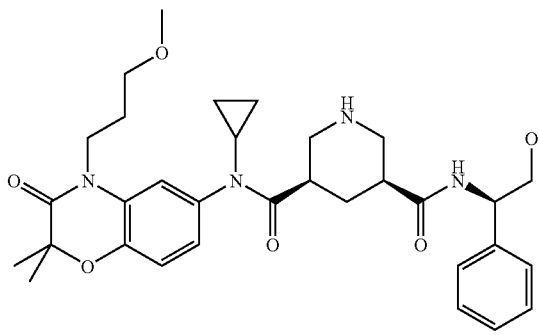

Example 262 is synthesized by deprotection of intermediate 262.1 analogously to the preparation of example 19. White material: M+H=607: $_C t_{Ret}$=3.06 min.

Intermediate 262.1

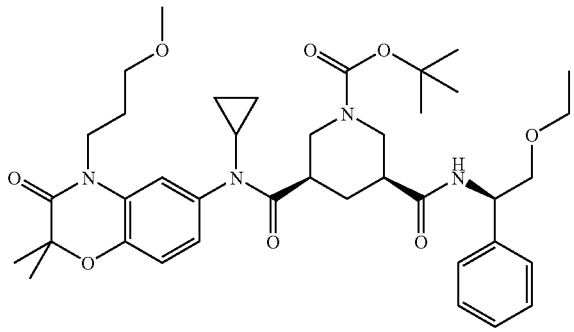

Intermediate 262.1 is synthesized by condensation of intermediate 108.2 (100 mg, 0.178 mmol) and α-ethoxymethyl-benzenemethanamine hydrochloride (EP691346) (47.3 mg, 0.23 mmol) analogously to the preparation of intermediate 32.3: ES-MS: M+H=707: $_C t_{Ret}$=4.13 min.

Example 263

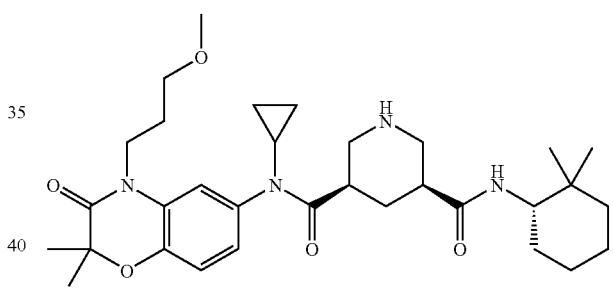

Example 263 is synthesized by deprotection of intermediate 263.1 (44 mg, 0.07 mmol) analogously to the preparation of example 123. White amorphous material, ES-MS: M+H=569: $_C t_{Ret}$=3.19 min.

Intermediate 263.1

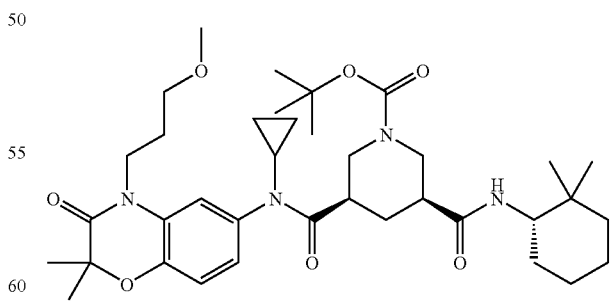

Intermediate 263.1 is synthesized by condensation of intermediate 108.2 (100 mg, 0.18 mmol) and (S)-2,2-dimethylcyclohexylamine (44 mg, 0.27 mmol) analogously to the preparation of intermediate 1.1. Colorless oil, ES-MS: M+H=669: $_B t_{Ret}$=2.23 min.

Example 264

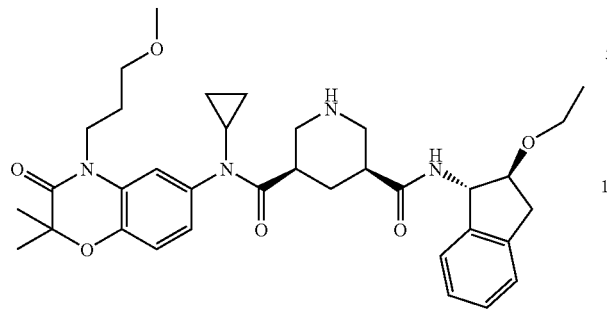

Example 264 is synthesized by deprotection of intermediate 264.1 analogously to the preparation of example 19: ES-MS: M+H=619: $_C t_{Ret}$=3.05 min.

Intermediate 264.1

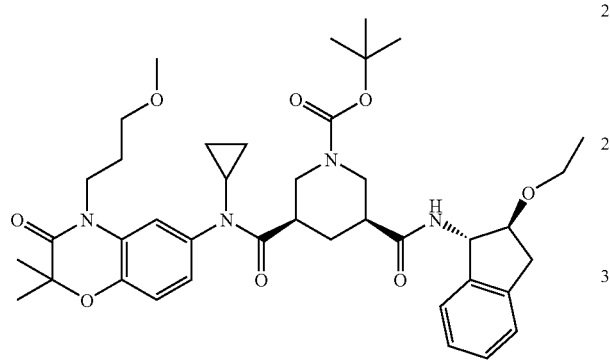

Intermediate 264.1 is synthesized by condensation of intermediate 108.2 (100 mg, 0.18 mmol) with intermediate 264.2 (47.0 mg, 0.22 mmol) analogously to the preparation of intermediate 32.3: white amorphous material, ES-MS: M+H=719: $_C t_{Ret}$=4.15 min.

Intermediate 264.2

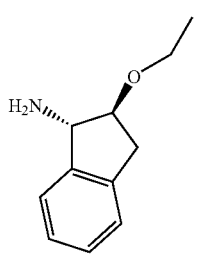

Intermediate 264.2 is synthesized by deprotection of intermediate 264.3 analogously to the preparation of example 19: ES-MS: M+H=178: $_B t_{Ret}$=1.32 min.

Intermediate 264.3

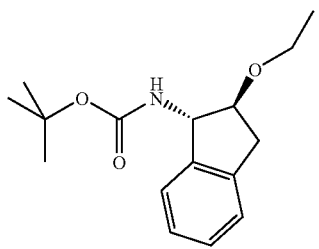

Intermediate 264.3 is synthesized by alkylation of ((1S, 2S)-2-hydroxy-indan-1-yl)-carbamic acid tert-butyl ester (140 mg, 0.56 mmol) with NaH (49.3 mg of 60 wt % in mineral oil, 1.23 mmol) and EtI (0.05 mL, 0.67 mmol) analogously to the preparation of intermediate 148.3. White amorphous material, ES-MS: M+H-$^t$Bu=222: $_B t_{Ret}$=2.06 min.

Example 265

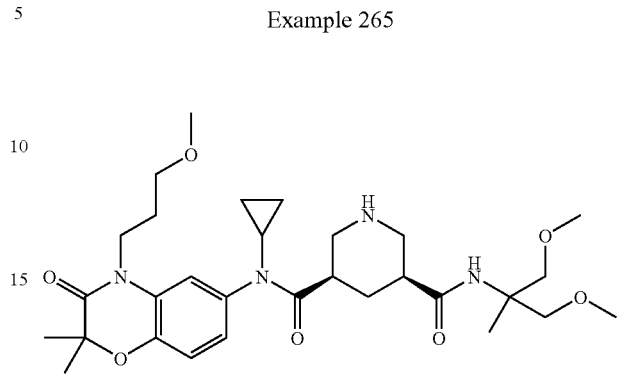

Example 265 is synthesized by deprotection of intermediate 265.1 analogously to the preparation of example 19. ES-MS: M+H=575: $_C t_{Ret}$=2.73 min.

Intermediate 265.1

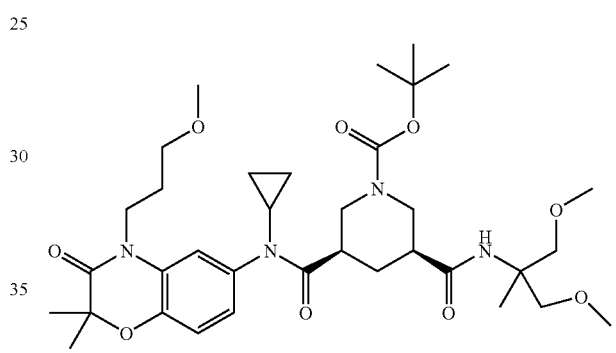

Intermediate 265.1 is synthesized by condensation of intermediate 108.2 (100 mg, 0.18 mmol) and 2-methoxy-1-methoxymethyl-1-methyl-ethylamine (37 mg, 0.22 mmol) analogously to the preparation of intermediate 32.3. ES-MS: M+H=675: $_C t_{Ret}$=3.80 min.

Intermediate 265.2

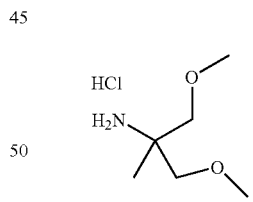

Intermediate 265.2 is synthesized by deprotection of intermediate 265.3 analogously to the preparation of example 19. The material is used in next step without further purification.

Intermediate 265.3

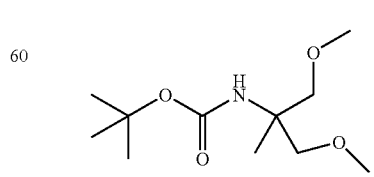

Intermediate 265.3 is synthesized by methylation of commercially available 2-tert-butoxycarbonylamino-2-methyl-1, 3-propanediol analogously to the preparation of intermediate 151.3. ES-MS: M+H=234: $_ct_{Ret}$=3.38 min.

Example 266

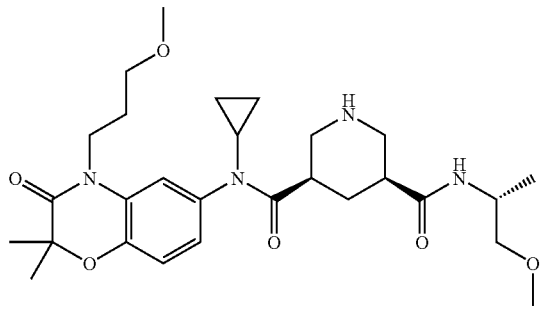

Example 266 is synthesized by deprotection of intermediate 266.1 (120 mg, 0.19 mmol) analogously to the preparation of intermediate 103.2. White amorphous material, ES-MS: M+H=531: $_ct_{Ret}$=2.54 min.

Intermediate 266.1

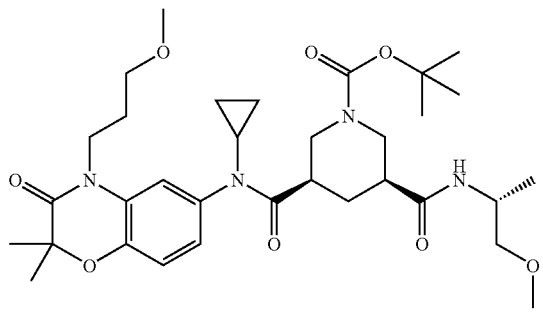

Intermediate 266.1 is synthesized by condensation of (R)-2-methoxy-1-methylethylamine (CAS No, 626220-76-6, 40 mg, 0.322 mmol) with intermediate 108.2 (120 mg, 0.214 mmol) analogously to the preparation of intermediate 1.1. White amorphous material, ES-MS: M+H=631: $_ct_{Ret}$=3.57 min.

Example 267

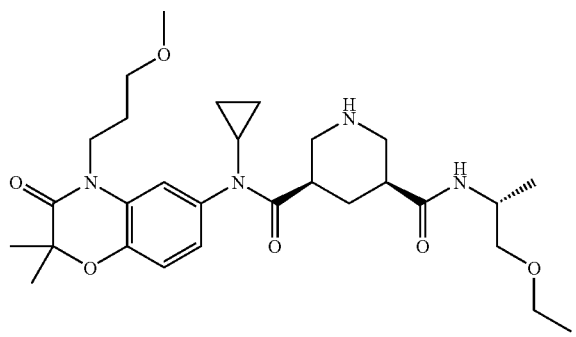

Example 267 is synthesized by deprotection of intermediate 267.1 (115 mg, 0.18 mmol) analogously to the preparation of intermediate 103.2. White amorphous material, ES-MS: M+H=545: $_ct_{Ret}$=2.68 min.

Intermediate 267.1

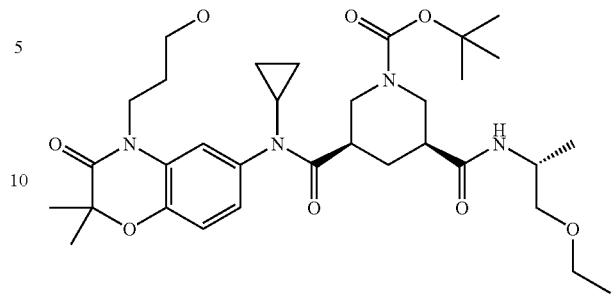

Intermediate 267.1 is synthesized by condensation of intermediate 267.2 (45 mg, 0.322 mmol) with intermediate 108.2 (120 mg, 0.214 mmol) analogously to the preparation of intermediate 1.1. White amorphous material, ES-MS: M+H=645: $_ct_{Ret}$=3.73 min.

Intermediate 267.2

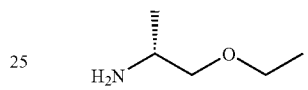

Intermediate 267.2 is synthesized by deprotection of intermediate 267.3 (441 mg, 2.17 mmol) analogously to the preparation of intermediate 103.2. White amorphous material, $^1$H-NMR (DMSO-d6, 400 MHz): δ 1.15 (3H, t), 1.17 (3H, d), 3.37-3.59 (5H, m), 8.00 (3H, br).

Intermediate 267.3

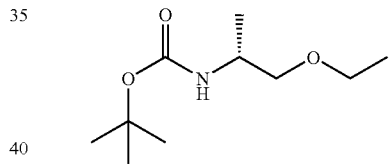

Intermediate 267.3 is synthesized by alkylation of ((R)-2-hydroxy-1-methylethyl) carbamic acid tert-butyl ester (898 mg, 5.13 mmol) analogously to the preparation of intermediate 148.3. White amorphous material, $^1$H-NMR (CDCl$_3$, 400 MHz): δ 1.17 (3H, t), 1.19 (3H, d), 1.45 (9H, s), 3.33-3.39 (2H, m), 3.43-3.52 (2H, m), 3.80 (1H, br), 4.69 (1H, br).

Example 268

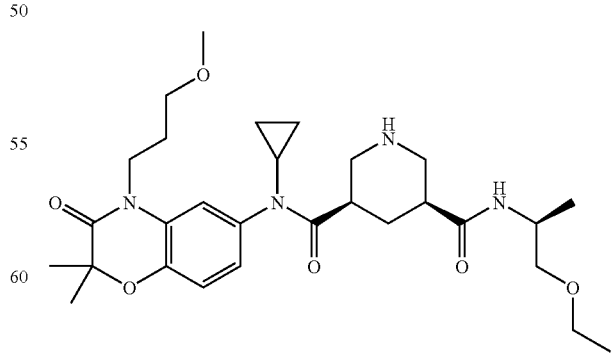

Example 268 is synthesized by deprotection of intermediate 268.1 (110 mg, 0.17 mmol) analogously to the preparation of intermediate 103.2. White amorphous material, ES-MS: M+H=545: $_ct_{Ret}$=2.68 min.

Intermediate 268.1

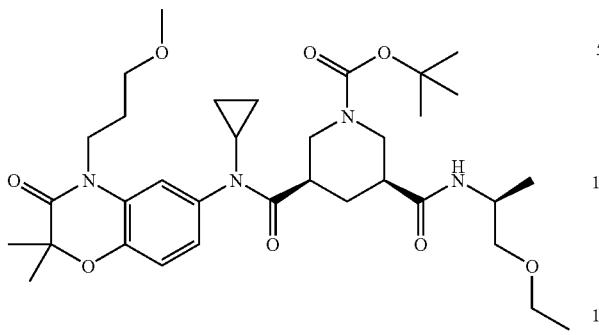

Intermediate 268.1 is synthesized by condensation of intermediate 268.2 (45 mg, 0.322 mmol) with intermediate 108.2 (120 mg, 0.214 mmol) analogously to the preparation of intermediate 1.1. White amorphous material, ES-MS: M+H=645: $c^tRet$=3.74 min.

Intermediate 268.2

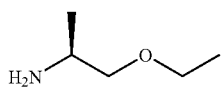

Intermediate 268.2 is synthesized by deprotection of intermediate 268.3 (221 mg, 1.06 mmol) analogously to the preparation of intermediate 103.2. White amorphous material: $^1$H-NMR (CDCl$_3$, 400 MHz): δ 1.24 (3H, t), 1.44 (3H, d), 3.52-3.67 (5H, m), 8.39 (3H, br).

Intermediate 268.3

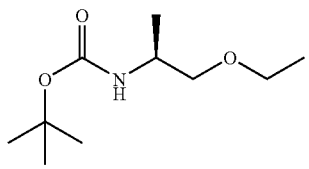

Intermediate 268.3 is synthesized by alkylation of ((S)-2-hydroxy-1-methylethyl) carbamic acid tert-butyl ester (936 mg, 5.34 mmol) analogously to the preparation of intermediate 148.3. White amorphous material: $^1$H-NMR (CDCl$_3$, 400 MHz): δ 1.17 (3H, t), 1.19 (3H, d), 1.45 (9H, s), 3.33-3.39 (2H, m), 3.43-3.52 (2H, m), 3.80 (1H, br), 4.69 (1H, br).

Example 269

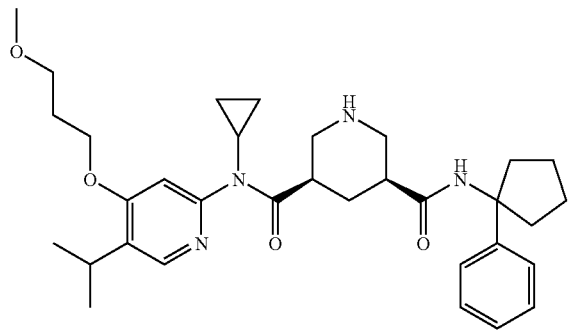

Example 269 is synthesized by deprotection of intermediate 269.1 (40 mg, 0.06 mmol) analogously to the preparation of intermediate 103.2. White amorphous material, ES-MS: M+H=563: $c^tRet$=3.48 min.

Intermediate 269.1

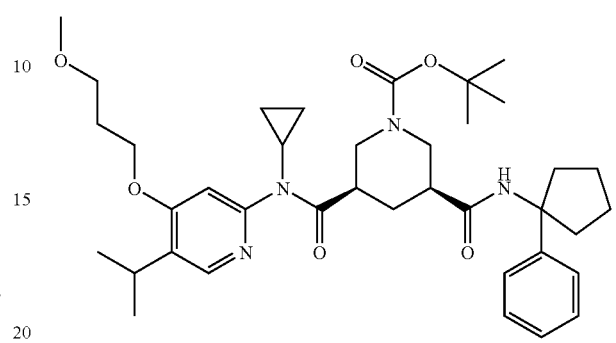

Intermediate 269.1 is synthesized by condensation of intermediate 269.2 (56 mg, 0.2 mmol) with intermediate 169.2 (70 mg, 0.17 mmol) analogously to the preparation of example 125. White amorphous material, ES-MS: M+H=663: $c^tRet$=3.85 min.

Intermediate 269.2

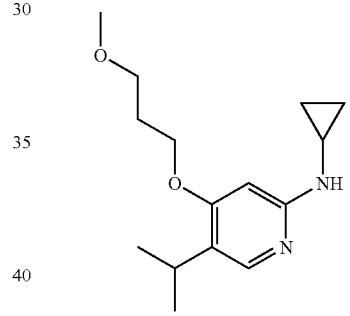

Intermediate 269.2 is synthesized by dehydration of intermediate 269.3 (400 mg, 1.5 mmol) analogously to the preparation of intermediate 90.3. White solid, ES-MS: M+H=265: $c^tRet$=2.59 min.

Intermediate 269.3

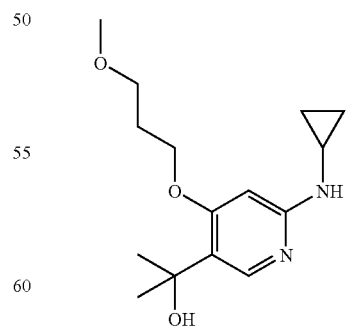

Intermediate 269.3 is synthesized by alkylation of intermediate 269.4 (500 mg, 1.5 mmol) analogously to the preparation of intermediate 89.3. White amorphous material, ES-MS: M+H=281: $c^tRet$=2.03 min.

Intermediate 269.4

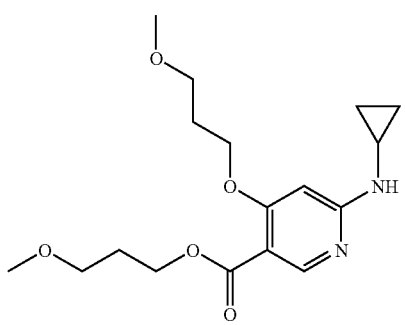

A mixture of methyl 2,4-dichloronicotinate (8 g, 39 mmol), 3-methoxypropanol (18 g, 195 mmol), and $K_2CO_3$ (16 g, 116 mmol) in DMF (70 mL) is stirred at 80° C. After stirring for 18 h, the reaction mixture is cooled down to room temperature, poured into ice/EtOAc (500/500 cc v/v), and separated. The organic phase is successively washed with $H_2O$ twice, and brine, then dried over $Na_2SO_4$ and concentrated in vacuo. The crude material is used for the next reaction without further purification.

A mixture of the crude product, cyclopropylamine, and $K_2CO_3$ in NMP is stirred at 80° C. After stirring for 28 h, the reaction mixture is cooled at room temperature, poured into ice/EtOAc (500/500 v/v) and extracted. The organic phase is successively washed with $H_2O$ twice, brine, dried over $Na_2SO_4$ and concentrated in vacuo. $SiO_2$ column chromatography purification affords intermediate 269.4: white solid, ES-MS: M+H=399: $_Ct_{Ret}$=2.19 min.

Example 270

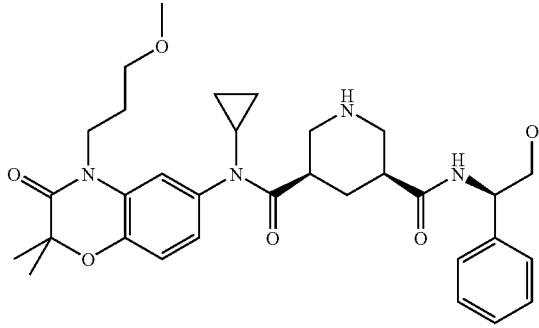

Example 270 is synthesized by deprotection of intermediate 270.1 analogously to the preparation of example 19. White material: M+H=593: $_Ct_{Ret}$=2.90 min.

Intermediate 270.1

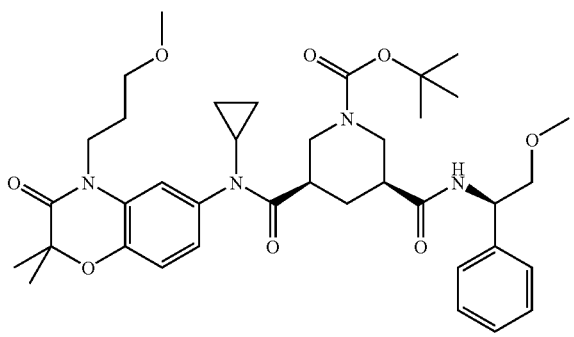

Intermediate 270.1 is synthesized by condensation of intermediate 108.2 (100 mg, 0.178 mmol) and (R)-(−)-1-amino-1-phenyl-2-methoxyethane hydrochloride (Organic Syntheses (1998), 75 19-30.) (33.2 mg, 0.178 mmol) analogously to the preparation of intermediate 32.3: ES-MS: M+H=693: $_Ct_{Ret}$=3.97 min.

Example 271

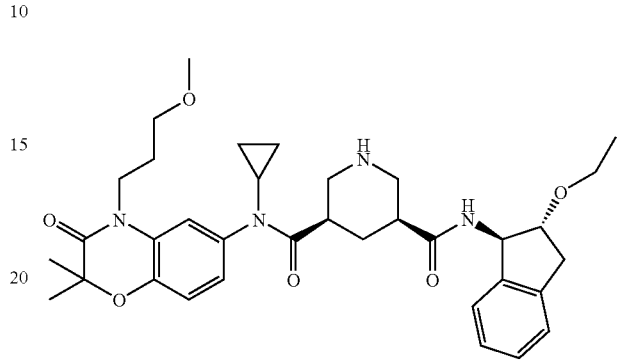

Example 271 is synthesized by deprotection of intermediate 271.1 analogously to the preparation of example 19: ES-MS: M+H=619: $_At_{Ret}$=2.70 min.

Intermediate 271.1

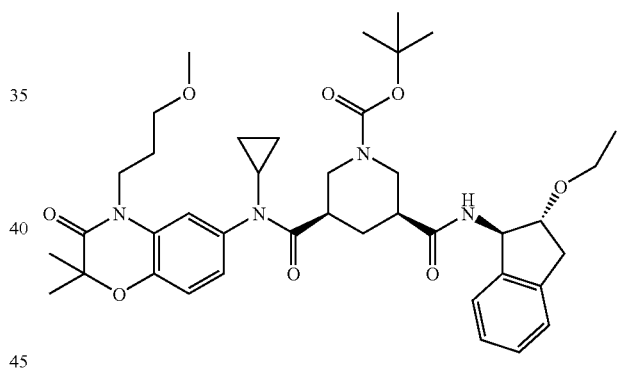

Intermediate 271.1 is synthesized by condensation of intermediate 108.2 (100 mg, 0.18 mmol) with intermediate 271.2 (47.0 mg, 0.22 mmol) analogously to the preparation of intermediate 32.3. White amorphous material, ES-MS: M+H=719: $_Bt_{Ret}$=2.17 min.

Intermediate 271.2

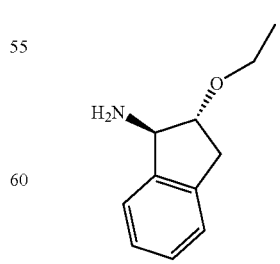

Intermediate 271.2 is synthesized by deprotection of intermediate 271.3 analogously to the preparation of example 19: ES-MS: M+H=178: $_Bt_{Ret}$=1.34 min.

Intermediate 271.3

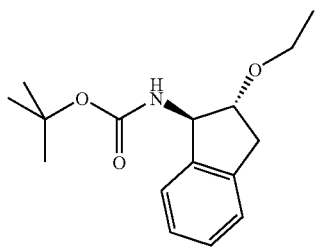

Intermediate 271.3 is synthesized by alkylation of ((1R, 2R)-2-hydroxy-indan-1-yl)-carbamic acid tert-butyl ester (*Adv. Synth. Catal.* 2005, 347, 255., 250 mg, 1.00 mmol) with NaH (88 mg of 60 wt % in mineral oil, 2.20 mmol) and EtI (0.09 mL, 1.1 mmol) analogously to the preparation of intermediate 148.3. White amorphous material, ES-MS: M+H-$^t$Bu=222: $_Bt_{Ret}$=2.07 min.

Example 272

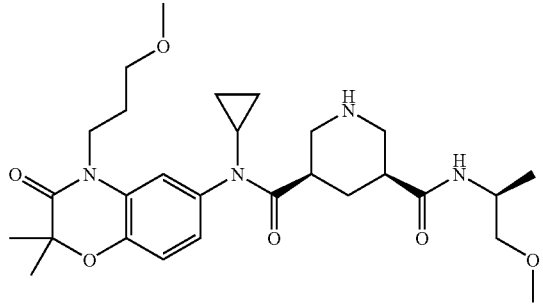

Example 272 is synthesized by deprotection of intermediate 272.1 (120 mg, 0.19 mmol) analogously to the preparation of intermediate 103.2. White amorphous material, ES-MS: M+H=531: $_Ct_{Ret}$=2.58 min.

Intermediate 272.1

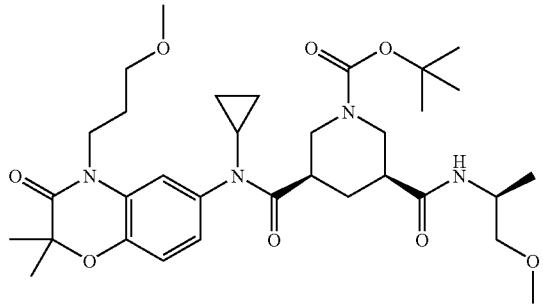

Intermediate 272.1 is synthesized by condensation of (S)-2-methoxy-1-methylethylamine (40 mg, 0.322 mmol) with intermediate 108.2 (120 mg, 0.214 mmol) analogously to the preparation of intermediate 1.1. White amorphous material, ES-MS: M+H=631: $_Ct_{Ret}$=3.59 min.

Example 273

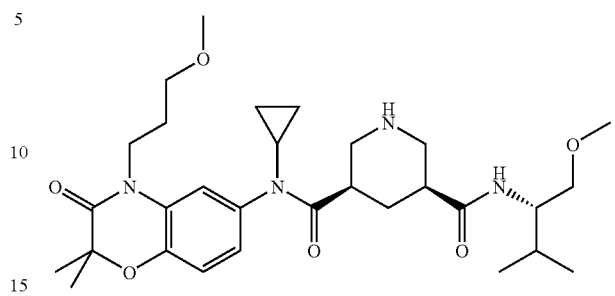

Example 273 is synthesized by deprotection of intermediate 273.1 analogously to the preparation of example 19. White material: M+H=559: $_Ct_{Ret}$=2.80 min Intermediate 273.1

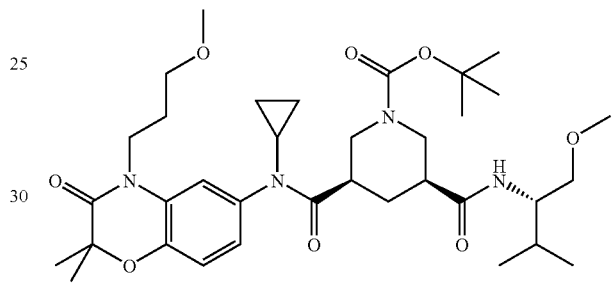

Intermediate 273.1 is synthesized by condensation of intermediate 108.2 (100 mg, 0.178 mmol) and (S)-1-methoxymethyl-2-methyl-propylamine (Journal of Organic Chemistry (1988), 53(13), 2991-9.) (27.3 mg, 0.178 mmol) analogously to the preparation of Intermediate 32.3. ES-MS: M+H=659: $_Ct_{Ret}$=3.85 min.

Example 274

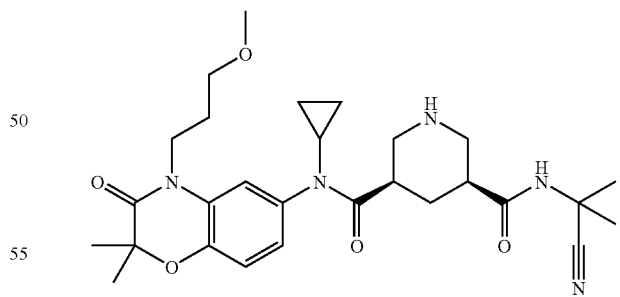

To a solution of intermediate 274.1 (110 mg, 0.18 mmol) in CH$_2$Cl$_2$ (3 mL) are added TMSOTf (98 μL, 0.54 mmol), 2,6-lutidine (64 μL, 0.54 mmol) at rt. Then the mixture is stirred at room temperature. After 5 h, the reaction mixture is quenched with H$_2$O and extracted with EtOAc. The combined organic phase is successively washed with H$_2$O, and concentrated under reduced pressure. The residue is purified by silica gel column chromatography to give example 274. White powder material; ES-MS: [M+H]$^+$=526; HPLC: $_Ct_{Ret}$=2.63 min.

Example 275

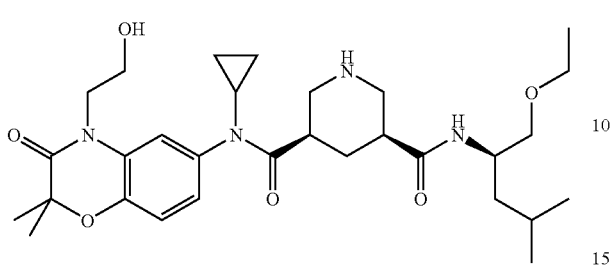

To a solution of intermediate 275.1 (140.9 mg, 0.19 mmol) in CH$_3$CN (2 mL)/H$_2$O (2 mL) at rt under N$_2$, TFA (2 mL) is added. The reaction mixture is stirred at rt for 5 h. Concentration under reduced pressure gives the crude product. The crude product is purified by reverse phase HPLC to give the desired example 275. ES-MS: M+H=559: $_c t_{Ret}$=2.94 min Intermediate 275.1

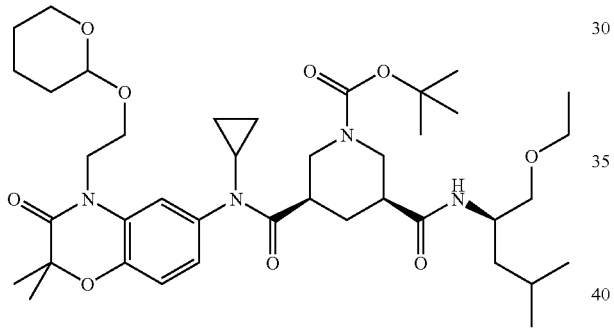

Intermediate 275.1 is synthesized by condensation of intermediate 275.2 (101.8 mg, 0.165 mmol) and intermediate 148.2 hydrochloride (36 mg, 0.198 mmol) analogously to the preparation of intermediate 32.3. ES-MS: M+H=743: $_c t_{Ret}$=4.63, 4.71 min.

Intermediate 275.2

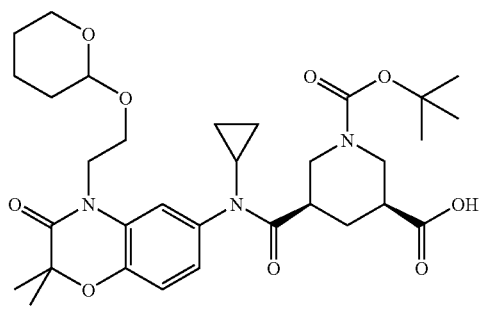

Intermediate 275.2 is synthesized by hydrolysis of intermediate 275.3 analogously to the preparation of intermediate 13.2. ES-MS: M+H=616: $_c t_{Ret}$=3.88 min.

Intermediate 275.3

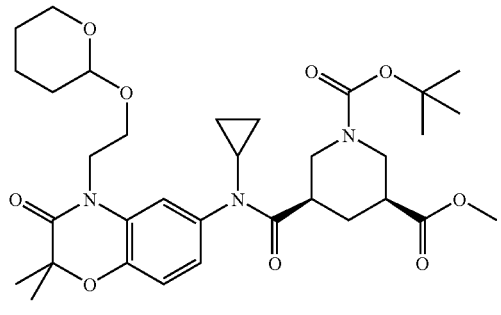

Intermediate 275.3 is synthesized by condensation of (3R, 5R)-starting material F (150 mg, 0.52 mmol) and intermediate 275.3 (192.9 mg, 0.535 mmol) analogously to the preparation of example 19.1. ES-MS: M+H=630: $_c t_{Ret}$=4.30 min.

Intermediate 275.4

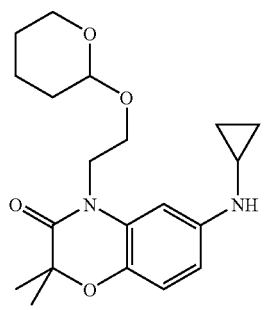

Intermediate 275.4 is synthesized by alkylation of 6-cyclopropylamino-2,2-dimethyl-4H-benzo[1,4]oxazin-3-one (776.8 mg, 3.34 mmol) and 2-(2-Bromoethoxy)-tetrahydro-2H-pyran (0.61 mL, 4.01 mmol) analogously to the preparation of intermediate 150.2. ES-MS: M+H-THP=277: $_c t_{Ret}$=3.33 min.

Example 276

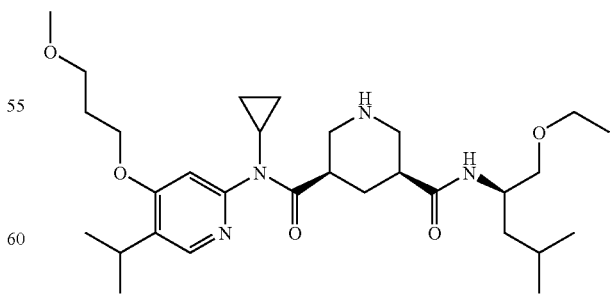

Example 276 is synthesized by deprotection of intermediate 276.1 (50 mg, 0.08 mmol) analogously to the preparation of intermediate 103.2. White amorphous material, ES-MS: M+H=547: $_c t_{Ret}$=2.86 min.

Intermediate 276.1

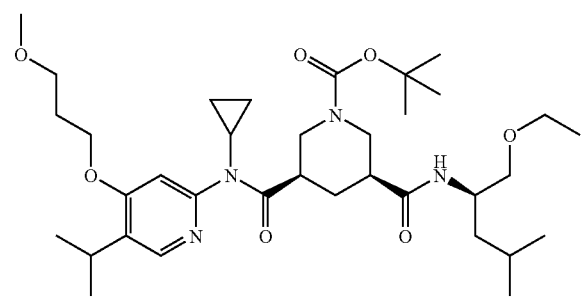

Intermediate 276.1 is synthesized by condensation of intermediate 269.2 (56 mg, 0.2 mmol) with intermediate 292.3 (67 mg, 0.17 mmol) analogously to the preparation of example 125. White amorphous material, ES-MS: M+H=647: $_ct_{Ret}$=3.83 min.

Example 277

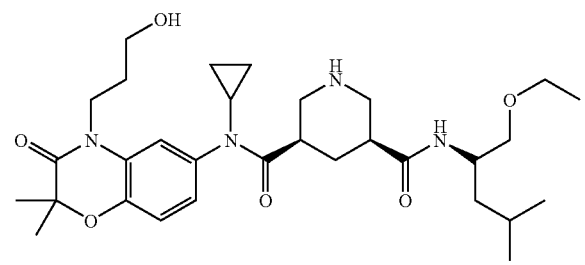

Example 277 is synthesized by deprotection of intermediate 277.1 (60 mg, 0.09 mmol) analogously to the preparation of intermediate 103.2. White amorphous material, ES-MS: M+H=573: $_ct_{Ret}$=2.93 min.

Intermediate 277.1

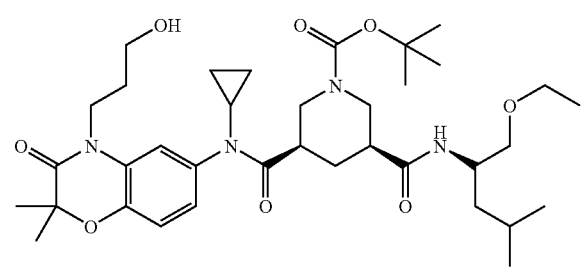

A mixture of intermediate 277.2 (100 mg, 0.132 mmol) and HCl in MeOH (0.5M in MeOH, 10 mL) is stirred at room temperature. After stirring for 1 h, the reaction mixture is diluted with H$_2$O (50 mL) and extracted with EtOAc (100 mL). The organic phase is successively washed with 5% KHSO$_4$aq, 5% NaHCO$_3$aq, H$_2$O, and brine, then dried over Na$_2$SO$_4$ and concentrated in vacuo. SiO$_2$ column chromatography purification affords intermediate 277.1: yellow amorphous material, ES-MS: M+H=673: $_ct_{Ret}$=3.96 min.

Intermediate 277.2

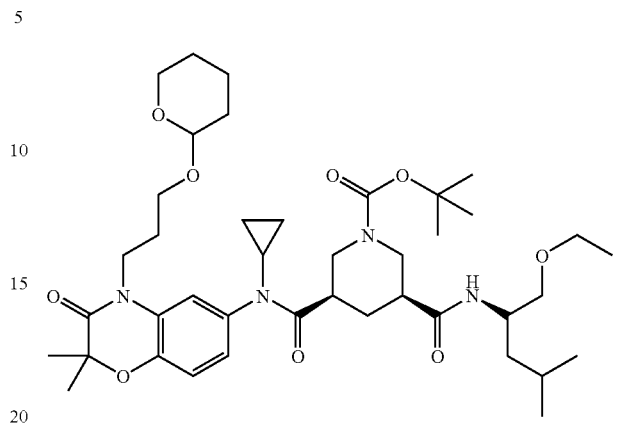

Intermediate 277.2 is synthesized by condensation of intermediate 148.2 (45 mg, 0.25 mmol) with intermediate 277.3 (130 mg, 0.21 mmol) analogously to the preparation of intermediate 1.1. White amorphous material, ES-MS: M+H=757: $_ct_{Ret}$=4.67 min.

Intermediate 277.3

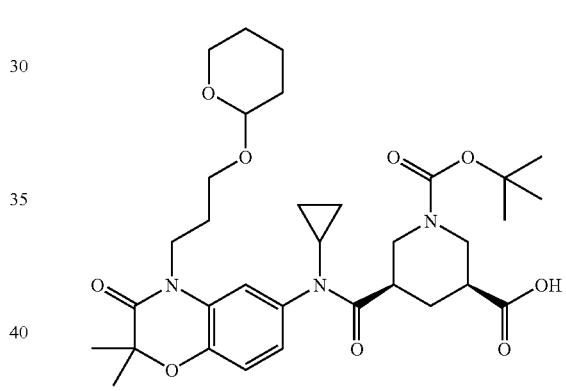

Intermediate 277.3 is synthesized by hydrolysis of intermediate 277.4 (610 mg, 0.95 mmol) analogously to the preparation of intermediate 13.2. Yellow amorphous material, ES-MS: M+H=630: $_ct_{Ret}$=3.93 min.

Intermediate 277.4

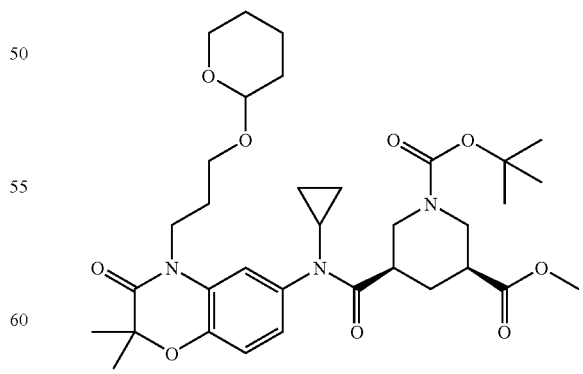

Intermediate 277.4 is synthesized by condensation of intermediate 277.5 (600 mg, 1.54 mmol) with (3R,5S)-Starting material-F (340 mg, 1.2 mmol) analogously to the preparation of intermediate 19.1. White amorphous material, ES-MS: M+H=644: $_ct_{Ret}$=4.32 min.

Intermediate 277.5

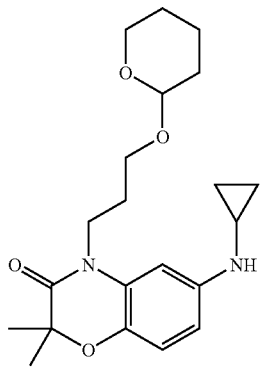

Intermediate 277.5 is synthesized by alkylation of 6-cyclopropylamino-2,2-dimethyl-4H-benzo[1,4]oxazin-3-one (500 mg, 2.15 mmol) with 2-(3-Bromopropoxy)tetrahydropyran (580 mg, 2.6 mmol) analogously to the preparation of intermediate 150.2. Yellow amorphous material, ES-MS: M+H=375: $_C t_{Ret}$=3.43 min.

Example 278

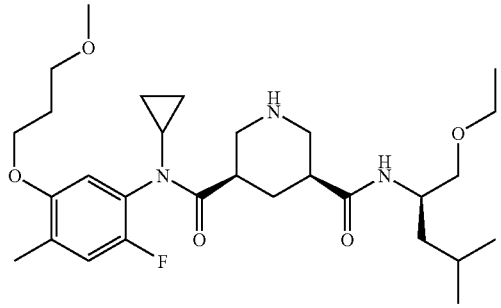

Example 278 is synthesized by deprotection of intermediate 278.1 (50 mg, 0.08 mmol) analogously to the preparation of example 123. White amorphous material, ES-MS: M+H=536: $_C t_{Ret}$=3.41 min.
Intermediate 278.1

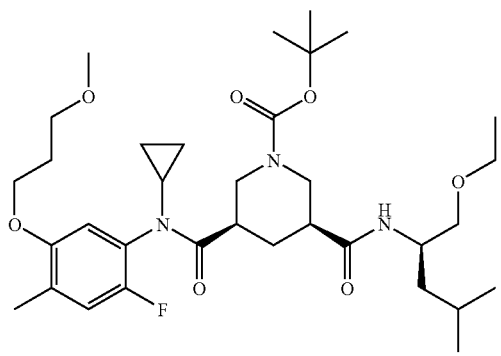

Intermediate 278.1 is synthesized by condensation of intermediate 249.2 (38 mg, 0.15 mmol) and intermediate 292.3 (60 mg, 0.15 mmol) analogously to the preparation of intermediate 1.1. Colorless oil, ES-MS: M+H=636: $_B t_{Ret}$=2.36 min.

Example 279

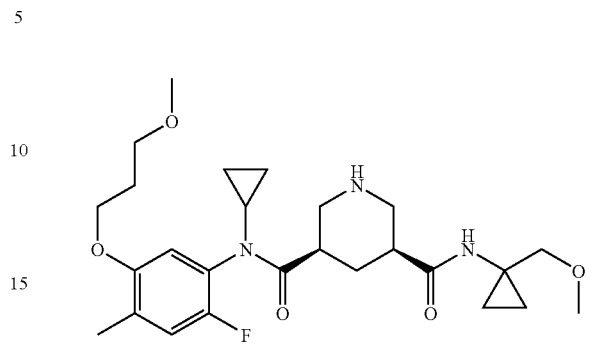

Example 279 is synthesized by deprotection of intermediate 279.1 (20 mg, 0.03 mmol) analogously to the preparation of example 123. White amorphous material, ES-MS: M+H=492: $_C t_{Ret}$=2.79 min.
Intermediate 279.1

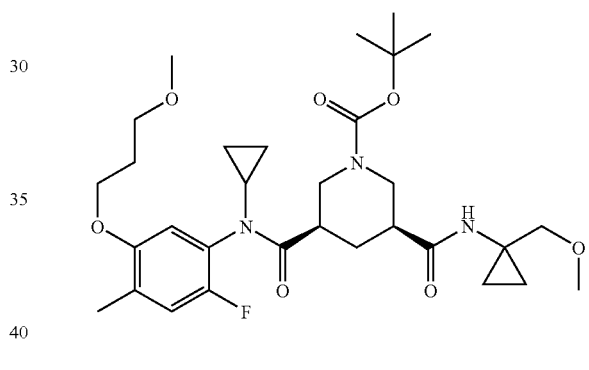

Intermediate 279.1 is synthesized by condensation of intermediate 249.2 (38 mg, 0.15 mmol) and intermediate 279.2 (54 mg, 0.15 mmol) analogously to the preparation of intermediate 1.1. Colorless oil, ES-MS: M+H=592: $_C t_{Ret}$=3.92 min.
Intermediate 279.2

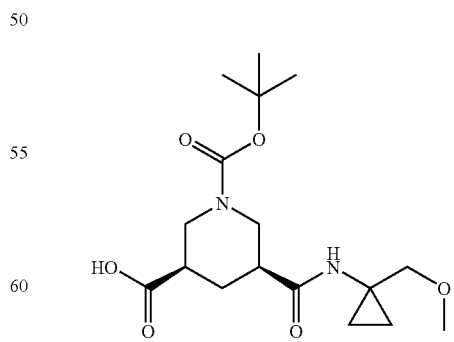

Intermediate 279.2 is synthesized by saponification of intermediate 279.3 (60 mg, 0.16 mmol) analogously to the preparation of intermediate 13.2. Colorless oil, ES-MS: M+H=357: $_B t_{Ret}$=1.58 min.

Intermediate 279.3

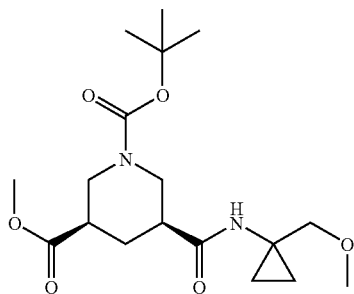

Intermediate 279.3 is synthesized by condensation of intermediate 213.2 (54 mg, 0.4 mmol) and (3S,5R)-Starting material-F (115 mg, 0.4 mmol) analogously to the preparation of intermediate 1.1. Colorless oil, ES-MS: M+H=371: $_Bt_{Ret}$=1.72 min.

Example 280

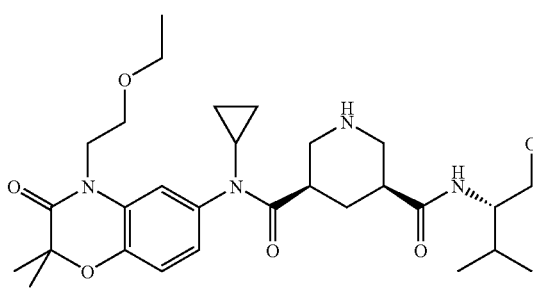

Example 280 is synthesized by deprotection of intermediate 280.1 analogously to the preparation of example 19. White material: M+H=573: $_Ct_{Ret}$=3.07 min.

Intermediate 280.1

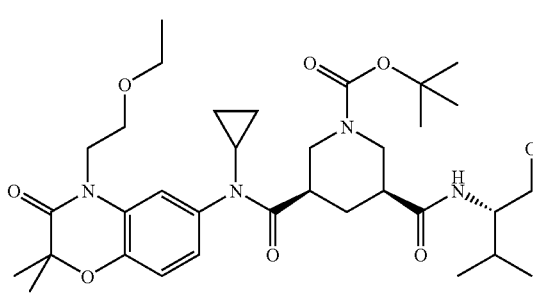

Intermediate 280.1 is synthesized by condensation of intermediate 104.2 (147.2 mg, 0.263 mmol) and intermediate 261.2 hydrochloride (44.9 mg, 0.268 mmol) analogously to the preparation of intermediate 32.3. ES-MS: M+H=673: $_Ct_{Ret}$=4.21 min.

Example 281

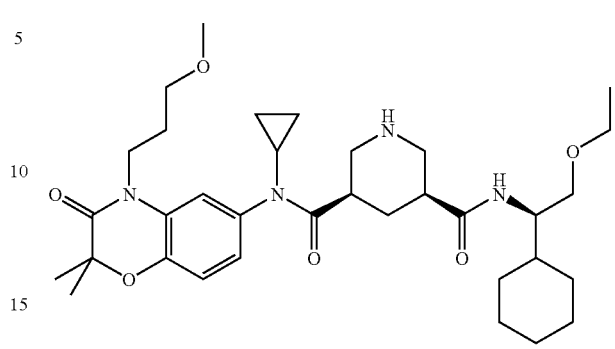

Example 281 is synthesized by deprotection of intermediate 281.1 analogously to the preparation of example 19. White material: M+H=613: $_Ct_{Ret}$=3.34 min.

Intermediate 281.1

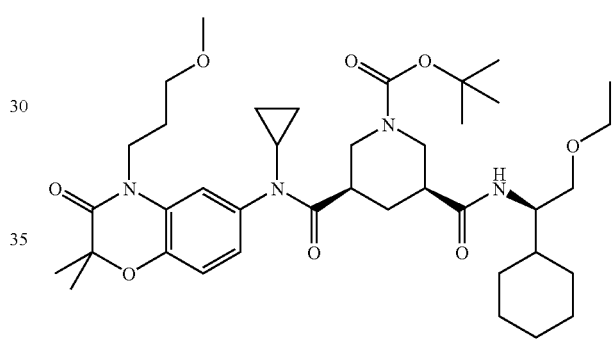

Intermediate 281.1 is synthesized by condensation of intermediate 108.2 (120 mg, 0.214 mmol) and intermediate 281.2 hydrochloride (70.8 mg, 0.34 mmol) analogously to the preparation of intermediate 32.3: ES-MS: M+H=713: $_Ct_{Ret}$=4.56 min.

Intermediate 281.2

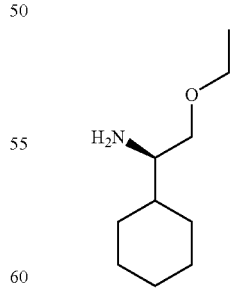

Intermediate 281.2 is synthesized by deprotection of intermediate 281.3 analogously to the preparation of example 19. White material: M+H=172: $_Bt_{Ret}$=1.48 min.

Intermediate 281.3

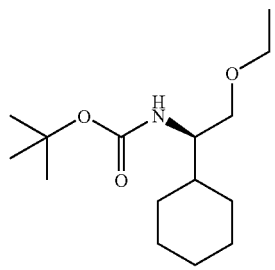

Intermediate 281.3 is synthesized by alkylation of commercially available Boc-D-cyclohexylgycinol analogously to the preparation of intermediate 151.3. M+H-Boc=172: $_B t_{Ret}$=2.34 min.

Example 282

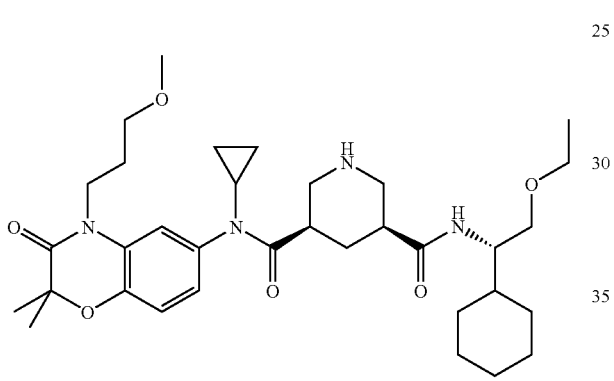

Example 282 is synthesized by deprotection of intermediate 282.1 analogously to the preparation of example 19. White material: M+H=613: $_C t_{Ret}$=3.39 min.

Intermediate 282.1

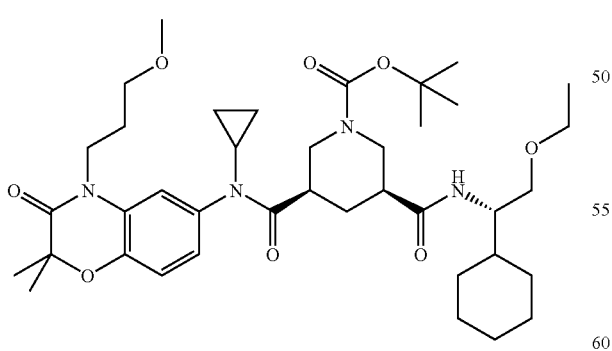

Intermediate 282.1 is synthesized by condensation of intermediate 108.2 (120 mg, 0.214 mmol) and intermediate 281.2 hydrochloride (50 mg, 0.24 mmol) analogously to the preparation of intermediate 32.3. ES-MS: M+H=713: $_C t_{Ret}$=4.53 min.

Intermediate 282.2

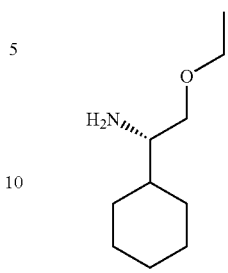

Intermediate 282.2 is synthesized by deprotection of intermediate 282.3 analogously to the preparation of example 19. ES-MS: M+H=172: $_B t_{Ret}$=1.55 min.

Intermediate 282.3

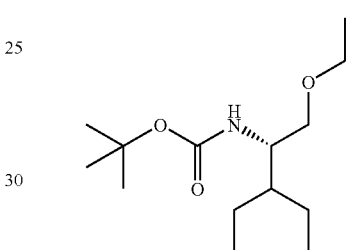

To a solution of commercially available N-Boc-L-cyclohexylglycinol (499 mg, 2.05 mmol) in DMF (8 mL) under $N_2$ at RT are added NaH (164 mg, 4.10 mmol) and EtI (179 μL, 2.26 mmol) at 0° C. The reaction mixture is stirred at RT for 2 h. Then, $H_2O$ is added to the resulting solution. The aqueous phase is extracted with $CH_2Cl_2$. The combined organic phases are dried over $Na_2SO_4$. Concentration under reduced pressure and purified with Silica gel column chromatography give intermediate 282.3: white amorphous material, ES-MS: M+H=272: $_B t_{Ret}$=2.46 min.

Example 283

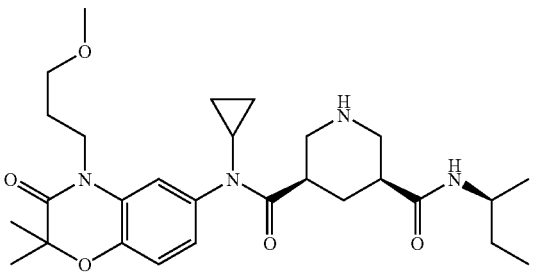

Example 283 is synthesized by deprotection of intermediate 283.1 analogously to the preparation of example 19. ES-MS: M+H=515: $_C t_{Ret}$=2.79 min.

Intermediate 283.1

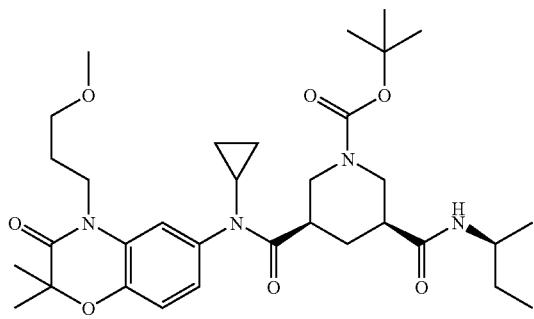

Intermediate 283.1 is synthesized by condensation of intermediate 108.2 (100 mg, 0.18 mmol) and (S)-(+)-sec-butylamine (22 μL, 0.22 mmol) analogously to the preparation of intermediate 32.3. ES-MS: M+H=615: $_c t_{Ret}$=3.90 min.

Example 284

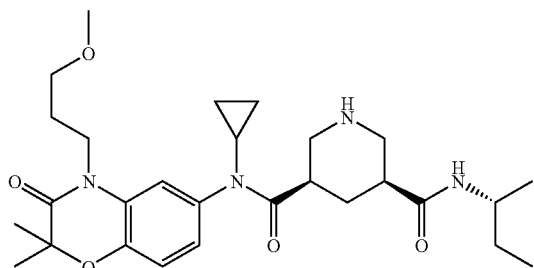

Example 284 is synthesized by deprotection of intermediate 284.1 analogously to the preparation of example 1.: ES-MS: M+H=515: $_c t_{Ret}$=2.81 min.

Intermediate 284.1

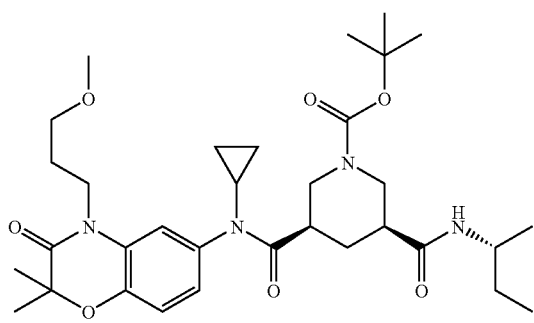

Intermediate 284.1 is synthesized by condensation of intermediate 108.2 (100 mg, 0.18 mmol) and (R)-(−)-sec-butylamine (22 μL, 0.22 mmol) analogously to the preparation of intermediate 32.3. ES-MS: M+H=615: $_c t_{Ret}$=3.89 min.

Example 285

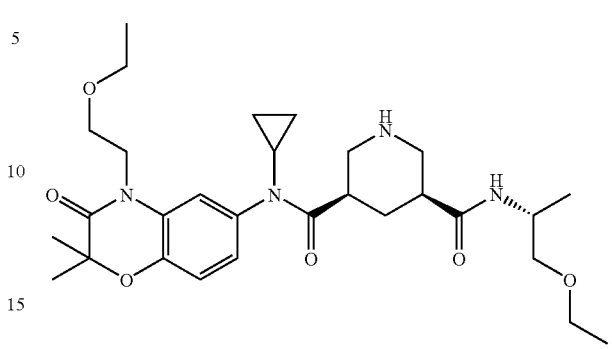

Example 285 is synthesized by deprotection of intermediate 285.1 analogously to the preparation of example 19. ES-MS: M+H=545: $_c t_{Ret}$=2.82 min.

Intermediate 285.1

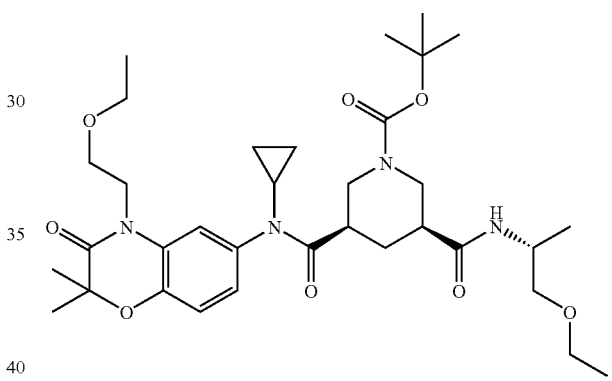

Intermediate 285.1 is synthesized by condensation of intermediate 208.2 (150 mg, 0.27 mmol) and intermediate 267.2 (41 mg, 0.30 mmol) analogously to the preparation of Intermediate 32.3. ES-MS: M+H=645: $_c t_{Ret}$=3.91 min.

Example 286

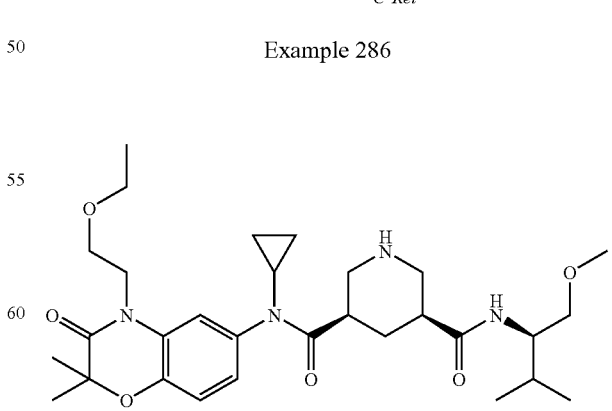

Example 286 is synthesized by deprotection of intermediate 286.1 analogously to the preparation of example 19. ES-MS: M+H=559: $_c t_{Ret}$=2.90 min.

Intermediate 286.1

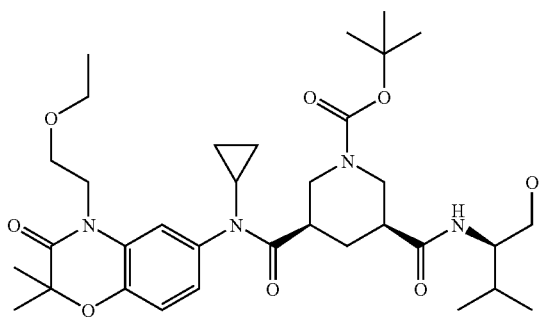

Intermediate 286.1 is synthesized by condensation of intermediate 208.2 (150 mg, 0.27 mmol) and (R)-1-methoxymethyl-2-methyl-propylamine (46 mg, 0.30 mmol) analogously to the preparation of intermediate 32.3. ES-MS: M+H=659: $_Ct_{Ret}$=4.05 min.

Example 287

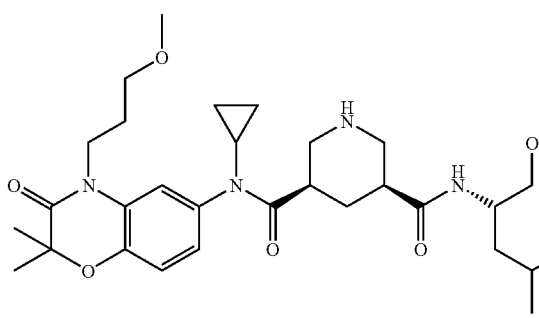

Example 287 is synthesized by deprotection of intermediate 287.1 analogously to the preparation of example 19. ES-MS: M+H=619: $_Ct_{Ret}$=2.70 min.
Intermediate 287.1

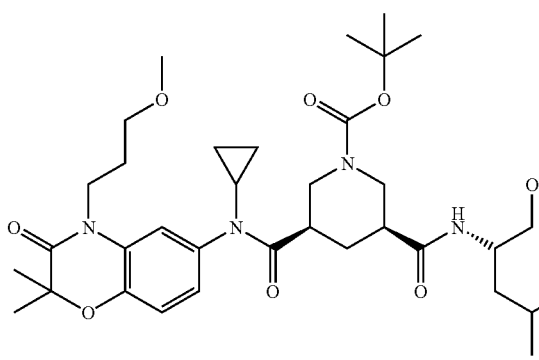

Intermediate 287.1 is synthesized by condensation of intermediate 108.2 (150 mg, 0.27 mmol) with (S)-1-methoxymethyl-3-methylbutylamine hydrochloride (*J. Org. Chem.* 1978, 43, 892, 68.7 mg, 0.41 mmol) analogously to the preparation of intermediate 32.3. White amorphous material, ES-MS: M+H=673: $_Ct_{Ret}$=4.11 min.

Example 288

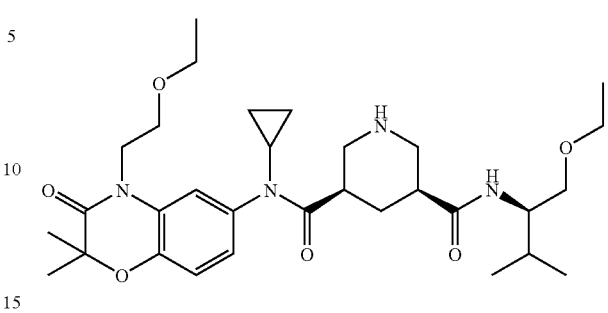

Example 288 is synthesized by deprotection of intermediate 288.1 analogously to the preparation of example 19. ES-MS: M+H=572: $_Ct_{Ret}$=3.08 min.
Intermediate 288.1

Intermediate 288.1 is synthesized by condensation of intermediate 208.2 (150 mg, 0.27 mmol) with intermediate 252.2 (60.0 mg, 0.35 mmol) analogously to the preparation of intermediate 32.3. White amorphous material, ES-MS: M+H=672: $_Bt_{Ret}$=2.23 min.

Example 289

Example 289 is synthesized by deprotection of intermediate 289.1 analogously to the preparation of example 19. White material: M+H=599: $_Ct_{Ret}$=3.18 min.

Intermediate 289.1

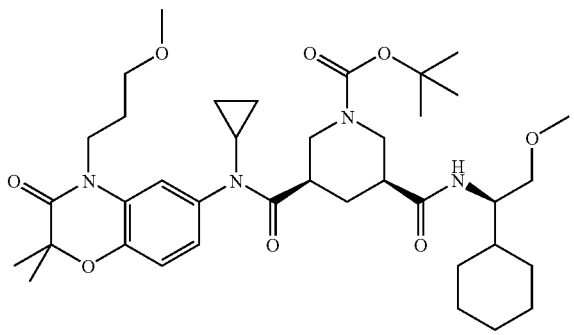

Intermediate 289.1 is synthesized by condensation of intermediate 108.2 (120 mg, 0.214 mmol) and intermediate 289.2 hydrochloride (41.3 mg, 0.214 mmol) analogously to the preparation of intermediate 32.3. ES-MS: M+H=699: $_C t_{Ret}$=4.38 min.

Intermediate 289.2

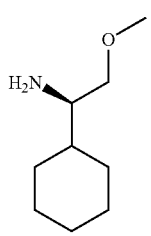

Intermediate 289.2 is synthesized by deprotection of intermediate 289.3 analogously to the preparation of example 19. White material: M+H=158: $_B t_{Ret}$=1.39 min.

Intermediate 289.3

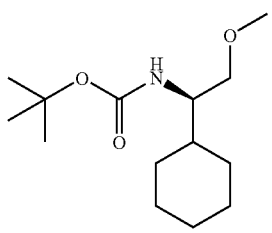

To a solution of commercially available N-Boc-D-cyclohexyl glycinol (500 mg, 2.05 mmol) in THF (10 mL) under $N_2$ at 0° C., NaH (102.6 mg of 60 wt % in mineral oil, 2.565 mmol) is added. The reaction mixture is stirred at that temperature for a few min. Methyl iodine is added. After stirring at rt for 30 min, the reaction is quenched with sat.KHSO$_4$ aq. and extracted with Et$_2$O, dried over MgSO$_4$. Concentration under reduced pressure gives the crude product. The crude product is purified with silica gel chromatography to afford the desired intermediate 289.3. M+H-Boc=158: $_B t_{Ret}$=2.24 min.

Example 290

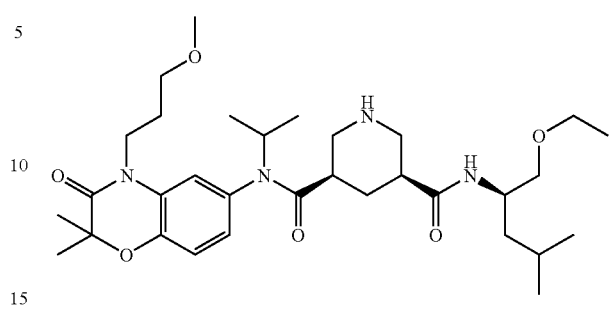

Example 290 is synthesized by deprotection of intermediate 290.1 (110 mg, 0.16 mmol) analogously to the preparation of intermediate 103.2. White amorphous material, ES-MS: M+H=589: $_C t_{Ret}$=3.34 min.

Intermediate 290.1

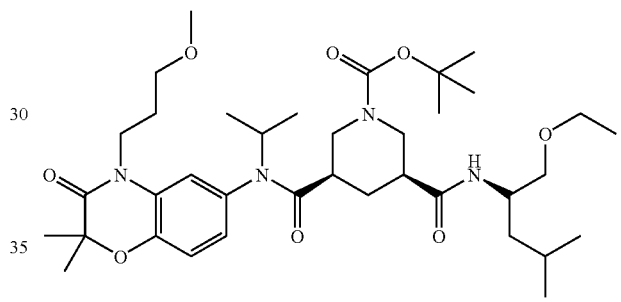

Intermediate 290.1 is synthesized by condensation of intermediate 148.2 (45 mg, 0.25 mmol) with intermediate 290.2 (110 mg, 0.2 mmol) analogously to the preparation of intermediate 1.1. White amorphous material, ES-MS: M+H=689: $_C t_{Ret}$=4.52 min.

Intermediate 290.2

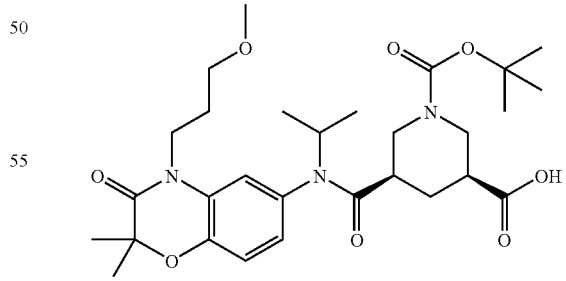

Intermediate 290.2 is synthesized by hydrolysis of intermediate 290.3 (350 mg, 0.6 mmol) analogously to the preparation of intermediate 13.2. White amorphous material, ES-MS: M+H=562: $_C t_{Ret}$=3.77 min.

Intermediate 290.3

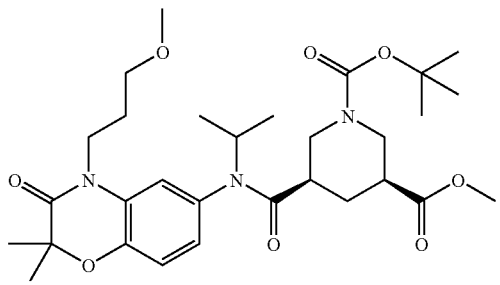

Intermediate 290.3 is synthesized by condensation of intermediate 207.2 (640 mg, 2.1 mmol) with (3R,5S)-Starting material-F (500 mg, 1.7 mmol) analogously to the preparation of intermediate 19.1. White amorphous material, ES-MS: M+H=576: $_c t_{Ret}$=4.20 min.

Example 291

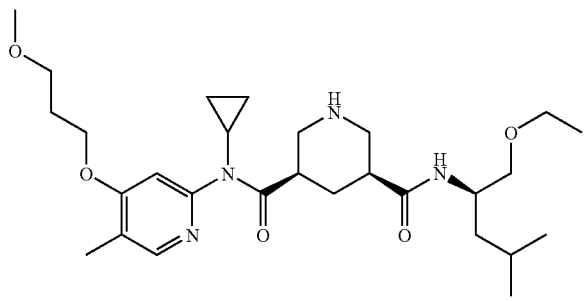

Example 291 is synthesized by deprotection of intermediate 291.1 (20 mg, 0.03 mmol) analogously to the preparation of intermediate 103.2. White amorphous material, ES-MS: M+H=519: $_c t_{Ret}$=2.64 min.

Intermediate 291.1

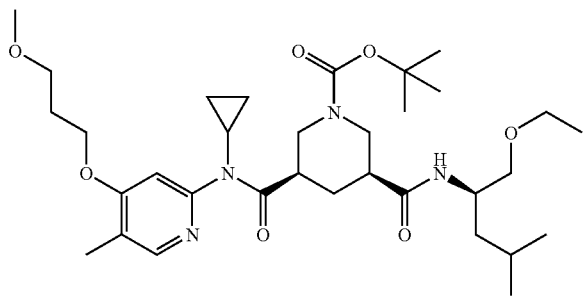

Intermediate 291.1 is synthesized by condensation of intermediate 291.2 (35 mg, 0.15 mmol) with intermediate 292.3 (54 mg, 0.14 mmol) analogously to the preparation of example 125. White amorphous material, ES-MS: M+H=619: $_c t_{Ret}$=3.57 min.

Intermediate 291.2

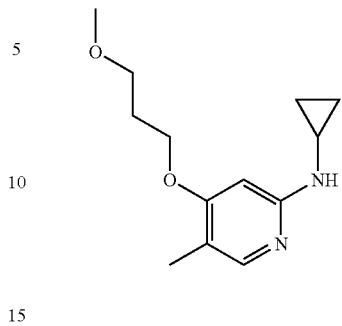

A mixture of intermediate 291.3 (100 mg, 0.4 mmol) and $SOCl_2$ (4 mL) is stirred at 0° C. After stirring for 3 h, the mixture is concentrated in vacuo. The residue is used for the next reaction without further purification.

A mixture of the residue and $NaBH_4$ (100 mg, 2.64 mmol) in DMSO (4 mL) is stirred at room temperature. After stirring for 1 h, the reaction mixture is diluted with $H_2O$ and extracted with $Et_2O$. The organic phase is washed with $H_2O$, and brine, then dried over $Na_2SO_4$ and concentrated in vacuo. RP-HPLC purification affords intermediate 291.2: white solid, ES-MS: M+H=237: $_c t_{Ret}$=2.20 min.

Intermediate 291.3

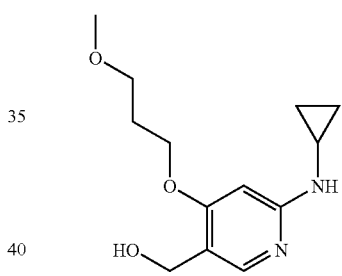

Intermediate 291.3 is synthesized by reduction of intermediate 269.4 (700 mg, 2.1 mmol) analogously to the preparation of intermediate 37.4. White amorphous material, ES-MS: M+H=253: $_c t_{Ret}$=1.70 min.

Example 292

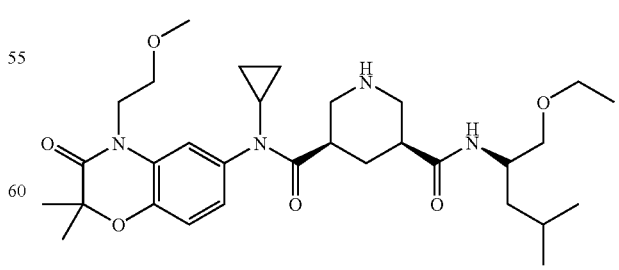

Example 292 is synthesized by deprotection of intermediate 292.1 (20 mg, 0.03 mmol) analogously to the preparation of intermediate 103.2. White amorphous material, ES-MS: M+H=573: $_c t_{Ret}$=3.12 min.

Intermediate 292.1

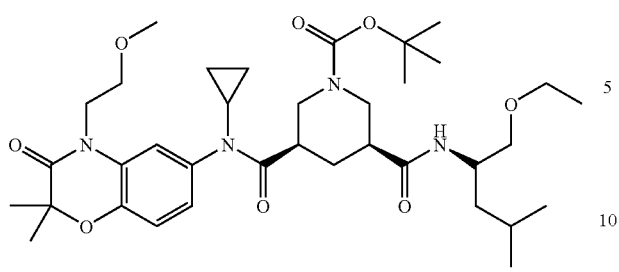

Intermediate 292.1 is synthesized by condensation of intermediate 292.2 (60 mg, 0.25 mmol) with intermediate 292.3 (85 mg, 0.21 mmol) analogously to the preparation of intermediate 19.1. White amorphous material, ES-MS: M+H=673: $_ct_{Ret}$=4.27 min.

Intermediate 292.2

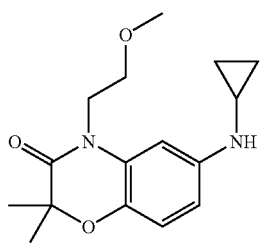

Intermediate 292.2 is synthesized by alkylation of 6-cyclopropylamino-2,2-dimethyl-4H-benzo[1,4]oxazin-3-one (500 mg, 2.15 mmol) with 1-bromo-2-methoxyethane (576 mg, 2.6 mmol) analogously to the preparation of intermediate 150.2: yellow amorphous material, ES-MS: M+H=291: $_ct_{Ret}$=2.72 min.

Intermediate 292.3

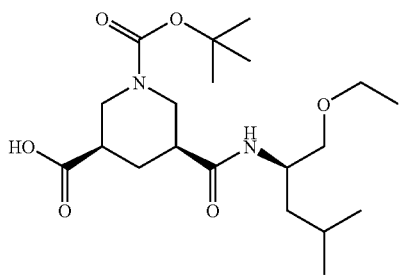

Intermediate 292.3 is synthesized by hydrolysis of intermediate 292.4 (450 mg, 1.1 mmol) analogously to the preparation of intermediate 13.2. White amorphous material, ES-MS: M+H=401: $_ct_{Ret}$=3.37 min.

Intermediate 292.4

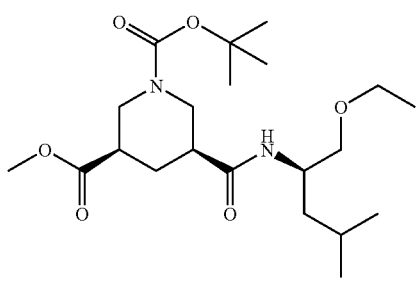

Intermediate 292.4 is synthesized by condensation of intermediate 148.2 (228 mg, 1.2 mmol) with (3S,5R)-Starting material-F (320 mg, 1.1 mmol) analogously to the preparation of intermediate 1.1. White amorphous material, ES-MS: M+H=415: $_ct_{Ret}$=3.77 min.

Example 293

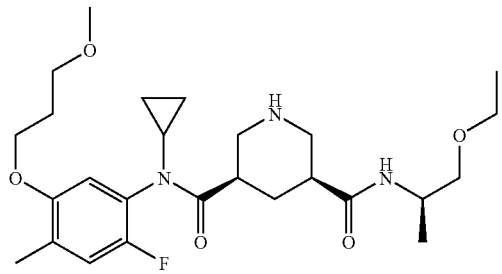

Example 293 is synthesized by deprotection of intermediate 293.1 (52 mg, 0.088 mmol) analogously to the preparation of example 123. White amorphous material, ES-MS: M+H=494: $_ct_{Ret}$=2.98 min.

Intermediate 293.1

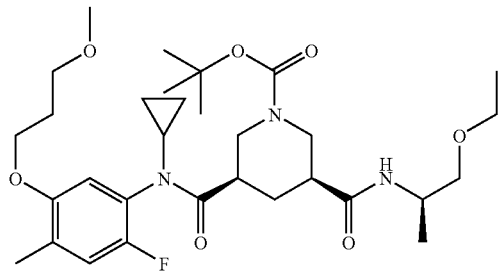

Intermediate 293.1 is synthesized by condensation of intermediate 293.2 (70 mg, 0.14 mmol) and (R)-1-ethoxymethyl propylamine hydrochloride (21 mg, 0.15 mmol) analogously to the preparation of intermediate 1.1. Colorless oil, ES-MS: M+H=592: $_ct_{Ret}$=3.92 min.

Intermediate 293.2

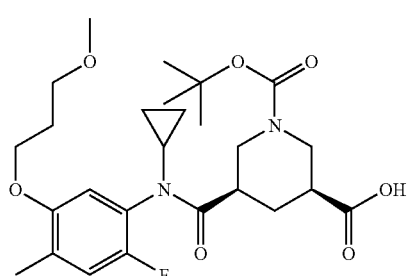

Intermediate 293.2 is synthesized by condensation of intermediate 249.2 (280 mg, 1.1 mmol) and (3S,5R)-Starting material-F (345 mg, 1.2 mmol) analogously to the preparation of example 125. Colorless oil, ES-MS: M+H=509: $_Bt_{Ret}$=3.95 min.

Example 294

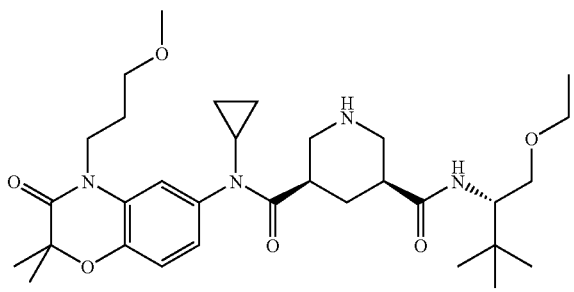

Example 294 is synthesized by deprotection of intermediate 294.1 analogously to the preparation of example 19. White material: M+H=587: $_{C}t_{Ret}$=3.17 min.

Intermediate 294.1

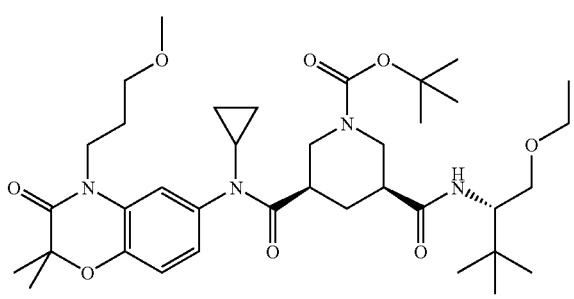

Intermediate 294.1 is synthesized by condensation of intermediate 108.2 (120 mg, 0.214 mmol) and intermediate 294.2 hydrochloride (44 mg, 0.242 mmol) analogously to the preparation of intermediate 32.3. ES-MS: M+H=687: $_{C}t_{Ret}$=4.26 min.

Intermediate 294.2

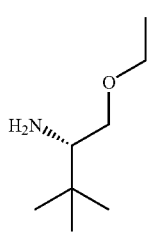

Intermediate 294.2 is synthesized by deprotection of intermediate 294.3 analogously to the preparation of example 19. White material: M+H=146: $_{B}t_{Ret}$=1.34 min.

Intermediate 294.3

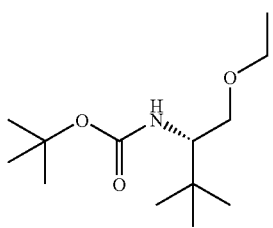

Intermediate 294.3 is synthesized by alkylation of ((S)-1-hydroxymethyl-2,2-dimethylpropyl)-carbamic acid tert-butyl ester (Chemical & Pharmaceutical Bulletin (2004), 52(1), 111-119) (300 mg, 1.38 mmol) analogously to the preparation of intermediate 151.3. White material: M+H-Boc=146: $_{B}t_{Ret}$=2.26 min.

Example 295

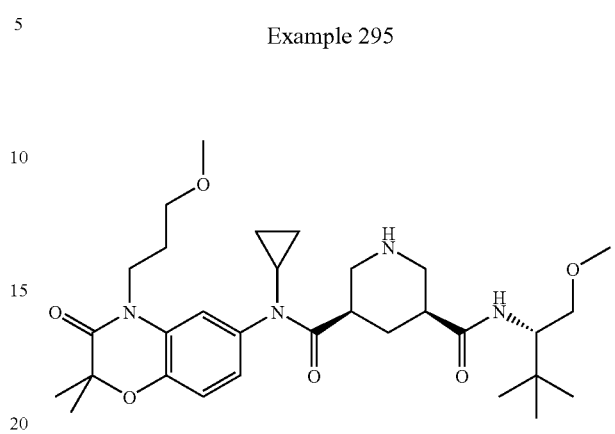

Example 295 is synthesized by deprotection of intermediate 295.1 analogously to the preparation of example 19. White material: M+H=573: $_{C}t_{Ret}$=3.05 min.

Intermediate 295.1

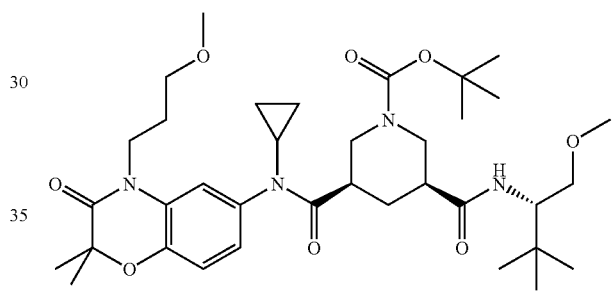

Intermediate 295.1 is synthesized by condensation of intermediate 108.2 (100 mg, 0.178 mmol) and (S)-1-methoxymethyl-2,2-dimethyl-propylamine hydrochloride (Tetrahedron Letters (1982), 23(36), 3711-14.) (37.2 mg, 0.221 mmol) analogously to the preparation of intermediate 32.3. ES-MS: M+H=673: $_{C}t_{Ret}$=4.07 min.

Example 296

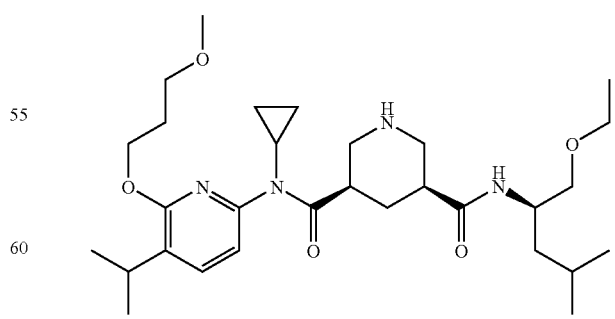

Example 296 is synthesized by deprotection of intermediate 296.1 analogously to the preparation of example 19. White solid; ES-MS: M+H=547: $_{C}t_{Ret}$=1.97 min.

Intermediate 296.1

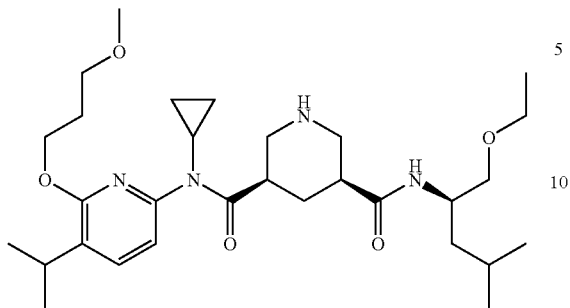

Intermediate 296.1 is synthesized by condensation of intermediate 296.2 (36 mg, 0.14 mmol) and intermediate 292.3 (42 mg, 0.11 mmol) analogously to the preparation of example 125. Pale yellow oil; ES-MS: M+H=647: $_ct_{Ret}$=2.54 min.

Intermediate 296.2

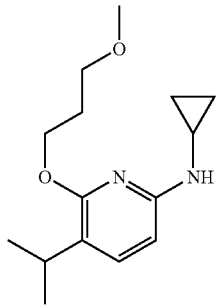

To a solution of intermediate 296.3 (1.0 g, 3.6 mmol) in THF, is dropped wise MeLi (14 mL, 14 mmol, 1.0 M in Et$_2$O) at −78° C. The reaction mixture is warmed up to 0° C. After stirring at 0° C. for 2 h, the reaction is quenched with aq. NH$_4$Cl and extracted with EtOAc. The combined organic extracts are washed with water and brine, dried over Mg$_2$SO$_4$, filtered, and concentrated in vacuo. To a solution of the resulting residue and triethylsilane (2.8 mL, 18 mmol, CAS: 617-86-7) in CH$_2$Cl$_2$, is added TFA (1.4 mL, 18 mmol) at 0° C. After stirring at room temperature for 4 h, the solvent is removed in vacuo. A solution of the residue in EtOAc is washed with sat. aq. NaHCO$_3$ and water, dried over Mg$_2$SO$_4$, filtered, and concentrated in vacuo. The residue is purified by silica gel column chromatography to afford intermediate 296.2 (897 mg, 3.4 mmol): colorless oil; ES-MS: M+H=265: $_ct_{Ret}$=2.12 min.

Intermediate 296.3

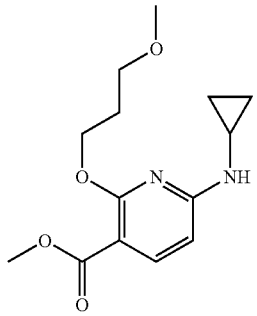

A mixture of intermediate 296.4 (2.0 g, 7.7 mmol) and cyclopropylamine (2.7 mL, 38.5 mmol) in N-methylpyrrolidone (NMP, 10 mL) is stirred with condenser at 90° C. for 8 h. After cooling down to room temperature and dilution with EtOAc, the mixture is washed with water and brine, dried over Mg$_2$SO$_4$, filtered, and concentrated in vacuo. The residue is purified by silica gel column chromatography to afford intermediate 296.3 (1.4 mg, 5.0 mmol): pale yellow oil; ES-MS: M+H=281: $_ct_{Ret}$=1.92 min.

Intermediate 296.4

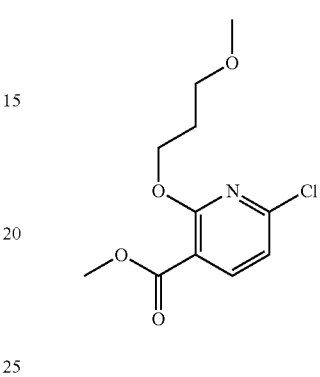

To a solution of 2,6-dichloronicotinic acid (10 g, 52 mmol. CAS: 38496-18-3) in 3-methoxy-1-propanol (26 mL, 90 mmol, CAS:1589-49-7), is dropped wise NaH (6.2 g, 160 mmol) at 0° C. The reaction mixture is warmed up to 60° C. After stirring at 60° C. for 4 h, the reaction is cooled down to room temperature and diluted with EtOAc. The combined organic extracts are washed with aq. citric acid and water, dried over Mg$_2$SO$_4$, filtered, and concentrated in vacuo. A mixture of the resulting residue, MeI (9.7 mL, 156 mmol) and K$_2$CO$_3$ (22 g, 156 mmol) in DMF (20 mL) is stirred at room temperature overnight. After addition of water, the mixture is extracted with EtOAc. The combined organic extracts are washed three times with water, dried over Mg$_2$SO$_4$, filtered, and concentrated in vacuo to afford intermediate 296.4 (13 g, 50 mmol): pale yellow oil; ES-MS: M+H=260: $_ct_{Ret}$=2.00 min.

Example 297

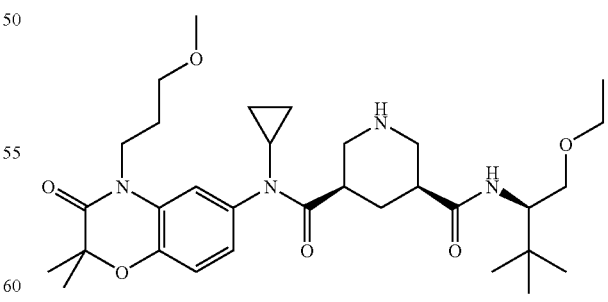

Example 297 is synthesized by deprotection of intermediate 297.1 analogously to the preparation of example 19. White material: M+H=587: $_ct_{Ret}$=3.15 min.

Intermediate 297.1

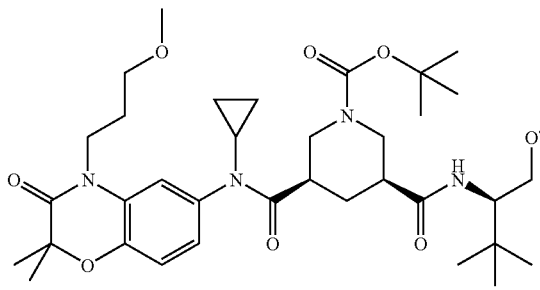

Intermediate 297.1 is synthesized by condensation of intermediate 108.2 (120 mg, 0.214 mmol) and intermediate 297.2 hydrochloride (38.8 mg, 0.214 mmol) analogously to the preparation of intermediate 32.3. ES-MS: M+H=686: $_C t_{Ret}$=4.31 min.

Intermediate 297.2

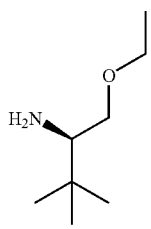

Intermediate 297.2 is synthesized by deprotection of intermediate 297.3 analogously to the preparation of example 19. White material: M+H=146: $_B t_{Ret}$=1.35 min.

Intermediate 297.3

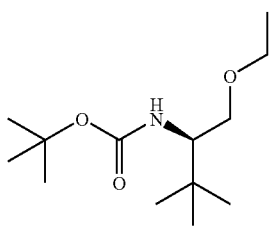

Intermediate 297.3 is synthesized by alkylation of ((R)-1-hydroxymethyl-2,2-dimethylpropyl)-carbamic acid tert-butyl ester (300 mg, 1.38 mmol) analogously to the preparation of intermediate 151.3. White material: M+H-Boc=146: $_B t_{Ret}$=2.25 min.

Example 298

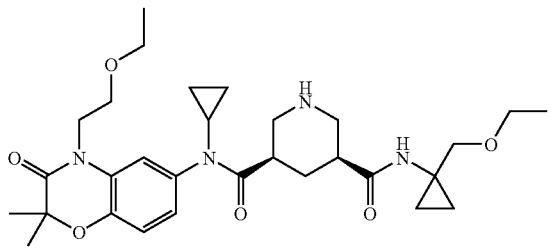

Example 298 is synthesized by deprotection of intermediate 298.1 analogously to the preparation of example 19. ES-MS: M+H=2.82: $_C t_{Ret}$=557 min.

Intermediate 298.1

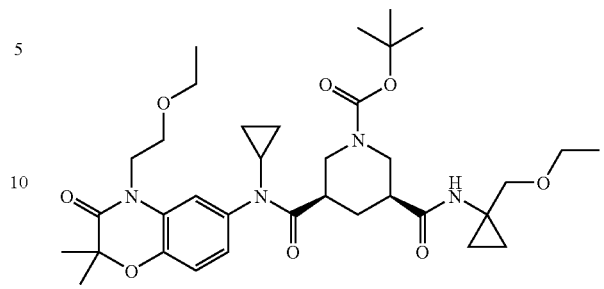

Intermediate 298.1 is synthesized by condensation of intermediate 208.2 (100 mg, 0.18 mmol) and intermediate 237.2 (33 mg, 0.22 mmol) analogously to the preparation of intermediate 32.3 in the presence of Et$_3$N (30 μL, 0.22 mmol). ES-MS: M+H=657: $_C t_{Ret}$=3.87 min.

Example 299

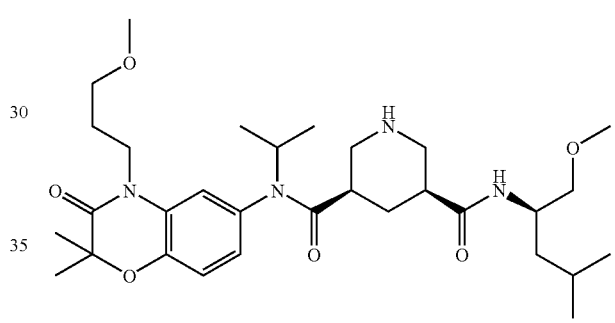

Example 299 is synthesized by deprotection of intermediate 299.1 analogously to the preparation of example 19. ES-MS: M+H=3.19: $_C t_{Ret}$=575 min.

Intermediate 299.1

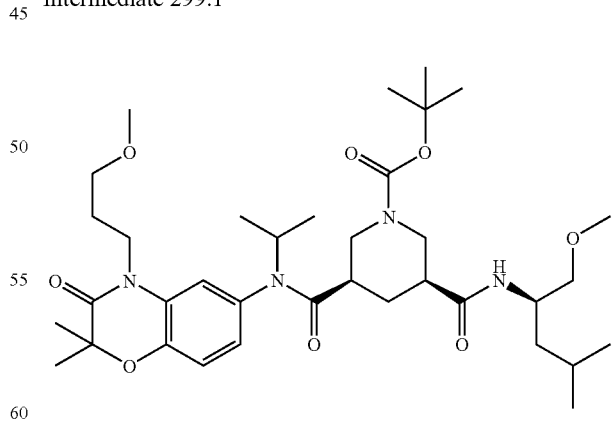

Intermediate 299.1 is synthesized by condensation of intermediate 299.2 (140 mg, 0.25 mmol) and (R)-1-methoxymethyl-3-methylbutylamine hydrochloride (*Org. Lett.* 2001, 3, 1241.) (46 mg, 0.28 mmol) analogously to the preparation of intermediate 32.3 in the presence of Et$_3$N (42 μL, 0.30 mmol). ES-MS: M+H=675: $_C t_{Ret}$=4.37 min.

Intermediate 299.2

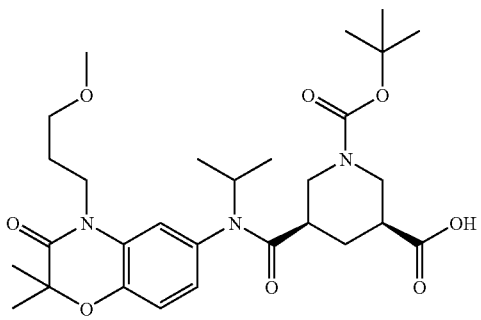

Intermediate 299.2 is synthesized by hydrolysis of intermediate 299.3 (1.9 g, 3.3 mmol) analogously to the preparation of intermediate 13.2. ES-MS: [M+H]⁺=562; HPLC: $_C t_{Ret}$=3.80 min.

Intermediate 299.3

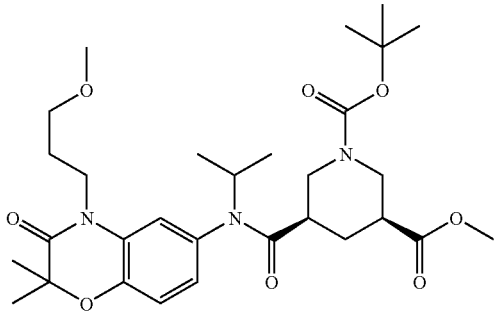

Intermediate 299.3 is synthesized by condensation of (3R, 5S)-Starting material (630 mg, 2.2 mmol) and intermediate 207.2 (670 mg, 2.2 mmol) analogously to the preparation of intermediate 19.1. ES-MS: M+H=562: $_C t_{Ret}$=3.80 min.

Example 300

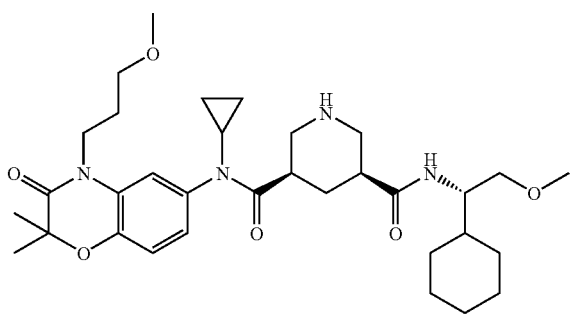

Example 300 is synthesized by deprotection of intermediate 300.1 analogously to the preparation of example 19. ES-MS: M+H=599: $_C t_{Ret}$=3.33 min.

Intermediate 300.1

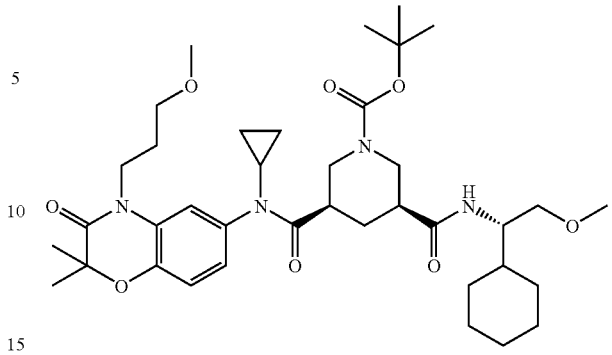

Intermediate 300.1 is synthesized by condensation of intermediate 108.2 (151 mg, 0.27 mmol) with intermediate 300.2 (57 mg, 0.30 mmol) analogously to the preparation of intermediate 32.3. ES-MS: M+H=699: $_C t_{Ret}$=4.39 min.

Intermediate 300.2

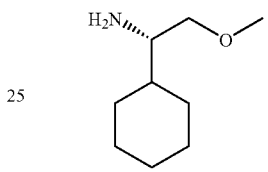

Intermediate 300.2 is synthesized by deprotection of intermediate 300.3 analogously to the preparation of example 19. ES-MS: M+H=158: $_B t_{Ret}$=1.49 min.

Intermediate 300.3

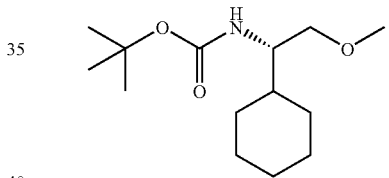

To a solution of N-Boc-L-cyclohexylglycinol (505 mg, 2.07 mmol) in THF (20 mL) under N₂ at rt are added NaH (91 mg, 2.28 mmol) and MeI (142 µL, 2.28 mmol) at 0° C. The reaction mixture is stirred at rt for 5 h. Then, H₂O is added to the resulting solution. The aqueous phase is extracted with CH₂Cl₂. The combined organic phases are dried over Na₂SO₄. Concentration under reduced pressure and purification by silica gel column chromatography gives intermediate 300.3: white amorphous material, ES-MS: M+H=258: $_B t_{Ret}$=2.35 min.

Example 301

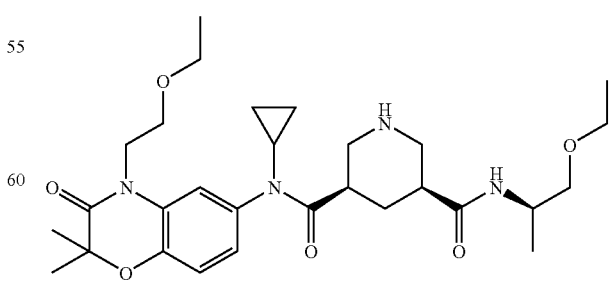

Example 301 is synthesized by deprotection of intermediate 301.1 analogously to the preparation of example 19. ES-MS: M+H=531: $_C t_{Ret}$=2.71 min.

Intermediate 301.1

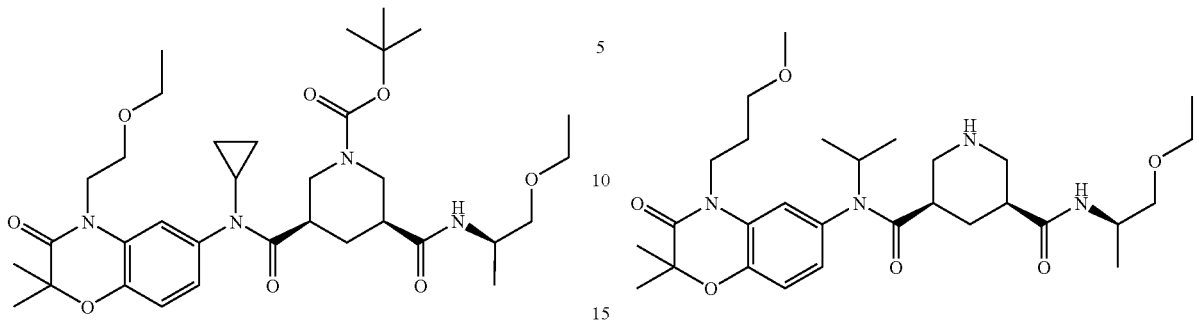

Intermediate 301.1 is synthesized by condensation of intermediate 208.2 (150 mg, 0.27 mmol) with intermediate 267.2 (44.0 mg, 0.35 mmol) analogously to the preparation of intermediate 32.3. White amorphous material, ES-MS: M+H=631: $_B t_{Ret}$=2.07 min.

Example 302

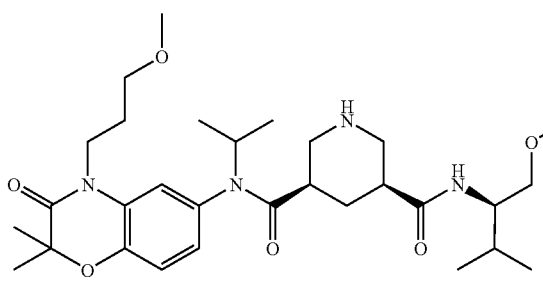

Example 302 is synthesized by deprotection of intermediate 302.1 analogously to the preparation of example 19. ES-MS: M+H=575: $_C t_{Ret}$=3.20 min.

Intermediate 302.1

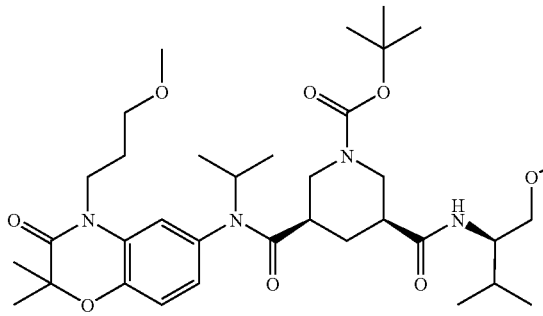

Intermediate 302.1 is synthesized by condensation of intermediate 299.2 (150 mg, 0.27 mmol) with intermediate 252.2 (45.0 mg, 0.35 mmol) analogously to the preparation of intermediate 32.3. White amorphous material, ES-MS: M+H=675: $_B t_{Ret}$=2.29 min.

Example 303

Example 303 is synthesized by deprotection of intermediate 303.1 analogously to the preparation of example 19. ES-MS: M+H=547: $_C t_{Ret}$=2.96 min.

Intermediate 303.1

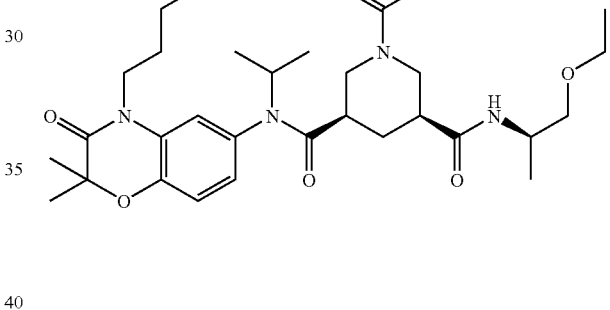

Intermediate 303.1 is synthesized by condensation of intermediate 299.2 (150 mg, 0.27 mmol) with intermediate 267.2 (45.0 mg, 0.32 mmol) analogously to the preparation of intermediate 32.3. White amorphous material, ES-MS: M+H=646: $_B t_{Ret}$=2.18 min.

Example 304

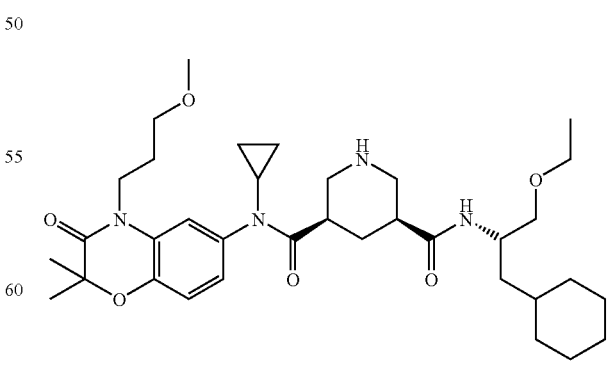

Example 304 is synthesized by deprotection of intermediate 304.1 analogously to the preparation of example 19. ES-MS: M+H=627: $_C t_{Ret}$=3.61 min.

Intermediate 304.1

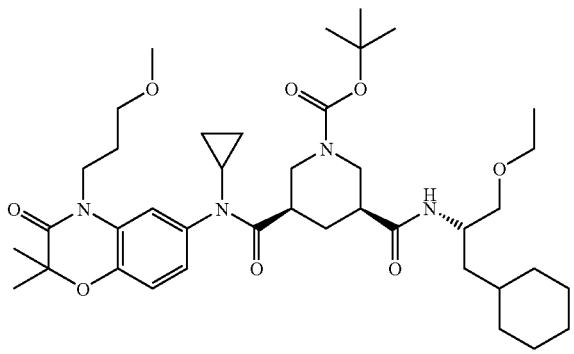

Example 305

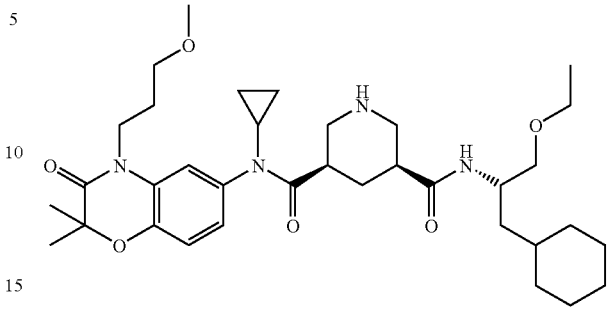

Intermediate 304.1 is synthesized by condensation of intermediate 108.2 (150 mg, 0.27 mmol) with intermediate 304.2 (71.5 mg, 0.32 mmol) analogously to the preparation of intermediate 32.3. White amorphous material, ES-MS: M+H=727: $_B t_{Ret}$=2.43 min.

Intermediate 304.2

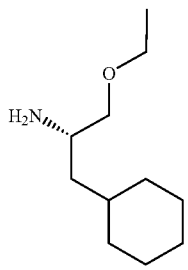

Intermediate 304.2 is synthesized by deprotection of intermediate 304.3 analogously to the preparation of example 19. ES-MS: M+H=186: $_B t_{Ret}$=1.68 min.

Intermediate 304.3

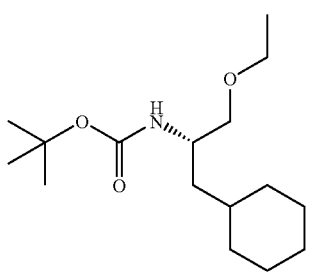

Intermediate 304.3 is synthesized by alkylation of N-Boc-(S)-2-amino-3-cyclohexyl-propan-1-ol (1.0 g, 3.88 mmol) with NaH (346 mg of 60 wt % in mineral oil, 8.56 mmol) and EtI (0.31 mL, 3.88 mmol) analogously to the preparation of intermediate 148.3. White amorphous material ES-MS: M+H=286: $_B t_{Ret}$=2.49 min.: Rf=0.75 (AcOEt:n-Hexane=1:2).

Example 305 is synthesized by deprotection of intermediate 305.1 analogously to the preparation of example 19. ES-MS: M+H=613: $_C t_{Ret}$=3.43 min.

Intermediate 305.1

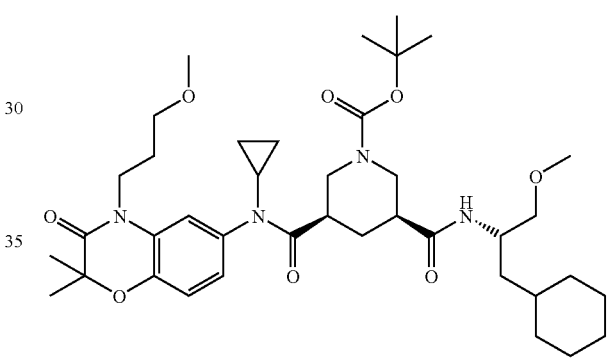

Intermediate 305.1 is synthesized by condensation of intermediate 108.2 (150 mg, 0.27 mmol) with intermediate 305.2 (67.0 mg, 0.33 mmol) analogously to the preparation of intermediate 32.3. White amorphous material, ES-MS: M+H=713: $_C t_{Ret}$=4.60 min.

Intermediate 305.2

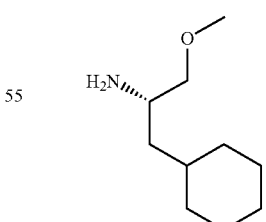

Intermediate 305.2 is synthesized by deprotection of intermediate 305.3 analogously to the preparation of example 19. ES-MS: M+H=172: $_B t_{Ret}$=1.57 min.

Intermediate 305.3

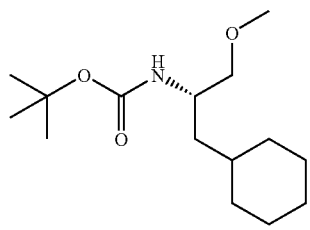

Intermediate 305.3 is synthesized by alkylation of N-Boc-(S)-2-amino-3-cyclohexyl-propan-1-ol (1.0 g, 3.88 mmol) with NaH (346 mg of 60 wt % in mineral oil, 8.56 mmol) and MeI (0.24 mL, 3.88 mmol) analogously to the preparation of intermediate 148.3. White amorphous material, ES-MS: M+H=272: $_B t_{Ret}$=2.40 min.

Example 306

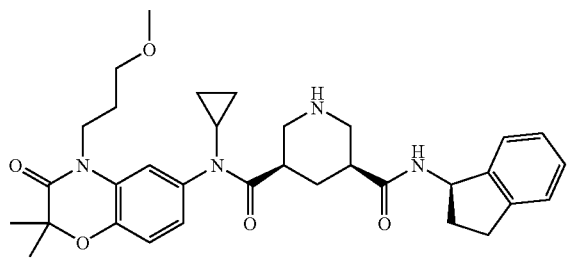

Example 306 is synthesized by deprotection of intermediate 306.1 (110 mg, 0.16 mmol) analogously to the preparation of example 123. White amorphous material, ES-MS: M+H=575: $_C t_{Ret}$=3.13 min.

Intermediate 306.1

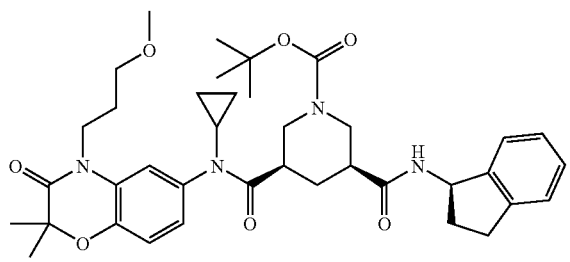

Intermediate 306.1 is synthesized by condensation of intermediate 108.2 (100 mg, 0.18 mmol) and (R)-1-aminoindan (31 mg, 0.23 mmol) analogously to the preparation of intermediate 1.1. Colorless oil, ES-MS: M+H=675: $_B t_{Ret}$=2.24 min.

Example 307

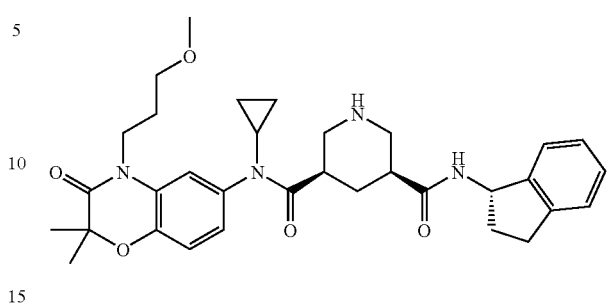

Example 307 is synthesized by deprotection of intermediate 307.1 (120 mg, 0.18 mmol) analogously to the preparation of example 123. White amorphous material, ES-MS: M+H=575: $_C t_{Ret}$=3.10 min.

Intermediate 307.1

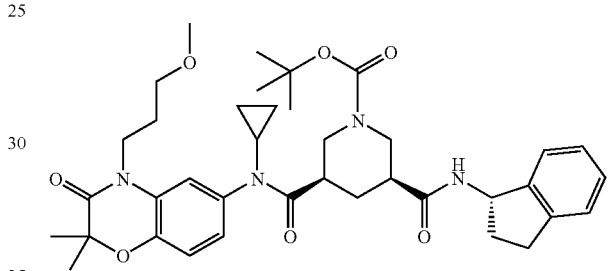

Intermediate 307.1 is synthesized by condensation of intermediate 108.2 (100 mg, 0.18 mmol) and (S)-1-aminoindan (31 mg, 0.23 mmol) analogously to the preparation of intermediate 1.1. Colorless oil, ES-MS: M+H=675: $_B t_{Ret}$=2.25 min.

Example 308

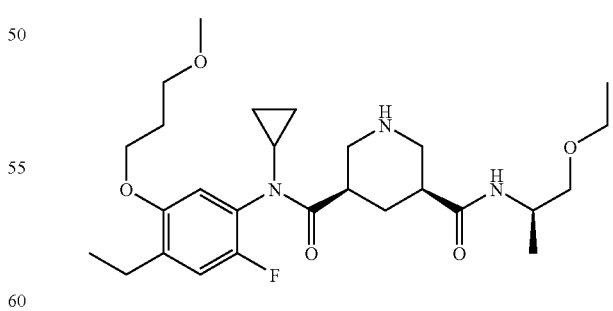

Example 308 is synthesized by deprotection of intermediate 308.1 (60 mg, 0.1 mmol) analogously to the preparation of example 123. White amorphous material, ES-MS: M+H=508: $_C t_{Ret}$=3.21 min.

Intermediate 308.1

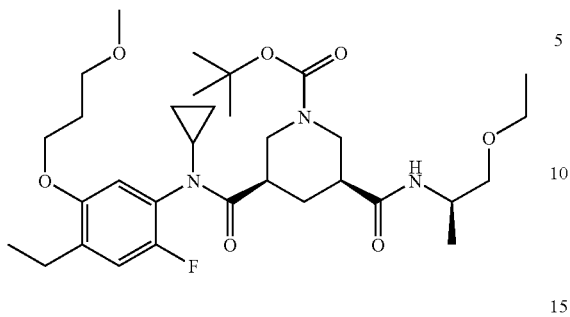

Intermediate 308.1 is synthesized by condensation of intermediate 308.2 (100 mg, 0.19 mmol) and (R)-1-ethoxymethyl propylamine hydrochloride (29 mg, 0.21 mmol) analogously to the preparation of intermediate 1.1. Colorless oil, ES-MS: M+H=608: $_Bt_{Ret}$=2.33 min.

Intermediate 308.2

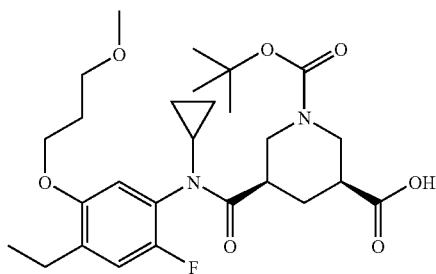

Intermediate 308.2 is synthesized by condensation of intermediate 308.3 (535 mg, 2 mmol) and (3R,5S)-starting material-F (575 mg, 2 mmol) analogously to the preparation of example 125. Colorless oil, ES-MS: M+H=523: $_Bt_{Ret}$=2.25 min.

Intermediate 308.3

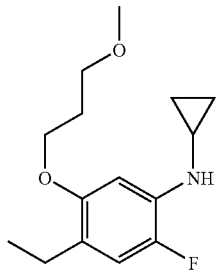

Intermediate 308.3 is prepared by cyclopropylation with intermediate 308.4 (2.9 g, 12.8 mmol) analogously to the preparation of intermediate 87.2. Colorless oil, ES-MS: M+H=308: $_Ct_{Ret}$=4.45 min.

Intermediate 308.4

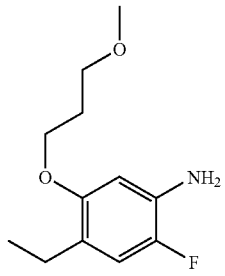

Intermediate 308.4 is prepared by hydrogenation with intermediate 308.5 (3.3 g, 12.8 mmol) analogously to the preparation of intermediate 32.5. Colorless oil, ES-MS: M+H=228: $_Bt_{Ret}$=1.76 min.

Intermediate 308.5

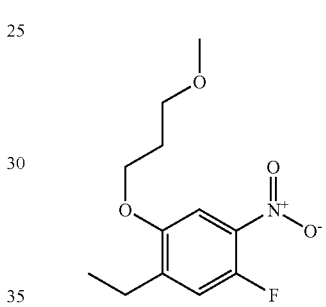

Intermediate 308.5 is prepared by alkylation with 2-ethyl-4-fluoro-5-nitrophenol (5.7 g, 30.78 mmol) analogously to the preparation of intermediate 37.5. Pale yellow oil, $_Bt_{Ret}$=1.96 min, TLC: Rf=0.5 (Hexane:AcOEt=3:1).

Example 309

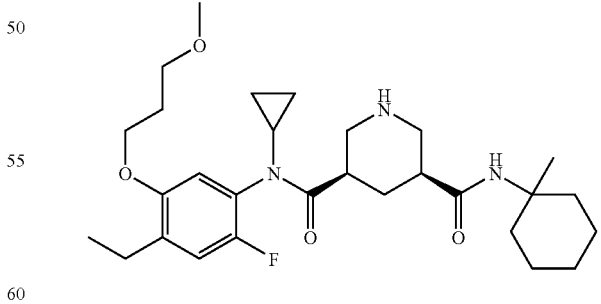

Example 309 is synthesized by deprotection of intermediate 309.1 (82 mg, 0.13 mmol) analogously to the preparation of example 123. White amorphous material, ES-MS: M+H=518: $_Ct_{Ret}$=3.65 min.

Intermediate 309.1

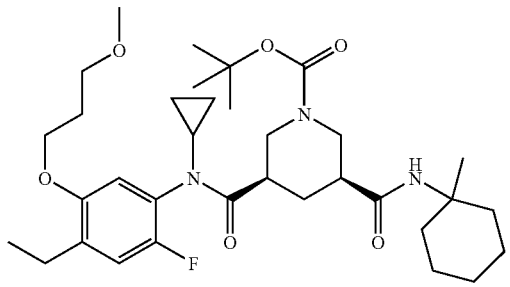

Intermediate 309.1 is synthesized by condensation of intermediate 308.2 (100 mg, 0.19 mmol) and 1-methylcyclohexylamine hydrochloride (38 mg, 0.21 mmol) analogously to the preparation of intermediate 1.1. Colorless oil, ES-MS: M+H=618: $_B t_{Ret}$=2.50 min.

Example 310

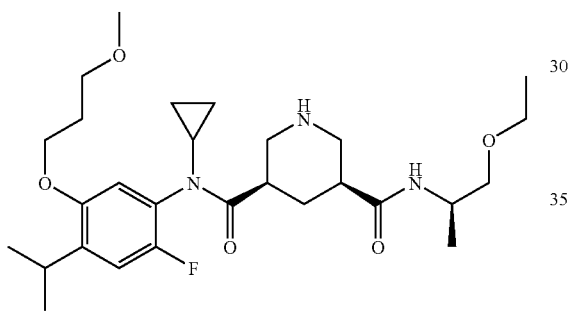

Example 310 is synthesized by deprotection of intermediate 310.1 (52 mg, 0.08 mmol) analogously to the preparation of example 123. White amorphous material, ES-MS: M+H=522: $_C t_{Ret}$=3.39 min.

Intermediate 310.1

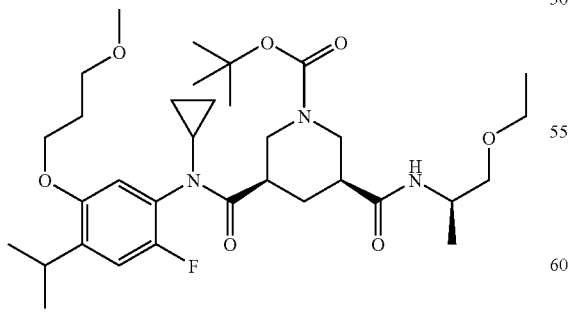

Intermediate 310.1 is synthesized by condensation of intermediate 310.2 (102 mg, 0.19 mmol) and (R)-1-ethoxymethyl propylamine hydrochloride (29 mg, 0.21 mmol) analogously to the preparation of intermediate 1.1. Colorless oil, ES-MS: M+H=622: $_B t_{Ret}$=2.40 min.

Intermediate 310.2

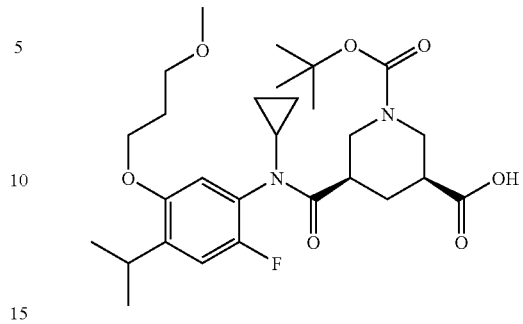

Intermediate 310.2 is synthesized by condensation of intermediate 308.3 (533 mg, 1.96 mmol) and (3R,5S)-starting material-F (564 mg, 1.96 mmol) analogously to the preparation of example 125. Colorless oil, ES-MS: M+H=391: $_A t_{Ret}$=3.97 min.

Intermediate 310.3

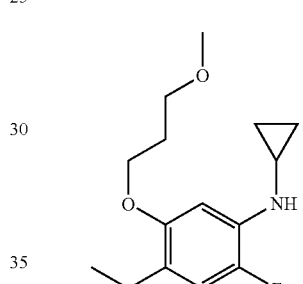

Intermediate 310.3 is prepared by cyclopropylation with intermediate 310.4 (1.84 g, 7.63 mmol) analogously to the preparation of intermediate 87.2. Colorless oil, ES-MS: M+H=281: $_C t_{Ret}$=2.42 min.

Intermediate 310.4

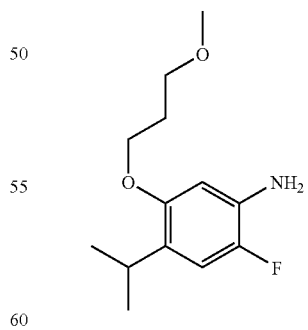

Intermediate 310.4 is prepared by hydrogenation with intermediate 310.5 (2.1 g, 7.74 mmol) analogously to the preparation of intermediate 32.5. Colorless oil, ES-MS: M+H=241: $_C t_{Ret}$=1.87 min.

Intermediate 310.5

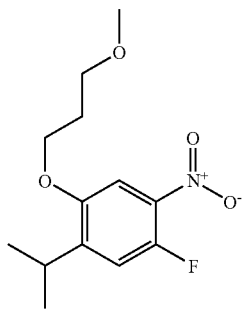

Intermediate 310.5 is prepared by alkylation with 2-isopropyl-4-fluoro-5-nitrophenol (2.83 g, 14.2 mmol) analogously to the preparation of intermediate 37.5. Pale yellow oil, $^1$H-NMR (CDCl$_3$, 400 MHz): δ 1.25 (6H, d), 2.10 (2H, quint.), 3.34 (1H, m), 3.36 (3H, s), 3.57 (2H, t), 4.13 (2H, t), 7.08 (1H, d), 7.51 (1H, d).

Example 311

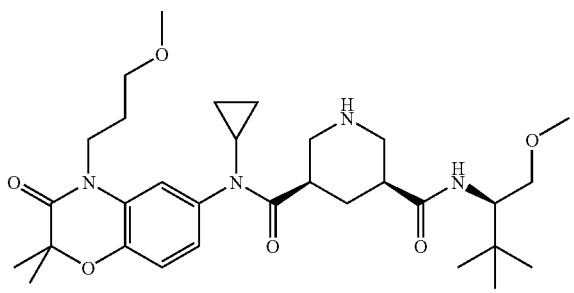

Example 311 is synthesized by deprotection of intermediate 311.1 analogously to the preparation of example 19. White material: M+H=573: $_ct_{Ret}$=3.01 min.
Intermediate 311.1

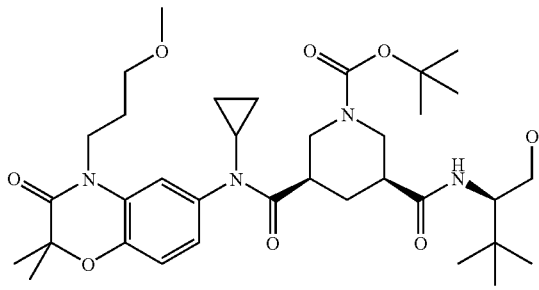

Intermediate 311.1 is synthesized by condensation of intermediate 108.2 (120 mg, 0.214 mmol) and (R)-1-methoxymethyl-2,2-dimethyl-propylamine hydrochloride (Tetrahedron Letters (1982), 23(36), 3711-14.) (32.7 mg, 0.25 mmol) analogously to the preparation of intermediate 32.3. ES-MS: M+H=676: $_ct_{Ret}$=4.16 min.

Example 312

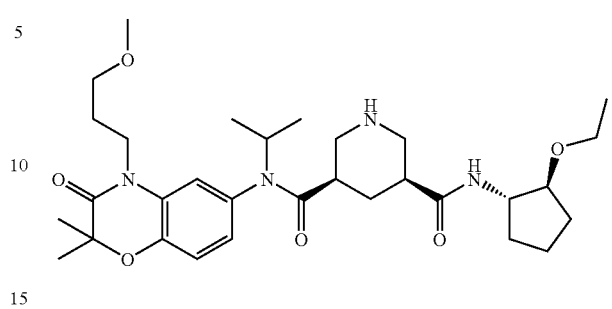

Example 312 is synthesized by deprotection of intermediate 312.1 analogously to the preparation of example 19. ES-MS: M+H=3.11: $_ct_{Ret}$=573 min.
Intermediate 312.1

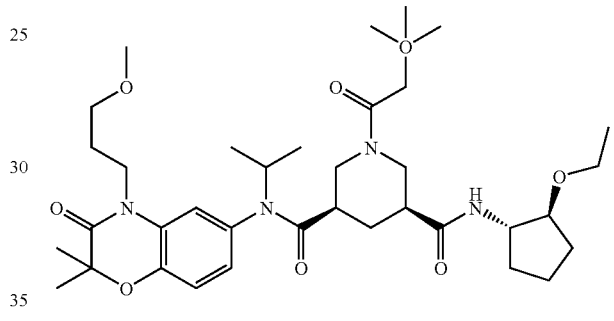

Intermediate 312.1 is synthesized by condensation of intermediate 299.2 (140 mg, 0.25 mmol) and intermediate 221.2 (46 mg, 0.28 mmol) analogously to the preparation of Intermediate 32.3 in the presence of Et$_3$N (42 μL, 0.30 mmol). ES-MS: M+H=673: $_ct_{Ret}$=4.20 min.

Example 313

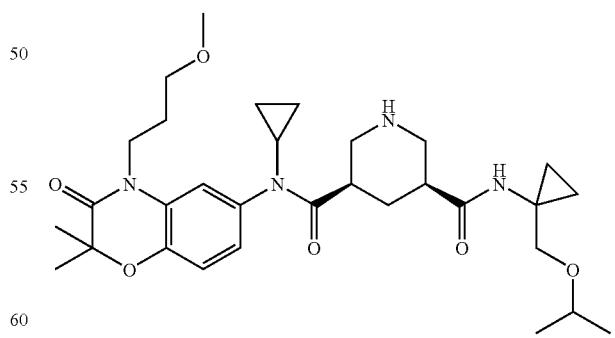

Example 313 is synthesized by deprotection of intermediate 313.1 analogously to the preparation of example 19. ES-MS: M+H=571: $_ct_{Ret}$=2.89 min.

Intermediate 313.1

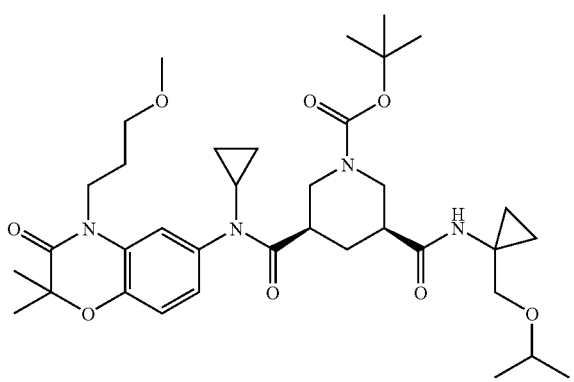

Intermediate 313.1 is synthesized by condensation of intermediate 108.2 (150 mg, 0.27 mmol) with intermediate 313.2 (54.0 mg, 0.32 mmol) analogously to the preparation of intermediate 32.3. White amorphous material, ES-MS: M+H=671: $_Bt_{Ret}$=2.15 min.

Intermediate 313.2

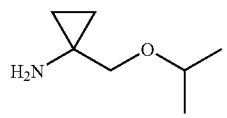

To a solution of intermediate 313.3 (0.1 M in methanol) is added palladium on charcoal (5 mol %). A slow stream of hydrogen was then passed through this solution for 1 d. From time to time, hydrochloric acid MeOH solution was added to acidify the solution. After filtration through a plug of Celite, the filtrate was concentrated in vacuo. The product is used for next reaction without purification: yellow oil. ES-MS: M+H=130: $_Bt_{Ret}$=1.39 min.

Intermediate 313.3

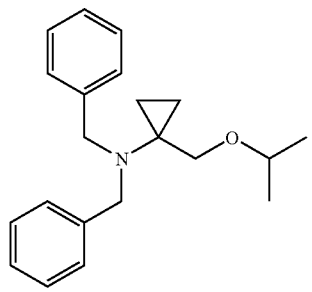

EtMgBr (8.85 mL, 8.85 mmol, 1 M in THF) is added under argon at 0° C. to a solution of intermediate 313.4 (700 mg, 2.36 mmol) and Ti(O$^i$Pr)$_4$ (1.14 mL, 3.89 mmol) in THF (10 mL). The solution is slowly warmed to room temperature, it is then stirred at rt for 30 min. Water (10 mL) is added, followed by 10% aq. HCl (10 mL) and Et$_2$O (20 mL). A 10% aq. NaOH solution is added to the resulting clear mixture until the pH becomes basic. The product is extracted with Et$_2$O (2×30 mL). The combined organic extracts are dried with Na$_2$SO$_4$. After evaporation of the solvent, the product is used for next reaction without purification: yellow oil. ES-MS: M+H=310: $_Bt_{Ret}$=1.85 min.

Intermediate 313.4

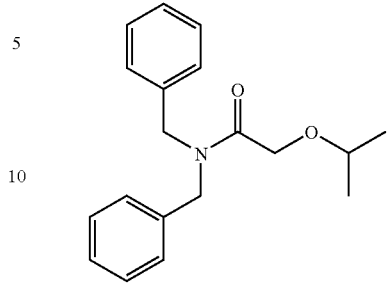

2-isopropoxyacetic acid (1.0 g, 8.47 mmol) is treated at room temp. with oxalyl chloride (0.87 mL, 11.0 mmol) in CH$_2$Cl$_2$ (20 mL) and the mixture is stirred for 1 h at this temperature The excess oxalyl chloride is then evaporated in vacuo. The residue is dissolved in CH$_2$Cl$_2$ (30 mL), and then Et$_3$N (3.38 g, 25.4 mmol) and dibenzylamine (2.51 g, 12.7 mmol) are added. After stirring for 3 h at room temp., the reaction mixture is washed with 1 N hydrochloric acid (20 mL), saturated NaHCO$_3$ solution (100 mL), and brine (100 mL), and dried with NaSO$_4$. Concentration under reduced pressure gives the crude product. The crude product is purified by silica gel chromatography to afford intermediate 313.4 (1.71 g): ES-MS: M+H=298: $_Bt_{Ret}$=2.13 min.

Example 314

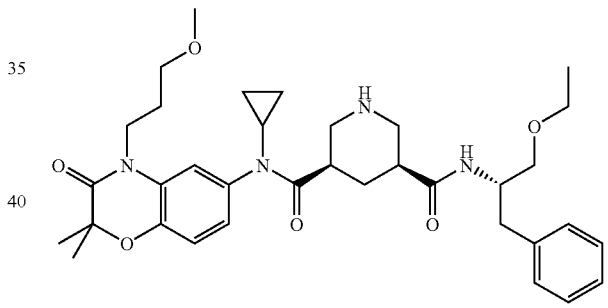

Example 314 is synthesized by deprotection of intermediate 314.1 analogously to the preparation of example 19. White material: M+H=621: $_Ct_{Ret}$=3.31 min.

Intermediate 314.1

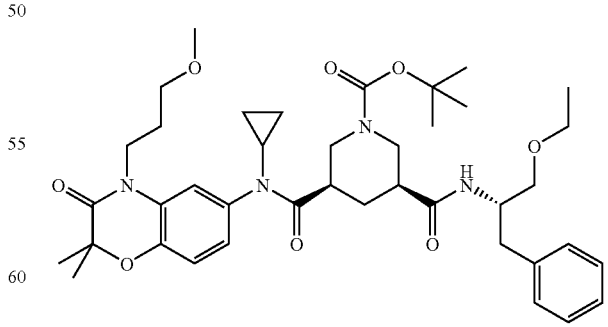

Intermediate 314.1 is synthesized by condensation of intermediate 108.2 (120 mg, 0.214 mmol) and intermediate 314.2 hydrochloride (46.1 mg, 0.214 mmol) analogously to the preparation of intermediate 32.3. ES-MS: M+H=721: $_Ct_{Ret}$=4.38 min.

Intermediate 314.2

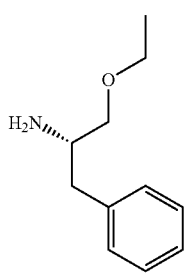

Intermediate 314.2 is synthesized by deprotection of intermediate 314.3 analogously to the preparation of example 19. White material: M+H=180: $_B t_{Ret}$=1.48 min.

Intermediate 314.3

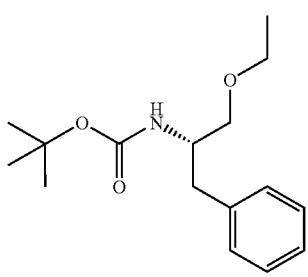

Intermediate 314.3 is synthesized by alkylation of N-Boc-(R)-phenyl-alaniol (Tetrahedron Letters (2004), 45(11), 2467-2471.) (200 mg, 0.795 mmol) analogously to the preparation of intermediate 151.3. White material: M+H-Boc=180: $_B t_{Ret}$=2.24 min.

Example 315

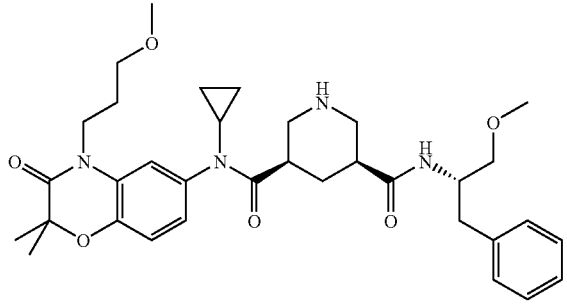

Example 315 is synthesized by deprotection of intermediate 315.1 analogously to the preparation of example 19. White material: M+H=607: $_C t_{Ret}$=3.19 min.

Intermediate-31 5.1

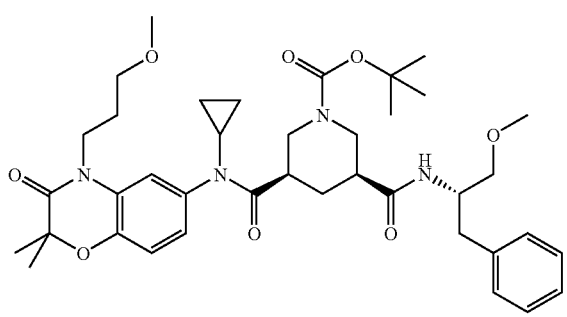

Intermediate 315.1 is synthesized by condensation of intermediate 108.2 (120 mg, 0.214 mmol) and (S)-1-methoxyethyl-2-phenyl-ethylamine hydrochloride (Journal of Organic Chemistry (1988), 53(13), 2991-9.) (43.16 mg, 0.214 mmol) analogously to the preparation of intermediate 32.3. ES-MS: M+H=707: $_C t_{Ret}$=4.18 min.

Example 316

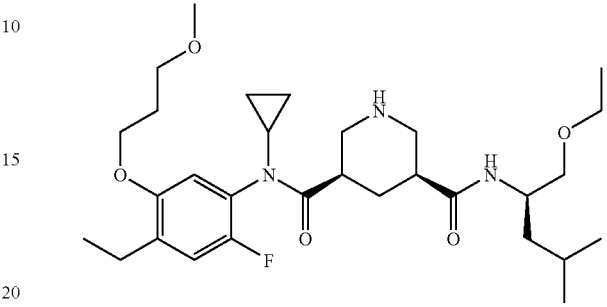

Example 316 is synthesized by deprotection of intermediate 316.1 (104 mg, 0.16 mmol) analogously to the preparation of example 123. White amorphous material, ES-MS: M+H=550: $_C t_{Ret}$=3.64 min.

Intermediate 316.1

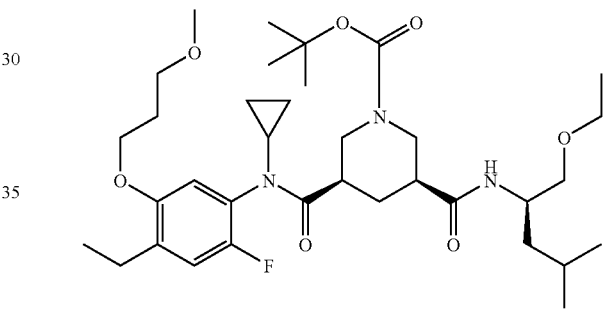

Intermediate 316.1 is synthesized by condensation of intermediate 308.2 (100 mg, 0.19 mmol) and (R)-1-ethoxymethyl-3-methyl butylamine hydrochloride (29 mg, 0.21 mmol) analogously to the preparation of intermediate 1.1. Colorless oil, ES-MS: M+H=650: $_B t_{Ret}$=2.50 min.

Example 317

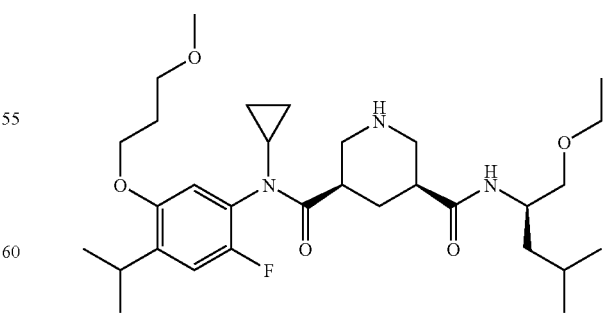

Example 317 is synthesized by deprotection of intermediate 317.1 (114 mg, 0.17 mmol) analogously to the preparation of example 123. White amorphous material, ES-MS: M+H=564: $_C t_{Ret}$=3.78 min.

Intermediate 317.1

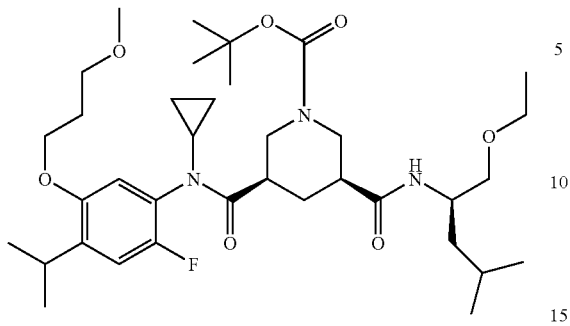

Intermediate 317.1 is synthesized by condensation of intermediate 310.2 (102 mg, 0.19 mmol) and (R)-1-ethoxymethyl-3-methyl butylamine hydrochloride (38 mg, 0.21 mmol) analogously to the preparation of intermediate 1.1. Colorless oil, ES-MS: M+H=664: $_B t_{Ret}$=2.56 min.

Example 318

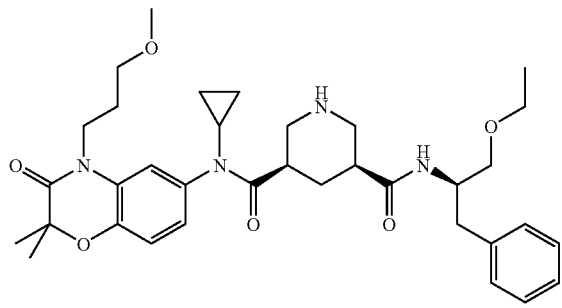

Example 318 is synthesized by deprotection of intermediate 318.1 analogously to the preparation of example 19. White material: M+H=621: $_C t_{Ret}$=3.29 min.

Intermediate 318.1

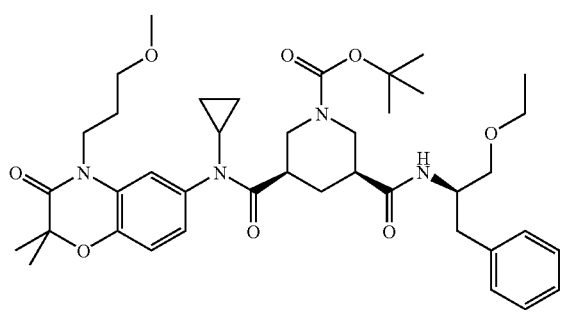

Intermediate 318.1 is synthesized by condensation of intermediate 108.2 (120 mg, 0.214 mmol) and intermediate 318.2 hydrochloride (46.1 mg, 0.214 mmol) analogously to preparation of Intermediate 32.3. ES-MS: M+H=721: $_C t_{Ret}$=4.42 min.

Intermediate 318.2

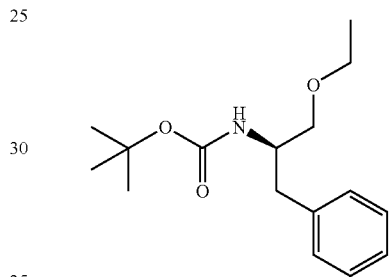

Intermediate 318.2 is synthesized by deprotection of intermediate 318.3 analogously to the preparation of example 19. White material: M+H=180: $_B t_{Ret}$=1.50 min.

Intermediate 318.3

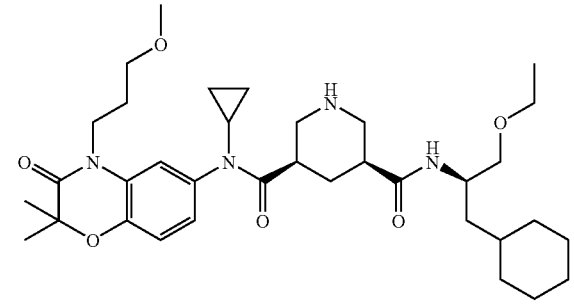

Intermediate 318.3 is synthesized by alkylation of N-Boc-(S)-phenyl-alaniol (Journal of Organic Chemistry (2000), 65(16), 5037-5042.) (200 mg, 0.795 mmol) analogously to the preparation of intermediate 151.3. White material: M+H-Boc=180: $_B t_{Ret}$=2.24 min.

Example 319

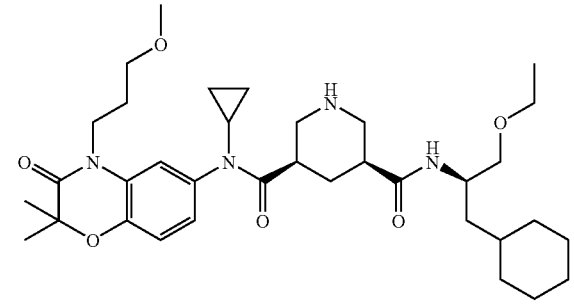

Example 319 is synthesized by deprotection of intermediate 319.1 analogously to the preparation of example 19. ES-MS: M+H=627: $_A t_{Ret}$=3.07 min.

Intermediate 319.1

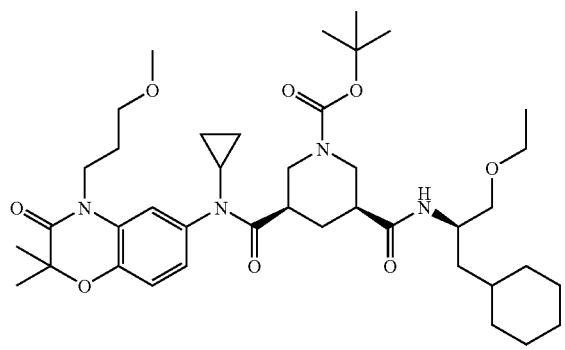

Example 320

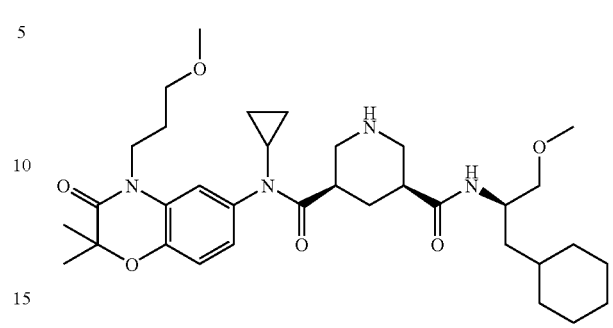

Intermediate 319.1 is synthesized by condensation of intermediate 108.2 (150 mg, 0.27 mmol) with intermediate 319.2 (67.0 mg, 0.33 mmol) analogously to the preparation of intermediate 32.3: White amorphous material, ES-MS: M+H=727: $_B t_{Ret}$=2.51 min.

Intermediate 319.2

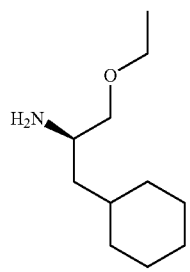

Intermediate 319.2 is synthesized by deprotection of intermediate 319.3 analogously to the preparation of example 19. ES-MS: M+H=186: $_B t_{Ret}$=1.70 min.

Intermediate 319.3

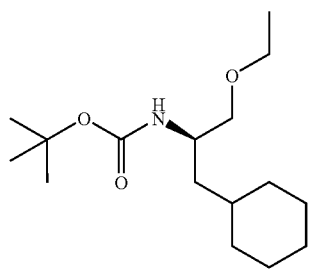

Intermediate 319.3 is synthesized by alkylation of N-Boc-(R)-2-amino-3-cyclohexyl-propan-1-ol (471 mg, 1.83 mmol) with NaH (161 mg of 60 wt % in mineral oil, 4.00 mmol) and EtI mL, 1.83 mmol) analogously to the preparation of intermediate 148.3. White amorphous material, ES-MS: M+H=286: $_B t_{Ret}$=2.53 min.

Example 320 is synthesized by deprotection of intermediate 320.1 analogously to the preparation of example 19: ES-MS: M+H=613: $_C t_{Ret}$=3.43 min.

Intermediate 320.1

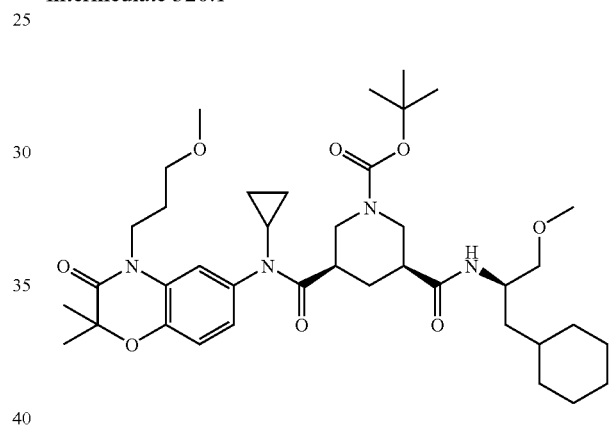

Intermediate 320.1 is synthesized by condensation of intermediate 108.2 (150 mg, 0.27 mmol) with intermediate 320.2 (68.5 mg, 0.33 mmol) analogously to the preparation of intermediate 32.3. White amorphous material, ES-MS: M+H=713: $_B t_{Ret}$=2.43 min.

Intermediate 320.2

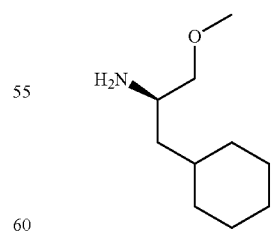

Intermediate 320.2 is synthesized by deprotection of intermediate 320.3 analogously to the preparation of example 19. ES-MS: M+H=172: $_B t_{Ret}$=1.63 min.

Intermediate 320.3

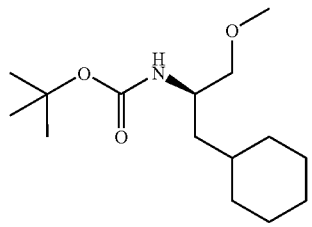

Intermediate 320.3 is synthesized by alkylation of N-Boc-(R)-2-amino-3-cyclohexyl-propan-1-ol (440 mg, 1.71 mmol) with NaH (151 mg of 60 wt % in mineral oil, 3.76 mmol) and MeI mL, 1.71 mmol) analogously to the preparation of intermediate 148.3. White amorphous material, ES-MS: M+H=272: $_B t_{Ret}$=2.43 min.

Example 321

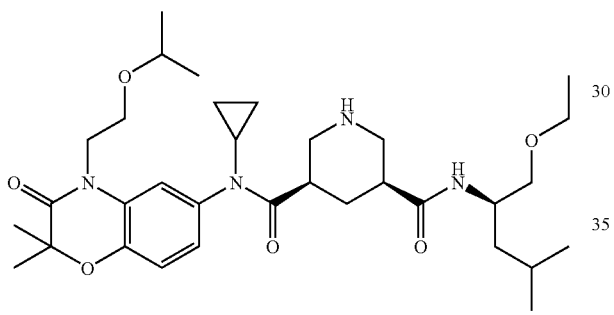

Example 321 is synthesized by deprotection of intermediate 321.1 analogously to the preparation of example 19. ES-MS: M+H=601: $_C t_{Ret}$=3.46 min.

Intermediate 321.1

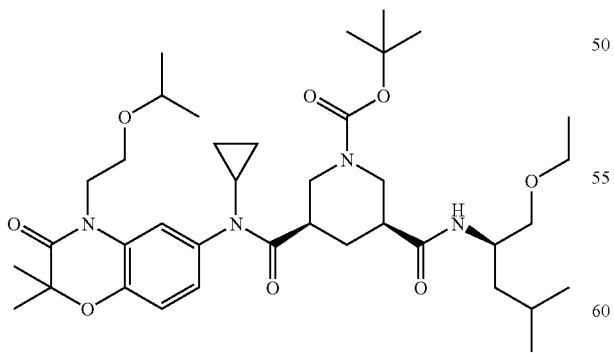

Intermediate 321.1 is synthesized by condensation of intermediate 292.3 (150 mg, 0.38 mmol) with intermediate 321.2 (130 mg, 0.41 mmol) analogously to the preparation of intermediate 19.1. White amorphous material, ES-MS: M+H=701: $_B t_{Ret}$=2.42 min.

Intermediate 321.2

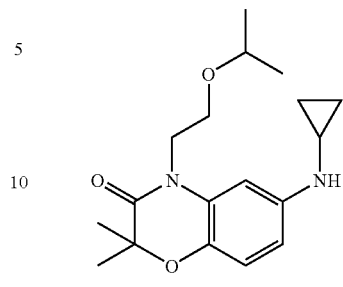

Intermediate 321.2 is synthesized by alkylation of intermediate 190.2, 6-cyclopropylamino-2,2-dimethyl-4H-benzo[1,4]oxazin-3-one (600 mg, 2.59 mmol) with NaH (113 mg of 60 wt % in mineral oil, 2.84 mmol), KI (471 mg, 2.84 mmol) and 2-Isopropoxyethyl p-toluenesulfonate (735 mg, 2.84 mmol, Macromolecules 1996, 29, 7544-7552) analogously to the preparation of intermediate 150.2. White amorphous material, ES-MS: M+H=319: $_B t_{Ret}$=2.02 min.

Example 322

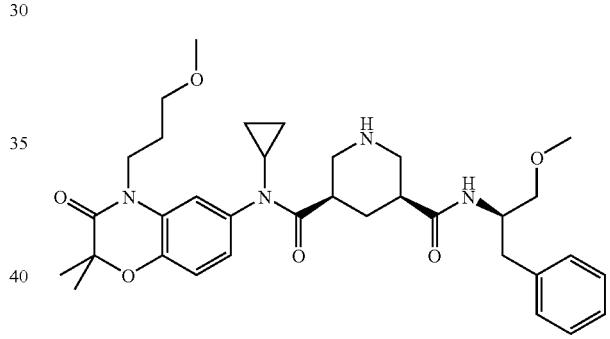

Example 322 is synthesized by deprotection of intermediate 322.1 analogously to the preparation of example 19. White material: M+H=607: $_C t_{Ret}$=3.20 min.

Intermediate 322.1

Intermediate 322.1 is synthesized by condensation of intermediate 108.2 (120 mg, 0.214 mmol) and (R)-1-methoxymethyl-2-phenyl-ethylamine hydrochloride (Tetrahedron Letters (1999), 40(7), 1241-1244.) (43.16 mg, 0.214 mmol) analogously to the preparation of Intermediate 32.3. ES-MS: M+H=707: $_C t_{Ret}$=4.25 min.

Example 323

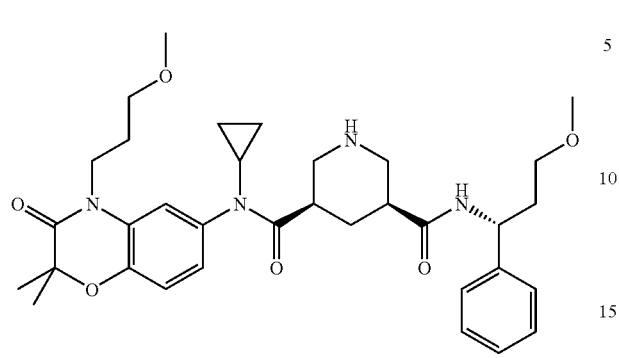

Example 323 is synthesized by deprotection of intermediate 323.1 analogously to the preparation of example 19. White material: M+H=607: $_Ct_{Ret}$=3.21 min.

Intermediate 323.1

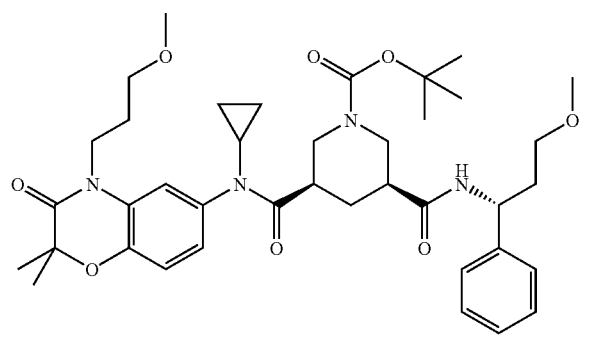

Intermediate 323.1 is synthesized by condensation of intermediate 108.2 (100 mg, 0.178 mmol) and intermediate 323.2 hydrochloride (35.9 mg, 0.178 mmol) analogously to the preparation of intermediate 32.3. ES-MS: M+H=707: $_Ct_{Ret}$=4.22 min.

Intermediate 323.2

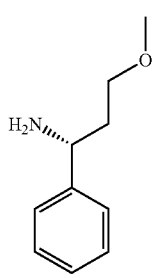

Intermediate 323.2 is synthesized by deprotection of intermediate 323.3 analogously to the preparation of example 19. White material: M+H=166: $_Bt_{Ret}$=1.39 min.

Intermediate 323.3

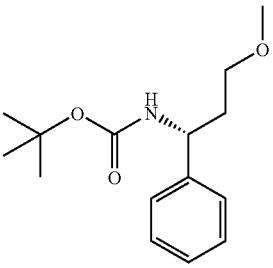

Intermediate 323.3 is synthesized by alkylation of ((R)-3-hydroxy-1-phenyl-propyl)-carbamic acid tert-butyl ester (WO2005009959) (200 mg, 0.795 mmol) analogously to the preparation of intermediate 289.3. White material: M+H-Boc=166: $_Bt_{Ret}$=2.15 min.

Example 324

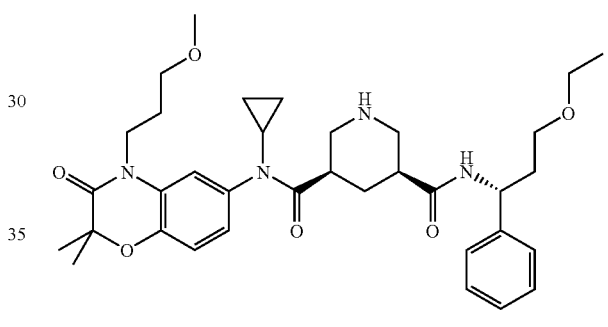

Example 324 is synthesized by deprotection of intermediate 324.1 analogously to the preparation of example 19. White material: M+H=621: $_Ct_{Ret}$=3.33 min.

Intermediate 324.1

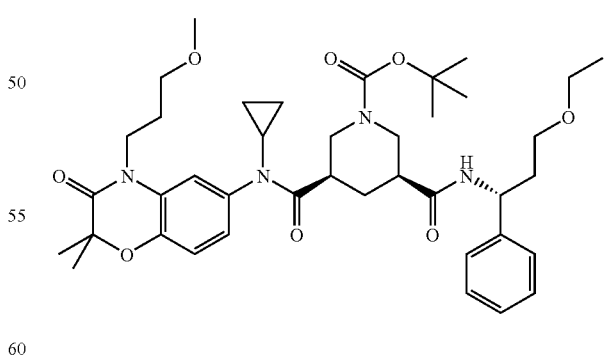

Intermediate 324.1 is synthesized by condensation of intermediate 108.2 (100 mg, 0.178 mmol) and intermediate 324.2 hydrochloride (38.3 mg, 0.178 mmol) analogously to the preparation of intermediate 32.3. ES-MS: M+H=721: $_Ct_{Ret}$=4.39 min.

Intermediate 324.2

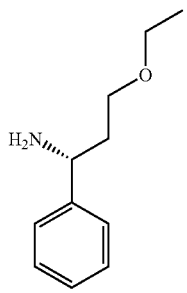

Intermediate 324.2 is synthesized by deprotection of intermediate 324.3 analogously to the preparation of example 19. White material: M+H=180: $_B t_{Ret}$=1.50 min.

Intermediate 324.3

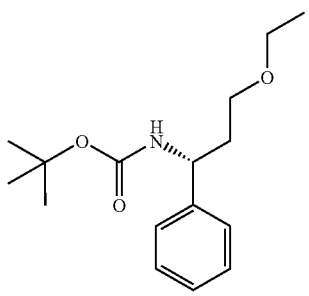

Intermediate 324.3 is synthesized by alkylation of ((R)-3-hydroxy-1-phenyl-propyl)-carbamic acid tert-butyl ester (WO2005009959) (200 mg, 0.795 mmol) analogously to the preparation of intermediate 151.3. White material: M+H-Boc=166: $_B t_{Ret}$=2.15 min.

Example 325

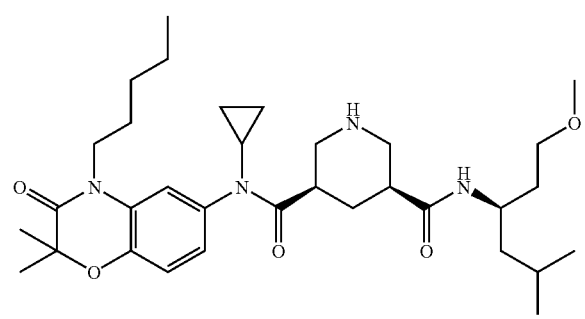

Example 325 is synthesized by deprotection of intermediate 325.1 analogously to the preparation of example 19. ES-MS: M+H=585: $_C t_{Ret}$=3.77 min.

Intermediate 325.1

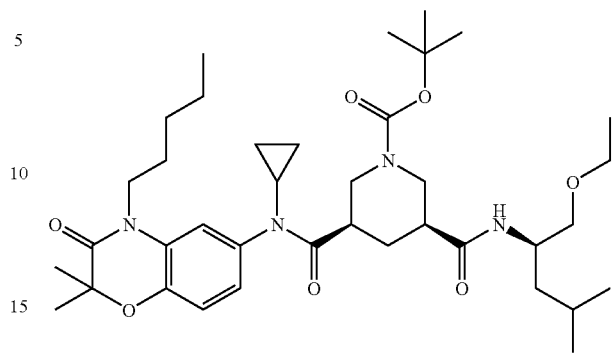

Intermediate 325.1 is synthesized by condensation of intermediate 292.3 (100 mg, 0.25 mmol) with intermediate 325.2 (83 mg, 0.28 mmol) analogously to the preparation of intermediate 19.1. White amorphous material, ES-MS: M+H=685: $_A t_{Ret}$=4.57 min.

Intermediate 325.2

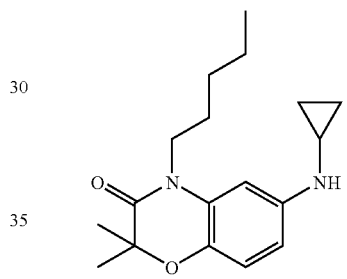

Intermediate 325.2 is synthesized by alkylation of intermediate 190.2, 6-cyclopropylamino-2,2-dimethyl-4H-benzo[1,4]oxazin-3-one (600 mg, 2.59 mmol) with NaH (113 mg of 60 wt % in mineral oil, 2.84 mmol) and 1-Iodopentane (0.37 mg, 2.84 mmol) analogously to the preparation of intermediate 150.2. White amorphous material, ES-MS: M+H=303: $_B t_{Ret}$=2.21 min.

Example 326

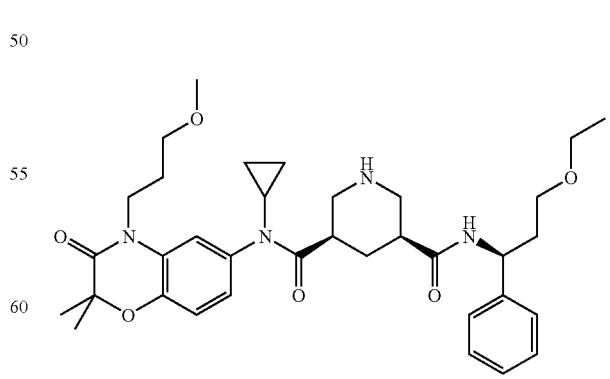

Example 326 is synthesized by deprotection of intermediate 326.1 analogously to the preparation of example 19. White material: M+H=621: $_C t_{Ret}$=3.29 min.

Intermediate 326.1

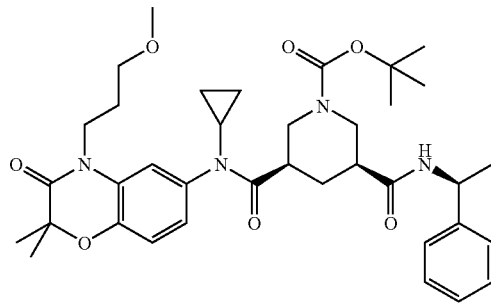

Intermediate 326.1 is synthesized by condensation of intermediate 108.2 (100 mg, 0.178 mmol) and intermediate 326.2 hydrochloride (38.3 mg, 0.178 mmol) analogously to the preparation of intermediate 32.3. ES-MS: M+H=721: $_Ct_{Ret}$=4.44 min.

Intermediate 326.2

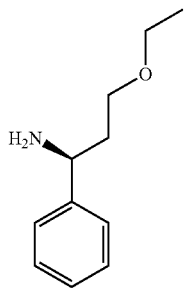

Intermediate 326.2 is synthesized by deprotection of intermediate 326.3 analogously to the preparation of example 19. White material: M+H=180: $_Bt_{Ret}$=1.46 min.

Intermediate 326.3

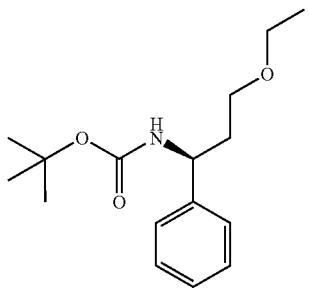

Intermediate 326.3 is synthesized by alkylation of ((S)-3-hydroxy-1-phenyl-propyl)-carbamic acid tert-butyl ester (Tetrahedron Letters (1994), 35(10), 1589-92.) (246 mg, 0.98 mmol) analogously to the preparation of intermediate 151.3. White material: M+H=280, $_Ct_{Ret}$=4.13 min.

Example 327

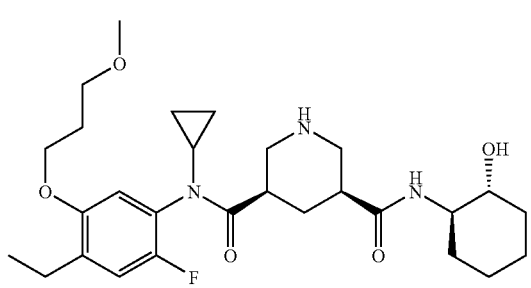

Example 327 is synthesized by deprotection of intermediate 327.1 (25 mg, 0.04 mmol) analogously to the preparation of example 123. White amorphous material, ES-MS: M+H=520: $_Ct_{Ret}$=3.09 min.

Intermediate 327.1

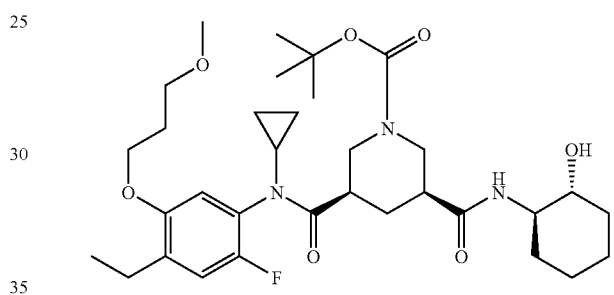

Intermediate 327.1 is synthesized by condensation of intermediate 308.2 (100 mg, 0.19 mmol) and (1R,2R)-2-aminocyclohexanol hydrochloride (32 mg, 0.21 mmol) analogously to the preparation of intermediate 1.1. Colorless oil, ES-MS: M+H=620: $_Bt_{Ret}$=2.28 min.

Example 328

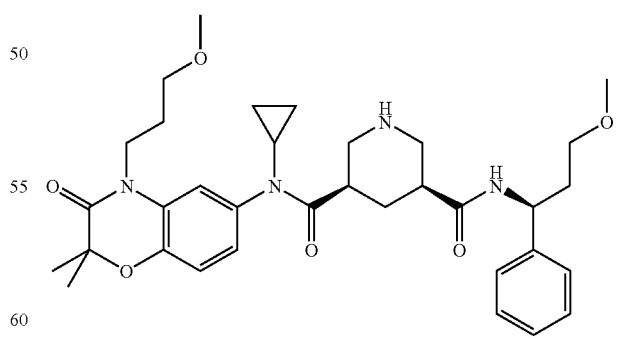

Example 328 is synthesized by deprotection of intermediate 328.1 analogously to the preparation of example 19. White material: M+H=607: $_Ct_{Ret}$=3.17 min.

Intermediate 328.1

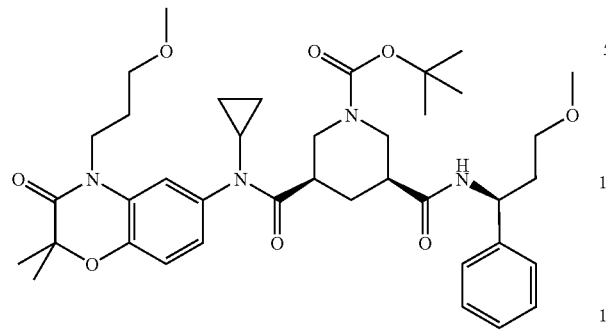

Intermediate 328.1 is synthesized by condensation of intermediate 108.2 (100 mg, 0.178 mmol) and intermediate 328.2 hydrochloride (35.9 mg, 0.178 mmol) analogously to the preparation of intermediate 32.3. ES-MS: M+H=707: $_Ct_{Ret}$=4.26 min.

Intermediate 328.2

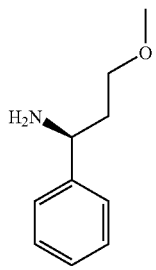

Intermediate 328.2 is synthesized by deprotection of intermediate 328.3 analogously to the preparation of example 19. White material: M+H=166: $_Bt_{Ret}$=1.41 min.

Intermediate 328.3

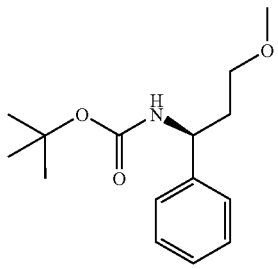

Intermediate 328.3 is synthesized by alkylation of ((S)-3-hydroxy-1-phenyl-propyl)-carbamic acid tert-butyl ester (Tetrahedron Letters (1994), 35(10), 1589-92.) (237 mg, 0.89 mmol) analogously to the preparation of intermediate 289.3. White material: M+H=266, 3.79 min.

Example 329

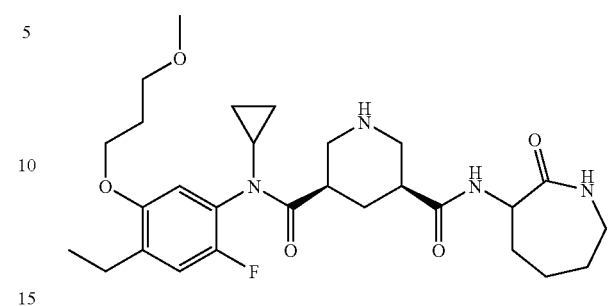

Example 329 is synthesized by deprotection of intermediate 329.1 (60 mg, 0.09 mmol) analogously to the preparation of example 123. White amorphous material, ES-MS: M+H=533: $_Ct_{Ret}$=2.95, 3.09 min.

Intermediate 329.1

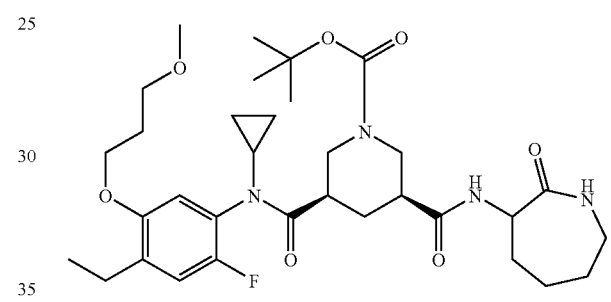

Intermediate 329.1 is synthesized by condensation of intermediate 308.2 (50 mg, 0.1 mmol) and alpha-amino-epsilon-caprolactam (15 mg, 0.12 mmol) analogously to the preparation of intermediate 1.1. Colorless oil, ES-MS: M+H=633: $_Bt_{Ret}$=2.18 min.

Example 330

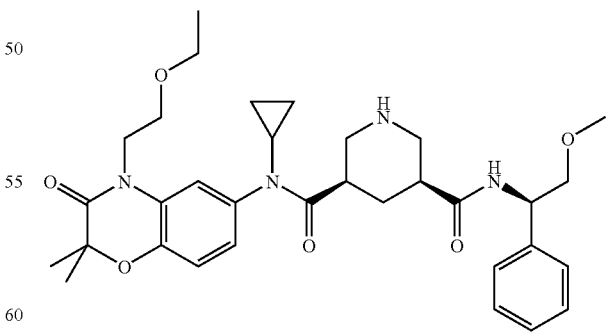

Example 330 is synthesized by deprotection of intermediate 330.1 analogously to the preparation of example 19. White material: M+H=593: $_Ct_{Ret}$=3.17 min Intermediate 330.1

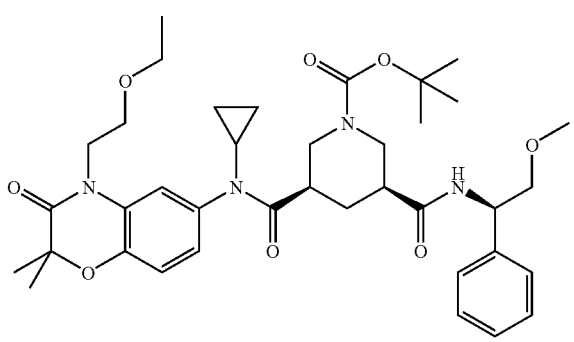

Intermediate 330.1 is synthesized by condensation of intermediate 208.2 (100 mg, 0.178 mmol) and (R)-(−)-1-amino-1-phenyl-2-methoxyethane hydrochloride (Organic Syntheses (1998), 75 19-30.) (36.1 mg, 0.19 mmol) analogously to the preparation of intermediate 32.3. ES-MS: M+H=693: $_C t_{Ret}$=4.19 min.

Example 331

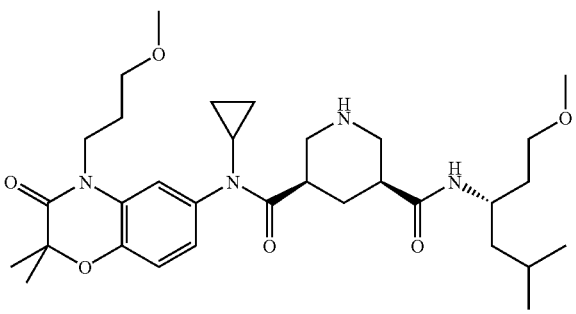

Example 331 is synthesized by deprotection of intermediate 331.1 analogously to the preparation of example 19. White material: M+H=587: $_C t_{Ret}$=3.32 min.

Intermediate 331.1

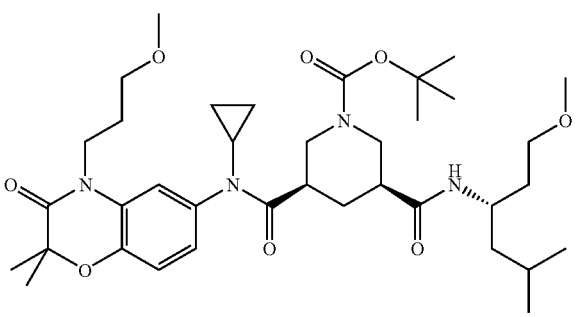

Intermediate 331.1 is synthesized by condensation of intermediate 108.2 (62.68 mg, 0.112 mmol) and intermediate 331.2 hydrochloride (24.5 mg, 0.13 mmol) analogously to the preparation of intermediate 32.3. ES-MS: M+H=687: $_C t_{Ret}$=4.31 min.

Intermediate 331.2

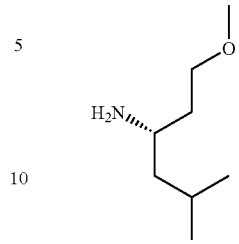

Intermediate 331.2 is synthesized by deprotection of intermediate 331.3 analogously to the preparation of example 19. White material: M+H=146: $_B t_{Ret}$=1.91 min Intermediate 331.3

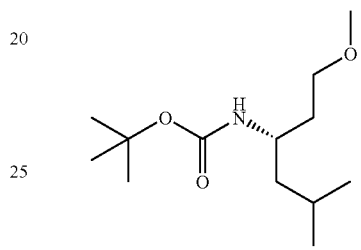

Intermediate 331.3 is synthesized by alkylation of [(S)-1-(2-hydroxy-ethyl)-3-methyl-butyl]-carbamic acid tert-butyl ester (U.S. Pat. No. 5,925,658) (61.2 mg, 0.264 mmol) analogously to the preparation of intermediate 289.3. White material: M+H-Boc=146: $_B t_{Ret}$=2.34 min.

Example 332

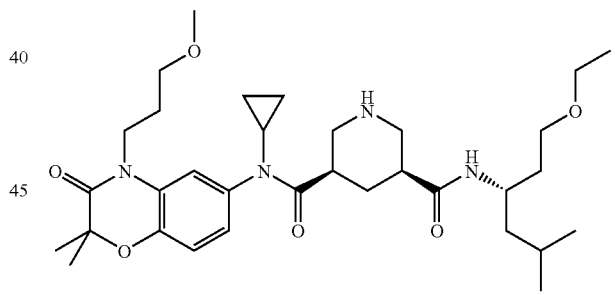

Example 332 is synthesized by deprotection of intermediate 332.1 analogously to the preparation of example 19. White material: M+H=601: $_C t_{Ret}$=3.51 min.

Intermediate 332.1

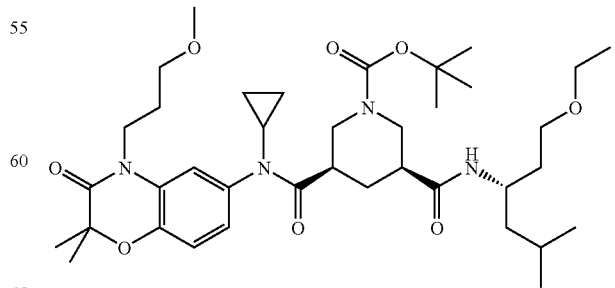

Intermediate 332.1 is synthesized by condensation of intermediate 108.2 (46.8 mg, 0.084 mmol) and intermediate 332.2 hydrochloride (16.4 mg, 0.084 mmol) analogously to the preparation of intermediate 32.3. ES-MS: M+H=701: $_C t_{Ret}$=4.55 min.

Intermediate 332.2

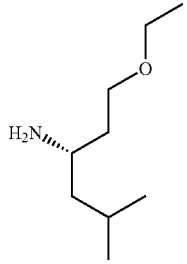

Intermediate 332.2 is synthesized by deprotection of intermediate 332.3 analogously to the preparation of example 19. White material: M+H=160: $_B t_{Ret}$=1.58 min.

Intermediate 332.3

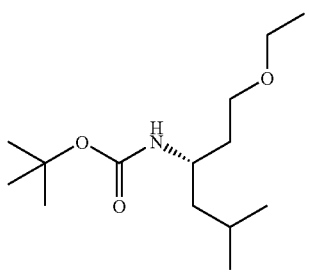

Intermediate 332.3 is synthesized by alkylation of [(S)-1-(2-hydroxy-ethyl)-3-methyl-butyl]carbamic acid tert-butyl ester (U.S. Pat. No. 5,925,658)(71.4 mg, 0.3086 mmol) analogously to the preparation of intermediate 151.3., White material: M+H-Boc=160: $_B t_{Ret}$=2.38 min.

Example 333

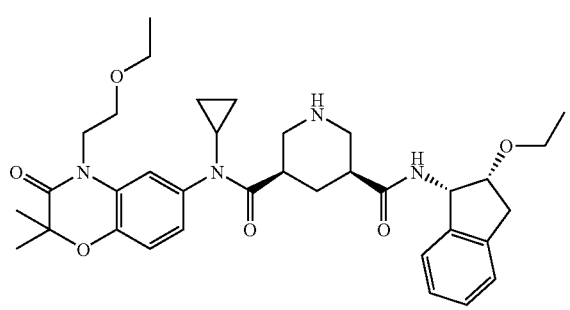

Example 333 is synthesized by deprotection of intermediate 333.1 analogously to the preparation of example 19. ES-MS: M+H=619: $_C t_{Ret}$=3.57 min.

Intermediate 333.1

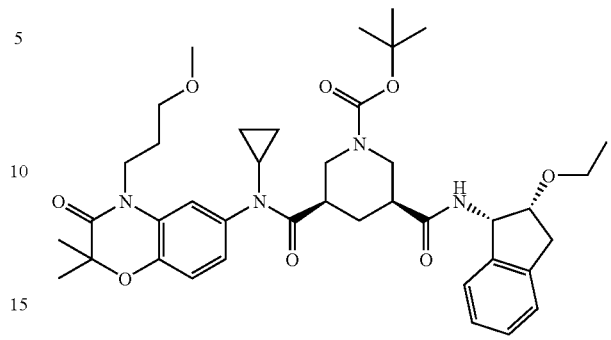

Intermediate 333.1 is synthesized by condensation of intermediate 208.2 (100 mg, 0.18 mmol) with intermediate 258.2 (46.2 mg, 0.22 mmol) analogously to the preparation of intermediate 32.3. White amorphous material, ES-MS: M+H=719: $_B t_{Ret}$=2.43 min.

Example 334

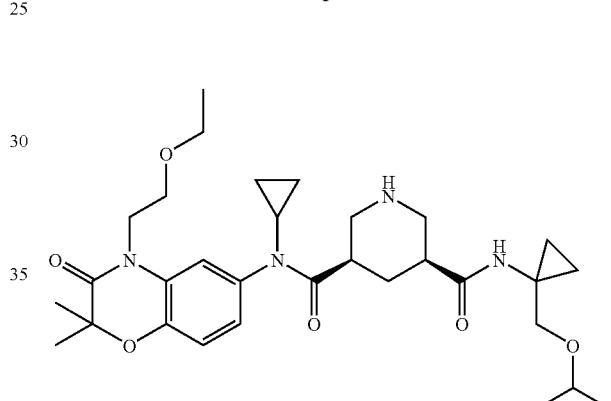

Example 334 is synthesized by deprotection of intermediate 334.1 analogously to the preparation of example 19. ES-MS: M+H=571: $_C t_{Ret}$=3.20 min.

Intermediate 334.1

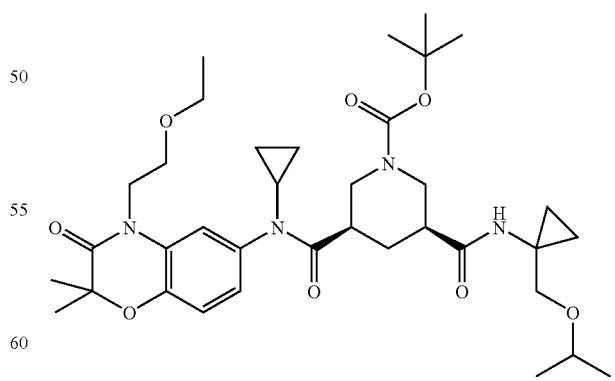

Intermediate 334.1 is synthesized by condensation of intermediate 208.2 (150 mg, 0.27 mmol) with intermediate 313.2 (54.0 mg, 0.32 mmol) analogously to the preparation of intermediate 32.3. White amorphous material, ES-MS: M+H=671: $_B t_{Ret}$=2.28 min.

Example 335

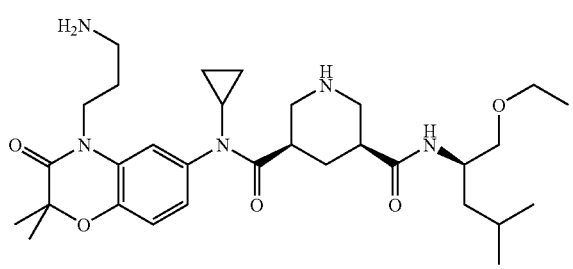

Example 335 is synthesized by deprotection of intermediate 335.1 analogously to the preparation of example 1. M+H=572, $_C t_{Ret}$=2.96 min.

Intermediate 335.1

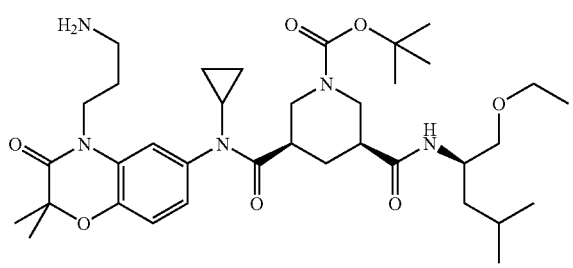

To a solution of intermediate 335.2 (212 mg, 0.265 mmol) in MeOH (10 mL) and CH$_2$Cl$_2$ (5 mL) is added hydrazine hydrate (66 mg, 1.32 mmol) at room temperature. After stirring for 30 h at room temperature, the reaction mixture is diluted with CH$_2$Cl$_2$ (20 mL) and washed with H$_2$O (50 mL). The organic layer is dried over MgSO$_4$ and concentrated in vacuo. The crude residue is purified by RP-HPLC to afford intermediate 335.1: colorless oil, ES-MS: M+H=672: $_B t_{Ret}$=2.05 min.

Intermediate 335.2

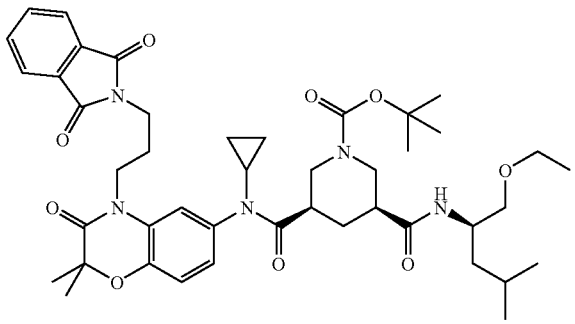

Intermediate 335.2 is synthesized by condensation of intermediate 292.3 (200 mg, 0.499 mmol) and intermediate 335.3 (230 mg, 0.549 mmol) analogously to the preparation of intermediate 32.3. ES-MS: M+H=802: $_B t_{Ret}$=2.43 min.

Intermediate 335.3

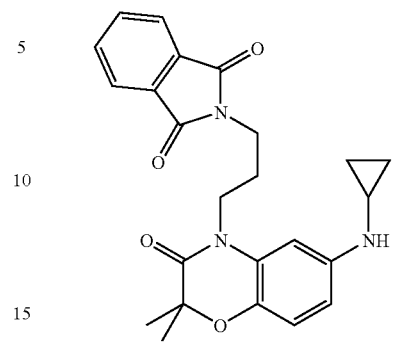

Intermediate 335.3 is synthesized by alkylation of intermediate 190.2, 6-cyclopropylamino-2,2-dimethyl-4H-benzo[1,4]oxazin-3-one (200 mg, 0.861 mmol) and 2-(3-Bromo-propyl)-isoindole-1,3-dione (254 mg, 0.947 mmol) analogously to the preparation of intermediate 150.2. M+H=420, $_B t_{Ret}$=2.07 min.

Example 336

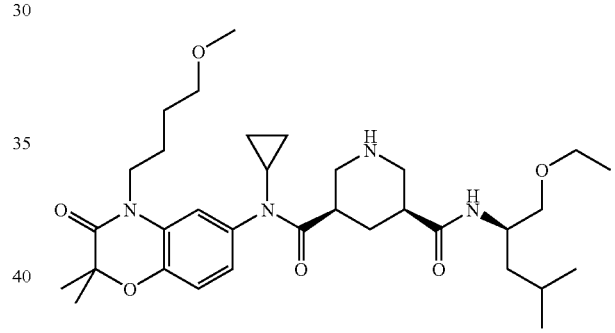

Example 336 is synthesized by deprotection of intermediate 336.1 analogously to the preparation of example 1. M+H=601, $_C t_{Ret}$=3.53 min.

Intermediate 336.1

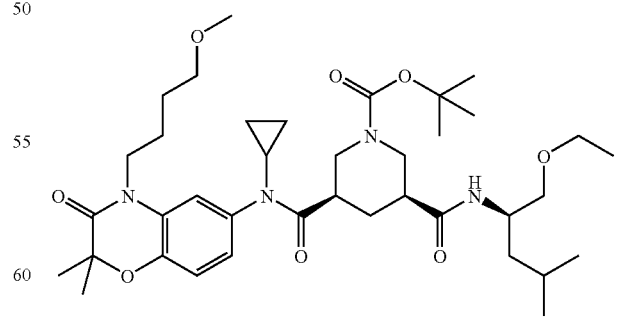

Intermediate 336.1 is synthesized by condensation of intermediate 292.3 (150 mg, 0.375 mmol) and intermediate 336.2 (179 mg, 0.562 mmol) analogously to the preparation of intermediate 32.3. ES-MS: M+H=7.1: $_B t_{Ret}$=2.45 min.

Intermediate 336.2

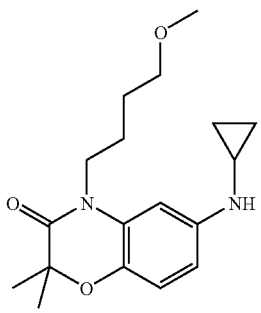

To a solution of intermediate 190.2, 6-cyclopropylamino-2,2-dimethyl-4H-benzo[1,4]oxazin-3-one (200 mg, 0.861 mmol) in DMF (10 mL) is added 60% NaH in mineral oil (38 mg, 0.95 mmol) at 0° C. The reaction mixture is stirred at room temperature for 10 min. After adding 1-chloro-4-methoxy-butane (116 mg, 0.947 mmol) and NaI (13 mg, 0.0861 mol) at room temperature, the mixture is stirred at room temperature for 3 h. The reaction mixture is added water (30 mL) and extracted with EtOAc. The combined organic extracts are dried (MgSO$_4$) and concentrated under reduced pressure. The residue is purified by silica-gel column chromatography to give intermediate 336.2: yellow amorphous, ES-MS: M+H=319: $_B$t$_{Ret}$=1.97.

Example 337

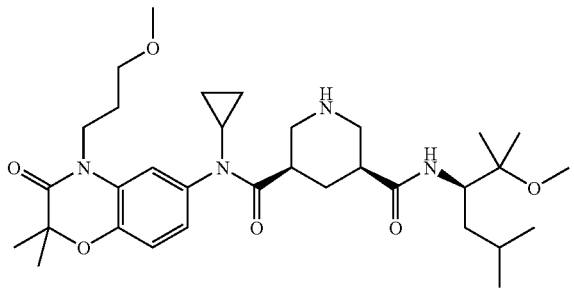

Example 337 is synthesized by deprotection of intermediate 337.1 analogously to the preparation of example 19. White material: M+H=601: $_A$t$_{Ret}$=2.77 min.

Intermediate 337.1

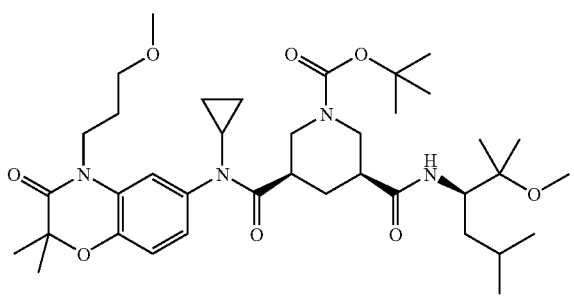

Intermediate 337.1 is synthesized by condensation of intermediate 108.2 (62.6 mg, 0.118 mmol) and intermediate 337.2 hydrochloride (21.9 mg, 0.118 mmol) analogously to the preparation of intermediate 32.3. ES-MS: M+H=701: $_A$t$_{Ret}$=4.03 min.

Intermediate 337.2

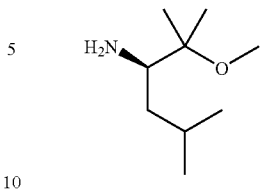

To a solution of intermediate 337.3 (47 mg, 0.14 mmol) in MeOH, 20% Pd(OH)$_2$/C is added and the reaction mixture hydrogenolyzed (4 kg/cm2) at RT overnight. After complete conversion, the catalyst is filtered off. Concentration under reduced pressure gave the cude. Then, 4N HCl in dioxane (1 mL) is added and the solvent is evaporated to give the salt. White material: M+H=160: $_A$t$_{Ret}$=1.61 min.

Intermediate 337.3

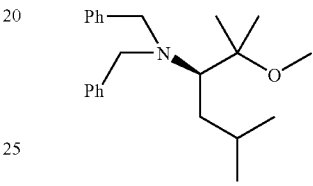

Intermediate 337.3 is synthesized by alkylation of intermediate 337.4 (182.4 mg, 0.56 mmol) analogously to the preparation of intermediate 289.3. White material: M+H=340: $_C$t$_{Ret}$=3.63 min Intermediate 337.4

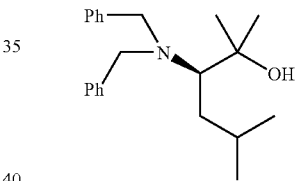

To a solution of (R)-2-dibenzylamino-4-methyl-pentanoic acid methyl ester (Journal of Organic Chemistry (1997), 62(7), 2292-2297.) (767.7 mg, 2.358 mmol) in THF (5 mL) under N$_2$ at 0° C., MeMgBr (7.6 mL of 0.93M in THF. 7.07 mmol) is added. The reaction mixture is stirred at rt for 3 h. The reaction is quenched with sat. KHSO$_4$ aq. and extracted with EtOAc, washed with brine and dried over MgSO$_4$. Concentration under reduced pressure gives the crude. The crude product is purified by the silica gel chromatography to give intermediate 337.4. M+H=326: $_C$t$_{Ret}$=3.30 min.

Example 338

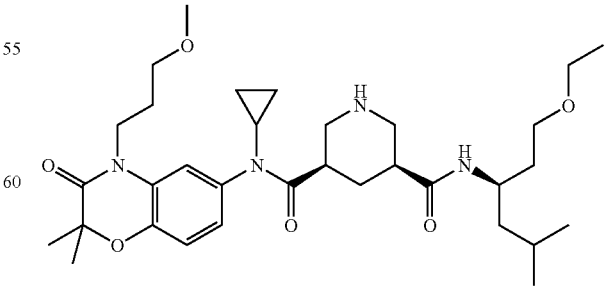

Example 338 is synthesized by deprotection of intermediate 338.1 analogously to the preparation of example 19. White material: M+H=601: $_C$t$_{Ret}$=3.14 min.

Intermediate 338.1

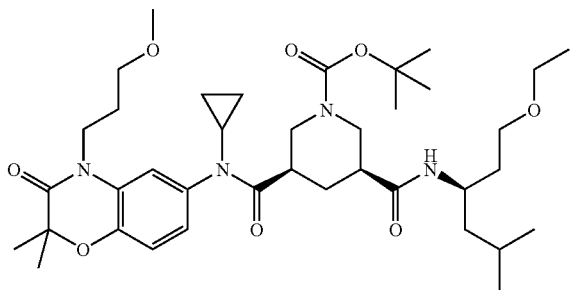

Intermediate 338.1 is synthesized by condensation of intermediate 108.2 (100 mg, 0.178 mmol) and intermediate 338.2 hydrochloride (36.3 mg, 0.185 mmol) analogously to the preparation of intermediate 32.3. ES-MS: M+H=701: $_C t_{Ret}$=4.25 min.

Intermediate 338.2

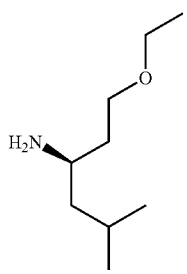

Intermediate 338.2 is synthesized by deprotection of intermediate 338.3 analogously to the preparation of example 19. White material: M+H=160: $_A t_{Ret}$=1.66 min.

Intermediate 338.3

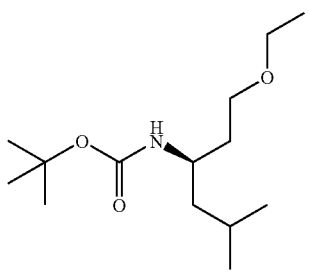

Intermediate 338.3 is synthesized by alkylation of intermediate 338.4 (201.5 mg, 0.87 mmol) analogously to the preparation of intermediate 151.3. White material: M+H-Boc=160: $_A t_{Ret}$=3.79 min.

Intermediate 338.4

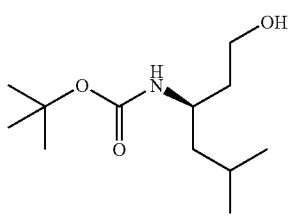

To a solution of (R)-3-tert-butoxycarbonylamino-5-methyl-hexanoic acid (471 mg, 1.92 mmol) (*Synthesis*, 1992, 1104) in THF (1 mL) under $N_2$ at 0° C., triethylamine (0.4 mL, 2.88 mmol) and isobutyl chloroformate (0.25 mL, 1.92 mmol) are added. The reaction mixture is stirred at that temperature for a few min. Filtration on Celite® and concentration under reduced pressure give the anhydride.

To a solution of the anhydride in MeOH under $N_2$ at 0° C., $NaBH_4$ (726 mg, 19.2 mmol) is added. The reaction mixture is stirred at that temperature for 2 h. Concentration under reduced pressure to remove the solvent (MeOH) gives a solid. Then, $KHSO_4$ aq. is added to the mixture, which is extracted with $CH_2Cl_2$, dried over $Na_2SO_4$. Concentration under reduced pressure gives the crude product. The crude is purified by silica gel chromatography to give intermediate 338.4.

Example 339

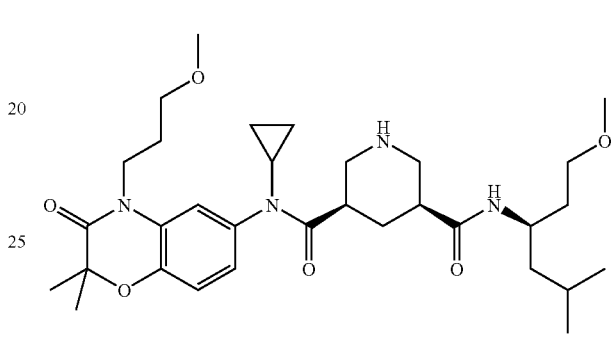

Example 339 is synthesized by deprotection of intermediate 339.1 analogously to the preparation of example 19. White material: M+H=587: $_C t_{Ret}$=2.49 min.

Intermediate 339.1

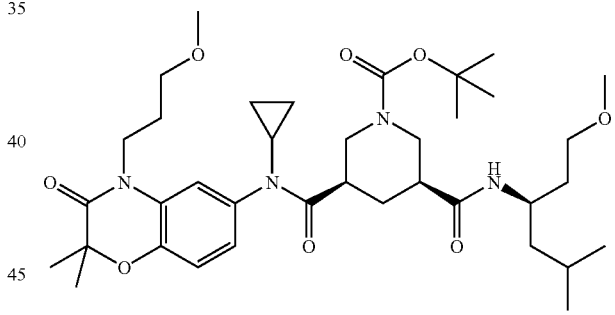

Intermediate 339.1 is synthesized by condensation of intermediate 108.2 (99.4 mg, 0.177 mmol) and intermediate 339.2 hydrochloride (48.5 mg, 0.27 mmol) analogously to the preparation of intermediate 32.3. ES-MS: M+H=687: $_C t_{Ret}$=4.09 min.

Intermediate 339.2

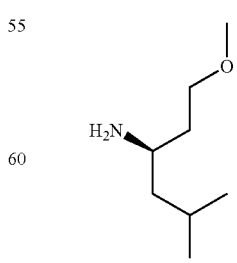

Intermediate 339.2 is synthesized by deprotection of intermediate 339.3 analogously to the preparation of example 19. White material: M+H=146: $_A t_{Ret}$=1.46 min.

Intermediate 339.3

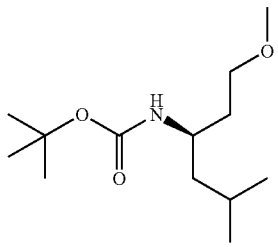

Intermediate 339.3 is synthesized by alkylation of intermediate 338.4 (200.4 mg, 0.87 mmol) analogously to the preparation of intermediate 289.3. White material: M+H-Boc=146: $_At_{Ret}$=3.48 min.

Example 340

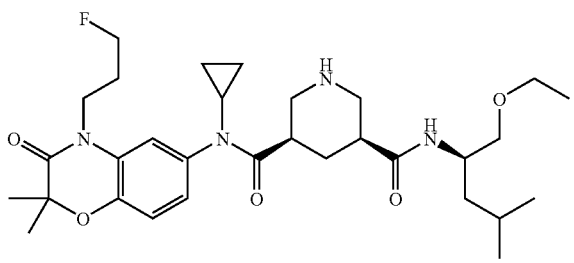

Example 340 is synthesized by deprotection of intermediate 340.1 (35 mg, 0.05 mmol) analogously to the preparation of intermediate 103.2. White amorphous material, ES-MS: M+H=575: $_Ct_{Ret}$=3.15 min.
Intermediate 340.1

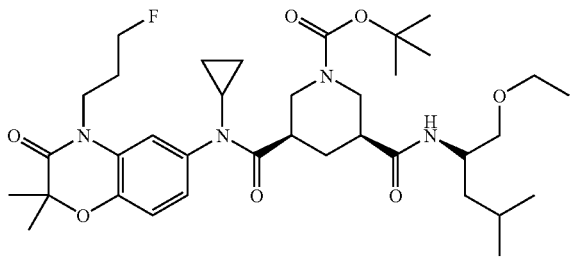

Intermediate 340.1 is synthesized by condensation of intermediate 340.2 (60 mg, 0.25 mmol) with intermediate 292.3 (85 mg, 0.21 mmol) analogously to the preparation of intermediate 19.1. White amorphous material, ES-MS: M+H=675: $_Ct_{Ret}$=4.24 min.
Intermediate 340.2

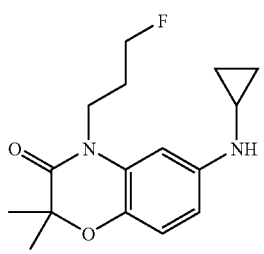

Intermediate 340.2 is synthesized by a alkylation of intermediate 190.2, 6-cyclopropylamino-2,2-dimethyl-4H-benzo [1,4]oxazin-3-one (465 mg, 2 mmol) with 3-fluoro-1-tosyloxypropane (557 mg, 2.64 mmol) analogously to the preparation of intermediate 59.2. Brown solid, ES-MS: M+H=293: $_Ct_{Ret}$=2.93 min.

Example 341

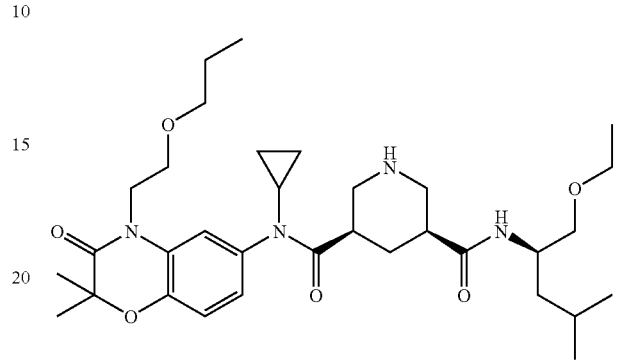

Example 342 is synthesized by deprotection of intermediate 341.1 analogously to the preparation of example 19 ES-MS: M+H=601: $_Ct_{Ret}$=3.38 min
Intermediate 341.1

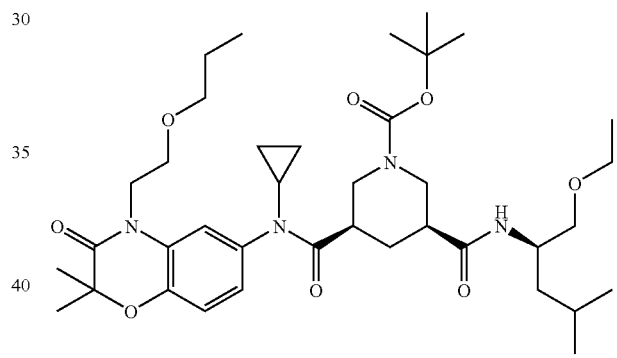

Intermediate 341.1 is synthesized by condensation of Intermediate 292.3 (108 mg, 0.27 mmol) with Intermediate 341.2 (98 mg, 0.28 mmol) analogously to the preparation of intermediate 19.1. White amorphous material, ES-MS: M+H=701: $_Bt_{Ret}$=2.27 min.
Intermediate 341.2

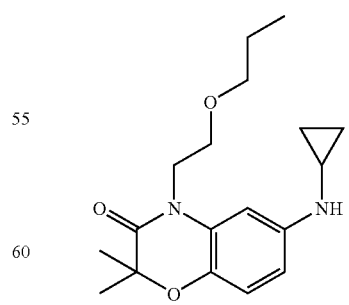

Intermediate 341.2 is synthesized by alkylation of intermediate 190.2, 6-cyclopropylamino-2,2-dimethyl-4H-benzo[1, 4]oxazin-3-one (500 mg, 2.15 mmol) with NaH (104 mg of 60 wt % in mineral oil, 2.58 mmol) and β-propoxyethyl iodide (505 mg, 2.37 mmol, JP2001011072) analogously to the preparation of intermediate 150.2. White amorphous material, ES-MS: M+H=319: $_B t_{Ret}$=1.88 min.

Example 342

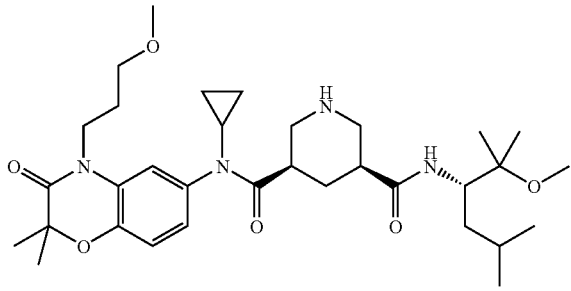

Example 342 is synthesized by deprotection of intermediate 342.1 analogously to the preparation of example 19. White material: M+H=601: $_C t_{Ret}$=3.18 min.

Intermediate 342.1

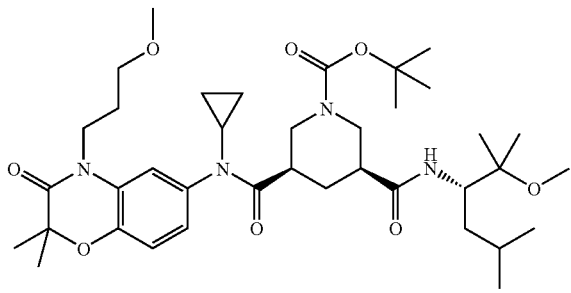

Intermediate 342.1 is synthesized by condensation of Intermediate 108.2 (140 mg, 0.25 mmol) and Intermediate 342.2 hydrochloride (54 mg, 0.28 mmol) analogously to the preparation of Intermediate 32.3. ES-MS: M+H=701: $_C t_{Ret}$=4.25 min Intermediate 342.2

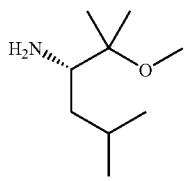

Intermediate 342.2 is synthesized by deprotection of Intermediate 342.3 (590 mg, 1.74 mmol) analogously to the preparation of Intermediate 337.2 ES-MS: M+H=160: $_B t_{Ret}$=1.38 min Intermediate 342.3

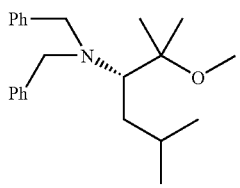

Intermediate 342.3 is synthesized by alkylation of Intermediate 342.4 (182.4 mg, 0.56 mmol) analogously to the preparation of intermediate 289.3. White material: M+H=340: $_C t_{Ret}$=3.59 min Intermediate 342.4

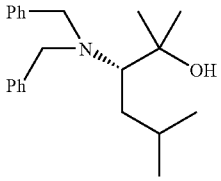

Intermediate 342.4 is synthesized by alkylation of (S)-2-dibenzylamino-4-methylpentanoic acid methyl ester (Eur. Pat. Appl. (1997), EP 767168 A2 19970409) (2.4 g, 7.25 mmol) analogously to the preparation of Intermediate 337.4. Colorless oil: M+H=326: $_C t_{Ret}$=3.23 min.

Example 343

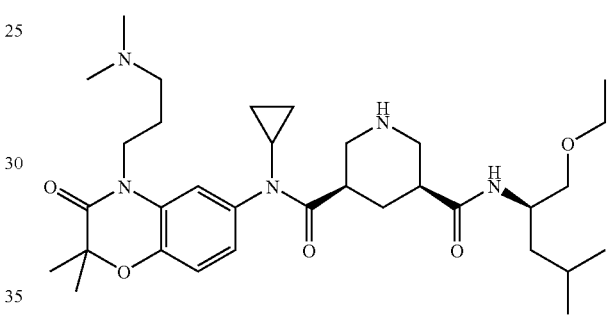

Example 343 is synthesized by deprotection of Intermediate 343.1 analogously to the preparation of example 19. White material: M+H=600: $_C t_{Ret}$=2.60 min.

Intermediate 343.1

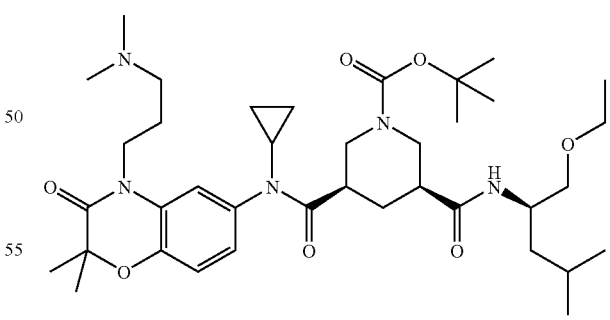

To a solution of Intermediate 343.2 (60 mg, 0.08 mmol) in DMF (3 mL) is added 2 M dimethylamine solution in THF (3 mL) at room temperature. After stirring for 6 h at 50° C., the reaction mixture is diluted with AcOEt (20 mL) and washed with H$_2$O, then dried over Na$_2$SO$_4$ and concentrated in vacuo. White amorphous, ES-MS: M+H=700: $_C t_{Ret}$=3.47 min.

Intermediate 343.2

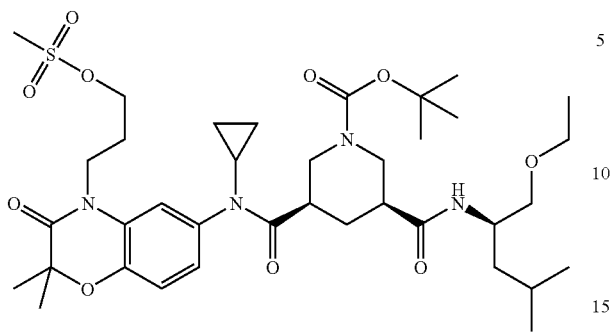

To a solution of Intermediate 277.1 (104 mg, 0.16 mmol) in CH$_2$Cl$_2$ (3 mL) are added Et$_3$N (27 μL, 0.19 mmol) and methanesulfonyl chloride (13 μL, 0.17 mmol) at room temperature. After stirring for 15 h at room temperature, the reaction mixture is diluted with CH$_2$Cl$_2$ (20 mL) and washed with H$_2$O, then dried over Na$_2$SO$_4$ and concentrated. White amorphous material, ES-MS: M+H=751: $_Ct_{Ret}$=4.08 min.

Example 348

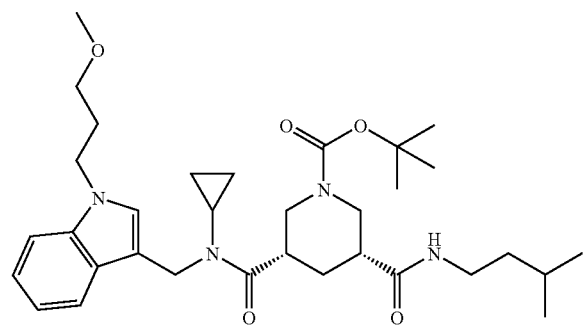

Example 348 is synthesized by deprotection of Intermediate 348.1 analogously to the preparation of example 1. ES-MS: M+H=483: $_At_{Ret}$=3.02 min.

Intermediate 348.1

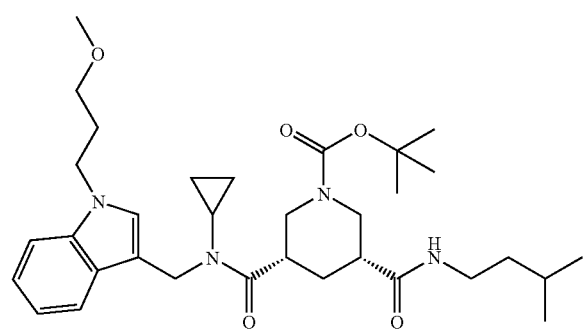

Intermediate 348.1 is synthesized by condensation of Intermediate 348.2 (72 mg, 0.14 mmol) with isoamylamine (18 mg, 0.21 mmol) analogously to the preparation of Intermediate 1.1. White amorphous material; ES-MS: [M+H]$^+$=583; HPLC: $_Ct_{Ret}$=4.13 min.

Intermediate 348.2

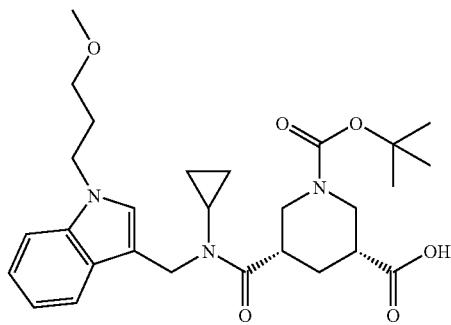

Intermediate 348.2 is synthesized by hydrolysis of Intermediate 348.3 (80 mg, 0.15 mmol) analogously to the preparation of Intermediate 13.2. White amorphous material; ES-MS: [M+H]$^+$=514; HPLC: $_Ct_{Ret}$=3.67 min.

Intermediate 348.3

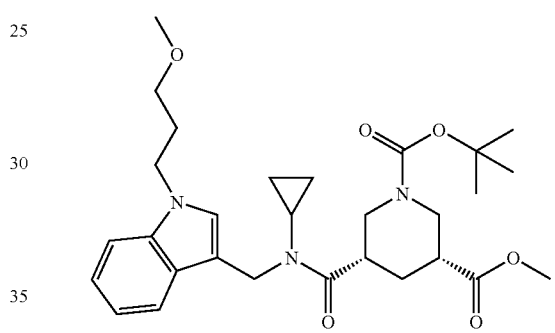

Intermediate 348.3 is synthesized by condensation of (3S, 5R)-Starting material-F (50 mg, mmol) with Intermediate 1.3 (54 mg, 0.21 mmol) analogously to the preparation of Intermediate 1.1. White amorphous material; ES-MS: [M]$^+$=528; HPLC: $_Ct_{Ret}$=4.14 min.

Examples 349-350 are synthesized by condensation and deprotection from (3S,5R)-Starting material-F analogously to the preparation of example 348.

Example 349

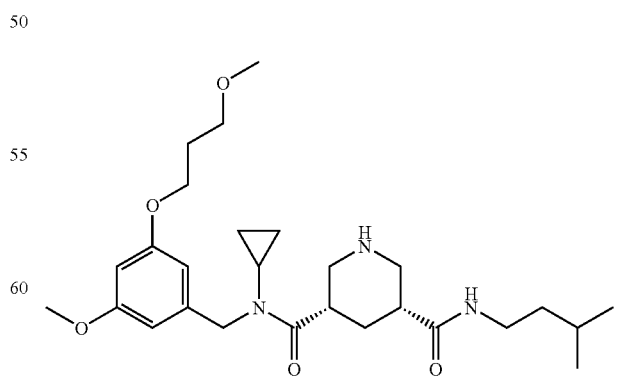

Example 349 is synthesized by deprotection of Intermediate 349.1 analogously to the preparation of example 19: ES-MS: M+H=490: $_Ct_{Ret}$=3.35 min.

Intermediate 349.1

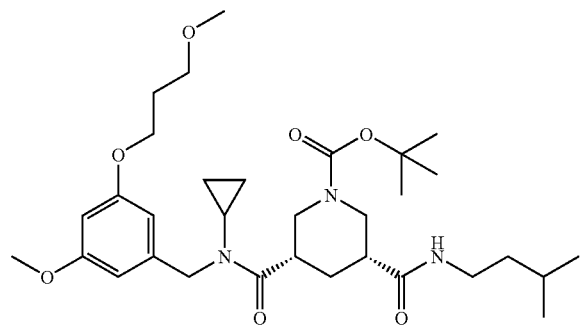

Intermediate 349.1 is synthesized by condensation of Intermediate 349.2 (112.5 mg, 0.33 mmol) with Intermediate 37.2 (150 mg, 0.57 mmol) analogously to the preparation of Intermediate 1.1. White amorphous material; ES-MS: [M+H]$^+$=590; HPLC: $_Bt_{Ret}$=2.12 minute.

Intermediate 349.2

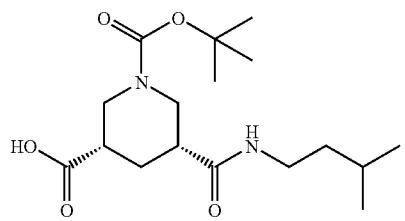

Intermediate 349.2 is synthesized by hydrolysis of Intermediate 349.3 (248.5 mg, 0.697 mmol) analogously to the preparation of Intermediate 13.2. White amorphous material; ES-MS: [M+H]$^+$=343; HPLC: $_Bt_{Ret}$=1.83 minute.

Intermediate 349.3

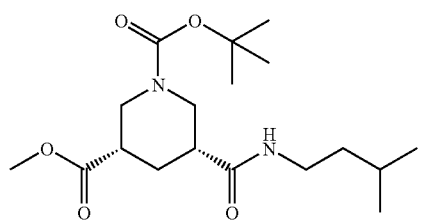

Intermediate 349.3 is synthesized by condensation of (3R, 5S)-Starting material-F (200 mg, 0.696 mmol) with isoamylamine (24 mg, 0.84 mmol) analogously to the preparation of Intermediate 1.1. White amorphous material; ES-MS: [M]$^+$ = 357; HPLC: $_At_{Ret}$=1.95 minute.

Example 350

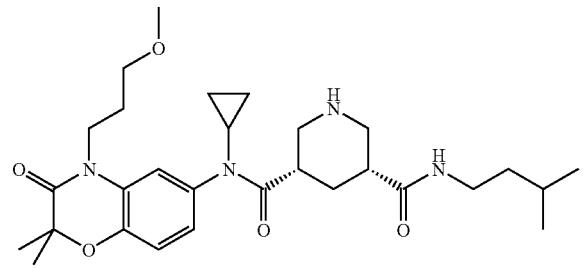

Example 350 is synthesized by deprotection of Intermediate 350.1 analogously to the preparation of example 19: ES-MS: M+H=501: $_Ct_{Ret}$=3.10 min.

Intermediate 350.1

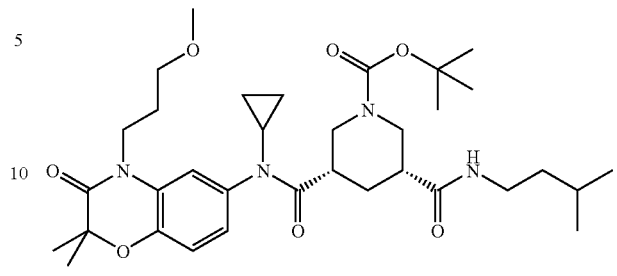

Intermediate 350.1 is synthesized by condensation of Intermediate 349.2 (122.5 mg, 0.36 mmol) with Intermediate 87.2 (99.4 mg, 0.36 mmol) analogously to the preparation of Intermediate 32.3. White amorphous material; ES-MS: [M+H]$^+$= 601; HPLC: $_Bt_{Ret}$=2.02 minute.

Example 351

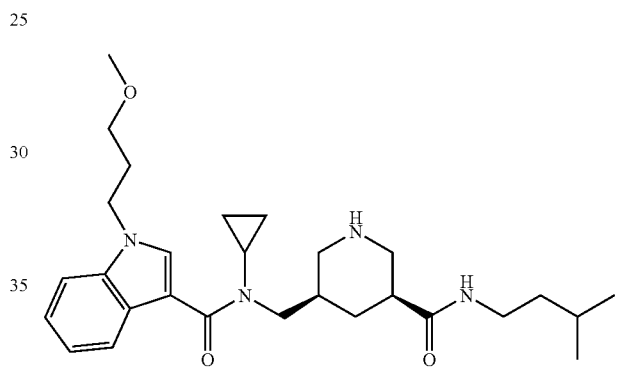

Example 351 is synthesized by deprotection of intermediate 351.1 analogously to the preparation of Example 1. ES-MS: M+H=482: $_Ct_{Ret}$=2.88 min.

Intermediate 351.1

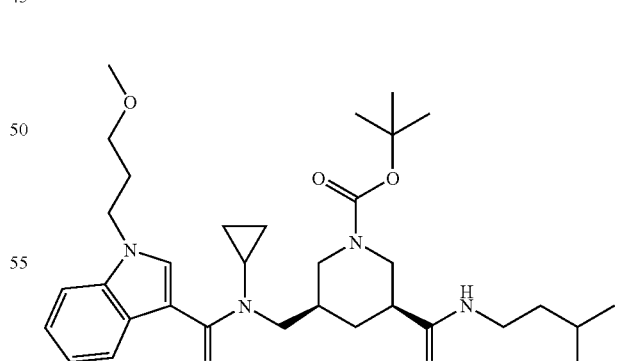

Intermediate 351.1 is synthesized by condensation of Intermediate 351.2 (121 mg, 0.33 mmol) with Intermediate 351.6 (100 mg, 0.47 mmol) analogously to the preparation of intermediate 32.3. White amorphous material, ES-MS: M+H=583: $_Ct_{Ret}$=3.93 min.

Intermediate 351.2

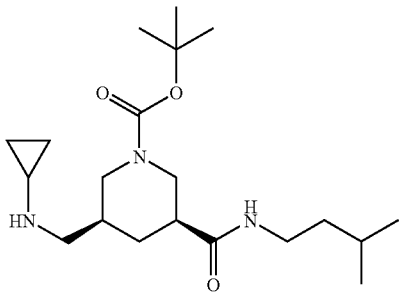

To a solution of intermediate 351.3 (141 mg, 0.43 mmol) in CH$_2$Cl$_2$ (5 mL) under N$_2$ at rt, AcOH (0.091 mL, 1.596 mmol), cyclopropylamine (0.11 mL, 1.57 mmol) and sodium triacethoxyborohydride (338 mg, 1.596 mmol) are added. The reaction mixture is stirred at rt overnight. Then, sat. NaHCO$_3$aq. is added to the resulting solution. The aqueous phase is extracted with CH$_2$Cl$_2$. The combined organic phase is dried over Na$_2$SO$_4$, concentrated under reduced pressure to afford the title compound. ES-MS: M+H=368: $ct_{Ret}$=2.65 min.

Intermediate 351.3

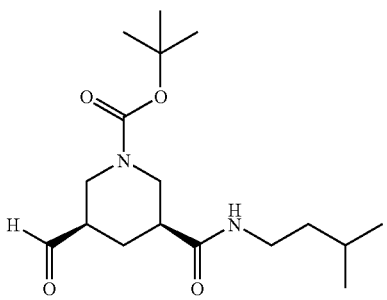

To a solution of intermediate 351.4 (436 mg, 1.33 mmol) in CH$_2$Cl$_2$ (5 mL) under N$_2$ at rt, Dess-Martin periodinane (670 mg, 1.58 mmol) is added. The reaction mixture is stirred at that temperature for 1 h and concentrated under reduced pressure to give crude product. The crude product is purified by silica gel chromatography to afford intermediate 351.3. ES-MS: M+H=327: $ct_{Ret}$=2.97 min.

Intermediate 351.4

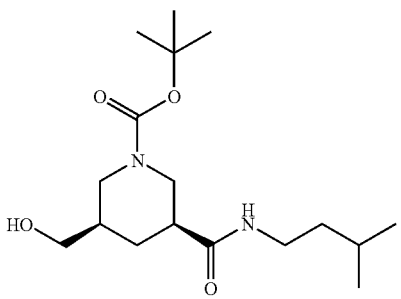

To a solution of intermediate 351.5 (1.42 g, 4.15 mmol) in THF (20 mL) under N$_2$ at 0° C., triethyl amine (0.78 mL, 5.6 mmol) and isobutyl chloroformate (0.61 mL, 4.68 mmol) are added. After stirring at the same temperature for 5 min, the reaction solution is filtered through Celite®, and concentrated under reduced pressure to afford the corresponding mixed anhydride.

To a solution of the anhydride in THF/MeOH (10 mL/10 mL) under N$_2$ at 0° C., NaBH$_4$ (324 mg, 8.58 mmol) is added. The reaction mixture is stirred at rt for 2 h. The reaction is quenched with sat. NH$_4$Cl aq and extracted with EtOAc. The combined organic phase is dried over Na$_2$SO$_4$ and concentrated under reduced pressure to give the crude product. The crude product is purified on silica gel to afford intermediate 351.4. ES-MS: M+H=329: $ct_{Ret}$=2.87 min.

Intermediate 351.5

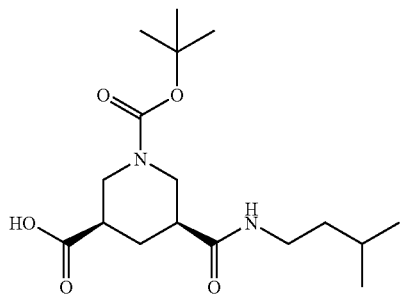

To a solution of triethylamine (7.1 mL, 0.051 mol) and 3-Methyl-butylamine (3 mL, 0.025 mol) in THF (49 mL) under N$_2$ at 0° C. is added starting material-E (1 g, 0.039 mol). After stirring at rt for 40 min, sat. KHSO$_4$ aq. is added. The aqueous phase is extracted with EtOAc and the combined organic phase is dried over Na$_2$SO$_4$. Concentration under reduced pressure gives intermediate 351.5. ES-MS: M+H=343: $ct_{Ret}$=3.00 min.

Intermediate 351.6

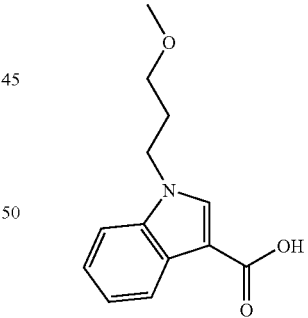

To a solution of intermediate 1.4 (1.5197 g, 0.069 mol) in $^t$BuOH (30 mL) and H$_2$O (15 mL) under N$_2$ at rt are added 2-methyl-2-butene (15.6 mL, 0.15 mol), NaH$_2$PO$_4$ (4.0 g, 0.033 mol) and NaClO$_2$ (2.88 g of 80%, 0.025 mmol). After stirring at that temperature overnight, brine is added. The aqueous phase is extracted with EtOAc, dried over Na$_2$SO$_4$ and concentrated under reduced pressure to give the crude product. The crude product is purified on silica gel chromatography to afford Intermediate 351.6. ES-MS: M+H=234: $ct_{Ret}$=2.61 min.

(rac)-trans-Starting material-G

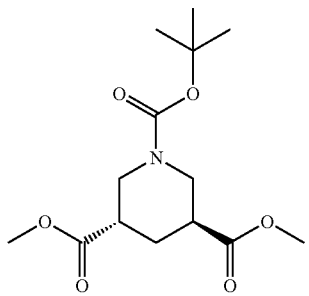

To a solution of starting material-B (4.97 g, 25 mmol) in CH$_2$Cl$_2$ (70 mL) under N$_2$, triethyl amine (5.2 mL, 37.5 mmol), Boc$_2$O (5.7 g, 26.1 mmol) and DMAP (116.6 mg, 0.95 mmol) are added at 0° C. The resulting solution is stirred at rt overnight. And then, sat.NH$_4$Cl aq. is added. The reaction mixture is extracted with CH$_2$Cl$_2$, dried over Na$_2$SO$_4$, concentared under reduced pressure and subjected to silica gel chromatography to give (rac)-trans-Starting material-G as a white syrup material. ES-MS: M+H-tBu=246; HPLC: $_At_{Ret}$=3.17 min for trans isomer, 3.30 min for cis isomer.
Ref. *Tetrahedron: Asymmetry* 2003, 14, 1541-1545.

(rac)-trans-Starting material-H

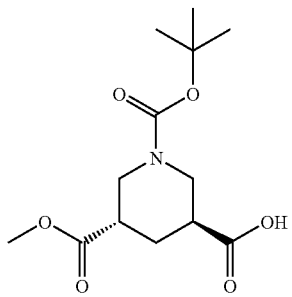

To a solution of (rac)-trans-Starting material-G (702.3 mg, 2.33 mmol) in MeOH (4.8 mL)-H$_2$O (1.2 mL) under N$_2$, Ba(OH)$_2$.8H$_2$O (367 mg, 1.16 mmol) is added at rt. After stirring at that temperature for 50 min, H$_2$O and sat. KHSO$_4$aq. is added. The reaction mixture is extracted with CH$_2$Cl$_2$, dried over Na$_2$SO$_4$, concentrated under reduced pressure and subjected to silica gel chromatography to give (rac)-trans-Starting material-H as a white syrup material. ES-MS: M+H-tBu=232; HPLC: $_At_{Ret}$=2.50 min for trans isomer.
Ref. *Aust., J. Chem.* 1986, 39, 2061

Example 352

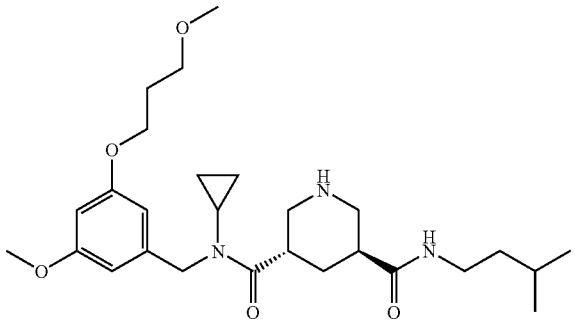

Example 352 is synthesized by deprotection of Intermediate 352.1 analogously to the preparation of example 1. White amorphous material; ES-MS: M+H=490; HPLC: $_At_{Ret}$=2.88 min.

Intermediate 352.1

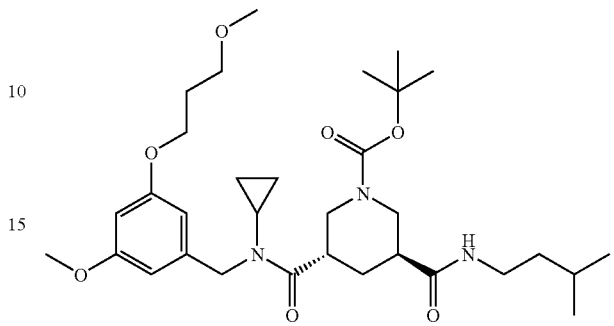

Intermediate 352.1 is synthesized by condensation of Intermediate 352.2 (117.4 mg, 0.34 mmol) and intermediate 37.2 (90.2 mg, 0.34 mmol) analogously to the preparation of Intermediate 1.1. White amorphous material; ES-MS: M+H=590; HPLC: $_At_{Ret}$=4.18 min.

Intermediate 352.2

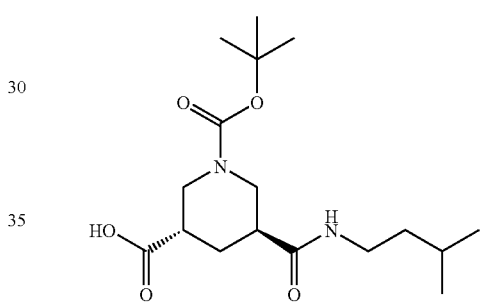

To a solution of intermediate 352.3 (505.0 mg, 1.42 mmol) in THF (8.5 mL), 1 N NaOH aq. is added at rt. After stirring at that temperature for 4 h, citric acid is added at 0° C. The organic phase is extracted with Et$_2$O, dried over Na$_2$SO$_4$ and concentrated under reduced pressure to give intermediate 352.2. White amorphous material; ES-MS: M+H=342; HPLC: $_Ct_{Ret}$=3.00 min for trans-isomer, 3.09 min for cis-isomer.

Intermediate 352.3

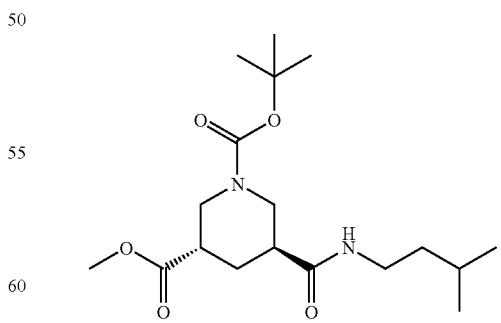

Intermediate 173.3 is synthesized by condensation of (rac)-trans-Starting material-H (2.5 g, 8.7 mmol) and 3-methyl-butylamine (1.2 mL, 10.44 mmol) analogously to the preparation of Intermediate 1.1. White amorphous material; ES-MS: M+H=356; HPLC: $_Bt_{Ret}$=1.82 min.

Example 353

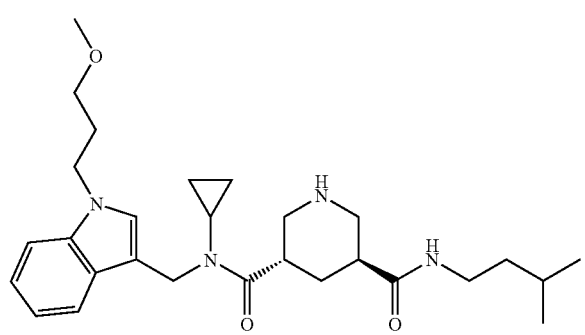

Example 353 is synthesized by deprotection of Intermediate 353.1 analogously to the preparation of example 1. White amorphous material; ES-MS: M+H=483; HPLC: $_A t_{Ret}$=2.97 min.

Intermediate 353.1

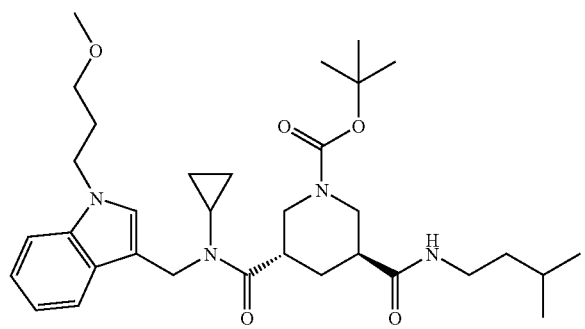

Intermediate 353.1 is synthesized by condensation of Intermediate 353.2 (71.3 mg, 0.21 mmol) and Intermediate 1.3 (53.7 mg, 0.21 mmol) analogously to the preparation of Intermediate 1.1. White amorphous material; ES-MS: M+H=583; HPLC: $_A t_{Ret}$=4.34 min.

Example 354

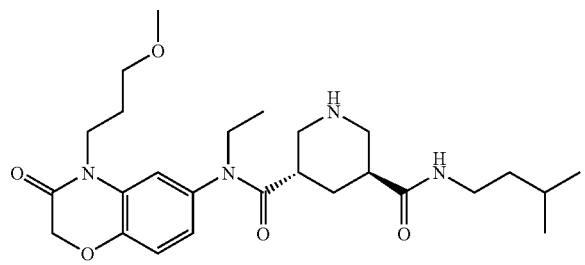

Example 354 is synthesized by deprotection of Intermediate 354.1 analogously to the preparation of example 1. White amorphous material; ES-MS: M+H=489; HPLC: $_A t_{Ret}$=2.54 min.

Intermediate 354.1

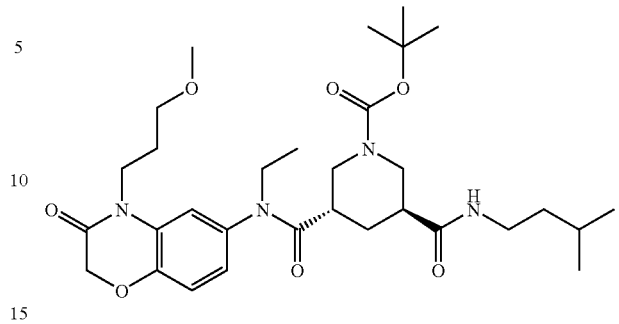

Intermediate 354.1 is synthesized by condensation of intermediate 352.2 (96.5 mg, 0.28 mmol) and 6-ethylamino-4-(3-methoxypropyl)-4H-benzo[1,4]oxazin-3-one (74 mg, 0.28 mmol) analogously to the preparation of Intermediate 59.1. White amorphous material; ES-MS: M+H=589; HPLC: $_A t_{Ret}$=3.67 min.

Example 355

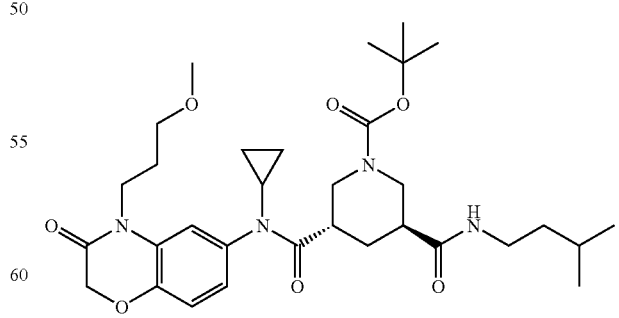

Example 355 is synthesized by deprotection of Intermediate 355.1 analogously to the preparation of example 1. White amorphous material; ES-MS: M+H=501; HPLC: $_A t_{Ret}$=2.54 min.

Intermediate 355.1

Intermediate 355.1 is synthesized by condensation of Intermediate 352.2 (59.2 mg, 0.18 mmol) and intermediate 19.3 (49.1 mg, 0.18 mmol) analogously to the preparation of Intermediate 59.1. White amorphous material; ES-MS: M+H=601; HPLC: $_A t_{Ret}$=3.68 min.

Example 356

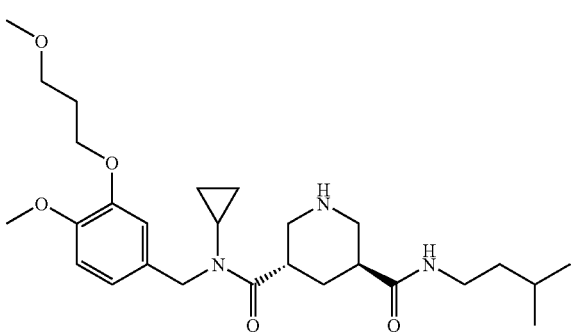

Example 356 is synthesized by deprotection of Intermediate 356.1 analogously to the preparation of example 1. White colorless oil; ES-MS: [M+H]$^+$=490; HPLC: $_At_{Ret}$=2.68 min.

Intermediate 356.1

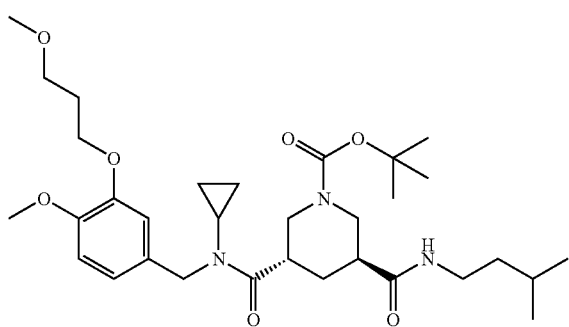

Intermediate 356.1 is synthesized by condensation of Intermediate 352.2 (60 mg, 0.226 mmol) with intermediate 101.2 (68.4 mg, 0.20 mmol) analogously to the preparation of Intermediate 1.1. White amorphous material; ES-MS: [M+H]$^+$=590; HPLC: $_Ct_{Ret}$=4.10 min.

Example 357

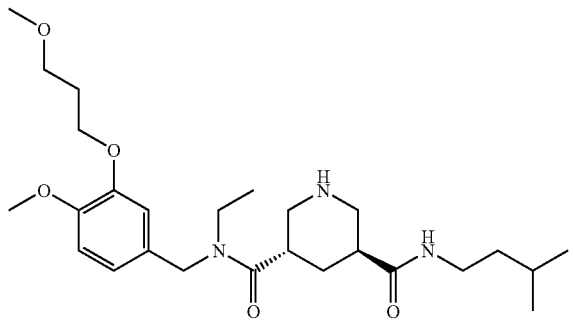

Example 357 is synthesized by deprotection of Intermediate 357.1 analogously to the preparation of example 1. White colorless oil; ES-MS: [M+H]$^+$=4.78; HPLC: $_At_{Ret}$=2.67 min.

Intermediate 357.1

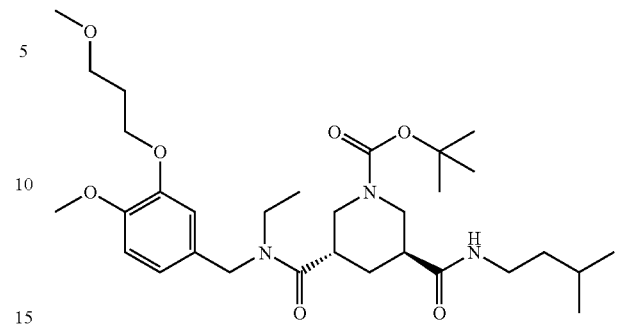

Intermediate 357.1 is synthesized by condensation of Intermediate 352.2 (36.6 mg, 0.144 mmol) with intermediate 58.2 (49.47 mg, 0.144 mmol) analogously to the preparation of Intermediate 1.1. White amorphous material; ES-MS: [M+H]$^+$=578; HPLC: $_At_{Ret}$=3.82 min.

Example 358

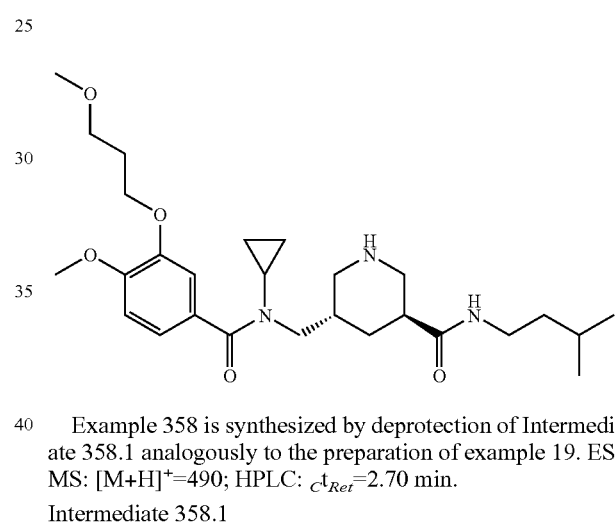

Example 358 is synthesized by deprotection of Intermediate 358.1 analogously to the preparation of example 19. ES-MS: [M+H]$^+$=490; HPLC: $_Ct_{Ret}$=2.70 min.

Intermediate 358.1

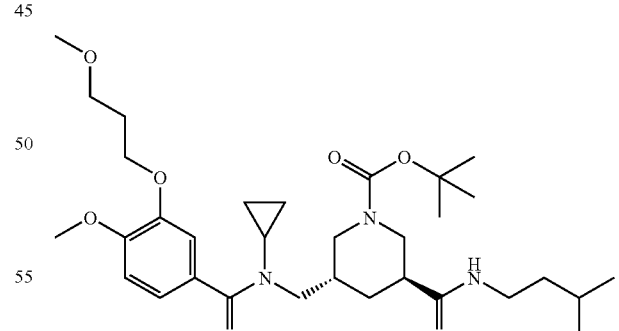

A mixture of intermediate 58.4 (49 mg, 0.22 mmol) and SOCl$_2$ (1.0 mL) in CH$_2$Cl$_2$ (1.0 mL) is stirred at 50° C. for 3 h. After the mixture is concentrated in vacuo, the resulting acid chloride is treated with intermediate 358.2 (53 mg, 0.14 mmol) and Et$_3$N (0.030 mL, 0.22 mmol) in CH$_2$Cl$_2$ (2.0 mL) at 0° C. for 1 h. After the mixture is concentrated in vacuo, the residue is purified by silica gel column chromatography to give intermediate 358.1: white amorphous material; ES-MS: [M+H]$^+$=590; HPLC: $_Bt_{Ret}$=1.97 min.

Intermediate 358.2

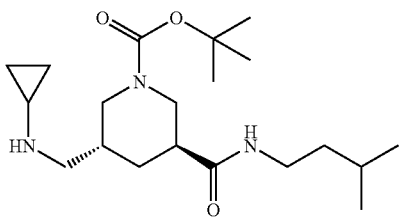

Intermediate 358.2 is synthesized by reductive alkylation of cyclopropylamine (0.5 mL, 7.15 mmol) with intermediate 358.3 (778 mg, 2.38 mmol) analogously to the preparation of Intermediate 1.3. White amorphous material; ES-MS: [M+H]$^+$=368; HPLC: $_C t_{Ret}$=2.67 min.

Intermediate 358.3

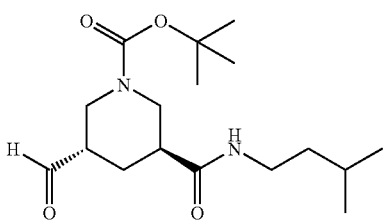

To the solution of intermediate 358.4 (926 mg, 2.82 mmol) in CH$_2$Cl$_2$ (14.1 mL) under N$_2$ at rt is added Dess-Martin periodinane (1.43 mg, 3.38 mmol). The reaction mixture is stirred at the same temperature for 1 h. After the reaction is quenched with sat NaHCO$_3$ aq and 5% Na$_2$SO$_3$ aq., under cooling with ice bath, the mixture is extracted with EtOAc. The combined organic phases are washed with water and brine, dried over Na$_2$SO$_4$ and concentrated under reduced pressure to afford Intermediate 358.3: white amorphous material, ES-MS: M+H=288: $_A t_{Ret}$=3.65 min.

Intermediate 358.4

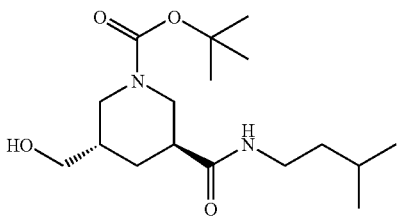

To a solution of intermediate 109.3 (1.06 g, 2.98 mmol) in THF (14 mL) under N$_2$ at rt is added LiBH$_4$ (129.8 mg, 5.96 mmol). The reaction mixture is stirred at the same temperature for 2 h. After the reaction is quenched by addition of H$_2$O, the mixture is extracted with CH$_2$Cl$_2$, dried over Na$_2$SO$_4$, filtered and concentrated under reduced pressure to afford Intermediate 358.4: white amorphous material, ES-MS: M+H=329: $_C t_{Ret}$=2.91 min.

Example 359

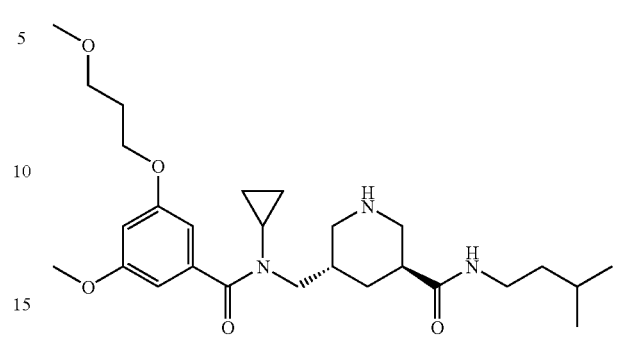

Example 359 is synthesized by deprotection of Intermediate 359.1 analogously to the preparation of example 19. ES-MS: [M+H]$^+$=490; HPLC: $_C t_{Ret}$=2.91 min.

Intermediate 359.1

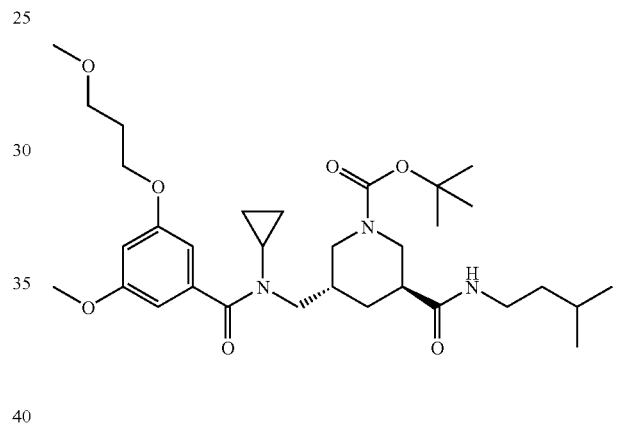

Intermediate 359.1 is synthesized by condensation of Intermediate 358.2 (56 mg, 0.15 mmol) with 3-methoxy-5-(3-methoxypropoxy)-benzoic acid (prepared by hydrolysis of intermediate 37.5) analogously to the preparation of Intermediate 358.1. White amorphous material; ES-MS: [M+H]$^+$=590; HPLC: $_C t_{Ret}$=4.03 min.

Example 360

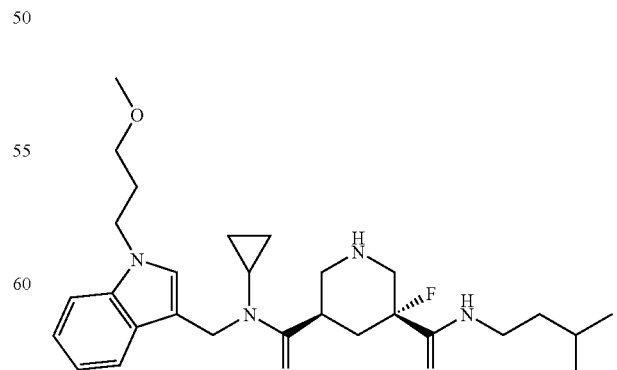

Example 360 is synthesized by deprotection of intermediate 360.1 analogously to the preparation of Example 1. ES-MS: M+H=501: $_C t_{Ret}$=3.19 min.

Example 361

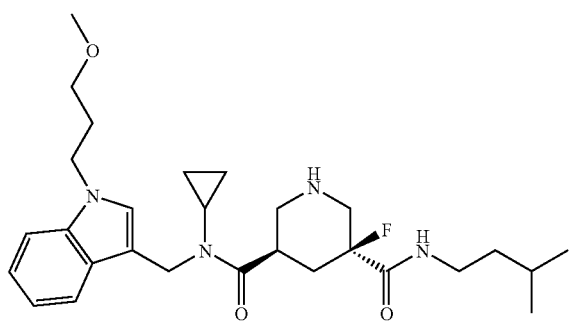

Example 361 is synthesized by deprotection of intermediate 361.1 analogously to the preparation of Example 1. ES-MS: M+H=501: $_A t_{Ret}$=3.00 min.

Intermediate 361.1

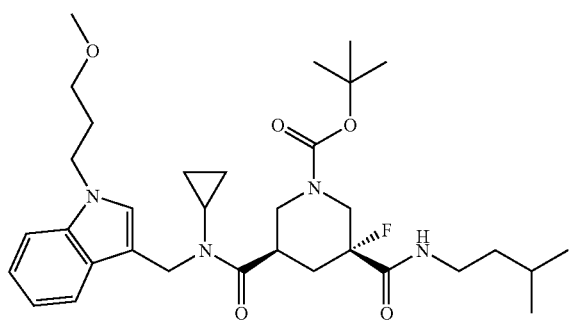

Intermediate 361.1 is synthesized by condensation of Intermediate 361.2 (121.7 mg, 0.229 mmol) with 3-methyl-butylamine (0.027 mL, 0.23 mmol) analogously to the preparation of intermediate 32.3. White amorphous material, ES-MS: M+H=601: $_A t_{Ret}$=4.74 min.

Intermediate 361.1

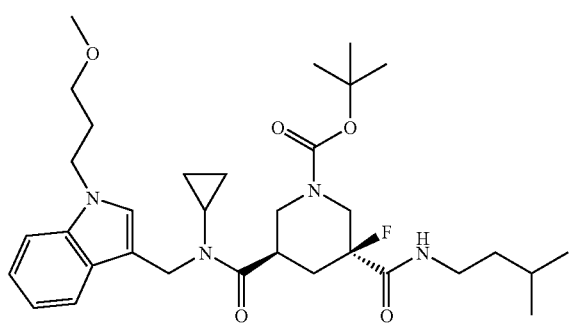

Intermediate 361.1 is synthesized by condensation of Intermediate 361.2 (180.8 mg, 0.34 mmol) with 3-methyl-butylamine (0.039 mL, 0.34 mmol) analogously to the preparation of intermediate 32.3. White amorphous material, ES-MS: M+H=601: $_B t_{Ret}$=2.19 min.

Intermediate 360.2

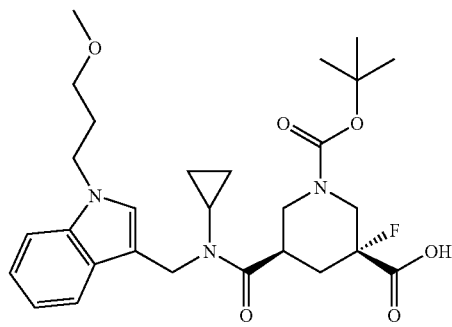

Intermediate 360.2 is synthesized by saponification of intermediate 360.3 analogously to the preparation of Intermediate 13.2. White amorphous material, ES-MS: M+H=532: $_A t_{Ret}$=3.65 min.

Intermediate 361.2

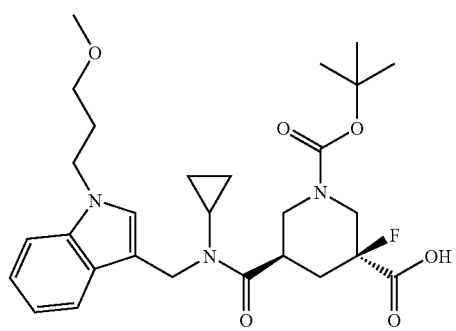

Intermediate 361.2 is synthesized by saponification of intermediate 361.3 analogously to the preparation of Intermediate 13.2. White amorphous material, ES-MS: M+H=532: $_A t_{Ret}$=3.68 min.

Intermediate 360.3 and 361.3

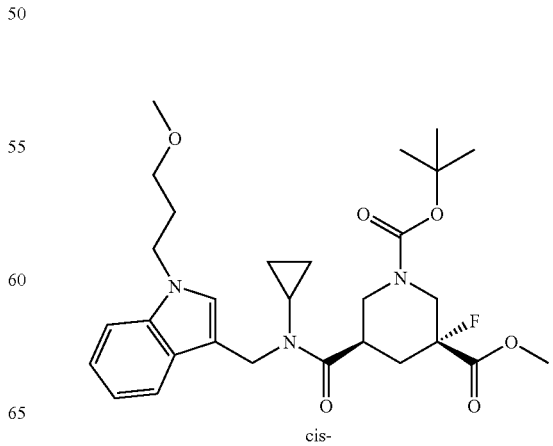

cis-

-continued

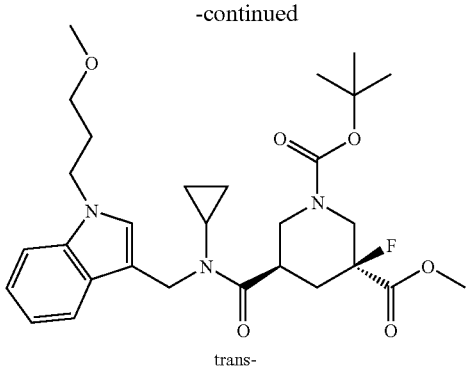

trans-

Intermediate 360.3 and 361.3 are synthesized by condensation of Intermediate 360.4 (266.8 mg, 0.87 mmol) with intermediate 1.3 (227 mL, 0.88 mmol) analogously to the preparation of intermediate 32.3. The corresponding cis-trans mixtures are separated by silica gel chromatography. cis-3,5-piperidine, intermediate 360.3: ES-MS: M+H=546: $_At_{Ret}$=4.27 min. trans-3,5-piperidine, intermediate 361.3: ES-MS: M+H=546: $_At_{Ret}$=4.25 min.

Intermediate 360.4

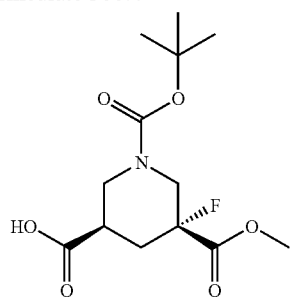

To a solution of (rac)-Piperidine-1,3,5-tricarboxylic acid 1-tert-butyl ester 3-methyl ester (214.2 mg, 0.74 mmol) in THF (20 mL) under N$_2$ at –78° C. is slowly added LDA (0.89 mL of 2 M in THF/heptane/2-ethylbenzene, 1.78 mmol). After stirring at the same temperature for 30 min, the reaction temperature is allowed to rise to 0° C. The solution is stirred at 0° C. for 15 min, then the reaction mixture is cooled to –78° C. N-fluorobenzene sulfonamide (682.8 mg, 2.16 mmol) is added to the solution. The resulting solution is stirred at rt overnight. The reaction is quenched with sat. NH$_4$Cl aq. and sat. KHSO$_4$ aq. The aqueous phase is extracted with EtOAc, the organic phase is dried over Na$_2$SO$_4$, filtered, and concentrated under reduced pressure to give the crude product. The crude product is purified by silica gel chromatography to afford intermediate 360.4 as a cis-trans 3,5-piperidine mixture. ES-MS: M+H-$^t$Bu=251: $_At_{Ret}$=2.64, 2.78 min Example 362

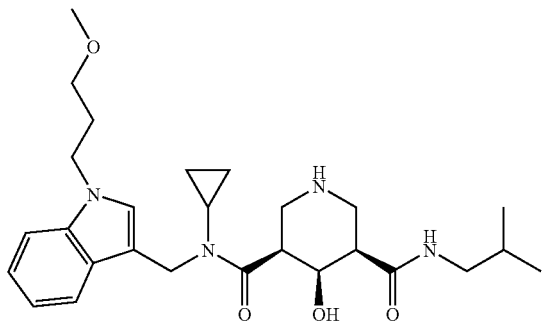

Example 362 is synthesized by deprotection of intermediate 362.1 analogously to the preparation of Example 1. ES-MS: M+H=499: $_Bt_{Ret}$=1.79 min.

Intermediate 362.1

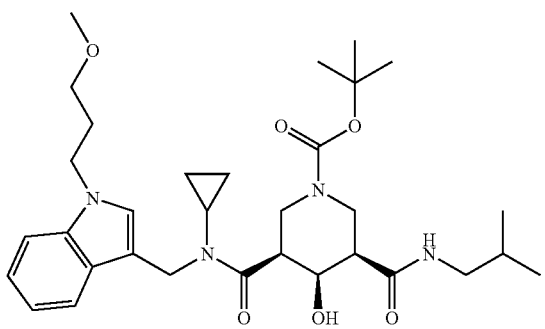

Intermediate 362.1 is synthesized by condensation of intermediate 362.2 (108 mg, 0.204 mmol) with isoamylamine (19.6 mg, 0.225 mmol) analogously to the preparation of intermediate 13.1. ES-MS: M+H=599: $_Bt_{Ret}$=2.16 min.

Intermediate 362.2

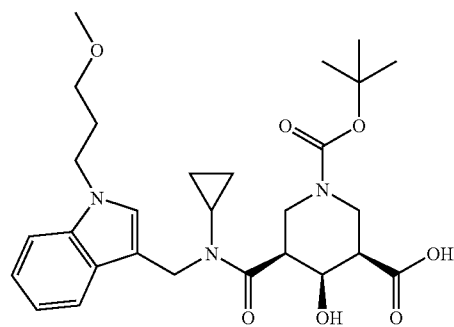

Intermediate 362.2 is synthesized by hydrolysis of intermediate 362.3 (136 mg, 0.25 mmol) analogously to the preparation of intermediate 13.2. ES-MS: M+H=530: $_Bt_{Ret}$=1.93 min.

Intermediate 362.3

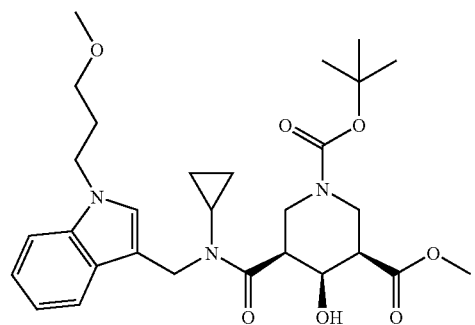

Intermediate 362.3 is synthesized by condensation of (3R,4R,5S)-4-hydroxypiperidine-1,3,5-tricarboxylic acid 1-tert-butyl ester 3-methyl ester (X. Liang, A. Lohse, M. Bols *J. Org. Chem.* 2000, 65, 7432.) (100 mg, 0.33 mmol) with intermediate 1.3 (94 mg, 0.363 mmol) analogously to the preparation of intermediate 13.3. ES-MS: M+H=544: $_Bt_{Ret}$=2.07 min.

Example 363

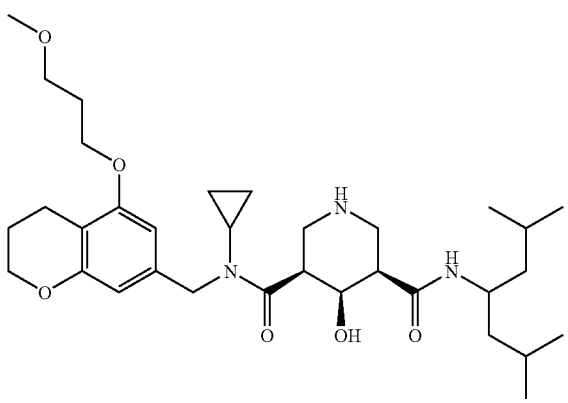

Example 363 is synthesized by deprotection of intermediate 363.1 analogously to the preparation of example 19: ES-MS: M+H=588: $ct_{Ret}$=3.48 min.

Intermediate 363.1

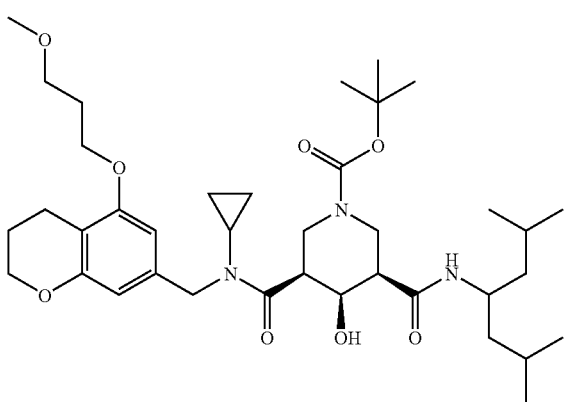

To a solution of intermediate 363.2 (170 mg, 0.3 mmol) and 1-isobutyl-3-methylbutylamine (65 mg, 0.36 mmol) in DMF (2 mL) are added EDCI.HCl (86 mg, 0.45 mmol), HOAt (61 mg, 0.45 mmol) at 0° C., then the mixture is stirred at room temperature. After 3 h, the reaction mixture is quenched with H$_2$O and extracted with EtOAc. The combined organic phase is successively washed with H$_2$O, then dried over Na$_2$SO$_4$ and concentrated under reduced pressure. The residue is purified by silica gel column chromatography to give intermediate 363.1. ES-MS: [M+H]$^+$=688; HPLC: $ct_{Ret}$=5.18 min.

Intermediate 363.2

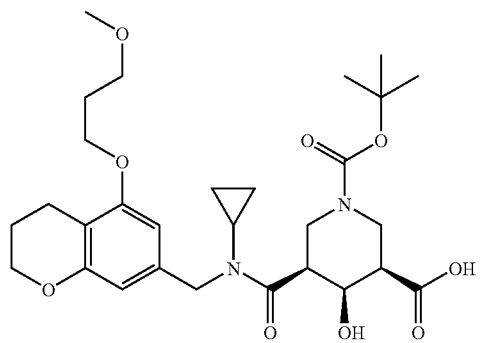

Intermediate 363.2 is synthesized by hydrolysis of intermediate 363.3 analogously to the preparation of intermediate 13.2: ES-MS: [M+H]$^+$=3.65; HPLC: $ct_{Ret}$=563 min.

Intermediate 363.3

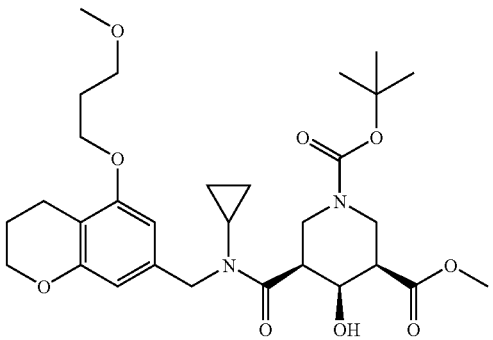

Intermediate 363.3 is synthesized by condensation of (3R,4R,5S)-4-hydroxypiperidine-1,3,5-tricarboxylic acid 1-tert-butyl ester 3-methyl ester (X. Liang, A. Lohse, M. Bols *J. Org. Chem.* 2000, 65, 7432.) (91 mg, 0.3 mmol) and cyclopropyl-[5-(3-methoxypropoxy)chroman-7-ylmethyl]amine (96 mg, 0.33 mmol) analogously to the preparation of Intermediate 363.1. White amorphous material; ES-MS: [M+H]$^+$=577; HPLC: $ct_{Ret}$=4.12 min.

Example 364

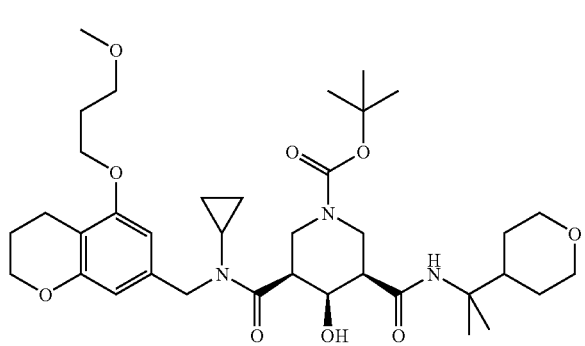

Example 364 is synthesized by deprotection of intermediate 364.1 analogously to the preparation of example 19 ES-MS: M+H=588: $ct_{Ret}$=2.99 min.

Intermediate 364.1

Intermediate 364.1 is synthesized by condensation of intermediate 363.2 (38 mg, 0.21 mmol) and 1-methyl-1-(tetrahydropyran-4-yl)-ethylamine (38 mg, 0.21 mmol) analogously to the preparation of intermediate 363.3: ES-MS: [M+H]+= 688; HPLC: $_ct_{Ret}$=4.24 min.

Example 365

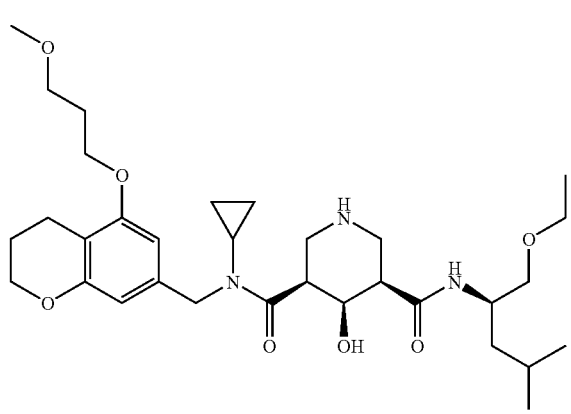

Example 365 is synthesized by deprotection of intermediate 365.1 analogously to the preparation of example 19: ES-MS: M+H=590: $_ct_{Ret}$=3.35 min.
Intermediate 365.1

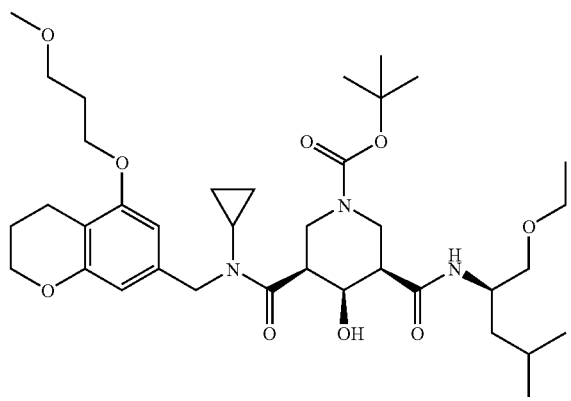

Intermediate 365.1 is synthesized by condensation of Intermediate 363.2 (120 mg, 0.2 mmol) and Intermediate 148.2 hydrochloride (37 mg, 0.2 mmol) analogously to the preparation of intermediate 363.3 in the presence of Et$_3$N (31 µL, 0.22 mmol): ES-MS: M+H=690: $_ct_{Ret}$=4.67 min.

Example 366

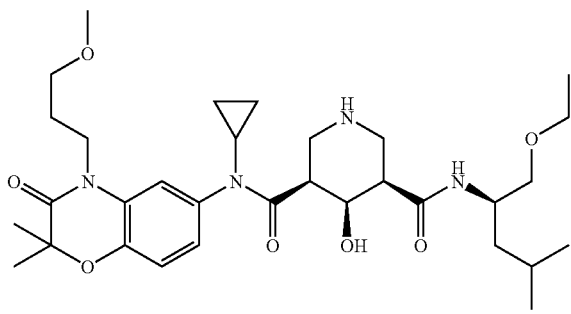

Example 366 is synthesized by deprotection of intermediate 366.1 analogously to the preparation of example 19: ES-MS: M+H=603: $_ct_{Ret}$=3.15 min.
Intermediate 366.1

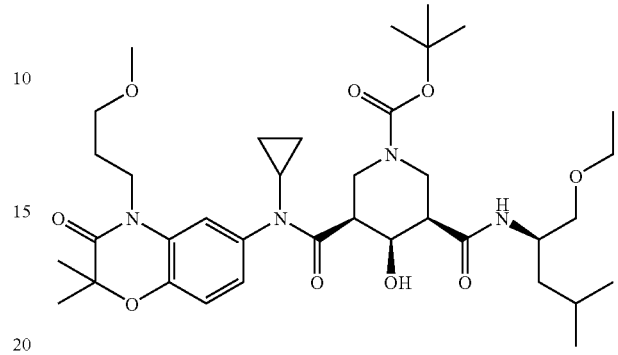

Intermediate 366.1 is synthesized by condensation of intermediate 366.2 (120 mg, 0.2 mmol) and intermediate 148.2 hydrochloride (25 mg, 0.13 mmol) analogously to the preparation of intermediate 363.3 in the presence of Et$_3$N (20 µL, 0.13 mmol): ES-MS: M+H=703: $_ct_{Ret}$=4.45 min.
Intermediate 366.2

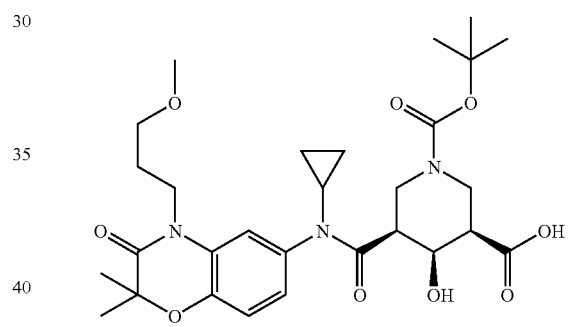

Intermediate 366.2 is synthesized by hydrolysis of intermediate 366.3 analogously to the preparation of intermediate 13.2: ES-MS: M+H=576: $_ct_{Ret}$=3.53 min.
Intermediate 366.3

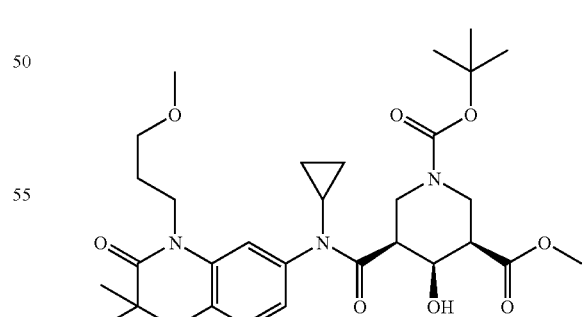

Intermediate 366.3 is synthesized by condensation of (3R, 4R,5S)-4-hydroxypiperidine-1,3,5-tricarboxylic acid 1-tert-butyl ester 3-methyl ester (X. Liang, A. Lohse, M. Bols *J. Org. Chem.* 2000, 65, 7432.) and Intermediate 87.2 analogously to the preparation of intermediate 19.1: ES-MS: M+H=590: $_ct_{Ret}$=3.86 min.

Example 367

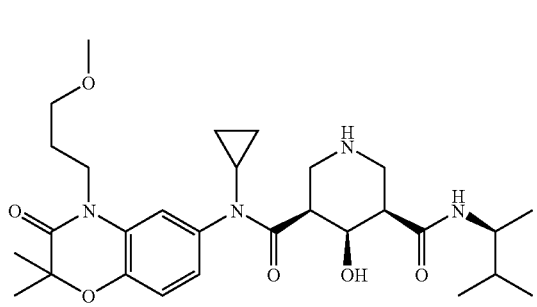

Example 367 is synthesized by deprotection of intermediate 367.1 analogously to the preparation of example 19: ES-MS: M+H=545: $_ct_{Ret}$=2.87 min.

Intermediate 367.1

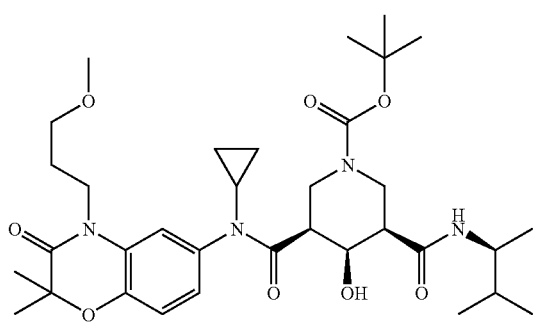

Intermediate 367.1 is synthesized by condensation of Intermediate 366.2 (60 mg, 0.1 mmol) and (S)-(+)-2-amino-3-methylbutane (14 μL, 0.12 mmol) analogously to the preparation of intermediate 363.3 in the presence of Et$_3$N (20 μL, 0.13 mmol): ES-MS: M+H=645: $_ct_{Ret}$=4.16 min.

Example 368

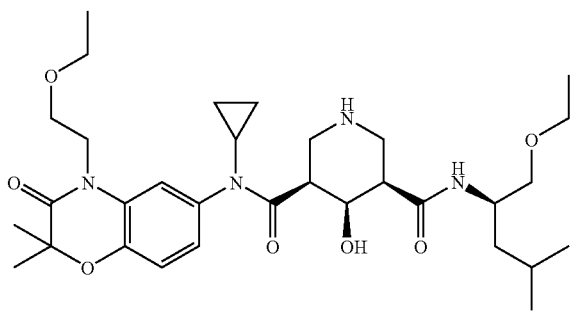

Example 368 is synthesized by deprotection of intermediate 368.1 analogously to the preparation of example 19: ES-MS: M+H=603: $_ct_{Ret}$=3.22 min.

Intermediate 368.1

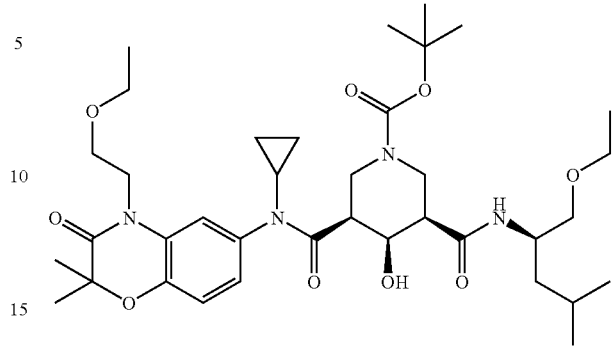

Intermediate 368.1 is synthesized by condensation of Intermediate 368.2 (100 mg, 0.18 mmol) and Intermediate 148.2 hydrochloride (35 mg, 0.19 mmol) analogously to the preparation of intermediate 363.3 in the presence of Et$_3$N (30 μL, 0.22 mmol): ES-MS: M+H=703: $_ct_{Ret}$=4.56 min.

Intermediate 368.2

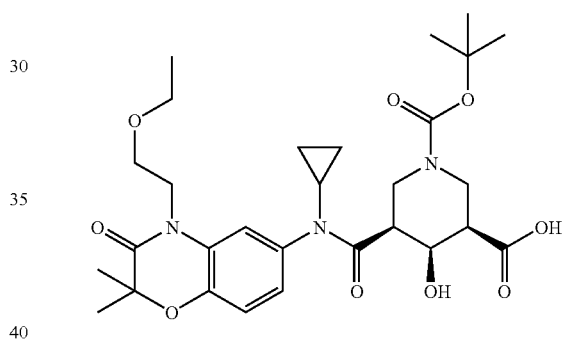

Intermediate 368.2 is synthesized by hydrolysis of intermediate 368.3 analogously to the preparation of Intermediate 13.2: ES-MS: M+H=576: $_ct_{Ret}$=3.66 min.

Intermediate 368.3

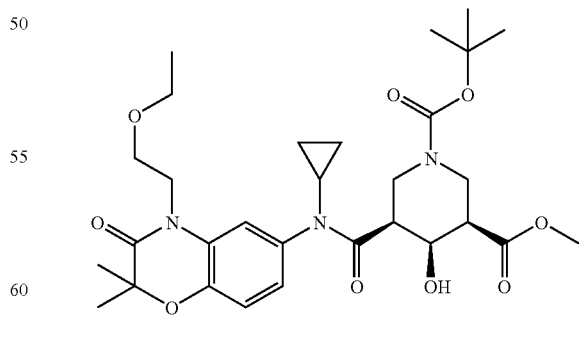

Intermediate 368.3 is synthesized by condensation of (3R, 4R,5S)-4-hydroxypiperidine-1,3,5-tricarboxylic acid 1-tert-butyl ester 3-methyl ester (X. Liang, A. Lohse, M. Bols *J. Org. Chem.* 2000, 65, 7432.) and Intermediate 150.2 analogously to the preparation of intermediate 19.1: ES-MS: M+H=590: $_ct_{Ret}$=4.03 min.

Example 369

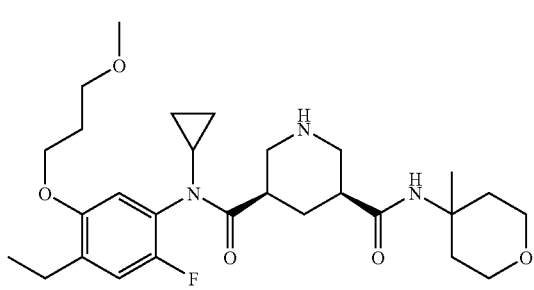

Example 369 is synthesized by deprotection of Intermediate 369.1 (60 mg, 0.1 mmol) analogously to the preparation of Example 123. Example 369. White amorphous material, ES-MS: M+H=520: $_C t_{Ret}$=3.17 min.

Intermediate 369.1

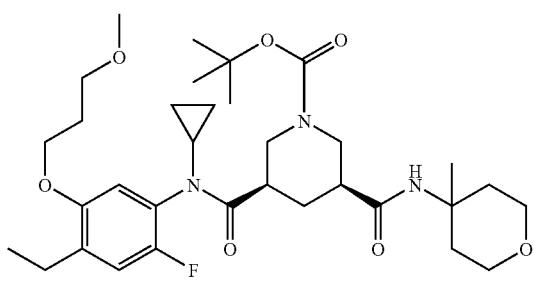

Intermediate 369.1 is synthesized by condensation of Intermediate 308.2 (100 mg, 0.19 mmol) and 4-methyl tetrahydropyran-4-yl amine (43 mg, 0.21 mmol) analogously to the preparation of Intermediate 1.1. Intermediate 369.1: colorless oil, ES-MS: M+H=620: $_A t_{Ret}$=3.85 min.

Example 370

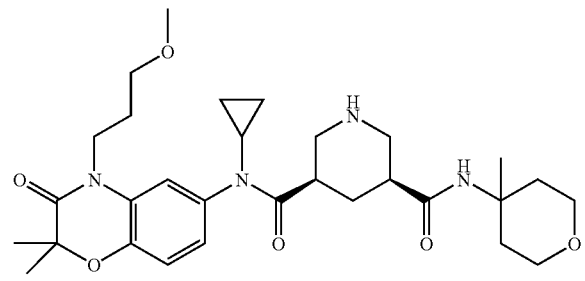

Example 370 is synthesized by deprotection of Intermediate 370.1 (62 mg, 0.09 mmol) analogously to the preparation of Example 123. White amorphous material, ES-MS: M+H=557: $_C t_{Ret}$=2.77 min.

Intermediate 370.1

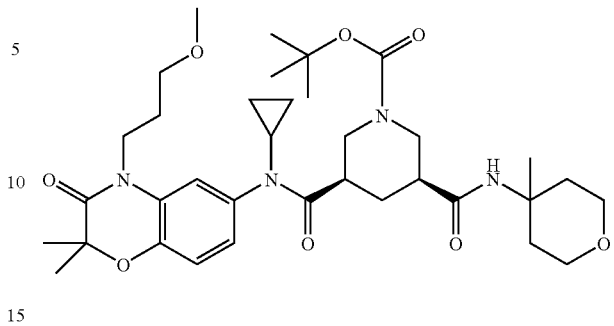

Intermediate 370.1 is synthesized by condensation of Intermediate 108.2 (100 mg, 0.18 mmol) and 4-methyl tetrahydropyran-4-yl amine (43 mg, 0.23 mmol) analogously to the preparation of Intermediate 1.1. Intermediate 370.1: colorless oil, ES-MS: M+H=657: $_A t_{Ret}$=3.32 min.

Example 371

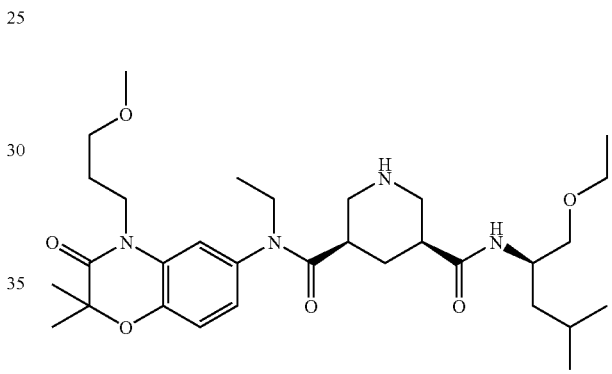

Example 371 is synthesized by deprotection of intermediate 371.1 analogously to the preparation of example 19. White material: M+H=575: $_A t_{Ret}$=3.33 min.

Intermediate 371.1

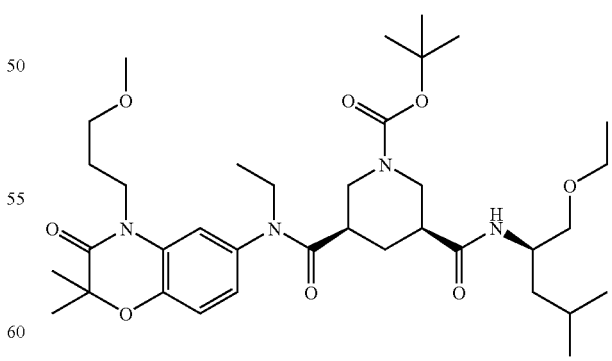

Intermediate 371.1 is synthesized by condensation of Intermediate 371.2 (100 mg, 0.18 mmol) and intermediate 148.2 hydrochloride (40 mg, 0.22 mmol) analogously to the preparation of Example 19 in the presence of Et₃N (31 µL, 0.22 mmol). Intermediate 371.1: ES-MS: M+H=675: $_A t_{Ret}$=4.51 min.

Intermediate 371.2

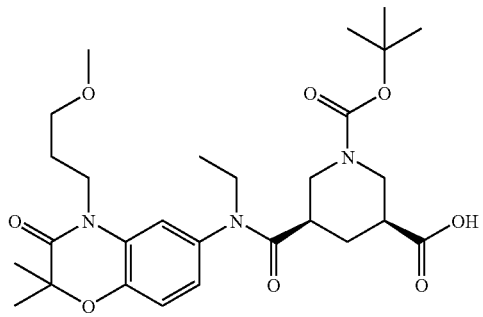

Intermediate 371.2 is synthesized by hydrolysis of intermediate 371.3 analogously to the preparation of Intermediate 13.2. ES-MS: M+H=548: $_c t_{Ret}$=3.25 min.

Intermediate 371.3

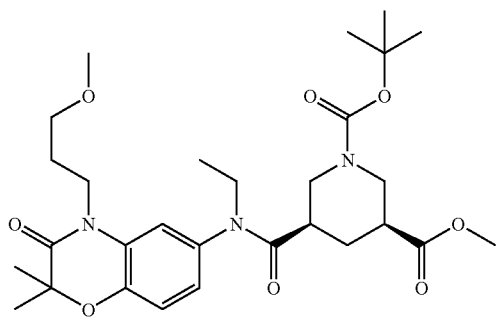

Intermediate 371.3 is synthesized by condensation of (3R, 5S)-starting material and Intermediate 127.2 analogously to the preparation of intermediate 19.1. Intermediate 371.3: ES-MS: M+H=562: $_A t_{Ret}$=4.16 min Example 372

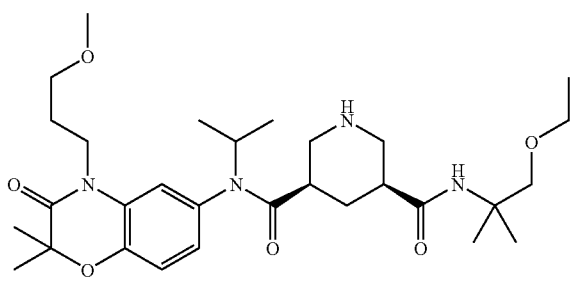

Example 372 is synthesized by deprotection of intermediate 372.1 analogously to the preparation of Example 19. ES-MS: M+H=561: $_c t_{Ret}$=3.28 min.

Intermediate 372.1

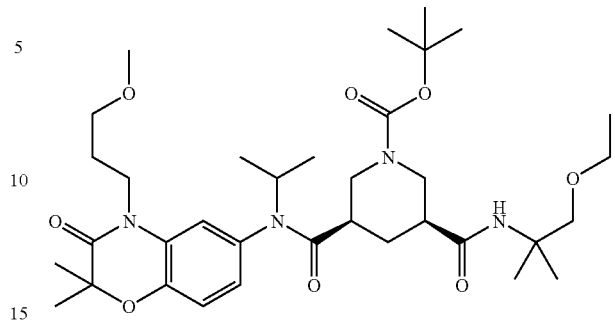

Intermediate 372.1 is synthesized by condensation of intermediate 207.2 (140 mg, 0.25 mmol) and Intermediate 246.2 (46 mg, 0.3 mmol) analogously to the preparation of example 19 in the presence of Et₃N (42 µL, 0.30 mmol). Intermediate 372.1: ES-MS: M+H=661: $_c t_{Ret}$=4.44 min.

Example 373

Soft Capsules 5000 soft gelatin capsules, each comprising as active ingredient 0.05 g of any one of the compounds of formula I mentioned in any one of the preceding Examples, are prepared as follows:

Composition

| Active ingredient | 250 g |
|---|---|
| Lauroglycol | 2 liters |

Preparation process: The pulverized active ingredient is suspended in Lauroglykol® (propylene glycol laurate, Gattefossé S. A., Saint Priest, France) and ground in a wet pulverizer to produce a particle size of about 1 to 3 µm. 0.419 g portions of the mixture are then introduced into soft gelatin capsules using a capsule-filling machine.

Example 375

Tablets Comprising Compounds of the Formula I

Tablets, comprising, as active ingredient, 100 mg of any one of the compounds of formula I in any one of the preceding Examples are prepared with the following composition, following standard procedures:

Composition

| Active Ingredient | 100 mg |
|---|---|
| crystalline lactose | 240 mg |
| Avicel | 80 mg |
| PVPPXL | 20 mg |
| Aerosil | 2 mg |
| ~~magnesium stearate~~ | ~~5 mg~~ |
| | 447 mg |

Manufacture: The active ingredient is mixed with the carrier materials and compressed by means of a tabletting machine (Korsch EKO, stamp diameter 10 mm).

Avicel® is microcrystalline cellulose (FMC, Philadelphia, USA). PVPPXL is polyvinylpolypyrrolidone, cross-linked (BASF, Germany). Aerosil® is silicon dioxide (Degussa, Germany).

The invention claimed is:
1. A compound of the formula I'

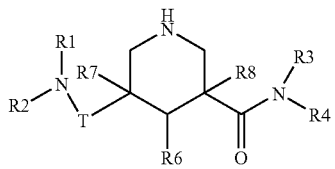

(I')

wherein
R1 is hydrogen, unsubstituted or substituted alkyl, unsubstituted or substituted alkenyl, unsubstituted or substituted alkynyl, unsubstituted or substituted aryl, unsubstituted or substituted heterocyclyl or unsubstituted or substituted cycloalkyl;
R2 is unsubstituted or substituted alkyl, unsubstituted or substituted alkenyl, unsubstituted or substituted alkynyl, unsubstituted or substituted aryl, unsubstituted or substituted heterocyclyl, unsubstituted or substituted cycloalkyl, or acyl;
R3 is hydrogen, unsubstituted or substituted aryl or unsubstituted or substituted alkyl;
R4 is unsubstituted or substituted alkyl, unsubstituted or substituted alkenyl, unsubstituted or substituted alkynyl, unsubstituted or substituted aryl, unsubstituted or substituted heterocyclyl, unsubstituted or substituted cycloalkyl, or acyl;
or R3 and R4 may form together a 3 to 7 membered nitrogen containing saturated hydrocarbon ring which can be unsubstituted or substituted;
R6 is hydrogen, halo, OH, unsubstituted alkyl or unsubstituted alkoxy;
R7 and R8 are independently of each other hydrogen or halo; and
T is methylene or carbonyl; wherein heterocyclyl is a mono or bicyclic heterocyclic moiety or a pharmaceutically acceptable salt thereof.

2. The compound according to claim 1 having a structure according to formula I

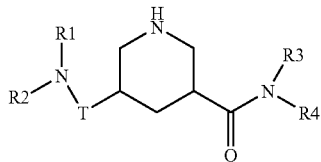

(I)

wherein
R1 is hydrogen, unsubstituted or substituted alkyl, unsubstituted or substituted alkenyl, unsubstituted or substituted alkynyl, unsubstituted or substituted aryl, unsubstituted or substituted heterocyclyl or unsubstituted or substituted cycloalkyl;
R2 is unsubstituted or substituted alkyl, unsubstituted or substituted alkenyl, unsubstituted or substituted alkynyl, unsubstituted or substituted aryl, unsubstituted or substituted heterocyclyl, unsubstituted or substituted cycloalkyl, or acyl;
R3 is hydrogen, unsubstituted or substituted aryl or unsubstituted or substituted alkyl;
R4 is unsubstituted or substituted alkyl, unsubstituted or substituted alkenyl, unsubstituted or substituted alkynyl, unsubstituted or substituted aryl, unsubstituted or substituted heterocyclyl, unsubstituted or substituted cycloalkyl, or acyl;
or R3 and R4 may form together a 3 to 7 membered nitrogen containing saturated hydrocarbon ring which can be unsubstituted or substituted; and
T is methylene or carbonyl; wherein heterocyclyl is a mono or bicyclic heterocyclic moiety or a pharmaceutically acceptable salt thereof.

3. The compound according to claim 1 wherein
R1 is hydrogen, unsubstituted or substituted alkyl or unsubstituted or substituted cycloalkyl;
R2 is unsubstituted or substituted alkyl, unsubstituted or substituted aryl or unsubstituted or substituted mono or bicyclic heterocyclyl;
R3 is hydrogen or unsubstituted or substituted alkyl,
R4 is unsubstituted or substituted alkyl, unsubstituted or substituted cycloalkyl or acyl;
or R3 and R4 may form together a 3 to 7 membered nitrogen containing saturated hydrocarbon ring which can be unsubstituted or substituted; and
T is carbonyl (C(=O));
or a pharmaceutically acceptable salt thereof.

4. The compound according to claim 1, wherein the moieties T-NR1R2 and NR3R4 are bound in cis configuration with regard to the central piperidine, or a pharmaceutically acceptable salt thereof.

5. The compound according to claim 1, wherein the moieties T-NR1R2 and NR3R4 are bound in trans configuration with regard to the central piperidine ring, or a pharmaceutically acceptable salt thereof.

6. The compound according to claim 4 which has the configuration shown in the following formula IA or I'A,

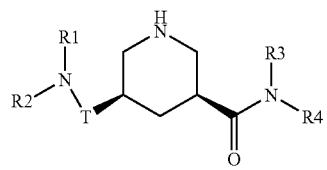

(IA)

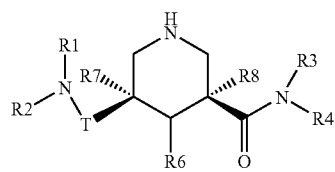

(I'A)

or a pharmaceutically acceptable salt thereof.

7. The compound according to claim 4 which has the configuration shown in the following formula IB or I'B,

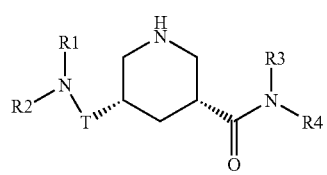

(IB)

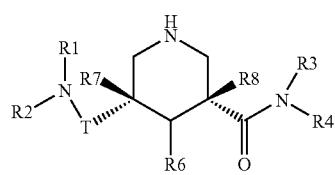

(I'B)

or a pharmaceutically acceptable salt thereof.

8. The compound according to claim 5 which has the configuration shown in the following formula IC or I'C,

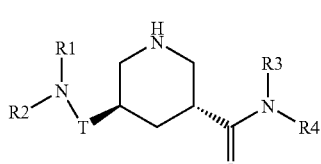
(IC)

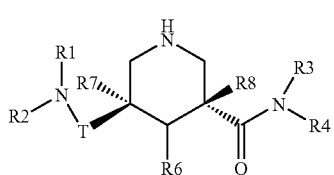
(I'C)

or a pharmaceutically acceptable salt thereof.

9. The compound of the formula I according to claim 5 which has the configuration shown in the following formula ID or I'D,

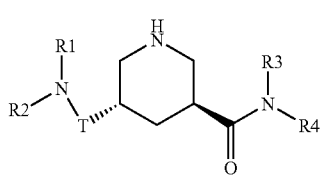
(ID)

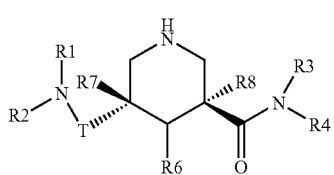
(I'D)

or a pharmaceutically acceptable salt thereof.

10. The compound according to claim 1, wherein
R1 is hydrogen, $C_1$-$C_7$-alkyl, $C_3$-$C_8$-cycloalkyl or phenyl-$C_1$-$C_7$-alkyl,
R2 is pyrimidyl, pyridyl, phenyl-$C_1$-$C_7$-alkyl, naphthyl-$C_1$-$C_7$-alkyl, pyridyl-$C_1$-$C_7$-alkyl, indolyl-$C_1$-$C_7$-alkyl, 1H-pyrrolo[2,3-b]pyridyl-$C_1$-$C_7$-alkyl, quinolinyl-$C_1$-$C_7$-alkyl, 1H-pyridin-2-onyl-$C_1$-$C_7$-alkyl, thiophenyl-$C_1$-$C_7$-alkyl, chromanyl-$C_1$-$C_7$-alkyl, 2,3-dihydrobenzofuranyl-$C_1$-$C_7$-alkyl, phenyl, 4H-benzo[1,4]oxazin-3-onyl, 3,4-dihydro-2H-benzo[1,4]oxazyl, 3,4-dihydro-1H-quinolin-2-onyl, or is acyl where each phenyl, naphthyl, pyridyl, pyrimidyl, indolyl, pyrrolo[2,3-b]pyridyl, quinolinyl 1H-pyridin-2-onyl, thiophenyl, chromanyl, 2,3-dihydrobenzofuranyl, 3,4-dihydro-1H-quinolin-2-onyl, 3,4-dihydro-2H-benzo[1,4]oxazyl or 4H-benzo[1,4]oxazin-3-on-yl mentioned for R2 so far as a substituent or part of a substituent is unsubstituted or substituted by one or more moieties independently selected from the group consisting of $C_1$-$C_7$-alkyl, $C_1$-$C_7$-alkoxy-$C_1$-$C_7$-alkyl, halo-$C_1$-$C_7$-alkyl, hydroxy-$C_1$-$C_7$-alkyl, phenyl, phenyl which is mono-, di- or tri-substituted with halo, hydroxy, $C_1$-$C_7$-alkoxy, and/or $C_1$-$C_7$-alkyl; halo, hydroxy, $C_1$-$C_7$-alkoxy, cyano, $C_1$-$C_7$-alkoxy-$C_1$-$C_7$-alkoxy-$C_1$-$C_7$-alkyl, $C_1$-$C_7$-alkoxy-$C_1$-$C_7$-alkylamino-$C_1$-$C_7$-alkyl, $C_1$-$C_7$-alkanoylamino, N-mono-$C_1$-$C_7$-alkoxy-$C_1$-$C_7$-alkylaminocarbonyl, $C_1$-$C_7$-alkanoyl, $C_1$-$C_7$-alkoxy-$C_1$-$C_7$-alkanoyl, amino-$C_1$-$C_7$-alkyl and $C_1$-$C_7$-alkoxy-$C_1$-$C_7$-alkoxy;
R3 is hydrogen, $C_1$-$C_7$-alkyl;
R4 is selected from the group consisting of:
branched $C_4$-$C_{10}$-alkyl which may be unsubstituted or substituted with one or more of the group consisting of:
unsubstituted or substituted heterocyclyl, each of which is unsubstituted or substituted; unsubstituted or substituted aryl; halo, hydroxy, $C_1$-$C_7$-alkoxy, halo-$C_1$-$C_7$-alkoxy, hydroxy-$C_1$-$C_7$-alkoxy, and N-mono- or N,N-di-($C_1$-$C_7$-alkyl)-aminocarbonyl; N-mono- or N,N-di-($C_1$-$C_7$-alkyl)-amino, aminocarbonyl, or cyano;
straight chain $C_1$-$C_7$-alkyl which may be bound to the terminal or non-terminal carbon and which may be unsubstituted or substituted with one or more of the group consisting of:
unsubstituted or substituted, heterocyclyl, each of which is unsubstituted or substituted;
unsubstituted or substituted aryl; unsubstituted or substituted $C_3$-$C_8$-cycloalkyl; halo, hydroxy, $C_1$-$C_7$-alkoxy, halo-$C_1$-$C_7$-alkoxy, hydroxy-$C_1$-$C_7$-alkoxy, N-mono- or N,N-di-($C_1$-$C_7$-alkyl)-amino, and N-mono- or N,N-di-($C_1$-$C_7$-alkyl)-aminocarbonyl;
unsubstituted or substituted $C_3$-$C_8$-cycloalkyl,
unsubstituted or substituted aryl,
unsubstituted or substituted heterocyclyl, or
acyl;
or R3 and R4 form together a pyrrolidine or piperidine ring that is unsubstituted or substituted by up to four moieties selected from $C_1$-$C_7$-alkyl, hydroxyl, halo, hydroxy-$C_1$-$C_7$-alkyl, halo-$C_1$-$C_7$-alkyl and cyano; and
T is carbonyl or methylene;
or a pharmaceutically acceptable salt thereof.

11. The compound according to claim 1, wherein R6 is OH, F, $C_1$-$C_4$-alkyl or $C_1$-$C_4$-alkoxy.

12. The compound according to claim 1, wherein R7 and R8 are independently of each other F.

13. The compound according to claim 1, wherein one of R7 and R8 is hydrogen and the other is F.

14. A pharmaceutical formulation, comprising:
the compound according to claim 1, or a pharmaceutically acceptable salt thereof and
at least one pharmaceutically acceptable carrier material.

15. A method of treating hypertension, comprising:
administering to a warm-blooded animal in need of such treatment a pharmaceutically effective amount of the compound according to claim 1 or a pharmaceutically acceptable salt thereof.

16. A process for the manufacture of the compound according to claim 1, or a pharmaceutically acceptable salt thereof, comprising:
reacting a compound of the formula II,

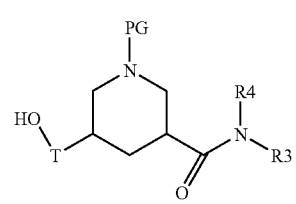
(II)

wherein T is methylene or carbonyl, PG is a protecting group, with a compound of the formula III,

R1-NH-R2 (III);

or
reacting a compound of the formula IV,

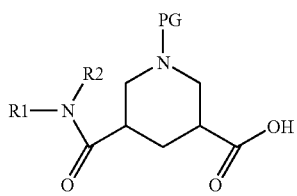
(IV)

wherein PG is a protecting group, with a compound of the formula V,

R3-NH-R4    (V);

and, if desired, subsequent to any one or more of the processes mentioned above converting an obtainable compound of the formula I or a protected form thereof into a different compound of the formula I, converting a salt of an obtainable compound of formula I into the free compound or a different salt, converting an obtainable free compound of formula I into a salt thereof, and/or separating an obtainable mixture of isomers of a compound of formula I into individual isomers;
where in any of the starting materials, in addition to specific protecting groups mentioned, further protecting groups may be present, and any protecting groups or bound resins are removed at an appropriate stage in order to obtain a corresponding compound of the formula I, or a salt thereof.

17. A process for the manufacture of a compound of formula VIIa or VIIb:

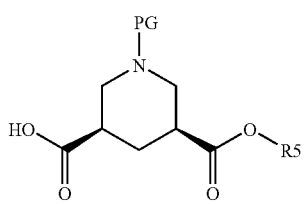
(VIIa)

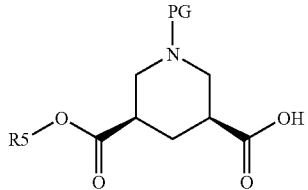
(VIIb)

wherein PG is a protecting group, with an alcohol R5OH, wherein R5 is unsubstituted or substituted alkyl or alkenyl, or a pharmaceutically acceptable salt thereof, comprising:
reacting a compound of the formula VI

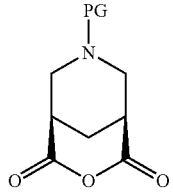
(VI)

wherein PG is as defined in formulae VIIa or VIIb, in the presence of a chiral amine catalyst.

18. The compound according to claim 1, wherein
R1 is $C_1$-$C_7$-alkyl or $C_3$-$C_8$-cycloalkyl;
R2 is pyrimidyl, pyridyl, phenyl-$C_1$-$C_7$-alkyl, naphthyl-$C_1$-$C_7$-alkyl, pyridyl-$C_1$-$C_7$-alkyl, indolyl-$C_1$-$C_7$-alkyl, 1H-pyrrolo[2,3-b]pyridyl-$C_1$-$C_7$-alkyl, quinolinyl-$C_1$-$C_7$-alkyl, 1H-pyridin-2-onyl-$C_1$-$C_7$-alkyl, thiophenyl-$C_1$-$C_7$-alkyl, chromanyl-$C_1$-$C_7$-alkyl, 2,3-dihydrobenzofuranyl-$C_1$-$C_7$-alkyl, phenyl, 4H-benzo[1,4]oxazin-3-onyl, 3,4-dihydro-2H-benzo[1,4]oxazyl, 3,4-dihydro-1H-quinolin-2-onyl, or is acyl such as phenylcarbonyl or indolylcarbonyl where each phenyl, naphthyl, pyridyl, pyrimidyl, indolyl, pyrrolo[2,3-b]pyridyl, quinolinyl 1H-pyridin-2-onyl, thiophenyl, chromanyl, 2,3-dihydrobenzofuranyl, 3,4-dihydro-1H-quinolin-2-onyl, 3,4-dihydro-2H-benzo[1,4]oxazyl or 4H-benzo[1,4]oxazin-3-on-yl mentioned for R2 so far as a substituent or part of a substituent is unsubstituted or substituted by one or more moieties independently selected from the group consisting of $C_1$-$C_7$-alkyl, $C_1$-$C_7$-alkoxy-$C_1$-$C_7$-alkyl, halo-$C_1$-$C_7$-alkyl, hydroxy-$C_1$-$C_7$-alkyl, phenyl, phenyl which is mono-, di- or tri-substituted with halo, hydroxy, $C_1$-$C_7$-alkoxy, and/or $C_1$-$C_7$-alkyl; halo, hydroxy, $C_1$-$C_7$-alkoxy, cyano, $C_1$-$C_7$-alkoxy-$C_1$-$C_7$-alkoxy-$C_1$-$C_7$-alkyl, $C_1$-$C_7$-alkoxy-$C_1$-$C_7$-alkylamino-$C_1$-$C_7$-alkyl, $C_1$-$C_7$-alkanoylamino, N-mono-$C_1$-$C_7$-alkoxy-$C_1$-$C_7$-alkylaminocarbonyl, $C_1$-$C_7$-alkanoyl, $C_1$-$C_7$-alkoxy-$C_1$-$C_7$-alkanoyl, amino-$C_1$-$C_7$-alkyl and $C_1$-$C_7$-alkoxy-$C_1$-$C_7$-alkoxy;
R3 is hydrogen, $C_1$-$C_7$-alkyl;
R4 is selected from the group consisting of:
branched $C_4$-$C_{10}$-alkyl which may be unsubstituted or substituted with one or more group consisting of:
unsubstituted pyrrolyl, furanyl, thienyl, thiazolyl, pyrazolyl, triazolyl, tetrazolyl, tetrahydropyranyl, pyridyl, or pyrimidinyl; unsubstituted phenyl; halo, hydroxy, $C_1$-$C_7$-alkoxy, halo-$C_1$-$C_7$-alkoxy, hydroxy-$C_1$-$C_7$-alkoxy, and N-mono- or N,N-di-($C_1$-$C_7$-alkyl)-aminocarbonyl; N-mono- or N,N-di-($C_1$-$C_7$-alkyl)-amino, aminocarbonyl, or cyano;
straight chain $C_1$-$C_7$-alkyl which may be bound to the terminal or non-terminal carbon and which may be unsubstituted or substituted with one or more, such as one or two of the group consisting of:
unsubstituted pyrazyl, isoxazolyl, morpholinyl, thiomorpholinyl, piperidinyl, piperazinyl, pyrrolidinyl, tetrahydrofuranyl, tetrahydropyranyl, tetrahydrothiophenyl, pyridyl, or pyrrolidin-2-onyl; unsubstituted phenyl; unsubstituted $C_3$-$C_8$-cycloalkyl; halo, hydroxy, $C_1$-$C_7$-alkoxy, halo-$C_1$-$C_7$-alkoxy, hydroxy-$C_1$-$C_7$-alkoxy, N-mono- or N,N-di-($C_1$-$C_7$-alkyl)-amino, and N-mono- or N,N-di-($C_1$-$C_7$-alkyl)-aminocarbonyl;
unsubstituted or substituted $C_3$-$C_8$-cycloalkyl, which is unsubstituted or substituted as described herein,
unsubstituted or substituted phenyl or indanyl, each of which is unsubstituted or substituted as described herein,
unsubstituted or substituted azepan-2-onyl, tetrahydropyranyl, 1H-pyridin-2-onyl, pyridyl, piperidinyl, piperazinyl or pyrrolidinyl, which is unsubstituted or substituted as described herein, or
(unsubstituted or substituted alkyl, unsubstituted or substituted aryl-$C_1$-$C_7$-alkyl, unsubstituted or substituted heterocyclyl-$C_1$-$C_7$-alkyl or unsubstituted or substituted cycloalkyl-$C_1$-$C_7$-alkyl)-sulfonyl;

or R3 and R4 form together a pyrrolidine or piperidine ring that is unsubstituted or substituted by up to four moieties selected from $C_1$-$C_7$-alkyl, hydroxyl, halo, hydroxy-$C_1$-$C_7$-alkyl, halo-$C_1$-$C_7$-alkyl and cyano; and T is carbonyl or methylene;

or a pharmaceutically acceptable salt thereof.

19. The compound according to claim 1 selected from the compounds of the formula:

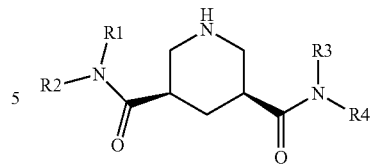

as represented in the following table:

| examples | R1 | R2 | R3 | R4 |
|---|---|---|---|---|
| 1 | cyclopropyl | 3-(indol-1-yl)propoxymethyl | H | isobutyl |
| 2 | cyclopropyl | 3-(indol-1-yl)propoxymethyl | H | neopentyl |
| 3 | cyclopropyl | 3-(indol-1-yl)propoxymethyl | H | isopentyl |
| 4 | cyclopropyl | 3-(indol-1-yl)propoxymethyl | H | benzyl |

-continued
| examples | R1 | R2 | R3 | R4 |
|---|---|---|---|---|
| 5 |  | 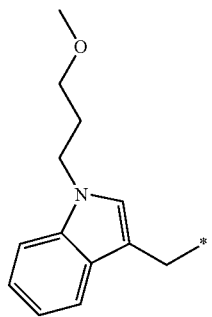 | H | 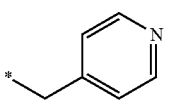 |
| 6 |  | 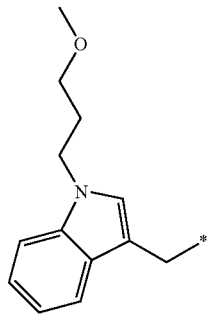 | H | 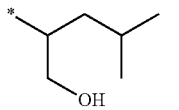 |
| 7 |  | 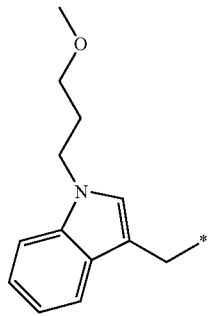 | H | 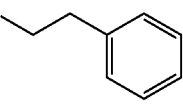 |
| 8 |  | 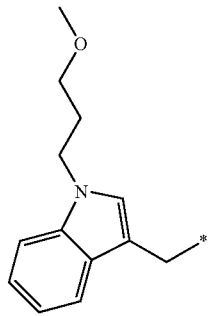 | Me | 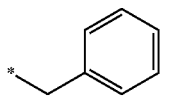 |
| 9 |  | 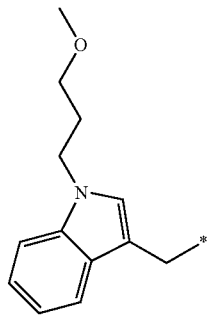 | Me | 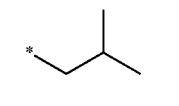 |

-continued
| examples | R1 | R2 | R3 | R4 |
|---|---|---|---|---|
| 10 | 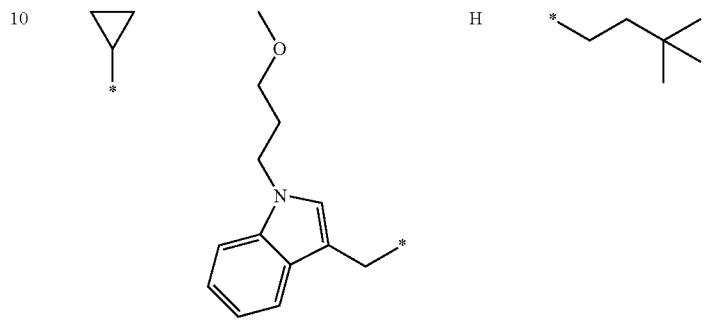 | | H | |
| 11 | 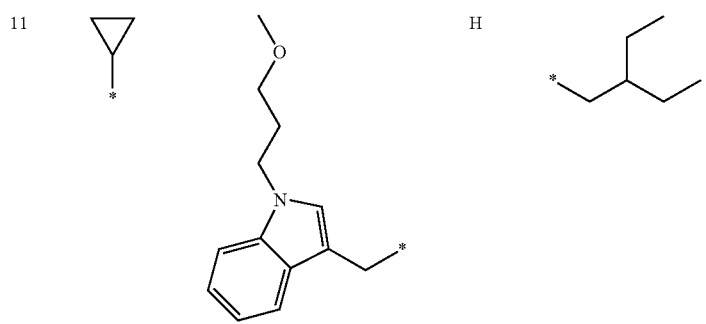 | | H | |
| 12 | 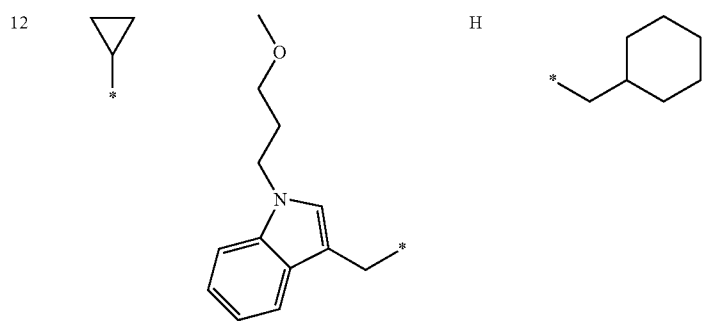 | | H | |
| 13 | 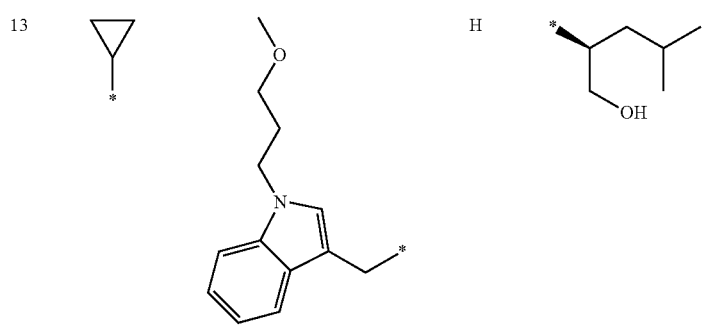 | | H | |

-continued
| examples | R1 | R2 | R3 | R4 |
|---|---|---|---|---|
| 14 |  | 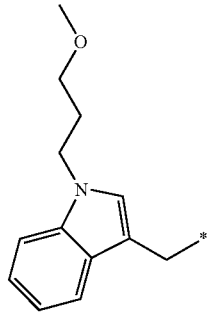 | H | 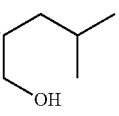 |
| 15 |  | 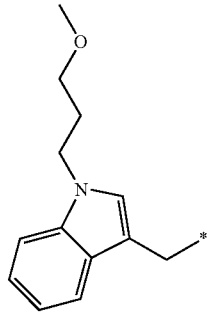 | H | 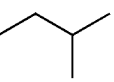 |
| 16 |  | 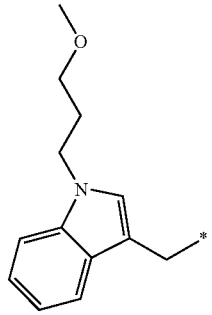 | H | 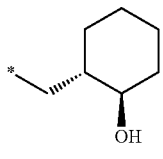 |
| 17 |  | 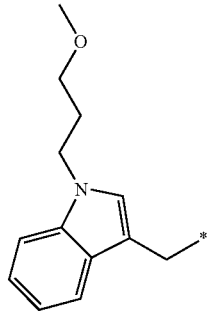 | H | 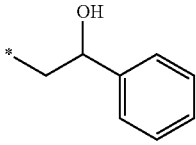 |
| 18 |  | 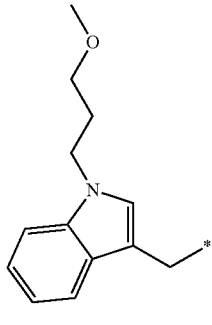 | H | 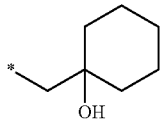 |

-continued

| examples | R1 | R2 | R3 | R4 |
|---|---|---|---|---|
| 19 | cyclopropyl-* | 6-substituted 4-(3-methoxypropyl)-2H-benzo[b][1,4]oxazin-3(4H)-yl | H | *-CH₂CH₂CH(CH₃)₂ (isopentyl) |
| 20 | cyclopropyl-* | 6-substituted 4-(3-methoxypropyl)-2H-benzo[b][1,4]oxazin-3(4H)-yl | H | *-CH₂CH₂-phenyl |
| 21 | cyclopropyl-* | 1-(3-methoxypropyl)-1H-indol-3-ylmethyl-* | H | *-CH(phenyl)CH₂CH₂OH |
| 22 | cyclopropyl-* | 1-(3-methoxypropyl)-1H-indol-3-ylmethyl-* | H | *-CH₂CH(OH)CH₂CH₃ |
| 23 | cyclopropyl-* | 1-(3-methoxypropyl)-1H-indol-3-ylmethyl-* | H | *-CH(CH₂OH)CH(OH)phenyl |

-continued

| examples | R1 | R2 | R3 | R4 |
|---|---|---|---|---|
| 24 | cyclopropyl | 1-(3-methoxypropyl)-1H-indol-3-ylmethyl | H | (2S)-2-benzyl-3-hydroxypropyl |
| 25 | cyclopropyl | 1-(3-methoxypropyl)-1H-pyrrolo[2,3-b]pyridin-3-ylmethyl | H | 2-(hydroxymethyl)-4-methylpentyl |
| 26 | cyclopropyl | 2-propoxyquinolin-4-ylmethyl | H | 2-(hydroxymethyl)-4-methylpentyl |
| 27 | cyclopropyl | 2-propoxyquinolin-4-ylmethyl | H | 2-(hydroxymethyl)-4-methylpentyl |
| 28 | cyclopropyl | 1-(3-methoxypropyl)-1H-indol-3-ylmethyl | H | 2-(hydroxymethyl)cyclohexyl |

-continued
| examples | R1 | R2 | R3 | R4 |
|---|---|---|---|---|
| 29 |  | 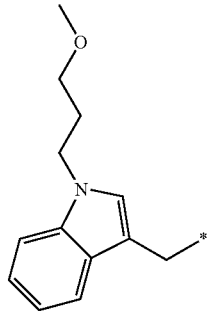 | H | 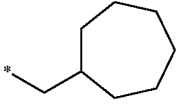 |
| 30 |  | 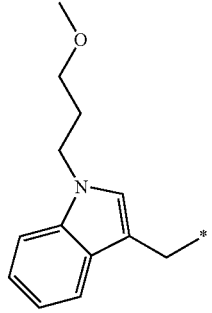 | H | 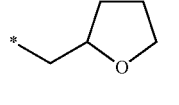 |
| 31 |  | 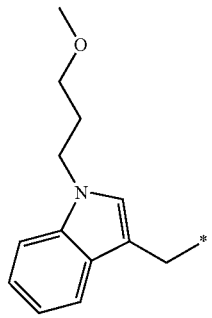 | H | 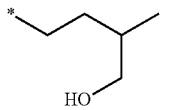 |
| 32 |  | 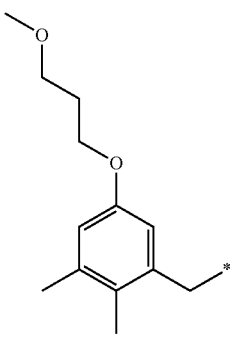 | H | 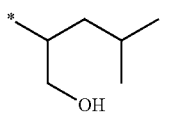 |
| 33 |  | 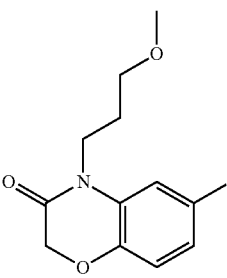 | H | 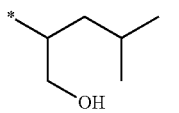 |

-continued

| examples | R1 | R2 | R3 | R4 |
|---|---|---|---|---|
| 34 | cyclopropyl | 1-(3-methoxypropyl)-1H-indol-3-ylmethyl | H | benzylsulfonyl |
| 35 | cyclopropyl | 1-(3-methoxypropyl)-1H-indol-3-ylmethyl | H | (S)-2-(2,2-dimethylpropyl)-3-hydroxypropyl |
| 36 | cyclopropyl | 1-(3-methoxypropyl)-1H-indol-3-ylmethyl | H | (R)-2-(2,2-dimethylpropyl)-3-hydroxypropyl |
| 37 | cyclopropyl | 3-(3-methoxypropoxy)-5-methoxybenzyl | H | 2-isobutyl-3-hydroxypropyl |
| 38 | cyclopropyl | 3-(2-methoxyethoxymethyl)-5-methoxybenzyl | H | 2-isobutyl-3-hydroxypropyl |

-continued
| examples | R1 | R2 | R3 | R4 |
|---|---|---|---|---|
| 39 |  | 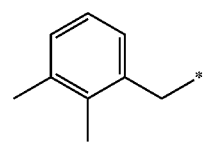 | H | 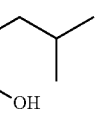 |
| 40 |  | 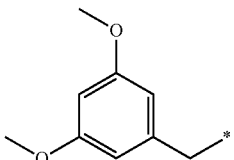 | H | 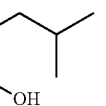 |
| 41 |  | 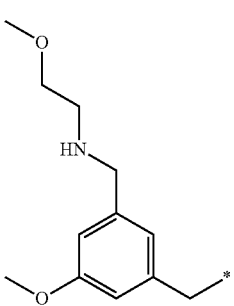 | H | 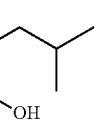 |
| 42 |  | 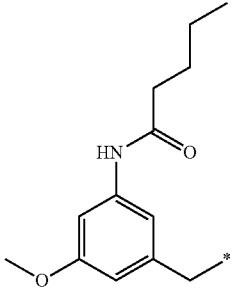 | H | 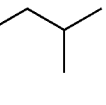 |
| 43 |  | 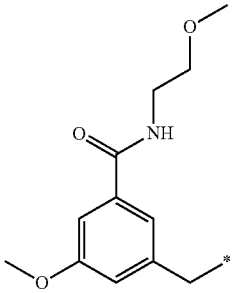 | H | 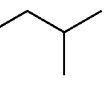 |
| 44 |  | 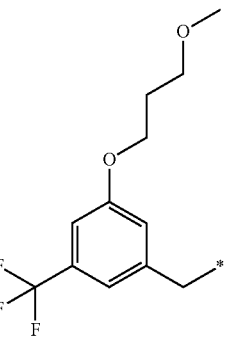 | H | 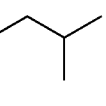 |

-continued

| examples | R1 | R2 | R3 | R4 |
|---|---|---|---|---|
| 45 | cyclopropyl | 1-(3-methoxypropyl)-1H-indol-3-ylmethyl | H | (S)-2-hydroxymethyl-3-phenylpropyl |
| 46 | cyclopropyl | 1-(3-methoxypropyl)-1H-indol-3-ylmethyl | H | (R)-2-hydroxymethyl-3-phenylpropyl |
| 47 | cyclopropyl | 1-(3-methoxypropyl)-1H-indol-3-ylmethyl | H | (S)-3-hydroxy-1-phenylpropyl |
| 48 | cyclopropyl | 1-(3-methoxypropyl)-1H-indol-3-ylmethyl | H | (R)-3-hydroxy-1-phenylpropyl |
| 49 | cyclopropyl | 1-(3-methoxypropyl)-1H-indol-3-ylmethyl | H | (S)-2-hydroxy-1-phenylethyl |

-continued
| examples | R1 | R2 | R3 | R4 |
|---|---|---|---|---|
| 50 |  | 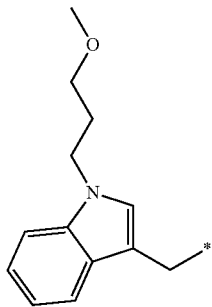 | H | 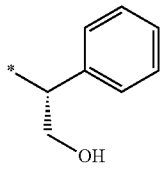 |
| 51 |  | 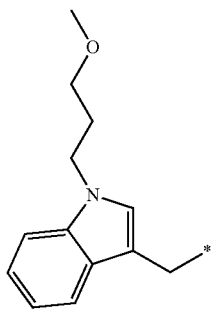 | H | 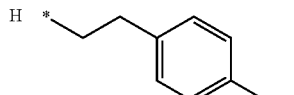 |
| 52 |  | 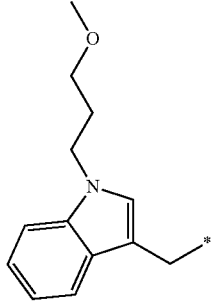 | H | 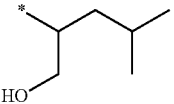 |
| 53 |  | 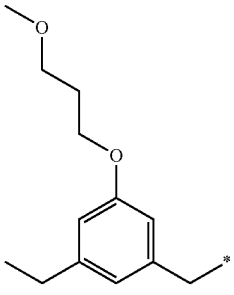 | H | 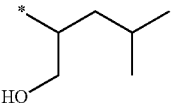 |
| 54 |  | 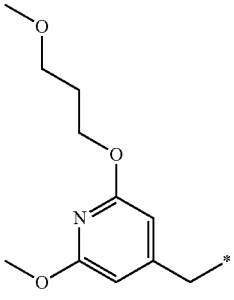 | H | 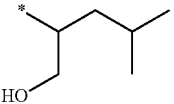 |

-continued

| examples | R1 | R2 | R3 | R4 |
|---|---|---|---|---|
| 55 | cyclopropyl | 1-(3-methoxypropyl)-1H-indol-3-ylmethyl | H | N,N-dimethyl-4-methylpentanamide |
| 56 | cyclopropyl | 1-(3-methoxypropyl)-2-oxo-1,2-dihydropyridin-5-ylmethyl | H | 2-hydroxymethyl-4-methylpentyl |
| 57 | cyclopropyl | [6-ethyl-2-(3-methoxypropoxy)pyridin-4-yl]methyl | H | 2-hydroxymethyl-4-methylpentyl |
| 58 | ethyl | [4-methoxy-3-(3-methoxypropoxy)phenyl]methyl | H | 2-hydroxymethyl-4-methylpentyl |
| 59 | cyclopropyl | 1-(3-methoxypropyl)-2-oxo-1,2,3,4-tetrahydroquinolin-7-yl | H | 2-hydroxymethyl-4-methylpentyl |

-continued

| examples | R1 | R2 | R3 | R4 |
| --- | --- | --- | --- | --- |
| 60 | cyclopropyl | 3-(methoxypropyl)-1H-indol-3-yl-methyl | H | (1-hydroxycyclohexyl)methyl |
| 61 | cyclopropyl | 3-(2-methoxyethoxy)-5-methoxybenzyl | H | 2-(hydroxymethyl)-4-methylpentyl |
| 62 | cyclopropyl | 3-(4-methoxybutoxy)-5-methoxybenzyl | H | 2-(hydroxymethyl)-4-methylpentyl |
| 63 | cyclopropyl | 1-(3-methoxypropyl)-1H-indol-3-yl-methyl | H | 3-hydroxy-5-methylhexan-2-yl |
| 64 | cyclopropyl | 2-(3-methoxypropoxy)-5-methylbenzyl | H | 2-(hydroxymethyl)-4-methylpentyl |

-continued
| examples | R1 | R2 | R3 | R4 |
|---|---|---|---|---|
| 65 | 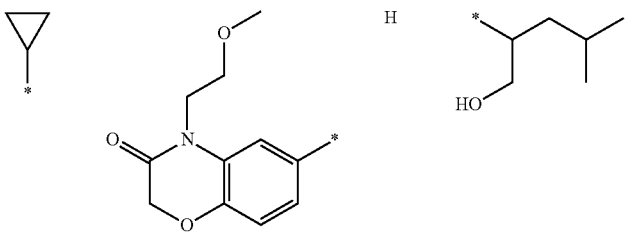 | 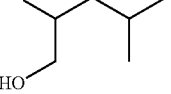 | H | 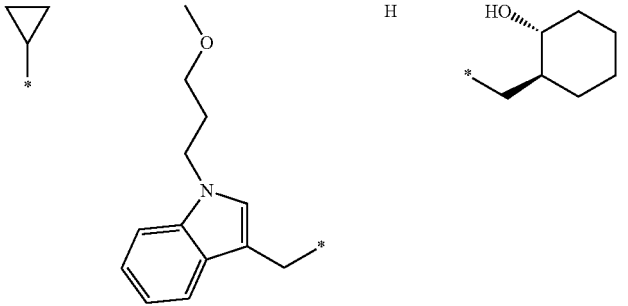 |
| 66 | 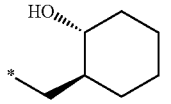 | 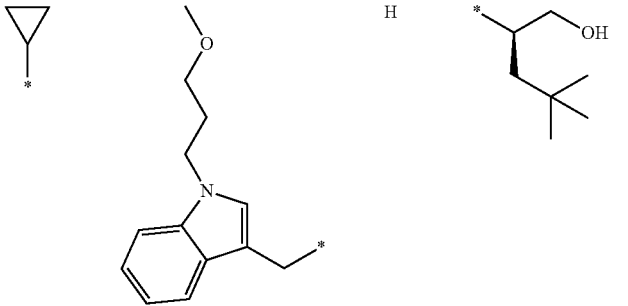 | H | 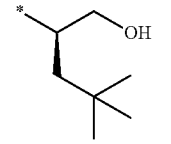 |
| 67 | 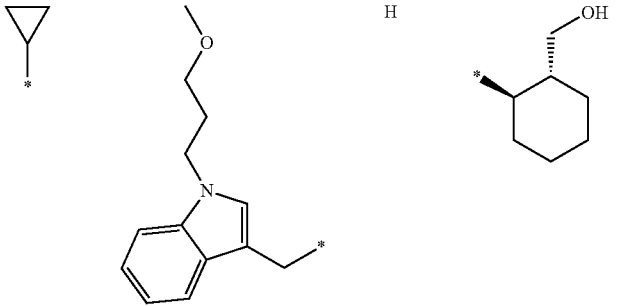 | 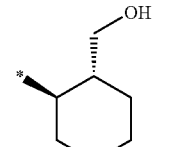 | H | 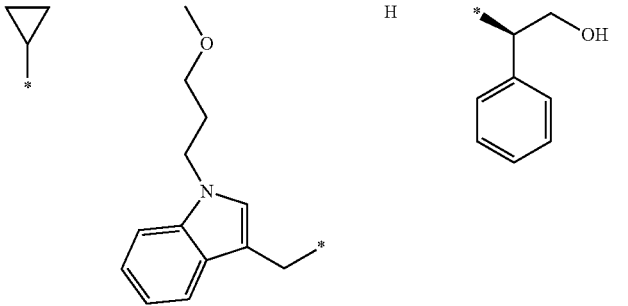 |
| 68 | 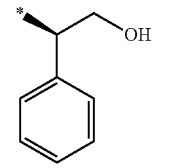 | | H | |
| 69 | | | H | |

-continued
| examples | R1 | R2 | R3 | R4 |
|---|---|---|---|---|
| 70 |  | 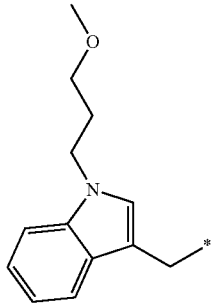 | H | 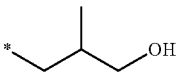 |
| 71 |  | 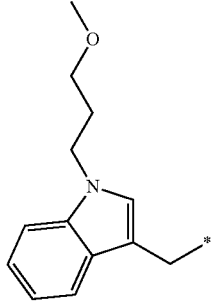 | H | 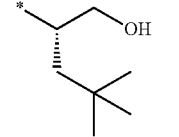 |
| 72 |  | 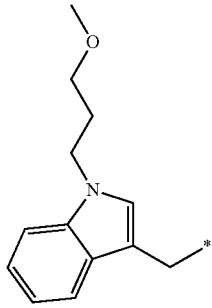 | H | 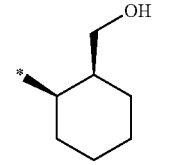 |
| 73 |  | 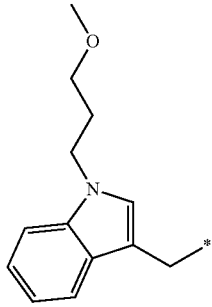 | H | 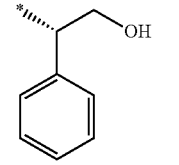 |
| 74 |  | 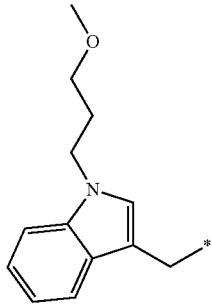 | H | 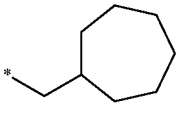 |

-continued

| examples | R1 | R2 | R3 | R4 |
|---|---|---|---|---|
| 75 | cyclopropyl | 3-(3-methoxypropyl)-1H-indol-3-ylmethyl | H | 2-methyl-4-hydroxybutyl |
| 76 | cyclopropyl | 1-(3-methoxypropyl)-1H-indol-3-ylmethyl | H | 2-(4-hydroxyphenyl)ethyl |
| 77 | cyclopropyl | 1-(3-methoxypropyl)-1H-indol-3-ylmethyl | H | 2,4-dimethylpentyl |
| 78 | cyclopropyl | 4-(3-methoxypropoxy)-3-methoxybenzyl | H | 2-hydroxymethyl-4-methylpentyl |
| 79 | cyclopropyl | 1-(3-methoxypropyl)-1H-indol-3-ylmethyl | H | 3-hydroxy-2,5-dimethylhexyl |

-continued

| examples | R1 | R2 | R3 | R4 |
|---|---|---|---|---|
| 80 | cyclopropyl* | 3-(3-methoxypropyl)-1H-indol-1-yl methyl* | H | (tetrahydrofuran-2-yl)methyl* |
| 81 | cyclopropyl* | 3-(3-methoxypropyl)-1H-indol-1-yl methyl* | H | *-CH2-CH(OH)-CH2-CH2-OH |
| 82 | cyclopropyl* | 4-(4-methoxybutyl)-3-oxo-3,4-dihydro-2H-benzo[b][1,4]oxazin-6-yl* | H | *-CH(CH2OH)-CH2-CH(CH3)2 |
| 83 | cyclopropyl* | 3-(3-methoxypropyl)-1H-indol-1-yl methyl* | H | *-C(CH3)(C(O)N(CH3)2)-CH2-CH(CH3)2 |
| 84 | cyclopropyl* | 3-(3-methoxypropyl)-1H-indol-1-yl methyl* | H | *-C(CH3)(C(O)N(CH3)2)-CH2-CH(CH3)2 |

-continued

| examples | R1 | R2 | R3 | R4 |
|---|---|---|---|---|
| 85 | cyclopropyl | 1-(3-methoxypropyl)-1H-indol-3-ylmethyl | H | (tetrahydro-2H-pyran-4-yl)methyl |
| 86 | cyclopropyl | 1-(3-methoxypropyl)-1H-indol-3-ylmethyl | H | 3-(hydroxymethyl)cyclohexyl |
| 87 | cyclopropyl | [4-(3-methoxypropyl)-2,2-dimethyl-3-oxo-3,4-dihydro-2H-benzo[1,4]oxazin-6-yl] | H | 1-hydroxy-4-methylpentan-2-yl |
| 88 | cyclopropyl | 1-(3-methoxypropyl)-1H-indol-3-ylmethyl | H | (3R)-5-methyl-3-hydroxymethyl... (3-hydroxy-5-methylhexyl) |
| 89 | cyclopropyl | 3-[3-(2-hydroxypropan-2-yl)-5-(3-methoxypropoxy)phenyl]methyl | H | 1-hydroxy-4-methylpentan-2-yl |

-continued

| examples | R1 | R2 | R3 | R4 |
|---|---|---|---|---|
| 90 | cyclopropyl | 3-(3-isopropyl-5-(methoxypropoxy)phenyl)methyl | H | 2-hydroxymethyl-4-methylpentyl |
| 91 | cyclopropyl | 1-(3-methoxypropyl)-1H-indol-3-ylmethyl | H | 2-methoxy-6-methylphenyl |
| 92 | cyclopropyl | 4-(3-methoxypropoxy)-2,3-dihydrobenzofuran-6-ylmethyl | H | 2-hydroxymethyl-4-methylpentyl |
| 93 | cyclopropyl | 2-(3-methoxypropoxy)quinolin-4-ylmethyl | H | 2-hydroxymethyl-4-methylpentyl |
| 94 | cyclopropyl | 5-ethyl-4-(3-methoxypropyl)thiophen-... ylmethyl | H | 2-hydroxymethyl-4-methylpentyl |

-continued

| examples | R1 | R2 | R3 | R4 |
|---|---|---|---|---|
| 95 | cyclopropyl | 5-(3-methoxypropoxy)chroman-7-ylmethyl | H | 2-hydroxymethyl-3-methylbutyl |
| 96 | cyclopropyl | 3-(3-methoxypropoxy)-5-methoxybenzyl | H | isopentyl |
| 97 | cyclopropyl | 4-(3-methoxypropyl)-3-oxo-3,4-dihydro-2H-benzo[1,4]oxazin-6-ylmethyl | H | isopentyl |
| 98 | (S)-sec-butyl | 3-(3-methoxypropoxy)-5-methoxybenzyl | H | 2-hydroxymethyl-3-methylbutyl |
| 99 | (R)-sec-butyl | 3-(3-methoxypropoxy)-5-methoxybenzyl | H | 2-hydroxymethyl-3-methylbutyl |

-continued

| examples | R1 | R2 | R3 | R4 |
|---|---|---|---|---|
| 100 | cyclopropyl | 2-tert-butyl-4-(3-methoxypropoxy)benzyl | H | 2-hydroxymethyl-4-methylpentyl |
| 101 | cyclopropyl | 2-methoxy-4-(3-methoxypropoxy)benzyl | H | 2-hydroxymethyl-4-methylpentyl |
| 102 | cyclopropyl | 4-acetyl-3-(3-methoxypropoxy)benzyl | H | 2-hydroxymethyl-4-methylpentyl |
| 103 | cyclopropyl | 1-(3-methoxypropyl)-1H-indol-3-ylmethyl | H | 1-phenylcyclopentyl |
| 104 | cyclopropyl | 3-methoxy-5-(3-methoxypropoxy)benzyl | H | 2,4-dimethylpentyl |

-continued

| examples | R1 | R2 | R3 | R4 |
|---|---|---|---|---|
| 105 | cyclopropyl | 4-(3-methoxypropyl)-2,2-dimethyl-3-oxo-3,4-dihydro-2H-benzo[1,4]oxazin-6-yl | H | 2,4-dimethylpentan-3-yl |
| 106 | cyclopropyl | 5-(3-methoxypropoxy)chroman-7-ylmethyl | H | 2,4-dimethylpentan-3-yl |
| 107 | cyclopropyl | 5-(2-methoxyethoxy)chroman-7-ylmethyl | H | 4-methyl-2-(hydroxymethyl)pentyl |
| 108 | cyclopropyl | 4-(3-methoxypropyl)-2,2-dimethyl-3-oxo-3,4-dihydro-2H-benzo[1,4]oxazin-6-yl | H | 2-methoxy-6-methylphenyl |
| 109 | cyclopropyl | 2-(3-methoxypropoxy)-5-methylphenyl | H | 2,4-dimethylpentan-3-yl |

-continued

| examples | R1 | R2 | R3 | R4 |
|---|---|---|---|---|
| 110 | cyclopropyl | 4-(3-methoxypropyl)-2,2-dimethyl-3-oxo-3,4-dihydro-2H-benzo[1,4]oxazin-6-yl | H | 2-hydroxy-4-methyl-1-isopropyl-pentyl (with OH) |
| 111 | cyclopropyl | 3-(3-methoxypropoxy)-5-methoxyphenyl-methyl | H | 2-methoxy-6-methylphenyl |
| 112 | cyclopropyl | 2-(3,5-difluorophenyl)-4-(3-methoxypropyl)-2-methyl-3-oxo-3,4-dihydro-2H-benzo[1,4]oxazin-6-yl (racemate) | H | 2,4-dimethylpentyl |
| 113 | cyclopropyl | 2-(3-methoxypropoxy)-4-methylphenyl | H | 2-hydroxy-4-methyl-1-isopropyl-pentyl (with OH) |
| 114 | cyclopropyl | 5-(3-methoxypropoxy)chroman-7-ylmethyl | H | 2-methoxy-6-methylphenyl |

-continued
| examples | R1 | R2 | R3 | R4 |
|---|---|---|---|---|
| 115 |  | 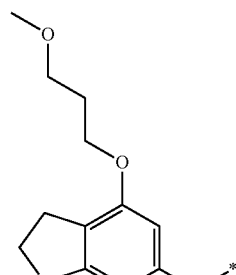 | H | 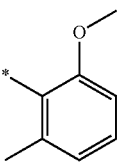 |
| 116 |  | 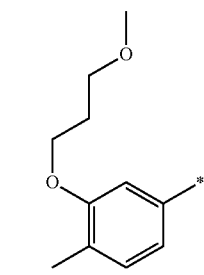 | H | 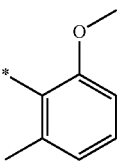 |
| 117 |  | 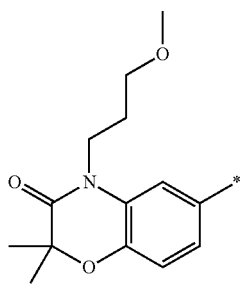 | H | 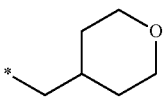 |
| 118 |  | 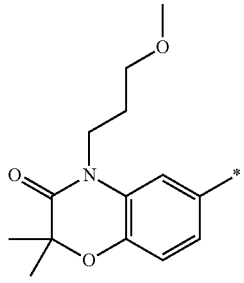 | H | 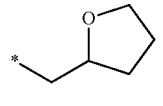 |
| 119 |  | 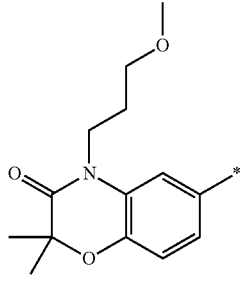 | H | 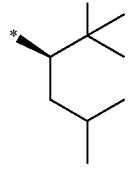 |

-continued

| examples | R1 | R2 | R3 | R4 |
|---|---|---|---|---|
| 120 | cyclopropyl | 4-(3-methoxypropyl)-2,2-dimethyl-3-oxo-3,4-dihydro-2H-benzo[1,4]oxazin-6-yl | H | 2-hydroxy-2,4-dimethylpentan-3-yl |
| 121 | cyclopropyl | 4-(3-methoxypropyl)-2,2-dimethyl-3-oxo-3,4-dihydro-2H-benzo[1,4]oxazin-6-yl | H | 4-methyl-1-hydroxypentan-2-yl |
| 122 | cyclopropyl | 4-(3-methoxypropyl)-2,2-dimethyl-3-oxo-3,4-dihydro-2H-benzo[1,4]oxazin-6-yl | H | 1-(pyridin-4-yl)cyclopentyl |
| 123 | cyclopropyl | 4-(3-methoxypropyl)-2,2-dimethyl-3-oxo-3,4-dihydro-2H-benzo[1,4]oxazin-6-yl | H | 4-fluoro-2-methoxy-3-methylphenyl |
| 124 | cyclopropyl | 4-(3-methoxypropyl)-2,2-dimethyl-3-oxo-3,4-dihydro-2H-benzo[1,4]oxazin-6-yl | H | 4-methyl-1-hydroxypentan-2-yl |

-continued

| examples | R1 | R2 | R3 | R4 |
|---|---|---|---|---|
| 125 | cyclopropyl | 2-(3-methoxypropoxy)-4-*-benzonitrile | H | 2,4-dimethylpentan-3-yl* |
| 126 | cyclopropyl | 2-(3-methoxypropoxy)-4-*-benzonitrile | H | 2-methoxy-6-methylphenyl* |
| 127 | ethyl* | 4-(3-methoxypropyl)-2,2-dimethyl-3-oxo-3,4-dihydro-2H-benzo[b][1,4]oxazin-6-yl* | H | 2-methoxy-6-methylphenyl* |
| 128 | cyclopropyl | 4-(3-methoxypropyl)-2,2-dimethyl-3-oxo-3,4-dihydro-2H-benzo[b][1,4]oxazin-6-yl* | H | *-CH2CH2-O-iPr |
| 129 | cyclopropyl | 4-(3-methoxypropyl)-2,2-dimethyl-3-oxo-3,4-dihydro-2H-benzo[b][1,4]oxazin-6-yl* | H | *-(CH2)3-(2-oxopyrrolidin-1-yl) |

-continued

| examples | R1 | R2 | R3 | R4 |
|---|---|---|---|---|
| 130 | cyclopropyl | 4-(3-methoxypropyl)-2,2-dimethyl-3-oxo-3,4-dihydro-2H-benzo[b][1,4]oxazin-6-yl | H | (1-hydroxycyclohexyl)methyl |
| 131 | cyclopropyl | 4-acetyl-3-(3-methoxypropoxy)phenyl | H | 2-methoxy-3-methylphenyl |
| 132 | cyclopropyl | 4-(3-methoxypropyl)-2,2-dimethyl-3-oxo-3,4-dihydro-2H-benzo[b][1,4]oxazin-6-yl | H | 2-methylphenyl |
| 133 | cyclopropyl | 4-(3-methoxypropyl)-2,2-dimethyl-3-oxo-3,4-dihydro-2H-benzo[b][1,4]oxazin-6-yl | H | 2-methoxyphenyl |
| 134 | cyclopropyl | 4-(3-methoxypropyl)-2,2-dimethyl-3-oxo-3,4-dihydro-2H-benzo[b][1,4]oxazin-6-yl | H | 2-methoxyphenyl |

-continued
| examples | R1 | R2 | R3 | R4 |
|---|---|---|---|---|
| 135 |  | 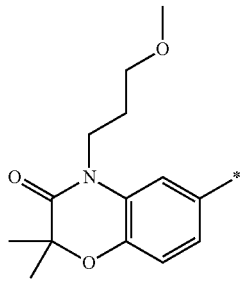 | H | 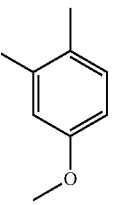 |
| 136 |  | 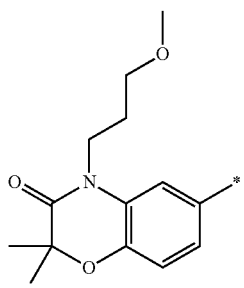 | H | 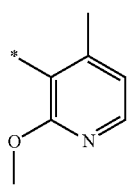 |
| 137 |  | 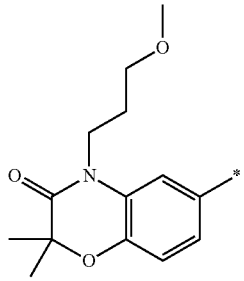 | H | 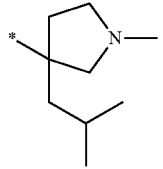 |
| 138 |  | 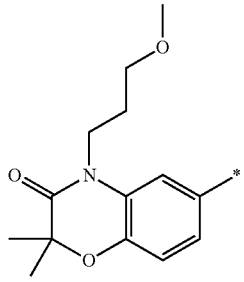 | H | 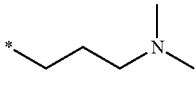 |
| 139 |  | 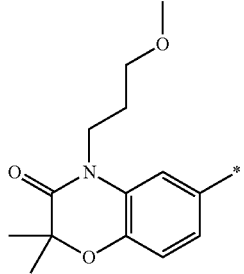 | H | 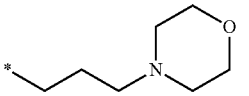 |

-continued

| examples | R1 | R2 | R3 | R4 |
|---|---|---|---|---|
| 140 | cyclopropyl | 4-(3-methoxypropyl)-2,2-dimethyl-3-oxo-3,4-dihydro-2H-benzo[1,4]oxazin-6-yl | H | -CH2CH2-N(CH2CH3)2 |
| 141 | cyclopropyl | 4-(3-methoxypropyl)-2,2-dimethyl-3-oxo-3,4-dihydro-2H-benzo[1,4]oxazin-6-yl | H | -CH2CH2-morpholin-4-yl |
| 142 | cyclopropyl | 4-(3-methoxypropyl)-2,2-dimethyl-3-oxo-3,4-dihydro-2H-benzo[1,4]oxazin-6-yl | H | 1-acetylpiperidin-4-yl |
| 143 | cyclopropyl | 4-(3-methoxypropyl)-2,2-dimethyl-3-oxo-3,4-dihydro-2H-benzo[1,4]oxazin-6-yl | H | -CH2CH2-(tetrahydropyran-4-yl) |
| 144 | cyclopropyl | 1-(3-methoxypropyl)-3,3-dimethyl-2-oxo-1,2,3,4-tetrahydroquinolin-7-yl | H | 1-(pyridin-4-yl)cyclopentyl |

-continued

| examples | R1 | R2 | R3 | R4 |
|---|---|---|---|---|
| 145 | cyclopropyl | 2-cyano-4-*-phenyl with O(CH2)3OMe at position 2 | H | 1-(pyridin-4-yl)cyclopentyl-* |
| 146 | cyclopropyl | 1-(3-methoxypropyl)-3,3-dimethyl-2-oxo-1,2,3,4-tetrahydroquinolin-7-yl-* | H | (tetrahydro-2H-pyran-4-yl)methyl-* |
| 147 | cyclopropyl | 4-(3-methoxypropyl)-2,2-dimethyl-3-oxo-3,4-dihydro-2H-benzo[b][1,4]oxazin-6-yl-* | H | (2S)-1-methoxy-4-methylpentan-2-yl-* |
| 148 | cyclopropyl | 4-(3-methoxypropyl)-2,2-dimethyl-3-oxo-3,4-dihydro-2H-benzo[b][1,4]oxazin-6-yl-* | H | (2S)-1-ethoxy-4-methylpentan-2-yl-* |
| 149 | cyclopropyl | 4-(3-methoxypropyl)-2,2-dimethyl-3-oxo-3,4-dihydro-2H-benzo[b][1,4]oxazin-6-yl-* | H | (2S)-N,N,4-trimethyl-2-*-pentyl-1-amine |

-continued

| examples | R1 | R2 | R3 | R4 |
|---|---|---|---|---|
| 150 | cyclopropyl-* | 4-(3-methoxypropyl)-2,2-dimethyl-3-oxo-3,4-dihydro-2H-benzo[b][1,4]oxazin-6-yl* | H | 4-methylpentan-2-yl* |
| 151 | cyclopropyl-* | 4-(3-methoxypropyl)-2,2-dimethyl-3-oxo-3,4-dihydro-2H-benzo[b][1,4]oxazin-6-yl* | H | (1-ethoxycyclohexyl)methyl* |
| 152 | cyclopropyl-* | 4-(3-methoxypropyl)-2,2-dimethyl-3-oxo-3,4-dihydro-2H-benzo[b][1,4]oxazin-6-yl* | H | 1-(tetrahydro-2H-pyran-4-yl)cyclopropyl* |
| 153 | cyclopropyl-* | N-(2-chloro-5-*-phenyl)-3-methoxypropanamide | H | 2-methoxy-6-methylphenyl* |
| 154 | cyclopropyl-* | 4-(3-methoxypropyl)-2,2-dimethyl-3-oxo-3,4-dihydro-2H-benzo[b][1,4]oxazin-6-yl* | H | (1S)-2-hydroxy-2-methyl-1-phenylpropyl* |

-continued
| examples | R1 | R2 | R3 | R4 |
|---|---|---|---|---|
| 155 |  | 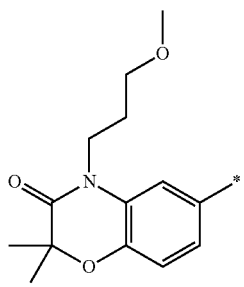 | H | 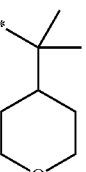 |
| 156 |  | 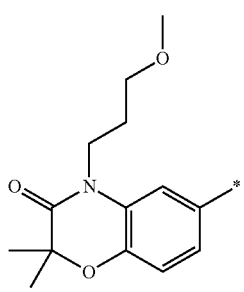 | H | 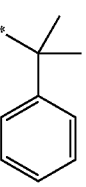 |
| 157 |  | 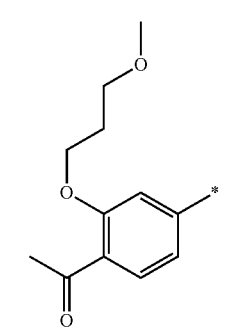 | H | 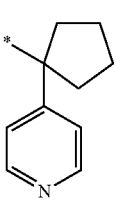 |
| 158 |  | 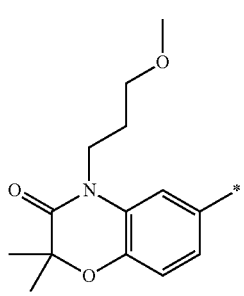 | H | 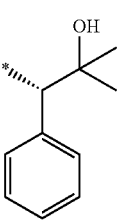 |
| 159 |  | 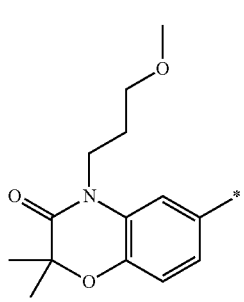 | H | 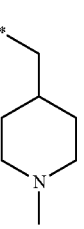 |

-continued
| examples | R1 | R2 | R3 | R4 |
|---|---|---|---|---|
| 160 |  | 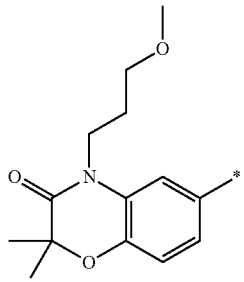 | H | 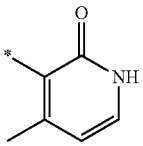 |
| 161 |  | 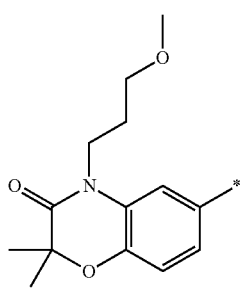 | H | 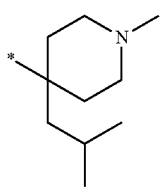 |
| 162 |  | 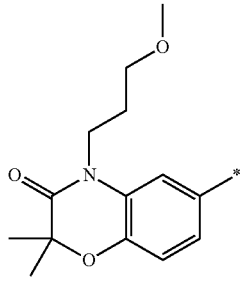 | H | 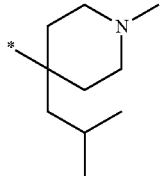 |
| 163 |  | 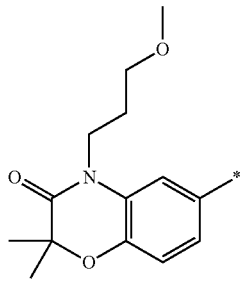 | H | 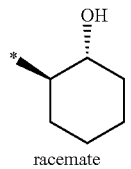racemate |
| 164 |  | 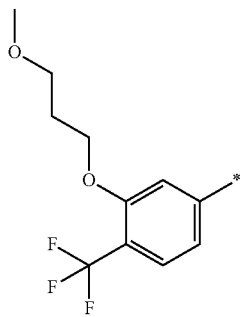 | H | 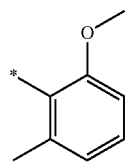 |

-continued
| examples | R1 | R2 | R3 | R4 |
|---|---|---|---|---|
| 165 |  | 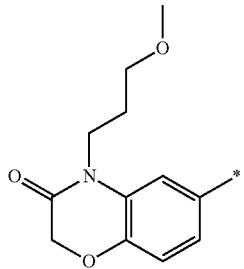 | H | 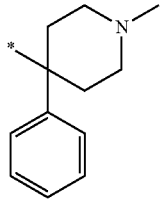 |
| 166 |  | 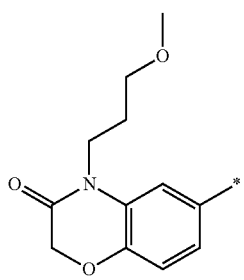 | H | 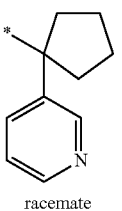 racemate |
| 167 |  | 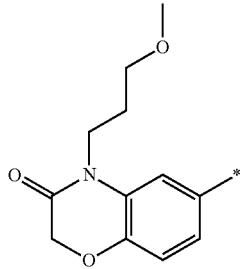 | H | 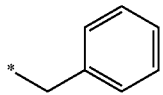 |
| 168 |  | 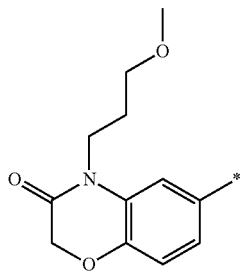 | H | 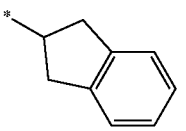 |
| 169 |  | 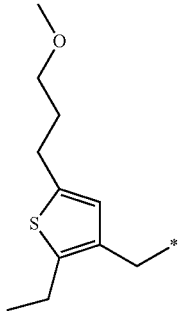 | H | 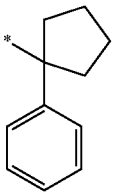 |

-continued
| examples | R1 | R2 | R3 | R4 |
|---|---|---|---|---|
| 170 |  | 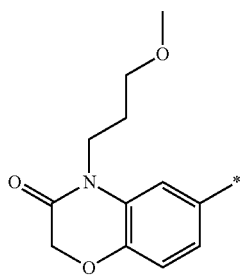 | H | 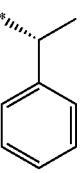 |
| 171 |  | 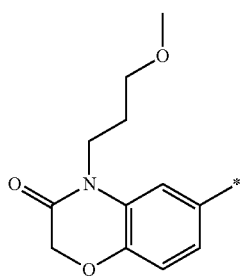 | H | 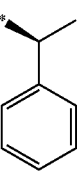 |
| 172 |  | 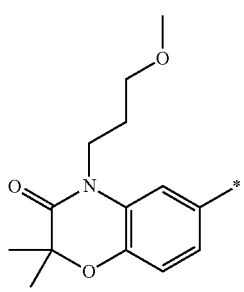 | H | 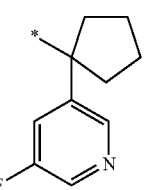 |
| 173 |  | 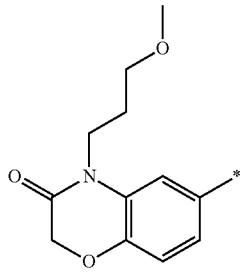 | H | 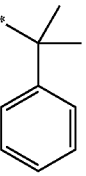 |
| 174 |  | 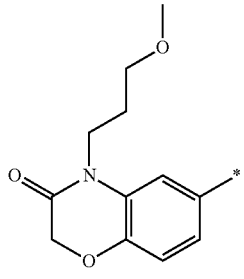 | H | 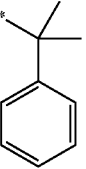 |

-continued
| examples | R1 | R2 | R3 | R4 |
|---|---|---|---|---|
| 175 |  | 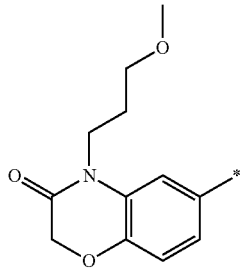 | H | 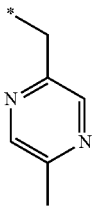 |
| 176 |  | 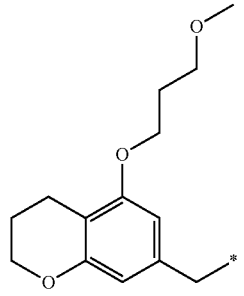 | H | 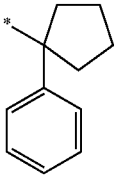 |
| 177 |  | 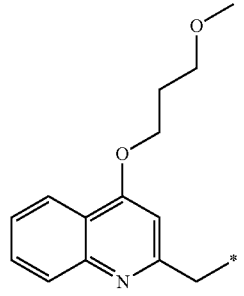 | H | 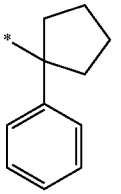 |
| 178 |  | 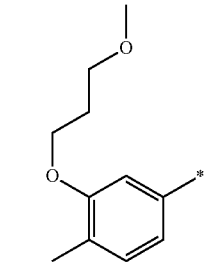 | H | 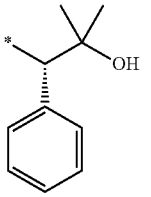 |
| 179 |  | 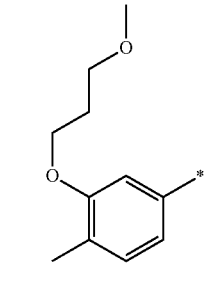 | H | 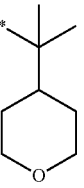 |

| examples | R1 | R2 | R3 | R4 |
|---|---|---|---|---|
| 180 | cyclopropyl | 4-(3-methoxypropyl)-2,2-dimethyl-3-oxo-3,4-dihydro-2H-benzo[1,4]oxazin-6-yl | H | (5-methylisoxazol-3-yl)methyl |
| 181 | cyclopropyl | 4-(3-methoxypropyl)-2,2-dimethyl-3-oxo-3,4-dihydro-2H-benzo[1,4]oxazin-6-yl | H | (1R,2S)-2-hydroxycyclopentyl |
| 182 | cyclopropyl | 4-(3-methoxypropyl)-2,2-dimethyl-3-oxo-3,4-dihydro-2H-benzo[1,4]oxazin-6-yl | H | (1S,2R)-2-hydroxycyclopentyl |
| 183 | cyclopropyl | 5-(3-methoxypropoxy)chroman-7-ylmethyl | H | 1-methyl-4-phenylpiperidin-4-yl |
| 184 | cyclopropyl | 4-(3-methoxypropyl)-2,2-dimethyl-3-oxo-3,4-dihydro-2H-benzo[1,4]oxazin-6-yl | H | 1-phenylcyclopropyl |

-continued
| examples | R1 | R2 | R3 | R4 |
|---|---|---|---|---|
| 185 |  | 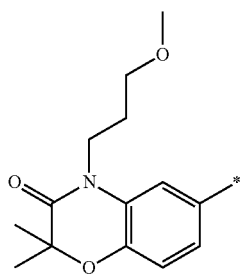 | H | 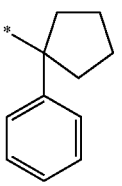 |
| 186 |  | 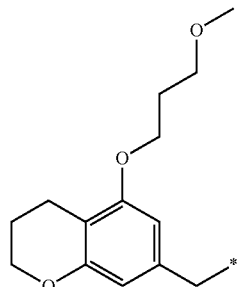 | H | 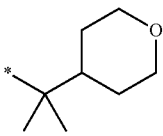 |
| 187 |  | 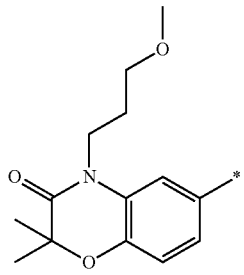 | H | 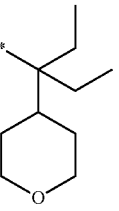 |
| 188 |  | 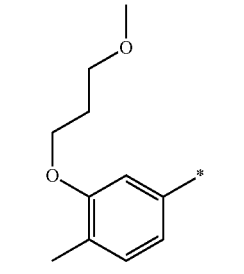 | H | 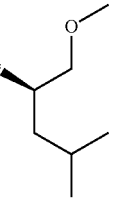 |
| 189 |  | 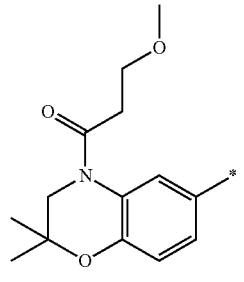 | H | 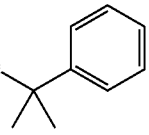 |
| 190 |  | 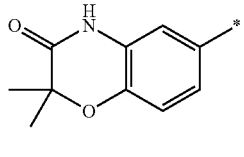 | H | 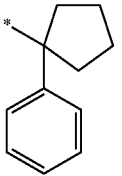 |

-continued
| examples | R1 | R2 | R3 | R4 |
|---|---|---|---|---|
| 191 | | | H | racemate |
| 192 | | | H | |
| 193 | | | H | |
| 194 | | | H | |
| 195 | | | H | |
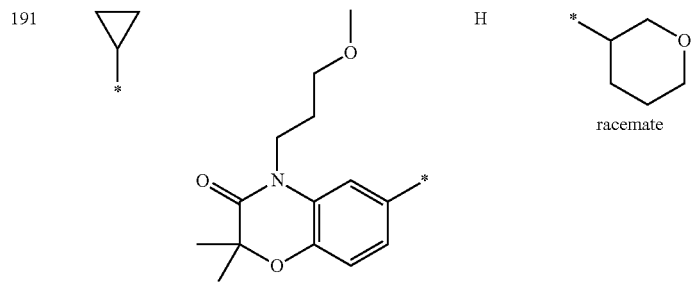
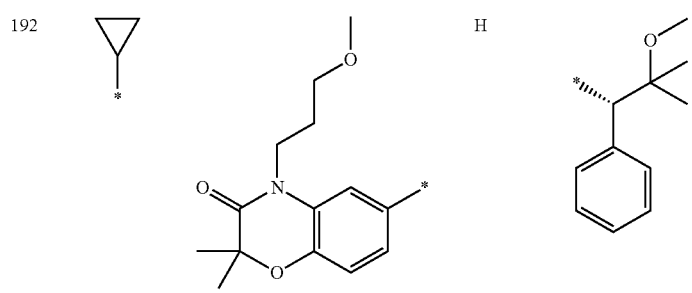
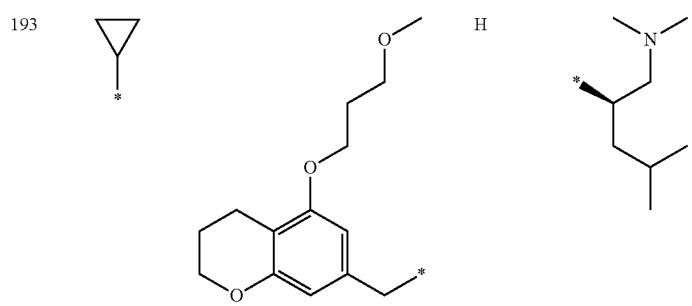
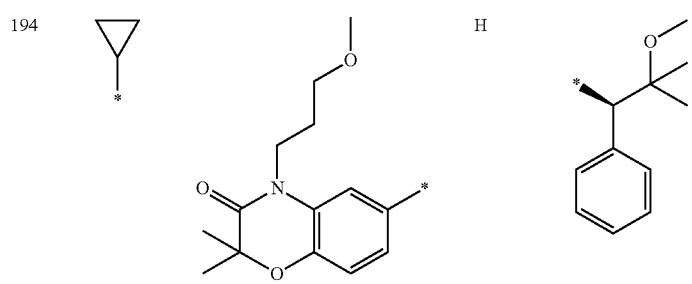
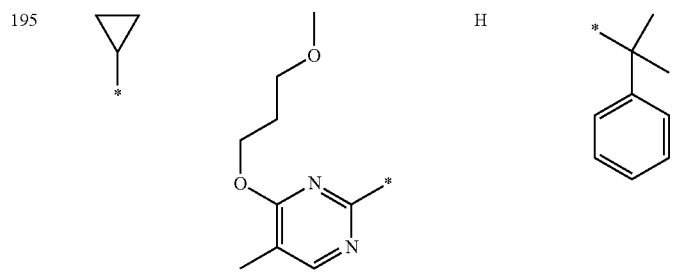

-continued
| examples | R1 | R2 | R3 | R4 |
|---|---|---|---|---|
| 196 |  |  | H |  |
| 197 |  |  | H |  |
| 198 |  | 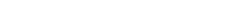 | H |  |
| 199 |  | 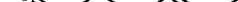 | H |  |
| 200 |  |  | H |  |

-continued

| examples | R1 | R2 | R3 | R4 |
|---|---|---|---|---|
| 201 | cyclopropyl | 1-(3-methoxypropyl)-2-oxo-1,2,3,4-tetrahydroquinolin-7-yl | H | 2-(tetrahydro-2H-pyran-4-yl)propan-2-yl |
| 202 | cyclopropyl | 1-(3-methoxypropyl)-2-oxo-1,2,3,4-tetrahydroquinolin-7-yl | H | (R)-1-phenylethyl |
| 203 | cyclopropyl | 3-(3-methoxypropoxy)-5-methoxy-4-methylbenzyl | H | 1-phenylcyclopentyl |
| 204 | cyclopropyl | 3-(3-methoxypropoxy)-5-methoxy-4-methylbenzyl | H | (R)-1-phenylethyl |
| 205 | cyclopropyl | 4-(3-methoxypropyl)-2,2-dimethyl-3-oxo-3,4-dihydro-2H-benzo[b][1,4]oxazin-6-yl | H | 1-acetyl-4-phenylpiperidin-4-yl |

-continued

| examples | R1 | R2 | R3 | R4 |
|---|---|---|---|---|
| 206 | cyclopropyl-* | 4-(3-methoxypropyl)-2,2-dimethyl-3-oxo-3,4-dihydro-2H-benzo[1,4]oxazin-6-yl* | H | 1-(methylsulfonyl)-4-phenylpiperidin-4-yl* |
| 207 | 2-methylprop-2-yl-* | 4-(3-methoxypropyl)-2,2-dimethyl-3-oxo-3,4-dihydro-2H-benzo[1,4]oxazin-6-yl* | H | 2-phenylpropan-2-yl* |
| 208 | cyclopropyl-* | 4-(2-ethoxyethyl)-2,2-dimethyl-3-oxo-3,4-dihydro-2H-benzo[1,4]oxazin-6-yl* | H | (2S)-1-(dimethylamino)-4-methylpentan-2-yl* |
| 209 | cyclopropyl-* | 4-(3-methoxypropyl)-2,2-dimethyl-3-oxo-3,4-dihydro-2H-benzo[1,4]oxazin-6-yl* | H | 1-cyclohexylethyl* |
| 210 | cyclopropyl-* | 4-(3-methoxypropyl)-2,2-dimethyl-3-oxo-3,4-dihydro-2H-benzo[1,4]oxazin-6-yl* | H | cyclopropyl* |

-continued
| examples | R1 | R2 | R3 | R4 |
|---|---|---|---|---|
| 211 |  | 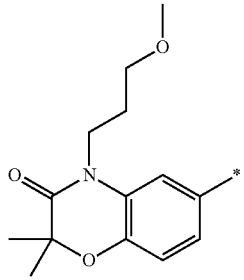 | H | 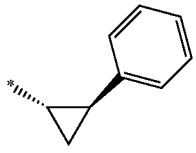 |
| 212 |  | 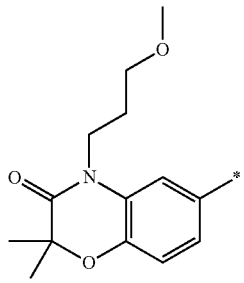 | H | 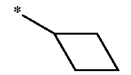 |
| 213 |  | 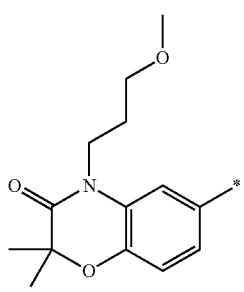 | H | 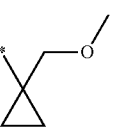 |
| 214 |  | 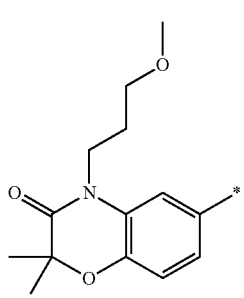 | H | 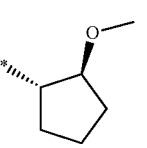 |
| 215 |  | 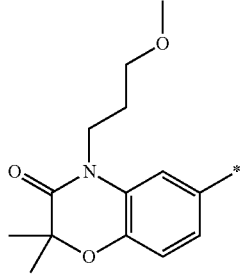 | H | 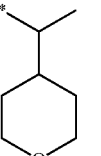<br>racemate |

-continued

| examples | R1 | R2 | R3 | R4 |
|---|---|---|---|---|
| 216 | cyclopropyl | 3-methoxy-5-(3-methoxypropoxy)benzyl | H | 1-phenylcyclopentyl |
| 217 | cyclopropyl | 4-(3-methoxypropyl)-2,2-dimethyl-3-oxo-3,4-dihydro-2H-benzo[b][1,4]oxazin-6-yl | H | 1-cyanocyclopentyl |
| 218 | cyclopropyl | 4-(3-methoxypropyl)-2,2-dimethyl-3-oxo-3,4-dihydro-2H-benzo[b][1,4]oxazin-6-yl | H | isopropyl |
| 219 | cyclopropyl | 4-(3-methoxypropyl)-2,2-dimethyl-3-oxo-3,4-dihydro-2H-benzo[b][1,4]oxazin-6-yl | H | 2-hydroxyethyl |
| 220 | cyclopropyl | 4-(3-methoxypropyl)-2,2-dimethyl-3-oxo-3,4-dihydro-2H-benzo[b][1,4]oxazin-6-yl | H | 2-ethoxyethyl |

-continued

| examples | R1 | R2 | R3 | R4 |
|---|---|---|---|---|
| 221 | cyclopropyl* | 4-(3-methoxypropyl)-2,2-dimethyl-3-oxo-3,4-dihydro-2H-benzo[1,4]oxazin-6-yl* | H | (1*,2)-2-ethoxycyclopentyl* |
| 222 | cyclopropyl* | 4-(2-ethoxyethyl)-2,2-dimethyl-3-oxo-3,4-dihydro-2H-benzo[1,4]oxazin-6-yl* | H | (2*S)-1-ethoxy-4-methylpentan-2-yl* |
| 223 | cyclopropyl* | 4-(3-methoxypropyl)-2,2-dimethyl-3-oxo-3,4-dihydro-2H-benzo[1,4]oxazin-6-yl* | H | 2,6-dimethylcyclohexyl* (cis-trans-mix.) |
| 224 | cyclopropyl* | 4-(3-methoxypropyl)-2,2-dimethyl-3-oxo-3,4-dihydro-2H-benzo[1,4]oxazin-6-yl* | H | (1*R)-1-phenylpropyl* |
| 225 | cyclopropyl* | 4-(3-methoxypropyl)-2,2-dimethyl-3-oxo-3,4-dihydro-2H-benzo[1,4]oxazin-6-yl* | H | (1*S)-1-phenylpropyl* |

-continued

| examples | R1 | R2 | R3 | R4 |
|---|---|---|---|---|
| 226 | cyclopropyl | 4-(2-ethoxyethyl)-2,2-dimethyl-3-oxo-3,4-dihydro-2H-benzo[1,4]oxazin-6-yl | H | (S)-1-methoxy-3-methylbutan-2-yl |
| 227 | cyclopropyl | 4-(2-ethoxyethyl)-2,2-dimethyl-3-oxo-3,4-dihydro-2H-benzo[1,4]oxazin-6-yl | H | 1-(tetrahydropyran-4-yl)cyclopropyl |
| 228 | cyclopropyl | 4-(2-ethoxyethyl)-2,2-dimethyl-3-oxo-3,4-dihydro-2H-benzo[1,4]oxazin-6-yl | H | (R)-1-ethoxy-3-methylbutan-2-yl |
| 229 | cyclopropyl | 4-(3-methoxypropyl)-2,2-dimethyl-3-oxo-3,4-dihydro-2H-benzo[1,4]oxazin-6-yl | H | 1-isobutylcyclopropyl |
| 230 | cyclopropyl | 4-(3-methoxypropyl)-2,2-dimethyl-3-oxo-3,4-dihydro-2H-benzo[1,4]oxazin-6-yl | H | 1-(methoxymethyl)cyclopentyl |

-continued

| examples | R1 | R2 | R3 | R4 |
|---|---|---|---|---|
| 231 | cyclopropyl | 4-(2-ethoxyethyl)-2,2-dimethyl-3-oxo-3,4-dihydro-2H-benzo[1,4]oxazin-6-yl | H | 2-methoxy-2-methyl-1-phenylpropyl |
| 232 | cyclopropyl | 2,2-dimethyl-4-(3-methoxypropyl)-3-oxo-3,4-dihydro-2H-benzo[1,4]oxazin-6-yl | H | (1S,2S)-2-hydroxycyclohexyl |
| 233 | cyclopropyl | 2,2-dimethyl-4-(3-methoxypropyl)-3-oxo-3,4-dihydro-2H-benzo[1,4]oxazin-6-yl | H | (1-methoxycyclohexyl)methyl |
| 234 | cyclopropyl | 2,2-dimethyl-4-(3-methoxypropyl)-3-oxo-3,4-dihydro-2H-benzo[1,4]oxazin-6-yl | H | (1R)-1-cyclohexylethyl |
| 235 | cyclopropyl | 2,2-dimethyl-4-(3-methoxypropyl)-3-oxo-3,4-dihydro-2H-benzo[1,4]oxazin-6-yl | H | (1S,2S)-2-ethoxycyclohexyl |

-continued

| examples | R1 | R2 | R3 | R4 |
|---|---|---|---|---|
| 236 | cyclopropyl | 4-(3-methoxypropyl)-2,2-dimethyl-3-oxo-3,4-dihydro-2H-benzo[1,4]oxazin-6-yl | H | 1-(4-fluorophenyl)cyclopropyl |
| 237 | cyclopropyl | 4-(3-methoxypropyl)-2,2-dimethyl-3-oxo-3,4-dihydro-2H-benzo[1,4]oxazin-6-yl | H | 1-(ethoxymethyl)cyclopropyl |
| 238 | cyclopropyl | 4-(3-methoxypropyl)-2,2-dimethyl-3-oxo-3,4-dihydro-2H-benzo[1,4]oxazin-6-yl | H | 1-(methoxymethyl)cyclopropyl |
| 239 | cyclopropyl | 4-(3-methoxypropyl)-2,2-dimethyl-3-oxo-3,4-dihydro-2H-benzo[1,4]oxazin-6-yl | H | tert-butyl |
| 240 | cyclopropyl | 4-(3-methoxypropyl)-2,2-dimethyl-3-oxo-3,4-dihydro-2H-benzo[1,4]oxazin-6-yl | H | (S)-1-methoxy-4-methylpentan-2-yl |

-continued

| examples | R1 | R2 | R3 | R4 |
|---|---|---|---|---|
| 241 | cyclopropyl | 4-(3-methoxypropyl)-2,2-dimethyl-3-oxo-3,4-dihydro-2H-benzo[b][1,4]oxazin-6-yl | H | (S)-1-ethoxy-4-methylpentan-2-yl |
| 242 | cyclopropyl | 2,2-dimethyl-3-oxo-3,4-dihydro-2H-benzo[b][1,4]oxazin-6-yl | H | (S)-1-ethoxy-4-methylpentan-2-yl |
| 243 | cyclopropyl | 4-(3-methoxypropyl)-2,2-dimethyl-3-oxo-3,4-dihydro-2H-benzo[b][1,4]oxazin-6-yl | H | cycloheptyl |
| 244 | cyclopropyl | 4-(3-methoxypropyl)-2,2-dimethyl-3-oxo-3,4-dihydro-2H-benzo[b][1,4]oxazin-6-yl | H | 1-(ethoxymethyl)cyclopentyl |
| 245 | cyclopropyl | 4-(3-methoxypropyl)-2,2-dimethyl-3-oxo-3,4-dihydro-2H-benzo[b][1,4]oxazin-6-yl | H | 1-methoxy-2,2-dimethylpropan-2-yl |

-continued
| examples | R1 | R2 | R3 | R4 |
|---|---|---|---|---|
| 246 |  | 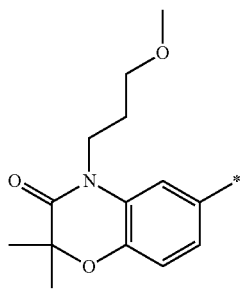 | H | 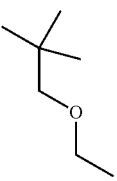 |
| 247 |  | 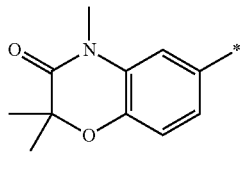 | H | 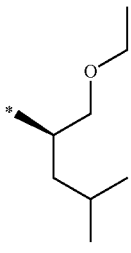 |
| 248 |  | 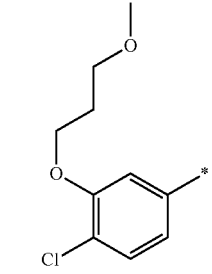 | H | 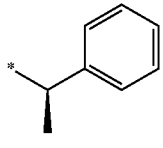 |
| 249 |  | 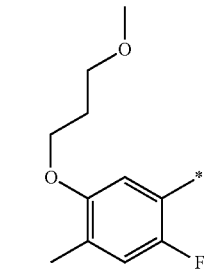 | H | 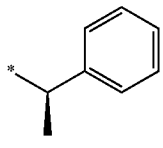 |
| 250 |  | 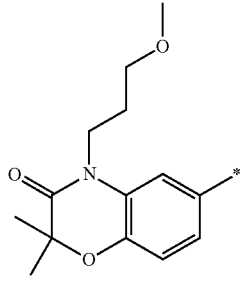 | H | 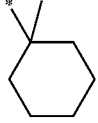 |

-continued
| examples | R1 | R2 | R3 | R4 |
|---|---|---|---|---|
| 251 |  | 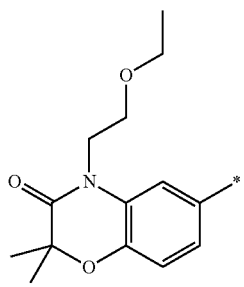 | H | 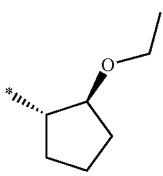 |
| 252 |  | 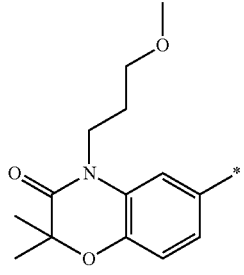 | H | 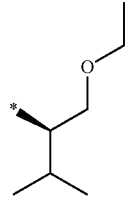 |
| 253 |  | 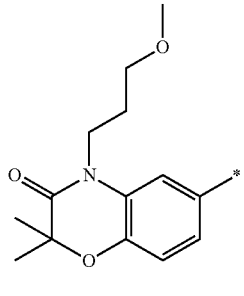 | H | 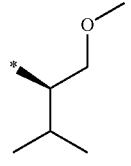 |
| 254 |  | 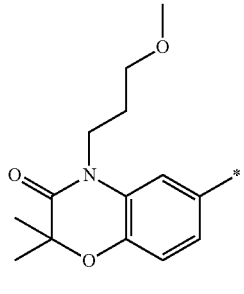 | H | 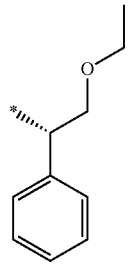 |
| 255 |  | 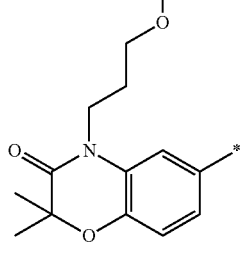 | H | 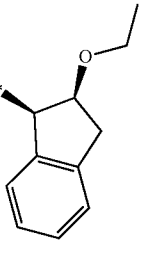 |

-continued

| examples | R1 | R2 | R3 | R4 |
|---|---|---|---|---|
| 256 | cyclopropyl | 4-(3-methoxypropyl)-2,2-dimethyl-3-oxo-3,4-dihydro-2H-benzo[1,4]oxazin-6-yl | H | 2-phenylpropan-2-yl |
| 257 | cyclopropyl | 4-(3-methoxypropyl)-2,2-dimethyl-3-oxo-3,4-dihydro-2H-benzo[1,4]oxazin-6-yl | H | (1S)-2-methoxy-1-phenylethyl |
| 258 | cyclopropyl | 4-(3-methoxypropyl)-2,2-dimethyl-3-oxo-3,4-dihydro-2H-benzo[1,4]oxazin-6-yl | H | (1R,2S)-2-ethoxy-2,3-dihydro-1H-inden-1-yl |
| 259 | cyclopropyl | 4-(3-methoxypropyl)-2,2-dimethyl-3-oxo-3,4-dihydro-2H-benzo[1,4]oxazin-6-yl | H | 1-carbamoyl-1-methylethyl |
| 260 | cyclopropyl | 4-(3-methoxypropyl)-2,2-dimethyl-3-oxo-3,4-dihydro-2H-benzo[1,4]oxazin-6-yl | H | (1S)-2,2-dimethylcyclohexyl |

-continued

| examples | R1 | R2 | R3 | R4 |
|---|---|---|---|---|
| 261 | cyclopropyl | 4-(3-methoxypropyl)-2,2-dimethyl-3-oxo-3,4-dihydro-2H-benzo[1,4]oxazin-6-yl | H | (S)-2-(ethoxymethyl)-3-methylbutyl |
| 262 | cyclopropyl | 4-(3-methoxypropyl)-2,2-dimethyl-3-oxo-3,4-dihydro-2H-benzo[1,4]oxazin-6-yl | H | (S)-2-ethoxy-1-phenylethyl |
| 263 | cyclopropyl | 4-(3-methoxypropyl)-2,2-dimethyl-3-oxo-3,4-dihydro-2H-benzo[1,4]oxazin-6-yl | H | 2,2-dimethylcyclohexyl |
| 264 | cyclopropyl | 4-(3-methoxypropyl)-2,2-dimethyl-3-oxo-3,4-dihydro-2H-benzo[1,4]oxazin-6-yl | H | trans-2-ethoxyindan-1-yl |
| 265 | cyclopropyl | 4-(3-methoxypropyl)-2,2-dimethyl-3-oxo-3,4-dihydro-2H-benzo[1,4]oxazin-6-yl | H | 3-methoxy-2-(methoxymethyl)-2-methylpropyl |

-continued

| examples | R1 | R2 | R3 | R4 |
|---|---|---|---|---|
| 266 | cyclopropyl | 4-(3-methoxypropyl)-2,2-dimethyl-3-oxo-3,4-dihydro-2H-benzo[1,4]oxazin-6-yl | H | (S)-1-methoxypropan-2-yl |
| 267 | cyclopropyl | 4-(3-methoxypropyl)-2,2-dimethyl-3-oxo-3,4-dihydro-2H-benzo[1,4]oxazin-6-yl | H | (S)-1-ethoxypropan-2-yl |
| 268 | cyclopropyl | 4-(3-methoxypropyl)-2,2-dimethyl-3-oxo-3,4-dihydro-2H-benzo[1,4]oxazin-6-yl | H | (R)-1-ethoxypropan-2-yl |
| 269 | cyclopropyl | 5-isopropyl-4-(3-methoxypropoxy)pyridin-2-yl | H | 1-phenylcyclopentyl |
| 270 | cyclopropyl | 4-(3-methoxypropyl)-2,2-dimethyl-3-oxo-3,4-dihydro-2H-benzo[1,4]oxazin-6-yl | H | (S)-2-methoxy-1-phenylethyl |

-continued
| examples | R1 | R2 | R3 | R4 |
|---|---|---|---|---|
| 271 |  | 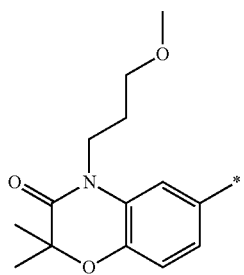 | H | 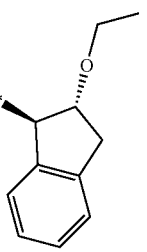 |
| 272 |  | 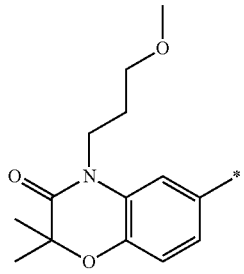 | H | 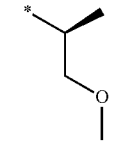 |
| 273 |  | 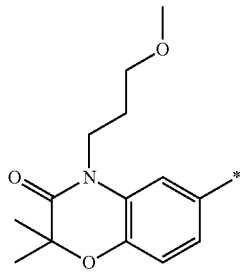 | H | 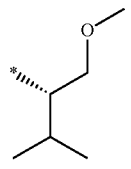 |
| 274 |  | 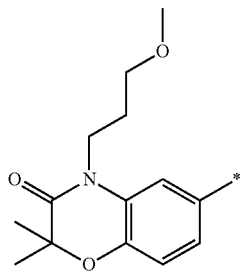 | H | 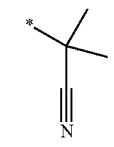 |
| 275 |  | 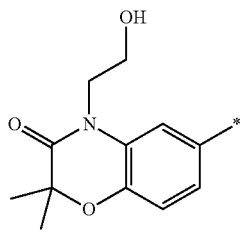 | H | 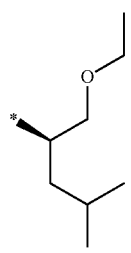 |

-continued

| examples | R1 | R2 | R3 | R4 |
|---|---|---|---|---|
| 276 | cyclopropyl-* | 5-isopropyl-4-(3-methoxypropoxy)pyridin-2-yl | H | (S)-1-ethoxy-4-methylpentan-2-yl |
| 277 | cyclopropyl-* | 4-(3-hydroxypropyl)-2,2-dimethyl-3-oxo-3,4-dihydro-2H-benzo[b][1,4]oxazin-6-yl | H | (S)-1-ethoxy-4-methylpentan-2-yl |
| 278 | cyclopropyl-* | 4-fluoro-5-(3-methoxypropoxy)-2-methylphenyl | H | (S)-1-ethoxy-4-methylpentan-2-yl |
| 279 | cyclopropyl-* | 4-fluoro-5-(3-methoxypropoxy)-2-methylphenyl | H | 1-(methoxymethyl)cyclopropyl |
| 280 | cyclopropyl-* | 4-(2-ethoxyethyl)-2,2-dimethyl-3-oxo-3,4-dihydro-2H-benzo[b][1,4]oxazin-6-yl | H | (S)-1-ethoxy-3-methylbutan-2-yl |

-continued
| examples | R1 | R2 | R3 | R4 |
|---|---|---|---|---|
| 281 |  | 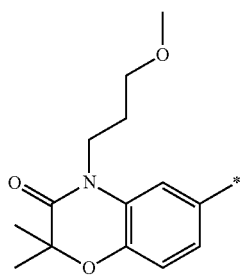 | H | 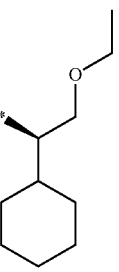 |
| 282 |  | 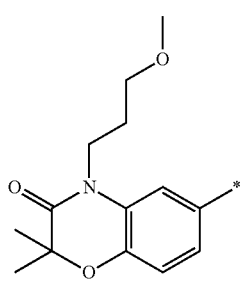 | H | 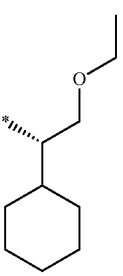 |
| 283 |  | 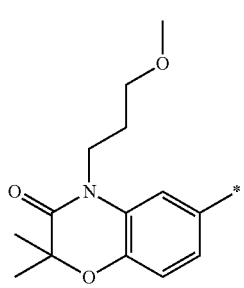 | H | 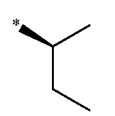 |
| 284 |  | 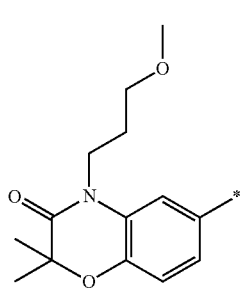 | H | 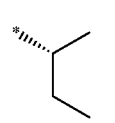 |
| 285 |  | 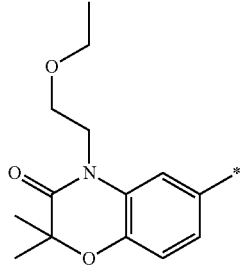 | H | 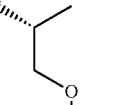 |

-continued

| examples | R1 | R2 | R3 | R4 |
|---|---|---|---|---|
| 286 | cyclopropyl-* | 4-(2-ethoxyethyl)-2,2-dimethyl-3-oxo-3,4-dihydro-2H-benzo[1,4]oxazin-6-yl* | H | (S)-1-methoxy-3-methylbutan-2-yl* |
| 287 | cyclopropyl-* | 2,2-dimethyl-4-(3-methoxypropyl)-3-oxo-3,4-dihydro-2H-benzo[1,4]oxazin-6-yl* | H | (S)-1-methoxy-4-methylpentan-2-yl* |
| 288 | cyclopropyl-* | 2,2-dimethyl-4-(3-methoxypropyl)-3-oxo-3,4-dihydro-2H-benzo[1,4]oxazin-6-yl* | H | (S)-1-ethoxy-3-methylbutan-2-yl* |
| 289 | cyclopropyl-* | 2,2-dimethyl-4-(3-methoxypropyl)-3-oxo-3,4-dihydro-2H-benzo[1,4]oxazin-6-yl* | H | (S)-2-cyclohexyl-1-methoxyethyl* |
| 290 | isopropyl-* | 2,2-dimethyl-4-(3-methoxypropyl)-3-oxo-3,4-dihydro-2H-benzo[1,4]oxazin-6-yl* | H | (S)-1-ethoxy-4-methylpentan-2-yl* |

-continued
| examples | R1 | R2 | R3 | R4 |
|---|---|---|---|---|
| 291 |  | 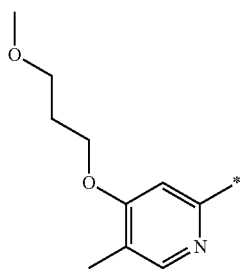 | H | 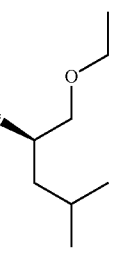 |
| 292 |  | 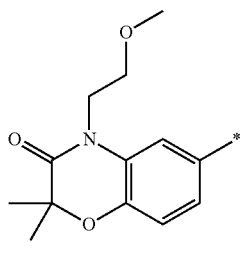 | H | 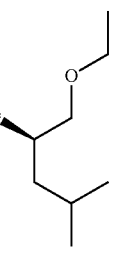 |
| 293 |  | 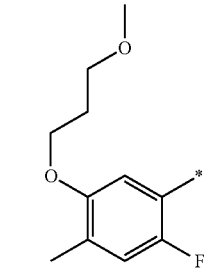 | H | 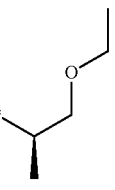 |
| 294 |  | 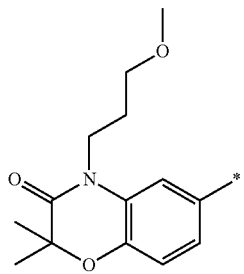 | H | 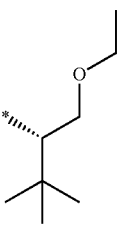 |
| 295 |  | 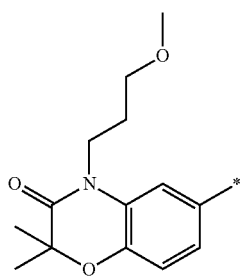 | H | 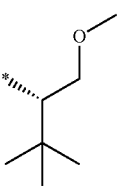 |

-continued

| examples | R1 | R2 | R3 | R4 |
|---|---|---|---|---|
| 296 | cyclopropyl | 3-isopropyl-6-(3-methoxypropoxy)pyridin-2-yl | H | (S)-1-ethoxy-4-methylpentan-2-yl |
| 297 | cyclopropyl | 4-(3-methoxypropyl)-2,2-dimethyl-3-oxo-3,4-dihydro-2H-benzo[b][1,4]oxazin-6-yl | H | (S)-1-ethoxy-3,3-dimethylbutan-2-yl |
| 298 | cyclopropyl | 4-(3-methoxypropyl)-2,2-dimethyl-3-oxo-3,4-dihydro-2H-benzo[b][1,4]oxazin-6-yl | H | 1-(ethoxymethyl)cyclopropyl |
| 299 | isopropyl | 4-(3-methoxypropyl)-2,2-dimethyl-3-oxo-3,4-dihydro-2H-benzo[b][1,4]oxazin-6-yl | H | (S)-1-methoxy-4-methylpentan-2-yl |
| 300 | cyclopropyl | 4-(3-methoxypropyl)-2,2-dimethyl-3-oxo-3,4-dihydro-2H-benzo[b][1,4]oxazin-6-yl | H | (R)-1-cyclohexyl-2-methoxyethyl |

-continued

| examples | R1 | R2 | R3 | R4 |
|---|---|---|---|---|
| 301 | cyclopropyl | 4-(2-ethoxyethyl)-2,2-dimethyl-3-oxo-3,4-dihydro-2H-benzo[b][1,4]oxazin-6-yl | H | (S)-1-methoxypropan-2-yl |
| 302 | isopropyl | 4-(2-ethoxyethyl)-2,2-dimethyl-3-oxo-3,4-dihydro-2H-benzo[b][1,4]oxazin-6-yl | H | (S)-1-ethoxy-3-methylbutan-2-yl |
| 303 | isopropyl | 2,2-dimethyl-4-(3-methoxypropyl)-3-oxo-3,4-dihydro-2H-benzo[b][1,4]oxazin-6-yl | H | (S)-1-ethoxypropan-2-yl |
| 304 | cyclopropyl | 2,2-dimethyl-4-(3-methoxypropyl)-3-oxo-3,4-dihydro-2H-benzo[b][1,4]oxazin-6-yl | H | (R)-1-cyclohexyl-3-ethoxypropan-2-yl |
| 305 | cyclopropyl | 2,2-dimethyl-4-(3-methoxypropyl)-3-oxo-3,4-dihydro-2H-benzo[b][1,4]oxazin-6-yl | H | (R)-1-cyclohexyl-3-methoxypropan-2-yl |

-continued
| examples | R1 | R2 | R3 | R4 |
|---|---|---|---|---|
| 306 |  | 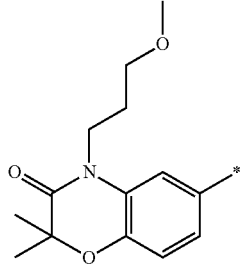 | H | 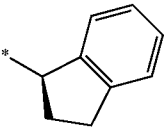 |
| 307 |  | 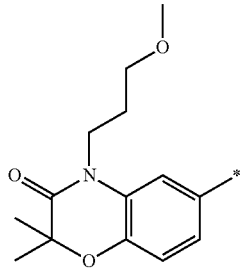 | H | 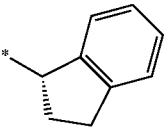 |
| 308 |  | 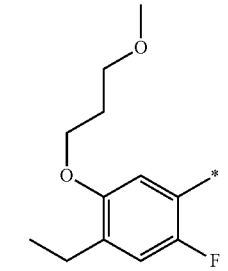 | H | 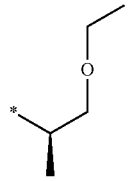 |
| 309 |  | 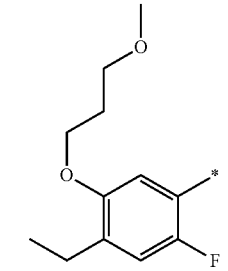 | H | 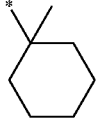 |
| 310 |  | 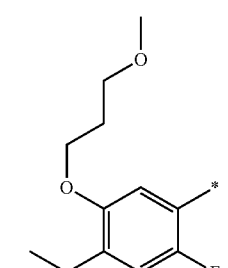 | H | 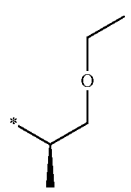 |

-continued

| examples | R1 | R2 | R3 | R4 |
|---|---|---|---|---|
| 311 | cyclopropyl | 4-(3-methoxypropyl)-2,2-dimethyl-3-oxo-3,4-dihydro-2H-benzo[b][1,4]oxazin-6-yl | H | (S)-1-methoxy-3,3-dimethylbutan-2-yl |
| 312 | isopropyl | 4-(3-methoxypropyl)-2,2-dimethyl-3-oxo-3,4-dihydro-2H-benzo[b][1,4]oxazin-6-yl | H | trans-2-ethoxycyclopentyl |
| 313 | cyclopropyl | 4-(3-methoxypropyl)-2,2-dimethyl-3-oxo-3,4-dihydro-2H-benzo[b][1,4]oxazin-6-yl | H | 1-(isopropoxymethyl)cyclopropyl |
| 314 | cyclopropyl | 4-(3-methoxypropyl)-2,2-dimethyl-3-oxo-3,4-dihydro-2H-benzo[b][1,4]oxazin-6-yl | H | (S)-1-ethoxy-3-phenylpropan-2-yl |
| 315 | cyclopropyl | 4-(3-methoxypropyl)-2,2-dimethyl-3-oxo-3,4-dihydro-2H-benzo[b][1,4]oxazin-6-yl | H | (R)-1-methoxy-3-phenylpropan-2-yl |

-continued

| examples | R1 | R2 | R3 | R4 |
|---|---|---|---|---|
| 316 | cyclopropyl-* | 4-fluoro-2-ethyl-5-[(3-methoxypropyl)amino]phenyl-* | H | (2S)-1-ethoxy-4-methylpentan-2-yl-* |
| 317 | cyclopropyl-* | 4-fluoro-2-isopropyl-5-(3-methoxypropoxy)phenyl-* | H | (2S)-1-ethoxy-4-methylpentan-2-yl-* |
| 318 | cyclopropyl-* | 4-(3-methoxypropyl)-2,2-dimethyl-3-oxo-3,4-dihydro-2H-benzo[1,4]oxazin-6-yl-* | H | (2S)-1-ethoxy-3-phenylpropan-2-yl-* |
| 319 | cyclopropyl-* | 4-(3-methoxypropyl)-2,2-dimethyl-3-oxo-3,4-dihydro-2H-benzo[1,4]oxazin-6-yl-* | H | (2S)-3-cyclohexyl-1-ethoxypropan-2-yl-* |
| 320 | cyclopropyl-* | 4-(3-methoxypropyl)-2,2-dimethyl-3-oxo-3,4-dihydro-2H-benzo[1,4]oxazin-6-yl-* | H | (2S)-3-cyclohexyl-1-methoxypropan-2-yl-* |

-continued

| examples | R1 | R2 | R3 | R4 |
|---|---|---|---|---|
| 321 | cyclopropyl | 4-(2-isopropoxyethyl)-2,2-dimethyl-3-oxo-3,4-dihydro-2H-benzo[1,4]oxazin-6-yl | H | (S)-1-ethoxymethyl-3-methylbutyl |
| 322 | cyclopropyl | 4-(2-isopropoxyethyl)-2,2-dimethyl-3-oxo-3,4-dihydro-2H-benzo[1,4]oxazin-6-yl | H | (S)-1-methoxymethyl-2-phenylethyl |
| 323 | cyclopropyl | 4-(2-isopropoxyethyl)-2,2-dimethyl-3-oxo-3,4-dihydro-2H-benzo[1,4]oxazin-6-yl | H | (R)-1-(2-methoxyethyl)-2-phenylethyl |
| 324 | cyclopropyl | 4-(2-isopropoxyethyl)-2,2-dimethyl-3-oxo-3,4-dihydro-2H-benzo[1,4]oxazin-6-yl | H | (R)-1-(2-ethoxyethyl)-2-phenylethyl |
| 325 | cyclopropyl | 2,2-dimethyl-3-oxo-4-pentyl-3,4-dihydro-2H-benzo[1,4]oxazin-6-yl | H | (S)-1-ethoxymethyl-3-methylbutyl |

-continued

| examples | R1 | R2 | R3 | R4 |
|---|---|---|---|---|
| 326 | cyclopropyl | 4-(3-methoxypropyl)-2,2-dimethyl-3-oxo-3,4-dihydro-2H-benzo[1,4]oxazin-6-yl | H | (S)-1-benzyl-3-ethoxypropyl |
| 327 | cyclopropyl | 4-ethyl-2-(3-methoxypropoxy)-5-fluorophenyl | H | (1R,2S)-2-hydroxycyclohexyl |
| 328 | cyclopropyl | 4-(3-methoxypropyl)-2,2-dimethyl-3-oxo-3,4-dihydro-2H-benzo[1,4]oxazin-6-yl | H | (S)-1-benzyl-3-methoxypropyl |
| 329 | cyclopropyl | 4-ethyl-2-(3-methoxypropoxy)-5-fluorophenyl | H | 2-oxoazepan-3-yl (racemate) |
| 330 | cyclopropyl | 4-(2-ethoxyethyl)-2,2-dimethyl-3-oxo-3,4-dihydro-2H-benzo[1,4]oxazin-6-yl | H | (S)-2-methoxy-1-phenylethyl |

-continued

| examples | R1 | R2 | R3 | R4 |
|---|---|---|---|---|
| 331 | cyclopropyl | 4-(3-methoxypropyl)-2,2-dimethyl-3-oxo-3,4-dihydro-2H-benzo[1,4]oxazin-6-yl | H | (S)-1-methoxy-3-methylpentan-4-yl |
| 332 | cyclopropyl | 4-(3-methoxypropyl)-2,2-dimethyl-3-oxo-3,4-dihydro-2H-benzo[1,4]oxazin-6-yl | H | (S)-1-ethoxy-3-methylpentan-4-yl |
| 333 | cyclopropyl | 4-(2-ethoxyethyl)-2,2-dimethyl-3-oxo-3,4-dihydro-2H-benzo[1,4]oxazin-6-yl | H | (1S,2S)-2-ethoxyindan-1-yl |
| 334 | cyclopropyl | 4-(2-ethoxyethyl)-2,2-dimethyl-3-oxo-3,4-dihydro-2H-benzo[1,4]oxazin-6-yl | H | 1-(isopropoxymethyl)cyclopropyl |
| 335 | cyclopropyl | 4-(3-aminopropyl)-2,2-dimethyl-3-oxo-3,4-dihydro-2H-benzo[1,4]oxazin-6-yl | H | (S)-1-ethoxy-3-methylpentan-4-yl |

-continued
| examples | R1 | R2 | R3 | R4 |
|---|---|---|---|---|
| 336 |  | 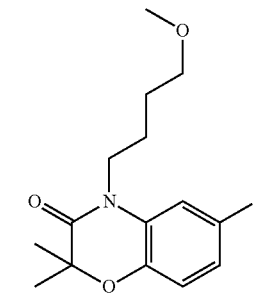 | H | 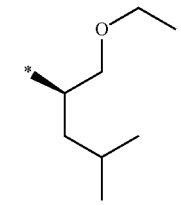 |
| 337 |  | 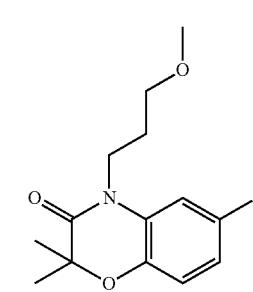 | H | 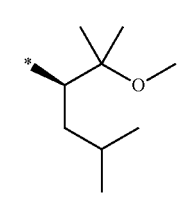 |
| 338 |  | 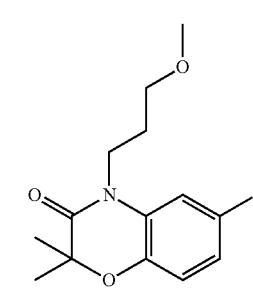 | H | 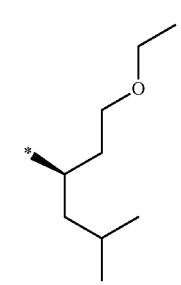 |
| 339 |  | 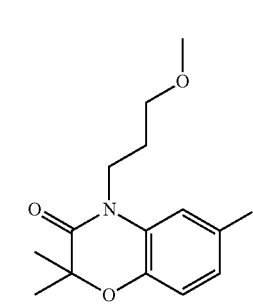 | H | 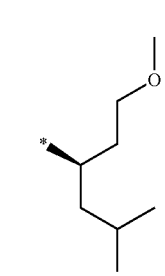 |
| 340 |  | 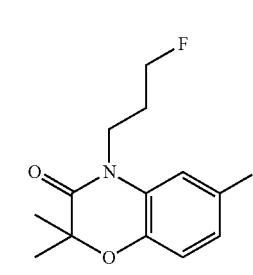 | H | 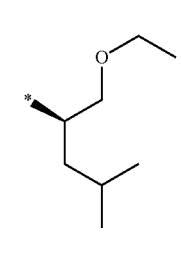 |

-continued
| examples | R1 | R2 | R3 | R4 |
|---|---|---|---|---|
| 341 |  | 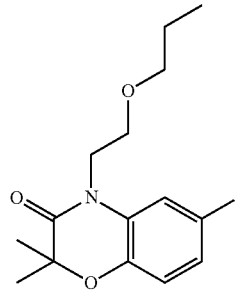 | H | 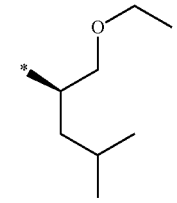 |
| 342 |  | 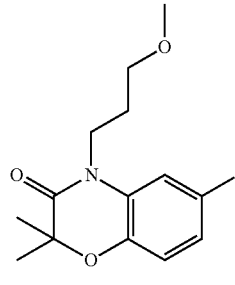 | H | 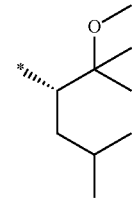 |
| 343 |  | 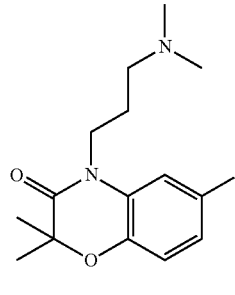 | H | 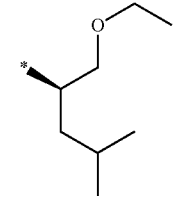 |
| 369 |  | 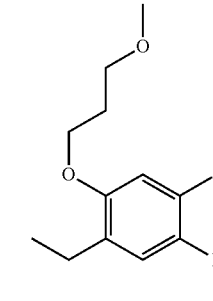 | H | 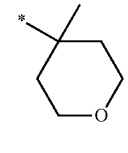 |
| 370 |  | 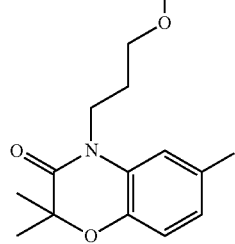 | H | 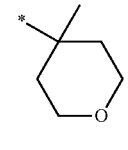 |

-continued
| examples | R1 | R2 | R3 | R4 |
|---|---|---|---|---|
| 371 |  | 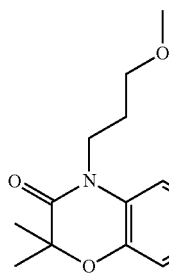 | H | 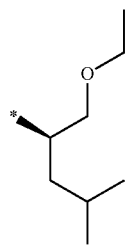 |
| 372 |  | 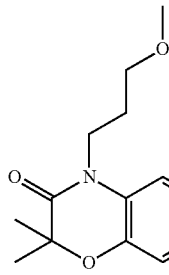 | H | 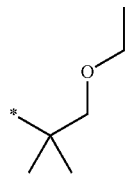 |
and compounds of the Formula:
| examples | R1 | R2 | R3,4 |
|---|---|---|---|
| 344 | 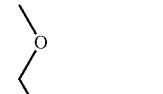 | 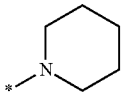 | 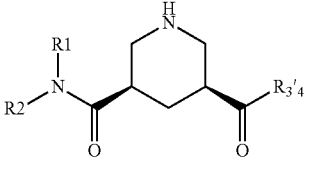 |
| 345 |  |  | 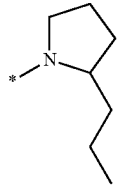 |
-continued
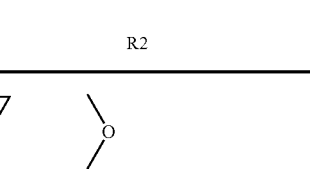
| examples | R1 | R2 | R3,4 |
|---|---|---|---|
| 346 |  | 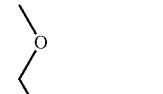 | 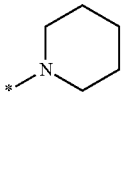 |
| 347 |  |  | 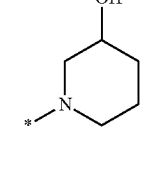 |

765
and compounds of the Formula:
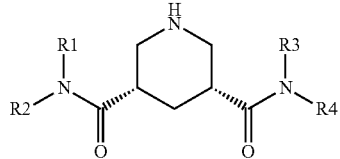
| example | R1 | R2 | R3 | R4 |
|---|---|---|---|---|
| 348 | 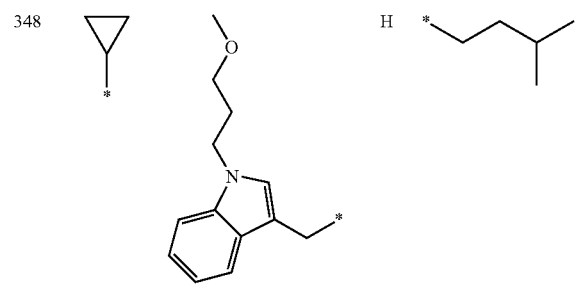 | | H | |
| 349 | 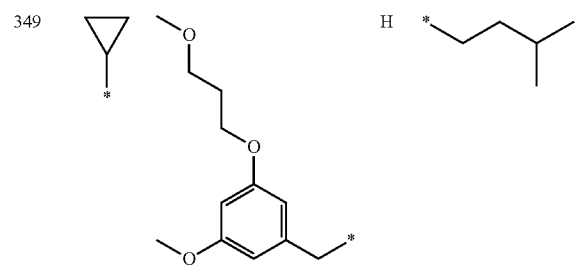 | | H | |
| 350 | 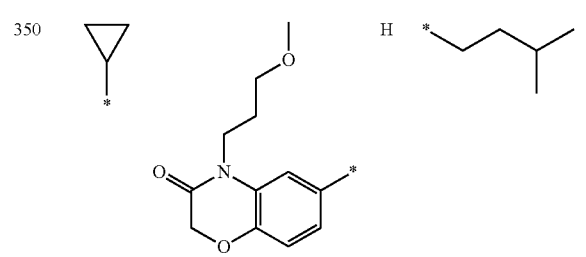 | | H | |
766
and compounds of the Formula:
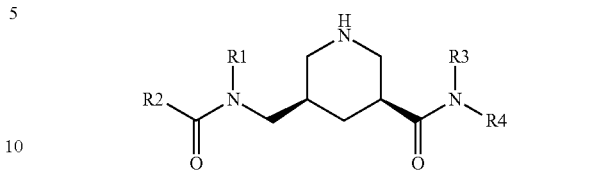
| example | R1 | R2 | R3 | R4 |
|---|---|---|---|---|
| 351 | 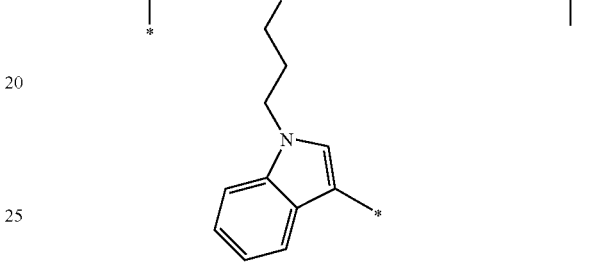 | | H | |
and compounds of Formula:
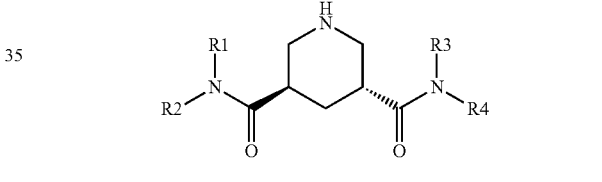
| examples | R1 | R2 | R3 |
|---|---|---|---|
| 352 | 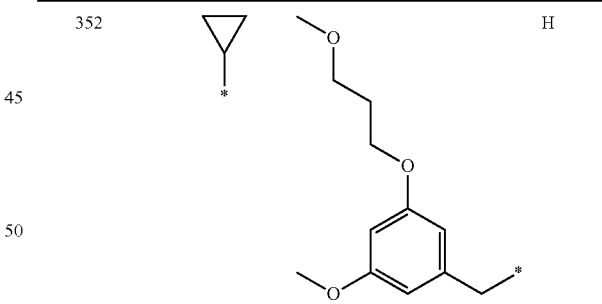 | | H |
| 353 | 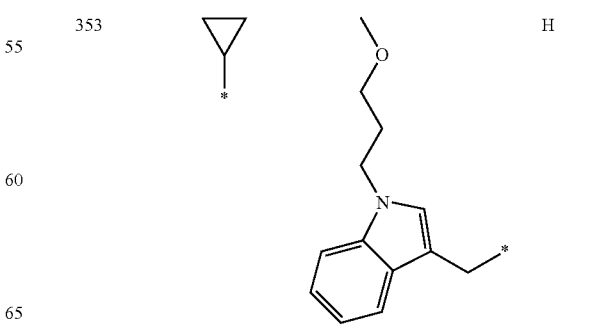 | | H |

767
-continued
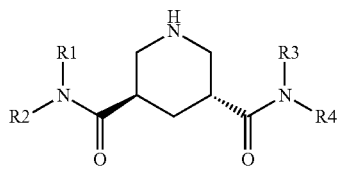
| examples | R1 | R2 | R3 |
|---|---|---|---|
| 354 | 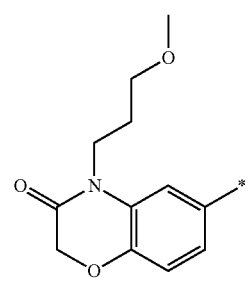 | | H |
| 355 | | | H |
| 356 | 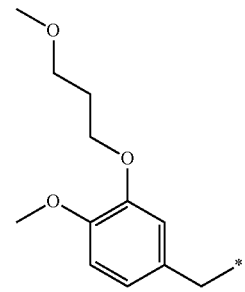 | | H |
| 357 | | 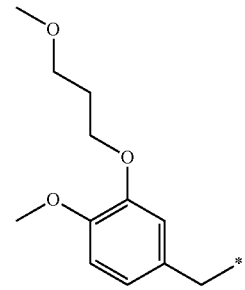 | H |
768
and compounds of Formula:
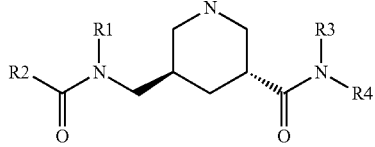
| example | R1 | R2 | R3 | R4 |
|---|---|---|---|---|
| 358 | | | H | |
| 359 | | | H | |
and compound of Formula:
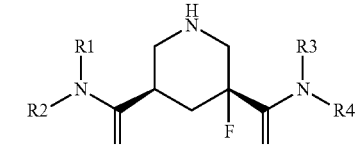
| example | R1 | R2 | R3 | R4 |
|---|---|---|---|---|
| 360 | 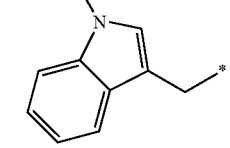 | | H | | and compound of Formula:
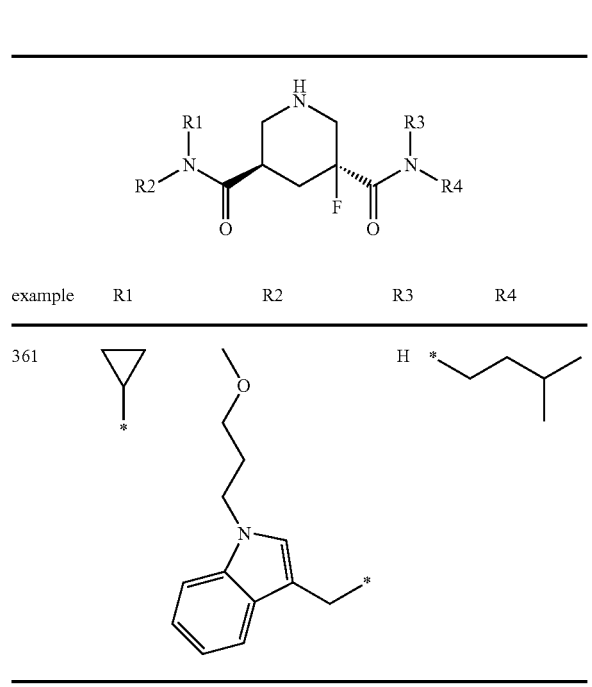
and compounds of Formula:
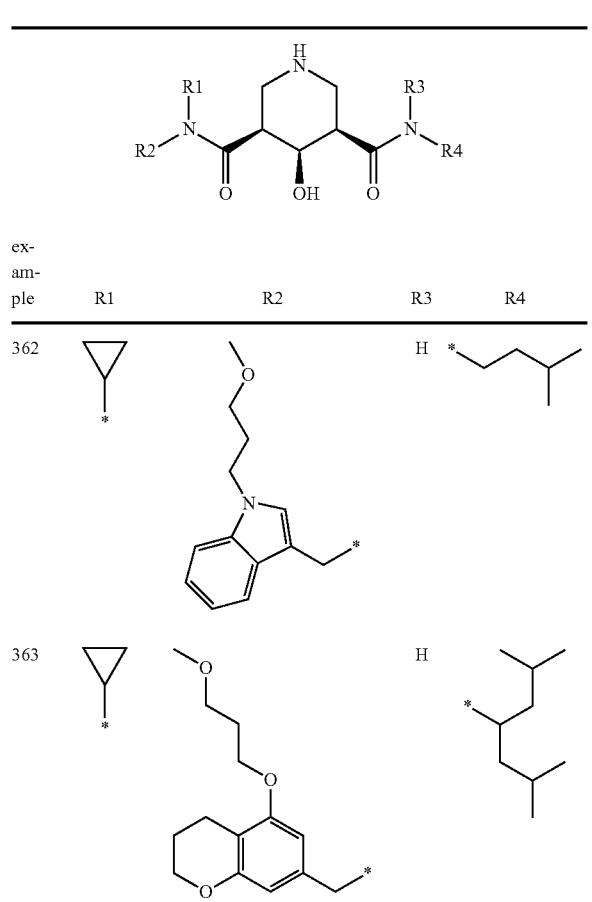
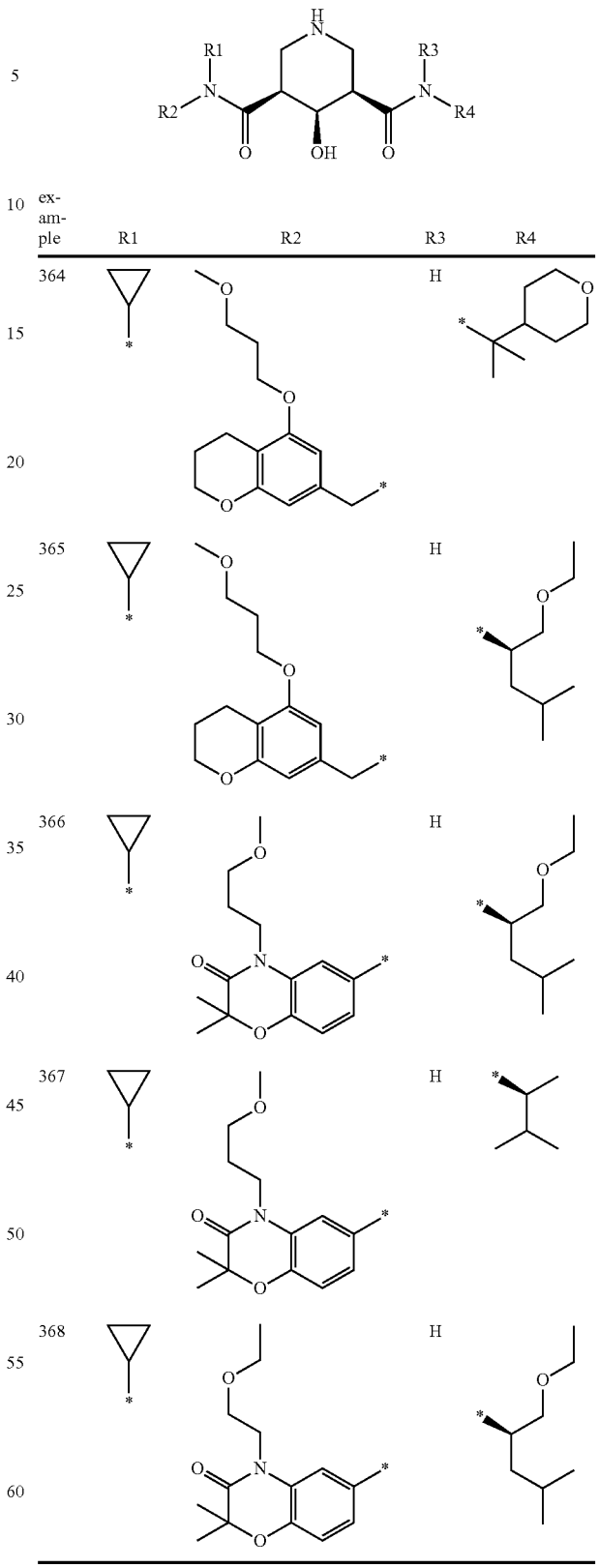
or a pharmaceutically acceptable salt thereof, respectively.
20. The compound according to claim 1 selected from the compounds of the formula:

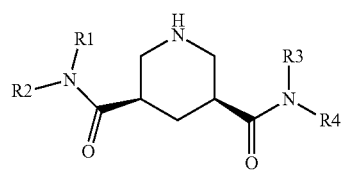
as represented in the following table:
| examples | R1 | R2 | R3 | R4 |
|---|---|---|---|---|
| 1 | cyclopropyl | 3-(1H-indol-3-ylmethyl)propyl methyl ether | H | isobutyl |
| 2 | cyclopropyl | 3-(1H-indol-3-ylmethyl)propyl methyl ether | H | neopentyl |
or a pharmaceutically acceptable-salt thereof, respectively.
* * * * *